US006627629B2

(12) United States Patent
Ko et al.

(10) Patent No.: US 6,627,629 B2
(45) Date of Patent: Sep. 30, 2003

(54) N-UREIDOHETEROCYCLOALKYL-PIPERIDINES AS MODULATORS OF CHEMOKINE RECEPTOR ACTIVITY

(75) Inventors: Soo S. Ko, Hockessin, DE (US); James R. Pruitt, Landenberg, PA (US); Dean A. Wacker, Chadds Ford, PA (US); Douglas G. Batt, Wilmington, DE (US)

(73) Assignee: Bristol-Myers Squibb Pharma, Princeton, NJ (US)

( * ) Notice: Subject to any disclaimer, the term of this patent is extended or adjusted under 35 U.S.C. 154(b) by 0 days.

(21) Appl. No.: 09/895,138

(22) Filed: Jun. 29, 2001

(65) Prior Publication Data

US 2003/0032654 A1 Feb. 13, 2003

Related U.S. Application Data

(60) Provisional application No. 60/215,215, filed on Jun. 30, 2000.
(51) Int. Cl.[7] .............. A61K 31/4525; A61K 31/4545; A61K 31/5377; C07D 401/06; C07D 405/14; C07D 413/14; A61P 29/00
(52) U.S. Cl. .................. 514/237.2; 514/222.2; 514/318; 514/319; 514/320; 514/321; 514/322; 514/323; 514/324; 514/326; 514/327; 514/212.03; 514/217.04; 540/524; 540/527; 540/597; 544/3; 544/129; 544/130; 546/187; 546/189; 546/191; 546/194; 546/197; 546/198; 546/199; 546/201; 546/207; 546/208; 546/209; 546/210; 546/211; 546/213; 546/214
(58) Field of Search .................. 546/187, 189, 546/191, 194, 197–199, 201, 207, 208–211, 213, 214; 544/3, 129, 130; 540/524, 597; 514/222.2, 237.2, 318–324, 326, 327, 212.03, 217.04

(56) References Cited

U.S. PATENT DOCUMENTS

| | | | |
|---|---|---|---|
| 3,461,120 A | 8/1969 | Zenitz et al. | |
| 5,236,921 A | 8/1993 | Emonds-Ai et al. | |
| 5,317,020 A | 5/1994 | Emonds-Alt et al. | |
| 5,547,966 A | 8/1996 | Atwal et al. | |
| 5,668,151 A | 9/1997 | Poindexter et al. | |
| 5,688,955 A | 11/1997 | Kruse et al. | |
| 5,872,135 A | 2/1999 | DeSolms et al. | |
| 5,889,016 A | 3/1999 | Bruce et al. | |
| 5,962,462 A | 10/1999 | Mills et al. | |
| 6,001,836 A | 12/1999 | Poindexter et al. | |
| 6,297,233 B1 * | 10/2001 | Stein ...................... | 514/212.03 |
| 6,331,541 B1 | 12/2001 | Ko et al. | |
| 6,331,545 B1 | 12/2001 | Ko et al. | |

FOREIGN PATENT DOCUMENTS

| | | |
|---|---|---|
| EP | 0350309 | 11/1992 |
| EP | 0903349 | 3/1999 |
| EP | 0747357 | 1/2002 |
| JP | 1261383 | 10/1989 |
| WO | 9320099 | 10/1993 |
| WO | 9422846 | 10/1994 |
| WO | 9427991 | 12/1994 |
| WO | 9427992 | 12/1994 |
| WO | 9518126 | 7/1995 |
| WO | 9519344 | 7/1995 |
| WO | 9610035 | 4/1996 |
| WO | 9626196 | 8/1996 |
| WO | 9717954 | 5/1997 |
| WO | 9718813 | 5/1997 |
| WO | 9719060 | 5/1997 |
| WO | 9722597 | 6/1997 |
| WO | 9724324 | 7/1997 |
| WO | 9724325 | 7/1997 |
| WO | 9727752 | 8/1997 |
| WO | 9736585 | 10/1997 |
| WO | 9736875 | 10/1997 |
| WO | 9736876 | 10/1997 |
| WO | 9736881 | 10/1997 |
| WO | 9736886 | 10/1997 |
| WO | 9736890 | 10/1997 |
| WO | 9736896 | 10/1997 |
| WO | 9736897 | 10/1997 |
| WO | 9736898 | 10/1997 |
| WO | 9736901 | 10/1997 |
| WO | 9738665 | 10/1997 |
| WO | 9748681 | 12/1997 |
| WO | 9805292 | 2/1998 |
| WO | 9825604 | 6/1998 |
| WO | 9825617 | 6/1998 |
| WO | 9831364 | 7/1998 |
| WO | 9850029 | 11/1998 |
| WO | 9850030 | 11/1998 |
| WO | 9850031 | 11/1998 |
| WO | 9904794 | 2/1999 |
| WO | 9909984 | 3/1999 |
| WO | 9927933 | 6/1999 |
| WO | 9954321 | 10/1999 |
| WO | 9967204 | 12/1999 |
| WO | 0035449 | 6/2000 |
| WO | 0035451 | 6/2000 |
| WO | 0035452 | 6/2000 |
| WO | 0035453 | 6/2000 |
| WO | 0035454 | 6/2000 |
| WO | 0035876 | 6/2000 |
| WO | 0035877 | 6/2000 |

OTHER PUBLICATIONS

Hesselgesser J et al. (1998) J. Biol. Chem. 273(25), 15687–15692.*
Howard OMZ et al. (1996) Tibtech 14, 46–51.*
Kim et al., "Migration and proliferation of guinea pig and human airway epithelial cells in response to tachykinins", Am. J. Physiol., 1995, vol. 269, pp. L119–L126 (Chem. Abstract No. 123:133809).
Kraneveld et al., "Airway hyperresponsiveness; first eosinophils and then neuropeptides", Int. J. Immunopharm., 1997, 19(9/10), pp. 517–527, (Chem. Abstract No. 129:107602).

* cited by examiner

*Primary Examiner*—Evelyn Mei Huang
(74) *Attorney, Agent, or Firm*—Mary K. VanAtten

(57) ABSTRACT

The present application describes modulators of CCR3 of formula (I):

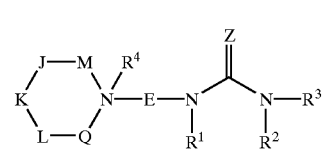

(I)

or pharmaceutically acceptable salt forms thereof, useful for the prevention of asthma and other allergic diseases.

24 Claims, No Drawings

N-UREIDOHETEROCYCLOALKYL-PIPERIDINES AS MODULATORS OF CHEMOKINE RECEPTOR ACTIVITY

This application claims the benefit of 60/215215, filed on Jun. 30, 2000.

FIELD OF THE INVENTION

This invention relates generally to modulators of chemokine receptor activity, pharmaceutical compositions containing the same, and methods of using the same as agents for treatment and prevention of inflammatory diseases such as asthma and allergic diseases, as well as autoimmune pathologies such as rheumatoid arthritis and atherosclerosis.

BACKGROUND OF THE INVENTION

Chemokines are chemotactic cytokines, of molecular weight 6–15 kDa, that are released by a wide variety of cells to attract and activate, among other cell types, macrophages, T and B lymphocytes, eosinophils, basophils and neutrophils (reviewed in Luster, New Eng. J Med., 338, 436–445 (1998) and Rollins, Blood, 90, 909–928 (1997)). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1, -2, and -3) are chemotactic for, among other cell types, macrophages, T lymphocytes, eosinophils, dendritic cells, and basophils. There also exist the chemokines lymphotactin-1, lymphotactin-2 (both C chemokines), and fractalkine (a CXXXC chemokine) that do not fall into either of the major chemokine subfamilies.

The chemokines bind to specific cell-surface receptors belonging to the family of G-protein-coupled seven-transmembrane-domain proteins (reviewed in Horuk, Trends Pharm. Sci., 15, 159–165 (1994)) which are termed "chemokine receptors." On binding their cognate ligands, chemokine receptors transduce an intracellular signal through the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns: CCR-1 (or "CKR-1" or "CC-CKR-1") [MIP-1α, MCP-3, MCP-4, RANTES] (Ben-Barruch, et al., Cell, 72, 415–425 (1993), Luster, New Eng. J. Med., 338, 436–445 (1998)); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo et al., Proc. Natl. Acad. Sci. USA, 91, 2752–2756 (1994), Luster, New Eng. J. Med., 338, 436–445 (1998)); CCR-3 (or "CKR-3" or "CC-CKR-3") [eotaxin-1, eotaxin-2, RANTES, MCP-3, MCP-4] (Combadiere, et al., J. Biol. Chem., 270, 16491–16494 (1995), Luster, New Eng. J. Med., 338, 436–445 (1998)); CCR-4 (or "CKR-4" or "CC-CKR-4") [TARC, MIP-1α, RANTES, MCP-1] (Power et al., J. Biol. Chem., 270, 19495–19500 (1995), Luster, New Eng. J. Med., 338, 436–445 (1998)); CCR-5 (or "CKR-5" OR "CC-CKR-5") [MIP-1α, RANTES, MIP-1β] (Sanson, et al., Biochemistry, 35, 3362–3367 (1996)); CCR-6 (or "CKR-6" or "CC-CKR-6") [LARC] (Baba et al., J. Biol. Chem., 272, 14893–14898 (1997)); CCR-7 (or "CKR-7" or "CC-CKR-7") [ELC] (Yoshie et al., J. Leukoc. Biol. 62, 634–644 (1997)); CCR-8 (or "CKR-8" or "CC-CKR-8") [I-309, TARC, MIP-1β] (Napolitano et al., J. Immunol., 157, 2759–2763 (1996), Bernardini et al., Eur. J. Immunol., 28, 582–588 (1998)); and CCR-10 (or "CKR-10" or "CC-CKR-10") [MCP-1, MCP-3] (Bonini et al, DNA and Cell Biol., 16, 1249–1256 (1997)).

In addition to the mammalian chemokine receptors, mammalian cytomegaloviruses, herpesviruses and poxviruses have been shown to express, in infected cells, proteins with the binding properties of chemokine receptors (reviewed by Wells and Schwartz, Curr. Opin. Biotech., 8, 741–748 (1997)). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

Chemokine receptors have been implicated as being important mediators of inflammatory, infectious, and immunoregulatory disorders and diseases, including asthma and allergic diseases, as well as autoimmune pathologies such as rheumatoid arthritis and atherosclerosis. For example, the chemokine receptor CCR-3 plays a pivotal role in attracting eosinophils to sites of allergic inflammation and in subsequently activating these cells. The chemokine ligands for CCR-3 induce a rapid increase in intracellular calcium concentration, increased expression of cellular adhesion molecules, cellular degranulation, and the promotion of eosinophil migration. Accordingly, agents which modulate chemokine receptors would be useful in such disorders and diseases. In addition, agents which modulate chemokine receptors would also be useful in infectious diseases such as by blocking infection of CCR3 expressing cells by HIV or in preventing the manipulation of immune cellular responses by viruses such as cytomegaloviruses.

A substantial body of art has accumulated over the past several decades with respect to substituted piperidines and pyrrolidines. These compounds have implicated in the treatment of a variety of disorders.

WO 98/25604 describes spiro-substituted azacycles which are useful as modulators of chemokine receptors:

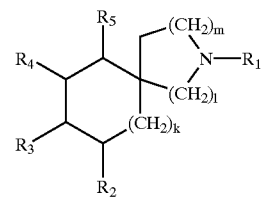

wherein $R_1$ is $C_{1-6}$ alkyl, optionally substituted with functional groups such as —$NR^6CONHR^7$, wherein $R^6$ and $R^7$ may be phenyl further substituted with hydroxy, alkyl, cyano, halo and haloalkyl. Such spiro compounds are not considered part of the present invention.

WO 95/13069 is directed to certain piperidine, pyrrolidine, and hexahydro-1H-azepine compounds of general formula:

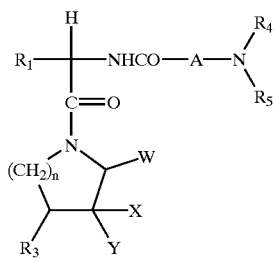

wherein A may be substituted alkyl or Z-substituted alkyl, with Z=$NR_{6a}$ or O. Compounds of this type are claimed to promote the release of growth hormone in humans and animals.

WO 93/06108 discloses pyrrolobenzoxazine derivatives as 5-hydroxytryptamine (5-HT) agonists and antagonists:

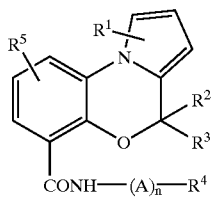

wherein A is lower alkylene and $R^4$ may be phenyl optionally substituted with halogen.

U.S. Pat. No. 5,668,151 discloses Neuropeptide Y (NPY) antagonists comprising 1,4-dihydropyridines with a piperidinyl or tetrahydropyridinyl-containing moiety attached to the 3-position of the 4-phenyl ring:

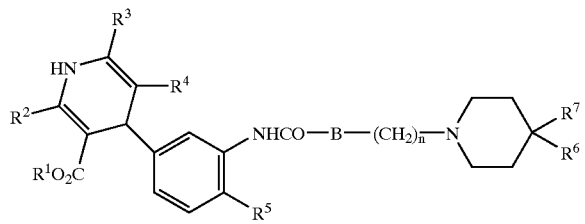

wherein B may be NH, $NR^1$, O, or a bond, and $R^7$ may be substituted phenyl, benzyl, phenethyl and the like.

Patent publication EP 0 903 349 A2 discloses CCR-3 receptor antagonists comprising cyclic amines of the following structure:

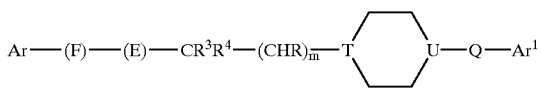

wherein T and U may be both nitrogen or one of T and U is nitrogen and the other is carbon and E may be —$NR^6CONR^5$— and others.

These reference compounds are readily distinguished structurally by either the nature of the urea functionality, the attachment chain, or the possible substitution of the present invention. The prior art does not disclose nor suggest the unique combination of structural fragments which embody these novel piperidine amides as having activity toward the chemokine receptors.

SUMMARY OF THE INVENTION

Accordingly, one object of the present invention is to provide novel agonists or antagonists of CCR-3, or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating inflammatory diseases and allergic disorders comprising administering to a host in need of such treatment a therapeutically effective amount of at least one of the compounds of the present invention or a pharmaceutically acceptable salt or prodrug form thereof.

It is another object of the present invention to provide novel N-ureidoheterocycloalkyl-piperidines for use in therapy.

It is another object of the present invention to provide the use of novel N-ureidoheterocycloalkyl-piperidines for the manufacture of a medicament for the treatment of allergic disorders.

These and other objects, which will become apparent during the following detailed description, have been achieved by the inventors' discovery that compounds of formula (I):

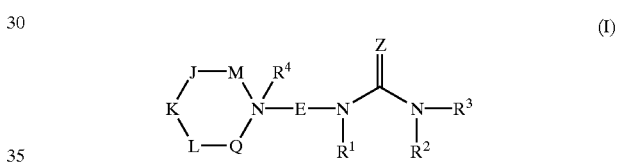

or stereoisomers or pharmaceutically acceptable salts thereof, wherein E, Z, M, J, K, L, Q, $R^1$, $R^2$, $R^3$, and $R^4$ are defined below, are effective modulators of chemokine activity.

DETAILED DESCRIPTION OF PREFERRED EMBODIMENTS

[1] Thus, in a first embodiment, the present invention provides novel compounds of formula (I):

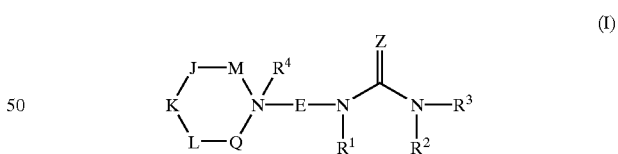

or stereoisomers or pharmaceutically acceptable salts thereof, wherein:

M is absent or selected from $CH_2$, $CHR^5$, $CHR^{13}$, $CR^{13}R^{13}$, and $CR^5R^{13}$;

Q is selected from $CH_2$, $CHR^5$, $CHR^{13}$, $CR^{13}R^{13}$, and $CR^5R^{13}$;

J and K are independently selected from $CH_2$, $CHR^5$, $CHR^6$, $CR^6R^6$ and $CR^5R^6$;

L is selected from $CHR^5$ and $CR^5R^6$;

with the proviso:
when M is absent, J is selected from $CH_2$, $CHR^5$, $CHR^{13}$, and $CR^5R^{13}$;

Z is selected from O, S, $NR^{1a}$, $C(CN)_2$, $CH(NO_2)$, and CHCN;

$R^{1a}$ is selected from H, $C_{1-6}$ alkyl, $C_{3-6}$ cycloalkyl, $CONR^{1b}R^{1b}$, $OR^{1b}$, CN, $NO_2$, and $(CH_2)_w$phenyl;

$R^{1b}$ is independently selected from H, $C_{1-3}$ alkyl, $C_{3-6}$ cycloalkyl, and phenyl;

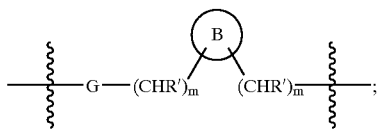

G is selected from a bond, C=O, and $SO_2$;

Ring B is a 5, 6, or 7 membered saturated heterocyclic ring wherein the heterocycle ring includes —$NR^9$—, —O—, —$S(O)_p$—, —$NR^{9d}C(O)$—, —$C(O)NR^{9d}$—, —$C(O)$O—, —$OC(O)$—, —$NR^{9d}C(O)NR^{9d}$, —$NR^{9d}C(O)O$—, —$NR^{9d}S(O)_2$—, —$S(O)_2NR^{9d}$, or —$OC(O)NR^{9d}$—, the heterocycle ring being optionally substituted by 0–2 $R^8$;

$R^1$ and $R^2$ are independently selected from H, $C_{1-8}$ alkyl, $C_{3-8}$ alkenyl, $C_{3-8}$ alkynyl, and $(CH_2)_rC_{3-6}$ cycloalkyl;

$R^3$ is selected from methyl substituted with 0–1 $R^{10}$, $C_{2-8}$ alkyl substituted with 0–3 $R^7$, $C_{3-8}$ alkenyl substituted with 0–3 $R^7$, $C_{3-8}$ alkynyl substituted with 0–3 $R^7$, $C_2$ fluoroalkyl, $C_{3-8}$ haloalkyl, a $(CR^{3'}R^{3''})_r$—$C_{3-10}$ carbocyclic residue substituted with 0–5 $R^{15}$ and a $(CR^{3'}R^{3''})_r$-5–10 membered heterocyclic system containing 1–4 heteroatoms selected from N, O, and S, substituted with 0–3 $R^{15}$;

$R^{3'}$ and $R^{3''}$, at each occurrence, are selected from H, $C_{1-6}$ alkyl, $(CH_2)_rC_{3-6}$ cycloalkyl, and phenyl;

$R^4$ is absent, taken with the nitrogen to which it is attached to form an N-oxide, or selected from $C_{1-8}$ alkyl, $C_{3-8}$ alkenyl, $C_{3-8}$ alkynyl, $(CH_2)_qC_{3-6}$ cycloalkyl, $(CH_2)_qC(O)R^{4b}$, $(CH_2)_qC(O)NR^{4a}R^{4a'}$, $(CH_2)_qC(O)OR^{4b}$, and a $(CH_2)_r$—$C_{3-10}$ carbocyclic residue substituted with 0–3 $R^{4c}$;

$R^{4a}$ and $R^{4a'}$, at each occurrence, are selected from H, $C_{1-6}$ alkyl, $(CH_2)_rC_{3-6}$ cycloalkyl, and phenyl;

$R^{4b}$, at each occurrence, is selected from $C_{1-6}$ alkyl, $C_{3-8}$ alkenyl, $(CH_2)_rC_{3-6}$ cycloalkyl, $C_{3-8}$ alkynyl, and phenyl;

$R^{4c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, $(CH_2)_rNR^{4a}R^{4a'}$, and $(CH_2)_r$phenyl;

$R^5$ is selected from a $(CR^{5'}R^{5''})_t$—$C_{3-10}$ carbocyclic residue substituted with 0–5 $R^{16}$ and a $(CR^{5'}R^{5''})_r$-5–10 membered heterocyclic system containing 1–4 heteroatoms selected from N, O, and S, substituted with 0–3 $R^{16}$;

$R^{5'}$ and $R^{5''}$, at each occurrence, are selected from H, $C_{1-6}$ alkyl, $(CH_2)_rC_{3-6}$ cycloalkyl, and phenyl;

$R^6$, at each occurrence, is selected from $C_{1-6}$ alkyl, $C_{2-8}$ alkenyl, $C_{2-8}$ alkynyl, $(CH_2)_rC_{3-6}$ cycloalkyl, $(CF_2)_rCF_3$, CN, $(CH_2)_rNR^{6a}R^{6a'}$, $(CH_2)_rOH$, $(CH_2)_rOR^{6b}$, $(CH_2)_rSH$, $(CH_2)_rSR^{6b}$, $(CH_2)_rC(O)OH$, $(CH_2)_rC(O)R^{6b}$, $(CH_2)_rC(O)NR^{6a}R^{6a'}$, $(CH_2)_rNR^{6d}C(O)R^{6a}$, $(CH_2)_rC(O)OR^{6b}$, $(CH_2)_rOC(O)R^{6b}$, $(CH_2)_rS(O)_pR^{6b}$, $(CH_2)_rS(O)_2NR^{6a}R^{6a'}$, $(CH_2)_rNR^{6d}S(O)_2R^{6b}$, and $(CH_2)_r$phenyl substituted with 0–3 $R^{6c}$;

$R^{6a}$ and $R^{6a'}$, at each occurrence, are selected from H, $C_{1-6}$ alkyl, $C_{3-6}$ cycloalkyl, and phenyl substituted with 0–3 $R^{6c}$;

$R^{6b}$, at each occurrence, is selected from $C_{1-6}$ alkyl, $C_{3-6}$ cycloalkyl, and phenyl substituted with 0–3 $R^{6c}$;

$R^{6c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{6d}R^{6d'}$;

$R^{6d}$, at each occurrence, is selected from H, $C_{1-6}$ alkyl, and $C_{3-6}$ cycloalkyl;

with the proviso that when any of J or K is $CR^6R^6$ and $R^6$ is cyano, or bonded to the carbon to which it is attached through a heteroatom, the other $R^6$ is not cyano, or bonded to the carbon to which it is attached through a heteroatom;

$R^7$ is selected from $NO_2$, CN, $NR^{7a}R^{7a'}$, OH, $OR^{7d}$, $C(O)H$, $C(O)OH$, $C(O)R^{7b}$, $C(O)NR^{7a}R^{7a'}$, $NR^{7f}C(O)OR^{7d}$, $OC(O)NR^{7a}R^{7a'}$, $NR^{7f}C(O)R^{7b}$, $NR^{7f}C(O)NR^{7f}R^{7f}$, $C(O)OR^{7d}$, $OC(O)R^{7b}$, $C(=NR^{7f})NR^{7a}R^{7a'}$, $NHC(=NR^{7f})NR^{7f}R^{7f}$, $S(O)_pR^{7b}$, $S(O)_2NR^{7a}R^{7a'}$, $NR^{7f}S(O)_2R^{7b}$, $C_{1-6}$ haloalkyl;

$R^{7a}$ and $R^{7a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0–5 $R^{7e}$, and a $(CH_2)_r$-5–10 membered heterocyclic system containing 1–4 heteroatoms selected from N, O, and S, substituted with 0–2 $R^{7e}$;

alternatively, $R^{7a}$ and $R^{7a'}$, along with the N to which they are attached, join to form a 5–6 membered heterocyclic system containing 1–2 heteroatoms selected from $NR^{7h}$, O, and S and optionally fused with a benzene ring or a 6-membered aromatic heterocycle;

$R^{7b}$, at each occurrence, is selected from H, $C_{1-6}$ alkyl, $C_{3-8}$ alkenyl, $C_{3-8}$ alkynyl, a $(CH_2)_r$—$C_{3-6}$ carbocyclic residue substituted with 0–3 $R^{7e}$, and $(CH_2)_r$-5–6 membered heterocyclic system containing 1–4 heteroatoms selected from N, O, and S, substituted with 0–2 $R^{7e}$;

$R^{7d}$, at each occurrence, is selected from $C_{3-8}$ alkenyl, $C_{3-8}$ alkynyl, methyl, $CF_3$, $C_{2-6}$ alkyl substituted with 0–3 $R^{7e}$, a $(CH_2)_r$—$C_{3-10}$ carbocyclic residue substituted with 0–3 $R^{7e}$, and a $(CH_2)_r$5–6 membered heterocyclic system containing 1–4 heteroatoms selected from N, O, and S, substituted with 0–3 $R^{7e}$;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, $C(O)OC_{1-6}$ alkyl, $C(O)OC_{1-6}$ alkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{7f}R^{7f}$, $(CH_2)_r$phenyl, and a heterocycle substituted with 0–1 $R^{7g}$, wherein the heterocycle is selected from imidazole, thiazole, oxazole, pyrazole, 1,2,4-triazole, 1,2,3-triazole, isoxazole, and tetrazole,;

$R^{7f}$, at each occurrence, is selected from H, $C_{1-6}$ alkyl, $C_{3-6}$ cycloalkyl, and phenyl;

$R^{7g}$ is selected from methyl, ethyl, acetyl, and $CF_3$;

$R^{7h}$ is selected from H, $C_{1-6}$ alkyl, $C_{3-6}$ cycloalkyl, $(CH_2)_p$phenyl, $C(O)R^{7f}$, $C(O)OR^{7i}$, and $SO_2R^{7i}$;

$R^{7i}$, at each occurrence, is selected from $C_{1-6}$ alkyl, $C_{3-6}$ cycloalkyl;

$R^8$ is selected from $C_{1-6}$ alkyl, $C_{2-8}$ alkenyl, $C_{2-8}$ alkynyl, $C_{1-6}$haloalkyl, a $(CH_2)_r$—$C_{3-10}$ carbocyclic residue substituted with 0–3 $R^{8c}$, and a $(CH_2)_r$-5–10 membered heterocyclic system containing 1–4 heteroatoms selected from N, O, and S, substituted with 0–2 $R^{8c}$;

$R^{8a}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{8e}$, and a $(CH_2)_r$-5–10 membered heterocyclic system containing 1–4 heteroatoms selected from N, O, and S, substituted with 0–3 $R^{8e}$;

$R^{8b}$, at each occurrence, is selected from $C_{1-6}$ alkyl, $C_{3-8}$ alkenyl, $C_{3-8}$ alkynyl, a $(CH_2)_r$—$C_{3-6}$ carbocyclic residue substituted with 0–2 $R^{8e}$, and a $(CH_2)_r$-5–6 membered heterocyclic system containing 1–4 heteroatoms selected from N, O, and S, substituted with 0–3 $R^{8e}$;

$R^{8c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{8f}R^{8f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{8a}$, $(CH_2)_rC(O)NR^{8f}R^{8f}$, $(CH_2)_rNR^{8f}C(O)R^{8a}$, $(CH_2)_rC(O)OC_{1-4}$ alkyl, $(CH_2)_rOC(O)R^{8b}$, $(CH_2)_rS(O)_pR^{8b}$, $(CH_2)_rS(O)_2NR^{8f}R^{8f}$, $(CH_2)_rNR^{8f}S(O)_2R^{8b}$, and $(CH_2)_r$phenyl substituted with 0–3 $R^{8e}$;

$R^{8e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSH$, $(CH_2)_rSC_{1-5}$ alkyl, $(CH_2)_rNR^{8f}R^{8f}$, and $(CH_2)_r$phenyl;

$R^{8f}$, at each occurrence, is selected from H, $C_{1-6}$ alkyl, and $C_{3-6}$ cycloalkyl;

$R^9$ is selected from H, $CH_3$, $C_{2-6}$ alkyl substituted with 0–3 $R^{9a}$, $C_{3-8}$ alkenyl, $C_{3-8}$ alkynyl, $C_{1-6}$haloalkyl, $(CHR')_rC(O)C_{1-6}$ alkyl substituted with 0–3 $R^{9j}$, $(CHR')_rC(O)OC_{1-6}$ alkyl substituted with 0–3 $R^{9b}$, $(CHR')_rC(O)NR^{9d}R^{9d'}$, $(CHR')_rS(O)_2C_{1-6}$ alkyl, $S(O)_2C_{1-6}$ haloalkyl, $(CHR')_rS(O)_2NR^{9d}R^{9d'}$, $R^{9i}$, $(CHR')_rC(O)R^{9i}$, $(CHR')_rC(O)NR^{9d}R^{9i}$, $(CHR')_rS(O)_2R^{9i}$, and $(CHR')_rS(O)_2NR^{9d}R^{9i}$;

$R^{9i}$, at each occurrence, is independently selected from $(CHR')_rC_{3-6}$ cycloalkyl substituted with 0–3 $R^{9e}$, $(CHR')_r$phenyl substituted with 0–3 $R^{9c}$, $(CHR')_r$-5–10 membered heterocyclic system containing 1–4 heteroatoms selected from N, O, and S, substituted with 0–3 $R^{9c}$, $R^{9a}$, at each occurrence, is selected from CN, $NO_2$, $OC_{1-5}$ alkyl, $CF_3$, OH, $OC_{1-5}$ alkyl, $OC(O)C_{1-5}$ alkyl, $SC_{1-5}$ alkyl, $S(O)_pC_{1-5}$ alkyl, and $NR^{9d}R^{9d'}$;

$R^{9b}$, at each occurrence, is selected from $C_{3-6}$ cycloalkyl, CN, $(CF_2)_rCF_3$, $(CH_2)_qOC_{1-5}$ alkyl, $(CH_2)_qOH$, $(CH_2)_qSC_{1-5}$ alkyl, $(CH_2)_qS(O)_pC_{1-5}$ alkyl, and $(CH_2)_qNR^{9d}R^{9d'}$;

$R^{9c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CHR')_rC(O)C_{1-5}$ alkyl, $(CHR')_rC(O)OC_{1-5}$ alkyl, $(CHR')_rC(O)NR^{9d}R^{9d'}$, $(CH_2)_rOH$, $(CH_2)_rSC_{1-5}$ alkyl, $(CH_2)_rS(O)_pC_{1-5}$ alkyl, and $(CH_2)_rNR^{9d}R^{9d'}$;

provided that if $R^{9c}$ is attached to a carbon attached to the nitrogen on Ring B, then $R^{9c}$ is selected from $(CH_2)_qOH$, $(CH_2)_qOC_{1-5}$ alkyl, $(CH_2)_qSC_{1-5}$ alkyl, $(CH_2)_qS(O)_qC_{1-5}$ alkyl, and $(CH_2)_qNR^{9d}R^{9d'}$;

$R^{9d}$ and $R^{9d'}$, at each occurrence, are independently selected from H, $C_{1-6}$ alkyl, $C_{3-6}$ cycloalkyl, and phenyl;

alternatively, $R^{9d}$ and $R^{9d'}$, along with the N to which they are attached, join to form a 5–6 membered heterocyclic system containing 1–2 heteroatoms selected from $NR^{9h}$, O, and S and optionally fused with a benzene ring or a 6-membered aromatic heterocycle;

$R^{9e}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rC_{1-5}$ alkyl, $(CHR')_rC(O)OC_{1-5}$ alkyl, $(CHR')_rC(O)NR^{9d}R^{9d'}$, $(CH_2)_rOH$, $(CH_2)_rSC_{1-5}$ alkyl, $(CH_2)_rS(O)_pC_{1-5}$ alkyl, and $(CH_2)_rNR^{9d}R^{9d'}$, or alternatively, two $R^{9e}$ on the same carbon atom form =O;

$R^{9h}$ is selected from H, $C_{1-6}$ alkyl, $C_{3-6}$ cycloalkyl, $(CH_2)_r$phenyl, $C(O)R^{9f}$, $C(O)OR^{9i}$, and $SO_2R^{9i}$;

$R^{9i}$, at each occurrence, is selected from $C_{1-6}$ alkyl, $C_{3-6}$ cycloalkyl;

$R^{9j}$, at each occurrence, is selected from $C_{3-6}$ cycloalkyl, CN, $(CF_2)_rCF_3$, $(CH_2)_rOC_{1-5}$ alkyl, $(CH_2)_rOH$, $(CH_2)_rSC_{1-5}$ alkyl, $(CH_2)_rS(O)_pC_{1-5}$ alkyl, and $(CH_2)_rNR^{9d}R^{9d'}$;

$R^{10}$ is selected from $C(O)H$, $C(O)OH$, $C(O)R^{10b}$, $C(O)NR^{10a}R^{10a'}$, $C(O)OR^{10d}$, $C(=NR^{10f})NR^{10a}R^{10a'}$, $S(O)R^{10b}$, $S(O)_2R^{10b}$, $S(O)_2NR^{10a}R^{10a'}$;

$R^{10a}$ and $R^{10a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0–5 $R^{10e}$, and a $(CH_2)_r$-5–10 membered heterocyclic system containing 1–4 heteroatoms selected from N, O, and S, substituted with 0–2 $R^{10e}$;

alternatively, $R^{10a}$ and $R^{10a'}$, along with the N to which they are attached, join to form a 5–6 membered heterocyclic system containing 1–2 heteroatoms selected from $NR^{10h}$, O, and S and optionally fused with a benzene ring or a 6-membered aromatic heterocycle;

$R^{10b}$, at each occurrence, is selected from $C_{1-6}$ alkyl, $C_{3-8}$ alkenyl, $C_{3-8}$ alkynyl, a $(CH_2)_r$—$C_{3-6}$ carbocyclic residue substituted with 0–3 $R^{10e}$, and $(CH_2)_r$-5–6 membered heterocyclic system containing 1–4 heteroatoms selected from N, O, and S, substituted with 0–2 $R^{10e}$;

$R^{10d}$, at each occurrence, is selected from $C_{3-8}$ alkenyl, $C_{3-8}$ alkynyl, methyl, $CF_3$, $C_{2-6}$ alkyl substituted with 0–3 $R^{10e}$, a $(CH_2)_r$—$C_{3-10}$ carbocyclic residue substituted with 0–3 $R^{10e}$, and a $(CH_2)_r$-5–6 membered heterocyclic system containing 1–4 heteroatoms selected from N, O, and S, substituted with 0–3 $R^{10e}$;

$R^{10e}$, at each occurrence, is selected from $C_{1-6}$ alkyl, $C_{2-8}$ alkenyl, $C_{2-8}$ alkynyl, $(CH_2)_rC_{3-6}$ cycloalkyl, $C(O)C_{1-6}$ alkyl, $C(O)OC_{1-6}$ alkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{10f}R^{10f}$, $(CH_2)_r$phenyl, and a heterocycle substituted with 0–1 $R^{10g}$, wherein the heterocycle is selected from imidazole, thiazole, oxazole, pyrazole, 1,2,4-triazole, 1,2,3-triazole, isoxazole, and tetrazole,;

$R^{10f}$, at each occurrence, is selected from H, $C_{1-6}$ alkyl, $C_{3-6}$ cycloalkyl, and phenyl;

$R^{10g}$ is selected from methyl, ethyl, acetyl, and $CF_3$;

$R^{10h}$ is selected from H, $C_{1-6}$ alkyl, $C_{3-6}$ cycloalkyl, $(CH_2)_r$phenyl, $C(O)R^{10f}$, $C(O)OR^{10i}$, and $SO_2R^{10i}$;

$R^{10i}$, at each occurrence, is selected from $C_{1-6}$ alkyl, $C_{3-6}$ cycloalkyl;

$R^{13}$, at each occurrence, is selected from $C_{1-6}$ alkyl, $C_{2-8}$ alkenyl, $C_{2-8}$ alkynyl, $C_{3-6}$ cycloalkyl, $(CF_2)_wCF_3$, $(CH_2)_q NR^{13a}R^{13a'}$, $(CH_2)_qOH$, $(CH_2)_qOR^{13b}$, $(CH_2)_qSH$, $(CH_2)_qSR^{13b}$, $(CH_2)_wC(O)OH$, $(CH_2)_wC(O)R^{13b}$, $(CH_2)_wC(O)NR^{13a}R^{13a'}$, $(CH_2)_wNR^{13d}C(O)R^{13a}$, $(CH_2)_wC(O)OR^{13b}$, $(CH_2)_qOC(O)R^{13b}$, $(CH_2)_wS(O)_pR^{13b}$, $(CH_2)_wS(O)_2NR^{13a}R^{13a'}$, $(CH_2)_wNR^{13d}S(O)_2R^{13b}$, and $(CH_2)_w$-phenyl substituted with 0–3 $R^{13c}$;

$R^{13a}$ and $R^{13a'}$, at each occurrence, are selected from H, $C_{1-6}$ alkyl, $C_{3-6}$ cycloalkyl, and phenyl substituted with 0–3 $R^{13c}$;

$R^{13b}$, at each occurrence, is selected from $C_{1-6}$ alkyl, $C_{3-6}$ cycloalkyl, and phenyl substituted with 0–3 $R^{13c}$;

$R^{13c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{13d}R^{13d}$;

$R^{13d}$, at each occurrence, is selected from H, $C_{1-6}$ alkyl, and $C_{3-6}$ cycloalkyl;

$R^{15}$, at each occurrence, is selected from =O, $C_{1-8}$ alkyl, $(CH_2)_rC_{3-6}$ cycloalkyl, Cl, Br, I, F, $NO_2$, CN, $(CHR')_rNR^{15a}R^{15a'}$, $(CHR')_rOH$, $(CHR')_rO(CHR')_rR^{15d}$, $(CHR')_rSH$, $(CHR')_rC(O)H$, $(CHR')_rC(O)OH$, $(CHR')_rC(O)(CHR')_rR^{15b}$, $(CHR')_rC(O)NR^{15a}R^{15a'}$, $(CHR')_rNR^{15f}C(O)O(CHR')_rR^{15d}$, $(CHR')_rOC(O)NR^{15a}R^{15a'}$, $(CHR')_rNR^{15f}C(O)(CHR')_rR^{15b}$, $(CHR')_rNR^{15f}C(O)NR^{15f}R^{15f}$, $(CHR')_rC(O)O(CHR')_rR^{15d}$, $(CHR')_rOC(O)(CHR')_rR^{15b}$, $(CHR')_rC(=NR^{15f})NR^{15a}R^{15a'}$, $(CHR')_rNHC(=NR^{15f})NR^{15f}R^{15f}$, $(CHR')_rS(O)_p(CHR')_rR^{15b}$, $(CHR')_rS(O)_2NR^{15a}R^{15a'}$, $(CHR')_rNR^{15f}S(O)_2(CHR')_rR^{15b}$, $C_{1-6}$haloalkyl, $C_{2-8}$ alkenyl substituted with 0–3 R', $C_{2-8}$ alkynyl substituted with 0–3 R', $(CHR')_r$phenyl substituted with 0–3 $R^{15e}$, and a $(CH_2)_r$-5–10 membered heterocyclic system containing 1–4 heteroatoms selected from N, O, and S, substituted with 0–2 $R^{15e}$;

R', at each occurrence, is independently selected from H, $C_{1-6}$ alkyl, $C_{3-8}$ alkenyl, $C_{3-8}$ alkynyl, $(CH_2)_rC_{3-6}$ cycloalkyl, and $(CH_2)_r$phenyl substituted with $R^{15e}$;

$R^{15a}$ and $R^{15a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0–5 $R^{15e}$, and a $(CH_2)_r$-5–10 membered heterocyclic system containing 1–4 heteroatoms selected from N, O, and S, substituted with 0–2 $R^{15e}$;

alternatively, $R^{15a}$ and $R^{15a'}$, along with the N to which they are attached, join to form a 5–6 membered heterocyclic system containing 1–2 heteroatoms selected from $NR^{15h}$, O, and S and optionally fused with a benzene ring or a 6-membered aromatic heterocycle;

$R^{15b}$, at each occurrence, is selected from $C_{1-6}$ alkyl, $C_{3-8}$ alkenyl, $C_{3-8}$ alkynyl, a $(CH_2)_r$—$C_{3-6}$ carbocyclic residue substituted with 0–3 $R^{15e}$, and $(CH_2)_r$-5–6 membered heterocyclic system containing 1–4 heteroatoms selected from N, O, and S, substituted with 0–2 $R^{15e}$;

$R^{15d}$, at each occurrence, is selected from $C_{3-8}$ alkenyl, $C_{3-8}$ alkynyl, methyl, $CF_3$, $C_{2-6}$ alkyl substituted with 0–3 $R^{15e}$, a $(CH_2)_r$—$C_{3-10}$ carbocyclic residue substituted with 0–3 $R^{15e}$, and a $(CH_2)_r$5–6 membered heterocyclic system containing 1–4 heteroatoms selected from N, O, and S, substituted with 0–3 $R^{15e}$;

$R^{15e}$, at each occurrence, is selected from $C_{1-6}$ alkyl, $C_{2-8}$ alkenyl, $C_{2-8}$ alkynyl, $(CH_2)_rC_{3-6}$ cycloalkyl, $C(O)C_{1-6}$ alkyl, $C(O)OC_{1-6}$ alkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{15f}R^{15f}$, $(CH_2)_r$phenyl, and a heterocycle substituted with 0–1 $R^{15g}$, wherein the heterocycle is selected from imidazole, thiazole, oxazole, pyrazole, 1,2,4-triazole, 1,2,3-triazole, isoxazole, and tetrazole,;

$R^{15f}$, at each occurrence, is selected from H, $C_{1-6}$ alkyl, $C_{3-6}$ cycloalkyl, and phenyl;

$R^{15g}$ is selected from methyl, ethyl, acetyl, and $CF_3$;

$R^{15h}$ is selected from H, $C_{1-6}$ alkyl, $C_{3-6}$ cycloalkyl, $(CH_2)_r$ phenyl, $C(O)R^{15f}$, $C(O)OR^{15i}$, and $SO_2R^{15i}$;

$R^{15i}$, at each occurrence, is selected from $C_{1-6}$ alkyl, $C_{3-6}$ cycloalkyl;

$R^{16}$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, (CHR')$_r$NR$^{16a}$R$^{16a'}$, (CHR')$_r$OH, (CHR')$_r$O (CHR')$_r$R$^{16d}$, (CHR')$_r$SH, (CHR')$_r$C(O)H, (CHR')$_r$C(O) OH, (CHR')$_r$C(O)(CHR')$_r$R$^{16b}$, (CHR')$_r$C(O)NR$^{16a}$R$^{16a'}$, (CHR')$_r$NR$^{16f}$C(O)(CHR')$_r$R$^{16b}$, (CHR')$_r$C(O)O(CHR')$_r$R$^{16d}$, (CHR')$_r$OC(O)(CHR')$_r$R$^{16b}$, (CHR')$_r$C(=NR$^{16f}$)NR$^{16a}$R$^{16a'}$, (CHR')$_r$NHC(=NR$^{16f}$)NR$^{16f}$R$^{16f}$, (CHR')$_r$S(O)$_p$(CHR')$_r$R$^{16b}$, (CHR')$_r$S(O)$_2$NR$^{16a}$R$^{16a'}$, (CHR')$_r$NR$^{16f}$S(O)$_2$(CHR')$_r$R$^{16b}$, $C_{1-6}$haloalkyl, $C_{2-8}$ alkenyl substituted with 0–3 R', $C_{2-8}$ alkynyl substituted with 0–3 R', and (CHR')$_r$phenyl substituted with 0–3 $R^{16e}$;

$R^{16a}$ and $R^{16a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0–5 $R^{16e}$, and a $(CH_2)_r$-5–10 membered heterocyclic system containing 1–4 heteroatoms selected from N, O, and S, substituted with 0–2 $R^{16e}$;

alternatively, $R^{16a}$ and $R^{16a'}$, along with the N to which they are attached, join to form a 5–6 membered heterocyclic system containing 1–2 heteroatoms selected from $NR^{16h}$, O, and S and optionally fused with a benzene ring or a 6-membered aromatic heterocycle;

$R^{16b}$, at each occurrence, is selected from $C_{1-6}$ alkyl, $C_{3-8}$ alkenyl, $C_{3-8}$ alkynyl, a $(CH_2)_rC_{3-6}$ carbocyclic residue substituted with 0–3 $R^{16e}$, and a $(CH_2)_r$-5–6 membered heterocyclic system containing 1–4 heteroatoms selected from N, O, and S, substituted with 0–2 $R^{16e}$;

$R^{16d}$, at each occurrence, is selected from $C_{3-8}$ alkenyl, $C_{3-8}$ alkynyl, $C_{1-6}$ alkyl substituted with 0–3 $R^{16e}$, a $(CH_2)_r$—$C_{3-10}$ carbocyclic residue substituted with 0–3 $R^{16e}$, and a $(CH_2)_r$-5–6 membered heterocyclic system containing 1–4 heteroatoms selected from N, O, and S, substituted with 0–3 $R^{16e}$;

$R^{16e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{16f}R^{16f}$, and $(CH_2)_r$phenyl;

$R^{16f}$, at each occurrence, is selected from H, $C_{1-5}$ alkyl, and $C_{3-6}$ cycloalkyl, and phenyl;

$R^{16h}$ is selected from H, $C_{1-6}$ alkyl, $C_{3-6}$ cycloalkyl, $(CH_2)_r$ phenyl, $C(O)R^{16f}$, $C(O)OR^{16i}$, and $SO_2R^{16i}$;

$R^{16i}$, at each occurrence, is selected from $C_{1-6}$ alkyl, $C_{3-6}$ cycloalkyl;

m, at each occurrence, is independently selected from 0, 1, and 2;

t, at each occurrence, is independently selected from 1 and 2;

w, at each occurrence, is independently selected from 0 and 1;

r, at each occurrence, is independently selected from 0, 1, 2, 3, 4, and 5;

q, at each occurrence, is independently selected from 1, 2, 3, 4, and 5; and p, at each occurrence, is independently selected from 0, 1, and 2.

[2] In another embodiment, the present invention provides novel compounds of formula (I), wherein:

$R^4$ is absent, taken with the nitrogen to which it is attached to form an N-oxide, or selected from $C_{1-8}$ alkyl, $(CH_2)_rC_{3-6}$ cycloalkyl, and $(CH_2)_r$-phenyl substituted with 0–3 $R^{4c}$;

$R^{4c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, $(CH_2)_rNR^{4a}R^{4a'}$, and $(CH_2)_r$phenyl;

$R^1$ and $R^2$ are independently selected from H and $C_{1-4}$ alkyl;

$R^6$, at each occurrence, is selected from $C_{1-4}$ alkyl, $C_{2-8}$ alkenyl, $C_{2-8}$ alkynyl, $(CH_2)_rC_{3-6}$ cycloalkyl, $(CF_2)_rCF_3$, CN, $(CH_2)_rOH$, $(CH_2)_rOR^{6b}$, $(CH_2)_rC(O)R^{6b}$, $(CH_2)_rC(O)NR^{6a}R^{6a'}$, $(CH_2)_rNR^{6d}C(O)R^{6a}$, and $(CH_2)_r$phenyl substituted with 0–3 $R^{6c}$;

$R^{6a}$ and $R^{6a'}$, at each occurrence, are selected from H, $C_{1-6}$ alkyl, $C_{3-6}$ cycloalkyl, and phenyl substituted with 0–3 $R^{6c}$;

$R^{6b}$, at each occurrence, is selected from $C_{1-6}$ alkyl, $C_{3-6}$ cycloalkyl, and phenyl substituted with 0–3 $R^{6c}$;

$R^{6c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{6d}R^{6d}$;

$R^{6d}$, at each occurrence, is selected from H, $C_{1-6}$ alkyl, and $C_{3-6}$ cycloalkyl;

$R^{13}$, at each occurrence, is selected from $C_{1-4}$ alkyl, $C_{3-6}$ cycloalkyl, $(CH_2)NR^{13a}R^{13a'}$, $(CH_2)OH$, $(CH_2)OR^{13b}$, $(CH_2)_wC(O)R^{13b}$, $(CH_2)_wC(O)NR^{13a}R^{13a'}$, $(CH_2)NR^{13d}C(O)R^{13a}$, $(CH_2)_wS(O)_2NR^{13a}R^{13a'}$, $(CH_2)NR^{13d}S(O)_2R_{13b}$, and $(CH_2)_w$-phenyl substituted with 0–3 $R^{13c}$;

$R^{13a}$ and $R^{13a'}$, at each occurrence, are selected from H, $C_{1-6}$ alkyl, $C_{3-6}$ cycloalkyl, and phenyl substituted with 0–3 $R^{13c}$;

$R^{13b}$, at each occurrence, is selected from $C_{1-6}$ alkyl, $C_{3-6}$ cycloalkyl, and phenyl substituted with 0–3 $R^{13c}$;

$R^{13c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, and $(CH_2)_rNR^{13d'}R^{13d}$;

$R^{13d}$, at each occurrence, is selected from H, $C_{1-6}$ alkyl, and $C_{3-6}$ cycloalkyl;

q is selected from 1, 2, and 3; and r is selected from 0, 1, 2, and 3.

[3] In another embodiment, the present invention provides novel compounds of formula (I), wherein:

$R^3$ is selected from a methyl substituted with 0–1 $R^{10}$, $C_{2-8}$ alkyl substituted with 0–3 $R^7$, a $(CR^{3'}H)_r$-carbocyclic residue substituted with 0–5 $R^{15}$, wherein the carbocyclic residue is selected from phenyl, $C_{3-6}$ cycloalkyl, naphthyl, and adamantyl; and a $(CR^{3'}H)_r$-heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indazolyl, isoxazolinyl, morpholinyl, pyrrolidinyl, tetrahydropyranyl, tetrahydrofuranyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^5$ is selected from $(CR^{5'}H)_r$-phenyl substituted with 0–5 $R^{16}$; and a $(CR^{5'}H)_r$-heterocyclic system substituted with 0–3 $R^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

[4] In another embodiment, the present invention provides novel compounds of formula (I), wherein:

Ring B is a 5 or 6 membered heterocycle ring wherein the heterocycle ring includes $-NR^9-$, $-O-$, $-S(O)_p-$, $-NR^{9d}C(O)-$, $-C(O)NR^{9d}-$, $-C(O)O-$, $-OC(O)-$, $-NR^{9d}C(O)NR^{9d}$, $-NR^{9d}C(O)O-$, $-OC(O)NR^{9d}-$, $-NR^{9d}S(O)_2-$, or $-S(O)_2NR^{9d}$, the heterocycle ring being optionally substituted by 0–2 $R^8$;

$R^9$ is selected from H, $CH_3$, $C_{2-6}$ alkyl substituted with 0–3 $R^{9a}$, $C_{3-8}$ alkenyl, $C_{3-8}$ alkynyl, $C_{1-3}$ haloalkyl, $(CH_2)_rC(O)C_{1-6}$ alkyl substituted with 0–2 $R^{9j}$, $(CH_2)_rC(O)OC_{1-6}$ alkyl substituted with 0–3 $R^{9b}$, $(CH_2)_rC(O)NR^{9d}R^{9d'}$, $(CH_2)_rS(O)_2C_{1-6}$ alkyl, $S(O)_2C_{1-6}$ trifluoromethyl, $(CH_2)_rC(O)R^{9'}$, $(CH_2)_rC(O)NR^{9d}R^{9'}$, $(CH_2)_rS(O)_2R^{9'}$, $R^{9'}$, and $(CH_2)_rS(O)_2NR^{9d}R^{9'}$;

$R^{9'}$, at each occurrence, is independently selected from $(CHR')_rC_{3-6}$ cycloalkyl substituted with 0–3 $R^{9e}$, wherein the cycloalkyl is selected from cyclopropyl, cyclobutyl, cyclopentyl, and cyclohexyl, $(CHR')_r$phenyl substituted with 0–3 $R^{9c}$, $(CHR')_r$5–6 membered heterocycle system containing 1–4 heteroatoms selected from N, O, and S, substituted with 0–3 $R^{9c}$, wherein the heterocycle is selected from oxadiazolyl, morpholinyl, piperidinyl, tetrahydropyranyl, tetrahydrothiopyranyl, tetrahydrothiopyranyl dioxide, thiophene, imidazolyl, pyrrolidinyl, pyrrolyl, thiazolyl, and furanyl, and $(CHR')_r$phenyl substituted with 0–3 $R^{9c}$;

$R^{9a}$, at each occurrence, is selected from CN, O-methyl, O-ethyl, $CF_3$, OH, OC(O)-methyl, S-methyl, S-ethyl, S-propyl, $S(O)_p$-methyl, $S(O)_p$-ethyl, $S(O)_p$-propyl, and $NR^{9d}R^{9d'}$;

$R^{9b}$, at each occurrence, is selected from cyclopropyl, cyclbutyl, cyclpentyl, CN, $CF_3$, $CH_2$-$OC_{1-5}$ alkyl, $CH_2$—OH, $CH_2$-$SC_{1-5}$ alkyl, and $CH_2$—$NR^{9d}R^{9d'}$;

$R^{9c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rC(O)OC_{1-5}$ alkyl, $(CH_2)_rC(O)C_{1-5}$ alkyl, $(CH_2)_rC(O)NR^{9d}R^{9d'}$, $(CH_2)_rOH$, $(CH_2)_rSC_{1-5}$ alkyl, $(CH_2)_rS(O)_pC_{1-5}$ alkyl, and $(CH_2)_rNR^{9d}R^{9d'}$;

provided that if $R^{9c}$ is attached to a carbon attached to the nitrogen on Ring B, then $R^{9c}$ is selected from $(CH_2)_qOH$, $(CH_2)_qOC_{1-5}$ alkyl, $(CH_2)_qSC_{1-5}$ alkyl, $(CH_2)_qS(O)_qC_{1-5}$ alkyl, and $(CH_2)_qNR^{9d}R^{9d'}$;

$R^{9d}$ and $R^{9d'}$, at each occurrence, are independently selected from H, methyl, ethyl, propyl, i-propyl, butyl, cyclopropyl, cyclobutyl, cyclopentyl, cyclohexyl and phenyl;

$R^{9e}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rC(O)OC_{1-5}$ alkyl, $(CH_2)_rC(O)NR^{9d}R^{9d'}$, $(CH_2)_rOH$, $(CH_2)_rSC_{1-5}$ alkyl, $(CH_2)_rS(O)_pC_{1-5}$ alkyl, and $(CH_2)_rNR^{9d}R^{9d'}$, or alternatively, two $R^{9e}$ on the same carbon atom form =O; and $R^{9j}$, at each occurrence, is selected from cyclpropyl, cyclobutyl, cyclopentyl, CN, $CF_3$, O-methyl, O-ethyl, O-propyl, O-i-propyl, O-butyl, OH, S-methyl, S-ethyl, and $NR^{9d}R^{9d'}$.

[5] In another embodiment, the present invention provides novel compounds of formula (I-i), wherein:

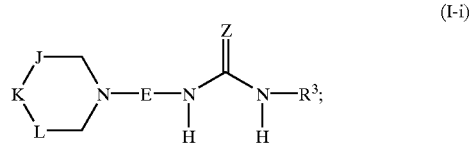

(I-i)

Z is selected from O, S, NCN, and $NCONH_2$;

$R^{16}$, at each occurrence, is selected from $C_{1-8}$ alkyl, $(CH_2)_rC_{3-6}$ cycloalkyl, $CF_3$, Cl, Br, I, F, $(CH_2)_rNR^{16a}R^{16a'}$, $NO_2$, CN, OH, $(CH_2)_rOR^{16d}$, $(CH_2)_rC(O)R^{16b}$, $(CH_2)_rC(O)NR^{16a}R^{16a'}$, $(CH_2)_rNR^{16f}C(O)R^{16b}$, $(CH_2)_rS(O)_pR^{16b}$, $(CH_2)_rS(O)_2NR^{16a}R^{16a'}$, $(CH_2)_rNR^{16f}S(O)_2R^{16b}$, and $(CH_2)_r$phenyl substituted with 0–3 $R^{16e}$;

$R^{16a}$ and $R^{16a'}$, at each occurrence, are selected from H, $C_{1-6}$ alkyl, $C_{3-6}$ cycloalkyl, and $(CH_2)_r$phenyl substituted with 0–3 $R^{16e}$;

$R^{16b}$, at each occurrence, is selected from H, $C_{1-6}$ alkyl, $C_{3-6}$ cycloalkyl, and $(CH_2)_r$phenyl substituted with 0–3 $R^{16e}$;

$R^{16d}$, at each occurrence, is selected from $C_{1-6}$ alkyl and phenyl;

$R^{16e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{16f}$, at each occurrence, is selected from H, and $C_{1-5}$ alkyl.

[6] In another embodiment, the present invention provides novel compounds of formula (I-ii), wherein:

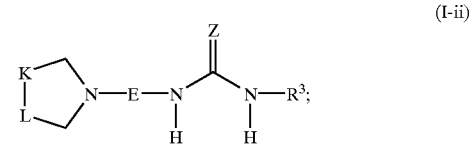

(I-ii)

Z is selected from O, S, NCN, and $NCONH_2$;

$R^{16}$, at each occurrence, is selected from $C_{1-8}$ alkyl, $(CH_2)_rC_{3-6}$ cycloalkyl, $CF_3$, Cl, Br, I, F, $(CH_2)_rNR^{16a}R^{16a'}$, $NO_2$, CN, OH, $(CH_2)_rOR^{16d}$, $(CH_2)_rC(O)R^{16b}$, $(CH_2)_rC(O)NR^{16a}R^{16a'}$, $(CH_2)_rNR^{16f}C(O)R^{16b}$, $(CH_2)_rS(O)_pR^{16b}$, $(CH_2)_rS(O)_2NR^{16a}R^{16a'}$, $(CH_2)_rNR^{16f}S(O)_2R^{16b}$, and $(CH_2)_r$phenyl substituted with 0–3 $R^{16e}$;

$R^{16a}$ and $R^{16a'}$, at each occurrence, are selected from H, $C_{1-6}$ alkyl, $C_{3-6}$ cycloalkyl, and $(CH_2)_r$phenyl substituted with 0–3 $R^{16e}$;

$R^{16b}$, at each occurrence, is selected from H, $C_{1-6}$ alkyl, $C_{3-6}$ cycloalkyl, and $(CH_2)_r$phenyl substituted with 0–3 $R^{16e}$;

$R^{16d}$, at each occurrence, is selected from $C_{1-6}$ alkyl and phenyl;

$R^{16e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{16f}$, at each occurrence, is selected from H, and $C_{1-5}$ alkyl.

[7] In another embodiment, the present invention provides novel compounds of formula (I-i), wherein:

Ring B is a 5 or 6 membered saturated heterocycle ring, wherein the heterocycle ring is selected from piperidine, tetrahydropyran, tetrahydrothiopyran, tetrahydrothiopyran 1,1-dioxide, tetrahydrothiopyran 1-monooxide, piperidin-2-one, tetrahydropyran-2-one, [1,2]thiazinane 1,1-dioxide, pyrrolidine, tetrahydrofuran, tetrahydrothiophene, pyrrolidin-2-one, dihydrofuran-2-one, and isothiazolidine 1,1-dioxide, the heterocycle ring being optionally substituted by 0–2 $R^8$;

$R^5$ is $CH_2$phenyl substituted with 0–3 $R^{16}$;

r is selected from 0, 1, and 2.

[8] In another embodiment, the present invention provides novel compounds of formula (I-ii), wherein:

Ring B is a 5 or 6 membered saturated heterocycle ring, wherein the heterocycle ring is selected from piperidine, tetrahydropyran, tetrahydrothiopyran, tetrahydrothiopyran 1,1-dioxide, tetrahydrothiopyran 1-monooxide, piperidin-2-one, tetrahydropyran-2-one, [1,2]thiazinane 1,1-dioxide, pyrrolidine, tetrahydrofuran, tetrahydrothiophene, pyrrolidin-2-one, dihydrofuran-2-one, and isothiazolidine 1,1-dioxide, the heterocycle ring being optionally substituted by 0–2 $R^8$;

$R^5$ is $CH_2$phenyl substituted with 0–3 $R^{16}$; and r is selected from 0, 1, and 2.

[9] In another embodiment, the present invention provides novel compounds of formula (I-i), wherein:

J is selected from $CH_2$ and $CHR^5$;

K is selected from $CH_2$ and $CHR^5$;

L is $CHR^5$;

$R^3$ is selected from a $C_{3-10}$ carbocyclic residue substituted with 0–3 $R^{15}$, wherein the carbocyclic residue is selected from cyclopropyl, cyclobutyl, cyclopentyl, cyclohexyl, phenyl, naphthyl and adamantyl, and a $(CR^{3'}H)_r$-heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, indazolyl, isoxazolinyl, morpholinyl, pyrrolidinyl, tetrahydropyranyl, tetrahydrofuranyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^{15}$, at each occurrence, is selected from $C_{1-8}$ alkyl, $(CH_2)_r$ $C_{3-6}$ cycloalkyl, $CF_3$, Cl, Br, I, F, $(CH_2)_rNR^{15a}R^{15a'}$, $NO_2$, CN, OH, $(CH_2)_rOR^{15d}$, $(CH_2)_rC(O)R^{15b}$, $(CH_2)_rC(O)NR^{15a}R^{15a'}$, $(CH_2)_rNR^{15f}C(O)R^{15b}$, $(CH_2)_rNR^{15f}C(O)O(CHR')_rR^{15d}$, $(CH_2)_rOC(O)NR^{15a}R^{15a'}$, $(CH_2)_rS(O)_pR^{15b}$, $(CH_2)_rS(O)_2NR^{15a}R^{15a'}$, $(CH_2)_rNR^{15f}S(O)_2R^{15b}$, $(CH_2)_r$phenyl substituted with 0–3 $R^{15e}$, and a $(CH_2)_r$-5–6 membered heterocyclic system containing 1–4 heteroatoms selected from N, O, and S, substituted with 0–2 $R^{15e}$, wherein the heterocyclic system is selected from tetrazolyl, piperidinyl, pyrrolidinyl, imidazolyl, thiazolyl, pyrazolyl, pyridyl, thienyl, furanyl, pyrrolyl, oxazolyl, isoxazolyl, triazolyl, pyridazinyl, pyrimidinyl, pyrazinyl, morpholinyl, oxadiazolyl, and thiadiazolyl;

$R^{15a}$ and $R^{15a'}$, at each occurrence, are selected from H, $C_{1-6}$ alkyl, $C_{3-6}$ cycloalkyl, and $(CH_2)_r$phenyl substituted with 0–3 $R^{15e}$;

alternatively, $R^{15a}$ and $R^{15a'}$, along with the N to which they are attached, join to form a 5–6 membered heterocyclic system containing 1–2 heteroatoms selected from $NR^{15h}$, O, and S and optionally fused with a benzene ring or a 6-membered aromatic heterocycle;

$R^{15b}$, at each occurrence, is selected from H, $C_{1-6}$ alkyl, $C_{3-6}$ cycloalkyl, and $(CH_2)_r$phenyl substituted with 0–3 $R^{15e}$;

$R^{15d}$, at each occurrence, is selected from $C_{1-6}$ alkyl and phenyl;

$R^{15e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{15f}$, at each occurrence, is selected from H, and $C_{1-5}$ alkyl.

[10] In another embodiment, the present invention provides novel compounds of formula (I-ii), wherein:

K is selected from $CH_2$ and $CHR^5$;

L is $CHR^5$;

$R^3$ is selected from a $C_{3-10}$ carbocyclic residue substituted with 0–3 $R^{15}$, wherein the carbocyclic residue is selected from cyclopropyl, cyclopentyl, cyclohexyl, phenyl, naphthyl and adamantyl, and a $(CR^{3'}H)_r$-heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indazolyl, isoxazolinyl, morpholinyl, pyrrolidinyl, tetrahydropyranyl, tetrahydrofuranyl, indolyl, indolinyl, isoindolyl, isothiadiazolyl, isoxazolyl, piperidinyl, pyrrazolyl, 1,2,4-triazolyl, 1,2,3-triaxolyl, tetrazolyl, thiadiazolyl, thiazolyl, oxazolyl, pyrazinyl, and pyrimidinyl; and $R^{15}$, at each occurrence, is selected from $C_{1-8}$ alkyl, $(CH_2)_r$ $C_{3-6}$ cycloalkyl, $CF_3$, Cl, Br, I, F, $(CH_2)_rNR^{15a}R^{15a'}$, $NO_2$, CN, OH, $(CH_2)_rOR^{15d}$, $(CH_2)_rC(O)R^{15b}$, $(CH_2)_rC(O)NR^{15a}R^{15a'}$, $(CH_2)_rNR^{15f}C(O)R^{15b}$, $(CH_2)_rNR^{15f}C(O)O(CHR')_rR^{15d}$, $(CH_2)_rOC(O)NR^{15a}R^{15a'}$, $(CH_2)_rS(O)_pR^{15b}$, $(CH_2)_rS(O)_2NR^{15a}R^{15a'}$, $(CH_2)_rNR^{15f}S(O)_2R^{15b}$, $(CH_2)_r$phenyl substituted with 0–3 $R^{15e}$, and a $(CH_2)_r$-5–6 membered heterocyclic system containing 1–4 heteroatoms selected from N, O, and S, substituted with 0–2 $R^{15e}$, wherein the heterocyclic system is selected from tetrazolyl, piperidinyl, pyrrolidinyl, imidazolyl, thiazolyl, pyrazolyl, pyridyl, thienyl, furanyl, pyrrolyl, oxazolyl, isoxazolyl, triazolyl, pyridazinyl, pyrimidinyl, pyrazinyl, morpholinyl, oxadiazolyl, and thiadiazolyl;

$R^{15a}$ and $R^{15a'}$ at each occurrence, are selected from H, $C_{1-6}$ alkyl, $C_{3-6}$ cycloalkyl, and $(CH_2)_r$phenyl substituted with 0–3 $R^{15e}$;

alternatively, $R^{15a}$ and $R^{15a'}$, along with the N to which they are attached, join to form a 5–6 membered heterocyclic system containing 1–2 heteroatoms selected from $NR^{15h}$, O, and S and optionally fused with a benzene ring or a 6-membered aromatic heterocycle;

$R^{15b}$, at each occurrence, is selected from H, $C_{1-6}$ alkyl, $C_{3-6}$ cycloalkyl, and $(CH_2)_r$phenyl substituted with 0–3 $R^{15e}$;

$R^{15d}$, at each occurrence, is selected from $C_{1-6}$ alkyl and phenyl;

$R^{15e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{15f}$, at each occurrence, is selected from H, and $C_{1-5}$ alkyl

[11] In another embodiment, the present invention provides novel compounds of formula (I), wherein the compound of formula (I) is:

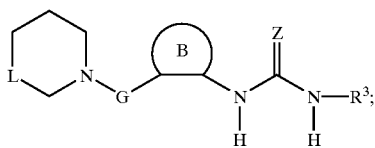

(I)

G is selected from CH$_2$ and C=O;
L is CHR$^5$;
B is selected from piperidine, tetrahydropyran, tetrahydrothiopyran, pyrrolidinyl, tetrahydrofuranyl, tetrahydrothiophenyl, tetrahydrothiophene 1-oxide, and tetrahydrothiophene 1,1-dioxide;
R$^3$ is selected from phenyl substituted with 1–2 R$^{15}$, —CH$_2$—CH$_2$-morpholin-1-yl substituted with 1–2 R$^{15}$, indazolyl substituted with 1–2 R$^{15}$, pyrazolyl substituted with 1–2 R$^{15}$ or thiazolyl substituted with 1–2 R$^{15}$;
R$^5$ is selected from a CH$_2$-phenyl substituted with 1–2 R$^{16}$;
R$^9$ is selected from H, C$_{2-6}$ alkyl substituted with 0–3 R$^{9a}$, wherein the alkyl is selected from methyl, ethyl, propyl, i-propyl, butyl, i-butyl, s-butyl, t-butyl, neo-pentyl; —CH$_2$CH=CH$_2$; —CH$_2$C≡CH; 2-fluoroethyl, 2,2-difluoroethyl, 2,2,2-trifluoroethyl, (CH$_2$)$_r$C(O)C$_{1-6}$ alkyl substituted with 0–2 R$^{9j}$, wherein the alkyl is selected from methyl, ethyl, propyl, i-propyl, butyl, t-butyl; C(O)Omethyl, C(O)Ot-butyl, So$_2$methyl, SO$_2$ethyl, SO$_2$propyl, SO$_2$i-propyl, SO$_2$t-butyl, SO$_2$CF$_3$, (CH$_2$)$_r$C(O)NR$^{9d}$R$^{9d'}$; (CH$_2$)$_r$C(O)R$^{9'}$, (CH$_2$)$_r$C(O)NR$^{9d}$R$^{9'}$, (CH$_2$)$_r$S(O)$_2$R$^{9'}$, R$^{9'}$, and (CH$_2$)$_r$S(O)$_2$NR$^{9d}$R$^{9'}$;
R$^{9'}$, at each occurrence, is independently selected from (CHR')$_r$C$_{3-6}$ cycloalkyl, wherein the cycloalkyl is selected from cyclopropyl, cyclobutyl, cyclopentyl, and cyclohexyl, (CHR')$_r$phenyl substituted with 0–3 R$^{9c}$, (CHR')$_r$5–6 membered heterocycle system containing 1–4 heteroatoms selected from N, O, and S, substituted with 0–3 R$^{9c}$, wherein the heterocycle is selected from oxadiazolyl, morpholinyl, piperidinyl, tetrahydropyranyl, tetrahydrothiopyranyl, tetrahydrothiopyranyl dioxide, thiophene, imidazolyl, pyrrolidinyl, pyrrolyl, thiazolyl, and furanyl, and (CHR')$_r$phenyl substituted with 0–3 R$^{9c}$;
R$^{9a}$, at each occurrence, is selected from CN, O-methyl, O-ethyl, CF$_3$, OH, OC(O)-methyl, S-methyl, S-ethyl, S-propyl, S(O)$_p$-methyl, S(O)$_p$-ethyl, S(O)$_p$-propyl, and NR$^{9d}$R$^{9d'}$;
R$^{9c}$, at each occurrence, is selected from methyl, ethyl, propyl, C(O)-methyl, C(O)O-t-butyl;
R$^{9d}$ and R$^{9d'}$, at each occurrence, are independently selected from H, methyl, ethyl, propyl, i-propyl, butyl, t-butyl;
R$^{9j}$, at each occurrence, is selected from O-methyl, O-ethyl, and NR$^{9d}$R$^{9d'}$;
R$^{15}$ is selected from Me, CF$_3$, OMe, OCF$_3$, F, Cl, Br, OH, OMe, C(O)Me, CH(OH)Me, CN, CO$_2$Me, CO$_2$Et, SO$_2$NH$_2$, NHC(O)Me, C(O)NH$_2$, C(O)NHMe, C(O)NHCH$_2$CH$_2$OMe, C(O)piperidinyl, C(O)pyrrolidinyl, C(O)morpholinyl, and a 5–6 membered heterocyclic system, wherein the heterocyclic system is selected from tetrazolyl, indazolyl, pyrazolyl, triazolyl, morpholinyl, and thiazolyl, the heterocyclic system substituted with 0–2 R$^{15e}$;
R$^{15e}$ is selected from methyl, ethyl, propyl, i-propyl, cyclopropyl, cyclopropylmethyl, acetyl, and t-butoxycarbonyl;
R$^{16}$ is selected from F, Cl, Br, and I;

[12] In another embodiment, the present invention provides novel compounds of formula (I), wherein the compounds are selected from:
(3R,4R)-4-[3-(3-acetyl-phenyl)-ureido]-3-[(S)-3-(4-fluorobenzyl)-piperidine-1-carbonyl]-piperidine-1-carboxylic acid t-butyl ester;
1-(3-acetyl-phenyl)-3-{(3R,4R)-3-[(S)-3-(4-fluoro-benzyl)-piperidine-1-carbonyl]-piperidin-4-yl}-urea;
(3R,4R)-3-[(S)-3-(4-fluoro-benzyl)-piperidine-1-carbonyl]-4-{3-[3-(1-methyl-1H-tetrazol-5-yl)-phenyl]-ureido}-piperidine-1-carboxylic acid t-butyl ester;
1-{(3R,4R)-3-[(S)-3-(4-fluoro-benzyl)-piperidine-1-carbonyl]-piperidin-4-yl}-3-[3-(1-methyl-1H-tetrazol-5-yl)-phenyl]-urea;
1-{1-(2,2-Dimethyl-propionyl)-3-[(3R,4R)-3-((S)-4-fluoro-benzyl)-piperidine-1-carbonyl]-piperidin-4-yl}-3-[3-(1-methyl-1H-tetrazol-5-yl)-phenyl]-urea;
1-{1-Acetyl-3-[(3R,4R)-3-((S)-4-fluoro-benzyl)-piperidine-1-carbonyl]-piperidin-4-yl}-3-[3-(1-methyl-1H-tetrazol-5-yl)-phenyl]-urea;
1-{(3R,4R)-3-[(S)-3-(4-Fluoro-benzyl)-piperidine-1-carbonyl]-1-methanesulfonyl-piperidin-4-yl}-3-[3-(1-methyl-1H-tetrazol-5-yl)-phenyl]-urea;
1-{(3R,4R)-3-[(S)-3-(4-Fluoro-benzyl)-piperidine-1-carbonyl]-1-methyl-piperidin-4-yl}-3-[3-(1-methyl-1H-tetrazol-5-yl)-phenyl]-urea;
5-(3-{(3R,4R)-1-tert-butoxycarbonyl-3-[(S)-3-(4-fluorobenzyl)-piperidine-1-carbonyl]-piperidin-4-yl}-ureido)-indazole-1-carboxylic acid t-butyl ester;
5-(3-{(3R,4R)-3-[(S)-3-(4-fluoro-benzyl)-piperidine-1-carbonyl]-piperidin-4-yl}-ureido)-indazole-1-carboxylic acid t-butyl ester;
(3R,4R)-4-[3-(5-acetyl-4-methyl-thiazol-2-yl)-ureido]-3-[(S)-3-(4-fluoro-benzyl)-piperidine-1-carbonyl]-piperidine-1-carboxylic acid t-butyl ester;
1-(5-acetyl-4-methyl-thiazol-2-yl)-3-{(3R,4R)-3-[(S)-3-(4-fluoro-benzyl)-piperidine-1-carbonyl]-piperidin-4-yl}-urea;
(3R,4S)-3-[3-(3-acetyl-phenyl)-ureido]-4-[(S)-3-(4-fluorobenzyl)-piperidine-1-carbonyl]-piperidine-1-carboxylic acid t-butyl ester;
1-(3-acetyl-phenyl)-3-{(3R,4R)-4-[(S)-3-(4-fluoro-benzyl)-piperidine-1-carbonyl]-piperidin-3-yl}-urea;
(3R,4R)-4-[3-(3-acetyl-phenyl)-ureido]-3-[(S)-3-(4-fluorobenzyl)-piperidin-1-ylmethyl]-piperidine-1-carboxylic acid t-butyl ester;
1-(3-acetyl-phenyl)-3-{(3S,4R)-3-[(S)-3-(4-fluoro-benzyl)-piperidin-1-ylmethyl]-piperidin-4-yl}-urea;
1-{(3R,4R)-1-acetyl-3-[(S)-3-(4-fluoro-benzyl)-piperidin-1-ylmethyl]-piperidin-4-yl}-3-(3-acetyl-phenyl)-urea;
1-(3-acetyl-phenyl)-3-{(3R,4R)-3-[(S)-3-(4-fluoro-benzyl)-piperidin-1-ylmethyl]-1-methanesulfonyl-piperidin-4-yl}-urea;
1-(3-acetyl-phenyl)-3-{(3S,4R)-3-[(S)-3-(4-fluoro-benzyl)-piperidin-1-ylmethyl]-1-methyl-piperidin-4-yl}-urea;
1-(3-acetyl-phenyl)-3-{(3R,4R)-3-[(S)-3-(4-fluoro-benzyl)-piperidin-1-ylmethyl]-1-isobutyl-piperidin-4-yl}-urea;
(3R,4R)-3-[(S)-3-(4-fluoro-benzyl)-piperidin-1-ylmethyl]-4-{3-[3-(1-methyl-1H-tetrazol-5-yl)-phenyl]-ureido}-piperidine-1-carboxylic acid t-butyl ester;
1-{(3S,4R)-3-[(S)-3-(4-fluoro-benzyl)-piperidin-1-ylmethyl]-piperidin-4-yl}-3-[3-(1-methyl-1H-tetrazol-5-yl)-phenyl]-urea;
5-(3-{(3R,4R)-1-t-butoxycarbonyl-3-[(S)-3-(4-fluorobenzyl)-piperidin-1-ylmethyl]-piperidin-4-yl}-ureido)-indazole-1-carboxylic acid t-butyl ester;

5-(3-{(3S,4R)-3-[(S)-3-(4-Fluoro-benzyl)-piperidin-1-ylmethyl]-piperidin-4-yl}-ureido)-indazole-1-carboxylic acid t-butyl ester;

(3R,4R)-4-[3-(5-acetyl-4-methyl-thiazol-2-yl)-ureido]-3-[(S)-3-(4-fluoro-benzyl)-piperidin-1-ylmethyl]-piperidine-1-carboxylic acid t-butyl ester;

1-(5-acetyl-4-methyl-thiazol-2-yl)-3-{(3S,4R)-3-[(S)-3-(4-fluoro-benzyl)-piperidin-1-ylmethyl]-piperidin-4-yl}-urea;

(3R,4R)-4-[3-(3-acetyl-phenyl)-ureido]-3-[(S)-3-(4-fluoro-benzyl)-piperidin-1-ylmethyl]-piperidine-1-carboxylic acid t-butyl ester;

1-(3-acetyl-phenyl)-3-{(3R,4S)-4-[(S)-3-(4-fluoro-benzyl)-piperidin-1-ylmethyl]-piperidin-3-yl}-urea;

(3S,4R)-4-[3-(3-acetyl-phenyl)-ureido]-3-[(S)-3-(4-fluoro-benzyl)-piperidine-1-carbonyl]-piperidine-1-carboxylic acid t-butyl ester;

1-(3-acetyl-phenyl)-3-{(3S,4R)-3-[(S)-3-(4-fluoro-benzyl)-piperidine-1-carbonyl]-piperidin-4-yl}-urea;

(3R,4R)-4-[3-(3-acetyl-phenyl)-ureido]-3-[(S)-3-(4-fluoro-benzyl)-piperidin-1-ylmethyl]-piperidine-1-carboxylic acid methyl ester;

1-(3-acetyl-phenyl)-3-{(3R,4R)-1-(2,2-dimethyl-propionyl)-3-[(S)-3-(4-fluoro-benzyl)-piperidin-1-ylmethyl]-piperidin-4-yl}-urea;

(3R,4S)-3-[3-(5-acetyl-4-methyl-thiazol-2-yl)-ureido]-4-[(S)-3-(4-fluoro-benzyl)-piperidine-1-carbonyl]-piperidine-2-carboxylic acid t-butyl ester;

1-(3-acetyl-phenyl)-3-{(3S,4R)-3-[(S)-3-(4-fluoro-benzyl)-piperidin-1-ylmethyl]-1-(2-fluoro-ethyl)-piperidin-4-yl}-urea;

1-(3-acetyl-phenyl)-3-{(3R,4R)-3-[(S)-3-(4-fluoro-benzyl)-piperidin-1-ylmethyl]-1-(2-oxo-propyl)-piperidin-4-yl}-urea;

1-(3-acetyl-phenyl)-3-{(3R,4S)-4-[(S)-3-(4-fluoro-benzyl)-piperidin-1-ylmethyl]-1-methyl-piperidin-3-yl}-urea;

1-{(3R,4S)-1-Acetyl-4-[(S)-3-(4-fluoro-benzyl)-piperidin-1-ylmethyl]-piperidin-3-yl}-3-(3-acetyl-phenyl)-urea;

1-{(3R,4R)-1-acetyl-3-[(S)-3-(4-fluoro-benzyl)-piperidin-1-ylmethyl]-piperidin-4-yl}-3-(1-methyl-1H-tetrazol-5-yl)-urea;

1-{(3S,4R)-3-[(S)-3-(4-fluoro-benzyl)-piperidin-1-ylmethyl]-1-methyl-piperidin-4-yl}-3-(1-methyl-1H-tetrazol-5-yl)-urea;

1-{(3R,4R)-3-[(S)-3-(4-fluoro-benzyl)-piperidin-1-ylmethyl]-1-methanesulfonyl-piperidin-4-yl}-3-(1-methyl-1H-tetrazol-5-yl)-urea;

1-{(3R,4R)-3-[(S)-3-(4-Fluoro-benzyl)-piperidine-1-carbonyl]-1-(2-oxo-propyl)-piperidin-4-yl}-3-[3-(1-methyl-1H-tetrazol-5-yl)-phenyl]-urea;

1-{(3R,4R)-3-[(S)-3-(4-Fluoro-benzyl)-piperidine-1-carbonyl]-1-(2-fluoro-ethyl)-piperidin-4-yl}-3-[3-(1-methyl-1H-tetrazol-5-yl)-phenyl]-urea;

1-{(3R,4R)-3-[(S)-3-(4-Fluoro-benzyl)-piperidine-1-carbonyl]-1-trifluoromethanesulfonyl-piperidin-4-yl}-3-[3-(1-methyl-1H-tetrazol-5-yl)-phenyl]-urea;

1-(3-Acetyl-phenyl)-3-{(2S,3R)-2-[(S)-3-(4-fluoro-benzyl)-piperidin-1-ylmethyl]-tetrahydro-pyran-3-yl}-urea;

1-{(2S,3R)-2-[(S)-3-(4-Fluoro-benzyl)-piperidin-1-ylmethyl]-tetrahydro-pyran-3-yl}-3-[3-(1-methyl-1H-tetrazol-5-yl)-phenyl]-urea;

1-{(2S,3R)-2-[(S)-3-(4-Fluoro-benzyl)-piperidin-1-ylmethyl]-tetrahydro-pyran-3-yl}-3-(5-acetyl-4-methyl-thiazol-2-yl)-urea;

1-(3-Acetyl-phenyl)-3-{(2S,3R)-2-[(S)-3-(4-fluoro-benzyl)-piperidine-1-carbonyl]-tetrahydro-pyran-3-yl}-urea;

1-{(2S,3R)-2-[(S)-3-(4-Fluoro-benzyl)-piperidine-1-carbonyl]-tetrahydro-pyran-3-yl}-3-[3-(1-methyl-1H-tetrazol-5-yl)-phenyl]-urea;

1-{(2S,3R)-2-[(S)-3-(4-Fluoro-benzyl)-piperidine-1-carbonyl]-tetrahydro-pyran-3-yl}-3-(5-acetyl-4-methyl-thiazol-2-yl)-urea;

1-{(3S,4R)-3-[(S)-3-(4-fluoro-benzyl)-piperidin-1-ylmethyl]-1-methyl-piperidin-4-yl}-3-(5-acetyl-4-methyl-thiazol-2-yl)-urea;

1-{(3R,4R)-1-acetyl-3-[(S)-3-(4-fluoro-benzyl)-piperidin-1-ylmethyl]-piperidin-4-yl}-3-(5-acetyl-4-methyl-thiazol-2-yl)-urea;

1-(5-Acetyl-4-methyl-thiazol-2-yl)-3-{(3R,4R)-3-[(S)-3-(4-fluoro-benzyl)-piperidin-1-ylmethyl]-1-isobutyryl-piperidin-4-yl}-urea;

1-{(3R,4R)-3-[(S)-3-(4-fluoro-benzyl)-piperidin-1-ylmethyl]-1-methanesulfonyl-piperidin-4-yl}-3-(5-acetyl-4-methyl-thiazol-2-yl)-urea;

1-{(3S,4R)-3-[(S)-3-(4-fluoro-benzyl)-piperidin-1-ylmethyl]-1-(2-fluoroethyl)-piperidin-4-yl}-3-(5-acetyl-4-methyl-thiazol-2-yl)-urea;

1-{(3R,4R)-3-[(S)-3-(4-fluoro-benzyl)-piperidin-1-ylmethyl]-1-(2-oxopropyl)-piperidin-4-yl}-3-(5-acetyl-4-methyl-thiazol-2-yl)-urea;

1-(3-Acetyl-phenyl)-3-{(3R,4R)-3-[(S)-3-(4-fluoro-benzyl)-piperidin-1-ylmethyl]-tetrahydro-pyran-4-yl}-urea;

1-{(3R,4R)-3-[(S)3-(4-Fluoro-benzyl)-piperidin-1-ylmethyl]-tetrahydro-pyran-4-yl}-3-[3-(1-methyl-1H-tetrazol-5-yl)-phenyl]-urea;

1-{(3R,4R)-3-[(S)3-(4-Fluoro-benzyl)-piperidin-1-ylmethyl]-tetrahydro-pyran-4-yl}-3-(5-acetyl-4-methyl-thiazol-2-yl)-urea;

1-(3-Acetyl-phenyl)-3-{(3R,4R)-3-[(S)-3-(4-fluoro-benzyl)-piperidine-1-carbonyl]-tetrahydro-pyran-4-yl}-urea;

1-{(3R,4R)-3-[(S)3-(4-Fluoro-benzyl)-piperidine-1-carbonyl]-tetrahydro-pyran-4-yl}-3-[3-(1-methyl-1H-tetrazol-5-yl)-phenyl]-urea;

1-{(3R,4R)-3-[(S)3-(4-Fluoro-benzyl)-piperidine-1-carbonyl]-tetrahydro-pyran-4-yl}-3-(5-acetyl-4-methyl-thiazol-2-yl)-urea;

1-{(3S,4R)-3-[(S)-3-(4-fluoro-benzyl)-piperidin-1-ylmethyl]-piperidin-4-yl}-3-(4-fluoro-phenyl)-urea;

(3R,4R)-3-[(S)-3-(4-fluoro-benzyl)-piperidin-1-ylmethyl]-4-[3-(4-fluoro-phenyl)-ureido]-piperidine-1-carboxylic acid t-butyl ester;

1-{(3R,4R)-1-acetyl-3-[(S)-3-(4-fluoro-benzyl)-piperidin-1-ylmethyl]-piperidin-4-yl}-3-(4-fluoro-phenyl)-urea;

1-{(3S,4R)-3-[(S)-3-(4-fluoro-benzyl)-piperidin-1-ylmethyl]-1-methyl-piperidin-4-yl}-3-(4-fluoro-phenyl)-urea;

1-{(3S,4R)-3-[(S)-3-(4-fluoro-benzyl)-piperidin-1-ylmethyl]-1-ethyl-piperidin-4-yl}-3-(4-fluoro-phenyl)-urea;

1-{(3R,4R)-3-[(S)-3-(4-fluoro-benzyl)-piperidin-1-ylmethyl]-1-[1,2,4]oxadiazol-3-ylmethyl-piperidin-4-yl}-3-(4-fluoro-phenyl)-urea;

2-{(3R,4R)-3-[(S)-3-(4-fluoro-benzyl)-piperidin-1-ylmethyl]-4-[3-(4-fluoro-phenyl)-ureido]-piperidin-1-yl}-N-isopropyl-acetamide;

1-((3R,4R)-3-[(S)-3-(4-fluoro-benzyl)-piperidin-1-ylmethyl]-1-prop-2-ynyl-piperidin-4-yl)-3-(4-fluoro-phenyl)-urea;

1-(3-acetyl-phenyl)-3-{(3R,4R)-3-[(S)-3-(4-fluoro-benzyl)-piperidin-1-ylmethyl]-[1,4']bipiperidinyl-4-yl}-urea;

1-{(3R,4R)-1'-acetyl-3-[(S)-3-(4-fluoro-benzyl)-piperidin-1-ylmethyl]-[1,4']bipiperidinyl-4-yl}-3-(3-acetyl-phenyl)-urea;

1-(3-acetyl-phenyl)-3-{(3R,4R)-3-[(S)-3-(4-fluoro-benzyl)-piperidin-1-ylmethyl]-1'-methyl-[1,4']bipiperidinyl-4-yl}-urea;

1-(3,5-diacetyl-phenyl)-3-{(3S,4R)-3-[(S)-3-(4-fluoro-benzyl)-piperidin-1-ylmethyl]-piperidin-4-yl}-urea;

(3R,4R)-3-[(S)-3-(4-fluoro-benzyl)-piperidin-1-ylmethyl]-4-[3-(3,5-diacetyl-phenyl)-ureido]-piperidine-1-carboxylic acid t-butyl ester;

1-(3,5-diacetyl-phenyl)-3-{(3R,4R)-1-acetyl-3-[(S)-3-(4-fluoro-benzyl)-piperidin-1-ylmethyl]-piperidin-4-yl}-urea;

1-(3,5-diacetyl-phenyl)-3-{(3S,4R)-3-[(S)-3-(4-fluoro-benzyl)-piperidin-1-ylmethyl]-1-methyl-piperidin-4-yl}-urea;

1-(3,5-diacetyl-phenyl)-3-{(3S,4R)-3-[(S)-3-(4-fluoro-benzyl)-piperidin-1-ylmethyl]-1-ethyl-piperidin-4-yl}-urea;

1-(3,5-diacetyl-phenyl)-3-{(3R,4R)-3-[(S)-3-(4-fluoro-benzyl)-piperidin-1-ylmethyl]-1-[1,2,4]oxadiazol-3-ylmethyl-piperidin-4-yl}-urea;

2-{(3R,4R)-3-[(S)-3-(4-Fluoro-benzyl)-piperidin-1-ylmethyl]-4-[3-(3,5-diacetyl-phenyl)-ureido]-piperidin-1-yl}-N-isopropyl-acetamide;

1-(3,5-diacetyl-phenyl)-3-{(3R,4R)-3-[(S)-3-(4-fluoro-benzyl)-piperidin-1-ylmethyl]-1-propargyl-piperidin-4-yl}-urea;

(3R,4R)-3-[(S)-3-(4-fluoro-benzyl)-piperidin-1-ylmethyl]-4-{3-[3-(1-methyl-1H-tetrazol-5-yl)-phenyl]-ureido}-piperidine-1-carboxylic acid methyl ester;

1-{(3S,4R)-3-[(S)-3-(4-fluoro-benzyl)-piperidin-1-ylmethyl]-piperidin-4-yl}-5-[3-methyl—S-(1-methyl-1H-tetrazol-5-yl)-phenyl]-urea;

(3R,4R)-3-[(S)-3-(4-fluoro-benzyl)-piperidin-1-ylmethyl]-4-{3-[3-methyl-5-(1-methyl-1H-tetrazol-5-yl)-phenyl]-ureido}-piperidine-1-carboxylic acid t-butyl ester;

1-{(3R,4R)-1-acetyl-3-[(S)-3-(4-fluoro-benzyl)-piperidin-1-ylmethyl]-piperidin-4-yl}-3-[3-methyl-5-(1-methyl-1H-tetrazol-5-yl)-phenyl]-urea;

1-{(3S,4R)-3-[(S)-3-(4-fluoro-benzyl)-piperidin-1-ylmethyl]-1-methyl-piperidin-4-yl}-3-[3-methyl-5-(1-methyl-1H-tetrazol-5-yl)-phenyl]-urea;

1-{(3S,4R)-3-[(S)-3-(4-fluoro-benzyl)-piperidin-1-ylmethyl]-1-ethyl-piperidin-4-yl}-3-[3-methyl-5-(1-methyl-1H-tetrazol-5-yl)-phenyl]-urea;

1-{(3R,4R)-3-[(S)-3-(4-fluoro-benzyl)-piperidin-1-ylmethyl]-1-[1,2,4]oxadiazol-3-ylmethyl-piperidin-4-yl}-3-[3-methyl-5-(1-methyl-1H-tetrazol-5-yl)-phenyl]-urea;

2-{(3R,4R)-3-[(S)-3-(4-fluoro-benzyl)-piperidin-1-ylmethyl]-4-{3-[3-methyl-5-(1-methyl-1H-tetrazol-5-yl)-phenyl]-ureido}-piperidin-1-yl}-N-isopropyl-acetamide;

1-{(3R,4R)-3-[(S)-3-(4-fluoro-benzyl)-piperidin-1-ylmethyl]-1-prop-2-ynyl-piperidin-4-yl}-3-[3-methyl-5-(1-methyl-1H-tetrazol-5-yl)-phenyl]-urea;

1-{(3S,4R)-3-[(S)-3-(4-fluoro-benzyl)-piperidin-1-ylmethyl]-piperidin-4-yl}-3-[3-bromo-5-(1-methyl-1H-tetrazol-5-yl)-phenyl]-urea;

(3R,4R)-3-[(S)-3-(4-fluoro-benzyl)-piperidin-1-ylmethyl]-4-{3-[3-bromo-5-(1-methyl-1H-tetrazol-5-yl)-phenyl]-ureido}-piperidine-1-carboxylic acid t-butyl ester;

1-{(3R,4R)-1-acetyl-3-[(S)-3-(4-fluoro-benzyl)-piperidin-1-ylmethyl]-piperidin-4-yl}-3-[3-bromo-5-(1-methyl-1H-tetrazol-5-yl)-phenyl]-urea;

1-{(3S,4R)-3-[(S)-3-(4-fluoro-benzyl)-piperidin-1-ylmethyl]-1-methyl-piperidin-4-yl}-3-[3-bromo-5-(1-methyl-1H-tetrazol-5-yl)-phenyl]-urea;

1-{(3S,4R)-3-[(S)-3-(4-fluoro-benzyl)-piperidin-1-ylmethyl]-1-ethyl-piperidin-4-yl}-3-[3-bromo-5-(1-methyl-1H-tetrazol-5-yl)-phenyl]-urea;

1-{(3R,4R)-3-[(S)-3-(4-fluoro-benzyl)-piperidin-1-ylmethyl]-1-[1,2,4]oxadiazol-3-ylmethyl-piperidin-4-yl}-3-[3-bromo-5-(1-methyl-1H-tetrazol-5-yl)-phenyl]-urea;

2-{(3R,4R)-3-[(S)-3-(4-fluoro-benzyl)-piperidin-1-ylmethyl]-4-{3-[3-bromo-5-(1-methyl-1H-tetrazol-5-yl)-phenyl]-ureido}-piperidin-1-yl}-N-isopropyl-acetamide;

1-{(3R,4R)-3-[(S)-3-(4-fluoro-benzyl)-piperidin-1-ylmethyl]-1-prop-2-ynyl-piperidin-4-yl}-3-[3-bromo-5-(1-methyl-1H-tetrazol-5-yl)-phenyl]-urea;

1-[(3R,4R)-3-[(S)-3-(4-fluoro-benzyl)-piperidin-1-ylmethyl]-1-(2-oxo-propyl)-piperidin-4-yl]-3-[3-(1-methyl-1H-tetrazol-5-yl)-phenyl]-urea;

1-{(3R,4R)-3-[(S)-3-(4-fluoro-benzyl)-piperidin-1-ylmethyl]-1-(2-oxo-propyl)-piperidin-4-yl}-3-(1-methyl-pyrazol-3-yl)-urea;

1-{(3R,4R)-3-[(S)-3-(4-fluoro-benzyl)-piperidin-1-ylmethyl]-1-(2-oxo-propyl)-piperidin-4-yl}-3-(thiazol-2-yl)-urea;

2-{3-[(3R,4R)-3-[(S)-3-(4-fluoro-benzyl)-piperidin-1-ylmethyl]-1-(2-oxo-propyl)-piperidin-4-yl]-ureido}-4-methyl-thiazole-5-carboxylic acid ethyl ester;

(3R,4R)-3-[(S)-3-(4-fluoro-benzyl)-piperidin-1-ylmethyl]-4-(5-acetyl-4-methyl-thiazol-2-yl)-ureido}-piperidine-1-carboxylic acid methyl ester;

(3R,4R)-4-[3-(5-acetyl-4-methyl-thiazol-2-yl)-ureido]-3-[(S)-3-(4-fluoro-benzyl)-piperidin-1-ylmethyl]-piperidine-1-carboxylic acid 3-hydroxy-2,2-dimethyl-propyl ester;

1-(5-acetyl-4-methyl-thiazol-2-yl)-3-{(3R,4R)-3-[(S)-3-(4-fluoro-benzyl)-piperidin-1-ylmethyl]-1-propionyl-piperidin-4-yl}-urea;

1-(5-acetyl-4-methyl-thiazol-2-yl)-3-{(3R,4R)-1-cyclopropanecarbonyl-3-[(S)-3-(4-fluoro-benzyl)-piperidin-1-ylmethyl]-piperidin-4-yl}-urea;

1-(5-acetyl-4-methyl-thiazol-2-yl)-3-{(3R,4R)-1-cyclopentanecarbonyl-3-[(S)-3-(4-fluoro-benzyl)-piperidin-1-ylmethyl]-piperidin-4-yl}-urea;

1-(5-acetyl-4-methyl-thiazol-2-yl)-3-[(3R,4R)-3-[(S)-3-(4-fluoro-benzyl)-piperidin-1-ylmethyl]-1-(tetrahydro-pyran-4-carbonyl)-piperidin-4-yl]-urea;

1-(5-acetyl-4-methyl-thiazol-2-yl)-3-[(3R,4R)-3-[(S)-3-(4-fluoro-benzyl)-piperidin-1-ylmethyl]-1-(2-methoxy-acetyl)-piperidin-4-yl]-urea;

1-(5-acetyl-4-methyl-thiazol-2-yl)-3-[(3R,4R)-3-[(S)-3-(4-fluoro-benzyl)-piperidin-1-ylmethyl]-1-(2-dimethylamino-acetyl)-piperidin-4-yl]-urea;

(3R,4R)-4-[3-(5-acetyl-4-methyl-thiazol-2-yl)-ureido]-3-[(S)-3-(4-fluoro-benzyl)-piperidin-1-ylmethyl]-piperidine-1-carboxylic acid methylamide;

(3R,4R)-4-[3-(5-acetyl-4-methyl-thiazol-2-yl)-ureido]-3-[(S)-3-(4-fluoro-benzyl)-piperidin-1-ylmethyl]-piperidine-1-carboxylic acid dimethylamide;

(3R,4R)-4-[3-(5-acetyl-4-methyl-thiazol-2-yl)-ureido]-3-[(S)-3-(4-fluoro-benzyl)-piperidin-1-ylmethyl]-piperidine-1-carboxylic acid ethylamide;

1-(5-acetyl-4-methyl-thiazol-2-yl)-3-{(3S,4R)-1-ethyl-3-[(S)-3-(4-fluoro-benzyl)-piperidin-1-ylmethyl]-piperidin-4-yl}-urea;

1-(5-acetyl-4-methyl-thiazol-2-yl)-3-{(3S,4R)-3-[(S)-3-(4-fluoro-benzyl)-piperidin-1-ylmethyl]-1-propyl-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-isopropyl-piperidin-4-yl}-urea;

1-(5-acetyl-4-methyl-thiazol-2-yl)-3-{(3R,4R)-1-cyclobutyl-3-[(S)-3-(4-fluoro-benzyl)-piperidin-1-ylmethyl]-piperidin-4-yl}-urea;

1-(5-acetyl-4-methyl-thiazol-2-yl)-3-{(3R,4R)-1-cyclopentyl-3-[(S)-3-(4-fluoro-benzyl)-piperidin-1-ylmethyl]-piperidin-4-yl}-urea;

1-(5-acetyl-4-methyl-thiazol-2-yl)-3-[(3R,4R)-3-[(S)-3-(4-fluoro-benzyl)-piperidin-1-ylmethyl]-1-(tetrahydro-pyran-4-yl)-piperidin-4-yl]-urea;

1-(5-acetyl-4-methyl-thiazol-2-yl)-3-[(3R,4R)-3-[(S)-3-(4-fluoro-benzyl)-piperidin-1-ylmethyl]-1-(tetrahydro-thiopyran-4-yl)-piperidin-4-yl]-urea;

1-(5-acetyl-4-methyl-thiazol-2-yl)-3-{(3R,4R)-1-(1,1-dioxo-hexahydro-1λ6-thiopyran-4-yl)-3-[(S)-3-(4-fluoro-benzyl)-piperidin-1-ylmethyl]-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-[1,4']bipiperidinyl-4-yl}-urea;

(3R,4R)-4-[3-(5-acetyl-4-methyl-thiazol-2-yl)-ureido]-3-[(S)-3-(4-fluoro-benzyl)-piperidin-1-ylmethyl]-[1,4']bipiperidinyl-1'-carboxylic acid tert-butyl ester;

1-{(3R,4R)-1'-acetyl-3-[(S)-3-(4-fluoro-benzyl)-piperidin-1-ylmethyl]-[1,4']bipiperidinyl-4-yl}-3-(5-acetyl-4-methyl-thiazol-2-yl)-urea;

1-(5-acetyl-4-methyl-thiazol-2-yl)-3-{(3R,4R)-3-[(S)-3-(4-fluoro-benzyl)-piperidin-1-ylmethyl]-1'-methyl-[1,4']bipiperidinyl-4-yl}-urea;

1-(5-acetyl-4-methyl-thiazol-2-yl)-3-{(3R,4R)-1-cyclopropylmethyl-3-[(S)-3-(4-fluoro-benzyl)-piperidin-1-ylmethyl]-piperidin-4-yl}-urea;

1-(5-acetyl-4-methyl-thiazol-2-yl)-3-{(3R,4R)-1-cyclobutylmethyl-3-[(S)-3-(4-fluoro-benzyl)-piperidin-1-ylmethyl]-piperidin-4-yl}-urea;

1-(5-acetyl-4-methyl-thiazol-2-yl)-3-{(3R,4R)-1-benzyl-3-[(S)-3-(4-fluoro-benzyl)-piperidin-1-ylmethyl]-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-furan-2-ylmethyl-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-furan-3-ylmethyl-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-thiophen-2-ylmethyl-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-thiophen-3-ylmethyl-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-imidazol-2-ylmethyl-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-imidazol-4-ylmethyl-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-thiazol-2-ylmethyl-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-[1,2,4]oxadiazol-3-ylmethyl-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-(2-hydroxyethyl)-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-(2-hydroxy-2-methylpropyl)-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-(2-hydroxy-3,3,3-trifluoropropyl)-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-(2-methoxy-ethyl)-piperidin-4-yl}-urea;

1-(5-acetyl-4-methyl-thiazol-2-yl)-3-{(3R,4R)-1-(2-ethoxy-ethyl)-3-[(S)-3-(4-fluoro-benzyl)-piperidin-1-ylmethyl]-piperidin-4-yl}-urea;

1-(5-acetyl-4-methyl-thiazol-2-yl)-3-{(3R,4R)-1-(2-ethylsulfanyl-ethyl)-3-[(S)-3-(4-fluoro-benzyl)-piperidin-1-ylmethyl]-piperidin-4-yl}-urea;

1-(5-acetyl-4-methyl-thiazol-2-yl)-3-{(3R, 4R)-1-(2-ethanesulfonyl-ethyl)-3-[(S)-3-(4-fluoro-benzyl)-piperidin-1-ylmethyl]-piperidin-4-yl}-urea;

1-(5-acetyl-4-methyl-thiazol-2-yl)-3-{(3R,4R)-1-(2-acetoxy-ethyl)-3-[(S)-3-(4-fluoro-benzyl)-piperidin-1-ylmethyl]-piperidin-4-yl}-urea;

1-(5-acetyl-4-methyl-thiazol-2-yl)-3-{(3R,4R)-1-cyanomethyl-3-[(S)-3-(4-fluoro-benzyl)-piperidin-1-ylmethyl]-piperidin-4-yl}-urea;

1-(5-acetyl-4-methyl-thiazol-2-yl)-3-{(3R,4R)-1-(2-diethylamino-ethyl)-3-[(S)-3-(4-fluoro-benzyl)-piperidin-1-ylmethyl]-piperidin-4-yl}-urea;

1-(5-acetyl-4-methyl-thiazol-2-yl)-3-{(3R,4R)-1-(2-diethylamino-ethyl)-3-[(S)-3-(4-fluoro-benzyl)-piperidin-1-ylmethyl]-piperidin-4-yl}-urea;

1-(5-acetyl-4-methyl-thiazol-2-yl)-3-[(3R,4R)-3-[(S)-3-(4-fluoro-benzyl)-piperidin-1-ylethyl]-1-(2-pyrrolidin-1-yl-ethyl)-piperidin-4-yl]-urea;

1-(5-acetyl-4-methyl-thiazol-2-yl)-3-[(3R,4R)-3-[(S)-3-(4-fluoro-benzyl)-piperidin-1-ylmethyl]-1-(2-morpholin-1-yl-ethyl)-piperidin-4-yl]-urea;

1-(5-acetyl-4-methyl-thiazol-2-yl)-3-[(3R,4R)-3-[(S)-3-(4-fluoro-benzyl)-piperidin-1-ylmethyl]-1-(2-pyrrol-1-yl-ethyl)-piperidin-4-yl]-urea;

1-(5-acetyl-4-methyl-thiazol-2-yl)-3-[(3R,4R)-3-[(S)-3-(4-fluoro-benzyl)-piperidin-1-ylmethyl]-1-(3-oxo-butyl)-piperidin-4-yl]-urea;

1-(5-acetyl-4-methyl-thiazol-2-yl)-3-[(3R,4R)-3-[(S)-3-(4-fluoro-benzyl)-piperidin-1-ylmethyl]-1-(2-methyl-3-oxo-butyl)-piperidin-4-yl]-urea;

1-(5-acetyl-4-methyl-thiazol-2-yl)-3-[(3R,4R)-3-[(S)-3-(4-fluoro-benzyl)-piperidin-1-ylmethyl]-1-(3-hydroxypropyl)-piperidin-4-yl]-urea;

1-(5-acetyl-4-methyl-thiazol-2-yl)-3-{(3R,4R)-3-[(S)-3-(4-fluoro-benzyl)-piperidin-1-ylmethyl]-1-[(S)-3-hydroxy-2-methylpropyl]-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-[(R)-3-hydroxy-2-methylpropyl]-piperidin-4-yl}-urea;

1-(5-acetyl-4-methyl-thiazol-2-yl)-3-{(3R,4R)-1-(3,3-dimethyl-2-oxo-butyl)-3-[(S)-3-(4-fluoro-benzyl)-piperidin-1-ylmethyl]-piperidin-4-yl}-urea;

2-{(3R,4R)-4-[3-(5-acetyl-4-methyl-thiazol-2-yl)-ureido]-3-[(S)-3-(4-fluoro-benzyl)-piperidin-1-ylmethyl]-piperidin-1-yl}-N-methyl-acetamide;

2-{(3R,4R)-4-[3-(5-acetyl-4-methyl-thiazol-2-yl)-ureido]-3-[(S)-3-(4-fluoro-benzyl)-piperidin-1-ylmethyl]-piperidin-1-yl}-N-isopropyl-acetamide;

2-{(3R,4R)-4-[3-(5-acetyl-4-methyl-thiazol-2-yl)-ureido]-3-[(S)-3-(4-fluoro-benzyl)-piperidin-1-ylmethyl]-piperidin-1-yl}-N-tert-butyl-acetamide;

2-{(3R,4R)-4-[3-(5-acetyl-4-methyl-thiazol-2-yl)-ureido]-3-[(S)-3-(4-fluoro-benzyl)-piperidin-1-ylmethyl]-piperidin-1-yl}-N,N-dimethyl-acetamide; 1-(5-acetyl-4-methyl-thiazol-2-yl)-3-[(3R,4R)-3-[(S)-3-(4-fluoro-benzyl)-piperidin-1-ylmethyl]-1-(2-oxo-cyclopentyl)-piperidin-4-yl]-urea;

1-(5-acetyl-4-methyl-thiazol-2-yl)-3-{(3R,4R)-1-allyl-3-[(S)-3-(4-fluoro-benzyl)-piperidin-1-ylmethyl]-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-prop-2-ynyl-piperidin-4-yl}-urea;

1-{(3R,4S)-4-[(S)-3-(4-fluoro-benzyl)-piperidin-1-ylmethyl]-piperidin-3-yl}-3-(4-fluoro-phenyl)-urea;

1-{(3R,4S)-1-acetyl-4-[(S)-3-(4-fluoro-benzyl)-piperidin-1-ylmethyl]-piperidin-3-yl}-3-(4-fluoro-phenyl)-urea;

1-[(3R,4S)-4-[(S)-3-(4-fluoro-benzyl)-piperidin-1-ylmethyl]-1-(2-methoxy-acetyl)-piperidin-3-yl]-3-(4-fluoro-phenyl)-urea;

1-{(3R,4S)-1-cyclopropylmethyl-4-[(S)-3-(4-fluoro-benzyl)-piperidin-1-ylmethyl]-piperidin-3-yl}-3-(4-fluoro-phenyl)-urea;

1-[(3R,4S)-4-[(S)-3-(4-fluoro-benzyl)-piperidin-1-ylmethyl]-1-(2-hydroxy-ethyl)-piperidin-3-yl]-3-(4-fluoro-phenyl)-urea;

1-(3-acetyl-phenyl)-3-[(3R,4S)-4-[(S)-3-(4-fluoro-benzyl)-piperidin-1-ylmethyl]-1-(2-methoxy-acetyl)-piperidin-3-yl]-urea;

1-(3-acetyl-phenyl)-3-{(3R,4S)-1-(2-dimethylamino-acetyl)-4-[(S)-3-(4-fluoro-benzyl)-piperidin-1-ylmethyl]-piperidin-3-yl}-urea;

(3R,4S)-3-[3-(3-acetyl-phenyl)-ureido]-4-[(S)-3-(4-fluoro-benzyl)-piperidin-1-ylmethyl]-piperidine-1-carboxylic acid ethylamide;

1-(3-acetyl-phenyl)-3-[(3R,4S)-4-[(S)-3-(4-fluoro-benzyl)-piperidin-1-ylmethyl]-1-(2-hydroxy-ethyl)-piperidin-3-yl]-urea;

(3R,4S)-4-[(S)-3-(4-fluoro-benzyl)-piperidin-1-ylmethyl]-3-{3-[3-(1-methyl-1H-tetrazol-5-yl)-phenyl]-ureido}-piperidine-1-carboxylic acid tert-butyl ester;

1-{(3R,4S)-1-acetyl-4-[(S)-3-(4-fluoro-benzyl)-piperidin-1-ylmethyl]-piperidin-3-yl}-3-[3-(1-methyl-1H-tetrazol-5-yl)-phenyl]-urea;

1-{(3R,4S)-1-(2,2-dimethyl-propionyl)-4-[(S)-3-(4-fluoro-benzyl)-piperidin-1-ylmethyl]-piperidin-3-yl}-3-[3-(1-methyl-1H-tetrazol-5-yl)-phenyl]-urea;

1-{(3R,4S)-4-[(S)-3-(4-fluoro-benzyl)-piperidin-1-ylmethyl]-1-methyl-piperidin-3-yl}-3-[3-(1-methyl-1H-tetrazol-5-yl)-phenyl]-urea;

1-{(3R,4S)-4-[(S)-3-(4-fluoro-benzyl)-piperidin-1-ylmethyl]-piperidin-3-yl}-3-[3-methyl-5-(1-methyl-1H-tetrazol-5-yl)-phenyl]-urea;

1-[(3R,4S)-4-[(S)-3-(4-fluoro-benzyl)-piperidin-1-ylmethyl]-1-(2-hydroxy-ethyl)-piperidin-3-yl]-3-[3-methyl-5-(1-methyl-1H-tetrazol-5-yl)-phenyl]-urea;

1-[3-bromo-5-(1-methyl-1H-tetrazol-5-yl)-phenyl]-3-{(3R,4S)-4-[(S)-3-(4-fluoro-benzyl)-piperidin-1-ylmethyl]-piperidin-3-yl}-urea;

1-[3-bromo-5-(1-methyl-1H-tetrazol-5-yl)-phenyl]-3-[(3R,4S)-4-[(S)-3-(4-fluoro-benzyl)-piperidin-1-ylmethyl]-1-(2-hydroxy-ethyl)-piperidin-3-yl]-urea;

1-{(3R,4S)-1-acetyl-4-[(S)-3-(4-fluoro-benzyl)-piperidin-1-ylmethyl]-piperidin-3-yl}-3-[3-(5-methyl-tetrazol-1-yl)-phenyl]-urea;

1-{(3R,4S)-1-acetyl-4-[(S)-3-(4-fluoro-benzyl)-piperidin-1-ylmethyl]-piperidin-3-yl}-3-(1-methyl-pyrazol-3-yl)-urea;

1-{(3R,4S)-1-acetyl-4-[(S)-3-(4-fluoro-benzyl)-piperidin-1-ylmethyl]-piperidin-3-yl}-3-(thiazol-2-yl)-urea;

2-(3-{(3R,4S)-1-acetyl-4-[(S)-3-(4-fluoro-benzyl)-piperidin-1-ylmethyl]-piperidin-3-yl}-ureido)-4-methyl-thiazole-5-carboxylic acid ethyl ester;

1-(5-acetyl-4-methyl-thiazol-2-yl)-3-{(3R,4S)-4-[(S)-3-(4-fluoro-benzyl)-piperidin-1-ylmethyl]-piperidin-3-yl}-urea;

(3R,4S)-3-[3-(5-acetyl-4-methyl-thiazol-2-yl)-ureido]-4-[(S)-3-(4-fluoro-benzyl)-piperidin-1-ylmethyl]-piperidine-1-carboxylic acid methyl ester;

(3R,4S)-3-[3-(5-acetyl-4-methyl-thiazol-2-yl)-ureido]-4-[(S)-3-(4-fluoro-benzyl)-piperidin-1-ylmethyl]-piperidine-1-carboxylic acid tert-butyl ester;

1-{(3R,4S)-1-acetyl-4-[(S)-3-(4-fluoro-benzyl)-piperidin-1-ylmethyl]-piperidin-3-yl}-3-(5-acetyl-4-methyl-thiazol-2-yl)-urea;

1-(5-acetyl-4-methyl-thiazol-2-yl)-3-{(3R,4S)-4-[(S)-3-(4-fluoro-benzyl)-piperidin-1-ylmethyl]-1-propionyl-piperidin-3-yl}-urea; 1-(5-acetyl-4-methyl-thiazol-2-yl)-3-{(3R,4S)-4-[(S)-3-(4-fluoro-benzyl)-piperidin-1-ylmethyl]-1-(2-methyl-propionyl)-piperidin-3-yl}-urea;

1-(5-acetyl-4-methyl-thiazol-2-yl)-3-{(3R,4S)-1-(2,2-dimethyl-propionyl)-4-[(S)-3-(4-fluoro-benzyl)-piperidin-1-ylmethyl]-piperidin-3-yl}-urea;

1-(5-acetyl-4-methyl-thiazol-2-yl)-3-{(3R,4S)-1-cyclopropanecarbonyl-4-[(S)-3-(4-fluoro-benzyl)-piperidin-1-ylmethyl]-piperidin-3-yl}-urea;

1-(5-acetyl-4-methyl-thiazol-2-yl)-3-{(3R, 4S)-1cyclobutanecarbonyl-4-[(S)-3-(4-fluoro-benzyl)-piperidin-1-ylmethyl]-piperidin-3-yl}-urea;

1-(5-acetyl-4-methyl-thiazol-2-yl)-3-{(3R,4S)-1-cyclopentanecarbonyl-4-[(S)-3-(4-fluoro-benzyl)-piperidin-1-ylmethyl]-piperidin-3-yl}-urea;

1-(5-acetyl-4-methyl-thiazol-2-yl)-3-{(3R,4S)-1-cyclohexanecarbonyl-4-[(S)-3-(4-fluoro-benzyl)-piperidin-1-ylmethyl]-piperidin-3-yl}-urea;

1-(5-acetyl-4-methyl-thiazol-2-yl)-3-{(3R,4S)-4-[(S)-3-(4-fluoro-benzyl)-piperidin-1-ylmethyl]-1-(tetrahydro-pyran-4-carbonyl)-piperidin-3-yl}-urea;

1-(5-acetyl-4-methyl-thiazol-2-yl)-3-{(3R,4S)-4-[(S)-3-(4-fluoro-benzyl)-piperidin-1-ylmethyl]-1-(2-methoxy-acetyl)-piperidin-3-yl}-urea;

1-(5-acetyl-4-methyl-thiazol-2-yl)-3-{(3R,4S)-1-(2-dimethylamino-acetyl)-4-[(S)-3-(4-fluoro-benzyl)-piperidin-1-ylmethyl]-piperidin-3-yl}-urea;

(3R,4S)-3-[3-(5-acetyl-4-methyl-thiazol-2-yl)-ureido]-4-[(S)-3-(4-fluoro-benzyl)-piperidin-1-ylmethyl]-piperidine-1-carboxylic acid methylamide;

(3R,4S)-3-[3-(5-acetyl-4-methyl-thiazol-2-yl)-ureido]-4-[(S)-3-(4-fluoro-benzyl)-piperidin-1-ylmethyl]-piperidine-1-carboxylic acid ethylamide;

(3R, 4S)-3-[3-(5-acetyl-4-methyl-thiazol-2-yl)-ureido]-4-[(S)-3-(4-fluoro-benzyl)-piperidin-1-ylmethyl]-piperidine-1-carboxylic acid propylamide;

(3R,4S)-3-[3-(5-acetyl-4-methyl-thiazol-2-yl)-ureido]-4-[(S)-3-(4-fluoro-benzyl)-piperidin-1-ylmethyl]-piperidine-1-carboxylic acid isopropylamide;

(3R,4S)-3-[3-(5-acetyl-4-methyl-thiazol-2-yl)-ureido]-4-[(S)-3-(4-fluoro-benzyl)-piperidin-1-ylmethyl]-piperidine-1-carboxylic acid allylamide;

(3R,4S)-3-[3-(5-acetyl-4-methyl-thiazol-2-yl)-ureido]-4-[(S)-3-(4-fluoro-benzyl)-piperidin-1-ylmethyl]-piperidine-1-carboxylic acid (5-acetyl-4-methyl-thiazol-2-yl)-amide;

1-(5-acetyl-4-methyl-thiazol-2-yl)-3-{(3R,4S)-4-[(S)-3-(4-fluoro-benzyl)-piperidin-1-ylmethyl]-1-methyl-piperidin-3-yl}-urea;

1-(5-acetyl-4-methyl-thiazol-2-yl)-3-{(3R,4S)-4-[(S)-3-(4-fluoro-benzyl)-piperidin-1-ylmethyl]-[1,4']bipiperidinyl-3-yl}-urea;

1-{(3R,4S)-1'-acetyl-4-[(S)-3-(4-fluoro-benzyl)-piperidin-1-ylmethyl]-[1,4']bipiperidinyl-3-yl}-3-(5-acetyl-4-methyl-thiazol-2-yl)-urea;

1-(5-acetyl-4-methyl-thiazol-2-yl)-3-{(3R,4S)-4-[(S)-3-(4-fluoro-benzyl)-piperidin-1-ylmethyl]-1'-methyl-[1,4']bipiperidinyl-3-yl}-urea;

1-(5-acetyl-4-methyl-thiazol-2-yl)-3-{(3R,4S)-1-cyclopropylmethyl-4-[(S)-3-(4-fluoro-benzyl)-piperidin-1-ylmethyl]-piperidin-3-yl}-urea;

1-(5-acetyl-4-methyl-thiazol-2-yl)-3-[(3R,4S)-4-[(S)-3-(4-fluoro-benzyl)-piperidin-1-ylmethyl]-1-(tetrahydro-pyran-2-ylmethyl)-piperidin-3-yl]-urea;

1-(5-acetyl-4-methyl-thiazol-2-yl)-3-{(3R,4S)-4-[(S)-3-(4-fluoro-benzyl)-piperidin-1-ylmethyl]-1-furan-2-ylmethyl-piperidin-3-yl}-urea;

1-(5-acetyl-4-methyl-thiazol-2-yl)-3-{(3R,4S)-4-[(S)-3-(4-fluoro-benzyl)-piperidin-1-ylmethyl]-1-furan-3-ylmethyl-piperidin-3-yl}-urea;

1-(5-acetyl-4-methyl-thiazol-2-yl)-3-{(3R,4S)-4-[(S)-3-(4-fluoro-benzyl)-piperidin-1-ylmethyl]-1-[1,2,4]oxadiazol-3-ylmethyl-piperidin-3-yl}-urea;

1-(5-acetyl-4-methyl-thiazol-2-yl)-3-{(3R,4S)-4-[(S)-3-(4-fluoro-benzyl)-piperidin-1-ylmethyl]-1-(2-fluoro-ethyl)-piperidin-3-yl}-urea;

1-(5-acetyl-4-methyl-thiazol-2-yl)-3-{(3R,4S)-4-[(S)-3-(4-fluoro-benzyl)-piperidin-1-ylmethyl]-1-(2-hydroxy-ethyl)-piperidin-3-yl}-urea;

1-(5-acetyl-4-methyl-thiazol-2-yl)-3-{(3R,4S)-1-(2-ethanesulfonyl-ethyl)-4-[(S)-3-(4-fluoro-benzyl)-piperidin-1-ylmethyl]-piperidin-3-yl}-urea;

1-(5-acetyl-4-methyl-thiazol-2-yl)-3-{(3R,4S)-1-cyanomethyl-4-[(S)-3-(4-fluoro-benzyl)-piperidin-1-ylmethyl]-piperidin-3-yl}-urea;

1-(5-acetyl-4-methyl-thiazol-2-yl)-3-{(3R,4S)-4-[(S)-3-(4-fluoro-benzyl)-piperidin-1-ylmethyl]-1-(2-hydroxy-propyl)-piperidin-3-yl}-urea;

1-(5-acetyl-4-methyl-thiazol-2-yl)-3-{(3R,4S)-4-[(S)-3-(4-fluoro-benzyl)-piperidin-1-ylmethyl]-1-[(S)-2-hydroxy-2-methyl-propyl]-piperidin-3-yl}-urea;

1-(5-acetyl-4-methyl-thiazol-2-yl)-3-{(3R,4S)-4-[(S)-3-(4-fluoro-benzyl)-piperidin-1-ylmethyl]-1-[(R)-2-hydroxy-2-methyl-propyl]-piperidin-3-yl}-urea;

1-(5-acetyl-4-methyl-thiazol-2-yl)-3-{(3R,4S)-4-[(S)-3-(4-fluoro-benzyl)-piperidin-1-ylmethyl]-1-(2-oxo-propyl)-piperidin-3-yl}-urea;

2-{(3R,4S)-3-[3-(5-acetyl-4-methyl-thiazol-2-yl)-ureido]-4-[(S)-3-(4-fluoro-benzyl)-piperidin-1-ylmethyl]-piperidin-1-yl}-N,N-dimethyl-acetamide;

1-{(3R,4S)-4-[(S)-3-(4-fluoro-benzyl)-piperidin-1-ylmethyl]-1-isobutyryl-piperidin-3-yl}-3-[3-(1-methyl-1H-tetrazol-5-yl)-phenyl]-urea;

1-{(3R,4S)-1-benzoyl-4-[(S)-3-(4-fluoro-benzyl)-piperidin-1-ylmethyl]-piperidin-3-yl}-3-[3-(1-methyl-1H-tetrazol-5-yl)-phenyl]-urea;

1-{(3R,4S)-4-[(S)-3-(4-fluoro-benzyl)-piperidin-1-ylmethyl]-1-(propane-2-sulfonyl)-piperidin-3-yl}-3-[3-(1-methyl-1H-tetrazol-5-yl)-phenyl]-urea;

1-{(3R,4S)-4-[(S)-3-(4-fluoro-benzyl)-piperidin-1-ylmethyl]-piperidin-3-yl}-3-(2-morpholin-4-yl-ethyl)-urea;

(3R,4S)-4-[(S)-3-(4-fluoro-benzyl)-piperidin-1-ylmethyl]-3-[3-(2-morpholin-4-yl-ethyl)-ureido]-piperidine-1-carboxylic acid methyl ester;

1-{(3R,4S)-1-acetyl-4-[(S)-3-(4-fluoro-benzyl)-piperidin-1-ylmethyl]-piperidin-3-yl}-3-(2-morpholin-4-yl-ethyl)-urea;

1-{(3R,4S)-4-[(S)-3-(4-fluoro-benzyl)-piperidin-1-ylmethyl]-1-propionyl-piperidin-3-yl}-3-(2-morpholin-4-yl-ethyl)-urea;

1-{(3R,4S)-1(2,2-dimethyl-propionyl)-4-[(S)-3-(4-fluoro-benzyl)-piperidin-1-ylmethyl]-piperidin-3-yl}-3-(2-morpholin-4-yl-ethyl)-urea;

1-{(3R,4S)-1-cyclobutanecarbonyl-4-[(S)-3-(4-fluoro-benzyl)-piperidin-1-ylmethyl]-piperidin-3-yl}-3-(2-morpholin-4-yl-ethyl)-urea;

1-{(3R,4S)-4-[(S)-3-(4-fluoro-benzyl)-piperidin-1-ylmethyl]-1-(tetrahydro-pyran-4-carbonyl)-piperidin-3-yl}-3-(2-morpholin-4-yl-ethyl)-urea;

1-{(3R,4S)-4-[(S)-3-(4-fluoro-benzyl)-piperidin-1-ylmethyl]-1-(2-methoxy-acetyl)-piperidin-3-yl}-3-(2-morpholin-4-yl-ethyl)-urea;

(3R,4S)-4-[(S)-3-(4-fluoro-benzyl)-piperidin-1-ylmethyl]-3-[3-(2-morpholin-4-yl-ethyl)-ureido]-piperidine-1-carboxylic acid dimethylamide;

(3R,4S)-4-[(S)-3-(4-fluoro-benzyl)-piperidin-1-ylmethyl]-3-[3-(2-morpholin-4-yl-ethyl)-ureido]-piperidine-1-carboxylic acid ethylamide;

1-{(3R,4S)-4-[(S)-3-(4-fluoro-benzyl)-piperidin-1-ylmethyl]-1-methanesulfonyl-piperidin-3-yl}-3-(2-morpholin-4-yl-ethyl)-urea;

1-{(3R,4S)-4-[(S)-3-(4-fluoro-benzyl)-piperidin-1-ylmethyl]-1-methyl-piperidin-3-yl}-3-(2-morpholin-4-yl-ethyl)-urea;

1-{(3R,4S)-1-ethyl-4-[(S)-3-(4-fluoro-benzyl)-piperidin-1-ylmethyl]-piperidin-3-yl}-3-(2-morpholin-4-yl-ethyl)-urea;

1-{(3R,4S)-4-[(S)-3-(4-fluoro-benzyl)-piperidin-1-ylmethyl]-1-isopropyl-piperidin-3-yl}-3-(2-morpholin-4-yl-ethyl)-urea;

1-{(3R,4S)-1-cyclopropylmethyl-4-[(S)-3-(4-fluoro-benzyl)-piperidin-1-ylmethyl]-piperidin-3-yl}-3-(2-morpholin-4-yl-ethyl)-urea;

1-{(3R,4S)-4-[(S)-3-(4-fluoro-benzyl)-piperidin-1-ylmethyl]-1-(2-oxo-propyl)-piperidin-3-yl}-3-(2-morpholin-4-yl-ethyl)-urea;

1-{(3R,4S)-4-[(S)-3-(4-fluoro-benzyl)-piperidin-1-ylmethyl]-tetrahydro-pyran-3-yl}-3-[3-(1-methyl-1H-tetrazol-5-yl)-phenyl]-urea;

1-{(3R,4S)-4-[(S)-3-(4-fluoro-benzyl)-piperidin-1-ylmethyl]-tetrahydro-pyran-3-yl}-3-[3-methyl-5-(1-methyl-1H-tetrazol-5-yl)-phenyl]-urea;

1-(5-acetyl-4-methyl-thiazol-2-yl)-3-{(3R,4S)-4-[(S)-3-(4-fluoro-benzyl)-piperidin-1-ylmethyl]-tetrahydro-pyran-3-yl}-urea;

(3R,4R)-3-[(S)-3-(4-fluoro-benzyl)-piperidin-1-ylmethyl]-4-[3-(4-fluoro-phenyl)-ureido]-piperidine-1-carboxylic acid methyl ester;

1-{(3R,4R)-1-(2-dimethylamino-acetyl)-3-[(S)-3-(4-fluoro-benzyl)-piperidin-1-ylmethyl]-piperidin-4-yl}-3-(4-fluoro-phenyl)-urea;

1-{(3R,4R)-3-[(S)-3-(4-fluoro-benzyl)-piperidin-1-ylmethyl]-1-methanesulfonyl-piperidin-4-yl}-3-(4-fluoro-phenyl)-urea;

1-{(3R,4R)-3-[(S)-3-(4-fluoro-benzyl)-piperidin-1-ylmethyl]-1-thiazol-2-ylmethyl-piperidin-4-yl}-3-(4-fluoro-phenyl)-urea;

1-[(3R, 4R)-3-[(S)-3-(4-fluoro-benzyl)-piperidin-1-ylmethyl]-1-(2-hydroxy-ethyl)-piperidin-4-yl]-3-(4-fluoro-phenyl)-urea;

1-[(3R,4R)-3-[(S)-3-(4-fluoro-benzyl)-piperidin-1-ylmethyl]-1-(2-methoxy-ethyl)-piperidin-4-yl]-3-(4-fluoro-phenyl)-urea;

1-[(3R,4R)-3-[(S)-3-(4-fluoro-benzyl)-piperidin-1-ylmethyl]-1-(2-morpholin-4-yl-ethyl)-piperidin-4-yl]-3-(4-fluoro-phenyl)-urea;

1-[(3S,4R)-3-[(S)-3-(4-fluoro-benzyl)-piperidin-1-ylmethyl]-1-(2-hydroxy-propyl)-piperidin-4-yl]-3-(4-fluoro-phenyl)-urea;

(3R,4R)-4-[3-(3,5-diacetyl-phenyl)-ureido]-3-[(S)-3-(4-fluoro-benzyl)-piperidin-1-ylmethyl]-piperidine-1-carboxylic acid methyl ester;

1-(3,5-diacetyl-phenyl)-3-{(3R,4R)-1-(2-dimethylamino-acetyl)-3-[(S)-3-(4-fluoro-benzyl)-piperidin-1-ylmethyl]-piperidin-4-yl}-urea;

1-(3,5-diacetyl-phenyl)-3-{(3R,4R)-3-[(S)-3-(4-fluoro-benzyl)-piperidin-1-ylmethyl]-1-methanesulfonyl-piperidin-4-yl}-urea;

1-(3,5-diacetyl-phenyl)-3-{(3R,4R)-1-(1,1-dioxo-hexahydro-1λ6-thiopyran-4-yl)-3-[(S)-3-(4-fluoro-benzyl)-piperidin-1-ylmethyl]-piperidin-4-yl}-urea;

1-(3,5-diacetyl-phenyl)-3-{(3R,4R)-3-[(S)-3-(4-fluoro-benzyl)-piperidin-1-ylmethyl]-1-thiazol-2-ylmethyl-piperidin-4-yl}-urea;

1-(3,5-diacetyl-phenyl)-3-[(3R,4R)-3-[(S)-3-(4-fluoro-benzyl)-piperidin-1-ylmethyl]-1-(2-hydroxy-ethyl)-piperidin-4-yl]-urea;

1-(3,5-diacetyl-phenyl)-3-[(3R,4R)-3-[(S)-3-(4-fluoro-benzyl)-piperidin-1-ylmethyl]-1-(2-methoxy-ethyl)-piperidin-4-yl]-urea;

1-(3,5-diacetyl-phenyl)-3-[(3R,4R)-3-[(S)-3-(4-fluoro-benzyl)-piperidin-1-ylmethyl]-1-(2-morpholin-4-yl-ethyl)-piperidin-4-yl]-urea;

1-(3,5-diacetyl-phenyl)-3-[(3S,4R)-3-[(S)-3-(4-fluoro-benzyl)-piperidin-1-ylmethyl]-1-(2-hydroxy-propyl)-piperidin-4-yl]-urea;

(3R,4R)-3-[(S)-3-(4-fluoro-benzyl)-piperidin-1-ylmethyl]-4-{3-[3-methyl-5-(1-methyl-1H-tetrazol-5-yl)-phenyl]-ureido}-piperidine-1-carboxylic acid methyl ester;

1-{(3R,4R)-1-(2-dimethylamino-acetyl)-3-[(S)-3-(4-fluoro-benzyl)-piperidin-1-ylmethyl]-piperidin-4-yl}-3-[3-methyl—S-(1-methyl-1H-tetrazol-5-yl)-phenyl]-urea;

1-{(3R,4R)-3-[(S)-3-(4-fluoro-benzyl)-piperidin-1-ylmethyl]-1-methanesulfonyl-piperidin-4-yl}-3-[3-methyl-5-(1-methyl-1H-tetrazol-5-yl)-phenyl]-urea;

1-{(3R,4R)-3-[(S)-3-(4-fluoro-benzyl)-piperidin-1-ylmethyl]-1-thiazol-2-ylmethyl-piperidin-4-yl}-3-[3-methyl-5-(1-methyl-1H-tetrazol-5-yl)-phenyl]-urea;

1-[(3R,4R)-3-[(S)-3-(4-fluoro-benzyl)-piperidin-1-ylmethyl]-1-(2-hydroxy-ethyl)-piperidin-4-yl]-3-[3-methyl-5-(1-methyl-1H-tetrazol-5-yl)-phenyl]-urea;

1-[(3R,4R)-3-[(S)-3-(4-fluoro-benzyl)-piperidin-1-ylmethyl]-1-(2-methoxy-ethyl)-piperidin-4-yl]-3-[3-methyl-5-(1-methyl-1H-tetrazol-5-yl)-phenyl]-urea;

1-[(3R,4R)-3-[(S)-3-(4-fluoro-benzyl)-piperidin-1-ylmethyl]-1-(2-morpholin-4-yl-ethyl)-piperidin-4-yl]-3-[3-methyl-5-(1-methyl-1H-tetrazol-5-yl)-phenyl]-urea;

1-[(3S,4R)-3-[(S)-3-(4-fluoro-benzyl)-piperidin-1-ylmethyl]-1-(2-hydroxy-propyl)-piperidin-4-yl]-3-[3-methyl-5-(1-methyl-1H-tetrazol-5-yl)-phenyl]-urea;

(3R,4R)-3-[(S)-3-(4-fluoro-benzyl)-piperidin-1-ylmethyl]-4-{3-[3-bromo-5-(1-methyl-1H-tetrazol-5-yl)-phenyl]-ureido}-piperidine-1-carboxylic acid methyl ester;

1-{(3R,4R)-1-(2-dimethylamino-acetyl)-3-[(S)-3-(4-fluoro-benzyl)-piperidin-1-ylmethyl]-piperidin-4-yl}-3-[3-bromo-5-(1-methyl-1H-tetrazol-5-yl)-phenyl]-urea;

1-{(3R,4R)-3-[(S)-3-(4-fluoro-benzyl)-piperidin-1-ylmethyl]-1-methanesulfonyl-piperidin-4-yl}-3-[3-bromo-5-(1-methyl-1H-tetrazol-5-yl)-phenyl]-urea;

1-{(3R,4R)-3-[(S)-3-(4-fluoro-benzyl)-piperidin-1-ylmethyl]-1-thiazol-2-ylmethyl-piperidin-4-yl}-3-[3-bromo-5-(1-methyl-1H-tetrazol-5-yl)-phenyl]-urea;

1-[(3R,4R)-3-[(S)-3-(4-fluoro-benzyl)-piperidin-1-ylmethyl]-1-(2-hydroxy-ethyl)-piperidin-4-yl]-3-[3-bromo-5-(1-methyl-1H-tetrazol-5-yl)-phenyl]-urea;

1-[(3R,4R)-3-[(S)-3-(4-fluoro-benzyl)-piperidin-1-ylmethyl]-1-(2-methoxy-ethyl)-piperidin-4-yl]-3-[3-bromo-5-(1-methyl-1H-tetrazol-5-yl)-phenyl]-urea;

1-[(3R,4R)-3-[(S)-3-(4-fluoro-benzyl)-piperidin-1-ylmethyl]-1-(2-morpholin-4-yl-ethyl)-piperidin-4-yl]-3-[3-bromo-5-(1-methyl-1H-tetrazol-5-yl)-phenyl]-urea;

1-[(3S,4R)-3-[(S)-3-(4-fluoro-benzyl)-piperidin-1-ylmethyl]-1-(2-hydroxy-propyl)-piperidin-4-yl]-3-[3-bromo-5-(1-methyl-1H-tetrazol-5-yl)-phenyl]-urea;

(3R,4S)-3-(3-benzyl-ureido)-4-[(S)-3-(4-fluoro-benzyl)-piperidin-1-ylmethyl]-piperidine-1-carboxylic acid tert-butyl ester;

1-benzyl-3-{(3R,4S)-4-[(S)-3-(4-fluoro-benzyl)-piperidin-1-ylmethyl]-piperidin-3-yl}-urea;

(3R,4S)-4-[(S)-3-(4-fluoro-benzyl)-piperidin-1-ylmethyl]-3-[3-(tetrahydro-pyran-4-ylmethyl)-ureido]-piperidine-1-carboxylic acid tert-butyl ester;

1-{(3R,4S)-4-[(S)-3-(4-fluoro-benzyl)-piperidin-1-ylmethyl]-piperidin-3-yl}-3-(tetrahydro-pyran-4-ylmethyl)-urea;

(3R,4S)-4-[(S)-3-(4-fluoro-benzyl)-piperidin-1-ylmethyl]-3-{3-[2-(tetrahydro-pyran-4-yl)-ethyl]-ureido}-piperidine-1-carboxylic acid tert-butyl ester;

1-{(3R,4S)-4-[(S)-3-(4-fluoro-benzyl)-piperidin-1-ylmethyl]-piperidin-3-yl}-3-[2-(tetrahydro-pyran-4-yl)-ethyl]-urea;

1-{(3S,4S)-4-[(S)-3-(4-Fluoro-benzyl)-piperidin-1-ylmethyl]-tetrahydro-pyran-3-yl}-3-[3-methyl-5-(1-methyl-1H-tetrazol-5-yl)-phenyl]-urea;

1-{(3S,4S)-4-[(S)-3-(4-fluoro-benzyl)-piperidin-1-ylmethyl]-tetrahydro-pyran-3-yl}-3-[3-(1-methyl-1H-tetrazol-5-yl)-phenyl]-urea;

1-{(3S,4S)-4-[(S)-3-(4-fluorobenzyl)-piperidin-1-ylmethyl]-tetrahydro-pyran-3-yl}-3-[5-acetyl-4-methylthiazol-2-yl]-urea;

1-{(3S,4S)-4-[(S)-3-(4-fluorobenzyl)-piperidin-1-ylmethyl]-tetrahydro-pyran-3-yl}-3-(3-acetylphenyl)-urea;

1-{(3S,4S)-4-[(S)-3-(4-fluorobenzyl)-piperidin-1-ylmethyl]-tetrahydro-pyran-3-yl}-3-(2-morpholin-4-yl-ethyl)-urea;

1-{(3S,4S)-4-[(S)-3-(4-fluorobenzyl)-piperidin-1-ylmethyl]-1,1-dioxo-tetrahydrothiophen-3-yl}-3-[5-acetyl-4-methylthiazol-2-yl]-urea;

1-{(3S,4S)-4-[(S)-3-(4-fluorobenzyl)-piperidin-1-ylmethyl]-1,1-dioxo-tetrahydrothiophen-3-yl}-3-[3-(1-methyl-1H-tetrazol-5-yl)-phenyl]-urea;

1-{(3S,4S)-4-[(S)-3-(4-fluorobenzyl)-piperidin-1-ylmethyl]-1,1-dioxo-tetrahydrothiophen-3-yl}-3-[3-acetylphenyl]-urea;

1-{(3S,4S)-4-[(S)-3-(4-fluorobenzyl)-piperidin-1-ylmethyl]-1,1-dioxo-tetrahydrothiophen-3-yl}-3-(2-morpholin-4-yl-ethyl)-urea;

1-(5-acetyl-4-methyl-thiazol-2-yl)-3-{(3R,4S)-4-[(S)-3-(4-fluorobenzyl)-piperidine-1-carbonyl]-1,1-dioxo-tetrahydro-1λ6-thiophen-3-yl}-urea;

1-{(3R,4S)-4-[(S)-3-(4-fluorobenzyl)-piperidine-1-carbonyl]-1,1-dioxo-tetrahydrothiophen-3-yl}-3-(2-morpholin-4-yl-ethyl)-urea;

(3S,4S)-3-[(S)-3-(4-fluorobenzyl)-piperidin-1-ylmethyl]-4-{3-[3-methyl-5-(1-methyl-1H-tetrazol-5-yl)-phenyl]-ureido}-pyrrolidine-1-carboxylic acid tert-butyl ester;

1-(5-acetyl-4-methylthiazol-2-yl)-3-{(3S,4S)-4-[(S)-3-(4-fluorobenzyl)-piperidin-1-ylmethyl]-pyrrolidin-3-yl}-urea.

In another embodiment, the present invention provides a pharmaceutical composition, comprising a pharmaceutically acceptable carrier and a therapeutically effective amount of a compound of the present invention.

In another embodiment, the present invention provides a method for modulation of chemokine receptor activity comprising administering to a patient in need thereof a therapeutically effective amount of a compound of the present invention.

In another embodiment, the present invention provides a method for treating inflammatory disorders comprising administering to a patient in need thereof a therapeutically effective amount of a compound of the present invention In another embodiment, the present invention provides a method for treating or preventing disorders selected from asthma, allergic rhinitis, atopic dermatitis, inflammatory bowel diseases, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, HIV infection, cystic fibrosis, Churg-Strauss syndrome, lymphoma, Hodgkin's disease, and colonic carcinoma.

In another embodiment, the present invention provides a method for treating or preventing disorders selected from asthma, allergic rhinitis, atopic dermatitis, and inflammatory bowel diseases.

In another embodiment, the present invention provides a method for treating or preventing asthma.

In another embodiment, the compound of Formula (I) is

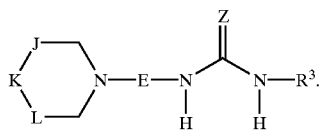

In another embodiment, the compound of Formula (I) is

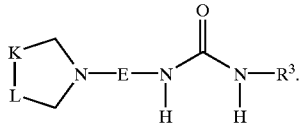

In another embodiment, J is $CH_2$, K is selected from $CH_2$ and $CHR^5$, and L is selected from $CH_2$ and $CHR^5$, wherein at least one of K or L contains an $R^5$.

In another embodiment, K is $CH_2$.
In another embodiment, L is $CH_2$.
In another embodiment, Z is selected from O, S, NCN, and $NCONH_2$.
In another embodiment, E is

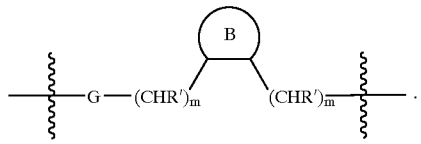

In another embodiment, E is

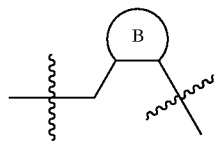

In another embodiment, Ring B is piperidine, tetrahydropyran, tetrahydrothiopyran, tetrahydrothiopyran 1,1-dioxide, piperidin-2-one, tetrahydropyran-2-one, [1,2] thiazinane 1,1-dioxide, pyrrolidine, tetrahydrofuran, tetrahydrothiophene, pyrrolidin-2-one, dihydrofuran-2-one, and isothiazolidine 1,1-dioxide.

In another embodiment, Ring B is piperidine, tetrahydropyran, tetrahydrothiopyran, tetrahydrothiopyran 1,1-dioxide, piperidin-2-one, tetrahydropyran-2-one, [1,2] thiazinane 1,1-dioxide, pyrrolidine, tetrahydrofuran, tetrahydrothiophene, pyrrolidin-2-one, dihydrofuran-2-one, and isothiazolidine 1,1-dioxide.

In another embodiment, Ring B is piperidine and tetrahydropyran.

In another embodiment, $R^1$ and $R^2$ are H.

In another embodiment, $R^3$ is selected from a $(CR^{3'}H)_r$-carbocyclic residue substituted with 0–5 $R^{15}$, wherein the carbocyclic residue is selected from phenyl, $C_{3-6}$ cycloalkyl, naphthyl, and adamantyl; and a $(CR^{3'}H)_r$-heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

In another embodiment, $R^3$ is selected from a methyl substituted with 0–2 $R^{10}$, $C_{2-8}$ alkyl substituted with 0–2 $R^7$, a $C_{3-10}$ carbocyclic residue substituted with 0–3 $R^{15}$, wherein the carbocyclic residue is selected from cyclopropyl, cyclobutyl, cyclopentyl, cyclohexyl, phenyl, naphthyl and adamantyl, and a $(CR^{3'}H)_r$-heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

In another embodiment, $R^3$ is selected from a phenyl substituted with 0–2 $R^{15}$; and a $(CH_2)_r$-5–10 membered heterocyclic system containing 1–4 heteroatoms selected from N, O, and S, substituted with 0–2 $R^{15}$, wherein the heterocyclic system is selected from pyridinyl, morpholinyl, pyrazolyl, indazolyl, thiazolyl and r is 0, 1, or 2.

In another embodiment, $R^5$ is selected from $(CR^{5'}H)_r$-phenyl substituted with 0–5 $R^{16}$; and a $(CR^{5'}H)_r$-heterocyclic system substituted with 0–3 $R^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

In another embodiment, $R^5$ is selected from a $CH_2$—$C_{3-10}$ carbocyclic residue substituted with 1–5 $R^{16}$ and a heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

In another embodiment, $R^5$ is $CH_2$-phenyl substituted with 0–3 $R^{16}$.

In another embodiment, $R^9$ is selected from H, $CH_3$, $C_{2-6}$ alkyl substituted with 0–3 $R^{9a}$, $C_{3-8}$ alkenyl, $C_{3-8}$ alkynyl, $C_{1-3}$haloalkyl, $(CH_2)_rC(O)C_{1-6}$ alkyl substituted with 0–2 $R^{9j}$, $(CH_2)_rC(O)OC_{1-6}$ alkyl substituted with 0–3 $R^{9b}$, $(CH_2)_rC(O)NR^{9d}R^{9d'}$, $(CH_2)_rS(O)_2C_{1-6}$ alkyl, $S(O)_2C_{1-6}$ trifluoromethyl, $(CH_2)_rC(O)R^{9'}$, $(CH_2)_rC(O)NR^{9d}R^{9'}$, $(CH_2)_rS(O)_2R^{9'}$, $R^{9'}$, and $(CH_2)_rS(O)_2NR^{9d}R^{9'}$;

$R^{9i}$, at each occurrence, is independently selected from $(CHR')_r C_{3-6}$ cycloalkyl substituted with 0–3 $R^{9e}$, wherein the cycloalkyl is selected from cyclopropyl, cyclobutyl, cyclopentyl, and cyclohexyl, $(CHR')_r$phenyl substituted with 0–3 $R^{9c}$, $(CHR')_r$5–6 membered heterocycle system containing 1–4 heteroatoms selected from N, O, and S, substituted with 0–3 $R^{9c}$, wherein the heterocycle is selected from oxadiazolyl, morpholinyl, piperidinyl, tetrahydropyranyl, tetrahydrothiopyranyl, tetrahydrothiopyranyl dioxide, thiophene, imidazolyl, pyrrolidinyl, pyrrolyl, thiazolyl, and furanyl, and $(CHR')_r$phenyl substituted with 0–3 $R^{9c}$;

$R^{9a}$, at each occurrence, is selected from CN, O-methyl, O-ethyl, $CF_3$, OH, OC(O)-methyl, S-methyl, S-ethyl, S-propyl, $S(O)_p$-methyl, $S(O)_p$-ethyl, $S(O)_p$-propyl, and $NR^{9d}R^{9d'}$;

$R^{9b}$, at each occurrence, is selected from cyclopropyl, cyclbutyl, cyclpentyl, CN, $CF_3$, $CH_2OC_{1-5}$ alkyl, $CH_2$-OH, $CH_2SC_{1-5}$ alkyl, and $CH_2NR^{9d}R^{9d'}$;

$R^{9c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_r OC_{1-5}$ alkyl, $(CH_2)_rC(O)OC_{1-5}$ alkyl, $(CH_2)_rC(O)C_{1-5}$ alkyl, $(CH_2)_rC(O)NR^{9d}R^{9d'}$, $(CH_2)_r OH$, $(CH_2)_rSC_{1-5}$ alkyl, $(CH_2)_rS(O)_pC_{1-5}$ alkyl, and $(CH_2)_r NR^{9d}R^{9d'}$;

provided that if $R^{9c}$ is attached to a carbon attached to the nitrogen on Ring B, then $R^{9c}$ is selected from $(CH_2)_q OH$, $(CH_2)_q OC_{1-5}$ alkyl, $(CH_2)_q SC_{1-5}$ alkyl, $(CH_2)_q S(O)_q C_{1-5}$ alkyl, and $(CH_2)_q NR^{9d}R^{9d'}$;

$R^{9d}$ and $R^{9d'}$, at each occurrence, are independently selected from H, methyl, ethyl, propyl, i-propyl, butyl, cyclopropyl, cyclobutyl, cyclopentyl, cyclohexyl and phenyl;

$R^{9e}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rC_{1-5}$ alkyl, $(CH_2)_rC(O)OC_{1-5}$ alkyl, $(CH_2)_rC(O)NR^{9d}R^{9d'}$, $(CH_2)_rOH$, $(CH_2)_rSC_{1-5}$ alkyl, $(CH_2)_rS(O)_pC_{1-5}$ alkyl, and $(CH_2)_rNR^{9d}R^{9d'}$, or alternatively, two $R^{9e}$ on the same carbon atom form =O; and $R^{9j}$, at each occurrence, is selected from cyclpropyl, cyclobutyl, cyclopentyl, CN, $CF_3$, O-methyl, O-ethyl, O-propyl, O-i-propyl, O-butyl, OH, S-methyl, S-ethyl, and $NR^{9d}R^{9d'}$.

In another embodiment, $R^9$ is selected from H, $C_{2-6}$ alkyl substituted with 0–3 $R^{9a}$, wherein the alkyl is selected from methyl, ethyl, propyl, i-propyl, butyl, i-butyl, s-butyl, t-butyl, neo-pentyl; $-CH_2CH=CH_2$; $-CH_2C\equiv CH$; 2-fluoroethyl, 2,2-difluoroethyl, 2,2,2-trifluoroethyl, $(CH_2)_r C(O)C_{1-6}$ alkyl substituted with 0–2 $R^{9j}$, wherein the alkyl is selected from methyl, ethyl, propyl, i-propyl, butyl, t-butyl; C(O)Omethyl, C(O)Ot-butyl, $SO_2$methyl, $SO_2$ethyl, $SO_2$propyl, $SO_2$i-propyl, $SO_2$t-butyl, $SO_2CF_3$, $(CH_2)_rC(O) NR^{9d}R^{9d'}$; $(CH_2)_rC(O)R^{9i}$, $(CH_2)_rC(O)NR^{9d}R^{9i}$, $(CH_2)_rS(O)_2R^{9i}$, $R^{9i}$, and $(CH_2)_rS(O)_2NR^{9d}R^{9i}$;

$R^{9i}$, at each occurrence, is independently selected from $(CHR')_rC_{3-6}$ cycloalkyl, wherein the cycloalkyl is selected from cyclopropyl, cyclobutyl, cyclopentyl, and cyclohexyl, $(CHR')_r$phenyl substituted with 0–3 $R^{9c}$, $(CHR')_r$5–6 membered heterocycle system containing 1–4 heteroatoms selected from N, O, and S, substituted with 0–3 $R^{9c}$, wherein the heterocycle is selected from oxadiazolyl, morpholinyl, piperidinyl, tetrahydropyranyl, tetrahydrothiopyranyl, tetrahydrothiopyranyl dioxide, thiophene, imidazolyl, pyrrolidinyl, pyrrolyl, thiazolyl, and furanyl, and $(CHR')_r$phenyl substituted with 0–3 $R^{9c}$;

$R^{9a}$, at each occurrence, is selected from CN, O-methyl, O-ethyl, $CF_3$, OH, OC(O)-methyl, S-methyl, S-ethyl, S-propyl, $S(O)_p$-methyl, $S(O)_p$-ethyl, $S(O)_p$-propyl, and $NR^{9d}R^{9d'}$;

$R^{9c}$, at each occurrence, is selected from methyl, ethyl, propyl, C(O)-methyl, C(O)O-t-butyl;

$R^{9d}$ and $R^{9d'}$, at each occurrence, are independently selected from H, methyl, ethyl, propyl, i-propyl, butyl, t-butyl;

$R^{9j}$, at each occurrence, is selected from O-methyl, O-ethyl, and $NR^{9d}R^{9d'}$.

The invention may be embodied in other specific forms without departing from the spirit or essential attributes thereof. This invention also encompasses all combinations of preferred aspects of the invention noted herein. It is understood that any and all embodiments of the present invention may be taken in conjunction with any other embodiment to describe additional even more preferred embodiments of the present invention. Furthermore, any elements of an embodiment are meant to be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

When any variable (e.g., $R^a$) occurs more than one time in any constituent or formula for a compound, its definition at each occurrence is independent of its definition at every other occurrence. Thus, for example, if a group is shown to be substituted with 0–2 $R^a$, then said group may optionally be substituted with up to two $R^a$ groups and $R^a$ at each occurrence is selected independently from the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-8}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl. $C_{1-8}$ alkyl, is intended to include $C_1$, $C_2$, $C_3$, $C_4$, $C_5$, $C_6$, $C_7$, and $C_8$ alkyl groups. "Alkenyl" is intended to include hydrocarbon chains of either a straight or branched configuration and one or more unsaturated carbon-carbon bonds which may occur in any stable point along the chain, such as ethenyl, propenyl, and the like. "Alkynyl" is intended to include hydrocarbon chains of either a straight or branched configuration and one or more unsaturated triple carbon-carbon bonds which may occur in any stable point along the chain, such as ethynyl, propynyl, and the like. "$C_{3-6}$ cycloalkyl" is intended to include saturated ring groups having the specified number of carbon atoms in the ring, including mono-, bi-, or poly-cyclic ring systems, such as cyclopropyl, cyclobutyl, cyclopentyl, cyclohexyl, and cycloheptyl in the case of $C_7$ cycloalkyl. $C_{3-6}$ cycloalkyl, is intended to include $C_3$, $C_4$, $C_5$, and $C_6$ cycloalkyl groups "Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

As used herein, the term "5–6-membered cyclic ketal" is intended to mean 2,2-disubstituted 1,3-dioxolane or 2,2-disubstituted 1,3-dioxane and their derivatives.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl,; [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" or "heterocyclic ring" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuran-2-one, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolidine 1,1-dioxide, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidin-2-one, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidin-2-one, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydropyranyl (THP), tetrahydroquinolinyl, tetrahydropyran-2-one, tetrahydrothiophenyl, 1-oxo-hexahydro-1$\lambda^4$-thiopyranyl, 1,1-dioxo-hexahydro-1$\lambda^6$-thiopyranyl, tetrahydrothiopyranyl (THTP), 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,1-dioxo-1$\lambda^6$-[1,2]thiazinanyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. Preferred heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, pyrimidinyl, tetrahydropyranyl, tetrahydrothiopyranyl, 1-oxo-hexahydro-1$\lambda^4$-thiopyranyl, 1,l-dioxo-hexahydro-1$\lambda^6$-thiopyranyl, piperidin-2-one, tetrahydropyran-2-one, 1,1-dioxo-1$\lambda^6$-[1,2]thiazinanyl, pyrrolidinyl, tetrahydrofuranyl, tetrahydrothiophenyl, pyrrolidin-2-one, dihydrofuran-2-one, and isothiazolidine 1,1-dioxide. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Stable compound" and "stable structure" are meant to indicate a compound that is sufficiently robust to survive isolation to a useful degree of purity from a reaction mixture, and formulation into an efficacious therapeutic agent.

Synthesis

The compounds of Formula I can be prepared using the reactions and techniques described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis,* Wiley and Sons, 1999).

Generally, compounds described in the scope of this patent application can be synthesized by the route described in Schemes 1, 2 or 3. In all schemes, P is a suitable protecting group as described in Greene and Wuts, Protective Groups in Organic Synthesis, 3rd edition, John Wiley & Sons, New York. In Scheme 1, the appropriately substituted pyrrolidine (n=0) or piperidine (n=1) 1 is alkylated by a N-protected alkylhalide (halide=Cl, Br, I), mesylate, tosylate or triflate, 2, (where E represents a linkage described within the scope of this application in its fully elaborated form with the appropriate protecting groups as understood by one skilled in the art or in a precursor form which can be later elaborated into its final form by methods familiar to one skilled in the art) with or without base or an acid scavenger to yield the piperidinyl- or pyrrolidinylalkyl protected amine 3. If the halide is not I, then KI can also be added to facilitate the displacement, provided the solvent is suitable, such as an alcohol, 2-butanone, DMF or DMSO, amongst others. The displacement can be performed at room temperature to the reflux temperature of the solvent. The protecting group is subsequently removed to yield amine 4. Protecting groups include phthalimide which can be removed by hydrazine, a reaction familiar to one skilled in the art; bis-BOC which can be removed by either TFA or HCl dissolved in a suitable solvent, both procedures being familiar to one skilled in the art; a nitro group instead of an amine which can be reduced to yield an amine by conditions familiar to one skilled in the art; 2,4-dimethyl pyrrole (S. P. Breukelman, et al. J. Chem. Soc. Perkin Trans. I, 1984, 2801); N-1,1,4,4-Tetramethyl-disilylazacyclopentane (STABASE) (S. Djuric, J. Venit, and P. Magnus Tet. Lett 1981, 22, 1787) and other protecting groups. Reaction with an isocyanate or isothiocyanate 5 (Z=O, S) yields urea or thiourea 6. Reaction with a chloroformate or chlorothioformate 7 (Z=O,S) such as o-, p-nitrophenyl-chloroformate or phenylchloroformate (or their thiocarbonyl equivalents), followed by displacement with an amine 9, also yields the corresponding urea or thiourea 6. Likewise, reaction of carbamate 8 (X=H, or 2- or 4-NO2) with disubstituted amine 10 yields trisubstituted urea or thiourea 12. Reaction of the amine 4 with an N,N-disubstituted carbamoyl chloride 11 (or its thiocarbonyl equivalent) yields the corresponding N,N-disubstituted urea or thiourea 12. Amine 4 can also be reductively aminated with aldehyde 13 to yield 14 by conditions familiar to one skilled in the art and by the following conditions: Abdel-Magid, A. F., et al. Tet. Lett. 1990, 31, (39) 5595–5598. This secondary amine can subsequently be reacted with isocyanates or isothiocyanates to yield trisubstituted ureas 15 or with carbamoyl chlorides to yield tetrasubstituted ureas 16.

Scheme 1

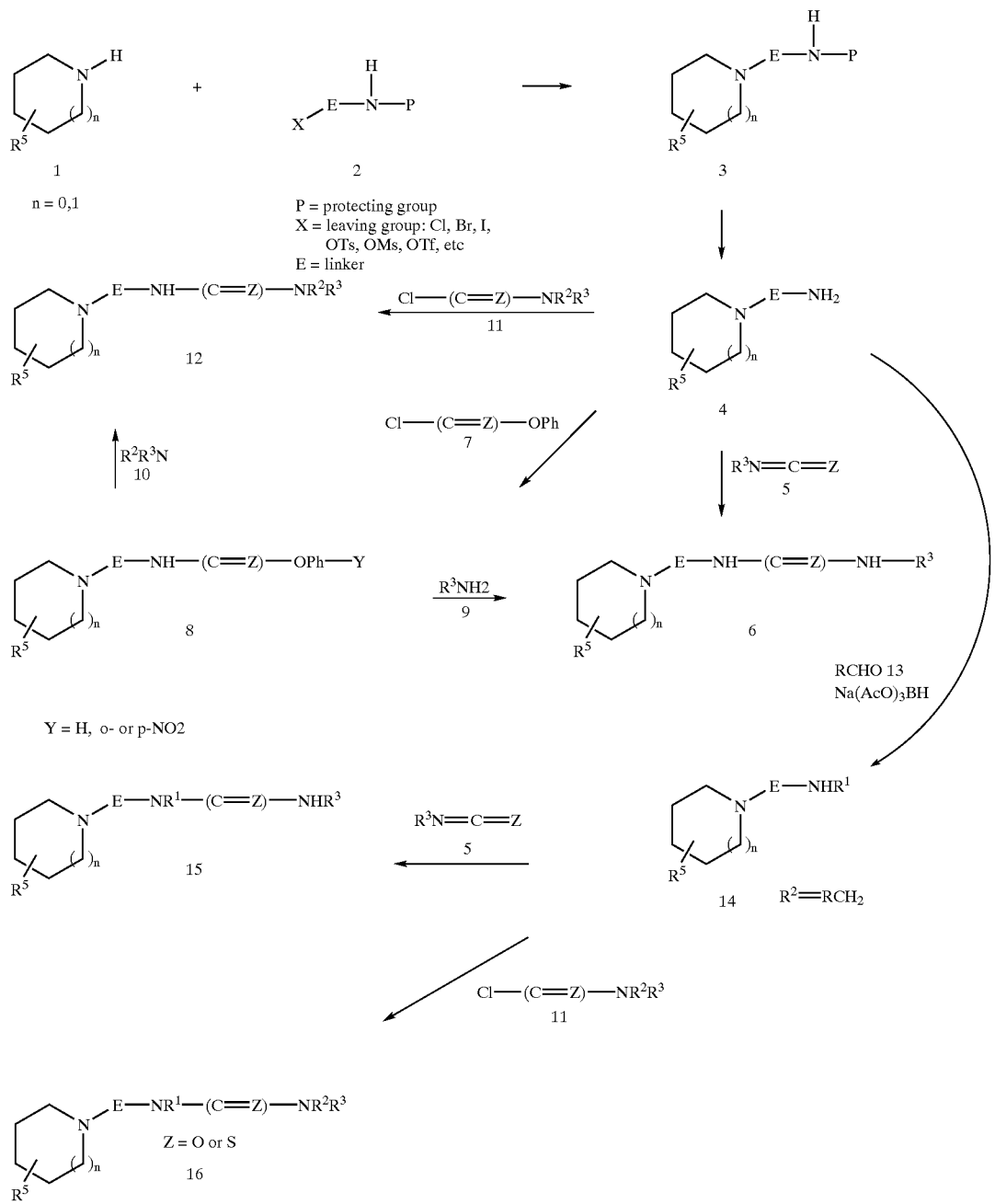

One can also convert amine 4 into an isocyanate, isothiocyanate, carbamoyl chloride or its thiocarbonyl equivalent (isocyanate: Nowakowski, J. J Prakt. Chem/Chem-Ztg 1996, 338 (7), 667–671; Knoelker, H.-J. et al., Angew. Chem. 1995, 107 (22), 2746–2749; Nowick, J. S.et al., J. Org. Chem. 1996, 61 (11), 3929–3934; Staab, H. A.; Benz, W.; Angew Chem 1961, 73; isothiocyanate: Strekowski L.et al., J. Heterocycl. Chem. 1996, 33 (6), 1685–1688; Kutschy, Pet al., Synlett. 1997, (3), 289–290) carbamoyl chloride: Hintze, F.; Hoppe, D.; Synthesis (1992) 12, 1216–1218; thiocarbamoyl chloride: Ried, W.; Hillenbrand, H.; Oertel, G.; Justus Liebigs Ann Chem 1954, 590) (these reactions are not shown in Scheme 1). These isocyanates, isothiocyanates, carbamoyl chlorides or thiocarbamoyl chlorides can then be reacted with $R^2R^3NH$ to yield di- or trisubstituted ureas or thioureas 12. An additional urea forming reaction involves the reaction of carbonyldiimidazole (CDI) (Romine, J. L.; Martin, S. W.; Meanwell, N. A.; Epperson, J. R.; Synthesis 1994 (8), 846–850) with 4 followed by reaction of the intermediate imidazolide with 9 or in the reversed sequence (9+CDI, followed by 4). Activation of imidazolide intermediates also facilitates urea formation (Bailey, R. A., et al., Tet. Lett. 1998, 39, 6267–6270). One can also use 14 and 10 with CDI. The urea forming reactions are done in an aprotic inert solvent such as THF, toluene, DMF, etc., at room temperature to the reflux temperature of the solvent and can employ the use of an acid scavenger or base when necessary such as carbonate and bicarbonate salts, triethylamine, DBU, Hunig's base, DMAP, etc.

Scheme 2 describes the synthesis of compounds with an carbonyl linking the appropriately substituted pyrrolidine (n=0) or piperidine (n=1) 1 and B. When carboxylic acid 17 is used, a wide variety of dehydrating coupling reagents may be used to prepare the amide 198 from amine 1. A review of the possible reaction conditions was prepared by Y. S. Klausner and M. Bodansky in Synthesis 1972, 9, 453–463. Additional references by E. Gross and J. Meienhofer can be found in the monograph series The Peptides, 4 vols.; Academic Press: New York, 1979–1983. Alternatively the acid chloride 18 can be prepared from carboxylic acid 17 via thionyl chloride or oxalyl chloride among other reagents (see Ansell in S. Patai, The Chemistry of Carboxylic Acids and Esters, Wiley Interscience: New York 1969, 35–68) and then coupled with amine 1 to give amide 19. Deprotection of amide 19 gives the required intermediate amine 20, which can be further elaborated to the final products by the procedures outlined in Scheme 1.

Substituted pyrrolidines and piperidines 1 can either be obtained commercially or be prepared as shown in the example of Scheme 4. Commercially available N-benzylpiperid-3-one 24 can be debenzylated and protected with a BOC group employing reactions familiar to one skilled in the art. Subsequent Wittig reaction followed by reduction and deprotection yields piperidine 28 employing reactions familiar to one skilled in the art. Substituted pyrrolidines may be made by a similar reaction sequence. Other isomers and analogs around the piperidine ring can also be made by a similar reaction sequence. Chiral pyrrolidines/piperidines can be synthesized via asymmetric hydrogenation of 18 using chiral catalysts (see Parshall, G. W. Homogeneous Catalysis, John Wiley and Sons, New York: 1980, pp. 43–45; Collman, J. P., Hegedus, L. S. Principles and Applications of Organotransition Metal Chemistry, University Science Books, Mill Valley, Calif., 1980, pp. 341–348).

Scheme 2

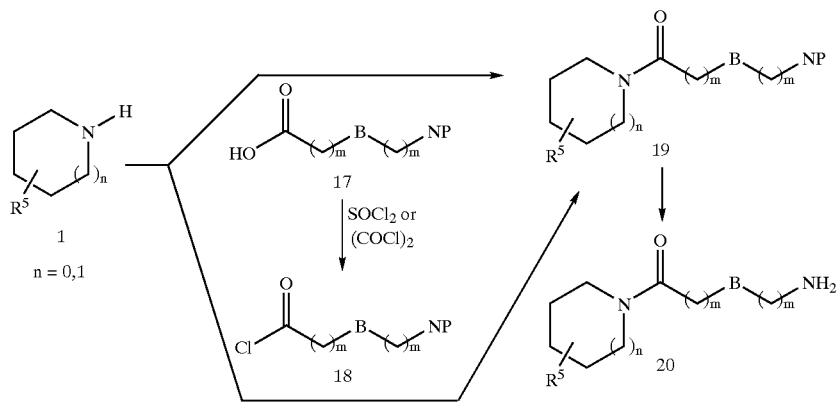

An alternative coupling of a alkyl linkage to the appropriately substituted pyrrolidine (n=0) or piperidine (n=1) 1 and B uses an reductive amination sequence (Abdel-Magid, A. F., et al. Tet. Lett. 1990, 31, (39) 5595–5598) shown in Scheme 3. The appropriately protected aldehyde 21 is reacted with amine 1 and the resulting imine is reduced with sodium triacetoxy-borohyride. Alternative hydride sources such as sodium cyanoborohydride may also be used. Deprotection of protected amine 22 gives the required intermediate amine 23, which can be further elaborated to the final products by the procedures outlined in Scheme 1.

Scheme 3

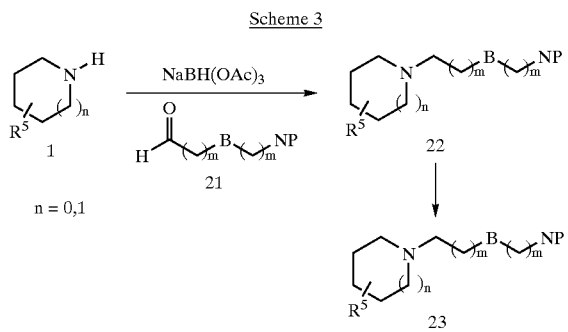

Scheme 4

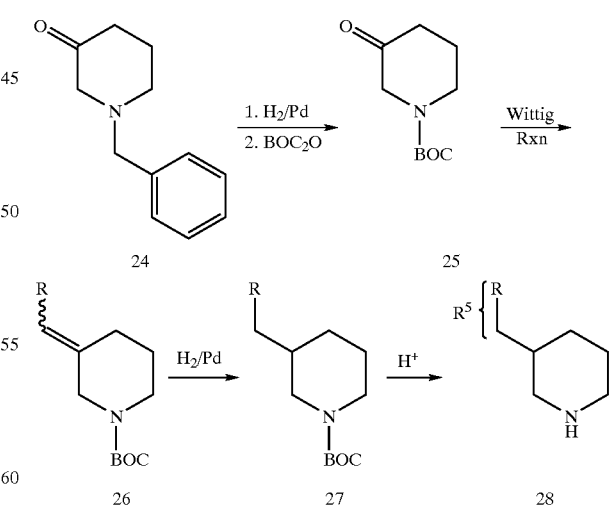

Guanidines (Z=NR$^{1a}$) can be synthesized by the methods outlined in Scheme 5. Compound 29 where Z=S can be methylated to yield the methylisothiourea 30. Displacement of the SMe group with amines yields substituted guanidines 31 (see H. King and I. M. Tonkin J. Chem. Soc. 1946, 1063 and references therein). Alternatively, reaction of thiourea 29 with amines in the presence of triethanolamine and "lac sulfur" which facilitates the removal of $H_2S$ yields substituted guanidines 31 (K. Ramadas, Tet. Lett. 1996, 37, 5161 and references therein). Finally, the use of carbonimidoyl-dichloride 32, or 33 followed by sequential displacements by amines yields the corresponding substituted guanidine 31 (S. Nagarajan, et al., Syn. Comm. 1992, 22, 1191–8 and references therein). In a similar manner, carbonimidoyldichlorides, $R^2$—N═C(Cl)$_2$ (not shown in Scheme 5) and $R^3$—N═C(Cl)$_2$ (not shown) can also be reacted sequentially with amines to yield di- and trisubstituted guanidine 23.

(Deng, J.; Hamada, Y.; Shioiri, T. Tet. Lett. 1996, 37, 2261) can provide the amine 38. To prepare the methylene derivative, borane reduction of amine 38 can give amine 39.

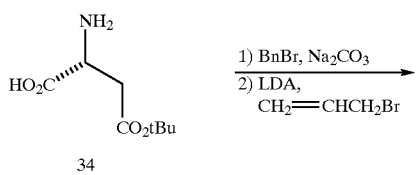

Scheme 6

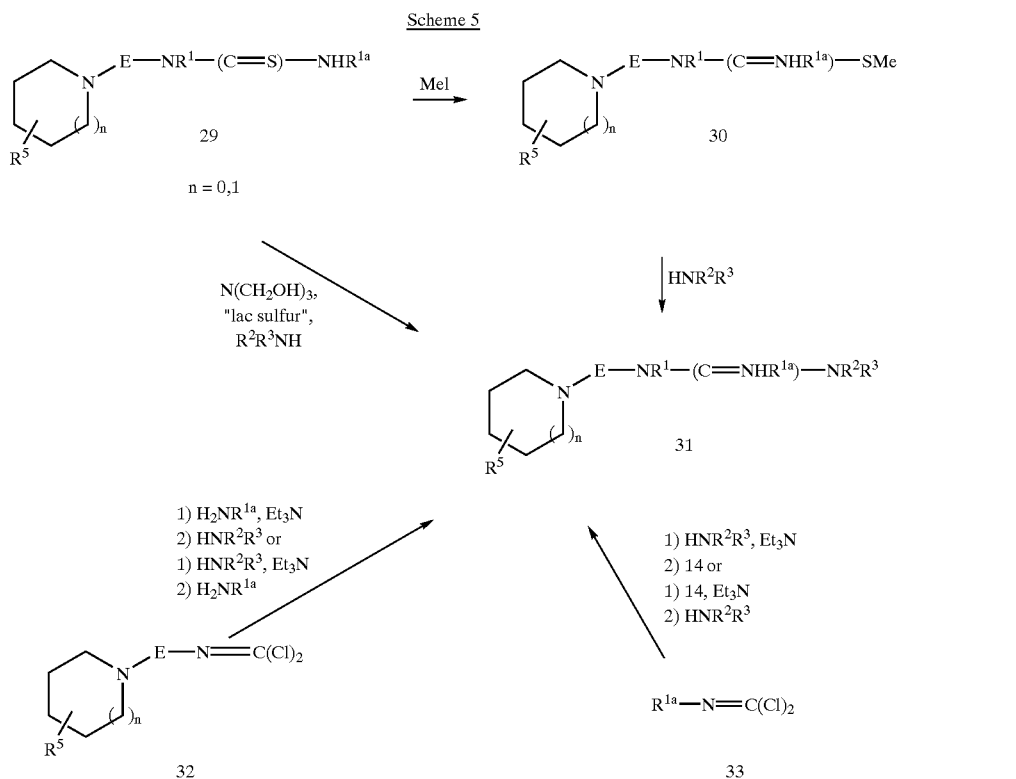

Scheme 5

Schemes 6 through 30 and Scheme 43 describe the syntheses of the variety of heterocyclic linkers, B. The protecting groups shown in the following schemes were chosen to maximize the utility of intermediates in a variety of schemes and may be interchanged with other compatible groups. While the synthesis of only one enantiomer is shown, the chiral precursors are available in both forms and therefore any isomer can be made from commercially available starting materials.

Scheme 6 describes the preparation of 2,3-disubstituted piperidines. The aspartic acid 34 can be exhaustively protected with benzyl bromide and the beta-carbon can be alkylated with allyl bromide to give the amino ester 35 as a mixture of diastereomers. Hydroboration can provide the alcohol 36 (H. C. Brown, J. C. Chen; J. Org. Chem. 1981, 46, 3978), with can be oxidized to an aldehyde (K. Omura, D. Swerm; Tet. Lett. 1978, 34, 1651) and the benzyl groups removed by catalytic hydrogenation. The intermediate aminoaldehyde cyclizes to an imine which can be further reduced to an aminoacid. Coupling this aminoacid with BOP-Cl (Castro, B.; Dormoy, J. R.; Evin, G.; Selve, C. Tet. Lett. 1975, 14, 1219) and the corresponding cyclic amine can give amide 37. Acidic hydrolysis of the ester, Boc protection of the amine, Curtius rearrangement via dppa

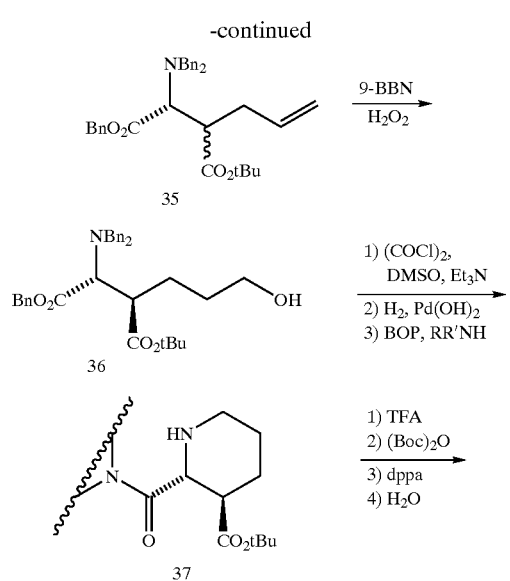

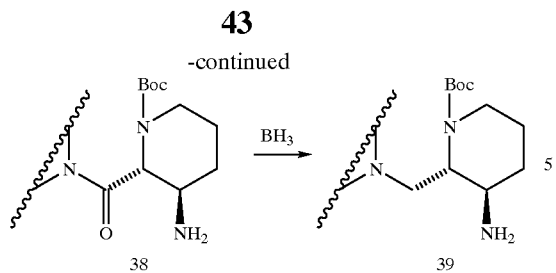

For the synthesis of 3,4-disubstituted piperidines, the sequence shown in Scheme 7 can be used. Following a procedure using an analog of a cyclohexanone derivative (Hayashi, Y.; Rohde, J. J.; Corey, E. J. J. Am. Chem. Soc. 1996, 118(23), 5502), the imine of 4-ketopiperidine 40 can be prepared by heating with (R)-alpha-methyl benzylamine with Dean-Stark trapping. Reduction with sodium triacetoxyborohyride can give the cis-amino ester 42. Epimerization can give the trans derivative 43. Hydrogenolysis of the benzyl group and protection as a benzyl carbamate 44 can provide a common intermediate for the hydrolysis and coupling to prepare amide 45 after deprotection. Alternatively, the ester can reduced to an alcohol, oxidized to an aldehyde, reductively aminated and deprotected to give amine 46.

Scheme 7

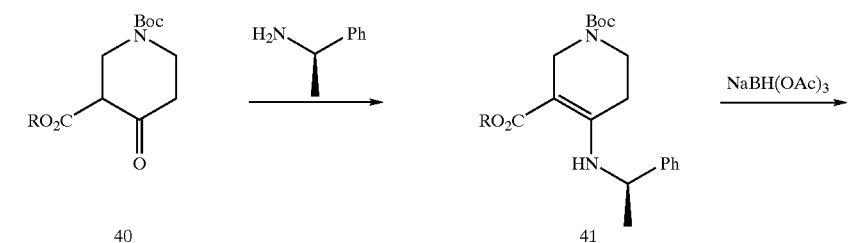

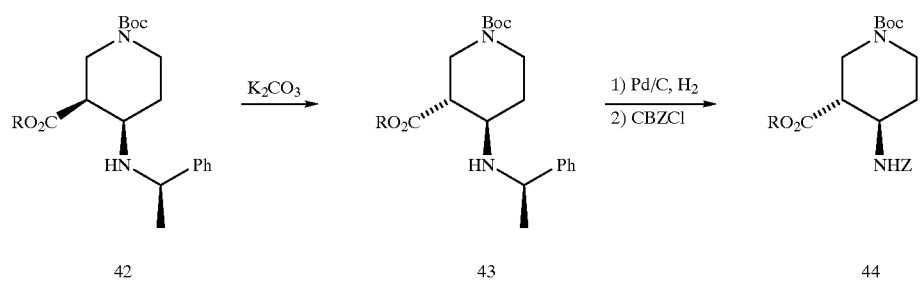

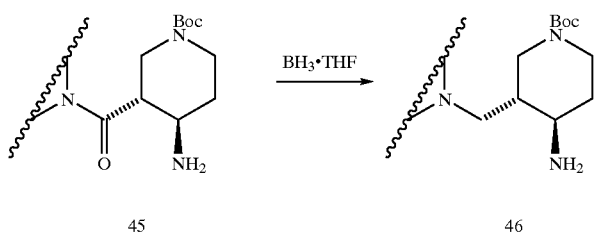

In a very similar manner, ketopiperidine 47 can be converted to amide 52 or amine 53 as shown in Scheme 8.

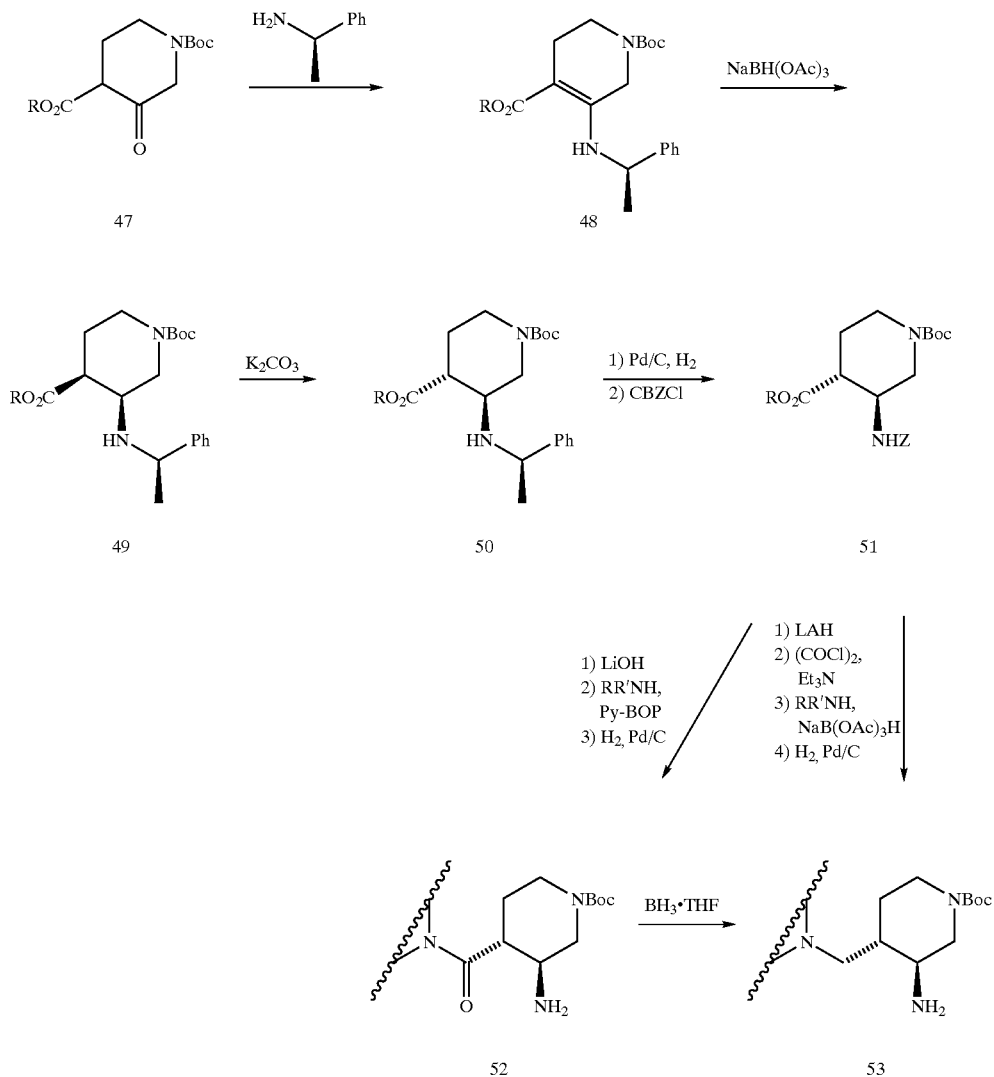

The synthesis of 2,3-disubstituted dihydropyrans is described in Scheme 9. Starting with diol 54, monoprotection and oxidation (Siedlecka, R.; Skarzewski, J. k; Mlochowski, J.; Tet. Lett. 1990, 31(15), 2177) can give acid 55. Acylation of the chiral auxiliary mediated by pivaloyl chloride can give oxazolinone 57. Sparteine-mediated aldol condensation with cinnamaldehyde sets up the required stereochemistry in alcohol 58 (Crimmins, M. T.; King, B. W.; Tabet, E. A.; J. Am. Chem. Soc. 1997, 119(33), 7883). Fluoride deprotection, triflate-mediated cyclization and lithium peroxide removal of the auxiliary can provide dihydropyran 59. Curtius rearrangement in the presence of t-butanol can produce the required protected amine. Oxidation with ozone and quenching with dimethyl sulfide can give the aldehyde 61. Oxidation of aldehyde 61 with TEMPO can give carboxylic acid 60.

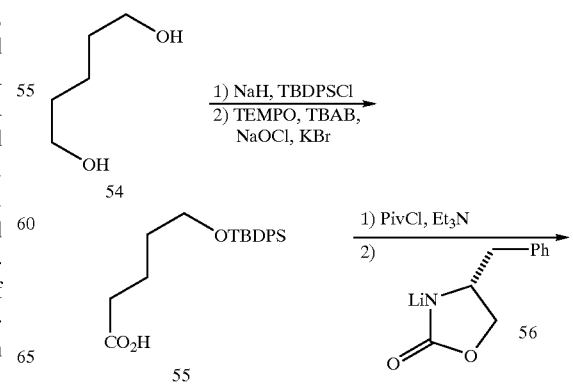

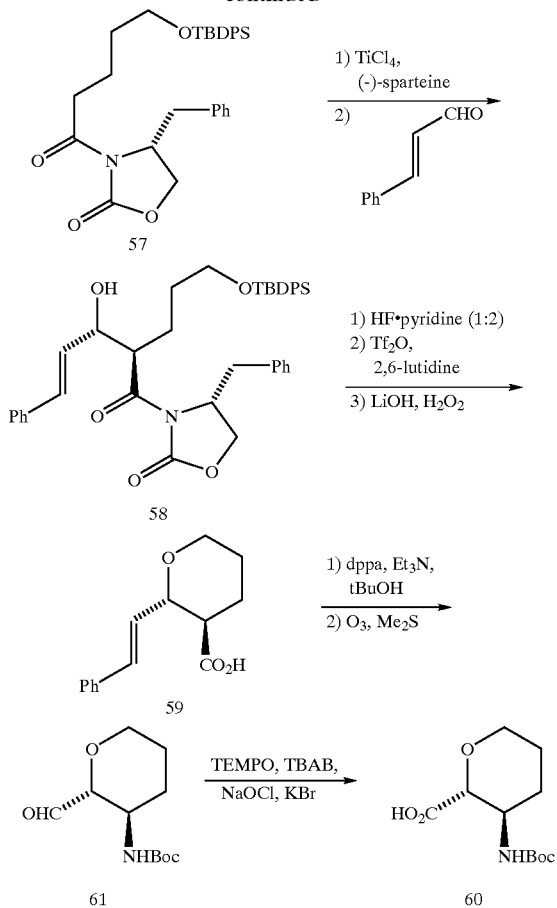

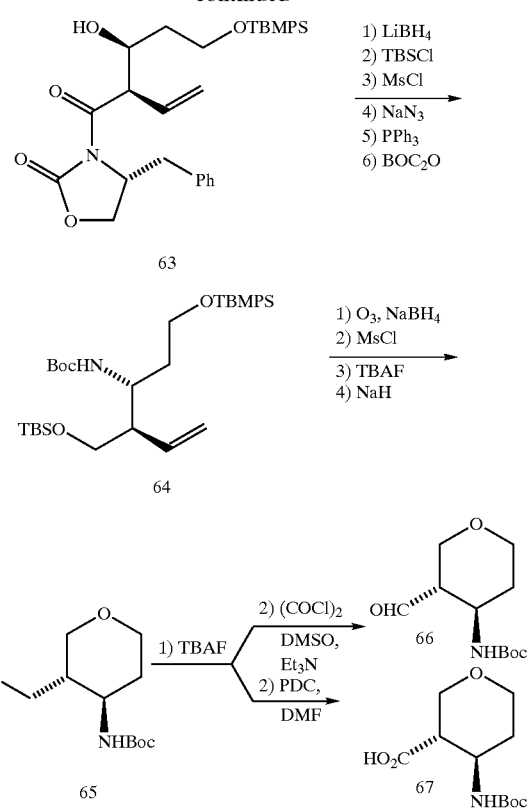

Scheme 10 describes the synthesis of 3,4-disubstituted dihydropyrans. Coupling of oxazolinone 56 with cinnamoyl chloride and subsequent boron-mediated aldol condensation (Galatsis, P.; Millan, S. D.; Ferguson, G.; J. Org. Chem. 1997, 62(15), 5048) with aldehyde 62 can give alcohol 63. Lithium borohydride auxiliary removal, protection of the primary alcohol with TBSCl, mesylate formation of the secondary alcohol, displacement of the mesylate with azide and reduction of the azide and protection of the resulting amine can give 64. Ozonolysis followed by reductive workup, mesylate formation of the alcohol, selective fluoride deprotection of the TBMP silyl ether (Guindon, Y.; Fortin, R.; Yaokim, C.; Gillard, J. W.; Tet. Lett. 1984, 25, 4717), and basic cyclization can provide dihydropyran 65. Fluoride deprotection followed by Swern oxidation can produce aldehyde 66 for reductive amination. Alternatively, the alcohol can be oxidized with PDC (Corey, E. J.; Schmidt, G. Tet. Lett. 1979, 5, 399) to acid 67.

The preparation of the regioisomeric 3,4-disubstituted dihydropyrans is shown in Scheme 11. One of the key differences between Schemes 11 and 10 is the aldol reaction with the shorter chain aldehyde 68. Instead of ozonolysis, the olefin 70 can be hydroborated, the resulting alcohol can be mesylated, and, after deprotection, undergoes ring closure to give the desired dihydropyran 71. Oxidation can give either 72 or 73.

Scheme 10

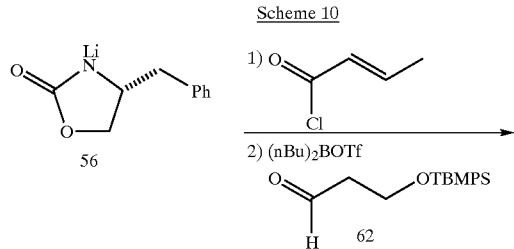

Scheme 11

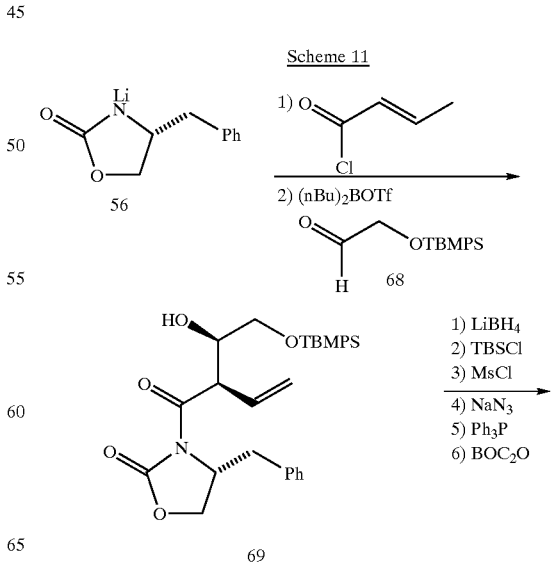

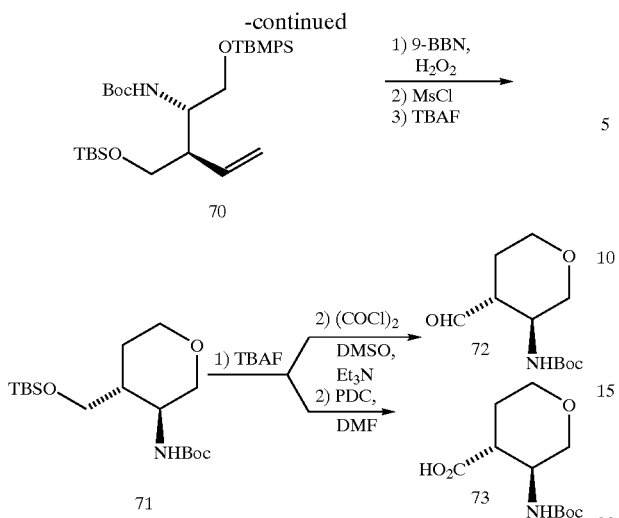

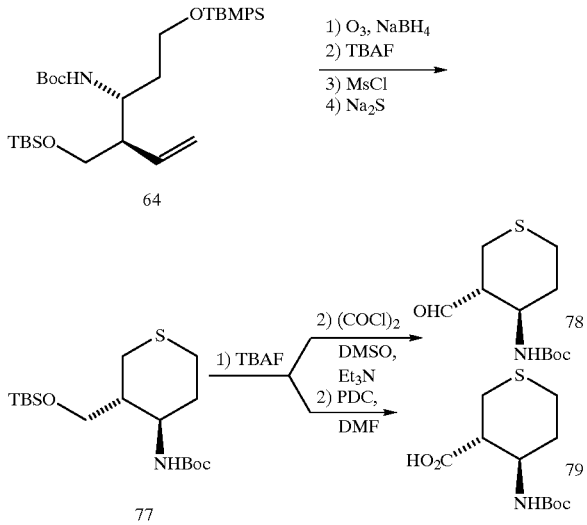

For the corresponding dihydrothiopyrans, advanced precursors from the dihydropyran syntheses were used.

Scheme 12 describes the synthesis of 2,3-disubstituted dihydrothiopyrans. Starting with alcohol 58, Lawesson'reagent displaces the hydroxyl with retention of configuration (Eberle, M. K.; Nuninger, F.; Weber, H-P.; J. Org. Chem. 1995, 60(8), 2610). Acidic fluoride deprotection removes the silyl group and catalyzes the cyclization to the dihydrothiopyran. Lithium hydroperoxide removes the chiral auxiliary and oxidizes the sulfur to the sulfone 74. Curtius rearrangement with Boc anhydride and ozonolysis with oxidative workup can give acid 75. Ozonolysis with reductive workup can give aldehyde 76.

Scheme 12

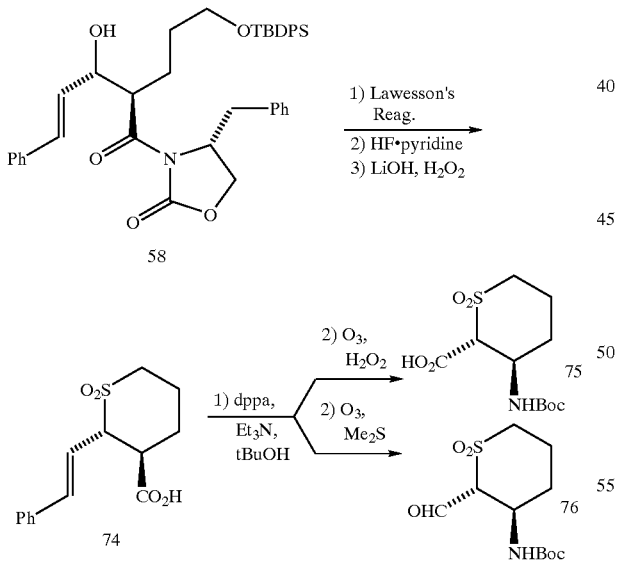

The preparation of the regioisomeric dihydrothiopyrans can be shown in Scheme 13. Ozonolysis of olefin 64 with reductive workup can provide an alcohol. Selective fluoride deprotection of the TBMP silyl group (discussed with scheme 10), mesylate formation on both alcohols, followed by displacement with sodium sulfide and subsequent ring closure can give sulfide 77. Fluoride deprotection and Swern oxidation can give aldehyde 78. Alternatively, PDC oxidation (Jeong, L. S.; Schinazi, R. F.; Beach, J. W.; Kim, H. O.; Shanmuganathan, K.; J. Med. Chem. 1993, 36(18), 2627) can give acid 79.

Scheme 13

The preparation of the other regioisomeric dihydrothiopyrans can be shown in Scheme 14. Selective fluoride deprotection of the TBMP silyl group on 70 (discussed previously), mesylate formation, can be followed by displacement of the mesylate with sodium sulfide. Reduction of the olefin initiates ring closure to give sulfide 80 (Aggarwal, V. K.; Ford, J. G.; Fonquerna, S.; Adams, H.; Jones, R. V. H.; Fieldhouse, R.; J. Am. Chem. Soc. 1998, 120, 30). Fluoride deprotection and Swern oxidation can give aldehyde 81. Alternatively, PDC oxidation can give acid 82.

Scheme 14

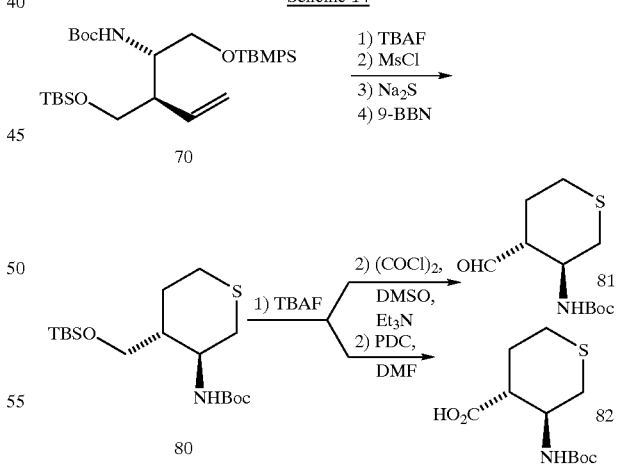

Scheme 15 shows the synthesis of the 5,6-disubstituted lactams. Alcohol 36 can be oxidized with PDC to the carboxylic acid, the ester and amine are deprotected by hydrogenolysis, heat can be applied to do a intramolecular cyclization, and the remaining carboxylic acid can be coupled with BOP-Cl with the amine 1 to give amide 83. Acidic ester hydrolysis with trifluoroacetic acid followed by Curtius rearrangement with dppa can provide amine 84.

Scheme 15

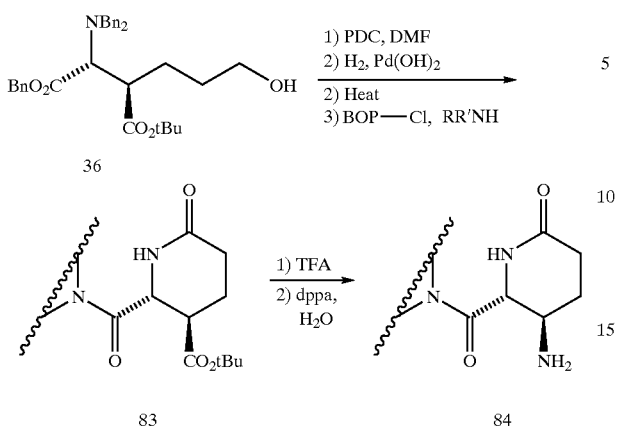

If the methylene linker can be desired for the 5,6-disubstituted lactams, then the synthesis can be outlined in Scheme 16. Alcohol 36 can be oxidized with PDC to the carboxylic acid, the ester and amine are deprotected by hydrogenolysis, heat can be applied to do a intramolecular cyclization, and the remaining carboxylic acid can be converted to the acid chloride, reduced to the alcohol and protected with the TBDP silyl group to give ester 85. Acidic ester hydrolysis with trifluoroacetic acid, Curtius rearrangement with dppa and Boc protection of the amine, fluoride deprotection and Swern oxidation can provide aldehyde 86.

Scheme 16

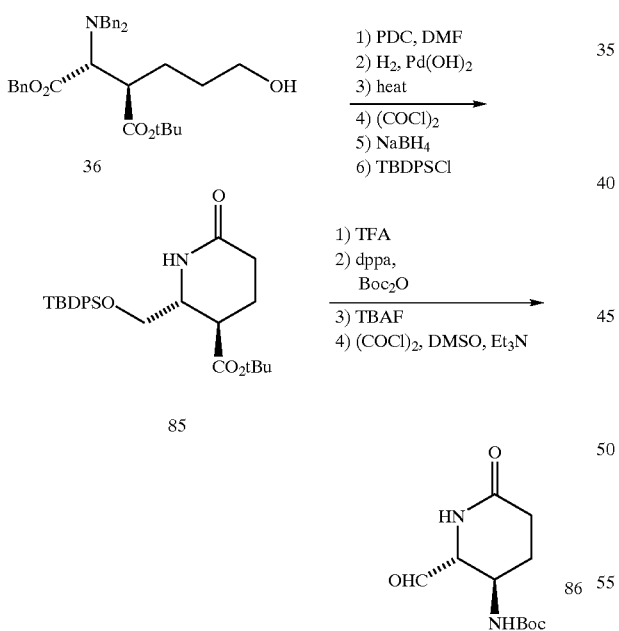

Scheme 17 describes the synthesis of 3,4-disubstituted lactams. Olefin 64 can be ozonolyzed with an oxidative workup. The resulting carboxylic acid can be converted to methyl ester 87 with trimethylsilyl diazomethane. Selective fluoride deprotection, mesylate formation, azide displacement of the mesylate, reduction of the azide and concomitant cyclization onto the ester can provide amide 88. Fluoride deprotection and Swern oxidation completes the synthesis of aldehyde 89.

Scheme 17

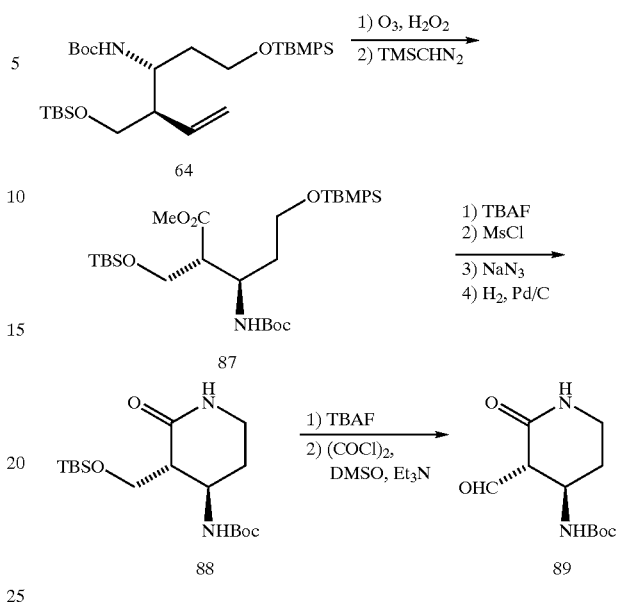

Scheme 18 describes the synthesis of 4,5-disubstituted lactams. Ether 64 can be selectively deprotected, oxidized to a carboxylic acid and esterified with trimethylsilyl diazomethane to give ester 90. Ozonolysis of the olefin with reductive workup, followed by mesylate formation of the resulting alcohol, azide displacement of the mesylate, reduction of the azide and concomitant cyclization onto the ester can provide amide 91. Fluoride deprotection and Swern oxidation completes the synthesis of aldehyde 92. Alternatively, oxidation with PDC can give acid 93.

Scheme 18

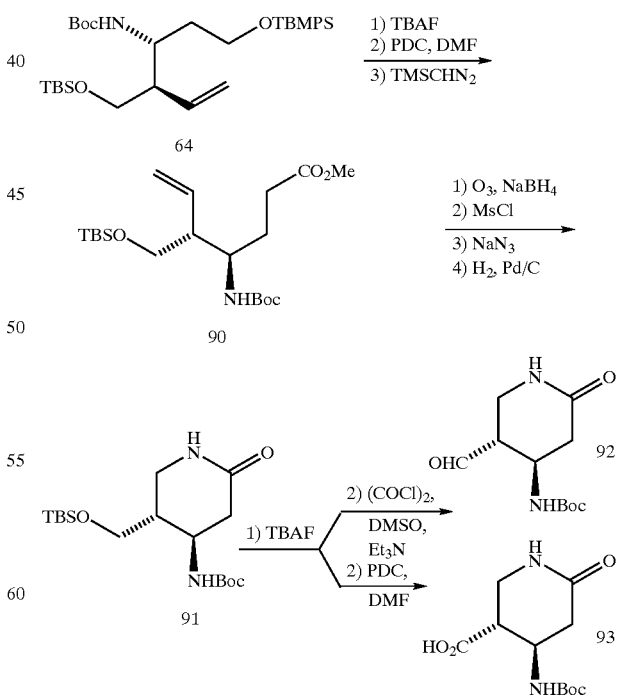

Scheme 19 describes the synthesis of regioisomeric 4,5-disubstituted lactams. Olefin 70 can be hydroborated, the resulting alcohol can be oxidized to a carboxylic acid and esterified with trimethylsilyl diazomethane to give ester 94. Selective fluoride deprotection, followed by mesylate formation of the resulting alcohol, azide displacement of the mesylate, reduction of the azide and concomitant cyclization onto the ester can provide amide 95. Fluoride deprotection and Swern oxidation completes the synthesis of aldehyde 96. Alternatively, oxidation with PDC can give acid 97.

Scheme 19

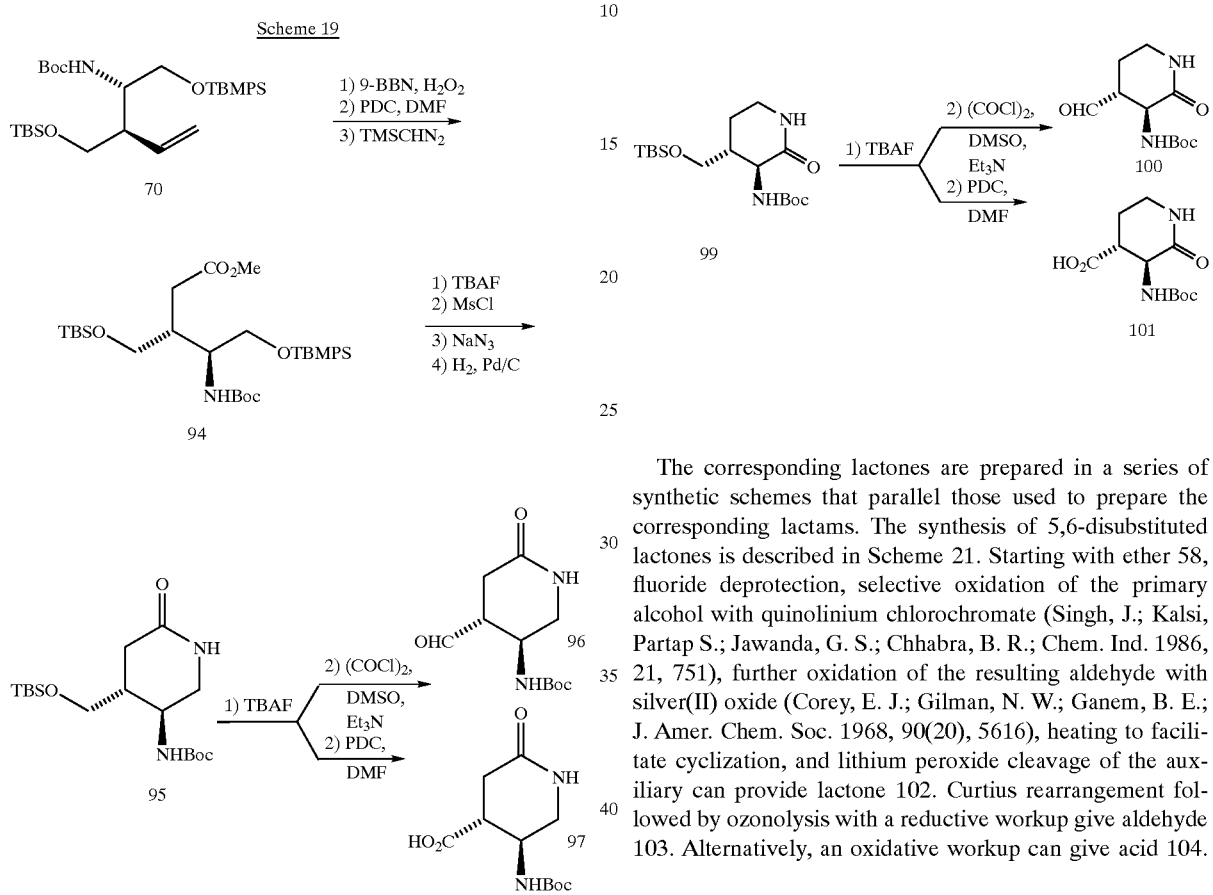

Scheme 20 describes the synthesis of regioisomeric 2,3-disubstituted lactams. Ether 70 can be selectively deprotected, the resulting alcohol can be oxidized to a carboxylic acid and esterified with trimethylsilyl diazomethane to give ester 98. Hydroboration, followed by mesylate formation of the resulting alcohol, azide displacement of the mesylate, reduction of the azide and concomitant cyclization onto the ester can provide amide 99. Fluoride deprotection and Swern oxidation completes the synthesis of aldehyde 100. Alternatively, oxidation with PDC can give acid 101.

Scheme 20

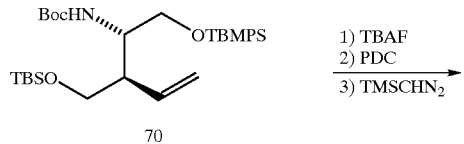

The corresponding lactones are prepared in a series of synthetic schemes that parallel those used to prepare the corresponding lactams. The synthesis of 5,6-disubstituted lactones is described in Scheme 21. Starting with ether 58, fluoride deprotection, selective oxidation of the primary alcohol with quinolinium chlorochromate (Singh, J.; Kalsi, Partap S.; Jawanda, G. S.; Chhabra, B. R.; Chem. Ind. 1986, 21, 751), further oxidation of the resulting aldehyde with silver(II) oxide (Corey, E. J.; Gilman, N. W.; Ganem, B. E.; J. Amer. Chem. Soc. 1968, 90(20), 5616), heating to facilitate cyclization, and lithium peroxide cleavage of the auxiliary can provide lactone 102. Curtius rearrangement followed by ozonolysis with a reductive workup give aldehyde 103. Alternatively, an oxidative workup can give acid 104.

Scheme 21

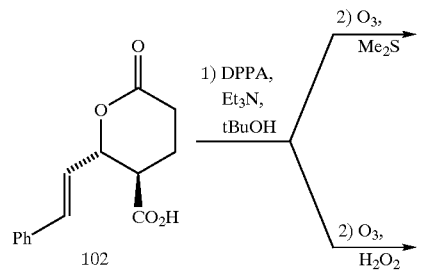

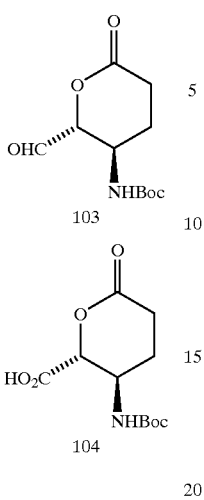

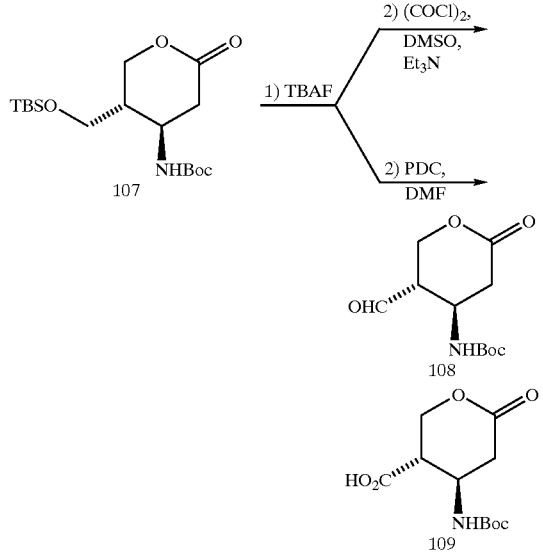

Scheme 22 describes the synthesis of 3,4-disubstituted lactones. Olefin 64 can be ozonolyzed with an oxidative workup. The TBMP silyl group can be selectively removed with fluoride, the alcohol can be heated and cyclizes with the carboxylic acid to give the lactone 105. Fluoride deprotection and Swern oxidation completes the synthesis of aldehyde 106.

Scheme 24 describes the synthesis of regioisomeric 4,5-disubstituted lactones. Olefin 70 can be hydroborated, the resulting alcohol can be oxidized to a carboxylic acid, the TBMP silyl can be selectively deprotected, and heated to promote cyclization to give amide 110. Fluoride deprotection and Swern oxidation completes the synthesis of aldehyde 111. Alternatively, oxidation with PDC can give acid 112.

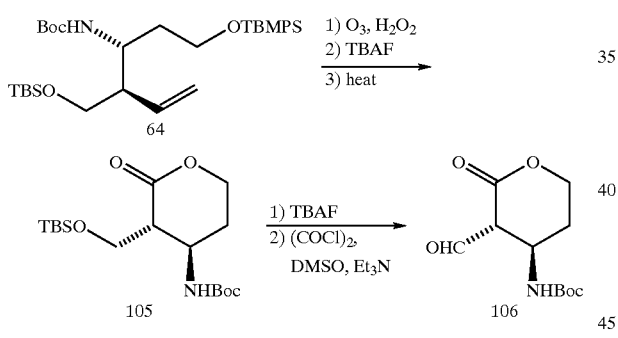

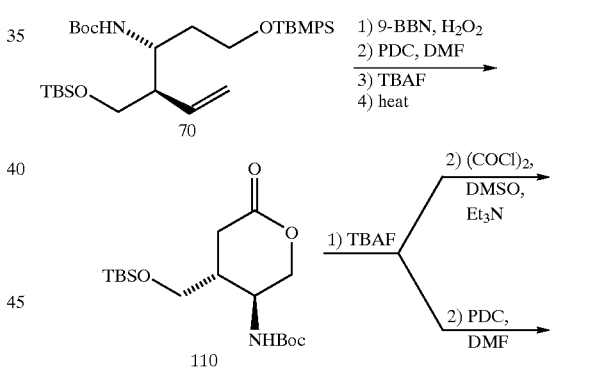

Scheme 23 describes the synthesis of 3,4-disubstituted lactones. The TBMP silyl group of ether 64 can be selectively removed with fluoride, the alcohol can be oxidized with PDC to a carboxylic acid, and the olefin can be ozonolyzed with an reductive workup to facilitate closure to the lactone 107. Fluoride deprotection and Swern oxidation completes the synthesis of aldehyde 108. Alternately, the alcohol can be oxidized with PDC to the carboxylic acid 109.

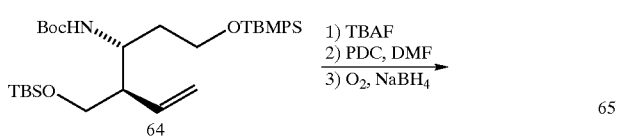

Scheme 25 describes the synthesis of regioisomeric 3,4-disubstituted lactones. The TBMP silyl group of ether 70 can be selectively removed with fluoride, the alcohol can be oxidized with PDC to a carboxylic acid, and the olefin can be hydroborated and heated to facilitate closure to the lactone 113. Fluoride deprotection and Swern oxidation completes the synthesis of aldehyde 114. Alternately, the alcohol can be oxidized with PDC to the carboxylic acid 115.

Scheme 25

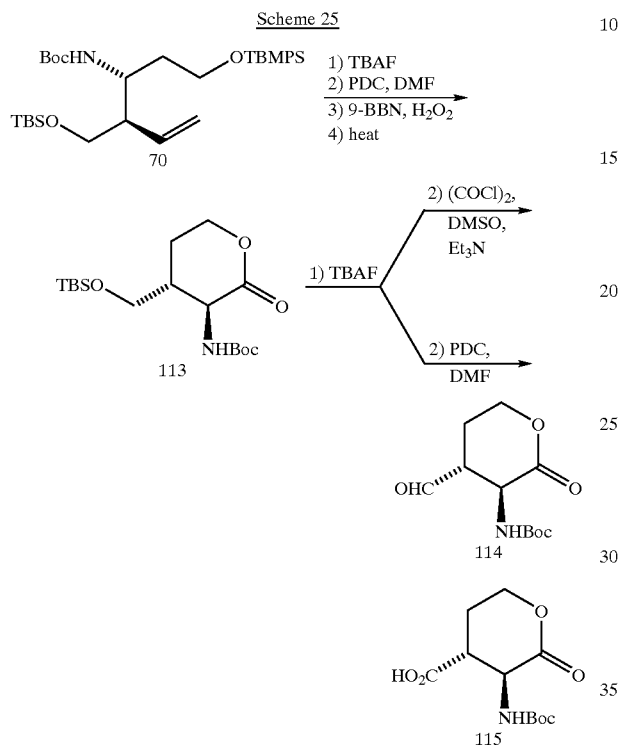

Scheme 26 shows the synthesis of the 5,6-disubstituted sulfonamides. Alcohol 36 can be converted to the thiol with Lawesson's reagent (Nishio, T.; J. Org. Chem. 1997, 62(4), 1106), the thiol can be oxidized with performic acid (Roberts, d. V.; J. biol. Chem. 1953, 204, 871), the benzyl groups were hydrogenolyzed and the mixture heated to facilitate cyclization to sulfonamide 116 (Selve, C.; Neiedercorn, F.; Nacro, M.; Castro, B.; Gabriel, M.; Tetrahedron 1981, 37, 1903). The carboxylic acid can be converted to the acid chloride with oxalyl chloride, reduced with sodium borohyride, and protected as a TBDP silyl ether 117. Acidic ester hydrolysis, Curtius rearrangement with dppa, fluoride deprotection, followed by Swern oxidation can provide aldehyde 118. Alternately, the alcohol can be oxidized with PDC to the carboxylic acid 119.

Scheme 26

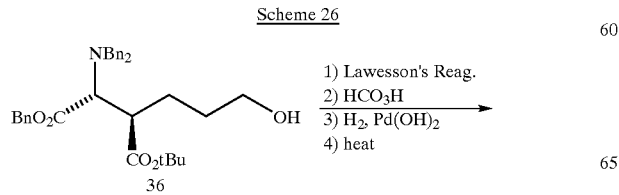

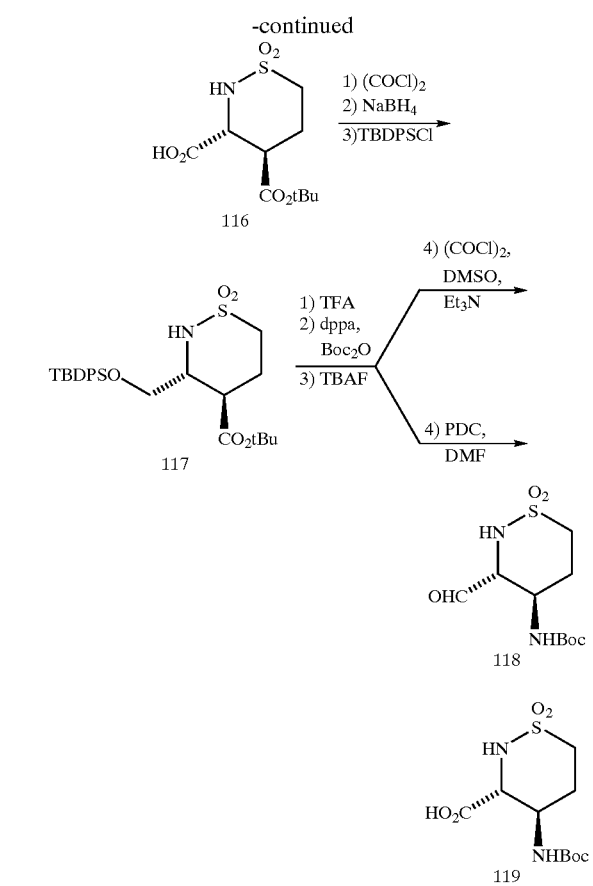

Scheme 27 describes the synthesis of 3,4-disubstituted sulfonamides. The olefin 64 can be ozonolyzed with reductive workup, the resulting alcohol can be converted to a thiol, and then oxidized to the sulfonic acid 120. Selective fluoride deprotection, mesylate formation, azide displacement and hydrogenation followed by cyclization can provide sulfonamide 121. Fluoride deprotection and Swern oxidation can give aldehyde 122.

Scheme 27

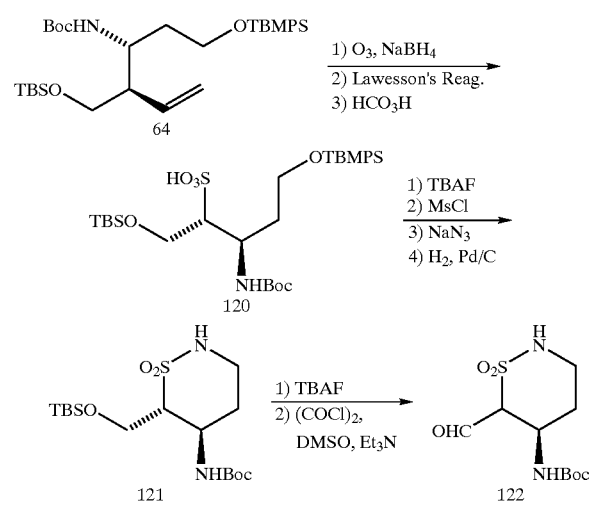

Scheme 28 describes the synthesis of 4,5-disubstituted sulfonamides. The ether 64 can be selectively fluoride deprotected, the resulting alcohol can be converted to a thiol, and then oxidized to the sulfonic acid 123. Ozonolysis with reductive workup, mesylate formation, azide displacement and hydrogenation followed by cyclization can provide sulfonamide 124. Fluoride deprotection and Swern oxidation can give aldehyde 125. Alternately, the alcohol can be oxidized with PDC to the carboxylic acid 126.

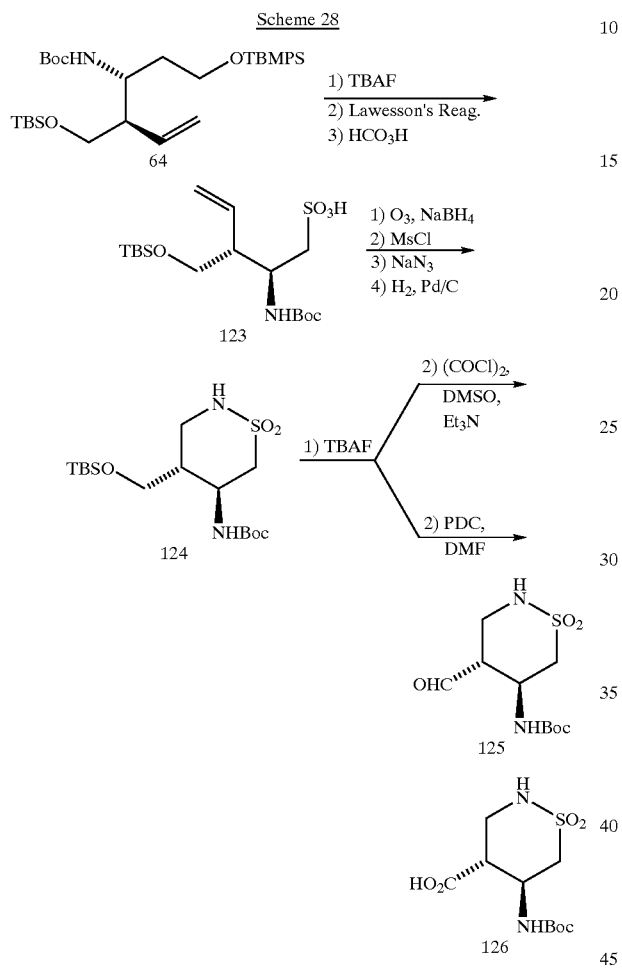

Scheme 29 describes the synthesis of 4,5-disubstituted sulfonamides. The olefin 64 can be hydroborated, the resulting alcohol can be converted to a thiol, and then oxidized to the sulfonic acid 127. Selective fluoride deprotection, mesylate formation, azide displacement and hydrogenation followed by cyclization can provide sulfonamide 128. Fluoride deprotection and Swern oxidation can give aldehyde 129. Alternately, the alcohol can be oxidized with PDC to the carboxylic acid 130.

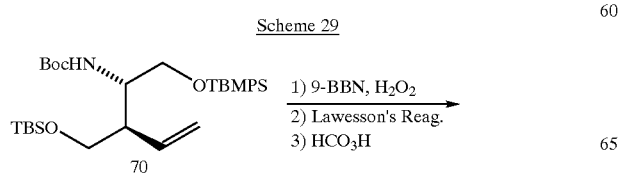

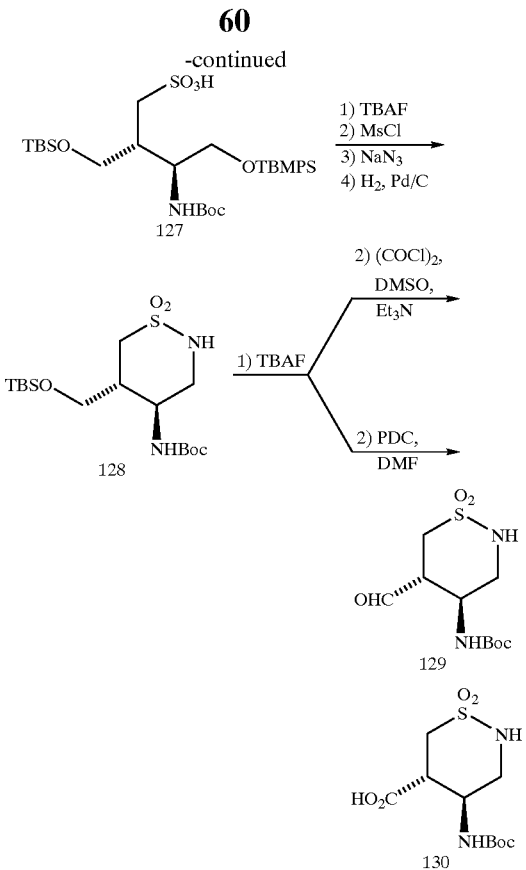

Scheme 30 describes the synthesis of 4,5-disubstituted sulfonamides. The ether 70 can be selectively fluoride deprotected, the resulting alcohol can be converted to a thiol, and then oxidized to the sulfonic acid 131. Hydroboration of the olefin, mesylate formation, azide displacement and hydrogenation followed by cyclization can provide sulfonamide 132. Fluoride deprotection and Swern oxidation can give aldehyde 133. Alternately, the alcohol can be oxidized with PDC to the carboxylic acid 134.

Scheme 30

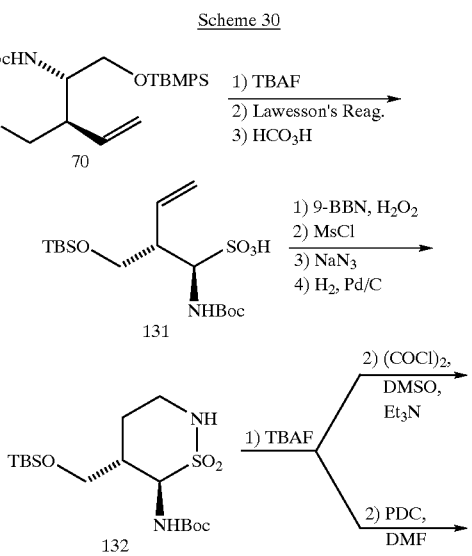

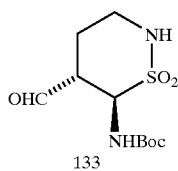

133

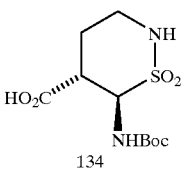

134

Multisubstituted pyrrolidines and piperidines may be synthesized by the methods outlined in Scheme 31. Monoalkylation of 135 via an enolate using LDA or potassium hexamethyldisilazane, or converting 135 first to an enamine, or by using other bases, all of which can be done in THF, ether, dioxane, benzene, or an appropriate non-hydroxylic solvent at −78° C. to room temperature with an alkylating agent such as methyl iodide, benzyl bromide, etc. where X can be as defined in Scheme 1, yields product 136. This product can subsequently undergo alkylation again under thermodynamic or kinetic conditions and afterwards, if need be, can undergo two more alkylations to produce tri- and tetrasubstituted analogs of 136. The thermodynamic or kinetic conditions yield regioselectively alkylated products (for a discussion on thermodynamic vs. kinetic alkylations see H. House Modern Synthetic Reactions, W. A. Benjamin, Inc. (Menlo Park, Calif.: 1972) chapter 9).

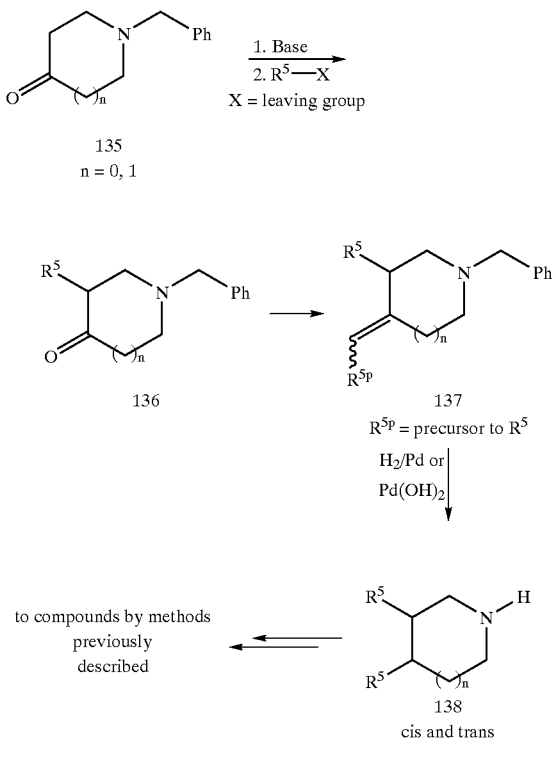

Subsequent Wittig olefination yields compound 137. Hydrogenation (asymmetric hydrogenation can be an option here: Parshall, G. W. Homogeneous Catalysis, John Wiley and Sons, New York: 1980, pp. 43–45; Collman, J. P., Hegedus, L. S. Principles and Applications of Organotransition Metal Chemistry, University Science Books, Mill Valley, Calif., 1980, pp. 341–348) yields pyrrolidine or piperidine 138 which can be resolved into its relative and/or absolute isomers at this stage or later on in the synthesis either by crystallization, chromatographic techniques, or other methods familiar to one skilled in the art. The amine 138 an then be elaborated into the compounds of this invention by methods discussed previously (Scheme 1). The carbonyl-containing intermediate 136 in Scheme 31 can also be reduced to the methylene analog via a Wolff-Kishner reduction and modifications thereof, or by other methods familiar to one skilled in the art. This piperidine or pyrrolidine can be deprotected and elaborated to the compounds of this invention by methods discussed earlier. Thus, mono-, di-, tri-, or tetraalkylated carbonyl-containing pyrrolidines or piperidines can be synthesized, which in turn can be reduced to the corresponding —CH2-analogs employing the Wolff-Kishner reduction or other methods.

Another method for synthesizing gem-substituted pyrrolidines and piperidines can be shown in Scheme 32. It can be understood by one skilled in the art that some of the steps in this scheme can be rearranged. It can be also understood that gem-disubstitution can be only shown at only one position on the piperidine ring and that similar transformations may be performed on other carbon atoms as well, both for piperidine and pyrrolidine. Thus, 3-carboethoxypiperidine 139 may be BOC-protected and alkylated employing a base such as LDA, KHMDS, LHDMS, etc., in THF, ether, dioxane, etc. at −78° C. to room temperature, and an alkylating agent $R^6X$ where X can be a halide (halide=Cl, Br, I), mesylate, tosylate or triflate, to yield 141. Reduction using DIBAL, for example, and if necessary followed by oxidation such as a Swern oxidation (S. L. Huang, K. Omura, D. Swern J. Org. Chem. 1976, 41, 3329–32) yields aldehyde 142. Wittig olefination (143) followed by deprotection yields 144 which may be elaborated as described previously into the compounds of this invention. Reduction of the Wittig adduct 143 yields 145 which may be deprotected to yield 146 which may be in turn elaborated as described previously into the compounds of this invention. Reaction of aldehyde 142 with an alkyllithium or Grignard reagent yields alcohol 147 which may be reduced catalytically or with $Et_3SiH$/TFA (J. Org. Chem. 1969, 34, 4; J. Org. Chem. 1987, 52, 2226) if $R^{5*}$ ($R^{5*}=R^5$ or a precursor thereof) can be aromatic to yield 148. If $R^{5*}$ can be not aromatic, then the OH may be reduced by the method of Barton (Barton, D. H. R.; Jaszberenyi, J. C. Tet. Lett. 1989, 30, 2619 and other references therein). Once tosylated, the alcohol can also be displaced with dialkyllithium cuprates (not shown) (Hanessian, S.; Thavonekham, B.; DeHoff, B.; J Org. Chem. 1989, 54, 5831). Deprotection if necessary yields 149 which may be elaborated as described previously into the compounds of this invention.

Scheme 32
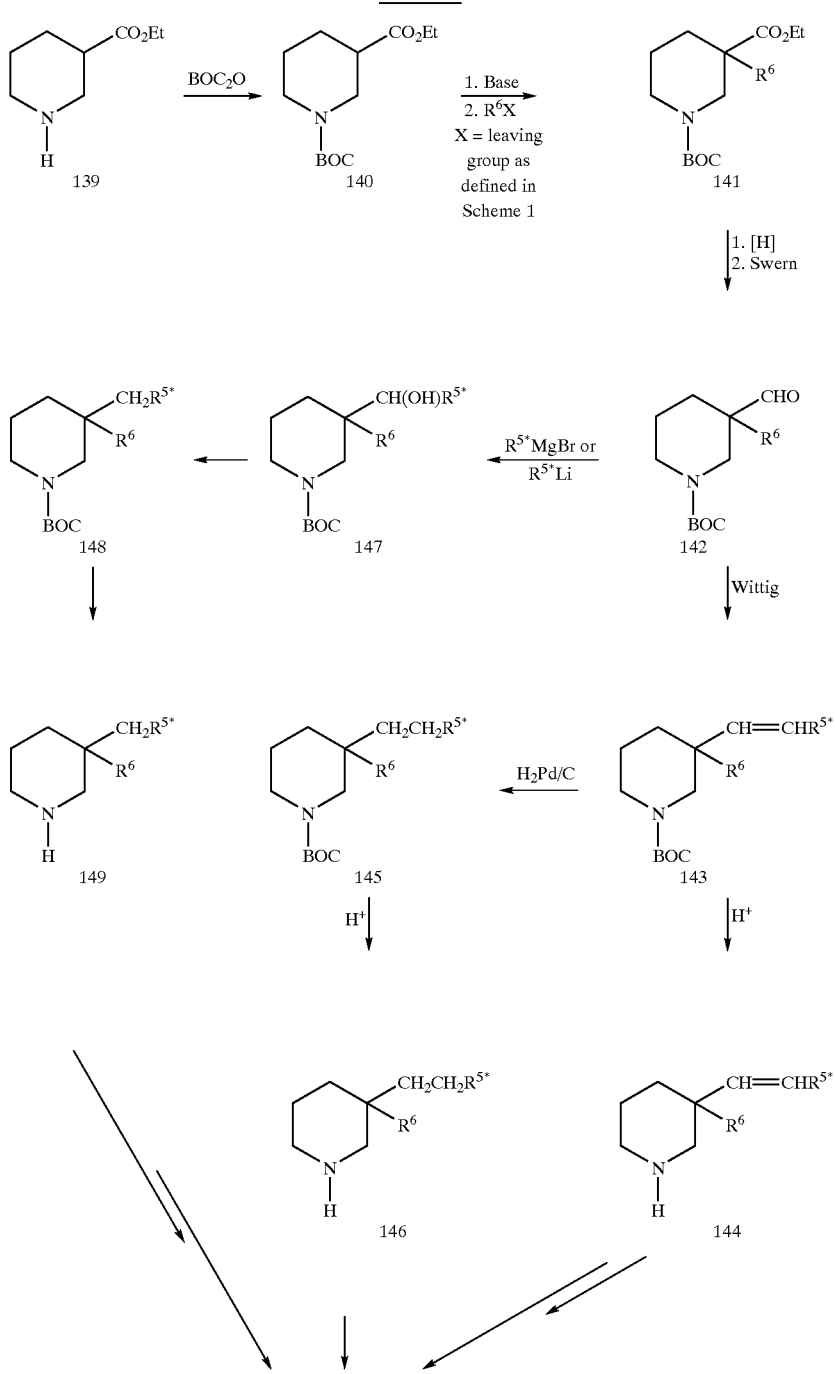
A method for the alkylation of alkyl groups, arylalkyl groups, allylic groups, propargylic groups, etc., and a variety of other electrophiles onto the pyrrolidinyl and/or piperidinyl alpha-carbons (alpha to the ring nitrogen atom) can be represented by the work of Peter Beak, et al. as shown in Scheme 33. It can be understood by one skilled in the art that the $R^5$ and $R^{13}$ groups are either in their precursor, protected, or final form. Only one $R^5$ group can be shown to be substituted on piperidine/pyrrolidine 150. However it can be understood by one skilled in the art that additional functionality may be present on the ring in either precursor, protected, or final form. Thus lithiation with an alkyllithium reagent such as n-BuLi or s-BuLi as shown, followed by quenching with an electrophilic species such as $R^5X$ or $R^{13}X$ where X can be as defined in Scheme 1 and $R^5$ and $R^{13}$ are in their precursor, protected, or final form, yields monoalkylated piperidine/pyrrolidine 151. This alkylation may occur either stereoselectively (P. Beak and W. K. Lee J. Org. Chem. 1990, 55, 2578–2580) or enantioselectively if sparteine can be included as a source of chirality (P. Beak, et al., J. Am. Chem. Soc. 1994, 116, 3231–3239). The alkylation process may be repeated up to three more times as shown in Scheme 33 to result in di-, tri-, and tetrasubstitution at the alpha-positions.

deprotonated with NaH or by other bases familiar to one skilled in the art, in a solvent such as DMF, THF, or another appropriate non-hydroxylic solvent and reacted with piperidine or pyrrolidine 155 at room temperature to the reflux temperature of the solvent. Deprotection and elaboration as described before yields compounds where $R^5$ contains an N-substituted heterocycle. If the nitrogen atom of the heterocycle can be sufficiently nucleophilic, then an acid scavenger, such as $K_2CO_3$, $KHCO_3$, $Na_2CO_3$, $NaHCO_3$, amongst others, can be used in place of NaH, employing THF, DMF, or methyl ethyl ketone as solvents. In this case hydroxylic solvents may be used as well, such as methanol, ethanol, etc. from room temperature to the reflux temperature of the solvent. Compound 155 as well as its other positional isomers are available, for example, from commercially available 4-hydroxymethylpiperidine, 2-, 3-, and 4-carboethoxypiperidine, L- or D-proline ethyl ester, or from methyl 1-benzyl-5-oxo-3-pyrrolidinecarboxylate by methods familiar to one skilled in the art and as discussed previously in this application.

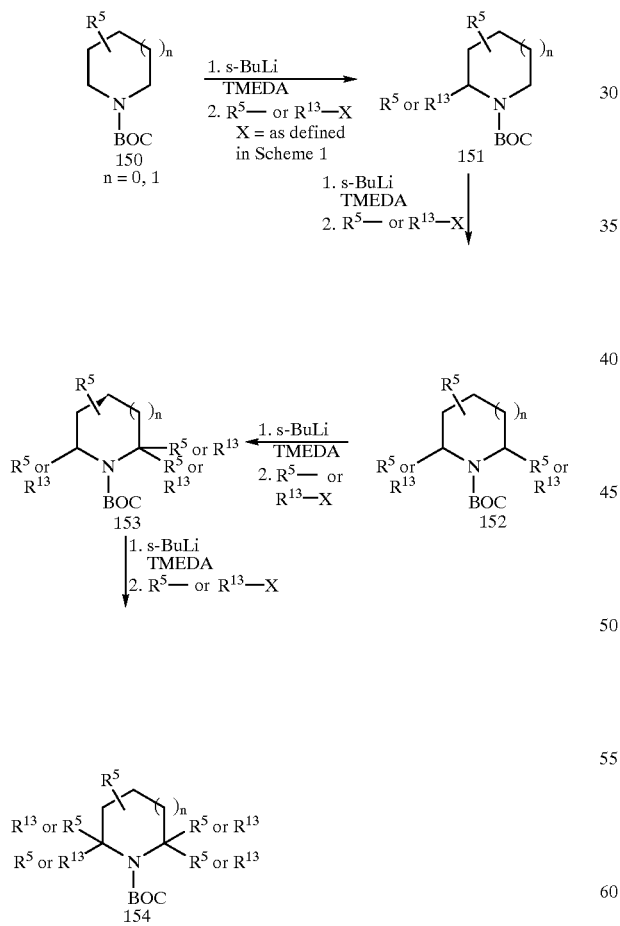

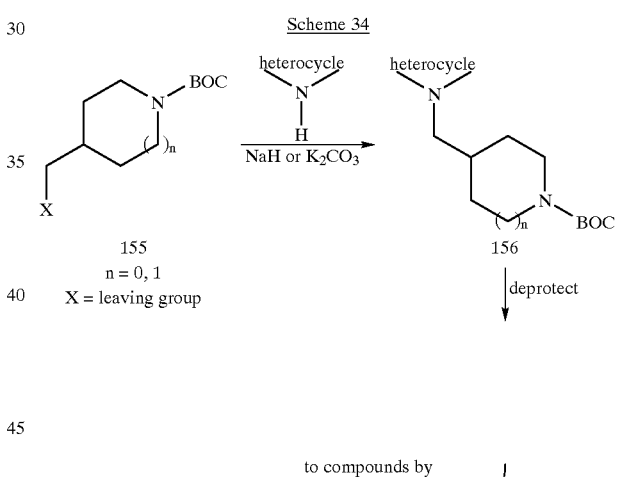

A method for the synthesis of N-substituted heterocycles at $R^5$ can be shown in Scheme 34. The heterocycle can be A method for the synthesis of C-substituted heterocycles at $R^5$ can be shown in Scheme 35. Many heterocycles such as the ones shown in Scheme 35, but not limited thereto, can be metallated with strong bases such as LDA, n-BuLi, sec-BuLi, t-BuLi, etc. to yield the corresponding anionic species. These anions may also be generated via halogen-metal exchange employing n-BuLi, or other alkyllithium reagents. These reactions may be performed in THF, ether, dioxane, DME, benzene, etc. at −78° C. to room temperature.

Scheme 35

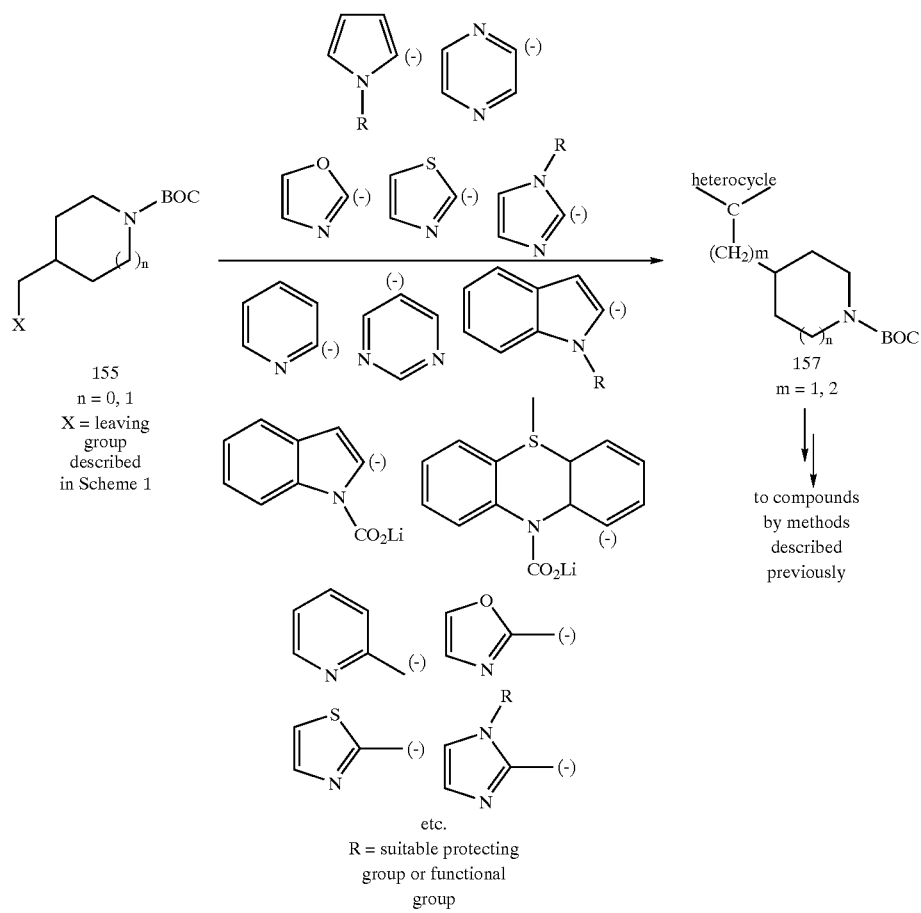

For reviews of these metallations and halogen-metal exchange reactions see Organometallics in Organic Synthesis, FMC Corp., Lithium Division, 1993, pp. 17–39; Lithium Link, FMC Corp., Spring 1993, pp. 2–17; n-Butyllithium in Organic Synthesis, Lithium Corp. of America, 1982, pp. 8–16; G. Heinisch, T. Langer, P. Lukavsky, J. Het. Chem. 1997, 34, 17–19. The anions can then be quenched with electrophile 155 or its positional isomers to yield the corresponding C-alkylated heterocyclic pyrrolidine or piperidine 157.

Another method for the synthesis of C-substituted heterocyclic-methylpyrrolidines or piperidines can be shown in Scheme 36. The protected aldehyde 158 can be reacted with the anion of the heterocycle (its generation as described previously) at −78° C. to room temperature with or without $CeCl_3$ in an inert solvent such as THF, ether, dioxane, DME, benzene, etc. to yield carbinol 159. Catalytic hydrogenation of the alcohol yields the corresponding methylene compound 157. Other reduction methods include $Et_3SiH/TFA$ (J. Org. Chem. 1969, 34, 4; J. Org. Chem. 1987, 52, 2226) amongst others familiar to one skilled in the art. It can be understood by one skilled in the art that the aldehyde group can be located in other positions instead of, for example, the 4-position of piperidine in compound 158 as depicted in Scheme 36. It can be to be understood that other heterocycles may also be used besides the ones shown in Scheme 35 and 36.

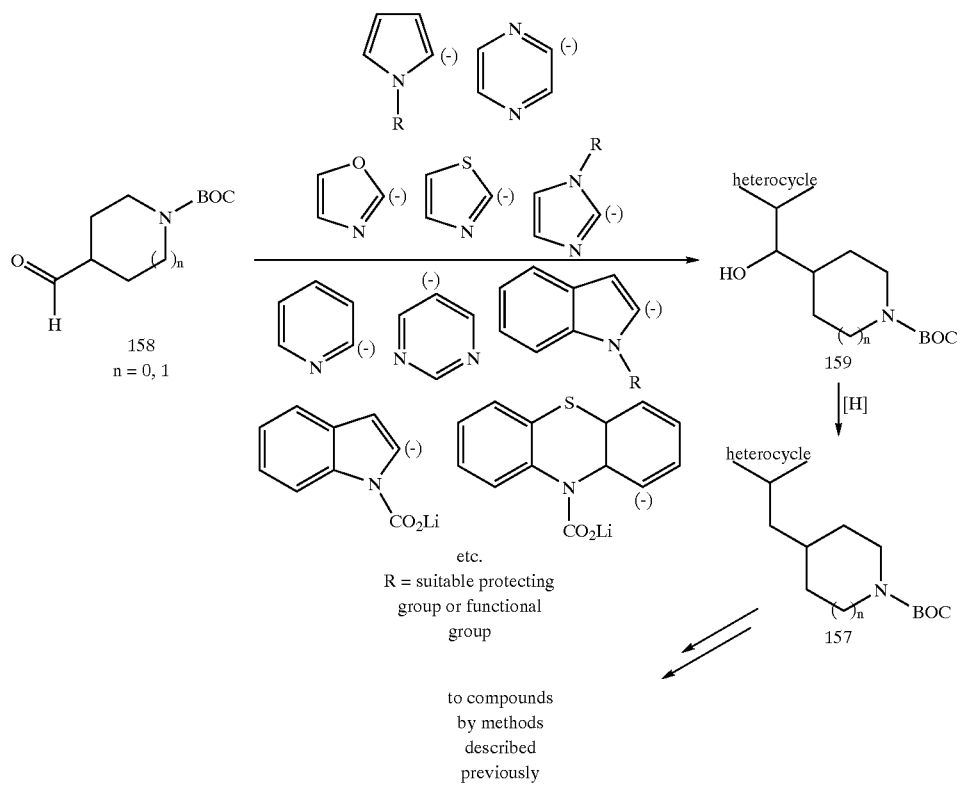

The anions of the methyl-substituted heterocycles may also be reacted with a BOC-protected piperidone or pyrrolidone (160) to yield alcohols 161 as shown in Scheme 22 (see above reviews on metallations for references). These alcohols may be reduced using $PtO_2$ and TFA (P. E. Peterson and C. Casey, J. Org. Chem. 1964, 29, 2325–9) to yield piperidines and pyrrolidines 162. These can subsequently be taken on to the compounds of this invention as described previously. It can be understood by one skilled in the art that the carbonyl group can be located in other positions instead of, for example, the 4-position of piperidine in compound 160 as depicted in Scheme 37. It can be to be understood that other heterocycles may also be used besides the ones shown in Scheme 37.

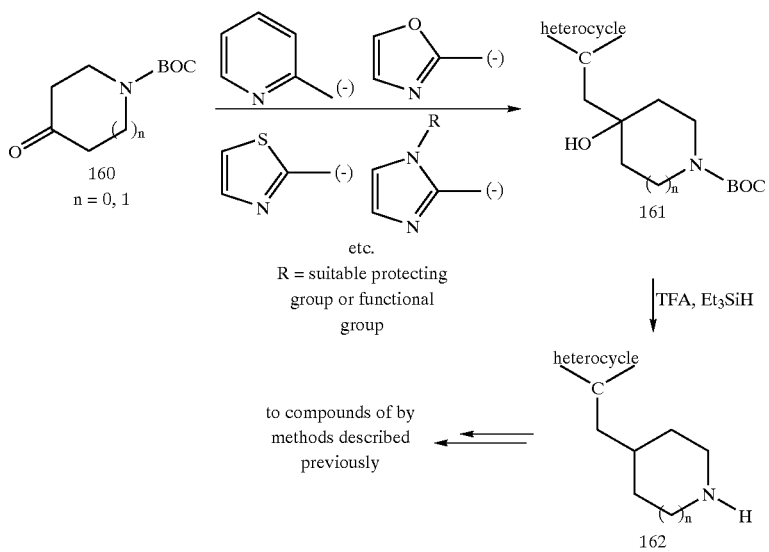

One may also react aryl (phenyl, naphthyl, etc.) anions, generated either by halogen-metal exchange or by ortho-directed metallation (Snieckus, V. Chem. Rev. 1990, 90, 879–933) using n- or s- or t-BuLi in a non-hydroxylic solvent such as THF, ether, etc., with or without TMEDA and allow them to react with compounds 155, 158, and 160 with subsequent elaboration to yield the compounds of this invention by the methods depicted in Schemes 34–37.

Another method for the preparation of C-substituted heterocycles can be shown in Scheme 38. Protected piperidone 160 undergoes a Wittig reaction with heterocyclic phosphorous ylides to yield 163. Hydrogenation over a noble metal catalyst such as Pd in an alcoholic solvent or with an optically active transition metal catalyst (see asymmetric hydrogenation references of Parshall and Coleman, op. cit.) yields 164 which can be further elaborated into the compounds of this invention by the procedures described previously. It will be appreciated by one skilled in the art that the carbonyl group can be located in other positions instead of, for example, the 4-position of piperidine in compound 160 as depicted in Scheme 38. It can be to be understood that other heterocycles may also be used besides the ones shown in Scheme 38.

catalytic hydrogenation, or via a number of chemical methods such as Zn/CaCl$_2$ (Sawicki, E. J Org Chem 1956, 21). The carbonyl insertion compounds (158) can also undergo reduction of the carbonyl group to either the CHOH or CH$_2$ linkages by methods already discussed (NaBH$_4$ or Et$_3$SiH, TFA, etc.). These amines can then be converted to isocyanate 5 via the following methods (Nowakowski, J. J Prakt Chem/Chem-Ztg 1996, 338 (7), 667–671; Knoelker, H.-J.et al., Angew Chem 1995, 107 (22), 2746–2749; Nowick, J. S.et al., J Org Chem 1996, 61 (11), 3929–3934; Staab, H. A.; Benz, W.; Angew Chem 1961, 73); to isothiocyanate 5 via the following methods (Strekowski L. et al., J Heterocycl Chem 1996, 33 (6), 1685–1688; Kutschy, Pet al., Synlett 1997, (3), 289–290); to carbamoyl chloride 11 (after 1168 or 170 can be reductively aminated with an R$^2$ group) (Hintze, F.; Hoppe, D.; Synthesis (1992) 12, 1216–1218); to thiocarbamoyl chloride 11 (after 168 or 170 can be reductively aminated with an R$^2$ group) (Ried, W.; Hillenbrand, H.; Oertel, G.; Justus Liebigs Ann Chem 1954, 590); or just used as 9, or 10 (after 168 or 170 can be reductively aminated with an R$^2$ group), in synthesizing the compounds of this invention by the methods depicted in Scheme 1.

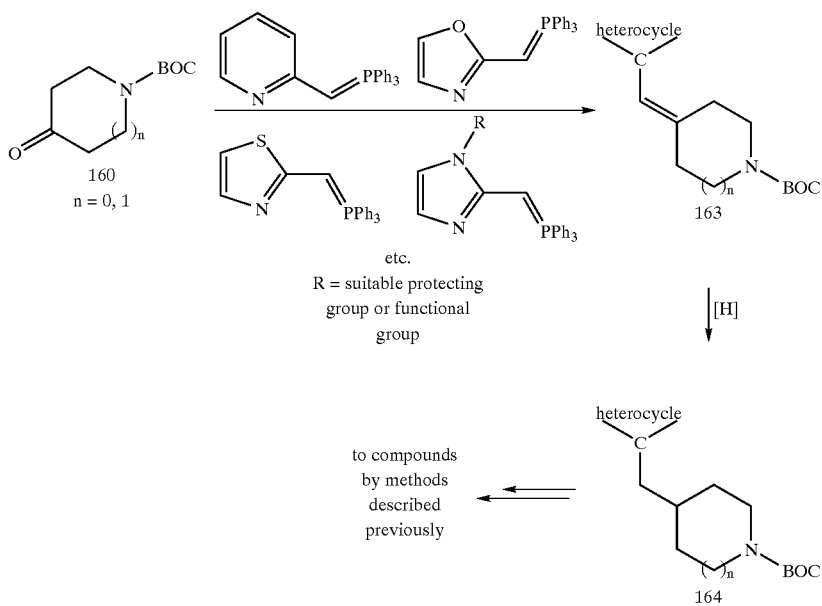

Syntheses of amines 9, 10, and the amines which are precursors to isocyanates or isothiocyanates 5 will now be discussed. For example, nitrobenzeneboronic acid (165: Scheme 39) can undergo Suzuki couplings (Suzuki, A. Pure Appl. Chem. 1991, 63, 419) with a wide variety of substituted iodo- or bromo aryls (aryls such as phenyl, naphthalene, etc.), heterocycles, alkyls, akenyls (Moreno-manas, M., et al., J. Org. Chem., 1995, 60, 2396), or alkynes. It can also undergo coupling with triflates of aryls, heterocycles, etc. (Fu, J.-m, Snieckus, V. Tet. Lett. 1990, 31, 1665–1668). Both of the above reactions can also undergo carbonyl insertion in the presence of an atmosphere of carbon monoxide (Ishiyama, et al., Tet. Lett. 1993, 34, 7595). These nitro-containing compounds (167 and 169) can then be reduced to the corresponding amines either via

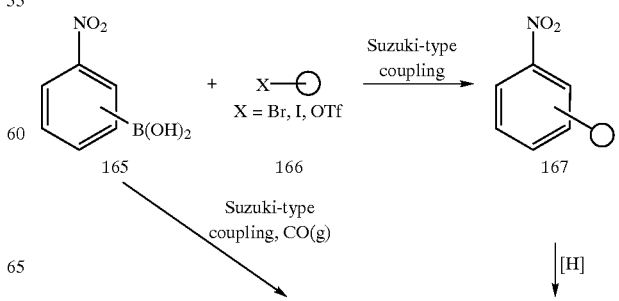

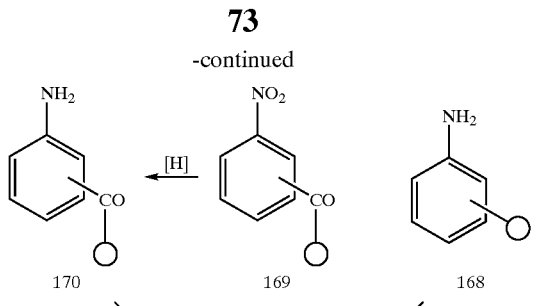

make isocyanate or
isothiocyanate 5,
or carbamoyl chlorides 11,
or used as 9 or 10 to make
the compounds of this
invention as described for
the compounds of Scheme 1

Likewise, protected aminobromobenzenes or triflates or protected aminobromoheterocycles or triflates 171 (Scheme 40) may undergo Suzuki-type couplings with arylboronic acids or heterocyclic boronic acids (172). These same bromides or triflates 171 may also undergo Stille-type coupling (Echavarren, A. M., Stille, J. K. J. Am. Chem. Soc., 1987, 109, 5478–5486) with aryl, vinyl, or heterocyclic stannanes 175. Bromides or triflates 171 may also undergo Negishi-type coupling with other aryl or heterocyclic bromides 176 (Negishi E. Accts. Chem. Res. 1982, 15, 340; M. Sletzinger, et al., Tet. Lett. 1985, 26, 2951). Deprotection of the amino group yields an amine with can be coupled to make a urea and other linkers containing Z as described above and for Scheme 1. Amino protecting groups include phthalimide, 2,4-dimethyl pyrrole (S. P. Breukelman, et al. J. Chem. Soc. Perkin Trans. I, 1984, 2801); N-1,1,4,4-Tetramethyldisilyl-azacyclopentane (STABASE) (S. Djuric, J. Venit, and P. Magnus Tet. Lett 1981, 22, 1787) and others familiar to one skilled in the art.

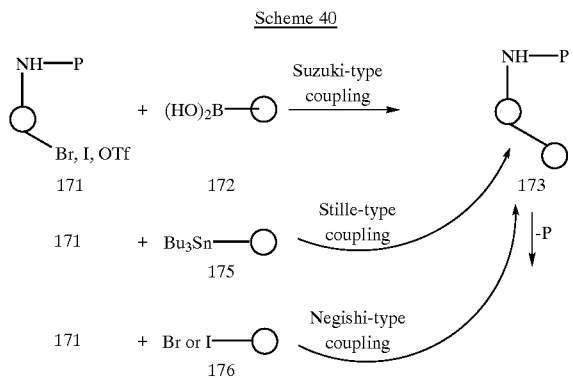

make isocyanate or
isothiocyanate 5,
or carbamoyl chlorides 11,
or used as 9 or 10 to make
the compounds of this
invention as described for
the compounds of Scheme 1

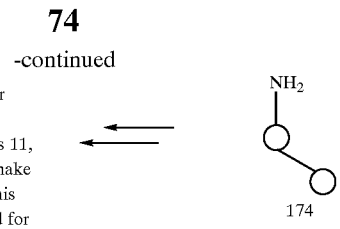

Many amines are commercially available and can be used as 9, 10, or used as precursors to isocyanates or isothiocyanates 5. There are numerous methods for the synthesis of non-commercially available amines familiar to one skilled in the art. For example, aldehydes and ketones may be converted to their O-benzyl oximes and then reduced with LAH to form an amine (Yamazaki, S.; Ukaji, Y.; Navasaka, K.; Bull Chem Soc Jpn 1986, 59, 525). Ketones and trifluoromethylketones undergo reductive amination in the presence of $TiCl_4$ followed by $NaCNBH_4$ to yield amines (Barney, C. L., Huber, E. W., McCarthy, J. R. Tet. Lett. 1990, 31, 5547–5550).

Aldehydes and ketones undergo reductive amination with $Na(AcO)_3BH$ as mentioned previously to yield amines (Abdel-Magid, A. F., et al. Tet. Lett. 1990, 31, (39) 5595–5598). Amines may also be synthesized from aromatic and heterocyclic OH groups (for example, phenols) via the Smiles rearrangement (Weidner, J. J., Peet, N. P. J. Het. Chem., 1997, 34, 1857–1860). Azide and nitrile displacements of halides, tosylates, mesylates, triflates, etc. followed by LAH or other types or reduction methods yield amines. Sodium diformyl amide (Yinglin, H., Hongwen, H. Synthesis 1989 122), potassium phthalimide, and bis-BOC-amine anion can all displace halides, tosylates, mesylates, etc., followed by standard deprotection methods to yield amines, procedures which are familiar to one skilled in the art. Other methods to synthesize more elaborate amines involve the Pictet-Spengler reaction, imine/immonium ion Diels-Alder reaction (Larsen, S. D.; Grieco, P. A. J. Am. Chem. Soc. 1985, 107, 1768–69; Grieco, P. A., et al., J. Org. Chem. 1988, 53, 3658–3662; Cabral, J. Laszlo, P. Tet. Lett. 1989, 30, 7237–7238; amide reduction (with LAH or diborane, for example), organometallic addition to imines (Bocoum, A. et al., J. Chem. Soc. Chem. Comm. 1993, 1542–4) and others all of which are familiar to one skilled in the art.

Compounds where Z=N—CN, $CHNO_2$, and $C(CN)_2$ can be synthesized by the methods shown in Scheme 41. Thus amine 108 reacts with malononitrile 179 neat or in an inert solvent at room temperature to the reflux temperature of the solvent, or at the melting point of the solid/solid mixture, to yield malononitrile 178. This in turn can undergo reaction with amine 177 under similar conditions stated just above to yield molononitrile 181. Likewise, a similar reaction sequence may be used to make 184 and 187 [for Z=$C(CN)_2$], see for example P. Traxler, et al., J. Med. Chem. (1997), 40, 3601–3616; for Z=N—CN, see K. S. Atwal, J. Med. Chem. (1998) 41, 271; for Z=$CHNO_2$, see J. M. Hoffman, et al., J. Med. Chem. (1983) 26, 140–144).

Scheme 41

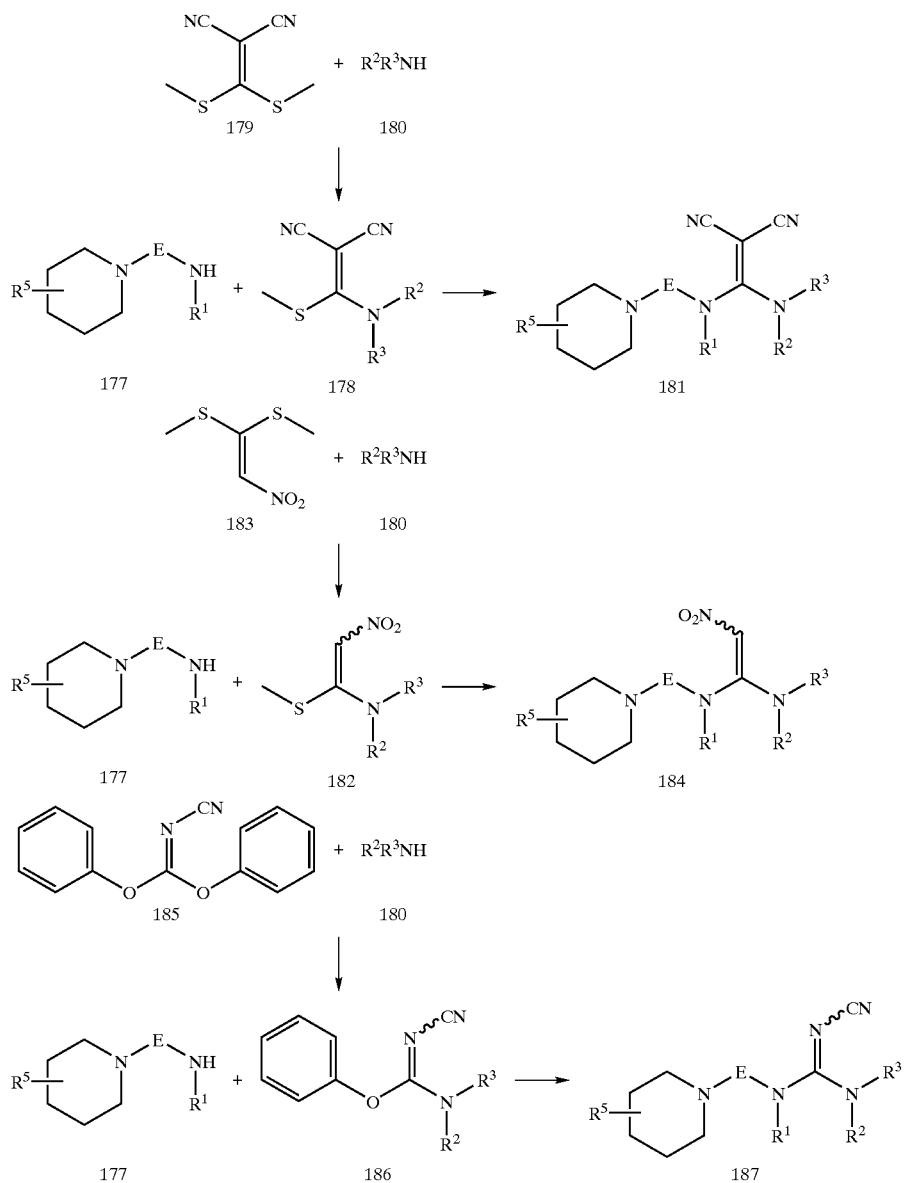

Additionally, the starting materials in the Schemes 6 through 29 can be modified with an a one-carbon longer or shorter length chain or ring size starting material and be applicable to the synthesis of five and seven-membered ring analogs. In some of the synthetic schemes, an intermediate may be easily modified to lengthen or shorten the chain length as shown in Scheme 42. To homologate alcohol 188, the mesylate can be displaced with cyanide. Lithium aluminum hydride reduction of the nitrile can give the amine 189. Alternatively, basic hydrolysis of the nitrile and lithium aluminum hydride reduction of the resulting acid can give the alcohol 190. To decrease the chain by one carbon, the mesylate of alcohol 188 can be eliminated to the olefin which upon treatment with ozone and reductive workup can give alcohol 191. In those schemes where an olefin can be hydroborated, to reduce the chain size by one carbon, the hydroboration step may be replaced with ozonolysis with an reductive workup (not shown in Scheme 42).

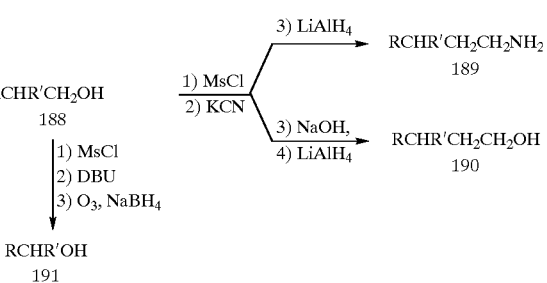

Scheme 43 describes the synthesis of carbamate- and urea-containing heterocycles. Olefin 70 can undergo ozonolysis with reductive workup, mesylate formation, azide displacement and catalytic reduction to give amine 192. Selective fluoride deprotection followed by ring closure with carbonyl diimidazole (Kaiser, A.; Balbi, M.; Tetrahedron: Asymmetry 1999, 10(5), 1001) can give carbamate 193. Fluoride deprotection and Swern oxidation completes the synthesis of aldehyde 194. Alternatively, oxidation with PDC can give acid 195. While only one regioisomer and ring size is shown, other regioisomers and ring sizes can be prepared by varying the chain lengths relative to the chiral centers as shown in the preceding schemes and then performing the ring closure.

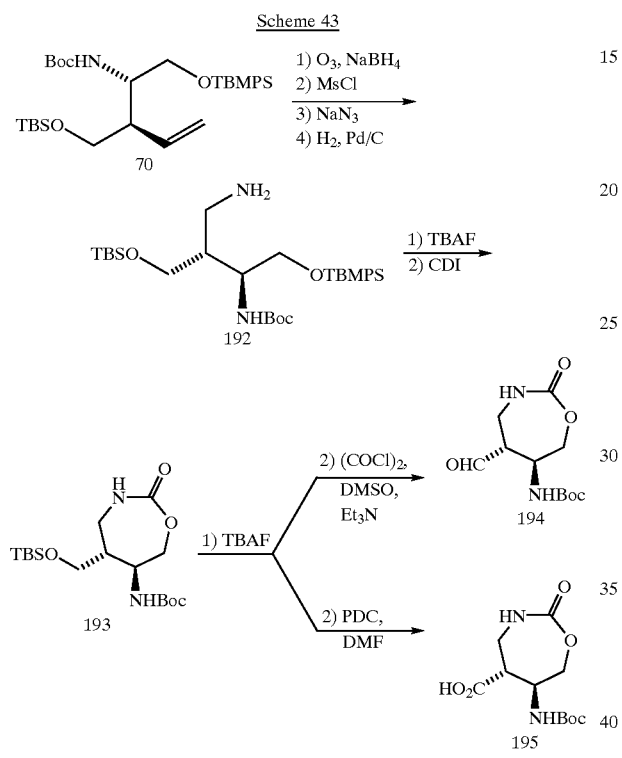

Scheme 44 describes the preparation of cyclic ureas, olefin 70 can undergo ozonolysis with reductive workup, mesylate formation, azide displacement and selective fluoride deprotection to give azide 196. Mesylate formation, azide displacement, catalytic hydrogenation followed by ring closure with carbonyl diimidazole can give urea 197. Fluoride deprotection and Swern oxidation completes the synthesis of aldehyde 198. Alternatively, oxidation with PDC can give acid 199.

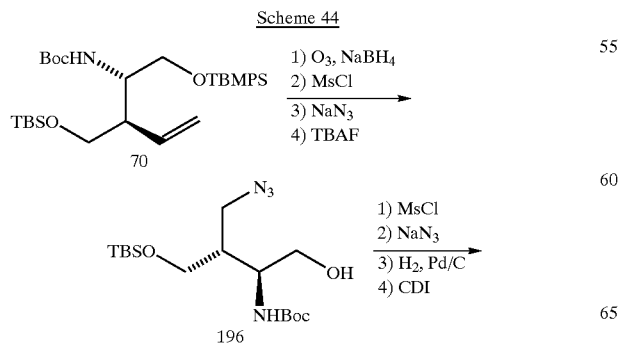

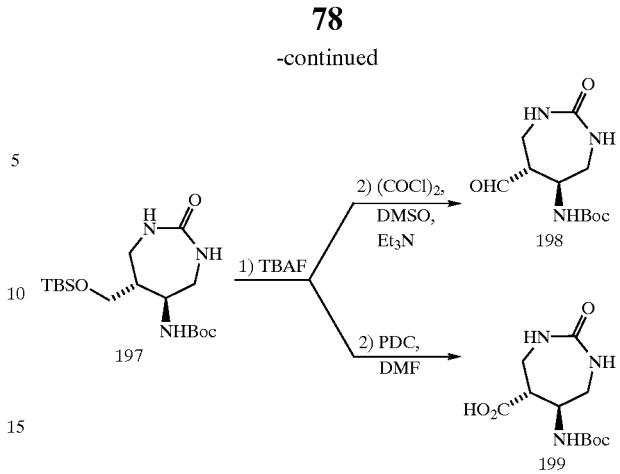

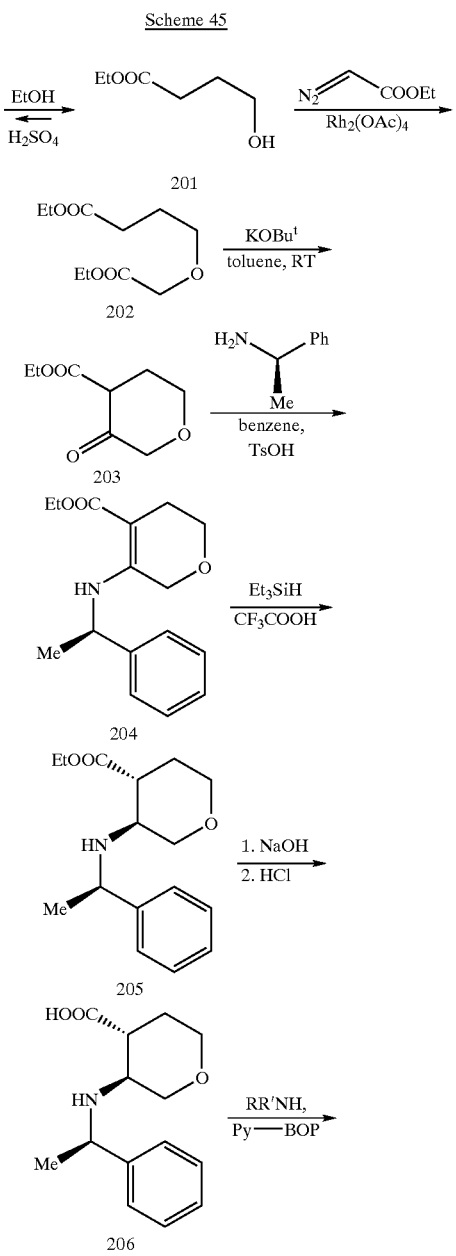

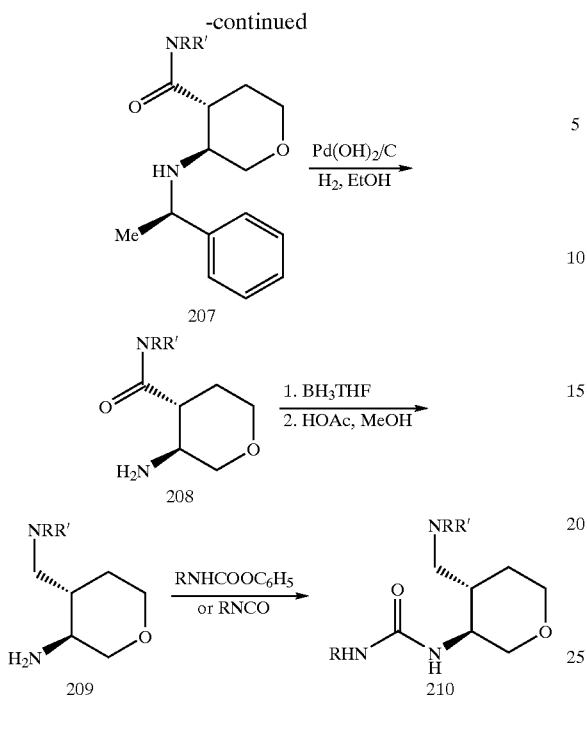

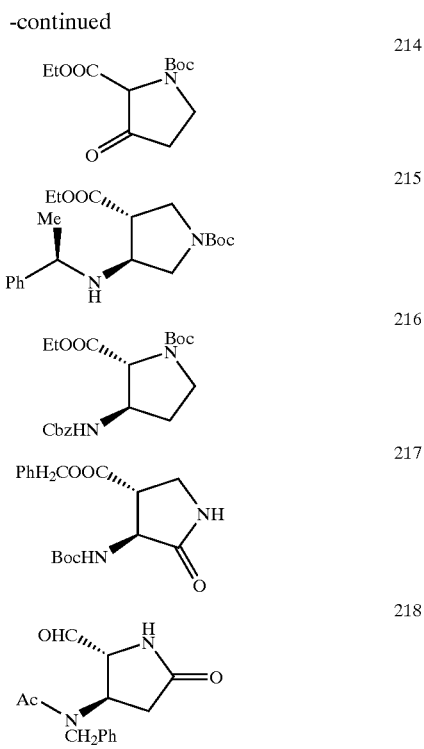

The regioisomeric 3,4-disubstituted dihydropyrans prepared in Scheme 11 can also be prepared using the route shown in Scheme 45. Acid-catalyzed trans-esterification of γ-butyrolactone 200 can provide the hydroxyester 201, which can undergo rhodium-catalyzed carbene insertion to provide the diester 202. Dieckmann cyclization can provide the ketoester 203, which can be converted to the β-aminoester 205 as already described for the preparation of other β-aminoesters. The trans isomer can be obtained either by reduction of the intermediate enamine 204 with sodium triacetoxyborohydride followed by base-catalyzed epimerization as already described, or by reduction of 204 with triethylsilane in trifluoroacetic acid. The ester can then be hydrolyzed to the acid 206, followed by coupling to give the amide 207. The benzyl group can be removed by hydrogenolysis to the amine 208, followed by reduction of the amide to 209 and reaction with an isocyanate or carbamate to provide the products 210.

Scheme 46

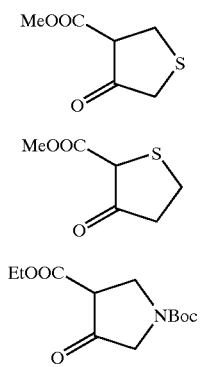

A number of 5-membered heterocyclic β-ketoesters can be prepared using methods demonstrated in the literature, and converted to the analogous products using reaction sequences similar to those already described. For example as in Scheme 46, methyl 4-keto-tetrahydrothiophene-3-carboxylate 211 and methyl 3-keto-tetrahydrothiophene-2-carboxylate 212 can be prepared as described by O. Hromatka, D. Binder and K. Eichinger, Monatsheft. Chem. 1973, 104, 1520. Ethyl 4-ketopyrrolidine-3-carboxylate 213 and ethyl 3-ketopyrrolidine-2-carboxylate 214, bearing a carbamate protecting group on the ring nitrogen atom, may be prepared as described by J. Blake, C. D. Willson and H. Rapoport, J. Am. Chem. Soc. 1964, 86, 5293, and converted to various products using chemistry analogous to that already described.

A synthetic route to (3R, 4S)-4-[(R)-1-phenylethylamino]-pyrrolidine-1,3-dicarboxylic acid 1-tert-butyl ester 3-ethyl ester 215 has been described by X. Wang, J. F. Espinosa and S. H. Gellman, J. Am. Chem. Soc. 2000, 122, 4821. A synthetic route to (2R, 3R)-3-benzyloxycarbonylamino-pyrrolidine-1,2-dicarboxylic acid 1-tert-butyl ester 2-ethyl ester 216 has been described by S. H. Gellman, D. H. Appella, L. A. Christianson, D. A. Klein, S. Krauthauser, Y. J. Chung, and X. Wang, U.S. Pat. No. 6,060,585. The preparation of 1-substituted analogs of (3R, 4S)-4-tert-butoxycarbonylamino-5-oxo-pyrrolidine-3-carboxylic acid benzyl ester 217 has been described by D. S. Garvey, P. D. May and A. M. Nadzan, J. Org. Chem. 1990, 55, 936. The preparation of the enantiomer of N-benzyl-N-[(2R,3R)-2-formyl-5-oxo-pyrrolidin-3-yl]-acetamide 218 has been described by N. Langlois and M. Radom, Tetrahedron Lett 1998, 39, 857. These intermediates may be converted to the corresponding final products using synthetic transformations disclosed herein.

EXAMPLES

Example 1

Part A: Preparation of 4-oxopiperidine-1,3-dicarboxylic acid 1-t-butyl ester 3-methyl ester In a dry flask 4-oxo-3-piperidinecarboxylic acid methyl ester hydrochloride (15.01 g, 77.52 mmol) was dissolved in tetrahydrofuran (100 mL) and triethylamine (22 mL, 158 mmol) was added. After stirring for 10 minutes, di-t-butyl dicarbonate (18.6 g, 85.2 mmol) was added and the reaction mixture was stirred for 6 hours. The mixture was concentrated in vacuo, dissolved in ethyl acetate (50 mL) and extracted twice with water (25 mL). The aqueous extracts were combined and extracted with ethyl acetate (50 mL). The combined organic extracts were dried with magnesium sulfate, filtered and concentrated in vacuo to give a light yellow oil (23.05 g, 100%) which was taken on without further purification. $^1$H NMR (300 MHz, CDCl$_3$), δ: 11.97 (s, 1H), 4.05 (s, 2H), 3.78 (s, 3H), 3.57 (t, 2H, J=6), 2.37 (t, 2H, J=6), 1.48 (s, 9H).

Part B: Preparation of (R)-4-(1-phenyl-ethylamino)-2,5-dihydro-2H-pyridine-1,3-dicarboxylic acid 1-tert-butyl ester 3-methyl ester In a dry flask equipped with a Dean-Stark trap and reflux condenser, 4-oxopiperidine-1,3-dicarboxylic acid 1-t-butyl ester 3-methyl ester (23.05 g, 85.2 mmol) was dissolved in toluene (300 mL). (R)-(+)-a-Methylbenzylamine (12.5 mL, 97.0 mmol) and p-toluenesulfonic acid monohydrate (0.23 g, 1.21 mmol) were added and the mixture heated to reflux for 18 hours. The crude reaction mixture was concentrated in vacuo to give the desired amine (36.92 g, quantitative) as a thick orange oil. $^1$H NMR (300 MHz, CDCl$_3$), δ: 9.25 (d, 1H, J=7), 7.26 (m, 5H), 4.61 (m, 1H), 4.06 (s, 2H), 3.72 (s, 3H), 3.41 (m, 1H), 3.30 (m, 1H), 2.39 (m, 1H), 2.04 (m, 1H), 1.50 (d, 3H, J=7), 1.43 (s, 9H).

Part C: Preparation of (3S,4R)-4-[(R)-1-phenyl-ethylamino]-piperidine-1,3-dicarboxylic acid 1-tert-butyl Ester 3-methyl Ester In a dry flask (R)-4-(1-phenyl-ethylamino)-2,5-dihydro-2H-pyridine-1,3-dicarboxylic acid 1-tert-butyl ester 3-methyl ester (26.72 g crude, 85.2 mmol) was dissolved in acetonitrile (250 mL) and glacial acetic acid (190 mL) and cooled to 0° C. Triacetoxyborohydride (82.31 g, 388 mmol) was added in two portions over a 140-minute period. The reaction mixture was allowed to stir at 0° C. for 30 minutes. The reaction mixture was concentrated in vacuo, removing 170 mL of acetonitrile. The reaction mixture was neutralized by the sequential addition of 1N sodium hydroxide (50 mL), 2N sodium hydroxide (50 mL), 5.7 M sodium hydroxide (50 mL) and concentrated aqueous sodium hydroxide (150 mL) to maintain the internal temperature of the flask below 18° C. Water was added to dissolve the solid sodium acetate. The resulting mixture was extracted with twice with dichloromethane (200 mL). The combined organic extracts were dried with magnesium sulfate, filtered, concentrated in vacuo, and then purified by flash chromatography with 20% ethyl acetate in hexanes to give a colorless oil (30.82 g, 83%). The $^1$H NMR showed a mixture of two rotation isomers. The major compound had the following $^1$H NMR (300 MHz, CDCl$_3$), δ: 7.32 (m, 4H), 7.24 (m, 1H), 4.00 (d, 1H, J=9), 3.86 (q, 1H, J=7), 3.72 (s, 3H), 3.67 (m, 1H), 3.16 (dd, 1H, J=14, J'=4), 2.98 (td, 1H, J=12, J'=4), 2.84 (m, 2H), 1.75 (m, 1H), 1.43 (s, 9H), 1.28 (d, 3H, J=7), 1.26 (m, 1H).

Part D: Preparation of (3R,4R)-4-[(R)-1-phenyl-ethylamino]-piperidine-1,3-dicarboxylic acid 1-tert-butyl ester 3-ethyl ester In a dry flask (3S,4R)-4-[(R)-1-phenyl-ethylamino]-piperidine-1,3-dicarboxylic acid 1-tert-butyl ester 3-methyl ester (13.78 g, 38.0 mmol) was dissolved in ethanol (400 mL) along with 3 Å molecular sieves (1.04 g). The mixture was heated to reflux over 2.5 hours. Potassium carbonate (26.3 g) was added and refluxing continued for 4 additional hours. The reaction mixture was cooled, filtered through a bed of celite, and concentrated in vacuo to give a crude oil (16.05 g). Purification by flash column chromatography (20–50% ethyl acetate/hexanes) provided a colorless oil (3.24 g, 23%). Unepimerized ethyl ester was also isolated (7.55 g, 53%). $^1$H NMR (300 MHz, CDCl$_3$), δ: 7.30 (m, 4H), 7.23 (m, 1H), 4.20 (m, 3H), 3.97 (bs, 1H), 3.82 (q, 1H, J=6), 2.89 (m, 2H), 2.66 (t, 1H, J=11), 2.31 (bs, 1H), 1.72 (m, 1H), 1.43 (s, 9H), 1.31 (m, 7H), 1.11 (m, 1H).

Part E: Preparation of (3R,4R)-4-aminopiperidine-1,3-dicarboxylic acid 1-tert-butyl ester 3-ethyl ester In a dry 500-mL Paar flask charged with Palladium hydroxide (20 wt % Pd, dry basis, on carbon, 1.50 g) was added ethanol (75 mL) and (3R,4R)-4-[(R)-1-phenyl-ethylamino]-piperidine-1,3-dicarboxylic acid 1-tert-butyl ester 3-ethyl ester (4.30 g, 11.4 mmol). The reaction mixture was hydrogenated at 53 psi for 20.5 hours with vigorous shaking. The reaction mixture was filtered through a plug of celite. The plug was washed with 20 mL of ethanol and the combined filtrates were concentrated in vacuo to give a colorless oil (3.07 g, 99%). $^1$H NMR (300 MHz, CDCl$_3$), δ: 4.32 (bs, 1H), 4.19 (q, 2H, J=7), 4.19 (bs, 1H), 3.08 (td, 1H, J=11, J'=3), 2.75 (bt, 2H, J=14), 2.29 (td, 1H, J=11, J'=4), 1.89 (m, 1H), 1.46 (s, 9H), 1.38 (td, 1H, J=12, J'=5), 1.28 (t, 3H, J=7).

Part F: Preparation of (3R,4R)-4-benzyloxycarbonylamino-piperidine-1,3-dicarboxylic acid 1-tert-butyl ester 3-ethyl ester In a dry flask (3R,4R)-4-aminopiperidine-1,3-dicarboxylic acid 1-tert-butyl ester 3-ethyl ester (3.07 g, 11.3 mmol) was dissolved in dichloromethane (100 mL) and triethylamine (2.1 mL, 15.1 mmol) and benzyl chloroformate (2.0 mL, 12.6 mmol) were added. The mixture was stirred for 22 hours. Water (30 mL) was added and the layers separated. The aqueous layer was extracted with dichloromethane (30 mL). The combined organic layers were dried with magnesium sulfate, filtered, and concentrated in vacuo to give a crude oil (4.91 g). Purification by flash column chromatography (40% ethyl acetate/hexanes) provided a colorless oil (2.37 g, 51%). $^1$H NMR (300 MHz, CDCl$_3$), δ: 7.33 (m, 5H), 5.08 (s, 2H), 4.71 (s, 1H), 4.12 (m, 4H), 3.90 (m, 1H), 2.98 (bs, 1H), 2.85 (t, 1H, J=13), 2.37 (m, 1H), 2.06 (d, 1H, J=7), 1.45 (s, 9H), 1.37 (m, 1H), 1.20 (t, 3H, J=7).

Part G: Preparation of (3R,4R)-4-benzyloxycarbonylamino-piperidine-1,3-dicarboxylic acid 1-tert-butyl ester In a flask (3R,4R)-4-benzyloxycarbonylamino-piperidine-1,3-dicarboxylic Acid 1-tert-butyl Ester 3-ethyl Ester (2.98 g, 7.33 mmol) was dissolved in tetrahydrofuran (120 mL) and lithium hydroxide (15 mL of a 1N aqueous solution, 15 mmol) was added. The mixture was stirred for 68 hours. The reaction was concentrated in vacuo to one-third the original volume. Water (50 mL) and diethyl ether (50 mL) were added and the layers separated. The aqueous layer was extracted with diethyl ether twice (30 mL). The aqueous layer was acidified with aqueous hydrochloric acid (6.5 mL of a 2M solution) and then extracted with ethyl acetate three times (30 mL). The combined organic layers were dried with magnesium sulfate, filtered, and concentrated in vacuo to give a crude white solid (3.11 g) which was used without further purification. $^1$H NMR (300 MHz, CDCl$_3$), δ: 7.36 (m, 5H), 5.12 (m, 2H), 4.91 (bs, 1H), 4.24 (bs, 1H), 4.09 (bs, 1H), 3.92 (bs, 1H), 3.01 (bs, 1H), 2.87 (m, 1H), 2.44 (m, 1H), 2.05 (bs, 1H), 1.45 (s, 9H), 1.40 (m, 1H).

Part H: Preparation of t-Butyl 3-oxo-1-piperidine-carboxylate

To a stirring solution of N-benzyl-3-piperidone hydrochloride hydrate (4.2 g, 18.6 mmol) and 10% palladium on carbon (0.8 g) in degassed methanol (200 mL) was added hydrogen gas to 55 psi. The reaction mixture was stirred for 16 hr and then filtered through a pad of celite. The celite was washed with methanol (200 mL). The filtrates were combined and concentrated in vacuo to a colorless oil. The oil was dissolved in tetrahydrofuran (200 mL) and then treated with di-t-butyl-dicarbonate (5.27 g, 24.1 mmol) and saturated aqueous. sodium bicarbonate (50 mL). The reaction was stirred for 4 hr and then concentrated in vacuo to a white solid. The solid was partitioned between ethyl acetate and 1N hydrochloric acid. The organic layer was separated, washed with 1N sodium hydroxide and brine, dried over Na$_2$SO$_4$, and evaporated in vacuo to a colorless oil. The oil was purified by flash chromatography (silica gel, hexane-:ethyl acetate 3:1) to yield 2.93 g as a colorless oil. $^1$H NMR (300 MHz, CDCl$_3$) δ3.99 (s, 2H), 3.58 (t, J=6, 2H), 2.46 (t, J=6, 2H), 1.97 (p, J=6, 2H), 1.45 (s, 9H).

Part I: Preparation of t-Butyl 3-(4-fluorobenzylidene)-1-piperidinecarboxylate To a stirring solution of (4-fluorophenylmethyl)-triphenylphosphonium chloride (17.68 g, 43.5 mmol) in dry tetrahydrofuran (60 mL) at −78° C. was added 2.5 M n-butyllithium in hexane (14.6 mL, 36.5 mmol). The reaction was warmed to 0° C. for 1 hr and t-Butyl 3-oxo-1-piperidinecarboxylate (3.46 g, 17.4 mmol) in tetrahydrofuran (60 mL) was added. The mixture was stirred at room temperature for 1 hr and the heated to reflux for 16 hr. The reaction was cooled to room temperature and quenched by the addition of saturated aqueous ammonium chloride. The reaction was extracted with ethyl acetate three times (100 mL). The organic layers were combined, washed with brine, dried over magnesium sulfate, and evaporated in vacuo to a pale yellow oil. The oil was purified by flash chromatography (silica gel, hexane:ethyl acetate 9:1) to yield 3.82 g of a mixture of E and Z isomers as a colorless oil. $^1$H NMR (300 MHz, CDCl$_3$) δ7.22–7.14 (m, 2H), 7.04–6.98 (m, 2H), 6.36 (s, 0.33H), 6.28 (s, 0.67H), 4.14 (s, 1.34 H), 4.00 (s, 0.66H) 3.50 (t, J=5, 2H), 2.47 (t, J=5, 0.66 H), 2.39 (t, J=5, 1.34H), 1.75–1.68 (m, 1.34H), 1.65–1.57 (m, 0.66H), 1.48 (s, 9H).

Part J: Preparation of t-Butyl (+)-3-(4-fluorobenzyl)-1-piperidinecarboxylate To a stirring solution of the t-Butyl 3-(4-fluorobenzylidene)-1-piperidinecarboxylate (3.82 g, 13.1 mmol) and 10% palladium on carbon (0.76 g) in degassed methanol (200 mL) was added hydrogen gas to 55 psi. The reaction was stirred for 16 h and then filtered through a pad of celite. The celite was washed with methanol (200 mL). The filtrates were combined and concentration in vacuo to yield 2.76 g as a colorless oil. $^1$H NMR (300 MHz, CDCl$_3$) δ7.12–7.07 (m, 2H), 6.98–6.93 (m, 2H), 3.89 (dt, J=13, J'=4, 1H), 3.84–3.74 (m, 1H), 2.57–2.43 (m, 4H), 1.75–1.60 (m, 4H), 1.42 (s, 9H), 1.15–1.09 (m, 1H).

Part K: Preparation of (3S)-3-(4-fluorobenzyl) piperidine, mandelic acid salt N-BOC-3-(4-fluorobenzyl) piperidine (5 g) was dissolved in 30 mL of 4N hydrochloric acid in dioxane. Some initial gassing occurred which eventually subsided. After one hour, the mixture was neutralized with aqueous Na$_2$CO$_3$, and the dioxane was evaporated off. The residue was then extracted with ether. The combined ether extracts were dried over magnesium sulfate and evaporated off to give 2.6 g of the free amine as a discolored oil. This crude material was used to make the diastereomeric salts.

Resolution of 3-(4-fluorobenzyl)piperidine

The crude racemic 3-(4-fluorobenzyl)piperidine (2.0 g) was dissolved in 25 mL acetonitrile and heated to reflux. The solution was hazy. To this was added 1.56 g (1 equiv.) of (R)-(−) mandelic acid dissolved in 15 mL acetonitrile. Some initial precipitation occurred when the cooler solution was added but it did redissolve when refluxing resumed. The heat was turned off and small amounts of enantiomerically pure salt was added as the temperature dropped. At first the seed crystals dissolved, but when the temperature dropped to 75° C., they remained suspended in the stirred solution. After a few more degrees of cooling, crystal growth was obvious. Cooling was continued at the rate of 1 degree/min. At 50° C., the solution was filtered to recover 0.9 g of salt, which melted at 164° C. It was recrystallized from acetonitrile twice to give (S)-(+)-3-(4-fluorobenzyl)piperidine mandelic acid salt in 98% ee, and melting at 168–171° C.

Part L: Preparation of (3R,4R)-4-benzyloxycarbonylamino-3-[(S)-3-(4-fluoro-benzyl)-piperidine-1-carbonyl]-pipreridine-1-carboxylic acid t-butyl ester (S)-3-(4-fluorobenzyl)-piperidine, mandelic acid salt (4.33 g, 12.5 mmol) is dissolved in 1N sodium hydroxide (100 mL) and extracted with ethyl acetate (50 mL) three times. The combined organic extracts were dried with magnesium sulfate, filtered, concentrated in vacuo and used without further purification.

In a flask (3R,4R)-4-benzyloxycarbonylamino-piperidine-1,3-dicarboxylic acid 1-tert-butyl ester (3.93 g, 10.4 mmol) was dissolved in dichloromethane (200 mL) and then benzotriazol-1-yloxy-tripyrrolidinophosphonium hexafluorophosphate (6.48 g, 12.5 mmol) and triethylamine (3.3 mL, 23.7 mmol) were added. After stirring for 5 minutes, (S)-3-(4-fluorobenzyl)-piperidine (2.21 g, 11.4 mmol) was added. The mixture was stirred for 16 hours. The reaction mixture was extracted with water (50 mL) and brine (50 mL). The organic layer was dried with magnesium sulfate, filtered, and concentrated in vacuo to give a crude orange glass (10.49 g). Purification by flash column chromatography (50–70% ethyl acetate/hexanes) provided a colorless oil (4.79 g, 83%). $^1$H NMR (300 MHz, CDCl$_3$), δ: 7.32 (m, 2H), 7.26 (m, 3H), 7.07 (m, 2H), 6.95 (m, 2H), 5.04 (m, 2H), 4.41 (d, 1H, J=13), 4.12 (bm, 2H), 3.83 (bm, 2H), 3.06 (bm, 1H), 2.76 (bs, 2H), 2.60 (dd, 2H, J=14, J'=6), 2.37 (m, 2H), 1.90 (bs, 1H), 1.63 (bm, 2H), 1.45 (m, 9H), 1.12 (m, 3H), 0.87 (m, 1H).

Part M: Preparation of (3R,4R)-4-amino-3-[(S)-3-(4-fluoro-benzyl)-piperidine-1-carbonyl]-piperidine-1-carboxylic acid t-butyl ester In a dry 500-mL Paar flask charged with 10 wt % palladium on carbon (0.050 g) and (3R,4R)-4- benzyloxycarbonylamino-3-[(S)-3-(4-fluoro-benzyl)-piperidine-1-carbonyl]-piperidine-1-carboxylic acid t-butyl ester (0.25 g, 0.451 mmol) was added methanol (15 mL). The reaction mixture was hydrogenated at 48 psi for 18 hours with vigorous shaking. The reaction mixture was filtered through a plug of celite. The plug was washed with 20 mL of methanol and the combined filtrates were concentrated in vacuo to give a white solid (0.183 g, 97%). $^1$H NMR (300 MHz, CDCl$_3$), δ: 8.11 (bs, 2H), 7.15 (m, 2H), 6.97 (t, 2H, J=8), 4.23 (bm, 3H), 3.88 (m, 1H), 3.67 (bs, 1H), 3.13 (m, 1H), 2.60 (bm, 5H), 2.31 (bd, 1H, J=12), 1.74 (bm, 6H), 1.47 (2s, 9H), 1.20 (m, 1H). MS (ESI), m$^+$/z: (M+H)$^+$=420.3.

Part N: Preparation of (3R,4R)-4-[3-(3-acetyl-phenyl)-ureido]-3-[(S)-3-(4-fluoro-benzyl)-piperidine-1-carbonyl]-piperidine-1-carboxylic acid t-butyl ester In a dry flask (3R,4R)-4-amino-3-[(S)-3-(4-fluoro-benzyl)-piperidine-1-carbonyl]-piperidine-1-carboxylic acid t-butyl ester (56 mg, 0.133 mmol) was dissolved in tetrahydrofuran (2 mL) and triethylamine (24 μL, 0.172 mmol) and 3-acetylphenylisocyanate (22 μL, 0.160 mmol) were added. The reaction mixture was stirred for 17 hours. One-half of the original reaction mixture (1 mL) was concentrated in vacuo then purified by preparative reverse-phase HPLC (10–80% acetonitrile in water with 0.05% trifluoroacetic acid) to give a white amorphous solid (24 mg, 62%). $^1$H NMR (400 MHz, DMSO, 120° C.), δ: 8.32 (s, 1H), 7.91 (t, 1H, J=2), 7.58 (m, 1H), 7.48 (m, 1H), 7.33 (t, 1H, J=8), 7.15 (m, 2H), 6.99 (m, 2H), 5.98 (d, 1H, J=10), 4.04 (bd, 1H, J=13), 3.89 (bm, 4H), 3.20 (bs, 2H), 2.96 (m, 2H), 2.86 (m, 2H), 2.50 (s, 3H), 2.46 (m, 2H), 1.90 (m, 1H), 1.62 (bm, 4H), 1.43 (2s, 9H), 1.20 (m, 1H). HRMS (ESI), C$_{32}$H$_{42}$FN$_4$O$_5$ m$^+$/z: calc.=581.3139, found=581.3141.

Example 2

Preparation of 1-(3-acetyl-phenyl)-3-{(3R,4R)-3-[(S)-3-(4-fluoro-benzyl)-piperidine-1-carbonyl]-piperidin-4-yl}-urea, trifluoroacetic acid salt In a dry flask (3R,4R)-4-[3-(3-acetyl-phenyl)-ureido]-3-[(S)-3-(4-fluoro-benzyl)-piperidine-1-carbonyl]-piperidine-1-carboxylic acid t-butyl ester 24 mg, 0.041 mmol in 1 mL of tetrahydrofuran) was concentrated in vacuo, redissolved in dichloromethane (1 mL), and trifluoroacetic acid (0.5 mL) was added. The reaction mixture was stirred for 5 hours. The reaction mixture was concentrated in vacuo then purified by preparative reverse-phase HPLC (10–80% acetonitrile in water with 0.05% trifluoroacetic acid) to give a white amorphous solid (22 mg, 89%). $^1$H NMR (400 MHz, DMSO, 120° C.), δ: 8.44 (bm, 3H), 7.96 (bs, 1H), 7.59 (m, 1H), 7.51 (m, 1H), 7.36 (t, 1H, J=8), 7.16 (m, 2H), 7.01 (t, 2H, J=9), 6.60 (d, 1H, J=7), 4.17 (d, 1H, J=13), 4.08 (bs, 1H), 3.90 (m, 1H), 3.43 (bs, 1H), 3.23 (m, 2H), 3.13 (m, 2H), 3.04 (bs, 2H), 2.51 (s, 3H), 2.46 (m, 2H), 1.97 (m, 2H), 1.67 (bd, 3H, J=9), 1.42 (bs, 1H), 1.19 (m, 1H). HRMS (ESI), C$_{27}$H$_{34}$FN$_4$O$_3$ m$^+$/z: calc.=481.2615, found=481.2614.

Example 3

Part A: Preparation of N-methyl-3-nitro-benzamide

In a dry flask 3-nitrobenzoyl chloride (7.00 g, 37.7 mmol) was dissolved in tetrahydrofuran (300 mL) and methylamine (41.5 mL of a 2.0 M solution in tetrahydrofuran, 82.9 mmol) was added. The reaction mixture was stirred for 2 hours. The reaction mixture was diluted with ethyl acetate (500 mL) and extracted with water three times (100 mL). The organic layer was dried with sodium sulfate, filtered, and concentrated in vacuo. The crude solid (6.38 g, 94%) was used with further purification. $^1$H NMR (300 MHz, CDCl$_3$), δ: 8.84 (bs, 1H), 8.67 (m, 1H), 8.37 (dd, J=8, J'=2, 1H), 8.28 (d, J=7, 1H), 7.78 (dd, J=8, J'=7, 1H), 2.83 (m, 3H). MS (ESI), m$^+$/z: (M+H)$^+$=181.

Part B: Preparation of 1-methyl-5-(3-nitrophenyl)-tetrazole

In a dry flask N-methyl-3-nitro-benzamide (30.0 g, 167 mmol) was dissolved in acetonitrile (835 mL) and sodium azide (10.9 g, 167 mmol) was added and the reaction cooled in an ice bath. Triflic anhydride (29 mL, 172 mmol) was added dropwise to maintain the internal temperature below 3° C. The reaction mixture was stirred for 3.5 hours at 0° C. The reaction mixture was poured into 1N aqueous sodium hydroxide (100 mL). The organic layer was separated dried with sodium sulfate, filtered, and concentrated in vacuo to 50 mL. The solution was diluted with dichloromethane and added water to precipitate a yellow solid (18.46 g, 54%). A second crop of crystals was obtained by concentrated the filtrate in vacuo and adding it to boiling ethyl acetate. Upon cooling to 0° C., 6.07 g (18%) of additional material was isolated upon filtration. further purification. $^1$H NMR (300 MHz, CDCl$_3$), δ: 3.67 (m, 1H), 8.49 (dd, J=8, J'=2, 1H), 8.31 (d, J=8, 1H), 7.94 (dd, J=8, J'=8, 1H), 4.22 (s, 3H).

Part C: Preparation of 1-methyl-5-(3-aminophenyl)-tetrazole

In a Paar flask 1-methyl-5-(3-nitrophenyl)-tetrazole (28.8 g, 140 mmol) was dissolved in ethyl acetate (430 mL) and methanol (1270 mL) and added to palladium on carbon (2.7 g, 10 wt %). The reaction mixture was hydrogenated for 1.5 hours with vigorous shaking. The reaction mixture was filtered, and concentrated in vacuo to give a white solid (24.0 g, 98%) was used with further purification. $^1$H NMR (300 MHz, CDCl$_3$), δ: 7.21 (dd, J=8, J'=7, 1H), 6.99 (s, 1H), 6.90 (d, J=7, 1H), 6.76 (d, J=8, 1H), 5.44 (bs, 2H), 4.10 (s, 3H).

Part D: Preparation of [3-(1-methyl-1H-tetrazol-5-yl)-phenyl]-carbamic acid phenyl ester In a dry flask of 1-methyl-5-(3-aminophenyl)-tetrazole (24.0 g, 137 mmol) was dissolved in dichloromethane (1.4 L) and 2,6-lutidine (44.1 g, 411 mmol) was added. Phenyl chloroformate (21.2 g, 136 mmol) was added in 4 portions over 15 minutes, then the reaction was stirred for 1.5 hours. The reaction was poured into 1N aqueous hydrochloric acid (200 mL) and the mixture was extracted with dichloromethane three times (200 mL). The combined organic layers were washed with brine, dried with sodium sulfate, filtered, and concentrated in vacuo. The crude brown material was dissolved in hot toluene, filtered, and allowed to precipitate at 0° C. to give 34.1 g of a white solid. The filtrate was concentrated and recrystallized from toluene again to give an additional crop of off-white crystals (3.44 g, 93% total). $^1$H NMR (300 MHz, CDCl$_3$), δ: 10.51 (bs, 1H), 8.01 (s, 1H), 7.71 (dt, J=7, J'=2, 1H), 7.55 (m, 2H), 7.41 (m, 2H), 7.24 (m, 2H), 4.14 (s, 3H).

Part E: Preparation of (3R,4R)-3-[(S)-3-(4-fluoro-benzyl)-piperidine-1-carbonyl]-4-{3-[3-(1-methyl-1H-tetrazol-5-yl)-phenyl]-ureido}-piperidine-1-carboxylic acid t-butyl ester In a dry flask (3R,4R)-4-amino-3-[(S)-3-(4-fluoro-benzyl)-piperidine-1-carbonyl]-piperidine-1-carboxylic acid t-butyl ester (350 mg, 0.834 mmol) was dissolved in dimethylformamide (5 mL) and [3-(1-methyl-1H-tetrazol-5-yl)-phenyl]-carbamic acid phenyl ester (285 mg, 0.965 mmol) was added. The reaction mixture was stirred for 19 hours. The reaction mixture was diluted with ethyl acetate and extracted three times with water. The combined aqueous extracts were extracted with ethyl acetate. The combined organic extracts were washed with brine, dried with sodium sulfate, filtered and concentrated in vacuo. The resulting oil was purified by flash column chromatography with 70–100% ethyl acetate/hexanes to give a solid (387 mg, 75%). A small amount was further purified by preparative reverse-phase HPLC (10–80% acetonitrile in water with 0.05% trifluoroacetic acid) to give a white amorphous solid (33 mg, 62%). $^1$H NMR (300 MHz, CDCl$_3$), δ: 7.88 (m, 1H), 7.49 (m, 2H), 7.40 (m, 1H), 7.19 (m, 1H), 7.01 (m, 1H), 6.95 (m, 1H), 6.86 (m, 1H), 4.31 (m, 1H), 4.17 (s, 3H), 4.03 (m, 4H), 3.16 (m, 1H), 3.05 (m, 1H), 2.88 (m, 3H), 2.67 (m, 1H), 2.50 (m, 2H), 2.37 (m, 1H), 1.95 (m, 1H), 1.65 (m, 5H), 1.47 (s, 9H), 1.23 (m ,1H). HRMS (ESI), $C_{32}H_{42}FN_8O_4$ m$^+$/z: calc.=621.3313, found=621.3337.

Example 4

Preparation of 1-{(3R,4R)-3-[(S)-3-(4-fluoro-benzyl)-piperidine-1-carbonyl]-piperidin-4-yl}-3-[3-(1-methyl-1H-tetrazol-5-yl)-phenyl]-urea, trifluoroacetic acid salt In a dry flask (3R,4R)-3-[(S)-3-(4-fluoro-benzyl)-piperidine-1-carbonyl]-4-{3-[3-(1-methyl-1H-tetrazol-5-yl)-phenyl]-ureido}-piperidine-1-carboxylic acid t-butyl ester (348 mg, 0.561 mmol) was dissolved in dichloromethane (8 mL), and trifluoroacetic acid (3 mL) was added. The reaction mixture was stirred for 2.5 hours. The reaction mixture was concentrated in vacuo then a small quantity was purified by preparative reverse-phase HPLC (10–80% acetonitrile in water with 0.05% trifluoroacetic acid) to give a white amorphous solid (37 mg). $^1$H NMR (300 MHz, CD$_3$OD), δ: 7.95 (d, 1H, J=10), 7.50 (m, 3H), 7.12 (m, 2H), 6.91 (m, 2H), 4.34 (bm, 2H), 4.16 (s, 3H), 3.99 (m, 1H), 3.55 (m, 1H), 3.38 (m, 3H), 3.15 (m, 2H), 2.96–2.61 (m, 1H), 2.47 (m, 2H), 2.07 (bm, 2H), 1.77 (m, 2H), 1.47 (bm, 2H), 1.24 (m, 1H). HRMS (ESI), $C_{27}H_{34}FN_8O_2$ m$^+$/z: calc. 521.2789, found=521.2803.

Example 5

Preparation of 1-{1-(2,2-Dimethyl-propionyl)-3-[(3R,4R)-3-((S)-4-fluoro-benzyl)-piperidine-1-carbonyl]-piperidin-4-yl}-3-[3-(1-methyl-1H-tetrazol-5-yl)-phenyl]-urea In a dry flask 1-((3R,4R)-3-[(S)-3-(4-fluoro-benzyl)-piperidine-1-carbonyl]-piperidin-4-yl}-3-[3-(1-methyl-1H-tetrazol-5-yl)-phenyl]-urea (63 mg, 0.10 mmol) was dissolved in dichloromethane (2 mL), and then triethylamine (70 μL, 0.50 mmol) and trimethylacetyl chloride (18 μL, 0.15 mmol) were added. The reaction mixture was stirred for 19 hours. The reaction mixture was concentrated in vacuo then was purified by preparative reverse-phase HPLC (10–80% acetonitrile in water with 0.05% trifluoroacetic acid) to give a white amorphous solid (42 mg, 70%). $^1$H NMR (300 MHz, CDCl$_3$), δ: 8.35 (s, 1H), 7.89 (t, 1H, J=2), 7.54 (dq, 1H, J=8, J'=1), 7.44 (t, 1H, J=8), 7.34 (dt, 1H, J=8, J'=1), 7.15 (m, 2H), 6.99 (t, 2H, J=9), 6.00 (d, 1H, J=8), 4.22 (m, 2H), 4.12 (s, 3H), 4.05 (d, 2H, J=14), 3.93 (m, 1H), 3.00 (m, 3H), 2.83 (m, 1H), 2.68 (t, 1H, J=11), 2.56 (dd, 1H, J=14, J'=6), 2.45 (dd, 1H, J=14, J'=7), 1.99 (m, 1H), 1.66 (m, 4H), 1.39 (m, 1H), 1.24 (s, 9H), 1.20 (m, 1H). HRMS (ESI), $C_{32}H_{42}FN_8O_3$ m$^+$/z: calc. 605.3363, found=605.3377.

Example 6

Preparation of 1-{1-Acetyl-3-[(3R,4R)-3-((S)-4-fluoro-benzyl)-piperidine-1-carbonyl]-piperidin-4-yl}-3-[3-(1-methyl-1H-tetrazol-5-yl)-phenyl]-urea In a dry flask 1-{(3R,4R)-3-[(S)-3-(4-fluoro-benzyl)-piperidine-1-carbonyl]-piperidin-4-yl}-3-[3-(1-methyl-1H-tetrazol-5-yl)-phenyl]-urea (65 mg, 0.10 mmol) was dissolved in dichloromethane (2 mL), and then triethylamine (70 μL, 0.50 mmol) and acetyl chloride (11 μL, 0.15 mmol) were added. The reaction mixture was stirred for 17 hours. The reaction mixture was concentrated in vacuo then was purified by preparative reverse-phase HPLC (10–80% acetonitrile in water with 0.05% trifluoroacetic acid) to give a white amorphous solid (37 mg, 64%). $^1$H NMR (400 MHz, DMSO-d6, 140° C.), δ: 8.39 (s, 1H), 7.89 (t, 1H, J=2), 7.54 (dq, 1H, J=8, J'=1), 7.44 (t, 1H, J=8), 7.35 (dt, 1H, J=8, J'=1), 7.15 (m, 2H), 6.99 (td, 2H, J=9, J'=2), 6.01 (d, 1H, J=8), 4.12 (s, 3H), 4.02 (bm, 5H), 2.99 (bm, 4H), 2.60 (bm, 2H), 2.44 (dd, 1H, J=14, J'=7), 2.01 (s, 3H), 1.95 (d, 1H, J=10), 1.66 (m, 4H), 1.39 (m, 1H), 1.19 (m, 1H). HRMS (ESI), $C_{25}H_{36}FN_8O_3$ m$^+$/z: calc. 563.2894, found=563.2865.

Example 7

Preparation of 1-{(3R,4R)-3-[(S)-3-(4-Fluoro-benzyl)-piperidine-1-carbonyl]-1-methanesulfonyl-piperidin-4-yl}-3-[3-(1-methyl-1H-tetrazol-5-yl)-phenyl]-urea In a dry flask 1-{(3R,4R)-3-[(S)-3-(4-fluoro-benzyl)-piperidine-1-carbonyl]-piperidin-4-yl}-3-[3-(1-methyl-1H-tetrazol-5-yl)-phenyl]-urea (67 mg, 0.11 mmol) was dissolved in dichloromethane (2 mL), and then triethylamine (65 ·L, 0.47 mmol) and methanesulfonyl chloride (9 μL, 0.11 mmol) were added. The reaction mixture was stirred for 25 minutes. The reaction mixture was concentrated in vacuo then was purified by preparative reverse-phase HPLC (10–80% acetonitrile in water with 0.05% trifluoroacetic acid) to give a white amorphous solid (38 mg, 60%). $^1$H NMR NMR (400 MHz, DMSO-d6, 140° C.), δ: 8.37 (s, 1H), 7.89 (t, 1H, J=2), 7.54 (d, 1H, J=6), 7.44(t, 1H, J=8), 7.35 (m, 1H), 7.14 (m, 2H), 6.99 (t, 2H, J=9), 6.05 (d, 1H, J=8), 4.12 (s, 3H), 4.05 (d, 2H, J=14), 3.85 (m, 1H), 3.63 (m, 2H), 3.16 (td, 1H, J=10, J'=4), 2.90 (m, 3H), 2.88 (s, 3H), 2.66 (m, 1H), 2.56 (dd, 1H, J=14, J'=6), 2.44 (dd, 1H, J=14, J'=8), 2.01 (m, 1H), 1.79 (qd, 1H, J=13, J'=4), 1.65 (bs, 3H), 1.40 (m, 1H), 1.20 (m, 1H). HRMS (ESI), $C_{28}H_{36}FN_8O_4S$ m$^+$/z: calc. 599.2564, found=599.2586.

Example 8

Preparation of 1-{(3R,4R)-3-[(S)-3-(4-Fluoro-benzyl)-piperidine-1-carbonyl]-1-methyl-piperidin-4-yl}-3-[3-(1-methyl-1H-tetrazol-5-yl)-phenyl]-urea, trifluoroacetic acid salt In a dry flask 1-{(3R,4R)-3-[(S)-3-(4-fluoro-benzyl)-piperidine-1-carbonyl]-piperidin-4-yl}-3-[3-(1-methyl-1H-tetrazol-5-yl)-phenyl]-urea (68 mg, 0.11 mmol) was dissolved in dichloroethane (4 mL), and then a solution of formaldehyde (250 μL in tetrahydrofuran) was added. The reaction mixture was stirred for 11 minutes then triacetoxyborohydride (36 mg, 0.17 mmol) was added. The mixture was stirred an additional 4.5 hours. The reaction was quenched with saturated aqueous sodium bicarbonate (1 mL) then diluted with water. The mixture was extracted with dichloromethane three times, dried with magnesium sulfate, filtered and concentrated in vacuo. Then it was purified by preparative reverse-phase HPLC (10–80% acetonitrile in water with 0.05% trifluoroacetic acid) to give a white amorphous solid (37 mg, 53%). $^1$H NMR (400 MHz, DMSO-d6, 140° C.), δ: 8.46 (s, 1H), 7.92 (s, 1H), 7.56 (d, 1H, J=8), 7.46 (t, 1H, J=8), 7.37 (d, 1H, J=8), 7.16 (m, 2H), 7.00 (t, 2H, J=9), 6.48 (bs, 1H), 4.13 (s, 3H), 4.12 (m, 2H), 3.87 (bs, 1H), 3.48 (bs, 1H), 3.21 (bs, 3H), 3.04 (bs, 3H), 2.72 (bs, 3H), 2.53 (m, 1H), 2.49 (m, 1H), 2.01 (m, 2H), 1.69 (m, 3H), 1.43 (bs, 1H), 1.21 (m, 1H). HRMS (ESI), $C_{28}H_{36}FN_8O_2$ m$^+$/z: calc. 535.2945, found=535.2945.

Example 9

Part A: Preparation of 5-nitro-indazole-1-carboxylic acid t-butyl ester

In a dry flask 5-nitro-indazole (1.03 g, 6.2 mmol) was dissolved in tetrahydrofuran (25 mL), cooled to 0° C. and sodium hydride (60% in mineral oil, washed with hexanes, 0.25 g) was added. The reaction was stirred for 10 minutes, di-t-butyl dicarbonate (1.35 g, 6.2 mmol) was added and the reaction stirred an additional 10 minutes. The reaction mixture was diluted with ethyl acetate extracted with water and brine, and concentrated in vacuo to give a white solid (1.61 g, 100%). $^1$H NMR (300 MHz, CDCl$_3$), δ: 8.71 (d, J=2, 1H), 8.43 (dd, J=9, J'=2, 1H), 8.35 (s, 1H), 8.34 (d, J=9, 1H), 1.75 (s, 9H).

Part B: Preparation of 5-amino-indazole-1-carboxylic acid t-butyl ester

In a Paar flask charged with palladium (10 wt % on carbon, 0.44 g) was added ethyl acetate (30 mL) and 5-nitro-indazole-1-carboxylic acid t-butyl ester (1.61 g, 6.2 mmol). The reaction mixture was hydrogenated at 50 psi for 30 minutes with vigorous shaking. The reaction mixture was filtered through a plug of celite. The plug was washed with 20 mL of methanol and the combined filtrates were concentrated in vacuo to give a white solid (1.4 g, 100%). $^1$H NMR (300 MHz, CDCl$_3$), δ: 7.99 (s, 1H), 7.97 (d, J=10, 1H), 6.94 (dd, J=10, J'=2, 1H), 6.92 (d, J=2, 1H), 1.71 (s, 9H).

Part C: Preparation of 5-phenoxycarbonylamino-indazole-1-carboxylic acid t-butyl ester In a dry flask 5-amino-indazole-1-carboxylic acid t-butyl ester (1.4 g, 6.0 mmol) was dissolved in tetrahydrofuran (20 mL) and triethylamine (1.0 g, 9.9 mmol) were added and the reaction mixture cooled to 0° C. Phenyl chloroformate (1.0 g, 6.4 mmol) was added dropwise and the mixture was stirred an additional 15 minutes after the addition was complete. The reaction mixture was diluted with ethyl acetate, washed with water, and concentrated in vacuo. The crude material was purified by flash chromatography with 35% ethyl acetate in hexanes to give a white solid (1.9 g, 90%). $^1$H NMR (300 MHz, CDCl$_3$), δ: 8.14 (d, J=10, 1H), 8.12 (s, 1H), 8.02 (bs, 1H), 7.40 (m, 3H), 7.24 (m, 4H), 1.73 (s, 9H).

Part D: Preparation of 5-(3-}(3R,4R)-1-tert-butoxycarbonyl-3-[(S)-3-(4-fluoro-benzyl)-piperidine-1-carbonyl]-piperidin-4-yl}-ureido)-indazole-1-carboxylic acid t-butyl ester In a dry flask (3R,4R)-4-Amino-3-[(S)-3-(4-fluoro-benzyl)-piperidine-1-carbonyl]-piperidine-1-carboxylic acid t-butyl ester (72 mg, 0.171 mmol) was dissolved in acetonitrile (2 mL) and triethylamine (25 μL, 0.179 mmol) and 5-(phenoxycarbonylamino)-1-indazolecarboxylic acid 1-tert-butyl ester (72 mg, 0.204 mmol) were added. The reaction mixture was stirred for 64 hours while heating to 60° C. The reaction mixture was cooled, diluted with ethyl acetate, washed twice with water and once with brine. The organic layer was dried with magnesium sulfate, filtered and concentrated in vacuo. The crude product was purified by preparative reverse-phase HPLC (10–80% acetonitrile in water with 0.05% trifluoroacetic acid) to give a white amorphous solid (71 mg, 61%). $^1$H NMR (300 MHz, CDCl$_3$), δ: 8.09 (m, 2H), 7.90 (2s, 1H), 7.44 (m, 1H), 7.10 (m, 1H), 6.99 (m, 1H), 6.83 (m, 2H), 4.90 (bs, 1H), 4.43 (bd, 1H, J=11), 4.22 (bs, 2H), 3.98 (bm, 2H), 3.14 (t, 1H, J=13), 2.75 (bm, 4H), 2.45 (bm, 3H), 1.94 (bm, 3H), 1.73 (2s, 9H), 1.48 (m, 9H), 1.45 (bm, 3H), 1.22 (bm, 1H). HRMS (ESI), $C_{36}H_{48}FN_6O_6$ m$^+$/z: calc. 679.3619, found=679.3621.

Example 10

Preparation of 5-(3-{(3R,4R)-3-[(S)-3-(4-fluoro-benzyl)-piperidine-1-carbonyl]-piperidin-4-yl}-ureido)-indazole-1-carboxylic acid t-butyl ester, trifluoroacetic acid salt In a dry flask 5-(3-{(3R,4R)-1-tert-butoxycarbonyl-3-[(S)-3-(4-fluoro-benzyl)-piperidine-1-carbonyl]-piperidin-4-yl}-ureido)-indazole-1-carboxylic acid t-butyl ester (51 mg, 0.075 mmol) was dissolved in dichloromethane (1.5 mL) and trifluoroacetic acid (0.5 mL) was added. The reaction mixture was stirred for 2.5 hours. The reaction mixture was concentrated in vacuo then purified by preparative reverse-phase HPLC (5–80% acetonitrile in water with 0.05% trifluoroacetic acid) to give a white amorphous solid (21 mg, 47%). $^1$H NMR (400 MHz, DMSO-d6, 140° C.), δ: 8.38 (bs, 2H), 8.03 (s, 1H), 7.89 (s, 1H), 7.75 (s, 1H), 7.41 (d, 1H, J=9), 7.28 (dd, 1H, J=9, J'=2), 7.16 (m, 2H), 7.00(t, 2H, J=9), 6.41 (d, 1H, J=7), 4.08 (m, 2H), 3.91 (m, 1H), 3.44 (m, 1H), 3.17 (bm, 5H), 2.50 (bm, 3H), 2.00 (m, 2H), 1.69 (d, 3H, J=11), 1.43 (bs, 1H), 1.21 (m, 1H). HRMS (ESI), $C_{26}H_{32}FN_6O_2$ m$^+$/z: calc.=479.2571, found=479.2564.

Example 11

Part A: Preparation of (5-acetyl-4-methyl-thiazol-2-yl)-carbamic acid phenyl ester In a round-bottom flask, NaH 60% dispersion in mineral oil (3.07 g, 77 mmol) was washed 2× with hexane and suspended in DMF. Then 2-amino-5-acetyl-4-methyl-thiazole (10.0 g, 64 mmol) was added and stirred while cooling in an ice bath. Stirring continued until the NaH was consumed. Diphenyl carbonate (34 g, 160 mmol) was added while cooling and after the addition was complete the reaction mixture was stirred for an additional ~30 minutes at room temperature. The dimethylformamide was removed on a rotary evaporator (high vacuum, 40° C.) to yield a brown residue. This residue was dissolved in 1 L of chloroform and washed successively with 2 L of 0.5N aqueous hydrochloric acid, twice with 1 L of water, and finally by 1 L of brine. The aqueous portions were back extracted twice with 300 mL of chloroform. The combined organic fractions were dried over anhydrous sodium sulfate, filtered and concentrated on a rotary evaporator to give a white solid. This was chromatographed on silica (15%–70% EtOAc/hexane) to give 15 g of the desired carbamate as a white solid. $^1$H NMR (300 MHz, CDCl$_3$) δ: 11.42 (bs, 1H), 7.47–7.40 (m, 2H), 7.33–7.27 (m, 1H), 7.22–7.18 (m, 2H), 2.72 (s, 3H), 2.50 (s, 3H). ESI MS: (M+H)$^+$=277.1.

Part B: Preparation of (3R,4R)-4-[3-(5-acetyl-4-methyl-thiazol-2-yl)-ureido]-3-[(S)-3-(4-fluoro-benzyl)-piperidine-1-carbonyl]-piperidine-1-carboxylic acid t-butyl ester In a dry flask (3R,4R)-4-Amino-3-[(S)-3-(4-fluoro-benzyl)-piperidine-1-carbonyl]-piperidine-1-carboxylic acid t-butyl ester (73 mg, 0.174 mmol) was dissolved in acetonitrile (2 mL) and triethylamine (25 µL, 0.179 mmol) and 4-acetyl-3-methyl-2-(phenoxycarbonylamino)-thiazole (58 mg, 0.21 mmol) were added. The reaction mixture was stirred for 64 hours while heating to 60° C. The reaction mixture was cooled, diluted with ethyl acetate, washed twice with water and once with brine. The organic layer was dried with magnesium sulfate, filtered and concentrated in vacuo. The crude product was purified by preparative reverse-phase HPLC (10–80% acetonitrile in water with 0.05% trifluoroacetic acid) to give a white amorphous solid (60 mg, 57%). $^1$H NMR (300 MHz, CDCl$_3$), δ: 7.14 (m, 1H), 6.98 (m, 2H), 6.88 (t, 1H, J=10), 4.39 (d, 1H, J=13), 4.09 (bs, 2H), 3.94 (bm, 2H), 3.12 (t, 1H, J=11), 2.74 (bm, 5H), 2.62 (m, 3H), 2.52 (m, 1H), 2.47 (m, 3H), 2.36 (m, 2H), 2.03 (bm, 3H), 1.74 (bm, 2H), 1.48 (2s, 9H), 1.40 (m, 1H), 1.22 (m, 1H). HRMS (ESI), $C_{30}H_{41}FN_5O_5S$ m$^+$/z: calc.=602.2813, found=602.2811.

Example 12

Preparation of 1-(5-acetyl-4-methyl-thiazol-2-yl)-3-{(3R,4R)-3-[(S)-3-(4-fluoro-benzyl)-piperidine-1-carbonyl]-piperidin-4-yl}-urea, trifluoroacetic acid salt In a dry flask (3R,4R)-4-[3-(5-acetyl-4-methyl-thiazol-2-yl)-ureido]-3-[(S)-3-(4-fluoro-benzyl)-piperidine-1-carbonyl]-piperidine-1-carboxylic acid t-butyl ester (47 mg, 0.078 mmol) was dissolved in dichloromethane (1.5 mL) and trifluoroacetic acid (0.5 mL) was added. The reaction mixture was stirred for 2 hours. The reaction mixture was concentrated in vacuo then purified by preparative reverse-phase HPLC (5–80% acetonitrile in water with 0.05% trifluoroacetic acid) to give a white amorphous solid (49 mg, 100%). $^1$H NMR (400 MHz, DMSO-d6, 120° C.), δ: 8.47 (bs, 2H), 7.15 (t, 2H, J=6), 7.03 (m, 3H), 4.12 (bs, 1H), 3.95 (m, 2H), 3.45 (m, 1H), 3.24 (m, 2H), 3.12 (m, 2H), 2.51 (s, 3H), 2.48 (bm, 3H), 2.40 (s, 3H), 1.98 (m, 2H), 1.67 (bd, 3H, J=10), 1.28 (bm, 3H). HRMS (ESI), $C_{25}H_{33}FN_5O_3S$ m$^+$/z: calc. 502.2288, found=502.2281.

Example 13

Part A: Preparation of ethyl 3-oxo-4-piperidinecarboxylate

In a dry 500-mL Paar flask charged with palladium hydroxide (20 wt % Pd, dry basis, on carbon, 0.43 g) was added methanol (20 mL) and ethyl 1-benzyl-3-oxo-4-piperidinecarboxylate hydrochloride (5.00 g, 16.8 mmol). The reaction mixture was hydrogenated at 60 psi for 16 hours with vigorous shaking. The reaction mixture was filtered through a plug of celite. The plug was washed with 20 mL of methanol and the combined filtrates were concentrated in vacuo to give a light yellow oil (2.88 g, 100%). $^1$H NMR (300 MHz, CDCl$_3$), δ: 4.23 (q, J=7, 2H), 3.84 (bs, 2H), 3.37 (m, 2H), 3.15 (m, 1H), 2.68 (m, 2H), 1.32 (t, J=7, 3H). MS (ESI), m$^+$/z: (M+H)$^+$+CH$_3$CN=213, (M+H)$^+$=172.

Part B: Preparation of ethyl 1-(t-butoxycarbonyl)-3-oxo-4-piperidinecarboxylate

In a dry flask, the crude ethyl 3-oxo-4-piperidinecarboxylate 2.88 g, 16.8 mmol) is dissolved in methanol (40 mL) and di-t-butyl dicarbonate (4.03 g, 18.5 mmol) and triethylamine (3.74 g, 36.9 mmol) were added. The reaction mixture was stirred under an argon atmosphere for 6 hours at room temperature. The reaction mixture was concentrated in vacuo and then water (30 mL) and ethyl acetate (30 mL) were added. The aqueous layer was separated and then extracted twice with ethyl acetate (30 mL). The combined organic extracts were dried with magnesium sulfate, filtered and concentrated in vacuo. Purification by flash column chromatography (20% ethyl acetate/hexanes) provided 4.19 g (92%) of a colorless oil. $^1$H NMR (300 MHz, CDCl$_3$), δ: 12.08 (bs, 1H), 4.23 (q, 2H, J=7), 4.03 (bs, 2H), 3.49 (t, 2H, J=6), 2.32 (bt, 2H, J=6), 1.47 (s, 9H), 1.31 (t, 3H, J=7).

Part C: Preparation of (R)-5-(1-phenyl-ethylamino)-3,6-dihydro-2H-pyridine-1,4-dicarboxylic acid 1-tert-butyl ester 4-ethyl ester In a dry flask equipped with a Dean-Stark trap and reflux condenser, ethyl 1-(t-butoxycarbonyl)-3-oxo-4-piperidinecarboxylate (4.19 g, 15.4 mmol) was dissolved in toluene (50 mL). (R)-(+)-a-Methylbenzylamine (1.91 g, 15.8 mmol) and p-toluenesulfonic acid monohydrate (0.019 g, 0.1 mmol) were added and the mixture heated to reflux for 6 hours. The crude reaction mixture was concentrated in vacuo to give the desired amine (5.78 g, 100%) as a thick orange oil. $^1$H NMR (300 MHz, CDCl$_3$), δ: 7.36 (t, J=3, 2H), 7.33 (t, J=4, 1H), 7.31 (dd, J=3, J'=4, 2H), 4.59 (m, 1H), 4.16 (q, J=7, 2H), 3.59 (m, 2H), 2.34 (m, 2H), 1.58 (bs, 2H), 1.52 (d, J=3, 3H), 1.29 (s, 9H), 1.26 (t, 3H, J=7). MS (ESI), m$^+$/z: (M+H)$^+$=375.

Part D: Preparation of (3R,4R)-3-[(R)-1-phenyl-ethylamino]-piperidine-1,4-dicarboxylic acid 1-tert-butyl Ester 4-ethyl Ester In a dry flask (R)-5-(1-phenyl-ethylamino)-3,6-dihydro-2H-pyridine-1,4-dicarboxylic acid 1-tert-butyl ester 4-ethyl ester (5.78 g, 15.4 mmol) was dissolved in acetonitrile (25 mL) and glacial acetic acid (25 mL) and cooled to 0° C. Triacetoxyborohydride (9.82 g, 46.3 mmol) was added over a 5-minute period. The reaction mixture was allowed to stir at 0° C. for 2 hours. Concentrated aqueous sodium hydroxide was carefully added to maintain the internal temperature of the flask below 10° C. The resulting solid sodium acetate was filtered and the mixture was extracted with ethyl acetate 3 times (50 mL). The combined organic extracts were dried with magnesium sulfate, filtered, concentrated in vacuo, and then purified by flash chromatography with 20% ethyl acetate in hexanes to give a colorless oil (2.6 g, 47%). The $^1$H NMR showed a mixture of two rotation isomers. The major compound had the following $^1$H NMR (300 MHz, CDCl$_3$), δ: 7.28 (t, J=5, 2H), 7.25 (t, J=2, 1H), 7.23 (d, J=4, 2H), 4.35 (m, 2H), 4.24 (q, 2H, J=7), 3.96 (m, 2H), 3.15 (bs, 1H), 2.99 (m, 1H), 2.75 (m, 1H) 2.48 (dt, 2H, J=10, 4), 1.86 (m, 1H), 1.68 (m, 1H), 1.39 (s, 9H), 1.26 (d, 3H, J=6), 1.26 (t, 3H, J=7).

Part E: Preparation of (3R,4S)-3-(1-phenyl-ethylamino)-piperidine-1,4-dicarboxylic acid 1-tert-butyl ester 4-ethyl ester In a dry flask (3R,4R)-3-[(R)-1-phenyl-ethylamino]-piperidine-1,4-dicarboxylic acid 1-tert-butyl ester 4-ethyl ester (31.32 g, 83.0 mmol) was dissolved in ethanol (400 mL). Potassium carbonate (68.72 g) was added and the mixture was refluxed for 6 hours. The reaction mixture was cooled, filtered through a bed of celite, and concentrated in vacuo to give a crude oil. Purification by flash column chromatography (20–50% ethyl acetate/hexanes) provided a colorless oil (4.59 g, 15%). Unepimerized ester was also isolated (23.49 g, 75%). $^1$H NMR (300 MHz, CDCl$_3$), δ: 7.25 (t, J=5, 2H), 7.245 (t, J=2, 2H), 7.20 (d, J=5, 1H), 4.19 (q, J=7, 2H), 3.94 (bd, J=13, 2H), 3.86 (m, 2H), 2.85 (m, 1H), 2.71 (m, 2H), 2.32 (d, J=7, 2H), 2.20 (d, J=15, 1H), 1.68 (bs, 3H), 1.51 (s, 9H). MS (ESI), m$^+$/z: (M+H)$^+$=377.

Part F: Preparation of (3R,4S)-3-amino-piperidine-1,4-dicarboxylic acid 1-t-butyl ester 4-ethyl ester In a dry 500-mL Paar flask charged with palladium hydroxide (20 wt % Pd, dry basis, on carbon, 1.62 g) was added methanol (50 mL) and (3R,4S)-4-[(R)-1-Phenyl-ethylamino]-piperidine-1,3-dicarboxylic acid 1-tert-butyl ester (5.41 g, 14.4 mmol). The reaction mixture was hydrogenated at 60 psi for 24 hours with vigorous shaking. The reaction mixture was filtered through a plug of celite. The plug was washed with 20 mL of ethanol and the combined filtrates were concentrated in vacuo to give a colorless oil (3.81 g, 100%). $^1$H NMR (300 MHz, CDCl$_3$), δ: 4.17 (q, J=7, 2H), 3.04 (m, 1H), 2.71 (m, 2H), 2.49 (m, 2H), 2.25 (m, 1H), 1.46 (s, 9H), 1.28 (t, J=7, 3H). MS (ESI), m$^+$/z: (M+H)$^+$=273.

Part G: Preparation of (3R,4S)-3-benzyloxycarbonylamino-piperidine-1,4-dicarboxylic acid 1-t-butyl ester 4-ethyl ester In a dry flask (3R,4S)-3-aminopiperidine-1,3-dicarboxylic acid 1-t-butyl ester 4-ethyl ester (3.81 g, 14.0 mmol) was dissolved in dichloromethane (40 mL) and triethylamine (3.9 mL, 28.0 mmol) and benzyl chloroformate (2.0 mL, 14.0 mmol) were added. The mixture was stirred for 18 hours. Water (30 mL) was added and the layers separated. The aqueous layer was extracted with ethyl acetate (30 mL). The combined organic layers were dried with magnesium sulfate, filtered, and concentrated in vacuo to give a crude oil. Purification by flash column chromatography (30% ethyl acetate/hexane) provided a colorless oil (1.19 g, 16%). $^1$H NMR (300 MHz, CDCl$_3$), δ: 7.35 (m, 5H), 5.09 (m, 2H), 4.13, (q, J=7, 2H), 3.88 (m, 2H), 3.78 (m, 1H), 3.17 (m, 2H), 2.62 (m, 1H), 1.86 (m, 2H), 1.45 (s, 9H), 1.22 (t, J=7, 9H). MS (ESI), m$^+$/z: (M+H)$^+$=407.

Part H: Preparation of (3R,4S)-3-benzyloxycarbonylamino-piperidine-1,4-dicarboxylic acid 1-tert-butyl ester In a flask (3R,4S)-3-benzyloxycarbonylamino-piperidine-1,4-dicarboxylic acid 1-tert-butyl ester 4-ethyl ester (1.19 g, 2.93 mmol) was dissolved in tetrahydrofuran (48 mL) and lithium hydroxide (12 mL of a 1N aqueous solution, 15 mmol) was added. The mixture was stirred for 60 hours. The reaction mixture was acidified with aqueous hydrochloric acid (3 mL of a 2M solution) and then extracted with ethyl acetate three times (30 mL). The combined organic layers were dried with magnesium sulfate, filtered, and concentrated in vacuo to give a crude white solid (1.13 g) which was used without further purification. $^1$H NMR (300 MHz, CDCl$_3$), δ: 7.35 (m, 5H), 5.10 (m, 2H), 3.91, (m, 2H), 3.19 (m, 1H), 2.71 (m, 2H), 1.92 (m, 1H), 1.74 (m, 2H), 1.45 (s, 9H). MS (APCI), m$^+$/z: (M+H)$^+$=379.

Part I: Preparation of (3R,4S)-3-benzyloxycarbonylamino-4-[(S)-3-(4-fluoro-benzyl)-piperidine-1-carbonyl]-piperidine-1-carboxylic acid t-butyl ester In a dry flask (3R,4S)-3-benzyloxycarbonylamino-piperidine-1,4-dicarboxylic acid 1-tert-butyl ester (1.13 g, 3.00 mmol) was dissolved in dichloromethane (100 mL) and then triethylamine (1.67 mL, 12.0 mmol) and benzotriazol-1-yloxy-tripyrrolidinophosphonium hexafluorophosphate (1.56 g, 3.00 mmol) were added. The reaction was stirred 18 hours. The reaction mixture was diluted with water (25 mL) and extracted three times with ethyl acetate (25 mL). The combined organic extracts were dried with magnesium sulfate, filtered and concentrated in vacuo. The mixture was purified by flash chromatography with 50% ethyl acetate/hexanes to give a white solid (153 mg, 56%). $^1$H NMR (300 MHz, CDCl$_3$), δ: 7.31 (m, 5H), 7.08 (m, 2H), 6.98 (m, 2H), 5.12 (m, 2H), 5.08 (m, 2H), 4.41 (m, 1H), 3.94 (m, 4H), 3.60 (m, 1H), 3.43 (m, 2H), 2.98 (m, 2H), 2.59 (m, 2H), 2.39 (m, 2H), 1.66 (m, 4H), 1.56 (s, 9H). MS (ESI), m$^+$/z: (M+H)$^+$=554.4.

Part J: Preparation of (3R,4S)-3-amino-4-[(S)-3-(4-fluoro-benzyl)-piperidine-1-carbonyl]-piperidine-1-carboxylic acid t-butyl ester In a Paar flask charged with palladium hydroxide (20 wt % on carbon, 0.423 g) was added (3R,4S)-3-benzyloxycarbonylamino-4-[(S)-3-(4-fluoro-benzyl)-piperidine-1-carbonyl]-piperidine-1-carboxylic acid t-butyl ester (1.41 g, 2.53 mmol) and methanol (30 mL). The reaction was hydrogenated at 60 psi with vigorous shaking for 65 hours. The reaction mixture was filtered through a bed of celite and then concentrated in vacuo to give a thick oil (1.19 g) which was used without further purification. $^1$H NMR (300 MHz, CDCl$_3$), δ: 7.06 (m, 4H), 4.45 (m, 2H), 4.21 (m, 2H), 3.81 (m, 2H), 3.62 (m, 2H), 3.23 (m, 2H), 3.08 (m, 1H), 2.67 (m, 2H), 2.45 (m, 2H), 2.21 (m, 1H), 1.45 (s, 9H). MS (APCI), m$^+$/z: (M+H)$^+$=420.3.

Part K: Preparation of (3R,4S)-3-[3-(3-acetyl-phenyl)-ureido]-4-[(S)-3-(4-fluoro-benzyl)-piperidine-1-carbonyl]-piperidine-1-carboxylic acid t-butyl ester In a dry flask (3R,4S)-3-amino-4-[(S)-3-(4-fluoro-benzyl)-piperidine-1-carbonyl]-piperidine-1-carboxylic acid t-butyl ester (77 mg, 0.18 mmol) was dissolved in tetrahydrofuran (2.5 mL) and triethylamine (20 µL, 0.143 mmol) and 3-acetylphenylisocyanate (50 µL, 0.36 mmol) were added. The reaction mixture was stirred for 16 hours. The reaction mixture was concentrated in vacuo and purified by preparative reverse-phase HPLC (10–90% acetonitrile in water with 0.05% trifluoroacetic acid) to give a white amorphous solid (40 mg, 38%). $^1$H NMR (300 MHz, CDCl$_3$), δ: 7.98 (d, J=8, 1H), 7.83 (m, 2H), 7.74 (m, 1H), 7.65 (m, 2H), 7.56 (m, 1H), 7.46 (m, 1H), 7.01 (m, 2H), 6.87 (m, 1H), 3.09 (m, 1H), 2.51–2.77 (m, 7H), 2.42 (m, 1H), 1.23–1.78 (m, 11H), 1.42 (s, 9H). HRMS (ESI), C$_{32}$H$_{42}$FN$_4$O$_5$ m$^+$/z: calc.=581.3139, found=581.3142.

Example 14

Preparation of 1-(3-acetyl-phenyl)-3-{(3R,4S)-4-[(S)-3-(4-fluoro-benzyl)-piperidine-1-carbonyl]-piperidin-3-yl}-urea, trifluoroacetic acid salt In a dry flask (3R,4S)-3-[3-(3-acetyl-phenyl)-ureido]-4-[(S)-3-(4-fluoro-benzyl)-piperidine-1-carbonyl]-piperidine-1-carboxylic acid t-butyl ester (25 mg, 0.043 mmol) was dissolved in trifluoroacetic acid. The reaction mixture was stirred for 4 hours. The reaction mixture was concentrated in vacuo then purified by preparative reverse-phase HPLC (10–90% acetonitrile in water with 0.05% trifluoroacetic acid) to give a white amorphous solid (19 mg, 50%). $^1$H NMR (300 MHz, CDCl₃), δ: 9.25 (bs, 2H), 8.26 (bs, 1H), 7.96 (m, 1H), 7.52 (m, 1H), 7.38 (m, 2H), 7.15 (m, 1H), 6.94 (m, 4H), 4.40 (m, 1H), 4.16 (m, 1H), 3.76 (m, 1H), 3.64 (m, 1H), 3.33 (m, 1H), 3.27 (m, 1H), 3.04 (m, 1H), 2.68 (m, 2H), 2.50 (s, 3H), 2.39 (m, 1H), 1.81 (m, 2H), 1.81 (m, 2H), 1.66 (m, 2H), 1.39 (m, 2H), 1.26 (m, 1H). HRMS (ESI), $C_{27}H_{36}FN_4O_2$ m⁺/z: calc.=481.2615, found=481.2622.

Example 15

Part A: Preparation of (3R,4R)-4-amino-3-[(S)-3-(4-fluoro-benzyl)-piperidin-1-ylmethyl]-piperidine-1-carboxylic acid t-butyl ester In a dry flask (3R,4R)-4-amino-3-[(S)-3-(4-fluoro-benzyl)-piperidine-1-carbonyl]-piperidine-1-carboxylic acid t-butyl ester (500 mg, 1.19 mmol) was dissolved in borane (50 mL of a 1M solution in tetrahydrofuran, 50 mmol). The reaction was stirred 19 hours. The reaction was poured into hydrochloric acid (70 mL of a 1M aqueous solution) and stirred vigorously for 4 hours. The reaction mixture was neutralized with saturated aqueous sodium bicarbonate. The layers were separated and the aqueous layer was extracted with ethyl acetate. The organic layers were combined, dried with magnesium sulfate, filtered and concentrated in vacuo. The mixture was purified by flash chromatography using 5–20% methanol in chloroform to give a yellow solid (371 mg, 77%). ¹H NMR (300 MHz, CDCl₃), δ: 7.08 (m, 2H), 6.97 (t, 2H, J=8), 4.08 (bs, 2H), 3.70 (bs, 1H), 3.34 (bs, 1H), 3.02 (bt, 1H, J=9), 2.68 (bm, 2H), 2.32 (bm, 7H), 1.98 (m, 1H), 1.75 (m, 5H), 1.44 (s, 9H), 0.89 (m, 1H).

Part B: Preparation of (3R,4R)-4-[3-(3-acetyl-phenyl)-ureido]-3-[(S)-3-(4-fluoro-benzyl)-pipiperidin-1-ylmethyl]-piperidine-1-carboxylic acid t-butyl ester, trifluoroacetic acid salt In a dry flask (3R,4R)-4-amino-3-[(S)-3-(4-fluoro-benzyl)-piperidin-1-ylmethyl]-piperidine-1-carboxylic acid t-butyl ester (42 mg, 0.103 mmol) was dissolved in tetrahydrofuran (2 mL) and triethylamine (20 μL, 0.143 mmol) and 3-acetylphenylisocyanate (17 μL, 0.124 mmol) were added. The reaction mixture was stirred for 16 hours. The reaction mixture was concentrated in vacuo and purified by preparative reverse-phase HPLC (10–80% acetonitrile in water with 0.05% trifluoroacetic acid) to give a white amorphous solid (56 mg, 74%). ¹H NMR (300 MHz, CD₃OD), δ: 8.04 (s, 1H), 7.64 (d, 1H, J=8), 7.58 (d, 1H, J=8), 7.39 (t, 1H, J=8), 7.18 (m, 2H), 6.99 (t, 2H, J=9), 4.02 (d, 1H, J=12), 3.86 (d, 1H, J=14), 3.62 (s, 4H), 3.53 (d, 2H, J=10), 3.24 (m, 2H), 3.08 (m, 2H), 2.93 (m, 2H), 2.62 (m, 2H), 2.56 (s, 3H), 1.97 (m, 4H), 1.77 (m, 2H), 1.57 (m, 1H), 1.46 (s, 9H), 1.23 (m, 1H). HRMS (ESI), $C_{32}H_{44}FN_4O_4$ m⁺/z: calc.=567.3346, found=567.3352.

Example 16

Preparation of 1-(3-acetyl-phenyl)-3-{(3S,4R)-3-[(S)-3-(4-fluoro-benzyl)-piperidin-1-ylmethyl]-piperidin-4-yl}-urea, bistrifluoroacetic acid salt In a dry flask (3R,4R)-4-[3-(3-acetyl-phenyl)-ureido]-3-[(S)-3-(4-fluoro-benzyl)-piperidin-1-ylmethyl]-piperidine-1-carboxylic acid t-butyl ester (31 mg, 0.055 mmol) was dissolved in dichloromethane (1.5 mL) and trifluoroacetic acid (0.5 mL) was added. The reaction mixture was stirred for 4 hours. The reaction mixture was concentrated in vacuo then purified by preparative reverse-phase HPLC (10–80% acetonitrile in water with 0.05% trifluoroacetic acid) to give a white amorphous solid (19 mg, 50%). ¹H NMR (300 MHz, CD₃OD), δ: 8.06 (s, 1H), 7.62 (m, 2H), 7.38 (m, 2H), 7.14 (m, 2H), 6.95 (t, 2H, J=9), 3.70 (m, 2H), 3.49 (m, 3H), 3.33 (m, 2H), 3.04 (m, 4H), 2.63 (m, 2H), 2.56 (s, 3H), 2.49 (m, 2H), 2.16 (m, 2H), 1.90 (m, 2H), 1.74 (m, 2H), 1.19 (m, 1H). HRMS (ESI), $C_{27}H_{36}FN_4O_2$ m⁺/z: calc.=467.2822, found=467.2822.

Example 17

Preparation of 1-{(3R,4R)-1-acetyl-3-[(S)-3-(4-fluoro-benzyl)-piperidin-1-ylmethyl]-piperidin-4-yl}-3-(3-acetyl-phenyl)-urea, trifluoroacetic acid salt In a dry flask 1-(3-acetyl-phenyl)-3-{(3R,4R)-3-[(S)-3-(4-fluoro-benzyl)-piperidin-1-ylmethyl]-piperidin-4-yl}-urea (55 mg, 0.079 mmol) was dissolved in dichloromethane (2 mL), and then triethylamine (55 μL, 0.39 mmol) and acetyl chloride (10 μL, 0.14 mmol) were added. The reaction mixture was stirred for 21 hours. The reaction mixture was concentrated in vacuo then was purified by preparative reverse-phase HPLC (10–80% acetonitrile in water with 0.05% trifluoroacetic acid) to give a white amorphous solid (26 mg, 53%). ¹H NMR (400 MHz, DMSO-d6, 60° C.), δ: 8.97 (bs, 1H), 8.79 (s, 1H), 8.01 (s, 1H), 7.63 (d, 1H, J=8), 7.53 (d, 1H, J=8), 7.39 (t, 1H, J=8), 7.20 (m, 2H), 7.08 (t, 2H, J=9), 6.45 (bs, 1H), 4.26 (m, 1H), 3.98 (bm, 2H), 3.61 (m, 2H), 3.47 (m, 2H), 3.26 (bs, 1H), 3.07 (m, 2H), 2.89 (bs, 1H), 2.61 (m, 2H), 2.52 (s, 3H), 2.01 (m, 5H), 1.84 (m, 2H), 1.59 (bm, 3H), 1.12 (m, 1H). HRMS (ESI), $C_{29}H_{38}FN_4O_3$ m⁺/z: calc. 509.2928, found=509.2942.

Example 18

Preparation of 1-(3-acetyl-phenyl)-3-{(3R,4R)-3-[(S)-3-(4-fluoro-benzyl)-piperidin-1-ylmethyl]-1-methanesulfonyl-piperidin-4-yl}-urea, trifluoroacetic acid salt In a dry flask 1-(3-acetyl-phenyl)-3-{(3R,4R)-3-[(S)-3-(4-fluoro-benzyl)-piperidin-1-ylmethyl]-piperidin-4-yl}-urea (70 mg, 0.10 mmol) was dissolved in dichloromethane (2 mL), and then triethylamine (140 μL, 1.0 mmol) and methanesulfonyl chloride (8 μL, 0.10 mmol) were added. The reaction mixture was stirred for 2 hours at 0° C. The reaction mixture was quenched with water, concentrated in vacuo then was purified by preparative reverse-phase HPLC (10–80% acetonitrile in water with 0.05% trifluoroacetic acid) to give a white amorphous solid (31 mg, 47%). ¹H NMR (300 MHz, CD₃OD), δ: 8.04 (s, 1H), 7.61 (m, 2H), 7.40 (t, 1H, J=12), 7.18 (m, 2H), 6.99 (t, 2H, J=9), 3.62 (bm, 6H), 3.13 (m, 3H), 2.93 (m, 2H), 2.87 (s, 3H), 2.59 (m, 2H), 2.56 (s, 3H), 2.23 (bs, 1H), 1.98 (bm, 3H), 1.77 (m, 3H), 1.20 (m, 1H). HRMS (ESI), $C_{28}H_{38}FN_4O_4S$ m⁺/z: calc. 545.2598, found=545.2591.

Example 19

Preparation of 1-(3-acetyl-phenyl)-3-{(3S,4R)-3-[(S)-3-(4-fluoro-benzyl)-piperidin-1-ylmethyl]-1-methyl-piperidin-4-yl}-urea, bistrifluoroacetic acid salt In a dry flask 1-(3-acetyl-phenyl)-3-{(3R,4R)-3-[(S)-3-(4-fluoro-benzyl)-piperidin-1-ylmethyl]-piperidin-4-yl}-urea (83 mg, 0.12 mmol) was dissolved in dichloroethane (5 mL), and then a solution of formaldehyde (240 μL in tetrahydrofuran) was added. The reaction mixture was stirred for 5 minutes then triacetoxyborohydride (41 mg, 0.19 mmol) was added. The mixture was stirred an additional 3 hours. The reaction was quenched with saturated aqueous sodium bicarbonate (1 mL) then diluted with water. The mixture was extracted with dichloromethane three times, dried with magnesium sulfate, filtered and concentrated in vacuo. Then it was purified by preparative reverse-phase HPLC (10–80% acetonitrile in water with 0.05% trifluoroacetic acid) to give a white amorphous solid (47 mg, 55%). $^1$H NMR (300 MHz, CD$_3$OD), δ: 8.07 (s, 1H), 7.62 (m, 2H), 7.40 (t, 1H, J=8), 7.14 (m, 2H), 6.96 (t, 2H, J=9), 3.74 (m, 2H), 3.55 (m, 3H), 3.35 (m, 2H), 3.07 (bm, 4H), 2.90 (s, 3H), 2.65 (m, 2H), 2.56 (s, 3H), 2.47 (m, 1H), 2.05 (bm, 4H), 1.73 (m, 2H), 1.17 (m, 1H). HRMS (ESI), C$_{28}$H$_{38}$FN$_4$O$_2$ m$^+$/z: calc. 481.2978, found=481.2986.

Example 20

Preparation of 1-(3-acetyl-phenyl)-3-{(3R,4R)-3-[(S)-3-(4-fluoro-benzyl)-piperidin-1-ylmethyl]-1-isobutyl-piperidin-4-yl}-urea, bistrifluoroacetic acid salt In a dry flask 1-(3-acetyl-phenyl)-3-{(3R,4R)-3-[(S)-3-(4-fluoro-benzyl)-piperidin-1-ylmethyl]-piperidin-4-yl}-urea (97 mg, 0.14 mmol) was dissolved in dichloroethane (5 mL), and i-butyraldehyde (15 μL, 0.165 mmol) was added. The reaction mixture was stirred for 5 minutes then triacetoxyborohydride (46 mg, 0.22 mmol) was added. The mixture was stirred an additional 2 hours. The reaction was quenched with saturated aqueous sodium bicarbonate (1 mL) then diluted with water. The mixture was extracted with dichloromethane three times, dried with magnesium sulfate, filtered and concentrated in vacuo. Then it was purified by preparative reverse-phase HPLC (10–80% acetonitrile in water with 0.05% trifluoroacetic acid) to give a white amorphous solid (38 mg, 36%). $^1$H NMR (300 MHz, CD$_3$OD), δ: 8.07 (s, 1H), 7.61 (m, 2H), 7.41 (m, 1H), 7.14 (m, 2H), 6.96 (m, 2H), 3.90 (bs, 1H), 3.61 (bm, 4H), 3.32 (m, 2H), 3.01 (bm, 6H), 2.62 (m, 2H), 2.56 (s, 3H), 2.49 (bs, 1H), 2.12 (bm, 4H), 1.88 (m, 1H), 1.73 (m, 2H), 1.17 (m, 1H), 1.03 (m, 6H) HRMS (ESI), C$_{31}$H$_{44}$FN$_4$O$_2$ m$^+$/z: calc. 523.3448, found=523.3453.

Example 21

Preparation of (3R,4R)-3-[(S)-3-(4-fluoro-benzyl)-piperidin-1-ylmethyl]-4-{3-[3-(1-methyl-1H-tetrazol-5-yl)-phenyl]-ureido}-piperidine-1-carboxylic acid t-butyl ester, trifluoroacetic acid salt In a dry flask (3R,4R)-4-amino-3-[(S)-3-(4-fluoro-benzyl)-piperidin-1-ylmethyl]-piperidine-1-carboxylic acid t-butyl ester (43 mg, 0.11 mmol) was dissolved in dimethylformamide (1 mL) and [3-(1-methyl-1H-tetrazol-5-yl)-phenyl]-carbamic acid phenyl ester (36 mg, 0.12 mmol) was added. The reaction mixture was stirred for 16 hours. The reaction mixture was diluted with ethyl acetate and extracted twice with water and once with brine. The combined organic extract was dried with sodium sulfate, filtered and concentrated in vacuo. Half of the resulting oil was purified by preparative reverse-phase HPLC (10–80% acetonitrile in water with 0.05% trifluoroacetic acid) to give a white amorphous solid (24 mg, 63%). $^1$H NMR (300 MHz, CD$_3$OD), δ: 7.98 (s, 1H), 7.52 (m, 2H), 7.42 (m, 1H), 7.17 (m, 2H), 6.99 (t, 2H, J=8), 4.18 (s, 3H), 4.03 (d, 1H, J=14), 3.86 (d, 1H, J=14), 3.64 (td, 1H, J=9, J'=5), 3.54 (d, 2H, J=13), 3.25 (m, 2H), 3.09 (m, 2H), 2.94 (t, 2H, J=10), 2.60 (m, 3H), 2.03 (bs, 2H), 1.94 (d, 2H, J=14), 1.77 (t, 2H, J=11), 1.57 (m, 1H), 1.46 (s, 9H), 1.21 (m, 1H). HRMS (ESI), C$_{32}$H$_{44}$FN$_8$O$_3$ m$^+$/z: calc.=607.3521, found=607.3518.

Example 22

Preparation of 1-{(3S,4R)-3-[(S)-3-(4-fluoro-benzyl)-piperidin-1-ylmethyl]-piperidin-4-yl}-3-[3-(1-methyl-1H-tetrazol-5-yl)-phenyl]-urea, bistrifluoroacetic acid salt In a dry flask (3R,4R)-3-[(S)-3-(4-fluoro-benzyl)-piperidin-1-ylmethyl]-4-{3-[3-(1-methyl-1H-tetrazol-5-yl)-phenyl]-ureido}-piperidine-1-carboxylic acid t-butyl ester (48 mg, 0.079 mmol) was dissolved in dichloromethane (1.5 mL), and trifluoroacetic acid (0.5 mL) was added. The reaction mixture was stirred for 3 hours. The reaction mixture was concentrated in vacuo then purified by preparative reverse-phase HPLC (10–80% acetonitrile in water with 0.05% trifluoroacetic acid) to give a white amorphous solid (22 mg, 38%). $^1$H NMR (500 MHz, CD$_3$OD, 30° C.), δ: 8.01 (t, 1H, J=1), 7.59 (dq, 1H, J=8, J'=1), 7.52 (t, 1H, J=8), 7.43 (dt, 1H, J=8, J'=1), 7.17 (m, 2H), 6.96 (t, 2H, J=9), 4.18 (s, 3H), 3.73 (m, 2H), 3.51 (m, 3H), 3.38 (d, 1H, J=13), 3.13 (m, 2H), 2.99 (m, 2H), 2.64 (dd, 2H, J=14, J'=6), 2.50 (bs, 2H), 2.21 (m, 1H), 2.11 (bs, 1H), 1.92 (m, 2H), 1.76 (m, 2H), 1.19 (m, 1H). HRMS (ESI), C$_{27}$H$_{36}$FN$_8$O M$^+$/z: calc. 507.2996, found=507.2976.

Example 23

Preparation of 5-(3-{(3R,4R)-1-t-butoxycarbonyl-3-[(S)-3-(4-fluoro-benzyl)-piperidin-1-ylmethyl]-piperidin-4-yl}-ureido)-indazole-1-carboxylic acid t-butyl ester, trifluoroacetic acid salt In a dry flask (3R,4R)-4-amino-3-[(S)-3-(4-fluoro-benzyl)-piperidin-1-ylmethyl]-piperidine-1-carboxylic acid t-butyl ester (48 mg, 0.118 mmol) was dissolved in dimethylformamide (1 mL) and 5-(phenoxycarbonylamino)-1-indazolecarboxylic acid 1-tert-butyl ester (47 mg, 0.133 mmol) was added. The reaction mixture was stirred for 16 hours. The reaction mixture was diluted with ethyl acetate, washed twice with water and once with brine.

The organic layer was dried with magnesium sulfate, filtered and concentrated in vacuo. Half of the crude product was purified by preparative reverse-phase HPLC (10–80% acetonitrile in water with 0.05% trifluoroacetic acid) to give a white amorphous solid (26 mg, 57%). $^1$H NMR (300 MHz, CD$_3$OD), δ: 8.20 (s, 1H) 8.02 (d, 1H, J=9), 35 7.95 (s, 1H), 7.47 (dd, 1H, J=9, J'=2), 7.17 (m, 2H), 6.99 (t, 2H, J=9), 4.02 (d, 1H, J=10), 3.89 (m, 1H), 3.64 (m, 1H), 3.52 (m, 2H), 3.25 (m, 2H), 3.10 (m, 2H), 2.94 (m, 2H), 2.61 (m, 4H), 1.97 (m, 4H), 1.78 (m, 2H), 1.69 (s, 9H), 1.57 (m, 1H), 1.46 (s, 9H), 1.20 (m, 1H). HRMS (ESI), C$_{36}$H$_{50}$FN$_6$O$_5$ m$^+$/z: calc.= 665.3827, found=665.3835.

Example 24

Preparation of 5-(3-{(3S,4R)-3-[(S)-3-(4-Fluoro-benzyl)-piperidin-1-ylmethyl]-piperidin-4-yl}-ureido)-indazole-1-carboxylic acid t-butyl ester, bistrifluoroacetic acid salt In a dry flask 5-(3-{(3R,4R)-1-t-butoxycarbonyl-3-[(S)-3-(4-fluoro-benzyl)-piperidin-1-ylmethyl]-piperidin-4-yl}-ureido)-indazole-1-carboxylic acid t-butyl ester (56 mg, 0.084 mmol) was dissolved in dichloromethane (1.5 mL) and trifluoroacetic acid (0.5 mL) was added. The reaction mixture was stirred for 3 hours. The reaction mixture was concentrated in vacuo then purified by preparative reverse-phase HPLC (10–80% acetonitrile in water with 0.05% trifluoroacetic acid) to give a white amorphous solid (29 mg, 43%). $^1$H NMR (300 MHz, CD$_3$OD), δ: 7.95 (s, 1H), 7.84 (s, 1H), 7.46 (d, 1H, J=9), 7.32 (dd, 1H, J=9, J'=2), 7.13 (m, 2H), 6.95 (t, 2H, J=9), 3.73 (m, 2H), 3.51 (m, 3H), 3.31 (m, 2H), 3.12 (m, 3H), 2.98 (t, 2H, J=12), 2.64 (m, 2H), 2.49 (m, 2H), 2.16 (m, 2H), 1.91 (m, 2H), 1.73 (m, 2H), 1.16 (m, 1H) HRMS (ESI), C$_{26}$H$_{34}$FN$_6$O m$^+$/z: calc.=465.2778, found=465.2780.

Example 25

Preparation of (3R,4R)-4-[3-(5-acetyl-4-methyl-thiazol-2-yl)-ureido]-3-[(S)-3-(4-fluoro-benzyl)-piperidin-1-ylmethyl]-piperidine-1-carboxylic acid t-butyl ester, trifluoroacetic acid salt In a dry flask (3R,4R)-4-amino-3-[(S)-3-(4-fluoro-benzyl)-piperidin-1-ylmethyl]-piperidine-1-carboxylic acid t-butyl ester (49 mg, 0.121 mmol) was dissolved in dimethylformamide (1 mL) and 4-acetyl-3-methyl-2-(phenoxycarbonylamino)-thiazole (38 mg, 0.138 mmol) was added. The reaction mixture was stirred for 16 hours. The reaction mixture was diluted with ethyl acetate, washed twice with water and once with brine. The organic layer was dried with magnesium sulfate, filtered and concentrated in vacuo. Half of the crude product was purified by preparative reverse-phase HPLC (10–80% acetonitrile in water with 0.05% trifluoroacetic acid) to give a white amorphous solid (18 mg, 42%). $^1$H NMR (300 MHz, CD$_3$OD), δ: 7.18 (t, 2H, J=8), 7.00 (t, 2H, J=8), 4.01 (d, 1H, J=11), 3.84 (d, 1H, J=14), 3.68 (m, 1H), 3.53 (d, 2H, J=10), 3.16 (bm, 5H), 2.94 (t, 2H, J=10), 2.59 (m, 3H), 2.55 (s, 3H), 2.46 (s, 3H), 2.06 (bs, 2H), 1.91 (m, 2H), 1.77 (m, 2H), 1.59(m, 1H), 1.46 (s, 9H), 1.23 (m, 1H). HRMS (ESI), C$_{30}$H$_{43}$FN$_5$O$_4$S m$^+$/z: calc.=588.3020, found=588.3040.

Example 26

Preparation of 1-(5-acetyl-4-methyl-thiazol-2-yl)-3-{(3S,4R)-3-[(S)-3-(4-fluoro-benzyl)-piperidin-1-ylmethyl]-piperidin-4-yl}-urea, bistrifluoroacetic acid salt In a dry flask (3R,4R)-4-[3-(5-acetyl-4-methyl-thiazol-2-yl)-ureido]-3-[(S)-3-(4-fluoro-benzyl)-piperidin-1-ylmethyl]-piperidine-1-carboxylic acid t-butyl ester (47 mg, 0.080 mmol) was dissolved in dichloromethane (1.5 mL) and trifluoroacetic acid (0.5 mL) was added. The reaction mixture was stirred for 3 hours. The reaction mixture was concentrated in vacuo then purified by preparative reverse-phase HPLC (10–80% acetonitrile in water with 0.05% trifluoroacetic acid) to give a white amorphous solid (24 mg, 42%). $^1$H NMR (300 MHz, CD$_3$OD), δ: 7.15 (m, 2H), 6.98 (t, 2H, J=9), 3.74 (m, 2H), 3.48 (m, 3H), 3.05 (bm, 5H), 2.59 (bm, 4H), 2.56 (s, 3H), 2.46 (s, 3H), 1.94 (bm, 4H), 1.74 (d, 2H, J=13), 1.16 (m, 1H). HRMS (ESI), C$_{25}$H$_{35}$FN$_5$O$_2$S m$^+$/z: calc.=488.2499, found=488.2496.

Example 27

Part A: Preparation of (3R,4S)-3-amino-4-[(S)-3-(4-fluoro-benzyl)-piperidin-1-ylmethyl]-piperidine-1-carboxylic acid t-butyl ester In a dry flask (3R,4R)-3-[3-(3-acetyl-phenyl)-ureido]-4-[(S)-3-(4-fluoro-benzyl)-piperidine-1-carbonyl]-piperidine-1-carboxylic acid t-butyl ester (1.19 g, 2.84 mmol) was dissolved in borane (100 mL of a 1M solution in tetrahydrofuran, 100 mmol). The reaction was stirred 19 hours. The reaction mixture was concentrated in vacuo and redissolved in 800 mL of ethyl acetate. The solution was poured into hydrochloric acid (140 mL of a 1M aqueous solution) and stirred vigorously for 16 hours. The reaction mixture was neutralized with saturated aqueous sodium bicarbonate. The layers were separated and the aqueous layer was extracted with ethyl acetate. The organic layers were combined, dried with magnesium sulfate, filtered and concentrated in vacuo. The mixture was purified by flash chromatography using 20–0% hexane/ethyl acetate to give a light yellow solid (0.259 g, 22%). $^1$H NMR (300 MHz, CD$_3$OD), δ: 7.18 (m, 2H), 7.04 (m, 2H), 4.37 (m, 2H), 4.19 (m, 2H), 3.47 (m, 1H), 3.20 (m, 1H), 2.89 (m, 1H), 2.68 (m, 2H), 2.52 (m, 4H), 1.88 (m, 2H), 1.75 (m, 2H), 1.55 (m, 2H), 1.45 (m, 2H), 1.44 (s, 9H). MS (ESI), m$^+$/z: (M+H)$^+$=406.

Part B: Preparation of (3R,4S)-4-[3-(3-acetyl-phenyl)-ureido]-3-[(S)-3-(4-fluoro-benzyl)-piperidin-1-ylmethyl]-piperidine-1-carboxylic acid t-butyl ester, trifluoroacetic acid salt In a dry flask (3R,4S)-4-amino-3-[(S)-3-(4-fluoro-benzyl)-piperidin-1-ylmethyl]-piperidine-1-carboxylic acid t-butyl ester (207 mg, 0.511 mmol) was dissolved in tetrahydrofuran (2 mL) and triethylamine (140 μL, 101 mmol) and 3-acetylphenylisocyanate (68 μL, 0.496 mmol) were added. The reaction mixture was stirred for 16 hours. The reaction mixture was concentrated in vacuo and purified by preparative reverse-phase HPLC (10–80% acetonitrile in water with 0.05% trifluoroacetic acid) to give a white amorphous solid (193 mg, 69%). $^1$H NMR (300 MHz, CD$_3$OD), δ: 8.57 (m, 1H), 8.20 (m, 1H), 7.60 (m, 2H), 6.90 (m, 4H), 4.28 (m, 2H), 3.66 (m, 2H), 3.30 (m, 2H), 2.33–2.61 (m, 12H), 2.02 (m, 2H), 1.79 (m, 2H), 1.65 (m, 2H), 1.46 (s, 9H). HRMS (ESI), C$_{32}$H$_{44}$FN$_4$O$_4$ m$^+$/z: calc.=567.3347, found=567.3346.

Example 28

Preparation of 1-(3-acetyl-phenyl)-3-{(3R,4S)-4-[(S)-3-(4-fluoro-benzyl)-piperidin-1-ylmethyl]-piperidin-3-yl}-urea, bistrifluoroacetic acid salt In a dry flask (3R,4S)-4-[3-(3-acetyl-phenyl)-ureido]-3-[(S)-3-(4-fluoro-benzyl)-piperidin-1-ylmethyl]-piperidine-1-carboxylic acid t-butyl ester was trifluoroacetic acid (10 mL) was added. The reaction mixture was stirred for 10 minutes. The reaction mixture was concentrated in vacuo then purified by preparative reverse-phase HPLC (10–80% acetonitrile in water with 0.05% trifluoroacetic acid) to give a white amorphous solid (13 mg, 38%). $^1$H NMR (400 MHz, DMSO-d6, 120° C.), δ: 10.02 (bs, 1H), 9.64 (bs, 1H), 9.25 (bs, 1H), 8.20 (s, 1H), 7.93 (bs, 1H), 7.51 (d, J=6, 1H), 7.33 (m, 2H), 6.99 (t, J=6, 2H), 6.88 (t, J=6, 2H), 3.91 (m, 1H), 3.78 (m, 1H), 3.67 (m, 1H), 3.43 (m, 2H), 3.09 (m, 2H), 2.80 (m, 2H), 2.55 (s, 3H), 2.53 (m, 3H), 2.22 (m, 2H), 1.82 (m, 6H), 1.08 (m, 1H). HRMS (ESI), C$_{27}$H$_{34}$FN$_4$O$_3$ m$^+$/z: calc.=467.2822, found=467.2828.

Example 29

Part A: Preparation of (3S,4R)-4-[(R)-1-Phenyl-ethylamino]-piperidine-1,3-dicarboxylic acid 1-tert-butyl ester In a dry flask (3R,4R)-4-[(R)-1-Phenyl-ethylamino]-piperidine-1,3-dicarboxylic acid 1-tert-butyl ester 3-methyl ester (4.50 g, 12.4 mmol) was dissolved in tetrahydrofuran (170 mL) and t-butanol (11 mL), and sodium t-butoxide (04.85 g, 50.5 mmol) was added. The reaction mixture was stirred for 16 hours. Water was added and the mixture was extracted with ethyl acetate five times. There was minimal residue after concentration in vacuo of the combined organic extracts. The aqueous extract was acidified to pH 3 with 1N hydrochloric acid, saturated with sodium chloride and then extracted five times with ethyl acetate. The combined organic layers were dried with magnesium sulfate, filtered and concentrated in vacuo to give an orange glass (2.11 g, 49%). MS (ESI), m$^+$/z: (M+H)$^+$=349.2.

Part B: Preparation of (3S,4R)-4-amino-piperidine-1,3-dicarboxylic acid 1-tert-butyl ester In a dry 500-mL Paar flask charged with Palladium hydroxide (20 wt % Pd, dry basis, on carbon, 0.22 g) was added methanol (50 mL) and (3S,4R)-4-[(R)-1-Phenyl-ethylamino]-piperidine-1,3-dicarboxylic acid 1-tert-butyl ester (2.11 g, 6.05 mmol). The reaction mixture was hydrogenated at 53 psi for 42 hours with vigorous shaking. The reaction mixture was filtered through a plug of celite. The plug was washed with 20 mL of ethanol and the combined filtrates were concentrated in vacuo to give a colorless oil (1.32 g, 89%). $^1$H NMR (300 MHz, CDCl$_3$), δ: 4.38 (bd, J=12, 1H), 4.16 (m, 1H), 3.30 (m, 1H), 2.70 (m, 2H), 1.90–2.40 (m, 5H), 1.45 (s, 9H). MS (ESI), m$^+$/z: (M+H)$^+$=245.1.

Part C: Preparation of (3S,4R)-4-benzyloxycarbonylamino-piperidine-1,3-dicarboxylic acid 1-t-butyl ester In a dry flask (3S,4R)-4-aminopiperidine-1,3-dicarboxylic acid 1-tert-butyl ester (1.32 g, 5.40 mmol) was dissolved in dichloromethane (30 mL) and triethylamine (1.0 mL, 7.2 mmol) and benzyl chloroformate (0.94 mL, 5.9 mmol) were added. The mixture was stirred for 18 hours. Water (30 mL) was added and the layers separated. The aqueous layer was extracted with dichloromethane (30 mL). The combined organic layers were washed with brine, dried with magnesium sulfate, filtered, and concentrated in vacuo to give a crude oil (2.13 g). Purification by flash column chromatography (5–20% methanol/chloroform) provided a colorless oil (1.29 g, 63%). $^1$H NMR (400 MHz, DMSO-d6, 120° C.), δ: 7.34 (m, 5H), 6.76 (bs, 1H), 5.04 (s, 2H), 4.01, (bs, 1H), 3.78 (dd, J=14, J'=7, 1H), 3.47 (m, 2H), 3.26 (m, 1H), 2.67 (dt, J=7, J'=4, 1H), 2.49 (m, 1H), 1.79 (m, 1H), 1.59 (m, 1H), 1.40 (s, 9H). MS (ESI), m$^+$/z: (M+Na)$^+$=401.

Part D: Preparation of (3S,4R)-4-benzyloxycarbonylamino-3-[(S)-3-(4-fluoro-benzyl)-piperidine-1-carbonyl]-piperidine-1-carboxylic acid t-butyl ester In a dry flask (3S,4R)-4-benzyloxycarbonylamino-piperidine-1,3-dicarboxylic acid 1-tert-butyl ester (0.18 g, 0.48 mmol) was dissolved in dichloromethane (7 mL) and then triethylamine (150 μL, 1.08 mmol) and benzotriazol-1-yloxy-tripyrrolidinophosphonium hexafluorophosphate (0.30 g, 0.58 mmol) were added. The reaction was stirred 18 hours. The reaction mixture was diluted with dichloromethane (25 mL) and extracted twice with water (15 mL). The combined aqueous extracts were extracted with dichloromethane (25 mL). The combined organic extracts were dried with magnesium sulfate, filtered and concentrated in vacuo. The mixture was purified by flash chromatography with 50% ethyl acetate/hexanes to give a white solid (153 mg, 56%). $^1$H NMR (300 MHz, CDCl$_3$), δ: 7.33 (m, 5H), 7.02 (m, 4H), 5.55 (m, 1H), 5.08 (m, 2H), 4.19–4.48 (m, 1H), 3.96 (bs, 1H), 3.50 (m, 5H), 3.00 (m, 1H), 2.51 (m, 4H), 2.05 (m, 1H), 1.63 (m, 5H), 1.42 (s, 9H), 1.20 (m, 1H). MS (ESI), m$^+$/z: (M+H)$^+$=554.4.

Part E: Preparation of (3S,4R)-4-amino-3-[(S)-3-(4-fluoro-benzyl)-piperidine-1-carbonyl]-piperidine-1-carboxylic acid t-butyl ester In a dry 500-mL Paar flask charged with palladium (10 wt % Pd, dry basis, on carbon, 31 mg) was added methanol (10 mL) and (3S,4R)-4-benzyloxycarbonylamino-3-[(S)-3-(4-fluoro-benzyl)-piperidine-1-carbonyl]-piperidine-1-carboxylic acid t-butyl ester (150 mg, 2.08 mmol). The reaction mixture was hydrogenated at 45 psi for 20.5 hours with vigorous shaking. The reaction mixture was filtered through a plug of celite. The plug was washed with 20 mL of ethanol and the combined filtrates were concentrated in vacuo to give a colorless oil (111 mg, 98%). $^1$H NMR (300 MHz, CDCl$_3$), δ: 8.75 (bs, 2H), 7.09 (m, 2H), 6.97 (m, 2H), 4.30 (m, 1H), 4.01 (m, 2H), 3.70 (m, 2H), 3.25 (m, 1H), 3.10 (m, 1H), 2.75 (m, 1H), 2.48 (m, 4H), 1.82 (m, 5H), 1.42 (s, 9H), 1.21 (m, 2H). MS (ESI), m$^+$/z: (M+H)$^+$=420.3.

Part F: Preparation of (3S,4R)-4-[3-(3-acetyl-phenyl)-ureido]-3-[(S)-3-(4-fluoro-benzyl)-piperidine-1-carbonyl]-piperidine-1-carboxylic acid t-butyl ester In a dry flask (3S,4R)-4-amino-3-[(S)-3-(4-fluoro-benzyl)-piperidine-1-carbonyl]-piperidine-1-carboxylic acid t-butyl ester (43 mg, 0.10 mmol) was dissolved in tetrahydrofuran (2 mL) and then triethylamine (19 μL, 0.14 mmol) and 3-acetylphenylisocyanate (17 μL, 0.12 mmol) were added. After stirring for 18 hours, removed half of the reaction mixture for purification. The remainder of the reaction mixture was taken onto the next reaction without purification. The aliquot was purified by preparative reverse-phase HPLC (10–80% acetonitrile in water with 0.05% trifluoroacetic acid) to give a white amorphous solid (17 mg, 57%). $^1$H NMR (400 MHz, DMSO-d6, 120° C.), δ: 8.64 (s, 1H), 7.94 (m, 1H), 7.57 (d, J=8, 1H), 7.46 (d, J=8, 1H), 7.33 (t, J=8, 1H), 7.17 (m, 2H), 7.00 (t, J=9, 2H), 6.13 (d, J=8, 1H), 4.07 (m, 1H), 3.87 (m, 1H), 3.61 (m, 1H), 3.42 (dd, J=14, J'=4, 1H), 3.32 (m, 1H), 2.98 (m, 2H), 2.70 (m, 1H), 2.50 (m, 1H), 2.49 (s, 3H), 2.02 (m, 1H), 1.73 (m, 3H), 1.53 (m, 1H), 1.39 (s, 9H), 1.22 (m, 2H). HRMS (ESI), C$_{32}$H$_{42}$FN$_4$O$_5$ m$^+$/z: calc.=581.3139, found=581.3149.

Example 30

Preparation of 1-(3-acetyl-phenyl)-3-{(3S,4R)-3-[(S)-3-(4-fluoro-benzyl)-piperidine-1-carbonyl]-piperidin-4-yl}-urea, trifluoroacetic acid salt In a dry flask (3S,4R)-4-[3-(3-acetyl-phenyl)-ureido]-3-[(S)-3-(4-fluoro-benzyl)-piperidine-1-carbonyl]-piperidine-1-carboxylic acid t-butyl ester (17 mg, 0.029 mmol in 1 mL of tetrahydrofuran) was concentrated in vacuo, redissolved in dichloromethane (1 mL), and trifluoroacetic acid (0.5 mL) was added. The reaction mixture was stirred for 4 hours. The reaction mixture was concentrated in vacuo then purified by preparative reverse-phase HPLC (10–80% acetonitrile in water with 0.05% trifluoroacetic acid) to give a white amorphous solid (13 mg, 38%). $^1$H NMR (400 MHz, DMSO-d6, 120° C.), δ: 8.49 (s, 1H), 8.24 (bs, 2H), 7.93 (s, 1H), 7.58 (d, J=9, 1H), 7.49 (d, J=7, 1H), 7.35 (t, J=8, 1H), 7.12 (t, J=8, 2H), 6.97 (t, J=9, 2H), 6.28 (d, J=8, 1H), 4.17

(m, 1H), 3.83 (m, 1H), 3.46 (bs, 1H), 3.27 (m, 1H), 3.13 (m, 3H), 2.97 (m, 3H), 2.47 (s, 3H), 2.01 (m, 1H), 1.82 (m, 2H), 1.67 (m, 2H), 1.37 (m, 1H), 1.20 (m, 1H). HRMS (ESI), $C_{27}H_{34}FN_4O_3$ m$^+$/z: calc.=481.2615, found=481.2632.

Example 31

Preparation of (3R,4R)-4-[3-(3-acetyl-phenyl)-ureido]-3-[(S)3-(4-fluoro-benzyl)-piperidin-1-ylmethyl]-piperidine-1-carboxylic acid methyl ester, trifluoroacetic acid salt In a dry flask 1-(3-acetyl-phenyl)-3-{(3R,4R)-3-[(S)-3-(4-fluoro-benzyl)-piperidin-1-ylmethyl]-piperidin-4-yl}-urea (47 mg, 0.07 mmol) was dissolved in dichloromethane (2 mL), and then triethylamine (70 µL, 0.50 mmol) and methyl chloroformate (7 µL, 0.09 mmol) were added. The reaction mixture was stirred for 17 hours. The reaction mixture was concentrated in vacuo then was purified by preparative reverse-phase HPLC (10–80% acetonitrile in water with 0.05% trifluoroacetic acid) to give a white amorphous solid (17 mg, 38%). $^1$H NMR (300 MHz, CD$_3$OD), δ: 8.04 (s, 1H), 7.63 (d, 1H, J=8), 7.57 (d, 1H), J=10), 7.39 (t, 1H, J=8), 7.18 (m, 2H), 6.99 (t, 2H, J=9), 4.05 (d, 1H, J=14), 3.88 (m, 1H), 3.69 (s, 3H), 3.64 (m, 1H), 3.52 (bm, 2H), 3.27 (m, 2H), 3.17–2.89 (m, 4H), 2.64 (m, 2H), 2.56 (s, 3H), 2.08 (bs, 2H), 1.94 (d, 2H, J=14), 1.77 (m, 2H), 1.60 (m, 1H), 1.23 (m, 1H). HRMS (ESI), $C_{29}H_{38}FN_4O_4$ m$^+$/z: calc.=525.2877, found=525.2879.

Example 32

Preparation of 1-(3-acetyl-phenyl)-3-{(3R,4R)-1-(2,2-dimethyl-propionyl)-3-[(S)3-(4-fluoro-benzyl)-piperidin-1-ylmethyl]-piperidin-4-yl}-urea In a dry flask 1-(3-acetyl-phenyl)-3-{(3R,4R)-3-[(S)-3-(4-fluoro-benzyl)-piperidin-1-ylmethyl]-piperidin-4-yl}-urea (43 mg, 0.07 mmol) was dissolved in dichloromethane (2 mL), and then triethylamine (65 µL, 0.47 mmol) and pivaloyl chloride (12 µL, 0.10 mmol) were added. The reaction mixture was stirred for 17 hours. The reaction mixture was concentrated in vacuo then was purified by preparative reverse-phase HPLC (10–80% acetonitrile in water with 0.05% trifluoroacetic acid) to give a white amorphous solid (18 mg, 38%). $^1$H NMR (300 MHz, CD$_3$OD), δ: 8.04 (s, 1H), 7.64 (d, 1H, J=7), 7.58 (dd, 1H, J=7, J'=1), 7.40 (t, 1H, J=8), 7.19 (m, 2H), 6.99 (t, 2H, J=9), 4.27 (d, 1H, J=14), 4.14 (d, 1H, J=15), 3.71 (m, 1H), 3.48 (bm, 3H), 3.25 (m, 2H), 3.07 (m, 1H), 2.95 (m, 2H), 2.66 (m, 2H), 2.57 (s, 3H), 1.98 (m, 4H), 1.76 (m, 2H), 1.62 (m, 1H), 1.28 (s, 9H), 1.20 (m, 1H). HRMS (ESI), $C_{32}H_{44}FN_4O_3$ m$^+$/z: calc. 551.3397, found=551.3402.

Example 44

Part A: Preparation of (R)-4-Benzyl-3-[5-(tert-butyl-diphenyl-silanyloxy)-pentanoyl]-oxazolidin-2-one To a stirring solution of pivaloyl chloride (3.39 mL, 27.5 mmol) and triethylamine (4.39 mL, 31.4 mmol) in dry ether in a flame-dried round bottom flask under N$_2$ at 0° C. was added 5-(tert-butyl-diphenyl-silanyloxy)-pentanoic acid prepared according to procedures of Barrett, A. G. M. ; et al J. Org. Chem. (1989), 54(14), 3321 (9.35 g, 26.2 mmol). The reaction was warmed to room temperature, and, after 25 min, the white precipitate was removed by filtration. The filtrate was concentrated in vacuo to a colorless oil. The oil was dissolved in dry ether (6 mL) and added via cannula to a solution of lithiated oxazolidinone prepared by treating a solution of oxazolidinone (4.64 g, 26.2 mmol) in dry THF (150 mL) in a flame-dried round bottom flask under N$_2$ at −78° C. with n-butyllithium in hexane (22.4 mL, 1.17 M) until the solution became pale yellow in color. The reaction was stirred for 40 min and then poured into 1N aqueous hydrogen chloride. The reaction was extracted with ethyl acetate (3×150 mL). The organic layers were combined, washed with saturated aqueous sodium bicarbonate, brine, dried over sodium sulfate, and concentrated in vacuo to a colorless oil. The oil was purified by flash chromatography (SiO$_2$, 5–30% ethyl acetate in hexanes) to yield 10.9 g (80.7%) of a white solid. MS (APCI), m$^+$/z: (M+H)$^+$=516.5.

Part B: Preparation of (4R)-4-Benzyl-3-{(2R,3R)-2-[3-(tert-butyl-diphenyl-silanyloxy)-propyl]-3-hydroxy-5-phenyl-pent-4-enoyl}-oxazolidin-2-one To a stirring solution of (R)-4-benzyl-3-[5-(tert-butyl-diphenyl-silanyloxy)-pentanoyl]-oxazolidin-2-one (1.64 g, 3.19 mmol) in dry methylene chloride (15.9 mL) in a flame dried round bottom flask under N$_2$ at 0° C. was added titanium(IV) chloride (386 µL, 3.51 mmol). After 5 min, (−)-sparteine (1.83 mL, 7.97 mmol) was added. After 20 min, trans-cinnamaldehyde (442 µL, 3.51 mmol) was added dropwise to the purple suspension, and the resulting pale green-yellow solution was stirred for 1 h . The reaction was quenched by the addition of 50% saturated ammonium chloride (50 mL), diluted with water (100 mL), and then extracted with methylene chloride (3×30 mL). The organic layers were combined, washed with brine, dried over sodium sulfate, and concentrated in vacuo to a colorless oil. The oil was purified by flash chromatography (SiO$_2$, 15–30% ethyl acetate in hexanes) to yield 1.72 g (83.1%) of the desired product as a white solid. MS (APCI), m$^+$/z: (M+H)$^+$=648.

Part C: Preparation of (4R)-4-Benzyl-3-[(2R,3R)-3-hydroxy-2-(3-hydroxy-propyl)-5-phenyl-pent-4-enoyl]-oxazolidin-2-one To a stirring solution of (4R)-4-benzyl-3-{(2R,3R)-2-[3-(tert-butyl-diphenyl-silanyloxy)-propyl]-3-hydroxy-5-phenyl-pent-4-enoyl}-oxazolidin-2-one (1.80 g, 2.78 mmol) in pyridine (7.20 mL) in a nalgene vial at 0° C. was added hydrogen fluoride-pyridine (3.6 mL). After 20 min, additional 1 mL aliquots of hydrogen fluoride-pyridine were added to the reaction solution until no starting material was detected by thin-layer chromatography. The reaction was made basic with saturated aqueous sodium bicarbonate, acidified with 6N aqueous hydrogen chloride (100 mL), and washed with ethyl acetate (3×50 mL). The combined organics were dried over sodium sulfate, concentrated in vacuo, and the resulting residue was purified by flash chrom. (SiO$_2$, 50–80% ethyl acetate in hexanes) to give 1.0 g (87.7%) of the desired diol as a foamy white solid. MS (ESI), m$^+$/z: (M+Na)$^+$=432.2.

Part D: Preparation of (4R)-4-Benzyl-3-[(2R,3R)-2-styryl-tetrahydro-pyran-3-carbonyl]-oxazolidin-2-one To a stirring solution of (4R)-4-benzyl-3-[(2R,3R)-3-hydroxy-2-(3-hydroxy-propyl)-5-phenyl-pent-4-enoyl]-oxazolidin-2-one (3.88 g, 9.49 mmol) in anhydrous methylene chloride (100 mL) in a flame-dried round bottom flask under N$_2$ at −78° C. was added 2,6-lutidine (2.76 mL, 23.7 mmol). Trifluoromethanesulfonic anhydride (1.68 mL, 9.96 mmol) was then added dropwise; after 5 min, the reaction was quenched with saturated aqueous sodium bicarbonate (50 mL), the layers were separated, and the aqueous layer was washed with methylene chloride (2×50 mL). The combined organic layers were dried over sodium sulfate, concentrated in vacuo, and purified by flash chromatography (SiO$_2$, 20–30% ethyl acetate in hexanes) to yield a pale yellow oil. The resulting oil was diluted with ethyl acetate (50 mL), the organic layer was washed once with 1N aqueous hydrogen chloride (50 mL) to remove residual 2,6-lutidine, and the ethyl acetate was concentrated in vacuo to yield the desired tetrahydropyran (2.35 g, 63.3%) as a pale yellow oil. MS (APCI), m$^+$/z: (M+H)$^+$=392.4.

Part E: Preparation of (2R,3R)-2-Styryl-tetrahydro-pyran-3-carboxylic acid

To a stirring solution of (4R)-4-benzyl-3-[(2R,3R)-2-styryl-tetrahydro-pyran-3-carbonyl]-oxazolidin-2-one (177 mg, 0.453 mmol) in 4:1 tetrohydrofuran:water (2.27 mL) at 0° C. was added lithium hydroxide (17.3 mg, 0.724 mmol) dissolved in 900 µL of water. To the resulting solution was added 30 wt % aqueous hydrogen peroxide (205 µL) dropwise, and the now pale yellow solution was stirred for 30 min. The solution was then poured into water (50 mL) containing a 1.5 mL-aliquot of 1.3 M sodium sulfite, and the resulting aqeuous layer was acidified with 6N aqueous hydrogen chloride (10 mL). The aqueous layer was washed with ethyl acetate (3×50 mL), and the combined organic layers were washed with brine (15 mL), dried over sodium sulfate, and concentrated in vacuo. The resulting residue was purified by flash chromatography (SiO$_2$, 33% ethyl acetate in hexanes) to yield the desired product 100 mg (95%) as a pale yellow oil. MS (ESI), m$^+$/z: (M+H)$^+$=233.2.

Part F: Preparation of [(2R,3R)-2-Styryl-tetrahydro-pyran-3-yl]-carbamic acid tert-butyl ester To a stirring solution of (2R,3R)-2-styryl-tetrahydro-pyran-3-carboxylic acid (106 mg, 0.456 mmol) in anhydrous tert-butanol (5 mL) under nitrogen in a flame-dried round bottom flask was added sequentially triethylamine (95 µL, 0.684 mmol) and diphenylphosphoryl azide (98 µL, 0.456 mmol). The reaction was warmed to reflux conditions and maintained at reflux for 15 h. The reaction solution was then cooled to 23° C., concentrated, and purified by flash chromatography (SiO$_2$, 30% ethyl acetate in hexanes) to yield the desired carbamate (76.4 mg, 55.5%) as a white solid. MS (ESI), m$^+$/z: (M+H)$^+$=304.3.

Part G: Preparation of [(2R,3R)-2-formyl-tetrahydro-pyran-3-yl]-carbamic acid tert-butyl ester Through a stirring solution of [(2R,3R)-2-styryl-tetrahydro-pyran-3-yl]-carbamic acid tert-butyl ester (27 mg, 0.089 mmol) in methanol (2 mL) at −78° C. was bubbled ozone until the reaction solution was blue in color. Excess triphenylphosine (500 mg) was added, and the reaction was allowed to warm to 23° C. The resulting mixture was concentrated and purified by flash chromatography (SiO$_2$, 7–40% ethyl acetate in hexanes) to give the desired aldehyde (20 mg, 98%) as a pale yellow oil. MS (APCI), m$^+$/z: (M+H)$^+$=230.

Part H: Preparation of {(2S,3R)-2-[(S)-3-(4-Fluoro-benzyl)-piperidin-1-ylmethyl]-tetrahydro-pyran-3-yl}-carbamic acid tert-butyl ester To a stirring solution of [(2R,3R)-2-formyl-tetrahydro-pyran-3-yl]-carbamic acid tert-butyl ester (20 mg, 0.0873 mmol) in 1,2-dichloroethane (2 mL) in a flame-dried round bottom flask under nitrogen was added (S)-(+)-3-(4-fluorobenzyl)piperidine (R)-mandelate (36.2 mg, 0.105 mmol). To this suspension was added methanol (200 µL), and the resulting solution was treated with sodium triacetoxyborohydride (36 mg, 0.170 mmol). The cloudy yellow suspension was stirred for 15 h and then poured into 1N hydrogen chloride (50 mL). The aqueous layer was basified with 12N aqueous sodium hydroxide and then extracted with ethyl acetate (3×50 mL). The combined organic layers were washed with brine (30 mL), dried over sodium sulfate, and concentrated in vacuo. The resulting residue was purified by flash chromatography to yield the desired carbamic acid (33.1 mg, 93.5%) as a yellow oil. MS (AP$^+$), m$^+$/z: (M+H)$^+$=407.5.

Part I: Preparation of (2S,3R)-2-[(S)-3-(4-Fluoro-benzyl)-piperidin-1-ylmethyl]-tetrahydro-pyran-3-ylamine To {(2S,3R)-2-[(S)-3-(4-fluoro-benzyl)-piperidin-1-ylmethyl]-tetrahydro-pyran-3-yl}-carbamic acid tert-butyl ester (33 mg, 0.0813 mmol) was added 4 M hydrogen chloride in dioxane (7 mL). After stirring for one hour, the solution was concentrated in vacuo to give (2S,3R)-2-[(S)-3-(4-fluoro-benzyl)-piperidin-1-ylmethyl]-tetrahydro-pyran-3-ylamine dihydrochloride as a pale yellow residue (30.8 mg, 100%). This residue was dissolved in ethyl acetate and poured into 1N sodium hydroxide (20 mL). The layers were separated, and the resulting aqueous layer was washed with ethyl acetate (3×50 mL). The combined organic layers were washed with brine (20 mL), dried over sodium sulfate, and concentrated in vacuo to yield (2S,3R)-2-[(S)-3-(4-fluoro-benzyl)-piperidin-1-ylmethyl]-tetrahydro-pyran-3-ylamine (24.9 mg, 100%) as a pale yellow oil. MS (APCI), m$^+$/z: (M+H)$^+$=307.4.

Part J: Preparation of 1-(3-Acetyl-phenyl)-3-{(2S,3R)-2-[(S)-3-(4-fluoro-benzyl)-piperidin-1-ylmethyl]-tetrahydro-pyran-3-yl}-urea To a solution of (2S,3R)-2-[(S)-3-(4-fluoro-benzyl)-piperidin-1-ylmethyl]-tetrahydro-pyran-3-ylamine dihydrochloride (16 mg, 0.043 mmol—prepared according to Part I) and excess triethylamine (100 µL, 0.719 mmol) in methylene chloride (1 mL) was added 3-acetylphenyl isocyanate (6.9 mg, 0.043) dissolved in methylene chloride (1 mL). The resulting yellow solution was shaken vigorously for 20 sec, and allowed to stand at 23° C. for 10 min. The solution was then concentrated in vacuo, and the resulting residue was purified by flash chromatography (5% methanol in methylene chloride) to yield the desired urea (13 mg, 65%) as a pale yellow oil. MS (ESI), m$^+$/z: (M+H)$^+$=468.3.

Example 45

Preparation of 1-{(2S,3R)-2-[(S)-3-(4-Fluoro-benzyl)-piperidin-1-ylmethyl]-tetrahydro-pyran-3-yl}-3-[3-(1-methyl-1H-tetrazol-5-yl)-phenyl]-urea, trifluoroacetic acid salt To a stirring solution of (2S,3R)-2-[(S)-3-(4-fluoro-benzyl)-piperidin-1-ylmethyl]-tetrahydro-pyran-3-ylamine (24 mg, 0.078 mmol) in anhydrous acetonitrile (1 mL) in a flame-dried round bottom flask under nitrogen was added [3-(1-methyl-1H-tetrazol-5-yl)-phenyl]-carbamic acid phenyl ester (22.8 mg, 0.077 mmol). The resulting solution was stirred for 15 h and was then concentrated. Purification of the resulting residue via flash chromatography (5% methanol in dichloromethane) gave 27.3 mg (68%) of a slightly impure off-white solid. This solid was further purified by preparative reverse-phase HPLC (10–90% acetonitrile in water with 0.05% trifluoroacetic acid) to give the desired product (12.7 mg, 31.8%) as an amorphous solid. MS (ESI), m$^+$/z: (M+H—CF$_3$CO$_2$)$^+$=508.4.

Example 46

Preparation of 1-[3-(5-Acetyl-4-methyl-thiazol-2-yl)-phenyl]-3-{(2S,3R)-2-[(S)-3-(4-fluoro-benzyl)-piperidin-1-ylmethyl]-tetrahydro-pyran-3-yl}-urea To a stirring solution of (2S,3R)-2-[(S)-3-(4-fluoro-benzyl)-piperidin-1-ylmethyl]-tetrahydro-pyran-3-ylamine (10 mg, 0.033 mmol) in anhydrous acetonitrile (1 mL) in a flame-dried round bottom flask was added [5-acetyl-4-methyl-thiazol-2-yl)-carbamic acid phenyl ester (11 mg, 0.039 mmol). The resulting solution was stirred for 15 h and was then concentrated. Purification of the resulting residue via flash chromatography (5% methanol in methylene chloride) followed by preparative reverse-phase HPLC (10–90% acetonitrile in water with 0.05% trifluoroacetic acid) gave an amorphous solid. The resulting amorphous solid was dissolved in ethyl acetate (10 mL) and washed with saturated aqueous sodium bicarbonate (20 mL). The aqueous layer was washed with ethyl acetate (10 mL) and the organic layers were combined, dried over sodium sulfate, and concentrated in vacuo to yield the desire product (10.2 mg, 63.8%) as an amorphous solid. MS (APCI), m$^+$/z: (M+H)$^+$=489.6.

Example 47

Part A: Preparation of (2R,3R)-3-tert-Butoxycarbonylamino-tetrahydro-pyran-2-carboxylic acid To a stirring solution of [(2R,3R)-2-formyl-tetrahydro-pyran-3-yl]-carbamic acid tert-butyl ester (57.7 mg, 0.251 mmol) in methylene chloride (2 mL) was added tetramethyl-ammonium bromide (4.1 mg, 0.012 mmol) and 2,2,6,6-tetramethyl-1-piperidinyloxy, free radical (1 mg, 0.003 mmmol), followed by a solution of potassium bromide (3 mg, 0.03 mmol) in water (1 mL). Upon cooling the mixture to 0° C., aqueous sodium hypochlorite (3.6 mL, 0.35 M) made pH 8.6 with sodium bicarbonate (50 mg/mL of 0.35 M NaOCl) was added, and the resulting yellow/orange mixture was stirred vigorously for 5 min. The reaction was poured into 1N aqueous sodium hydroxide (50 mL), acidified with 1N aqueous hydrogen chloride (55 mL), and washed with ethyl acetate (3×50 mL). The combined organic layers were dried over sodium sulfate, concentrated in vacuo, and the resulting residue was purified by flash chromatography (SiO$_2$, 30–50% ethyl acetate in hexanes then 70% ethyl acetate in hexanes containing 5% acetic acid and 1% methanol) to give the desired product (55.5 mg, 89.5%) as a foamy solid. MS (ESI), m$^+$/z: (M$^+$H)$^+$=244.

Part B: Preparation of {(2R,3R)-2-[(S)-3-(4-Fluoro-benzyl)-piperidine-1-carbonyl]-tetrahydro-Pyran-3-yl}-carbamic acid tert-butyl ester To a stirring solution of (2R,3R)-3-tert-butoxy-carbonylamino-tetrahydro-pyran-2-carboxylic acid (55.5 mg, 0.226 mmol) in dichloromethane (2.5 mL) in a flame-dried round bottom flask under nitrogen was added benzotriazol-1-yloxytripyrrolidinophosphonium hexafluorophosphate (110 mg, 0.249 mmol) and triethylamine (63 µL, 0.452 mmol). The reaction was allowed to stir for 10 min before the addition of (S)-3-(4-fluoro-benzyl)-piperidine (52.3 mg, 0.271 mmol) in one portion. After an additional 10 min, the solution was poured into saturated aqueous sodium bicarbonate (20 mL), and the aqueous layer was washed with ethyl acetate (3×50 mL). The combined organic layers were washed with saturated aqueous sodium chloride (20 mL), dried over sodium sulfate, and concentrated. The resulting residue was purified by flash chromatography (SiO$_2$, 10–30% ethyl acetate in hexanes) to yield the desired carbamic acid (56 mg, 59%) as a white solid. MS (APCI), m$^+$/z: (M+H)$^+$=421.5.

Part C: Preparation of (2R,3R)-(3-Amino-tetrahydro-pyran-2-yl)-[(S)-3-(4-fluoro-benzyl)-piperidin-1-yl]-methanone Hydrochloride To {(2R,3R)-2-[(S)-3-(4-fluoro-benzyl)-piperidine-1-carbonyl]-tetrahydro-pyran-3-yl}-carbamic acid tert-butyl ester (56 mg, 0.133 mmol) was added 4 M hydrogen chloride in dioxane (10 mL). The resulting pale yellow solution was allowed to stir for 20 min and was then concentrated to give the desired product (43 mg, 100%) as a pale yellow oil. MS (ESI), m$^+$/z: (M+H)$^+$=321.3.

Part D: Preparation of 1-(3-Acetyl-phenyl)-3-{(2R,3R)-2-[(S)-3-(4-fluoro-benzyl)-piperidine-1-carbonyl]-tetrahydro-pyran-3-yl}-urea To a solution of (2R,3R)-(3-amino-tetrahydro-pyran-2-yl)-[(S)-3-(4-fluoro-benzyl)-piperidin-1-yl]-methanone hydrochloride (14 mg, 0.044 mmol) in dichloromethane (500 µL) containing an excess of triethylamine (100 µL, 0.719 mmol) was added 3-acetylphenyl isocyanate (7.0 mg, 0.044 mmol) in methylene chloride (500 µL). The resulting yellow solution was shaken vigorously for 20 sec and allowed to sit at 23° C. before being concentrated. The resulting residue was purified by flash chormatography (SiO$_2$, 50–90 ethyl acetate in hexanes, then 90% ethyl acetate in hexanes containing 2% methanol) to yield the desired urea (18 mg, 85.3%) as a white solid. MS (ESI), m$^+$/z: (M+H)$^+$=482.6.

Example 48

Preparation of 1-{(2R,3R)-2-[(S)-3-(4-Fluoro-benzyl)-piperidine-1-carbonyl]-tetrahydro-pyran-3-yl}-3-[3-(1-methyl-1H-tetrazol-5-yl)-phenyl]-urea In a single portion was added [3-(1-methyl-1H-tetrazol-5-yl)-phenyl]-carbamic acid phenyl ester (14.2 mg, 0.0481 mmol) in anhydrous acetonitrile (1 mL) to (2R,3R)-(3-amino-tetrahydro-pyran-2-yl)-[(S)-3-(4-fluoro-benzyl)-piperidin-1-yl]-methanone (14 mg, 0.044 mmol) that had been derived from treatment of (2R,3R)-(3-amino-tetrahydro-pyran-2-yl)-[(S)-3-(4-fluoro-benzyl)-piperidin-1-yl]-methanone hydrochloride in ethyl acetate with 1N sodium hydroxide, brine, and concentration in vacuo. The pale yellow solution containing carbamic acid pheny ester and methanone was treated with N,N-dimethylformamide (500 µL) and stirred for 15 hours. Additional carbamic acid phenyl ester (14.2 mg, 0.0481 mmol) was added, the resulting solution was heated for 6 hr at 35° C., and it was then cooled to room temperature. After stirring for an additional 12 hours, the reaction was concentrated and the resulting residue was purified by flash chromatography (45% methylene chloride in ethyl acetate containing 5% methanol) to yield the desired urea (14 mg, 59%) as an off white solid. MS (ESI), m$^+$/z: (M+H)$^{30}$ =522.5.

Example 49

Preparation of 1-[3-(5-Acetyl-4-methyl-thiazol-2-yl)-phenyl]-3-{(2R-3R)-2-[(S)-3-(4-fluoro-benzyl)-piperidine-1-carbonyl]-tetrahydro-pyran-3-yl}-urea To (2R,3R)-(3-amino-tetrahydro-pyran-2-yl)-[(S)-3-(4-fluoro-benzyl)-piperidin-1-yl]-methanone (15 mg, 0.044 mmol-prepared as in Example 50) in anhydrous acetonitrile (1 mL) was added [5-acetyl-4-methyl-thiazol-2-yl)-carbamic acid phenyl ester (13.3 mg, 0.0481 mmol). The resulting pale yellow solution was stirred for 15 hours, and additional carbamic acid phenyl ester (13.3 mg, 0.0481 mmol) was added as well as N,N-dimethylformamide (500 µL). The resulting cloudy mixture was then heated for 3 hr at 35° C. before being cooled to 23° C. Upon concentration, the resulting residue was purified by flash chromatography (5% methanol in methylene chloride) to yield the desired urea (18 mg, 82%) as a white solid. MS (ESI), m+/z: (M+H)+=503.5.

Example 283

Part A. Preparation of Ethyl 4-hydroxybutyric acid ethyl ester

A solution of γ-butyrolactone (86.1 g, 1 mole) in absolute ethanol (1.5 l) was treated with concentrated sulfuric acid (20.4 g, 200 mmol) and stirred at room temperature for 18 h. The mixture was neutralized by slowly adding a solution of sodium metal (9.2 g, 400 mmol) in ethanol (200 mL). The mixture was concentrated in vacuo, and the residue was filtered through celite. The filtrate was distilled through a packed column (0.08 Torr) to provide recovered lactone (bp 27° C., 14.47 g, 17%) and the product as a colorless liquid (bp 52° C., 41.48 g, 31%). 1H NMR (300 mHz, CDCl3) δ4.14 (q, J=7.0 Hz, 2H), 3.69 (t, J=6.0 Hz, 2H), 2.44 (t, J=6.9 Hz, 2H), 1.89 (m, 3H), 1.27 (t, J=7.0 Hz, 3H).

Part B. Preparation of 4-ethoxycarbonylmethoxybutyric acid ethyl ester

A solution of ethyl 4-hydroxybutyric acid ethyl ester (13.2 g, 100 mmol) and rhodium (II) acetate dimer (440 mg, 1 mmol) in dichloromethane (350 mL) was treated with a solution of ethyl diazoacetate (17.1 g, 150 mmol) in dichloromethane (70 mL) over 4 h. The mixture was stirred at room temperature for 20 h, and concentrated in vacuo. The residue was distilled on a Kugelrohr apparatus (80–90° C., 0.2 Torr) to provide the product as a colorless liquid, contaminated with about 10% by weight of a 1:1 mixture of diethyl maleate and diethyl fumarate (22.02 g, 91%). 1H NMR (300 mHz, CDCl3) δ4.21 (q, J=7.4 Hz, 2H), 4.13 (q, J=7.0 Hz, 2H), 4.06 (s, 2H), 3.58 (t, J=6.2 Hz, 2H), 2.44 (t, J=7.3 Hz, 2H), 1.94 (m, 2H), 1.29 (t, J=7.3 Hz, 3H), 1.26 (t, J=7.0 Hz, 3H).

Part C. Preparation of 3-oxo-tetrahydro-pyran-4-carboxylic acid ethyl ester

A solution of 4-ethoxycarbonylmethoxybutyric acid ethyl ester (90%, 15.0 g, 61.9 mmol) in toluene (300 mL) was stirred at room temperature and treated over 5 min with a solution of potassium tert-butoxide in tetrahydrofuran (1.0 M, 74.2 mL, 74.2 mmol). The mixture was stirred at room temperature for 24 h, then was poured into 1 N hydrochloric acid. The phases were separated, and the aqueous phase was extracted with ether. The combined organic phases were dried (Na2SO4), filtered and concentrated in vacuo. The residue was purified by flash column chromatography (5% ethyl acetate/hexanes) to provide the product as a pale yellow liquid (5.06 g, 48%). 1H NMR (300 mHz, CDCl3) δ11.85 (s, 1H), 4.24 (q, J=7.3 Hz, 2H), 4.14 (t, J=1.7 Hz, 2H), 3.79 (t, J=5.5 Hz, 2H), 2.35 (tt, J=5.5, 1.7 Hz, 2H), 1.32 (t, J=7.3 Hz, 3H).

Part D. Preparation of (R)-5-(1-Phenyl-ethylamino)-3,6-dihydro-2H-pyran-4-carboxylic acid ethyl ester A solution of 3-oxo-tetrahydro-pyran-4-carboxylic acid ethyl ester (3.03 g, 17.6 mmol), R-(+)-α-methylbenzylamine (2.35 g, 19.4 mmol) and p-toluenesulfonic acid hydrate (67 mg, 230 µmol) in benzene (60 mL) was heated at reflux under a Dean-Stark trap for 16 h. The cooled mixture was concentrated in vacuo to provide the product as a yellow oily semisolid (5.05 g), used without further purification. 1H NMR (300 mHz, CDCl3) δ8.97 (bd, J=7.3 Hz, 1H), 7.3–7.2 (m, 5H), 4.41 (m, 1H), 4.30 (d, J=16.1 Hz, 1H), 4.18 (q, J=7.3 Hz, 2H), 3.91 (d, J=16.1 Hz, 1H), 3.64 (m, 2H), 2.34 (m, 2H), 1.48 (d, J=6.5 Hz, 3H), 1.30 (t, J=7.3 Hz, 3H).

Part E. Preparation of (3S,4R)-3-[(R)-1-Phenyl-ethylamino]-tetrahydro-pyran-4-carboxylic acid ethyl ester A solution of crude (R)-5-(1-Phenyl-ethylamino)-3,6-dihydro-2H-pyran-4-carboxylic acid ethyl ester (4.53 g, ca. 16.5 mmol) was dissolved in trifluoroacetic acid (45 mL) and treated with triethylsilane (7.9 mL, 49.4 mmol). The mixture was stirred for 17 h and then concentrated. The residue was dissolved in water and adjusted to pH 10 with 50% sodium hydroxide. The mixture was extracted with dichloromethane, and the combined organic phases were dried (Na2SO4) and concentrated. The residue was purified by flash column chromatography (40% diethyl ether/petroleum ether) to provide the product as a colorless oil (1.63 g, 36%). 1H NMR (300 mHz, CDCl3) δ7.22 (m, 4H), 7.16 (m, 1H), 4.14 (q, J=7.3 Hz, 2H), 3.77 (m, 2H), 3.60 (q, J=7.3 Hz, 1H), 3.23 (m, 1H), 2.83 (m, 2H), 2.31 (m, 1H), 1.77 (m, 2H), 1.24 (m, 6H), ESI MS: (M+H)+=278.1 (100%).

Part F. Preparation of (3S,4R)-3-[(R)-1-Phenyl-ethylamino]-tetrahydro-pyran-4-carboxylic acid A solution of (3S,4R)-3-[(R)-1-Phenyl-ethylamino]-tetrahydro-pyran-4-carboxylic acid ethyl ester (726 mg, 2.6 mmol) in tetrahydrofuran (6 mL) was treated with 1.0 M sodium hydroxide solution (5.2 mL, 5.2 mmol) and the heterogeneous mixture was stirred at room temperature. After 16 h, the now homogeneous solution was treated with 1.0 M hydrochloric acid (5.2 mL, 5.2 mmol) and concentrated in vacuo. The residue was dissolved in water and lyophilized to provide the product, along with sodium chloride, as a fluffy white solid (943 mg, quantitative), used without further purification. 1H NMR (300 mHz, CDCl3) δ7.41 (m, 5H), 4.09 (q, J=6.6 Hz, 1H), 3.98 (dd, J=11.7, 4.0 Hz, 1H), 3.77 (m, 1H), 3.33 (m, 1H), 3.08 (m, 2H), 2.37 (m, 1H), 2.19 (m, 1H), 1.79 (m, 1H), 1.61 (d, J=6.6 Hz, 3H), ESI MS: (M+H)+=250.3 (100%).

Part G. Preparation of [(S)-3-(4-Fluoro-benzyl)-piperidin-1-yl]-[(3S,4R)-3-((R)-1-phenyl-ethylamino)-tetrahydro-pyran-4-yl]-methanone (S)-3-(4-fluorobenzyl)-piperidine, mandelic acid salt (1.16 g, 3.35 mmol) was dissolved in 1.0 M sodium hydroxide (30 mL) and extracted with ethyl acetate (4×10 mL). The combined organic phases were dried (Na2SO4) and concentrated in vacuo. The free base was used without further purification.

A cloudy solution of (3S,4R)-3-[(R)-1-Phenyl-ethylamino]-tetrahydro-pyran-4-carboxylic acid (containing sodium chloride; 943 mg, 2.57 mmol) in dichloromethane (25 mL) was treated with benzotriazol-1-yloxy-tripyrrolidinophosphonium hexafluorophosphate (1.61 g, 3.09 mmol) and triethylamine (826 μL, 5.92 mmol) and stirred for 5 minutes. A solution of the (S)-3-(4-fluorobenzyl)-piperidine prepared above in dichloromethane (5 mL) was added and the mixture was stirred at room temperature. After 18 h, the mixture was washed with water and saturated NaHCO3, dried (Na2SO4) and concentrated. The residue was purified by flash column chromatography (75% ethyl acetate/hexanes) to provide the product as a gum (1.10 g, 100%). 1H NMR (300 mHz, CDCl3) δ7.4–7.3 (m, 5H), 7.12 (m, 2H), 6.99 (t, 2H), 4.55 (bd, 1H), 3.87 (m, 2H), 3.70 (m, 2H), 3.4–2.8 (m, 3H), 2.66 (m, 2H), 2.42 (m, 2H), 2.0–1.1 (m, 9H), 1.34 (d, J=6.6 Hz, 3H), ESI MS: (M+H)+=425.3.

Part H. Preparation of [(S)-3-(4-Fluoro-benzyl)-piperidin-1-yl]-[(3S,4R)-3-aminotetrahydro-pyran-4-yl]-methanone

[(S)-3-(4-Fluoro-benzyl)-piperidin-1-yl]-[(3S,4R)-3-((R)-1-phenyl-ethylamino)-tetrahydro-pyran-4-yl]-methanone (1.10 g, 2.6 mmol), palladium hydroxide (20 weight % on carbon, dry basis; 440 mg) and ethanol (40 mL) were combined in a pressure bottle and shaken under a hydrogen atmosphere (55–60 psig) for 20 h. The mixture was filtered through Celite, and the solids were washed thoroughly with ethanol. The filtrate was concentrated to give the product as a glassy foam (803 mg, 96%), used without further purification. 1H NMR (300 mHz, CD3OD) δ7.22 (m, 2H), 7.04 (m, 2H), 4.50 and 4.30 (2m, 1H), 4.1–3.6 (3H), 3.5–3.4 (2H), 3.3–2.9 (2H), 2.8–2.4 (4H), 2.0–1.2 (7H), ESI MS: (M+H)+=321.2.

Part I. Preparation of (3S,4S)-4-[(S)-3-(4-Fluoro-benzyl)-piperidin-1-ylmethyl]-tetrahydro-pyran-3-ylamine

[(S)-3-(4-Fluoro-benzyl)-piperidin-1-yl]-[(3S,4R)-3-aminotetrahydro-pyran-4-yl]-methanone (367 mg, 1.14 mmol) was treated with borane-tetrahydrofuran complex in tetrahydrofuran (1.0 M; 46 mL, 46 mmol) and stirred for 20 h. The mixture was treated slowly with 20% acetic acid in methanol (25 mL), and the resulting mixture was stirred at room temperature for 3 h. The solvents were removed, and the residue was dissolved in water, made basic (pH 11) with 50% sodium hydroxide, and extracted with dichloromethane. The combined organic phases were dried (Na2SO4) and concentrated to provide a gum (313 mg). A portion of this material (175 mg) was purified by flash column chromatography (5% methanol/dichloromethane, containing 0.5% ammonium hydroxide) to provide the product (103 mg, 52%) as an oil which solidified on standing. 1H NMR (300 mHz, CD3OD) δ7.15 (m, 2H), 6.98 (m, 2H), 3.87 (dd, J=10.3, 3.6 Hz, 1H), 3.78 (dd, J=11.1, 4.4 Hz, 1H), 3.37 (dd, J=12.0, 2.4 Hz, 1H), 3.03 (bd, 1H), 3.00 (dd, J=11.0, 10.2 Hz, 1H), 2.78 (bd, 1H), 2.59 (m, 1H), 2.49 (d, J=6.6 Hz, 2H), 2.42 (dd, J=12.8, 8.8 Hz, 1H), 2.23 (dd, J=12.8, 4.4 Hz, 1H), 1.9–1.4 (8H), 1.2 (m, 1H), 1.0 (m, 1H), ESI MS: (M+H)+=307.1.

Part J. Preparation of 1-{(3S,4S)-4-[(S)-3-(4-Fluoro-benzyl)-piperidin-1-ylmethyl]-tetrahydro-pyran-3-yl}-3-[3-methyl-5-(1-methyl-1H-tetrazol-5-yl)-phenyl]-urea, trifluoroacetate salt (3S,4S)-4-[(S)-3-(4-Fluoro-benzyl)-piperidin-1-ylmethyl]-tetrahydro-pyran-3-ylamine (41 mg, 133 μmol) and [3-methyl-5-(1-methyl-1H-tetrazol-5-yl)-phenyl]-carbamic acid phenyl ester (46 mg, 147 μmol) were dissolved in acetonitrile (1 mL) and the mixture was stirred at room temperature. After 24 h, the mixture was concentrated, dissolved in ethyl acetate, washed with water, dried (Na2SO4) and concentrated. The residue was purified by reverse phase high pressure liquid chromatography ($C_{18,\ 10-100}$% acetonitrile in water, containing 0.05% trifluoroacetic acid). After isolation, the product was lyophilized to provide a fluffy white solid (32 mg, 38%). 1H NMR (300 mHz, CD3OD) δ7.79 (s, 1H), 7.39 (s, 1H), 7.25 (s, 1H), 7.19 (m, 2H), 7.00 (m, 2H), 4.18 (s, 3H), 3.90 (m, 2H), 3.6 (m, 3H), 3.5 (m, 1H), 3.2 (m, 1H), 2.94 (bt, 1H), 2.7 (m, 2H), 2.6 (m, 1H), 2.41 (s, 3H), 2.2–1.6 (8H), 1.5 (m, 1H), 1.2 (m, 1H), ESI MS: (M+H)+=522.4.

Example 284

Preparation of 1-{(3S,4S)-4-[(S)-3-(4-fluorobenzyl)-piperidin-1-ylmethyl]-tetrahydro-pyran-3-yl}-3-[3-(1-methyl-1H-tetrazol-5-yl)-phenyl]-urea (3S,4S)-4-[(S)-3-(4-Fluoro-benzyl)-piperidin-1-ylmethyl]-tetrahydro-pyran-3-ylamine (44 mg, 143 μmol) and [3-(1-methyl-1H-tetrazol-5-yl)-phenyl]-carbamic acid phenyl ester (47 mg, 158 μmol) were dissolved in acetonitrile (1 mL) and the mixture was stirred at room temperature. After 24 h, the mixture was concentrated, dissolved in ethyl acetate, washed with water, dried (Na2SO4) and concentrated. The residue was purified by reverse phase high pressure liquid chromatography (C18, 10–100% acetonitrile in water, containing 0.05% trifluoroacetic acid), then by flash column chromatography (5% methanol in dichloromethane, containing 0.5% ammonium hydroxide) to provide the product as a glass (16 mg, 23%). 1H NMR (300 mHz, CD3OD) δ7.95 (s, 1H), 7.52 (m, 2H), 7.43 (m, 1H), 7.05 (m, 2H), 6.86 (m, 2H), 4.19 (s, 3H), 3.94 (dd, J=10.7, 4.4 Hz, 1H), 3.87 (bd, 1H), 3.50 (td, J=9.9, 4.4 Hz, 1H), 3.39 (m, 1H), 3.09 (t, J=10.2 Hz, 1H), 2.93 (bd, 1H), 2.85 (bd, 1H), 2.56 (dd, J=12.8, 5.2 Hz, 1H), 2.45 (m, 2H), 2.30 (dd, J=12.4, 6.6 Hz, 1H), 2.04 (bt, 1H), 1.9–1.5 (7H), 1.40 (m, 1H), 0.95 (m, 1H), ESI MS: (M+H)+=508.3 (100%).

Example 285

Preparation of 1-{(3S,4S)-4-[(S)-3-(4-fluorobenzyl)-piperidin-1-ylmethyl]-tetrahydro-pyran-3-yl}-3-[5-acetyl-4-methylthiazol-2-yl]-urea (3S,4S)-4-[(S)-3-(4-Fluoro-benzyl)-piperidin-1-ylmethyl]-tetrahydro-pyran-3-ylamine (49 mg, 160 μmol) and (5-acetyl-4-methylthiazol-2-yl)-carbamic acid phenyl ester (49 mg, 176 μmol) were dissolved in acetonitrile (1 mL) and the mixture was stirred at room temperature. After 24 h, the mixture was concentrated, dissolved in ethyl acetate, washed with water, dried (Na2SO4) and concentrated. The residue was purified by reverse phase high pressure liquid chromatography (C18, 10–100% acetonitrile in water, containing 0.05% trifluoroacetic acid), then by flash column chromatography (5% methanol in dichloromethane, containing 0.5% ammonium hydroxide) to provide the product as a glass (18 mg, 23%). 1H NMR (300 mHz, CD3OD) δ7.05 (m, 2H), 6.87 (m, 2H), 3.90 (dd, J=11.0, 4.4 Hz, 1H), 3.84 (m, 1H), 3.53 (td, J=9.5, 4.3 Hz, 1H), 3.40 (bt, 1H), 3.10 (m, 1H), 2.90 (bd, 1H), 2.75 (bd, 1H), 2.58 (s, 3H), 2.48 (s, 3H), 2.45 (m, 3H), 2.21 (dd, J=13.6, 6.3 Hz, 1H), 1.91 (bt, 1H), 1.8–1.5 (7H), 1.37 (m, 1H), 0.92 (m, 1H), ESI MS: (M+H)+=489.4 (100%).

Example 286

Preparation of 1-{(3S,4S)-4-[(S)-3-(4-fluorobenzyl)-piperidin-1-ylmethyl]-tetrahydro-pyran-3-yl}-3-(3-acetylphenyl)-urea trifluoroacetate salt (3S,4S)-4-[(S)-3-(4-Fluorobenzyl)-piperidin-1-ylmethyl]-tetrahydro-pyran-3-ylamine (45 mg, 146 μmol), 3-acetylphenyl isocyanate (20 μL, 146 μmol) and triethylamine (21 μL, 146 μmol) were dissolved in tetrahydrofuran (1 mL) and the mixture was stirred at room temperature. After 22.5 h, the mixture was concentrated. The residue was purified by flash column chromatography (5% methanol in dichloromethane, containing 0.5% ammonium hydroxide), then by reverse phase high pressure liquid chromatography (C18, 10–100% acetonitrile in water, containing 0.05% trifluoroacetic acid) to provide the product as a glass. After lyophilizing the product was a fluffy white powder (42 mg, 49%). 1H NMR (300 mHz, CD3OD) δ8.09 (t, J=1.9 Hz, 1H), 7.61 (m, 2H), 7.39 (t, J=8.1 Hz, 1H), 7.17 (m, 2H), 6.99 (m, 2H), 3.91 (m, 2H), 3.57 (m, 3H), 3.45 (m, 1H), 3.4–3.2 (m, 2H), 3.12 (dd, J=13.2, 8.2 Hz, 1H), 2.93 (m, 1H), 2.7–2.45 (m, 3H), 2.57 (s, 3H), 2.2–1.7 (m, 6H), 1.50 (m, 1H), 1.20 (m, 1H), ESI MS: (M+H)+=468.5 (100%).

Example 287

Preparation of 1-{(3S,4S)-4-[(S)-3-(4-fluorobenzyl)-piperidin-1-ylmethyl]-tetrahydro-pyran-3-yl}-3-(2-morpholin-4-yl-ethyl)-urea bis-trifluoroacetate salt (3S,4S)-4-[(S)-3-(4-Fluorobenzyl)-piperidin-1-ylmethyl]-tetrahydro-pyran-3-ylamine (44 mg, 144 μmol), (2-morpholin-4-yl-ethyl)-carbamic acid 4-nitro-phenyl ester hydrochloride (58 mg, 173 μmol) and triethylamine (24 μL, 173 pmol) were dissolved in N,N-dimethylformamide (1 mL) and the mixture was stirred at room temperature. After 22.5 h, the mixture was concentrated. The residue was dissolved in ethyl acetate, washed with 1N sodium hydroxide, water, and brine, and dried (Na2SO4) and concentrated. The residue was purified by flash column chromatography (5% methanol in dichloromethane, containing 0.5% ammonium hydroxide), then by reverse phase high pressure liquid chromatography (C18, 10–100% acetonitrile in water, containing 0.05% trifluoroacetic acid) to provide the product as a glass. After lyophilizing the product was a glass (63 mg, 63%). 1H NMR (300 mHz, CD3OD) δ7.19 (m, 2H), 7.02 (m, 2H), 4.03 (m, 2H), 3.88 (m, 2H), 3.79 (m, 2H), 3.7–3.3 (m, 8H), 3.3–3.0 (m, 7H), 2.92 (m, 1H), 2.7–2.5 (m, 3H), 2.1–1.7 (m, 6H), 1.50 (m, 1H), 1.20 (m, 1H), AP MS: (M+H)+=463.2 (100%).

Example 288

Part A. Preparation of (R)-4-(1-phenyl-ethylamino)-2,5-dihydrothiophene-3-carboxylic acid methyl ester A solution of 4-oxo-tetrahydrothiophene-3-carboxylic acid methyl ester (prepared according to the procedure of O. Hromatka, D. Binder and K. Eichinger, Monatsheft. Chem. 1973, 104, 1520; 3.20 g, 20 mmol), R-(+)-α-methylbenzylamine (2.85 mL, 22 mmol), acetic acid (2.85 mL, 50 mmol) and benzene (100 mL) was heated at reflux under a Dean-Stark trap for 4.5 h. The cooled mixture was concentrated in vacuo to provide the product as a viscous yellowish oil (6.2 g) which contained residual acetic acid. The material, which solidified on standing, was used without further purification. 1H NMR (300 mHz, CDCl3) δ8.27 (bd, J=7.4 Hz, 1H), 7.35 (m, 2H), 7.25 (m, 3H), 4.54 (m, 1H), 3.87 (m, 1H), 3.82 (m, 2H), 3.75 (s, 3H), 3.54 (m, 1H), 1.54 (d, J=6.6 Hz, 3H).

Part B. Preparation of (3R,4S)-4-[(R)-1-phenyl-ethylamino]-tetrahydrothiophene-3-carboxylic acid methyl ester A solution of crude (R)-4-(1-Phenyl-ethylamino)-2,5-dihydrothiophene-3-carboxylic acid methyl ester (2.82 g, ca. 9.1 mmol) was dissolved in trifluoroacetic acid (50 mL) and treated with triethylsilane (4.4 mL, 27.4 mmol). The mixture was stirred for 20 h, when TLC indicated residual starting material. Additional triethylsilane (1.5 mL) was added and the mixture was heated at reflux for 3 h, then was cooled and concentrated. The residue was dissolved in water and adjusted to pH 10 with 50% sodium hydroxide. The mixture was extracted with ether, and the combined organic phases were dried (Na2SO4) and concentrated. The residue was purified by flash column chromatography (15–30% diethyl ether/petroleum ether) to provide the product as a colorless oil (673 mg, 28%). 1H NMR (300 mHz, CDCl3) δ7.33 (m, 4H), 7.27 (m, 1H), 3.84 (q, J=6.6 Hz, 1H), 3.73 (s, 3H), 3.61 (m, 1H), 3.1–3.0 (m, 3H), 2.80 (dd, J=11.0, 5.8 Hz, 1H), 2.54 (dd, J=11.0, 6.6 Hz, 1H), 1.37 (d, J=6.6 Hz, 3H), ESI MS: (M+H)+=266.1.

Part C. Preparation of (3R,4S)-4-[(R)-1-phenyl-ethylamino]-tetrahydrothiophene-3-carboxylic acid A solution of Preparation of (3R,4S)-4-[(R)-1-phenyl-ethylamino]-tetrahydrothiophene-3-carboxylic acid methyl ester (673 mg, 2.54 mmol) in tetrahydrofuran (5 mL) was treated with 1.0 M sodium hydroxide solution (5.0 mL, 5.0 mmol) and the heterogeneous mixture was stirred at room temperature. After 75 min, the now homogeneous solution was treated with 1.0 M hydrochloric acid (5.0 mL, 5.0 mmol) and concentrated in vacuo. The residue was dissolved in water and lyophilized to provide the product, along with sodium chloride, as a fluffy white solid (928 mg, quantitative), used without further purification. 1H NMR (300 mHz, DMSO-d6) δ7.4–7.2 (m, 5H), 3.87 (q, J=6.6 Hz, 1H), 3.27 (dd, J=13.6, 7.0 Hz, 1H), 3.0–2.8 (m, 3H), 2.5 (m, 2H), 1.26 (d, J=6.6, 3H), ESI MS: (M+H)+252.0.

Part D. Preparation of [(S)-3-(4-fluorobenzyl)-piperidin-1-yl]-[(3R,4S)-4-((R)-1-phenyl-ethylamino)-tetrahydrothiophen-3-yl]-methanone (S)-3-(4-fluorobenzyl)-piperidine, mandelic acid salt (1.14 g, 3.30 mmol) was stirred in ethyl acetate (20 mL) and 1.0 M sodium hydroxide (25 mL) until the solid dissolved. The layers were separated and the organic phase was extracted with ethyl acetate (2×25 mL). The combined organic phases were dried (Na2SO4) and concentrated in vacuo. The free base was used without further purification.

A cloudy solution of (3R,4S)-4-[(R)-1-phenyl-ethylamino]-tetrahydrothiophene-3-carboxylic acid (containing sodium chloride; 928 mg, 2.54 mmol) in dichloromethane (20 mL) was treated with benzotriazol-1-yloxy-tripyrrolidinophosphonium hexafluorophosphate (1.59 g, 3.05 mmol) and triethylamine (814 μL, 5.84 mmol) and stirred for 5 minutes. A solution of the (S)-3-(4-fluorobenzyl)-piperidine prepared above in dichloromethane (5 mL) was added and the mixture was stirred at room temperature. After 21.5 h, the mixture was diluted with dichloromethane, washed with water and saturated NaHCO3, dried (Na2SO4) and concentrated. The residue was purified by flash column chromatography (55% ethyl acetate/hexanes) to provide the product as a gum (1.05 g, 94%). 1H NMR (300 mHz, CDCl3) δ7.32 (m, 4H), 7.27 (m, 1H), 7.10 (m, 2H), 6.99 (m, 2H), 4.47 (m, 1H), 3.9–3.6 (m, 3H), 3.2 (m, 1H), 2.95 (m, 2H), 2.8–2.4 (m, 6H), 1.9–1.6 (m, 4H), 1.4 (m, 1H), 1.37 (m, 3H), 1.2 (m, 1H), ESI MS: (M+H)+=427.4.

Part E. Preparation of [1,1-dioxo-(3R,4S)-4-[(R)-1-phenyl-ethylamino]-tetrahydrothiophen-3-yl]-[(S)-3-(4-fluorobenzyl)-piperidin-1-yl]-methanone

[(S)-3-(4-fluorobenzyl)-piperidin-1-yl]-[(3R,4S)-4-[(R)-1-phenyl-ethylamino]-tetrahydro-thiophen-3-yl]-methanone (1.02 g, 2.39 mmol) was dissolved in methanol (10 mL) and acetone (10 mL) and stirred on ice. Water (10 mL) was added, and the resulting heterogeneous mixture was treated with potassium peroxymonosulfate (Oxone®, 3.67 g, 5.98 mmol). After 5 min the cooling bath was removed and the mixture was stirred at room temperature. After 20.5 h, the mixture was concentrated and diluted with water. The pH was adjusted to ca. 11 with 1N sodium hydroxide, and the mixture was extracted with ethyl acetate. The combined extracts were dried (Na2SO4) and concentrated, and the residue was purified by flash column chromatography (2.5% 2-propanol/chloroform) to provide the product as a glass (790 mg, 72%). 1H NMR (300 mHz, CDCl3) δ7.31 (m, 5H), 7.11 (m, 2H), 7.06 (m, 2H), 4.50 (m, 1H), 4.0–3.7 (m, 3H), 3.5–2.9 (m, 5H), 2.7–2.5 (m, 4H), 1.9–1.6 (m, 4H), 1.43 (m, 1H), 1.33 (m, 3H), 1.20 (m, 1H), ESI MS: (M+H)+=459.3.

Part F. Preparation of [(3R,4S)-4-amino-1,1-dioxo-tetrahydrothiophen-3-yl]-[(S)-3-(4-fluorobenzyl)-piperidin-1-yl]-methanone

[1,1-Dioxo-(3R,4S)-4-[(R)-1-phenyl-ethylamino]-tetrahydrothiophen-3-yl]-[(S)-3-(4-fluoro-benzyl)-piperidin-1-yl]-methanone (790 mg, 1.72 mmol), palladium hydroxide (20 weight % on carbon, dry basis; 1.1 g) and methanol (50 mL) were combined in a pressure bottle and shaken under a hydrogen atmosphere (55–60 psig) for 20.5 h. The mixture was filtered through Celite, and the solids were washed thoroughly with methanol. The filtrate was concentrated to give the product as a solid (660 mg, quantitative), used without further purification. 1H NMR (300 mHz, CD3OD) δ7.20 (m, 2H), 7.00 (m, 2H), 4.45 and 4.32 (2m, 1H), 4.09 (m, 1H), 3.90 and 3.79 (2m, 1H), 3.7–3.4 (m, 2H), 3.13 (m, 2H), 2.87 and 2.69 (2m, 1H), 2.56 (m, 2H), 1.79 (m, 3H), 1.28 (m, 3H), 0.88 (m, 1H), ESI MS: (M+H)+=355.2.

Part G. Preparation of (3S,4S)-4-[(S)-3-(4-fluorobenzyl)-piperidin-1-ylmethyl]-1,1-dioxo-tetrahydro-thiophen-3-ylamine

[(3R,4S)-4-Amino-1,1-dioxo-tetrahydrothiophen-3-yl]-[(S)-3-(4-fluorobenzyl)-piperidin-1-yl]-methanone (560 mg, 1.46 mmol) was treated with borane-tetrahydrofuran complex in tetrahydrofuran (1.0 M; 58 mL, 58 mmol) and stirred for 16.5 h. The mixture was treated slowly with 20% acetic acid in methanol (38 mL), and the resulting mixture was stirred at room temperature for 5.5 h. The solvents were removed, and the residue was dissolved in water, made basic (pH 11) with 50% sodium hydroxide, and extracted with dichloromethane. The combined organic phases were dried (Na2SO4) and concentrated to provide a gum. This was purified by flash column chromatography (4% methanol/dichloromethane, containing 0.4% ammonium hydroxide) to provide the product (304 mg, 61%) as a white solid. 1H NMR (300 mHz, CD3OD) δ7.13 (m, 2H), 6.96 (m, 2H), 3.36 (m, 3H), 2.87 (m, 3H), 2.78 (m, 1H), 2.56 (m, 1H), 2.49 (m, 2H), 2.40 (m, 2H), 1.95 (m, 1H), 1.8–1.6 (m, 4H), 1.50 (m, 1H), 0.95 (m, 1H), ESI MS: (M+H)+=341.2.

Part H. Preparation of 1-{(3S,4S)-4-[(S)-3-(4-fluorobenzyl)-piperidin-1-ylmethyl]-1,1-dioxo-tetrahydro-thiophen-3-yl}-3-[5-acetyl-4-methylthiazol-2-yl]-urea, trifluoroacetate salt (3S,4S)-4-[(S)-3-(4-fluorobenzyl)-piperidin-1-ylmethyl]-1,1-dioxo-tetrahydrothiophen-3-ylamine (39 mg, 115 μmol) and [5-acetyl-4-methylthiazol-2-yl]-carbamic acid phenyl ester (35 mg, 126 pmol) were dissolved in N,N-dimethylformamide (0.8 mL) and treated with triethylamine (16 μL, 115 μmol). The mixture was stirred at room temperature for 19 h, and then concentrated. The residue was purified by flash column chromatography (3% methanol/dichloromethane containing 0.3% aqueous ammonium hydroxide). After isolation, the product was treated with trifluoroacetic acid (1 drop), dissolved in water/acetonitrile and lyophilized to provide a fluffy white solid (50 mg, 68%). 1H NMR (300 mHz, CD3OD) δ7.23 (m, 2H), 7.04 (m, 2H), 4.48 (bm, 1H), 3.62 (m, 4H), 3.45 (m, 1H), 3.3 (m, 2H), 3.1 (m, 2H), 2.85 (m, 2H), 2.6 (m, 2H), 2.58 (s, 3H), 2.47 (s, 3H0, 2.20 (m, 1H), 1.9 (m, 3H), 1.25 (m, 1H), ESI MS: (M+H)+=523.3.

Example 289

Preparation of 1-{(3S,4S)-4-[(S)-3-(4-fluorobenzyl)-piperidin-1-ylmethyl]-1,1-dioxo-tetrahydrothiophen-3-yl}-3-[3-(1-methyl-1H-tetrazol-5-yl)-phenyl]-urea, trifluoroacetate salt (3S,4S)-4-[(S)-3-(4-fluorobenzyl)-piperidin-1-ylmethyl]-1,1-dioxo-tetrahydrothiophen-3-ylamine (41 mg, 120 μmol) and [3-(1-methyl-1H-tetrazol-5-yl)-phenyl]-carbamic acid phenyl ester (39 mg, 131 μmol) were dissolved in N,N-dimethylformamide (1 mL) and treated with triethylamine (19 μL, 131 μmol). The mixture was stirred at room temperature for 66 h, and then concentrated. The residue was purified by flash column chromatography (3% methanol/dichloromethane containing 0.3% aqueous ammonium hydroxide). After isolation, the product was treated with trifluoroacetic acid (1 drop), dissolved in water/acetonitrile and lyophilized to provide a fluffy white solid (70 mg, 89%). 1H NMR (300 mHz, CD3OD) δ7.95 (t, J=1.4 Hz, 1H), 7.6–7.4 (3H), 7.10 (m, 2H), 6.95 (m, 2H), 4.33 (q, J=7.7 Hz, 1H), 4.19 (s, 3H), 3.56 (dd, J=13.6, 7.7 Hz, 1H), 3.38 (dd, J=13.5, 8.4 Hz, 1H), 3.05 (m, 2H), 2.79 (m, 2H), 2.7–2.4 (5H), 2.05 (m, 1H), 1.9–1.5 (5H), 0.97 (m, 1H), ESI MS: (M+H)+=542.5.

Example 290

Preparation of 1-{(3S,4S)-4-[(S)-3-(4-fluorobenzyl)-piperidin-1-ylmethyl]-1,1-dioxo-tetrahydrothiophen-3-yl}-3-[3-acetylphenyl]-urea, trifluoroacetate salt (3S,4S)-4-[(S)-3-(4-fluorobenzyl)-piperidin-1-ylmethyl]-1,1-dioxo-tetrahydrothiophen-3-ylamine (41 mg, 120 μmol) and 3-acetylphenyl isocyanate (16.5 μL, 120 μmol) were dissolved in N,N-dimethylformamide (1 mL) and treated with triethylamine (17 μL, 120 μmol). The mixture was stirred at room temperature for 66 h, and then concentrated. The residue was purified by flash column chromatography (3% methanol/dichloromethane containing 0.3% ammonium hydroxide). After isolation, the product was treated with trifluoroacetic acid (1 drop), dissolved in water/acetonitrile and lyophilized to provide a fluffy white solid (71 mg, 95%). 1H NMR (300 mHz, CD3OD) δ8.01 (s, 1H), 7.61 (m, 2H), 7.40 (t, J=8.0 Hz, 1H), 7.09 (m, 2H), 6.92 (m, 2H), 4.32 (q, J=8.0 Hz, 1H), 3.56 (dd, J=9.4, 8.1 Hz, 1H), 3.38 (dd, J=13.6, 7.4 Hz, 1H), 3.03 (m, 2H), 2.79 (m, 2H), 2.7–2.4 (5H), 2.57 (s, 3H), 2.04 (m, 1H), 1.8–1.4 (5H), 0.94 (m, 1H), ESI MS: (M+H)+=502.5.

Example 291

Preparation of 1-{(3S,4S)-4-[(S)-3-(4-fluorobenzyl)-piperidin-1-ylmethyl]-1,1-dioxo-tetrahydrothiophen-3-yl}-3-(2-morpholin-4-yl-ethyl)-urea, bis-hydrochloride salt (3S,4S)-4-[(S)-3-(4-fluorobenzyl)-piperidin-1-ylmethyl]-1,1-dioxo-tetrahydrothiophen-3-ylamine (47 mg, 137 μmol)

and (2-morpholin-4-yl-ethyl)-carbamic acid 4-nitro-phenyl ester hydrochloride (55 mg, 164 μmol) were dissolved in N,N-dimethylformamide (1 mL) and treated with triethylamine (23 μL, 164 μmol). The mixture was stirred at room temperature for 67 h, and then concentrated. The residue was purified by flash column chromatography (3% methanol/dichloromethane containing 0.3% aqueous ammonium hydroxide). After isolation, the product was dissolved in 1N hydrochloric acid and water and lyophilized to provide a fluffy white solid (70 mg, 90%). 1H NMR (300 mHz, CD3OD) δ7.15 (m, 2H), 6.98 (m, 2H), 4.21 (q, J=8.1 Hz, 1H), 3.68 (m, 4H), 3.49 (dd, J=13.6, 8.1 Hz, 1H), 3.35 (m, 1H), 3.25 (t, J=6.6 Hz, 2H), 2.98 (m, 2H), 2.78 (m, 2H), 2.6–2.4 (11H), 2.07 (m, 1H), 1.9–1.5 (5H), 0.98 (m, 1H), ESI MS: (M+H)+=497.1.

Example 292

Preparation of 1-(5-acetyl-4-methyl-thiazol-2-yl)-3-{(3R,4S)-4-[(S)-3-(4-fluorobenzyl)-piperidine-1-carbonyl]-1,1-dioxo-tetrahydro-1λ6-thiophen-3-yl}-urea

[(3R,4S)-4-Amino-1,1-dioxo-tetrahydrothiophen-3-yl]-[(S)-3-(4-fluorobenzyl)-piperidin-1-yl]-methanone (50 mg, 141 μmol) and [5-acetyl-4-methylthiazol-2-yl]-carbamic acid phenyl ester (43 mg, 155 μmol) were dissolved in N,N-dimethylformamide (1 mL) and treated with triethylamine (22 μL, 155 μmol). The mixture was stirred at room temperature for 94 h, and then concentrated. The residue was purified by flash column chromatography (4% methanol/dichloromethane containing 0.4% aqueous ammonium hydroxide) to provide a white solid (41 mg, 55%). 1H NMR (300 mHz, CD3OD) δ7.16 (m, 2H), 6.95 (m, 2H), 4.74 (m, 1H), 4.32 (m, 1H), 4.1–3.8 (m, 2H), 3.6–3.5 (m, 2H), 3.4–3.2 (m, 2H), 3.2–2.8 (m, 2H), 2.54 (s, 3H), 2.5 (m, 2H), 2.46+2.44 (2s, 3H), 1.75 (m, 3H), 1.43 (m, 1H), 1.23 (m, 1H), ESI MS: (M+H)+=537.4.

Example 293

Preparation of 1-{(3R,4S)-4-[(S)-3-(4-fluorobenzyl)-piperidine-1-carbonyl]-1,1-dioxo-tetrahydrothiophen-3-yl}-3-(2-morpholin-4-yl-ethyl)-urea, trifluoroacetate salt

[(3R,4S)-4-amino-1,1-dioxo-tetrahydrothiophen-3-yl]-[(S)-3-(4-fluorobenzyl)-piperidin-1-yl]-methanone (48 mg, 135 μmol) and (2-morpholin-4-yl-ethyl)-carbamic acid 4-nitro-phenyl ester hydrochloride (54 mg, 162 μmol) were dissolved in N,N-dimethylformamide (1 mL) and treated with triethylamine (75 μL, 540 μmol). The mixture was stirred at room temperature for 15 h, and then concentrated. The residue was purified by flash column chromatography (4% methanol/dichloromethane containing 0.4% aqueous ammonium hydroxide), then by reverse-phase preparative HPLC ($C_{18}$, 10–90% acetonitrile/water containing 0.05% trifluoroacetic acid, 35 min, 35 mL/in). After isolation, the product was dissolved in water and lyophilized to provide a fluffy white solid (35 mg, 41%). 1H NMR (300 mHz, CD3OD) δ7.24 (m, 2H), 7.00 (m, 2H), 4.70 (m, 1H), 4.42 +4.32 (2m, 1H), 4.1–3.4 (12H), 3.3–3.0 (7H), 2.85 +2.66 (2m, 1H), 2.57 (m, 2H), 1.9–1.6 (m, 3H), 1.5–1.2 (m, 2H), ESI MS: (M+H)+=511.4.

Example 294

Part A. Preparation of (3R, 4S)-4-[(R)-1-phenyl-ethylamino]-pyrrolidine-1,3-dicarboxylic acid 1-tert-butyl ester.

A solution of (3R,4S)-4-[(R)-1-phenyl-ethylamino]-pyrrolidine-1,3-dicarboxylic acid 1-tert-butyl ester 3-ethyl ester (prepared according to the procedure of X. Wang, J. F. Espinosa and S. H. Gellman, J. Am. Chem. Soc. 2000, 122, 4821; 107 mg, 295 μmol) in tetrahydrofuran (2 mL) was treated with 1.0 M sodium hydroxide solution (600 μL, 600 μmol) and the heterogenous mixture was stirred at room temperature. After 18 h, the now homogenous solution was treated with 1.0 M hydrochloric acid (600 μL, 600 μmol) and concentrated in vacuo. The residue was dissolved in water and lyophilized to provide the product, along with sodium chloride, as a white solid (115 mg, quantitative), used without further purification. 1H NMR (300 mHz, CD3OD) δ7.48 (m, 5H), 4.44 (m, 1H), 3.89 (m, 1H), 3.78 (m, 1H), 3.44–3.14 (3H), 1.67 (d, 3H), 1.4 (bs, 9H); mass spec. (ES+) m/z 335.3.

Part B. Preparation of (3R,4S)-3-[(S)-3-(4-fluorobenzyl)-piperidine-1-carbonyl]-4-[(R)-1-phenyl-ethylamino]-pyrrolidine-1-carboxylic acid tert-butyl ester.

(S)-3-(4-flourobenzyl)-piperdine, mandelic acid salt (100 mg, 290 μmol) was dissolved in 1.0 M sodium hydroxide (4mL) and extracted with ethyl acetate (4×5mL). The combined organic phases were dried (Na2SO4) and concentrated in vacuo. The free base was used without further purification.

A cloudy solution of (3R,4S)-4-[(R)-1-phenyl-ethylamino]-pyrrolidine-1,3-dicarboxylic acid 1-tert-butyl ester (80 mg, 240 μmol) in methylene chloride (5 mL) was treated with benzotriazol-1-yloxy-tripyrrolidinophosphonium hexafluorophosphate (151 mg, 290 μmol) and triethylamine (77 μL, 550 μmol) and stirred for 5 minutes. A solution of the (S)-3-(4-flourobenzyl)-piperdine prepared above in methylene chloride (5 mL) was added and the mixture was stirred at room temperature. After 18 h, the mixture was washed with water and saturated NaHCO3, dried (Na2SO4) and concentrated. The residue was purified by flash column chromatography (50% ethyl acetate/hexanes) to provide the product as a gum (100 mg, 82%). 1H NMR (300 mHz, CD3OD) δ7.32–6.95 (7H), 4.42–4.30 (1H), 3.90–2.48 (14H), 1.80–1.62 (3H), 1.40 (bs, 9H), 1.29 (d, 3H); mass spec. (ES+) m/z 510.4.

Part C. Preparation of (3S,4R)-3-amino-4-[(S)-3-(4-fluorobenzyl)-piperidine-1-carbonyl]-pyrrolidine-1-carboxylic acid tert-butyl ester.

(3R,4S)-3-[(S)-3-(4-fluorobenzyl)-piperidine-1-carbonyl]-4-[(R)-1-phenyl-ethylamino]-pyrrolidine-1-carboxylic acid tert-butyl ester (99 mg, 195 μmol), palladium hydroxide (20 weight % on carbon, dry basis; 40 mg) and ethanol (7 mL) were combined in a pressure bottle and shaken under hydrogen atmosphere (50–55 psig) for 20 h. The mixture was filtered through Celite, and the solids were rinsed with ethanol. The filtrate was concentrated to give the product as a glassy foam (75 mg, 95%), used without further purification. 1H NMR (300mHz, CDCl3) δ7.26 (m, 2H), 6.96 (m, 2H), 4.57–4.36 (1H), 3.84–2.41 (10H), 1.93–1.70 (6H), 1.44–1.39 (9H); mass spec. (ES+) m/z 406.4.

Part D. Preparation of (3S,4S)-3-amino-4-[(S)-3-(4-fluorobenzyl)-piperidin-1-ylmethyl]-pyrrolidine-1-carboxylic acid tert-butyl ester.

(3S,4R)-3-Amino-4-[(S)-3-(4-fluorobenzyl)-piperidine-1-carbonyl]-pyrrolidine-1-carboxylic acid tert-butyl ester (75 mg, 185 μmol) was treated with borane-tetrahydrofuran complex in tetrahydrofuran (1.0 M; 7.4 mL, 7.4 mmol) and stirred for 20 h. The mixture was treated slowly with 20% acetic acid in methanol (10 mL), and the resulting mixture was stirred at room temperature for 1 h . The solvents were removed, and the residue was dissolved in water, made basic (pH 11) with 50% sodium hydroxide, and extracted with methylene chloride. The combined organic phases were dried (Na2SO4) and concentrated. The residue was purified by flash column chromatography (5% methanol/ dichloromethane) to provide the product (30 mg, 40%). 1H NMR (300 mHz, CD3OD) δ7.20 (m, 2H), 6.98 (m, 2H), 3.18–2.42 (15H), 1.80–1.50 (4H), 1.41 (s, 9H); mass spec. (ES+) m/z 392.4.

Part E. Preparation of (3S,4S)-3-[(S)-3-(4-fluorobenzyl)-piperidin-1-ylmethyl]-4-{3-[3-methyl-5-(1-methyl-1H-tetrazol-5-yl)-phenyl]-ureido}-pyrrolidine-1-carboxylic acid tert-butyl ester, trifluoroacetate salt.

(3S,4S)-3-amino-4-[(S)-3-(4-fluorobenzyl)-piperidin-1-ylmethyl]-pyrrolidine-1-carboxylic acid tert-butyl ester (21 mg, 54 μmol) and [3-methyl-5-(1-methyl-1H-tetrazol-5yl)-phenyl]-carbamic acid phenyl ester (20 mg, 65 pmol) were dissolved in acetonitrile (1 mL) and the mixture was stirred at room temperature. After 24 h , the mixture was concentrated and purified by flash chromatography (5% methanol/ dichloromethane containing 0.5% ammonium hydroxide). After isolation, the product was dissolved in water with a small amount of trifluoroacetic acid and the solution was lyophilized to provide a white solid (10 mg, 31%). 1H NMR (300 mHz, CD3OD) δ7.79 (s, 1H), 7.39 (s, 1H), 7.21 (s, 1H), 7.15–6.94 (4H), 4.19 (s, 3H), 4.02 (m, 1H), 3.76–3.6 (3H), 3.21–2.82 (7H), 2.50 (m, 2H), 2.41 (s, 3H), 2.36 (m, 1H), 1.80–1.60 (5H), 1.45 (s, 9H); mass spec. (ES+) m/z 607.4.

Example 295

Preparation of 1-(5-acetyl-4-methylthiazol-2-yl)-3-{(3S,4S)-4-[(S)-3-(4-fluorobenzyl)-piperidin-1-ylmethyl]-pyrrolidin-3-yl}-urea, bis-trifluoroacetate salt Part A. Preparation of (3S,4S)-3-[(S)-3-(4-fluorobenzyl)-piperidin-1-ylmethyl]-4-[(R)-1-phenyl-ethylamino]-pyrrolidine-1-carboxylic acid tert-butyl ester (3R,4S)-3-[(S)-3-(4-fluorobenzyl)-piperidine-1-carbonyl]-4-[(R)-1-phenyl-ethylamino]-pyrrolidine-1-carboxylic acid tert-butyl ester (150 mg, 294 μmol) ) was treated with borane-tetrahydrofuran complex in tetrahydrofuran (1.0 M; 11.64 mL, 11.64 mmol) and stirred for 20 h . The mixture was treated slowly with 20% acetic acid in methanol (20 mL), and the resulting mixture was stirred at room temperature for 36 h . The solvents were removed, and the residue was dissolved in water, made basic (pH 11) with 50% sodium hydroxide, and extracted with dichloromethane. The combined organic phases were dried (Na2SO4) and concentrated. The residue was purified by flash column chromatography (60% ethyl acetate/hexane) to provide the product (100 mg, 68%). 1H NMR (300 mHz, CD3OD) δ7.31–7.00 (9H), 3.78 (m, 1H), 3.42 (m, 1H), 3.22–1.62 (18H), 1.39 (d, 3H), 1.34 (s, 9H); mass spec. (ES+) m/z 496.5.

Part B. Preparation of (3S,4S)-3-amino-4-[(S)-3-(4-fluorobenzyl)-piperidin-1-ylmethyl]-pyrrolidine-1-carboxylic acid tert-butyl ester (3S, 4S)-3-[(S)-3-(4-Fluorobenzyl)-piperidin-1-ylmethyl]-4-[(R)-1-phenyl-ethylamino]-pyrrolidine-1-carboxylic acid tert-butyl ester (100 mg, 0.201 mmol), palladium hydroxide (20 weight % on carbon, dry basis; 40 mg) and methanol (7 mL) were combined in a pressure bottle and shaken under hydrogen atmosphere (50–55 psig) for 20 h . The mixture was filtered through Celite, and the solids were rinsed with ethanol. The filtrate was concentrated to give the product as a glassy foam (75 mg, 95%), used without further purification. 1H NMR (300 mHz, CD3OD) δ7.20 (m, 2H), 6.98 (m, 2H), 3.18–2.42 (15H), 1.80–1.50 (4H), 1.41 (s, 9H); mass spec. (ES+) m/z 392.4.

Part C. Preparation of 1-(5-acetyl-4-methylthiazol-2-yl)-3-{(3S,4S)-4-[(S)-3-(4-fluorobenzyl)-piperidin-1-ylmethyl]-pyrrolidin-3-yl}-urea, bis-trifluoroacetate salt (3S,4S)-3-Amino-4-[(S)-3-(4-fluorobenzyl)-piperidin-1-ylmethyl]-pyrrolidine-1-carboxylic acid tert-butyl ester (21 mg, 0.054 mmol) and [5-acetyl-4-methylthiazol-2-yl]-carbamic acid phenyl ester (18 mg, 0.065 mmol) were dissolved in DMF (1 mL) and treated with triethylamine (9 μL, 0.065 mmol) and the mixture was stirred at room temperature. After 24 h , the mixture was concentrated and purified by flash column chromatography (5% methanol/ dichloromethane containing 0.5% ammonium hydroxide). After isolation, the product was stirred in trifluoroacetic acid for 4 h . The mixture was concentrated and the residue dissolved in water and lyophilized to provide a white solid (10 mg, 31%). 1H NMR (300mHz, CD3OD) δ7.46–7.22 (4H), 4.19–3.40 (4H), 2.61 (s, 3H), 2.45 (s, 3H), 2.24 (m, 1H), 1.64–1.23 (15H); mass spec. (ES+) m/z 474.5.

The compounds shown below were made using the procedures described above.

TABLE 1

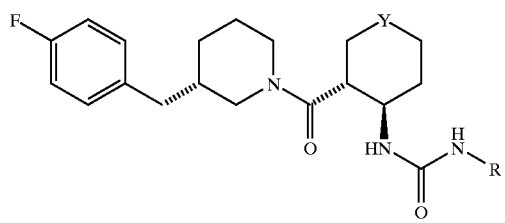

core a

TABLE 1-continued
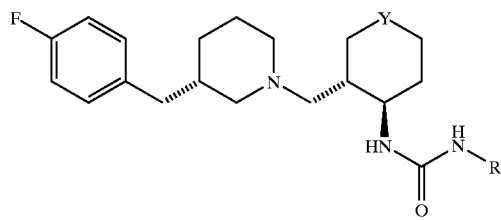
core b
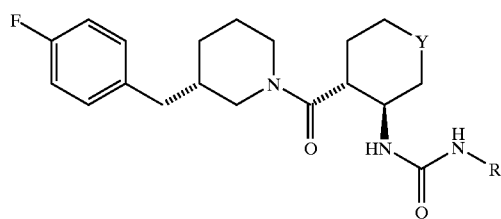
core c
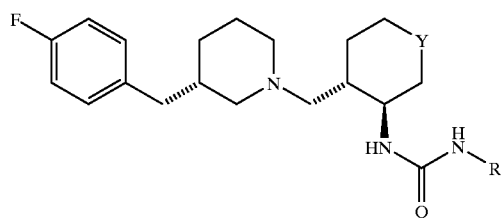
core d
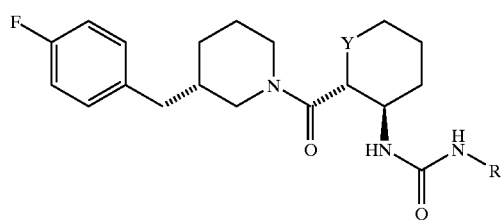
core e
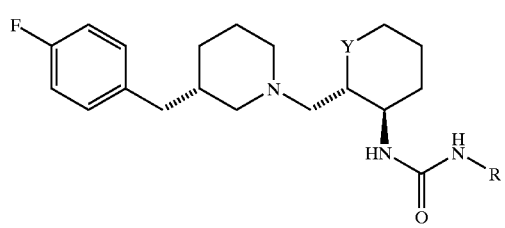
core f
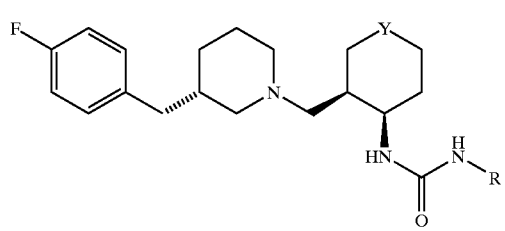
core g TABLE 1-continued

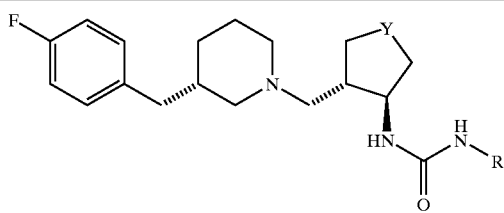

core h

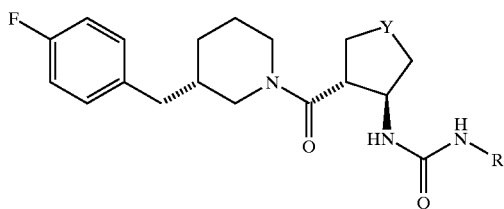

core i

| Ex # | Core | Y | R | MS m/z |
|---|---|---|---|---|
| 1 | a | NBoc | 3-Ac—Ph | 581 |
| 2 | a | NH | 3-Ac—Ph | 481 |
| 3 | a | NBoc | 3-(1-Me-5-tetrazole)-Ph | 621 |
| 4 | a | NH | 3-(1-Me-5-tetrazole)-Ph | 521 |
| 5 | a | NCOtBu | 3-(1-Me-5-tetrazole)-Ph | 605 |
| 6 | a | NAc | 3-(1-Me-5-tetrazole)-Ph | 563 |
| 7 | a | NSO$_2$Me | 3-(1-Me-5-tetrazole)-Ph | 599 |
| 8 | a | NMe | 3-(1-Me-5-tetrazole)-Ph | 535 |
| 9 | a | NBoc | 1-Boc-5-indazole | 679 |
| 10 | a | NH | 5-indazole | 479 |
| 11 | a | NBoc | 5-Ac-4-Me-2-thiazole | 602 |
| 12 | a | NH | 5-Ac-4-Me-2-thiazole | 502 |
| 13 | c | NBoc | 3-Ac-Ph | 581 |
| 14 | c | NH | 3-Ac-Ph | 481 |
| 15 | b | NBoc | 3-Ac-Ph | 567 |
| 16 | b | NH | 3-Ac-Ph | 467 |
| 17 | b | NAc | 3-Ac-Ph | 509 |
| 18 | b | NSO$_2$Me | 3-Ac-Ph | 545 |
| 19 | b | NMe | 3-Ac-Ph | 481 |
| 20 | b | NiBu | 3-Ac-Ph | 523 |
| 21 | b | NBoc | 3-(1-Me-5-tetrazole)-Ph | 607 |
| 22 | b | NH | 3-(1-Me-5-tetrazole)-Ph | 507 |
| 23 | b | NBoc | 1-Boc-5-indazole | 665 |
| 24 | b | NH | 5-indazole | 485 |
| 25 | b | NBoc | 5-Ac-4-Me-2-thiazole | 588 |
| 26 | b | NH | 5-Ac-4-Me-2-thiazole | 488 |
| 27 | d | NBoc | 3-Ac-Ph | 567 |
| 28 | d | NH | 3-Ac-Ph | 467 |
| 29 | g | NBoc | 3-Ac-Ph | 581 |
| 30 | g | NH | 3-Ac-Ph | 481 |
| 31 | b | NCO$_2$Me | 3-Ac-Ph | 525 |
| 32 | b | NCOtBu | 3-Ac-Ph | 551 |
| 33 | c | NBoc | 3-(1-Me-5-tetrazole)-Ph | 621 |
| 34 | b | NCH$_2$CH$_2$F | 3-Ac-Ph | 513 |
| 35 | b | NCH$_2$COMe | 3-Ac-Ph | 523 |

TABLE 1-continued

| | | | | |
|---|---|---|---|---|
| 36 | d | NMe | 3-Ac-Ph | 481 |
| 37 | d | NAc | 3-Ac-Ph | 509 |
| 38 | b | NAc | 3-(1-Me-5-tetrazole)-Ph | 549 |
| 39 | b | NMe | 3-(1-Me-5-tetrazole)-Ph | 521 |
| 40 | b | NSO$_2$Me | 3-(1-Me-5-tetrazole)-Ph | 584 |
| 41 | a | NCH$_2$COMe | 3-(1-Me-5-tetrazole)-Ph | 577 |
| 42 | a | NCH$_2$CH$_2$F | 3-(1-Me-5-tetrazole)-Ph | 567 |
| 43 | a | NSO$_2$CF$_3$ | 3-(1-Me-5-tetrazole)-Ph | 653 |
| 44 | f | O | 3-Ac-Ph | 468 |
| 45 | f | O | 3-(1-Me-5-tetrazole)-Ph | 508 |
| 46 | f | O | 5-Ac-4-Me-2-thiazole | 489 |
| 47 | e | O | 3-Ac-Ph | 482 |
| 48 | e | O | 3-(1-Me-5-tetrazole)-Ph | 522 |
| 49 | e | O | 5-Ac-4-Me-2-thiazole | 503 |
| 50 | b | NMe | 5-Ac-4-Me-2-thiazole | 502 |
| 51 | b | NAc | 5-Ac-4-Me-2-thiazole | 530 |
| 52 | b | NCOi-Pr | 5-Ac-4-Me-2-thiazole | 558 |
| 53 | b | NSO$_2$Me | 5-Ac-4-Me-2-thiazole | 566 |
| 54 | b | NCH2CH2F | 5-Ac-4-Me-2-thiazole | 534 |
| 55 | b | NCH2COMe | 5-Ac-4-Ne-2-thiazole | 544 |
| 56 | b | O | 3-Ac-Ph | 468 |
| 57 | b | O | 3-(1-Me-5-tetrazole)-Ph | 508 |
| 58 | b | O | 5-Ac-4-Me-2-thiazole | 467 |
| 59 | a | O | 3-Ac-Ph | 482 |
| 60 | a | O | 3-(1-Me-5-tetrazole)-Ph | 522 |
| 61 | a | O | 5-Ac-4-Me-2-thiazole | 503 |
| 62 | b | NH | 4-F-Ph | 443 |
| 63 | b | NBoc | 4-F-Ph | 543 |
| 64 | b | NAc | 4-F-Ph | 485 |
| 65 | b | NMe | 4-F-Ph | 457 |
| 66 | b | NEt | 4-F-Ph | 471 |
| 67 | b | NCH2 [1,2,4]oxadiazol-3-yl | 4-F-Ph | 525 |
| 68 | b | NCH2CONHiPr | 4-F-Ph | 542 |
| 69 | b | NCH2C≡CH | 4-F-Ph | 481 |
| 70 | b | N-piperidin-4-yl | 3-Ac-Ph | 550 |
| 71 | b | N-1-Ac-piperidin-4-yl | 3-Ac-Ph | 592 |
| 72 | b | N-1-Me-piperidin-4-yl | 3-Ac-Ph | 564 |
| 73 | b | NH | 3,5-diAc-Ph | 509 |
| 74 | b | NBoc | 3,5-diAc-Ph | 609 |
| 75 | b | NAc | 3,5-diAc-Ph | 551 |
| 76 | b | NMe | 3,5-diAc-Ph | 523 |
| 77 | b | NEt | 3,5-diAc-Ph | 537 |
| 78 | b | NCH2 [1,2,4] oxadiazol-3-yl | 3,5-diAc-Ph | 591 |
| 79 | b | NCH2CONHiPr | 3,5-diAc-Ph | 608 |
| 80 | b | NCH2C≡CH | 3,5-diAc-Ph | 547 |
| 81 | b | NCO2Me | 3-(1-Me-5-tetrazole)-Ph | 565 |
| 82 | b | NH | 3-Me-5-(1-Me-5-tetrazole)-Ph | 521 |
| 83 | b | NBoc | 3-Me-5-(1-Me-5-tetrazole)-Ph | 621 |
| 84 | b | NAc | 3-Me-5-(1-Me-5-tetrazole)-Ph | 563 |
| 85 | b | NMe | 3-Me-5-(1-Me-5-tetrazole)-Ph | 535 |

TABLE 1-continued

| | | | | |
|---|---|---|---|---|
| 86 | b | NEt | 3-Me-5-(1-Me-5-tetrazole)-Ph | 549 |
| 87 | b | NCH2 [1,2,4] oxadiazol-3-yl | 3-Me-5-(1-Me-5-tetrazole)-Ph | 603 |
| 88 | b | NCH2CONHiPr | 3-Me-5-(1-Me-5-tetrazole)-Ph | 620 |
| 89 | b | NCH2C≡CH | 3-Me-5-(1-Me-5-tetrazole)-Ph | 559 |
| 90 | b | NH | 3-Br-5-(1-Me-5-tetrazole)-Ph | 585 |
| 91 | b | NBoc | 3-Br-5-(1-Me-5-tetrazole)-Ph | 685 |
| 92 | b | NAc | 3-Br-5-(1-Me-5-tetrazole)-Ph | 627 |
| 93 | b | NMe | 3-Br-5-(1-Me-5-tetrazole)-Ph | 599 |
| 94 | b | NEt | 3-Br-5-(1-Me-5-tetrazole)-Ph | 613 |
| 95 | b | NCH2[1,2,4]oxadiazol-3-yl | 3-Br-5-(1-Me-5-tetrazole)-Ph | 667 |
| 96 | b | NCH2CONHiPr | 3-Br-5-(1-Me-5-tetrazole)-Ph | 684 |
| 97 | b | NCH2C≡CH | 3-Br-5-(1-Me-5-tetrazole)-Ph | 623 |
| 98 | b | NCH2COCH3 | 3-(5-Me-1-tetrazole)-Ph | 563 |
| 99 | b | NCH2COCH3 | 1-Me-pyrazol-3-yl | 485 |
| 100 | b | NCH2COCH3 | thiazol-2-yl | 488 |
| 101 | b | NCH2COCH3 | 4-Me-5-CO2Et-thiazol-2-yl | 574 |
| 102 | b | NCO2Me | 5-Ac-4-Me-2-thiazole | 546 |
| 103 | b | NCO2CH2CMe2CH2OH | 5-Ac-4-Me-2-thiazole | 618 |
| 104 | b | NCOEt | 5-Ac-4-Me-2-thiazole | 544 |
| 105 | b | NCO-cyclopropyl | 5-Ac-4-Me-2-thiazole | 556 |
| 106 | b | NCO-cyclopentyl | 5-Ac-4-Me-2-thiazole | 584 |
| 107 | b | NCO-4-tetrahydropyran | 5-Ac-4-Me-2-thiazole | 600 |
| 108 | b | NCOCH2OMe | 5-Ac-4-Me-2-thiazole | 560 |
| 109 | b | NCOCH2NMe2 | 5-Ac-4-Me-2-thiazole | 573 |
| 110 | b | NCONHMe | 5-Ac-4-Me-2-thiazole | 545 |
| 111 | b | NCONMe2 | 5-Ac-4-Me-2-thiazole | 559 |
| 112 | b | NCONHEt | 5-Ac-4-Me-2-thiazole | 559 |
| 113 | b | NEt | 5-Ac-4-Ne-2-thiazole | 516 |
| 114 | b | NPr | 5-Ac-4-Me-2-thiazole | 530 |
| 115 | b | NiPr | 5-Ac-4-Me-2-thiazole | 530 |
| 116 | b | N-cyclobutyl | 5-Ac-4-Me-2-thiazole | 542 |
| 117 | b | N-cyclopentyl | 5-Ac-4-Me-2-thiazole | 556 |
| 118 | b | N-4-tetrahydropyran | 5-Ac-4-Me-2-thiazole | 572 |
| 119 | b | N-4-tetrahydrothiopyran | 5-Ac-4-Me-2-thiazole | 588 |
| 120 | b | N-4-tetrahydrothiopyran-dioxide | 5-Ac-4-Me-2-thiazole | 620 |
| 121 | b | N-4-piperidine | 5-Ac-4-Me-2-thiazole | 571 |
| 122 | b | N-4-piperidinyl-Boc | 5-Ac-4-Me-2-thiazole | 671 |
| 123 | b | N-4-piperidinyl-AC | 5-Ac-4-Me-2-thiazole | 613 |
| 124 | b | N-4-piperidinyl-Me | 5-Ac-4-Me-2-thiazole | 585 |

TABLE 1-continued

| | | | | |
|---|---|---|---|---|
| 125 | b | NCH2-cyclopropyl | 5-Ac-4-Me-2-thiazole | 542 |
| 126 | b | NCH2-cyclobutyl | 5-Ac-4-Me-2-thiazole | 556 |
| 127 | b | NCH2Ph | 5-Ac-4-Me-2-thiazole | 578 |
| 128 | b | NCH2-2-furan | 5-Ac-4-Me-2-thiazole | 572 |
| 129 | b | NCH2-3-furan | 5-Ac-4-Me-2-thiazole | 572 |
| 130 | b | NCH2-2-thiophene | 5-Ac-4-Me-2-thiazole | 584 |
| 131 | b | NCH2-3-thiophene | 5-Ac-4-Me-2-thiazole | 584 |
| 132 | b | NCH2-2-imidazole | 5-Ac-4-Me-2-thiazole | 568 |
| 133 | b | NCH2-4-imidazole | 5-Ac-4-Me-2-thiazole | 568 |
| 134 | b | NCH2-2-thiazole | 5-Ac-4-Me-2-thiazole | 585 |
| 135 | b | NCH2[1,2,4]oxadiazol-3-yl | 5-Ac-4-Me-2-thiazole | 570 |
| 136 | b | NCH2CH2OH | 5-Ac-4-Me-2-thiazole | 532 |
| 137 | b | NCH2CMe2OH | 5-Ac-4-Ne-2-thiazole | 560 |
| 138 | b | NCH2CHOHCF3 | 5-Ac-4-Me-2-thiazole | 600 |
| 139 | b | NCH2CH2OMe | 5-Ac-4-Me-2-thiazole | 546 |
| 140 | b | NCH2CH2OEt | 5-Ac-4-Me-2-thiazole | 560 |
| 141 | b | NCH2CH2SEt | 5-Ac-4-Me-2-thiazole | 576 |
| 142 | b | NCH2CH2SO2Et | 5-Ac-4-Me-2-thiazole | 608 |
| 143 | b | NCH2CH2OAc | 5-Ac-4-Me-2-thiazole | 574 |
| 144 | b | NCH2CN | 5-Ac-4-Me-2-thiazole | 527 |
| 145 | b | NCH2CH2NMe2 | 5-Ac-4-Me-2-thiazole | 559 |
| 146 | b | NCH2CH2NEt2 | 5-Ac-4-Me-2-thiazole | 587 |
| 147 | b | NCH2CH2pyrrolidine | 5-Ac-4-Me-2-thiazole | 585 |
| 148 | b | NCH2CH2morpholine | 5-Ac-4-Me-2-thiazole | 601 |
| 149 | b | NCH2CH2pyrrole | 5-Ac-4-Me-2-thiazole | 581 |
| 150 | b | NCH2CH2COMe | 5-Ac-4-Me-2-thiazole | 558 |
| 151 | b | NCH2CHMeCOMe | 5-Ac-4-Me-2-thiazole | 572 |
| 152 | b | NCH2CH2CH2OH | 5-Ac-4-Me-2-thiazole | 546 |
| 153 | b | (R)-NCH2CHMeCH2OH | 5-Ac-4-Me-2-thiazole | 560 |
| 154 | b | (S)-NCH2CHMeCH2OH | 5-Ac-4-Me-2-thiazole | 560 |
| 155 | b | NCH2COtBu | 5-Ac-4-Me-2-thiazole | 586 |
| 156 | b | NCH2CONHMe | 5-Ac-4-Me-2-thiazole | 559 |
| 157 | b | NCH2CONHiPr | 5-Ac-4-Me-2-thiazole | 587 |
| 158 | b | NCH2CONHtBu | 5-Ac-4-Me-2-thiazole | 601 |
| 159 | b | NCH2CONMe2 | 5-Ac-4-Me-2-thiazole | 573 |
| 160 | b | N-2-oxocyclopentane | 5-Ac-4-Me-2-thiazole | 570 |
| 161 | b | N-allyl | 5-Ac-4-Me-2-thiazole | 528 |
| 162 | b | N-propargyl | 5-Ac-4-Me-2-thiazole | 526 |
| 163 | d | NH | 4-F-Ph | 443 |
| 164 | d | NAc | 4-F-Ph | 485 |
| 165 | d | NCOCH2OMe | 4-F-Ph | 515 |

TABLE 1-continued

| | | | | |
|---|---|---|---|---|
| 166 | d | NCH2cyclopropyl | 4-F-Ph | 497 |
| 167 | d | NCH2CH2OH | 4-F-Ph | 487 |
| 168 | d | NCOCH2OMe | 3-Ac-Ph | 539 |
| 169 | d | NCOCH2NMe2 | 3-Ac-Ph | 552 |
| 170 | d | NCONHEt | 3-Ac-Ph | 538 |
| 171 | d | NCH2CH2OH | 3-Ac-Ph | 511 |
| 172 | d | NCO2tBu | 3-(1-Me-5-tetrazole)-Ph | 607 |
| 173 | d | NAc | 3-(1-Me-5-tetrazole)-Ph | 549 |
| 174 | d | NCOtBu | 3-(1-Me-5-tetrazole)-Ph | 591 |
| 175 | d | NMe | 3-(1-Me-5-tetrazole)-Ph | 520 |
| 176 | d | NH | 3-Me-5-(1-Me-5-tetrazole)-Ph | 521 |
| 177 | d | NCH2CH2OH | 3-Me-5-(1-Me-5-tetrazole)-Ph | 565 |
| 178 | d | NH | 3-Br-5-(1-Me-5-tetrazole)-Ph | 584 |
| 179 | d | NCH2CH2OH | 3-Br-5-(1-Ne-5-tetrazole)-Ph | 629 |
| 180 | d | NAc | 3-(5-Me-1-tetrazole)-Ph | 549 |
| 181 | d | NAc | 1-Me-pyrazol-3-yl | 471 |
| 182 | d | NAc | thiazol-2-yl | 474 |
| 183 | d | NAc | 4-Me-5-CO2Et-thiazol-2-yl | 560 |
| 184 | d | NH | 5-Ac-4-Me-2-thiazole | 488 |
| 185 | d | NCO2Me | 5-Ac-4-Me-2-thiazole | 546 |
| 186 | d | NCO2tBu | 5-Ac-4-Me-2-thiazole | 588 |
| 187 | d | NAc | 5-Ac-4-Me-2-thiazole | 530 |
| 188 | d | NCOEt | 5-Ac-4-Ne-2-thiazole | 544 |
| 189 | d | NCOiPr | 5-Ac-4-Me-2-thiazole | 558 |
| 190 | d | NCOtBu | 5-Ac-4-Me-2-thiazole | 572 |
| 191 | d | NCO-cyclopropyl | 5-Ac-4-Me-2-thiazole | 556 |
| 192 | d | NCO-cyclobutyl | 5-Ac-4-Me-2-thiazole | 570 |
| 193 | d | NCO-cyclopentyl | 5-Ac-4-Me-2-thiazole | 584 |
| 194 | d | NCO-cyclohexyl | 5-Ac-4-Me-2-thiazole | 598 |
| 195 | d | NCO-4-tetrahydropyran | 5-Ac-4-Me-2-thiazole | 600 |
| 196 | d | NCOCH2OMe | 5-Ac-4-Me-2-thiazole | 560 |
| 197 | d | NCOCH2NMe2 | 5-Ac-4-Me-2-thiazole | 573 |
| 198 | d | NCONHMe | 5-Ac-4-Me-2-thiazole | 545 |
| 199 | d | NOONHEt | 5-Ac-4-Me-2-thiazole | 559 |
| 200 | d | NCONHPr | 5-Ac-4-Me-2-thiazole | 573 |
| 201 | d | NCONHiPr | 5-Ac-4-Me-2-thiazole | 573 |
| 202 | d | NCONH-allyl | 5-Ac--4-Me-2-thiazole | 571 |
| 203 | d | NCONH-(5-Ac-4-Me-thiazol-2-yl) | 5-Ac-4-Me-2-thiazole | 670 |
| 204 | d | NMe | 5-Ac-4-Me-2-thiazole | 502 |
| 205 | d | N-4-piperidine | 5-Ac-4-Me-2-thiazole | 571 |
| 206 | d | N-4-piperidinyl-Ac | 5-Ac-4-Me-2-thiazole | 613 |
| 207 | d | N-4-piperidinyl-Me | 5-Ac-4-Me-2-thiazole | 585 |
| 208 | d | NCH2-cyclopropyl | 5-Ac-4-Me-2-thiazole | 542 |

TABLE 1-continued

| | | | | |
|---|---|---|---|---|
| 209 | d | NCH2-2-tetrahydropyran | 5-Ac-4-Ne-2-thiazole | 586 |
| 210 | d | NCH2-2-furan | 5-Ac-4-Me-2-thiazole | 568 |
| 211 | d | NCH2-3-furan | 5-Ac-4-Me-2-thiazole | 568 |
| 212 | d | NCH2[1,2,4]oxadiazol-3-yl | 5-Ac-4-Me-2-thiazole | 570 |
| 213 | d | NCH2CH2F | 5-Ac-4-Me-2-thiazole | 534 |
| 214 | d | NCH2CH2OH | 5-Ac-4-Me-2-thiazole | 532 |
| 215 | d | NCH2CH2SO2Et | 5-Ac-4-Me-2-thiazole | 608 |
| 216 | d | NCH2CN | 5-Ac-4-Me-2-thiazole | 527 |
| 217 | d | NCH2CH2CH2OH | 5-Ac-4-Me-2-thiazole | 546 |
| 218 | d | (R)-NCH2CHMeCH2OH | 5-Ac-4-Me-2-thiazole | 560 |
| 219 | d | (S)-NCH2CHMeCH2OH | 5-Ac-4-Me-2-thiazole | 560 |
| 220 | d | NCH2COMe | 5-Ac-4-Me-2-thiazole | 544 |
| 221 | d | NCH2CONMe2 | 5-Ac-4-Me-2-thiazole | 573 |
| 222 | a | NCOiPr | 3-(5-Me-1-tetrazole)-Ph | 591 |
| 223 | a | NCOPh | 3-(5-Me-1-tetrazole)-Ph | 625 |
| 224 | a | NSO2iPr | 3-(5-Me-1-tetrazole)-Ph | 627 |
| 225 | d | NH | CH2CH2-morpholin-1-yl | 462 |
| 226 | d | NCO2Me | CH2CH2-morpholin-1-yl | 520 |
| 227 | d | NAc | CH2CH2-morpholin-1-yl | 504 |
| 228 | d | NCOEt | CH2CH2-morpholin-1-yl | 518 |
| 229 | d | NCOtBu | CH2CH2-morpholin-1-yl | 546 |
| 230 | d | NCO-cyclobutyl | CH2CH2-morpholin-1-yl | 544 |
| 231 | d | NCO-4-tetrahydropyran | CH2CH2-morpholin-1-yl | 574 |
| 232 | d | NCOCH2OMe | CH2CH2-morpholin-1-yl | 534 |
| 233 | d | NCONMe2 | CH2CH2-morpholin-1-yl | 533 |
| 234 | d | NCONHEt | CH2CH2-morpholin-1-yl | 533 |
| 235 | d | NSO2Me | CH2CH2-morpholin-1-yl | 540 |
| 236 | d | NMe | CH2CH2-morpholin-1-yl | 476 |
| 237 | d | NEt | CH2CH2-morpholin-1-yl | 490 |
| 238 | d | NiPr | CH2CH2-morpholin-1-yl | 504 |
| 239 | d | NCH2cPr | CH2CH2-morpholin-1-yl | 516 |
| 240 | d | NCH2COMe | CH2CH2-morpholin-1-yl | 518 |
| 241 | d | O | 3-(5-Me-1-tetrazole)-Ph | 508 |
| 242 | d | O | 3-Me-5-(1-Me-5-tetrazole)-Ph | 522 |
| 243 | d | O | 5-Ac-4-Me-2-thiazole | 489 |
| 244 | b | NCO2Me | 4-F-Ph | 501 |
| 245 | b | COCH2NMe2 | 4-F-Ph | 528 |
| 246 | b | NSO2Me | 4-F-Ph | 521 |
| 247 | b | NCH2-thiazol-2-yl | 4-F-Ph | 540 |
| 248 | b | NCH2CH2OH | 4-F-Ph | 487 |
| 249 | b | NCH2CH2OMe | 4-F-Ph | 501 |
| 250 | b | NCH2CH2-morpholin-1-yl | 4-F-Ph | 556 |
| 251 | b | NCH2CH2CH2OH | 4-F-Ph | 501 |

TABLE 1-continued

| | | | | |
|---|---|---|---|---|
| 252 | b | NCO2Me | 3,5-diAc-Ph | 567 |
| 253 | b | COCH2NMe2 | 3,5-diAc-Ph | 594 |
| 254 | b | NSO2Me | 3,5-diAc-Ph | 587 |
| 255 | b | N-4-THTP-dioxide | 3,5-diAc-Ph | 641 |
| 256 | b | NCH2-thiazol-2-yl | 3,5-diAc-Ph | 606 |
| 257 | b | NCH2CH2OH | 3,5-diAc-Ph | 553 |
| 258 | b | NCH2CH2OMe | 3,5-diAc-Ph | 557 |
| 259 | b | NCH2CH2-morpholin-1-yl | 3,5-diAc-Ph | 622 |
| 260 | b | NCH2CH2CH2OH | 3,5-diAc-Ph | 567 |
| 261 | b | NCO2Me | 3-Me-5-(1-Me-5-tetrazole)-Ph | 579 |
| 262 | b | COCH2NMe2 | 3-Me-5-(1-Me-5-tetrazole)-Ph | 606 |
| 263 | b | NSO2Me | 3-Me-5-(1-Me-5-tetrazole)-Ph | 599 |
| 264 | b | NCH2-thiazol-2-yl | 3-Me-5-(1-Me-5-tetrazole)-Ph | 618 |
| 265 | b | NCH2CH2OH | 3-Me-5-(1-Me-5-tetrazole)-Ph | 565 |
| 266 | b | NCH2CH2OMe | 3-Me-5-(1-Me-5-tetrazole)-Ph | 579 |
| 267 | b | NCH2CH2-morpholin-1-yl | 3-Me-5-(1-Me-5-tetrazole)-Ph | 634 |
| 268 | b | NCH2CH2CH2OH | 3-Me-5-(1-Me-5-tetrazole)-Ph | 579 |
| 269 | b | NCO2Me | 3-Br-5-(1-Me-5-tetrazole)-Ph | 643 |
| 270 | b | COCH2NMe2 | 3-Br-5-(1-Me-5-tetrazole)-Ph | 670 |
| 271 | b | NSO2Me | 3-Br-5-(1-Me-5-tetrazole)-Ph | 663 |
| 272 | b | N-4-THTP-dioxide | 3-Br-5-(1-Me-5-tetrazole)-Ph | 717 |
| 273 | b | NCH2-thiazol-2-yl | 3-Br-5-(1-Me-5-tetrazole)-Ph | 682 |
| 274 | b | NCH2CH2OH | 3-Br-5-(1-Me-5-tetrazole)-Ph | 629 |
| 275 | b | NCH2CH2OMe | 3-Br-5-(1-Me-5-tetrazole)-Ph | 643 |
| 276 | b | NCH2CH2CH2OH | 3-Br-5-(1-Me-5-tetrazole)-Ph | 643 |
| 277 | d | NBoc | benzyl | 539 |
| 278 | d | NH | benzyl | 439 |
| 279 | d | NBoc | THP-4-ylmethyl | 547 |
| 280 | d | NH | THP-4-ylmethyl | 447 |
| 281 | d | NBoc | THP-4-ylethyl | 561 |
| 282 | d | NH | THP-4-ylethyl | 461 |
| 283 | d | O | 3-Me-5-(1-Me-5-tetrazole)-Ph | 522 |
| 284 | d | O | 3-(1-Me-5-tetrazole)-Ph | 508 |
| 285 | d | O | 5-Ac-4-Me-2-thiazole | 489 |
| 286 | d | O | 3-Ac-Ph | 468 |
| 287 | d | O | CH2CH2-morpholin-1yl | 463 |
| 288 | h | SO2 | 5-Ac-4-Me-2-thiazole | 523 |
| 289 | h | SO2 | 3-(1-Me-5-tetrazole)-Ph | 542 |
| 290 | h | SO2 | 3-Ac-Ph | 502 |
| 291 | h | SO2 | CH2CH2-morpholin-1yl | 497 |
| 292 | i | SO2 | 5-Ac-4-Me-2-thiazole | 537 |
| 293 | i | SO2 | CH2CH2-morpholin-1yl | 511 |
| 294 | h | NBoc | 3-Me-5-(1-Me-5-tetrazole)-Ph | 607 |
| 295 | h | NBOC | 5-Ac-4-Me-2-thiazole | 474 |

The following tables contain representative examples of the present invention, and may be prepared by procedures described above, or methods familiar to one skilled in the art. Each entry in each table is intended to be paired with each formulae at the start of the table. For example, Entry 1 in Table 2 is intended to be paired with each of formulae 1–12. (All stereocenters are (+/−) unless otherwise indicated)

TABLE 2
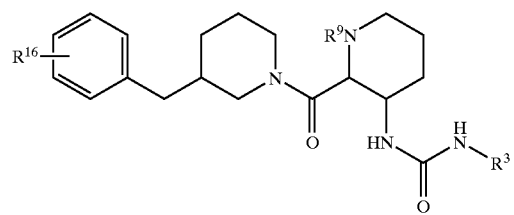
1
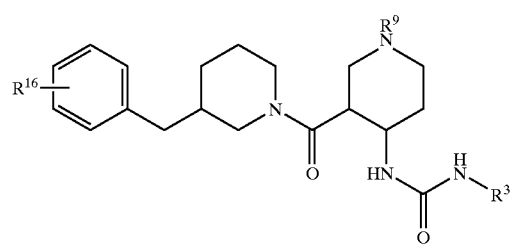
2
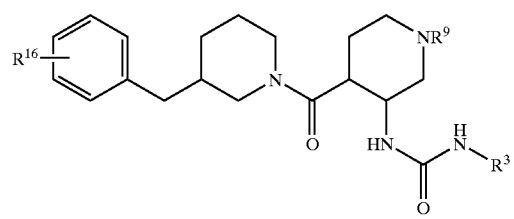
3
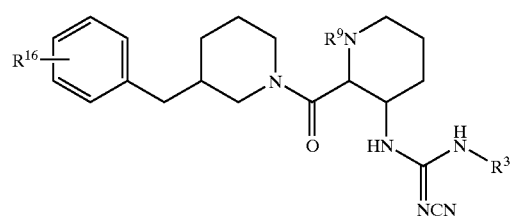
4
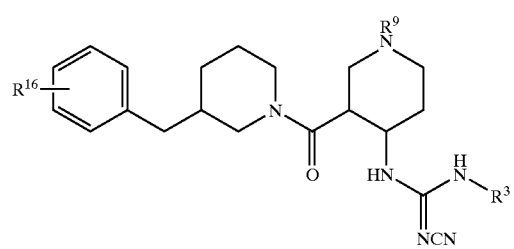
5
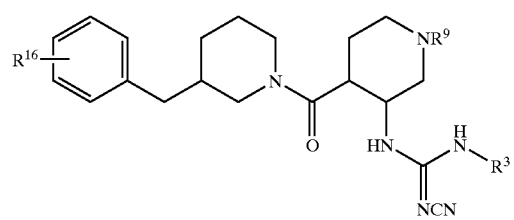
6
TABLE 2-continued
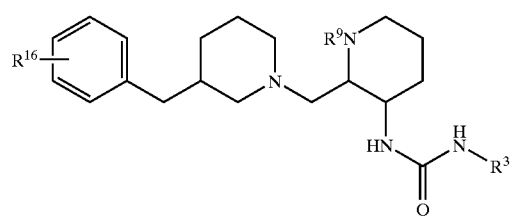
7
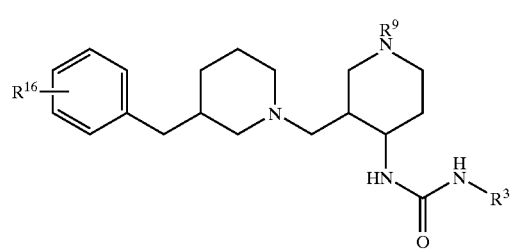
8
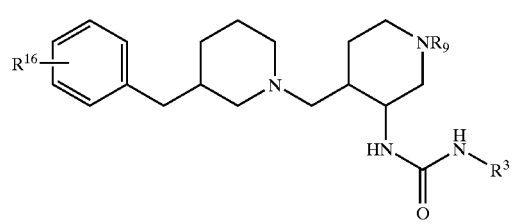
9
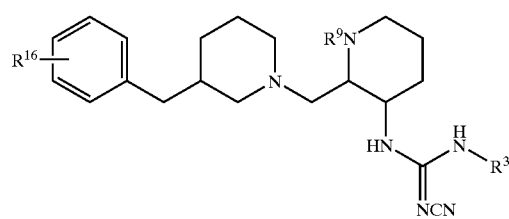
10
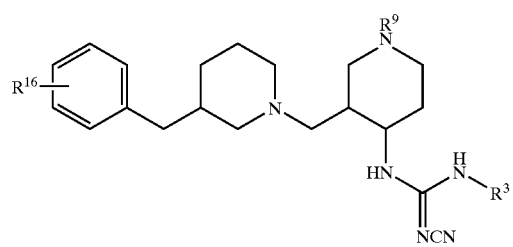
11

TABLE 2-continued

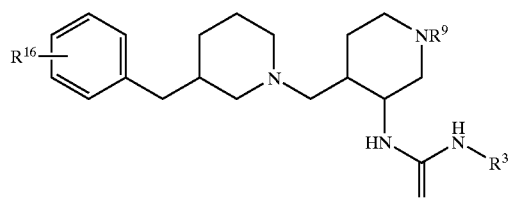

12

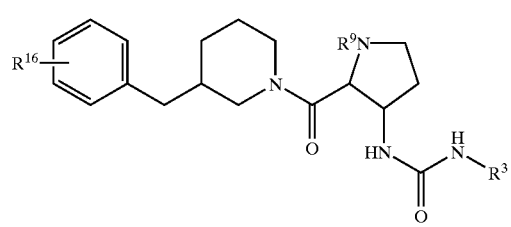

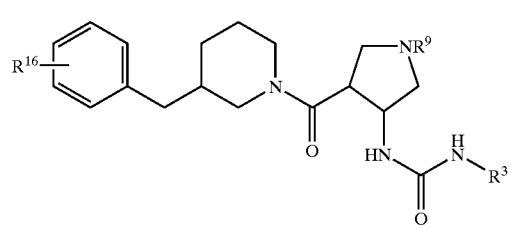

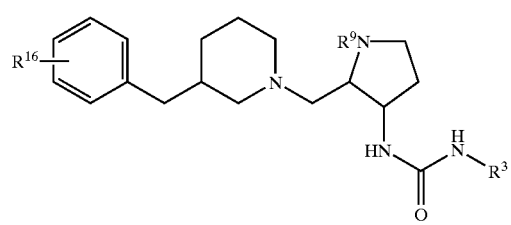

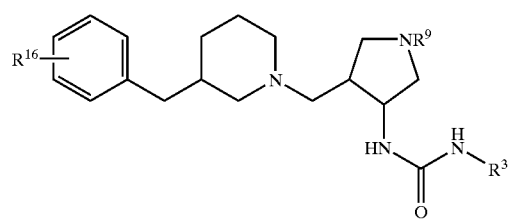

| Entry | R16 | R9 | R3 |
|---|---|---|---|
| 1 | 2-F | H | Ph |
| 2 | 2-F | H | 3-CN—Ph |
| 3 | 2-F | H | 3-COMe—Ph |
| 4 | 2-F | H | 3-CO2Me—Ph |
| 5 | 2-F | H | 3-CONH2—Ph |
| 6 | 2-F | H | 3-CONHMe—Ph |
| 7 | 2-F | H | 3-F—Ph |
| 8 | 2-F | H | 3-Cl—Ph |
| 9 | 2-F | H | 3-Br—Ph |
| 10 | 2-F | H | 3-SO2NH2—Ph |
| 11 | 2-F | H | 3-SO2NHMe—Ph |
| 12 | 2-F | H | 3-CF3—Ph |
| 13 | 2-F | H | 3-OMe—Ph |
| 14 | 2-F | H | 3-SMe—Ph |
| 15 | 2-F | H | 3-SOMe—Ph |
| 16 | 2-F | H | 3-SO2Me—Ph |
| 17 | 2-F | H | 3-OH—Ph |
| 18 | 2-F | H | 3-CH2OH—Ph |
| 19 | 2-F | H | 3-CHOHMe—Ph |
| 20 | 2-F | H | 3-COH(Me)2—Ph |
| 21 | 2-F | H | 3-Me—Ph |
| 22 | 2-F | H | 3-Et—Ph |
| 23 | 2-F | H | 3-iPr—Ph |
| 24 | 2-F | H | 3-tBu—Ph |
| 25 | 2-F | H | 3-CH2CO2Me—Ph |
| 26 | 2-F | H | 3-(1-piperidinyl)-Ph |
| 27 | 2-F | H | 3-(1-pyrrolidinyl)-Ph |
| 28 | 2-F | H | 3-(2-imidazolyl)-Ph |
| 29 | 2-F | H | 3-(1-imidazolyl)-Ph |
| 30 | 2-F | H | 3-(2-thiazolyl)-Ph |
| 31 | 2-F | H | 3-(3-pyrazolyl)-Ph |
| 32 | 2-F | H | 3-(1-pyrazolyl)-Ph |
| 33 | 2-F | H | 3-(5-Me-1-tetrazolyl)-Ph |
| 34 | 2-F | H | 3-(1-Me-5-tetrazolyl)-Ph |
| 35 | 2-F | H | 3-(2-pyridyl)-Ph |
| 36 | 2-F | H | 3-(2-thienyl)-Ph |
| 37 | 2-F | H | 3-(2-furanyl)-Ph |
| 38 | 2-F | H | 4-CN—Ph |
| 39 | 2-F | H | 4-COMe—Ph |
| 40 | 2-F | H | 4-CO2Me—Ph |
| 41 | 2-F | H | 4-CONH2—Ph |
| 42 | 2-F | H | 4-CONHMe—Ph |
| 43 | 2-F | H | 4-CONHPh—Ph |
| 44 | 2-F | H | 4-F—Ph |
| 45 | 2-F | H | 4-Cl—Ph |
| 46 | 2-F | H | 4-Br—Ph |
| 47 | 2-F | H | 4-SO2NH2—Ph |
| 48 | 2-F | H | 4-SO2NHMe—Ph |
| 49 | 2-F | H | 4-CF3—Ph |
| 50 | 2-F | H | 4-OMe—Ph |
| 51 | 2-F | H | 4-SMe—Ph |
| 52 | 2-F | H | 4-SOMe—Ph |
| 53 | 2-F | H | 4-SO2Me—Ph |
| 54 | 2-F | H | 4-OH—Ph |
| 55 | 2-F | H | 4-CH2OH—Ph |
| 56 | 2-F | H | 4-CHOHMe—Ph |
| 57 | 2-F | H | 4-COH(Me)2—Ph |
| 58 | 2-F | H | 4-Me—Ph |
| 59 | 2-F | H | 4-Et—Ph |
| 60 | 2-F | H | 4-iPr—Ph |
| 61 | 2-F | H | 4-tBu—Ph |
| 62 | 2-F | H | 4-CH2CO2Me—Ph |
| 63 | 2-F | H | 4-(1-piperidinyl)-Ph |
| 64 | 2-F | H | 4-(1-pyrrolidinyl)-Ph |
| 65 | 2-F | H | 4-(2-imidazolyl)-Ph |
| 66 | 2-F | H | 4-(1-imidazolyl)-Ph |
| 67 | 2-F | H | 4-(2-thiazolyl)-Ph |
| 68 | 2-F | H | 4-(3-pyrazolyl)-Ph |
| 69 | 2-F | H | 4-(1-pyrazolyl)-Ph |
| 70 | 2-F | H | 4-(5-Me-1-tetrazolyl)-Ph |
| 71 | 2-F | H | 4-(1-Me-5-tetrazolyl)-Ph |
| 72 | 2-F | H | 4-(2-pyridyl)-Ph |
| 73 | 2-F | H | 4-(2-thienyl)-Ph |
| 74 | 2-F | H | 4-(2-furanyl)-Ph |
| 75 | 2-F | H | 2-CN—Ph |
| 76 | 2-F | H | 2-COMe—Ph |
| 77 | 2-F | H | 2-CO2Me—Ph |
| 78 | 2-F | H | 2-CONH2—Ph |
| 79 | 2-F | H | 2-CONHMe—Ph |
| 80 | 2-F | H | 2-F—Ph |
| 81 | 2-F | H | 2-Cl—Ph |
| 82 | 2-F | H | 2-Br—Ph |
| 83 | 2-F | H | 2-SO2NH2—Ph |
| 84 | 2-F | H | 2-SO2NHMe—Ph |
| 85 | 2-F | H | 2-CF3—Ph |
| 86 | 2-F | H | 2-OMe—Ph |
| 87 | 2-F | H | 2-SMe—Ph |
| 88 | 2-F | H | 2-SOMe—Ph |
| 89 | 2-F | H | 2-SO2Me—Ph |
| 90 | 2-F | H | 2-OH—Ph |
| 91 | 2-F | H | 2-CH2OH—Ph |
| 92 | 2-F | H | 2-CHOHMe—Ph |
| 93 | 2-F | H | 2-COH(Me)2—Ph |
| 94 | 2-F | H | 2-Me—Ph |
| 95 | 2-F | H | 2-Et—Ph |
| 96 | 2-F | H | 2-iPr—Ph |
| 97 | 2-F | H | 2-tBu—Ph |
| 98 | 2-F | H | 2-CH2CO2Me—Ph |
| 99 | 2-F | H | 2-(1-piperidinyl)-Ph |

TABLE 2-continued

| | | | |
|---|---|---|---|
| 100 | 2-F | H | 2-(1-pyrrolidiflyl)-Ph |
| 101 | 2-F | H | 2-(2-imidazolyl)-Ph |
| 102 | 2-F | H | 2-(1-imidazolyl)-Ph |
| 103 | 2-F | H | 2-(2-thiazolyl)-Ph |
| 104 | 2-F | H | 2-(3-pyrazolyl)-Ph |
| 105 | 2-F | H | 2-(1-pyrazolyl)-Ph |
| 106 | 2-F | H | 2-(5-Me-1-tetrazolyl)-Ph |
| 107 | 2-F | H | 2-(1-Me-5-tetrazolyl)-Ph |
| 108 | 2-F | H | 2-(2-pyridyl)-Ph |
| 109 | 2-F | H | 2-(2-thieriyl)-Ph |
| 110 | 2-F | H | 2-(2-furanyl)-Ph |
| 111 | 2-F | H | 2,4-diF—Ph |
| 112 | 2-F | H | 2,5-diF—Ph |
| 113 | 2-F | H | 2,6-diF—Ph |
| 114 | 2-F | H | 3,4-diF—Ph |
| 115 | 2-F | H | 3,5-diF—Ph |
| 115 | 2-F | H | 2,4-diCl—Ph |
| 117 | 2-F | H | 2,5-diCl—Ph |
| 118 | 2-F | H | 2,6-diCl—Ph |
| 119 | 2-F | H | 3,4-diCl—Ph |
| 120 | 2-F | H | 3,5-diCl—Ph |
| 121 | 2-F | H | 3,4-diCF3—Ph |
| 122 | 2-F | H | 3,5-diCF3—Ph |
| 123 | 2-F | H | 5-Cl-2-MeO—Ph |
| 124 | 2-F | H | 5-Cl-2-Me—Ph |
| 125 | 2-F | H | 2-F-5-Me—Ph |
| 126 | 2-F | H | 3-F-5-morpholino-Ph |
| 127 | 2-F | H | 3,4-OCH2O—Ph |
| 128 | 2-F | H | 3,4-OCH2CH2O—Ph |
| 129 | 2-F | H | 2-MeO-5-CONH2—Ph |
| 130 | 2-F | H | 2-MeO-4-(1-Me-5-tetrazolyl)-Ph |
| 131 | 2-F | H | 2-MeO-5-(1-Me-5-tetrazolyl)-Ph |
| 132 | 2-F | H | 3-CONH2-5-(1-Me-5-tetrazolyl)-Ph |
| 133 | 2-F | H | 1-naphthyl |
| 134 | 2-F | H | 2-naphthyl |
| 135 | 2-F | H | 2-thienyl |
| 136 | 2-F | H | 3-thienyl |
| 137 | 2-F | H | 2-furanyl |
| 138 | 2-F | H | 3-furanyl |
| 139 | 2-F | H | 2-pyridyl |
| 140 | 2-F | H | 3-pyridyl |
| 141 | 2-F | H | 4-pyridyl |
| 142 | 2-F | H | 2-indolyl |
| 143 | 2-F | H | 3-indolyl |
| 144 | 2-F | H | 5-indolyl |
| 145 | 2-F | H | 6-indolyl |
| 146 | 2-F | H | 3-indazolyl |
| 147 | 2-F | H | 5-indazolyl |
| 148 | 2-F | H | 6-indazolyl |
| 149 | 2-F | H | 2-imidazolyl |
| 150 | 2-F | H | 3-isoxazoyl |
| 151 | 2-F | H | 3-pyrazolyl |
| 152 | 2-F | H | 2-thiadiazolyl |
| 153 | 2-F | H | 2-thiazolyl |
| 154 | 2-F | H | 5-Ac-4-Me-2-thiazolyl |
| 155 | 2-F | H | 5-tetrazolyl |
| 156 | 2-F | H | 2-benzimidazolyl |
| 157 | 2-F | H | 5-benzimidazolyl |
| 158 | 2-F | H | 2-benzothiazolyl |
| 159 | 2-F | H | 5-benzothiazolyl |
| 160 | 2-F | H | 2-benzoxazolyl |
| 161 | 2-F | H | 5-benzoxazolyl |
| 162 | 2-F | H | 1-adamantyl |
| 163 | 2-F | H | 2-adamantyl |
| 164 | 2-F | H | i-Pr |
| 165 | 2-F | H | t-Bu |
| 166 | 2-F | H | c-Hex |
| 167 | 2-F | H | CH2CH2OMe |
| 168 | 2-F | H | CH2CONH2 |
| 169 | 2-F | H | CH2CO2Me |
| 170 | 2-F | H | CH(CH2Ph)CO2Me |
| 171 | 2-F | H | CH2CH2NMe2 |
| 172 | 2-F | H | benzyl |
| 173 | 2-F | H | phenethyl |
| 174 | 2-F | H | 2-(morpholin-1-yl)-Et |
| 175 | 2-F | Me | Ph |
| 176 | 2-F | Me | 3-CN—Ph |
| 177 | 2-F | Me | 3-COMe—Ph |
| 178 | 2-F | Me | 3-CO2Me—Ph |
| 179 | 2-F | Me | 3-CONH2—Ph |
| 180 | 2-F | Me | 3-CONHMe—Ph |
| 181 | 2-F | Me | 3-F—Ph |
| 182 | 2-F | Me | 3-Cl—Ph |
| 183 | 2-F | Me | 3-Br—Ph |
| 184 | 2-F | Me | 3-SO2NH2—Ph |
| 185 | 2-F | Me | 3-SO2NHMe—Ph |
| 186 | 2-F | Me | 3-CF3—Ph |
| 187 | 2-F | Me | 3-OMe—Ph |
| 188 | 2-F | Me | 3-SMe—Ph |
| 189 | 2-F | Me | 3-SOMe—Ph |
| 190 | 2-F | Me | 3-SO2Me—Ph |
| 191 | 2-F | Me | 3-OH—Ph |
| 192 | 2-F | Me | 3-CH2OH—Ph |
| 193 | 2-F | Me | 3-CHOHMe—Ph |
| 194 | 2-F | Me | 3-COH(Me)2—Ph |
| 195 | 2-F | Me | 3-Me—Ph |
| 196 | 2-F | Me | 3-Et—Ph |
| 197 | 2-F | Me | 3-iPr—Ph |
| 198 | 2-F | Me | 3-tBu—Ph |
| 199 | 2-F | Me | 3-CH2CO2Me—Ph |
| 200 | 2-F | Me | 3-(1-piperidinyl)-Ph |
| 201 | 2-F | Me | 3-(1-pyrrolidinyl)-Ph |
| 202 | 2-F | Me | 3-(2-imidazolyl)-Ph |
| 203 | 2-F | Me | 3-(1-imidazolyl)-Ph |
| 204 | 2-F | Me | 3-(2-thiazolyl)-Ph |
| 205 | 2-F | Me | 3-(3-pyrazolyl)-Ph |
| 206 | 2-F | Me | 3-(1-pyrazolyl)-Ph |
| 207 | 2-F | Me | 3-(5-Me-1-tetrazolyl)-Ph |
| 208 | 2-F | Me | 3-(1-Me-5-tetrazolyl)-Ph |
| 209 | 2-F | Me | 3-(2-pyridyl)-Ph |
| 210 | 2-F | Me | 3-(2-thienyl)-Ph |
| 211 | 2-F | Me | 3-(2-furanyl)-Ph |
| 212 | 2-F | Me | 4-CN—Ph |
| 213 | 2-F | Me | 4-COMe—Ph |
| 214 | 2-F | Me | 4-CO2Me—Ph |
| 215 | 2-F | Me | 4-CONH2—Ph |
| 216 | 2-F | Me | 4-CONHMe—Ph |
| 217 | 2-F | Me | 4-CONHPh—Ph |
| 218 | 2-F | Me | 4-F—Ph |
| 219 | 2-F | Me | 4-Cl—Ph |
| 220 | 2-F | Me | 4-Br—Ph |
| 221 | 2-F | Me | 4-SO2NH2—Ph |
| 222 | 2-F | Me | 4-SO2NHMe—Ph |
| 223 | 2-F | Me | 4-CF3—Ph |
| 224 | 2-F | Me | 4-OMe—Ph |
| 225 | 2-F | Me | 4-SMe—Ph |
| 226 | 2-F | Me | 4-SOMe—Ph |
| 227 | 2-F | Me | 4-SO2Me—Ph |
| 228 | 2-F | Me | 4-OH—Ph |
| 229 | 2-F | Me | 4-CH2OH—Ph |
| 230 | 2-F | Me | 4-CHOHMe—Ph |
| 231 | 2-F | Me | 4-COH(Me)2—Ph |
| 232 | 2-F | Me | 4-Me—Ph |
| 233 | 2-F | Me | 4-Et—Ph |
| 234 | 2-F | Me | 4-iPr—Ph |
| 235 | 2-F | Me | 4-tBu—Ph |
| 236 | 2-F | Me | 4-CH2CO2Me—Ph |
| 237 | 2-F | Me | 4-(1-piperidinyl)-Ph |
| 238 | 2-F | Me | 4-(1-pyrrolidinyl)-Ph |
| 239 | 2-F | Me | 4-(2-imidazolyl)-Ph |
| 240 | 2-F | Me | 4-(1-imidazolyl)-Ph |
| 241 | 2-F | Me | 4-(2-thiazolyl)-Ph |
| 242 | 2-F | Me | 4-(3-pyrazolyl)-Ph |
| 243 | 2-F | Me | 4-(1-pyrazolyl)-Ph |
| 244 | 2-F | Me | 4-(5-Me-1-tetrazolyl)-Ph |
| 245 | 2-F | Me | 4-(1-Me-5-tetrazolyl)-Ph |
| 246 | 2-F | Me | 4-(2-pyridyl)-Ph |
| 247 | 2-F | Me | 4-(2-thienyl)-Ph |
| 248 | 2-F | Me | 4-(2-furanyl)-Ph |
| 249 | 2-F | Me | 2-CN—Ph |
| 250 | 2-F | Me | 2-COMe—Ph |
| 251 | 2-F | Me | 2-CO2Me—Ph |
| 252 | 2-F | Me | 2-CONH2—Ph |
| 253 | 2-F | Me | 2-CONHMe—Ph |
| 254 | 2-F | Me | 2-F—Ph |
| 255 | 2-F | Me | 2-Cl—Ph |
| 256 | 2-F | Me | 2-Br—Ph |
| 257 | 2-F | Me | 2-SO2NH2—Ph |

TABLE 2-continued

| | | | |
|---|---|---|---|
| 258 | 2-F | Me | 2-SO2NHMe—Ph |
| 259 | 2-F | Me | 2-CF3—Ph |
| 260 | 2-F | Me | 2-OMe—Ph |
| 261 | 2-F | Me | 2-SMe—Ph |
| 262 | 2-F | Me | 2-SOMe—Ph |
| 263 | 2-F | Me | 2-SO2Me—Ph |
| 264 | 2-F | Me | 2-OH—Ph |
| 265 | 2-F | Me | 2-CH2OH—Ph |
| 266 | 2-F | Me | 2-CHOHMe—Ph |
| 267 | 2-F | Me | 2-COH(Me)2—Ph |
| 268 | 2-F | Me | 2-Me—Ph |
| 269 | 2-F | Me | 2-Et—Ph |
| 270 | 2-F | Me | 2-iPr—Ph |
| 271 | 2-F | Me | 2-tBu—Ph |
| 272 | 2-F | Me | 2-CH2CO2Me—Ph |
| 273 | 2-F | Me | 2-(1-piperidinyl)-Ph |
| 274 | 2-F | Me | 2-(1-pyrrolidinyl)-Ph |
| 275 | 2-F | Me | 2-(2-imidazolyl)-Ph |
| 276 | 2-F | Me | 2-(1-imidazolyl)-Ph |
| 277 | 2-F | Me | 2-(2-thiazolyl)-Ph |
| 278 | 2-F | Me | 2-(3-pyrazolyl)-Ph |
| 279 | 2-F | Me | 2-(1-pyrazolyl)-Ph |
| 280 | 2-F | Me | 2-(5-Me-1-tetrazolyl)-Ph |
| 281 | 2-F | Me | 2-(1-Me-5-tetrazolyl)Ph |
| 282 | 2-F | Me | 2-(2-pyridyl)-Ph |
| 283 | 2-F | Me | 2-(2-thienyl)-Ph |
| 284 | 2-F | Me | 2-(2-furanyl)-Ph |
| 285 | 2-F | Me | 2,4-diF—Ph |
| 286 | 2-F | Me | 2,5-diF—Ph |
| 287 | 2-F | Me | 2,6-diF—Ph |
| 288 | 2-F | Me | 3,4-diF—Ph |
| 289 | 2-F | Me | 3,5-diF—Ph |
| 290 | 2-F | Me | 2,4-diCl—Ph |
| 291 | 2-F | Me | 2,5-diCl—Ph |
| 292 | 2-F | Me | 2,6-diCl—Ph |
| 293 | 2-F | Me | 3,4-diCl—Ph |
| 294 | 2-F | Me | 3,5-diCl—Ph |
| 295 | 2-F | Me | 3,4-diCF3—Ph |
| 296 | 2-F | Me | 3,5-diCF3—Ph |
| 297 | 2-F | Me | 5-Cl-2-MeO—Ph |
| 298 | 2-F | Me | 5-Cl-2-Me—Ph |
| 299 | 2-F | Me | 2-F-5-Me—Ph |
| 300 | 2-F | Me | 3-F-5-morpholino-Ph |
| 301 | 2-F | Me | 3,4-OCH2O—Ph |
| 302 | 2-F | Me | 3,4-OCH2CH2O—Ph |
| 303 | 2-F | Me | 2-MeO-5-CONH2—Ph |
| 304 | 2-F | Me | 2-MeO-4-(1-Me-5-tetrazolyl)-Ph |
| 305 | 2-F | Me | 2-MeO-5-(1-Me-5-tetrazolyl)-Ph |
| 306 | 2-F | Me | 3-CONH2-5-(1-Me-5-tetrazolyl)-Ph |
| 307 | 2-F | Me | 1-naphthyl |
| 308 | 2-F | Me | 2-naphthyl |
| 309 | 2-F | Me | 2-thienyl |
| 310 | 2-F | Me | 3-thienyl |
| 311 | 2-F | Me | 2-furanyl |
| 312 | 2-F | Me | 3-furanyl |
| 313 | 2-F | Me | 2-pyridyl |
| 314 | 2-F | Me | 3-pyridyl |
| 315 | 2-F | Me | 4-pyridyl |
| 316 | 2-F | Me | 2-indolyl |
| 317 | 2-F | Me | 3-indolyl |
| 318 | 2-F | Me | 5-indolyl |
| 319 | 2-F | Me | 6-indolyl |
| 320 | 2-F | Me | 3-indazolyl |
| 321 | 2-F | Me | 5-indazolyl |
| 322 | 2-F | Me | 6-indazolyl |
| 323 | 2-F | Me | 2-imidazolyl |
| 324 | 2-F | Me | 3-isoxazoyl |
| 325 | 2-F | Me | 3-pyrazolyl |
| 326 | 2-F | Me | 2-thiadiazolyl |
| 327 | 2-F | Me | 2-thiazolyl |
| 328 | 2-F | Me | 5-Ac-4-Me-2-thiazolyl |
| 329 | 2-F | Me | 5-tetrazolyl |
| 330 | 2-F | Me | 2-benzimidazolyl |
| 331 | 2-F | Me | 5-benzimidazolyl |
| 332 | 2-F | Me | 2-benzothiazolyl |
| 333 | 2-F | Me | 5-benzothiazolyl |
| 334 | 2-F | Me | 2-benzoxazolyl |
| 335 | 2-F | Me | 5-benzoxazolyl |
| 336 | 2-F | Me | 1-adamantyl |
| 337 | 2-F | Me | 2-adamantyl |
| 338 | 2-F | Me | i-Pr |
| 339 | 2-F | Me | t-Bu |
| 340 | 2-F | Me | c-Hex |
| 341 | 2-F | Me | CH2CH2OMe |
| 342 | 2-F | Me | CH2CONH2 |
| 343 | 2-F | Me | CH2CO2Me |
| 344 | 2-F | Me | CH(CH2Ph)CO2Me |
| 345 | 2-F | Me | CH2CH2NMe2 |
| 346 | 2-F | Me | benzyl |
| 347 | 2-F | Me | phenethyl |
| 348 | 2-F | Me | 2-(morpholin-1-yl)-Et |
| 349 | 2-F | 2-F—Et | Ph |
| 350 | 2-F | 2-F—Et | 3-CN—Ph |
| 351 | 2-F | 2-F—Et | 3-COMe—Ph |
| 352 | 2-F | 2-F—Et | 3-CO2Me—Ph |
| 353 | 2-F | 2-F—Et | 3-CONH2—Ph |
| 354 | 2-F | 2-F—Et | 3-CONHMe—Ph |
| 355 | 2-F | 2-F—Et | 3-F—Ph |
| 356 | 2-F | 2-F—Et | 3-Cl—Ph |
| 357 | 2-F | 2-F—Et | 3-Br—Ph |
| 358 | 2-F | 2-F—Et | 3-SO2NH2—Ph |
| 359 | 2-F | 2-F—Et | 3-SO2NHMe—Ph |
| 360 | 2-F | 2-F—Et | 3-CF3—Ph |
| 361 | 2-F | 2-F—Et | 3-OMe—Ph |
| 362 | 2-F | 2-F—Et | 3-SMe—Ph |
| 363 | 2-F | 2-F—Et | 3-SOMe—Ph |
| 364 | 2-F | 2-F—Et | 3-SO2Me—Ph |
| 365 | 2-F | 2-F—Et | 3-OH—Ph |
| 366 | 2-F | 2-F—Et | 3-CH2OH—Ph |
| 367 | 2-F | 2-F—Et | 3-CHOHMe—Ph |
| 368 | 2-F | 2-F—Et | 3-COH(Me)2—Ph |
| 369 | 2-F | 2-F—Et | 3-Me—Ph |
| 370 | 2-F | 2-F—Et | 3-Et—Ph |
| 371 | 2-F | 2-F—Et | 3-iPr—Ph |
| 372 | 2-F | 2-F—Et | 3-tBu—Ph |
| 373 | 2-F | 2-F—Et | 3-CH2CO2Me—Ph |
| 374 | 2-F | 2-F—Et | 3-(1-piperidinyl)-Ph |
| 375 | 2-F | 2-F—Et | 3-(1-pyrrolidinyl)-Ph |
| 376 | 2-F | 2-F—Et | 3-(2-imidazolyl)-Ph |
| 377 | 2-F | 2-F—Et | 3-(1-imidazolyl)-Ph |
| 378 | 2-F | 2-F—Et | 3-(2-thiazolyl)-Ph |
| 379 | 2-F | 2-F—Et | 3-(3-pyrazolyl)-Ph |
| 380 | 2-F | 2-F—Et | 3-(1-pyrazolyl)-Ph |
| 381 | 2-F | 2-F—Et | 3-(5-Me-1-tetrazolyl)-Ph |
| 382 | 2-F | 2-F—Et | 3-(1-Me-5-tetrazolyl)-Ph |
| 383 | 2-F | 2-F—Et | 3-(2-pyridyl)-Ph |
| 384 | 2-F | 2-F—Et | 3-(2-thienyl)-Ph |
| 385 | 2-F | 2-F—Et | 3-(2-furanyl)-Ph |
| 386 | 2-F | 2-F—Et | 4-CN—Ph |
| 387 | 2-F | 2-F—Et | 4-COMe—Ph |
| 388 | 2-F | 2-F—Et | 4-CO2Me—Ph |
| 389 | 2-F | 2-F—Et | 4-CONH2—Ph |
| 390 | 2-F | 2-F—Et | 4-CONHMe—Ph |
| 391 | 2-F | 2-F—Et | 4-CONHPh—Ph |
| 392 | 2-F | 2-F—Et | 4-F—Ph |
| 393 | 2-F | 2-F—Et | 4-Cl—Ph |
| 394 | 2-F | 2-F—Et | 4-Br—Ph |
| 395 | 2-F | 2-F—Et | 4-SO2NH2—Ph |
| 396 | 2-F | 2-F—Et | 4-SO2NHMe—Ph |
| 397 | 2-F | 2-F—Et | 4-CF3—Ph |
| 398 | 2-F | 2-F—Et | 4-OMe—Ph |
| 399 | 2-F | 2-F—Et | 4-SMe—Ph |
| 400 | 2-F | 2-F—Et | 4-SOMe—Ph |
| 401 | 2-F | 2-F—Et | 4-SO2Me—Ph |
| 402 | 2-F | 2-F—Et | 4-OH—Ph |
| 403 | 2-F | 2-F—Et | 4-CH2OH—Ph |
| 404 | 2-F | 2-F—Et | 4-CHOHMe—Ph |
| 405 | 2-F | 2-F—Et | 4-COH(Me)2—Ph |
| 406 | 2-F | 2-F—Et | 4-Me—Ph |
| 407 | 2-F | 2-F—Et | 4-Et—Ph |
| 408 | 2-F | 2-F—Et | 4-iPr—Ph |
| 409 | 2-F | 2-F—Et | 4-tBu—Ph |
| 410 | 2-F | 2-F—Et | 4-CH2CO2Me—Ph |
| 411 | 2-F | 2-F—Et | 4-(1-piperidinyl)-Ph |
| 412 | 2-F | 2-F—Et | 4-(1-pyrrolidinyl)-Ph |
| 413 | 2-F | 2-F—Et | 4-(2-imidazolyl)-Ph |
| 414 | 2-F | 2-F—Et | 4-(1-imidazolyl)-Ph |
| 415 | 2-F | 2-F—Et | 4-(2-thiazolyl)-Ph |

TABLE 2-continued

| | | | |
|---|---|---|---|
| 416 | 2-F | 2-F—Et | 4-(3-pyrazolyl)-Ph |
| 417 | 2-F | 2-F—Et | 4-(1-pyrazolyl)-Ph |
| 418 | 2-F | 2-F—Et | 4-(5-Me-1-tetrazolyl)-Ph |
| 419 | 2-F | 2-F—Et | 4-(1-Me-5-tetrazolyl)-Ph |
| 420 | 2-F | 2-F—Et | 4-(2-pyridyl)-Ph |
| 421 | 2-F | 2-F—Et | 4-(2-thienyl)-Ph |
| 422 | 2-F | 2-F—Et | 4-(2-furanyl)-Ph |
| 423 | 2-F | 2-F—Et | 2-CN—Ph |
| 424 | 2-F | 2-F—Et | 2-COMe—Ph |
| 425 | 2-F | 2-F—Et | 2-CO2Me—Ph |
| 426 | 2-F | 2-F—Et | 2-CONH2—Ph |
| 427 | 2-F | 2-F—Et | 2-CONHMe—Ph |
| 428 | 2-F | 2-F—Et | 2-F—Ph |
| 429 | 2-F | 2-F—Et | 2-Cl—Ph |
| 430 | 2-F | 2-F—Et | 2-Br—Ph |
| 431 | 2-F | 2-F—Et | 2-SO2NH2—Ph |
| 432 | 2-F | 2-F—Et | 2-SO2NHMe—Ph |
| 433 | 2-F | 2-F—Et | 2-CF3—Ph |
| 434 | 2-F | 2-F—Et | 2-OMe—Ph |
| 435 | 2-F | 2-F—Et | 2-SMe—Ph |
| 436 | 2-F | 2-F—Et | 2-SOMe—Ph |
| 437 | 2-F | 2-F—Et | 2-SO2Me—Ph |
| 438 | 2-F | 2-F—Et | 2-OH—Ph |
| 439 | 2-F | 2-F—Et | 2-CH2OH—Ph |
| 440 | 2-F | 2-F—Et | 2-CHOHMe—Ph |
| 441 | 2-F | 2-F—Et | 2-COH(Me)2-Ph |
| 442 | 2-F | 2-F—Et | 2-Me—Ph |
| 443 | 2-F | 2-F—Et | 2-Et—Ph |
| 444 | 2-F | 2-F—Et | 2-iPr—Ph |
| 445 | 2-F | 2-F—Et | 2-tBu—Ph |
| 446 | 2-F | 2-F—Et | 2-CH2CO2Me—Ph |
| 447 | 2-F | 2-F—Et | 2-(1-piperidinyl)-Ph |
| 448 | 2-F | 2-F—Et | 2-(1-pyrrolidinyl)-Ph |
| 449 | 2-F | 2-F—Et | 2-(2-imidazolyl)-Ph |
| 450 | 2-F | 2-F—Et | 2-(1-imidazolyl)-Ph |
| 451 | 2-F | 2-F—Et | 2-(2-thiazolyl)-Ph |
| 452 | 2-F | 2-F—Et | 2-(3-pyrazolyl)-Ph |
| 453 | 2-F | 2-F—Et | 2-(1-pyrazolyl)-Ph |
| 454 | 2-F | 2-F—Et | 2-(5-Me-1-tetrazolyl)-Ph |
| 455 | 2-F | 2-F—Et | 2-(1-Me-5-tetrazolyl)-Ph |
| 456 | 2-F | 2-F—Et | 2-(2-pyridyl)-Ph |
| 457 | 2-F | 2-F—Et | 2-(2-thienyl)-Ph |
| 458 | 2-F | 2-F—Et | 2-(2-furanyl)-Ph |
| 459 | 2-F | 2-F—Et | 2,4-diF—Ph |
| 460 | 2-F | 2-F—Et | 2,5-diF—Ph |
| 461 | 2-F | 2-F—Et | 2,6-diF—Ph |
| 462 | 2-F | 2-F—Et | 3,4-diF—Ph |
| 463 | 2-F | 2-F—Et | 3,5-diF—Ph |
| 464 | 2-F | 2-F—Et | 2,4-diCl—Ph |
| 465 | 2-F | 2-F—Et | 2,5-diCl—Ph |
| 466 | 2-F | 2-F—Et | 2,6-diCl—Ph |
| 467 | 2-F | 2-F—Et | 3,4-diCl—Ph |
| 468 | 2-F | 2-F—Et | 3,5-diCl—Ph |
| 469 | 2-F | 2-F—Et | 3,4-diCF3—Ph |
| 470 | 2-F | 2-F—Et | 3,5-diCF3—Ph |
| 471 | 2-F | 2-F—Et | 5-Cl-2-MeO—Ph |
| 472 | 2-F | 2-F—Et | 5-Cl-2-Me—Ph |
| 473 | 2-F | 2-F—Et | 2-F-S-Me—Ph |
| 474 | 2-F | 2-F—Et | 3-F-5-morpholino-Ph |
| 475 | 2-F | 2-F—Et | 3,4-OCH2O—Ph |
| 476 | 2-F | 2-F—Et | 3,4-OCH2CH2O—Ph |
| 477 | 2-F | 2-F—Et | 2-MeO-5-CONH2—Ph |
| 478 | 2-F | 2-F—Et | 2-MeO-4-(1-Me-5-tetrazolyl)-Ph |
| 479 | 2-F | 2-F—Et | 2-MeO-5-(1-Me-5-tetrazolyl)-Ph |
| 480 | 2-F | 2-F—Et | 3-CONH2-5-(1-Me-5-tetrazolyl)-Ph |
| 481 | 2-F | 2-F—Et | 1-naphthyl |
| 482 | 2-F | 2-F—Et | 2-naphthyl |
| 483 | 2-F | 2-F—Et | 2-thienyl |
| 484 | 2-F | 2-F—Et | 3-thienyl |
| 485 | 2-F | 2-F—Et | 2-furanyl |
| 486 | 2-F | 2-F—Et | 3-furanyl |
| 487 | 2-F | 2-F—Et | 2-pyridyl |
| 488 | 2-F | 2-F—Et | 3-pyridyl |
| 489 | 2-F | 2-F—Et | 4-pyridyl |
| 490 | 2-F | 2-F—Et | 2-indolyl |
| 491 | 2-F | 2-F—Et | 3-indolyl |
| 492 | 2-F | 2-F—Et | 5-indolyl |
| 493 | 2-F | 2-F—Et | 6-indolyl |
| 494 | 2-F | 2-F—Et | 3-indazolyl |
| 495 | 2-F | 2-F—Et | 5-indazolyl |
| 496 | 2-F | 2-F—Et | 6-indazolyl |
| 497 | 2-F | 2-F—Et | 2-imidazolyl |
| 498 | 2-F | 2-F—Et | 3-isoxazoyl |
| 499 | 2-F | 2-F—Et | 3-pyrazolyl |
| 500 | 2-F | 2-F—Et | 2-thiadiazolyl |
| 501 | 2-F | 2-F—Et | 2-thiazolyl |
| 502 | 2-F | 2-F—Et | 5-Ac-4-Me-2-thiazolyl |
| 503 | 2-F | 2-F—Et | 5-tetrazolyl |
| 504 | 2-F | 2-F—Et | 2-benzimidazolyl |
| 505 | 2-F | 2-F—Et | 5-benzimidazolyl |
| 506 | 2-F | 2-F—Et | 2-benzothiazolyl |
| 507 | 2-F | 2-F—Et | 5-benzothiazolyl |
| 508 | 2-F | 2-F—Et | 2-benzoxazolyl |
| 509 | 2-F | 2-F—Et | 5-benzoxazolyl |
| 510 | 2-F | 2-F—Et | 1-adamantyl |
| 511 | 2-F | 2-F—Et | 2-adamantyl |
| 512 | 2-F | 2-F—Et | i-Pr |
| 513 | 2-F | 2-F—Et | t-Bu |
| 514 | 2-F | 2-F—Et | c-Hex |
| 515 | 2-F | 2-F—Et | CH2CH2OMe |
| 516 | 2-F | 2-F—Et | CH2CONH2 |
| 517 | 2-F | 2-F—Et | CH2CO2Me |
| 518 | 2-F | 2-F—Et | CH(CH2Ph)CO2Me |
| 519 | 2-F | 2-F—Et | CH2CH2NMe2 |
| 520 | 2-F | 2-F—Et | benzyl |
| 521 | 2-F | 2-F—Et | phenethyl |
| 522 | 2-F | 2-F—Et | 2-(morpholin-1-yl)-Et |
| 523 | 2-F | CO2Me | Ph |
| 524 | 2-F | CO2Me | 3-CN—Ph |
| 525 | 2-F | CO2Me | 3-COMe—Ph |
| 526 | 2-F | CO2Me | 3-CO2Me—Ph |
| 527 | 2-F | CO2Me | 3-CONH2—Ph |
| 528 | 2-F | CO2Me | 3-CONHMe—Ph |
| 529 | 2-F | CO2Me | 3-F—Ph |
| 530 | 2-F | CO2Me | 3-Cl—Ph |
| 531 | 2-F | CO2Me | 3-Br—Ph |
| 532 | 2-F | CO2Me | 3-SO2NH2—Ph |
| 533 | 2-F | CO2Me | 3-SO2NHMe—Ph |
| 534 | 2-F | CO2Me | 3-CF3—Ph |
| 535 | 2-F | CO2Me | 3-OMe—Ph |
| 536 | 2-F | CO2Me | 3-SMe—Ph |
| 537 | 2-F | CO2Me | 3-SOMe—Ph |
| 538 | 2-F | CO2Me | 3-SO2Me—Ph |
| 539 | 2-F | CO2Me | 3-OH—Ph |
| 540 | 2-F | CO2Me | 3-CH2OH—Ph |
| 541 | 2-F | CO2Me | 3-CHOHMe—Ph |
| 542 | 2-F | CO2Me | 3-COH(Me)2-Ph |
| 543 | 2-F | CO2Me | 3-Me—Ph |
| 544 | 2-F | CO2Me | 3-Et—Ph |
| 545 | 2-F | CO2Me | 3-iPr—Ph |
| 546 | 2-F | CO2Me | 3-tBu—Ph |
| 547 | 2-F | CO2Me | 3-CH2CO2Me—Ph |
| 548 | 2-F | CO2Me | 3-(1-piperidinyl)-Ph |
| 549 | 2-F | CO2Me | 3-(1-pyrrolidinyl)-Ph |
| 550 | 2-F | CO2Me | 3-(2-imidazolyl)-Ph |
| 551 | 2-F | CO2Me | 3-(1-imidazolyl)-Ph |
| 552 | 2-F | CO2Me | 3-(2-thiazolyl)-Ph |
| 553 | 2-F | CO2Me | 3-(3-pyrazolyl)-Ph |
| 554 | 2-F | CO2Me | 3-(1-pyrazolyl)-Ph |
| 555 | 2-F | CO2Me | 3-(5-Me-1-tetrazolyl)-Ph |
| 556 | 2-F | CO2Me | 3-(1-Me-5-tetrazolyl)-Ph |
| 557 | 2-F | CO2Me | 3-(2-pyridyl)-Ph |
| 558 | 2-F | CO2Me | 3-(2-thienyl)-Ph |
| 559 | 2-F | CO2Me | 3-(2-furanyl)-Ph |
| 560 | 2-F | CO2Me | 4-CN—Ph |
| 561 | 2-F | CO2Me | 4-COMe—Ph |
| 562 | 2-F | CO2Me | 4-CO2Me—Ph |
| 563 | 2-F | CO2Me | 4-CONH2—Ph |
| 564 | 2-F | CO2Me | 4-CONHMe—Ph |
| 565 | 2-F | CO2Me | 4-CONHPh—Ph |
| 566 | 2-F | CO2Me | 4-F—Ph |
| 567 | 2-F | CO2Me | 4-Cl—Ph |
| 568 | 2-F | CO2Me | 4-Br—Ph |
| 569 | 2-F | CO2Me | 4-SO2NH2—Ph |
| 570 | 2-F | CO2Me | 4-SO2NHMe—Ph |
| 571 | 2-F | CO2Me | 4-CF3—Ph |
| 572 | 2-F | CO2Me | 4-OMe—Ph |
| 573 | 2-F | CO2Me | 4-SMe—Ph |

TABLE 2-continued

| | | | |
|---|---|---|---|
| 574 | 2-F | CO2Me | 4-SOMe—Ph |
| 575 | 2-F | CO2Me | 4-SO2Me—Ph |
| 576 | 2-F | CO2Me | 4-OH—Ph |
| 577 | 2-F | CO2Me | 4-CH2OH—Ph |
| 578 | 2-F | CO2Me | 4-CHOHMe—Ph |
| 579 | 2-F | CO2Me | 4-COH(Me)2—Ph |
| 580 | 2-F | CO2Me | 4-Me—Ph |
| 581 | 2-F | CO2Me | 4-Et—Ph |
| 582 | 2-F | CO2Me | 4-iPr—Ph |
| 583 | 2-F | CO2Me | 4-tBu—Ph |
| 584 | 2-F | CO2Me | 4-CH2CO2Me—Ph |
| 585 | 2-F | CO2Me | 4-(1-piperidinyl)-Ph |
| 586 | 2-F | CO2Me | 4-(1-pyrrolidinyl)-Ph |
| 587 | 2-F | CO2Me | 4-(2-imidazolyl)-Ph |
| 588 | 2-F | CO2Me | 4-(1-imidazolyl)-Ph |
| 589 | 2-F | CO2Me | 4-(2-thiazolyl)-Ph |
| 590 | 2-F | CO2Me | 4-(3-pyrazolyl)-Ph |
| 591 | 2-F | CO2Me | 4-(1-pyrazolyl)-Ph |
| 592 | 2-F | CO2Me | 4-(5-Me-1-tetrazolyl)-Ph |
| 593 | 2-F | CO2Me | 4-(1-Me-5-tetrazolyl)-Ph |
| 594 | 2-F | CO2Me | 4-(2-pyridyl)-Ph |
| 595 | 2-F | CO2Me | 4-(2-thienyl)-Ph |
| 596 | 2-F | CO2Me | 4-(2-furanyl)-Ph |
| 597 | 2-F | CO2Me | 2-CN—Ph |
| 598 | 2-F | CO2Me | 2-COMe—Ph |
| 599 | 2-F | CO2Me | 2-CO2Me—Ph |
| 600 | 2-F | CO2Me | 2-CONH2—Ph |
| 601 | 2-F | CO2Me | 2-CONHMe—Ph |
| 602 | 2-F | CO2Me | 2-F—Ph |
| 603 | 2-F | CO2Me | 2-Cl—Ph |
| 604 | 2-F | CO2Me | 2-Br—Ph |
| 605 | 2-F | CO2Me | 2-SO2NH2—Ph |
| 606 | 2-F | CO2Me | 2-SO2NHMe—Ph |
| 607 | 2-F | CO2Me | 2-CF3—Ph |
| 608 | 2-F | CO2Me | 2-OMe—Ph |
| 609 | 2-F | CO2Me | 2-SMe—Ph |
| 610 | 2-F | CO2Me | 2-SOMe—Ph |
| 611 | 2-F | CO2Me | 2-SO2Me—Ph |
| 612 | 2-F | CO2Me | 2-OH—Ph |
| 613 | 2-F | CO2Me | 2-CH2OH—Ph |
| 614 | 2-F | CO2Me | 2-CHOHMe—Ph |
| 615 | 2-F | CO2Me | 2-COH(Me)2—Ph |
| 616 | 2-F | CO2Me | 2-Me—Ph |
| 617 | 2-F | CO2Me | 2-Et—Ph |
| 618 | 2-F | CO2Me | 2-iPr—Ph |
| 619 | 2-F | CO2Me | 2-tBu—Ph |
| 620 | 2-F | CO2Me | 2-CH2CO2Me—Ph |
| 621 | 2-F | CO2Me | 2-(1-piperidinyl)-Ph |
| 622 | 2-F | CO2Me | 2-(1-pyrrolidinyl)-Ph |
| 623 | 2-F | CO2Me | 2-(2-imidazolyl)-Ph |
| 624 | 2-F | CO2Me | 2-(1-imidazolyl)-Ph |
| 625 | 2-F | CO2Me | 2-(2-thiazolyl)-Ph |
| 626 | 2-F | CO2Me | 2-(3-pyrazolyl)-Ph |
| 627 | 2-F | CO2Me | 2-(1-pyrazolyl)-Ph |
| 628 | 2-F | CO2Me | 2-(5-Me-1-tetrazolyl)-Ph |
| 629 | 2-F | CO2Me | 2-(1-Me-5-tetrazolyl)-Ph |
| 630 | 2-F | CO2Me | 2-(2-pyridyl)-Ph |
| 631 | 2-F | CO2Me | 2-(2-thienyl)-Ph |
| 632 | 2-F | CO2Me | 2-(2-furanyl)-Ph |
| 633 | 2-F | CO2Me | 2,4-diF—Ph |
| 634 | 2-F | CO2Me | 2,5-diF—Ph |
| 635 | 2-F | CO2Me | 2,6-diF—Ph |
| 636 | 2-F | CO2Me | 3,4-diF—Ph |
| 637 | 2-F | CO2Me | 3,5-diF—Ph |
| 638 | 2-F | CO2Me | 2,4-diCl—Ph |
| 639 | 2-F | CO2Me | 2,5-diCl—Ph |
| 640 | 2-F | CO2Me | 2,6-diCl—Ph |
| 641 | 2-F | CO2Me | 3,4-diCl—Ph |
| 642 | 2-F | CO2Me | 3,5-diCl—Ph |
| 643 | 2-F | CO2Me | 3,4-diCF3—Ph |
| 644 | 2-F | CO2Me | 3,5-diCF3—Ph |
| 645 | 2-F | CO2Me | 5-Cl-2-MeO—Ph |
| 646 | 2-F | CO2Me | 5-Cl-2-Me—Ph |
| 647 | 2-F | CO2Me | 2-F-5-Me—Ph |
| 648 | 2-F | CO2Me | 3-F-5-morpholino-Ph |
| 649 | 2-F | CO2Me | 3,4-OCH2O—Ph |
| 650 | 2-F | CO2Me | 3,4-OCH2CH2O—Ph |
| 651 | 2-F | CO2Me | 2-MeO-5-CONH2—Ph |
| 652 | 2-F | CO2Me | 2-MeO-4-(1-Me-5-tetrazolyl)-Ph |
| 653 | 2-F | CO2Me | 2-MeO-5-(1-Me-5-tetrazolyl)-Ph |
| 654 | 2-F | CO2Me | 3-CONH2-5-(1-Me-5-tetrazolyl)-Ph |
| 655 | 2-F | CO2Me | 1-naphthyl |
| 656 | 2-F | CO2Me | 2-naphthyl |
| 657 | 2-F | CO2Me | 2-thienyl |
| 658 | 2-F | CO2Me | 3-thienyl |
| 659 | 2-F | CO2Me | 2-furanyl |
| 660 | 2-F | CO2Me | 3-furanyl |
| 661 | 2-F | CO2Me | 2-pyridyl |
| 662 | 2-F | CO2Me | 3-pyridyl |
| 663 | 2-F | CO2Me | 4-pyridyl |
| 664 | 2-F | CO2Me | 2-indolyl |
| 665 | 2-F | CO2Me | 3-indolyl |
| 666 | 2-F | CO2Me | 5-indolyl |
| 667 | 2-F | CO2Me | 6-indolyl |
| 668 | 2-F | CO2Me | 3-indazolyl |
| 669 | 2-F | CO2Me | 5-indazolyl |
| 670 | 2-F | CO2Me | 6-indazolyl |
| 671 | 2-F | CO2Me | 2-imidazolyl |
| 672 | 2-F | CO2Me | 3-isoxazoyl |
| 673 | 2-F | CO2Me | 3-pyrazolyl |
| 674 | 2-F | CO2Me | 2-thiadiazolyl |
| 675 | 2-F | CO2Me | 2-thiazolyl |
| 676 | 2-F | CO2Me | 5-Ac-4-Me-2-thiazolyl |
| 677 | 2-F | CO2Me | 5-tetrazolyl |
| 678 | 2-F | CO2Me | 2-benzimidazolyl |
| 679 | 2-F | CO2Me | 5-benzimidazolyl |
| 680 | 2-F | CO2Me | 2-benzothiazolyl |
| 681 | 2-F | CO2Me | 5-benzothiazolyl |
| 682 | 2-F | CO2Me | 2-benzoxazolyl |
| 683 | 2-F | CO2Me | 5-benzoxazolyl |
| 684 | 2-F | CO2Me | 1-adamantyl |
| 685 | 2-F | CO2Me | 2-adamantyl |
| 686 | 2-F | CO2Me | i-Pr |
| 687 | 2-F | CO2Me | t-Bu |
| 688 | 2-F | CO2Me | c-Hex |
| 689 | 2-F | CO2Me | CH2CH2OMe |
| 690 | 2-F | CO2Me | CH2CONH2 |
| 691 | 2-F | CO2Me | CH2CO2Me |
| 692 | 2-F | CO2Me | CH(CH2Ph)CO2Me |
| 693 | 2-F | CO2Me | CH2CH2NMe2 |
| 694 | 2-F | CO2Me | benzyl |
| 695 | 2-F | CO2Me | phenethyl |
| 696 | 2-F | CO2Me | 2-(morpholin-1-yl)-Et |
| 697 | 2-F | Ac | Ph |
| 698 | 2-F | Ac | 3-CN—Ph |
| 699 | 2-F | Ac | 3-COMe—Ph |
| 700 | 2-F | Ac | 3-CO2Me—Ph |
| 701 | 2-F | Ac | 3-CONH2—Ph |
| 702 | 2-F | Ac | 3-CONHMe—Ph |
| 703 | 2-F | Ac | 3-F—Ph |
| 704 | 2-F | Ac | 3-Cl—Ph |
| 705 | 2-F | Ac | 3-Br—Ph |
| 706 | 2-F | Ac | 3-SO2NH2—Ph |
| 707 | 2-F | Ac | 3-SO2NHMe—Ph |
| 708 | 2-F | Ac | 3-CF3—Ph |
| 709 | 2-F | Ac | 3-OMe—Ph |
| 710 | 2-F | Ac | 3-SMe—Ph |
| 711 | 2-F | Ac | 3-SOMe—Ph |
| 712 | 2-F | Ac | 3-SO2Me—Ph |
| 713 | 2-F | Ac | 3-OH—Ph |
| 714 | 2-F | Ac | 3-CH2OH—Ph |
| 715 | 2-F | Ac | 3-CHOHMe—Ph |
| 716 | 2-F | Ac | 3-COH(Me)2—Ph |
| 717 | 2-F | Ac | 3-Me—Ph |
| 718 | 2-F | Ac | 3-Et—Ph |
| 719 | 2-F | Ac | 3-iPr—Ph |
| 720 | 2-F | Ac | 3-tBu—Ph |
| 721 | 2-F | Ac | 3-CH2CO2Me—Ph |
| 722 | 2-F | Ac | 3-(1-piperidinyl)-Ph |
| 723 | 2-F | Ac | 3-(1-pyrrolidinyl)-Ph |
| 724 | 2-F | Ac | 3-(2-imidazolyl)-Ph |
| 725 | 2-F | Ac | 3-(1-imidazolyl)-Ph |
| 726 | 2-F | Ac | 3-(2-thiazolyl)-Ph |
| 727 | 2-F | Ac | 3-(3-pyrazolyl)-Ph |
| 728 | 2-F | Ac | 3-(1-pyrazolyl)-Ph |
| 729 | 2-F | Ac | 3-(5-Me-1-tetrazolyl)-Ph |
| 730 | 2-F | Ac | 3-(1-Me-5-tetrazolyl)-Ph |
| 731 | 2-F | Ac | 3-(2-pyridyl)-Ph |

TABLE 2-continued

| | | | |
|---|---|---|---|
| 732 | 2-F | Ac | 3-(2-thienyl)-Ph |
| 733 | 2-F | Ac | 3-(2-furanyl)-Ph |
| 734 | 2-F | Ac | 4-CN—Ph |
| 735 | 2-F | Ac | 4-COMe—Ph |
| 736 | 2-F | Ac | 4-CO2Me—Ph |
| 737 | 2-F | Ac | 4-CONH2—Ph |
| 738 | 2-F | Ac | 4-CONHMe—Ph |
| 739 | 2-F | Ac | 4-CONHPh—Ph |
| 740 | 2-F | Ac | 4-F—Ph |
| 741 | 2-F | Ac | 4-Cl—Ph |
| 742 | 2-F | Ac | 4-Br—Ph |
| 743 | 2-F | Ac | 4-SO2NH2—Ph |
| 744 | 2-F | Ac | 4-SO2NHMe—Ph |
| 745 | 2-F | Ac | 4-CF3—Ph |
| 746 | 2-F | Ac | 4-OMe—Ph |
| 747 | 2-F | Ac | 4-SMe—Ph |
| 748 | 2-F | Ac | 4-SOMe—Ph |
| 749 | 2-F | Ac | 4-SO2Me—Ph |
| 750 | 2-F | Ac | 4-OH—Ph |
| 751 | 2-F | Ac | 4-CH2OH—Ph |
| 752 | 2-F | Ac | 4-CHOHMe—Ph |
| 753 | 2-F | Ac | 4-COH(Me)2—Ph |
| 754 | 2-F | Ac | 4-Me—Ph |
| 755 | 2-F | Ac | 4-Et—Ph |
| 756 | 2-F | Ac | 4-iPr—Ph |
| 757 | 2-F | Ac | 4-tBu—Ph |
| 758 | 2-F | Ac | 4-CH2CO2Me—Ph |
| 759 | 2-F | Ac | 4-(1-piperidinyl)-Ph |
| 760 | 2-F | Ac | 4-(1-pyrrolidinyl)-Ph |
| 761 | 2-F | Ac | 4-(2-imidazolyl)-Ph |
| 762 | 2-F | Ac | 4-(1-imidazolyl)-Ph |
| 763 | 2-F | Ac | 4-(2-thiazolyl)-Ph |
| 764 | 2-F | Ac | 4-(3-pyrazolyl)-Ph |
| 765 | 2-F | Ac | 4-(1-pyrazolyl)-Ph |
| 766 | 2-F | Ac | 4-(5-Me-1-tetrazolyl)-Ph |
| 767 | 2-F | Ac | 4-(1-Me-5-tetrazolyl)-Ph |
| 768 | 2-F | Ac | 4-(2-pyridyl)-Ph |
| 769 | 2-F | Ac | 4-(2-thienyl)-Ph |
| 770 | 2-F | Ac | 4-(2-furanyl)-Ph |
| 771 | 2-F | Ac | 2-CN—Ph |
| 772 | 2-F | Ac | 2-COMe—Ph |
| 773 | 2-F | Ac | 2-CO2Me—Ph |
| 774 | 2-F | Ac | 2-CONH2—Ph |
| 775 | 2-F | Ac | 2-CONHMe—Ph |
| 776 | 2-F | Ac | 2-F—Ph |
| 777 | 2-F | Ac | 2-Cl—Ph |
| 778 | 2-F | Ac | 2-Br—Ph |
| 779 | 2-F | Ac | 2-SO2NH2—Ph |
| 780 | 2-F | Ac | 2-SO2NHMe—Ph |
| 781 | 2-F | Ac | 2-CF3—Ph |
| 782 | 2-F | Ac | 2-OMe—Ph |
| 783 | 2-F | Ac | 2-SMe—Ph |
| 784 | 2-F | Ac | 2-SOMe—Ph |
| 785 | 2-F | Ac | 2-SO2Me—Ph |
| 786 | 2-F | Ac | 2-OH—Ph |
| 787 | 2-F | Ac | 2-CH2OH—Ph |
| 788 | 2-F | Ac | 2-CHoHMe—Ph |
| 789 | 2-F | Ac | 2-COH(Me)2—Ph |
| 790 | 2-F | Ac | 2-Me—Ph |
| 791 | 2-F | Ac | 2-Et—Ph |
| 792 | 2-F | Ac | 2-iPr—Ph |
| 793 | 2-F | Ac | 2-tBu—Ph |
| 794 | 2-F | Ac | 2-CH2CO2Me—Ph |
| 795 | 2-F | Ac | 2-(1-piperidinyl)-Ph |
| 796 | 2-F | Ac | 2-(1-pyrrolidinyl)-Ph |
| 797 | 2-F | Ac | 2-(2-imidazolyl)-Ph |
| 798 | 2-F | Ac | 2-(1-imidazolyl)-Ph |
| 799 | 2-F | Ac | 2-(2-thiazolyl)-Ph |
| 800 | 2-F | Ac | 2-(3-pyrazolyl)-Ph |
| 801 | 2-F | Ac | 2-(1-pyrazolyl)-Ph |
| 802 | 2-F | Ac | 2-(5-Me-1-tetrazolyl)-Ph |
| 803 | 2-F | Ac | 2-(1-Me-5-tetrazolyl)-Ph |
| 804 | 2-F | Ac | 2-(2-pyridyl)-Ph |
| 805 | 2-F | Ac | 2-(2-thienyl)-Ph |
| 806 | 2-F | Ac | 2-(2-furanyl)-Ph |
| 807 | 2-F | Ac | 2,4-diF—Ph |
| 808 | 2-F | Ac | 2,5-diF—Ph |
| 809 | 2-F | Ac | 2,6-diF—Ph |
| 810 | 2-F | Ac | 3,4-diF—Ph |
| 811 | 2-F | Ac | 3,5-diF—Ph |
| 812 | 2-F | Ac | 2,4-diCl—Ph |
| 813 | 2-F | Ac | 2,5-diCl—Ph |
| 814 | 2-F | Ac | 2,6-diCl—Ph |
| 815 | 2-F | Ac | 3,4-diCl—Ph |
| 816 | 2-F | Ac | 3,5-diCl—Ph |
| 817 | 2-F | Ac | 3,4-diCF3—Ph |
| 818 | 2-F | Ac | 3,5-diCF3—Ph |
| 819 | 2-F | Ac | 5-Cl-2-MeO—Ph |
| 820 | 2-F | Ac | 5-Cl-2-Me—Ph |
| 821 | 2-F | Ac | 2-F-5-Me—Ph |
| 822 | 2-F | Ac | 3-F-5-morpholino-Ph |
| 823 | 2-F | Ac | 3,4-OCH2O—Ph |
| 824 | 2-F | Ac | 3,4-OCH2CH2O—Ph |
| 825 | 2-F | Ac | 2-MeO-5-CONH2—Ph |
| 826 | 2-F | Ac | 2-MeO-4-(1-Me-5-tetrazolyl)-Ph |
| 827 | 2-F | Ac | 2-MeO-5-(1-Me-5-tetrazolyl)-Ph |
| 828 | 2-F | Ac | 3-CONH2-5-(1-Me-5-tetrazolyl)-Ph |
| 829 | 2-F | Ac | 1-naphthyl |
| 830 | 2-F | Ac | 2-naphthyl |
| 831 | 2-F | Ac | 2-thienyl |
| 832 | 2-F | Ac | 3-thienyl |
| 833 | 2-F | Ac | 2-furanyl |
| 834 | 2-F | Ac | 3-furanyl |
| 835 | 2-F | Ac | 2-pyridyl |
| 836 | 2-F | Ac | 3-pyridyl |
| 837 | 2-F | Ac | 4-pyridyl |
| 838 | 2-F | Ac | 2-indolyl |
| 839 | 2-F | Ac | 3-indolyl |
| 840 | 2-F | Ac | 5-indolyl |
| 841 | 2-F | Ac | 6-indolyl |
| 842 | 2-F | Ac | 3-indazolyl |
| 843 | 2-F | Ac | 5-indazolyl |
| 844 | 2-F | Ac | 6-indazolyl |
| 845 | 2-F | Ac | 2-imidazolyl |
| 846 | 2-F | Ac | 3-isoxazoyl |
| 847 | 2-F | Ac | 3-pyrazolyl |
| 848 | 2-F | Ac | 2-thiadiazolyl |
| 849 | 2-F | Ac | 2-thiazolyl |
| 850 | 2-F | Ac | 5-Ac-4-Me-2-thiazolyl |
| 851 | 2-F | Ac | 5-tetrazolyl |
| 852 | 2-F | Ac | 2-benzimidazolyl |
| 853 | 2-F | Ac | 5-benzimidazolyl |
| 854 | 2-F | Ac | 2-benzothiazolyl |
| 855 | 2-F | Ac | 5-benzothiazolyl |
| 856 | 2-F | Ac | 2-benzoxazolyl |
| 857 | 2-F | Ac | 5-benzoxazolyl |
| 858 | 2-F | Ac | 1-adamantyl |
| 859 | 2-F | Ac | 2-adamantyl |
| 860 | 2-F | Ac | i-Pr |
| 861 | 2-F | Ac | t-Bu |
| 862 | 2-F | Ac | c-Hex |
| 863 | 2-F | Ac | CH2CH2OMe |
| 864 | 2-F | Ac | CH2CONH2 |
| 865 | 2-F | Ac | CH2CO2Me |
| 866 | 2-F | Ac | CH(CH2Ph)CO2Me |
| 867 | 2-F | Ac | CH2CH2NMe2 |
| 868 | 2-F | Ac | benzyl |
| 869 | 2-F | Ac | phenethyl |
| 870 | 2-F | Ac | 2-(morpholin-1-yl)-Et |
| 871 | 2-F | COtBu | Ph |
| 872 | 2-F | COtBu | 3-CN—Ph |
| 873 | 2-F | COtBu | 3-COMe—Ph |
| 874 | 2-F | COtBu | 3-CO2Me—Ph |
| 875 | 2-F | COtBu | 3-CONH2—Ph |
| 876 | 2-F | COtBu | 3-CONHMe—Ph |
| 877 | 2-F | COtBu | 3-F—Ph |
| 878 | 2-F | COtBu | 3-Cl—Ph |
| 879 | 2-F | COtBu | 3-Br—Ph |
| 880 | 2-F | COtBu | 3-SO2NH2—Ph |
| 881 | 2-F | COtBu | 3-SO2NHMe—Ph |
| 882 | 2-F | COtBu | 3-CF3—Ph |
| 883 | 2-F | COtBu | 3-OMe—Ph |
| 884 | 2-F | COtBu | 3-SMe—Ph |
| 885 | 2-F | COtBu | 3-SOMe—Ph |
| 886 | 2-F | COtBu | 3-SO2Me—Ph |
| 887 | 2-F | COtBu | 3-OH—Ph |
| 888 | 2-F | COtBu | 3-CH2OH—Ph |
| 889 | 2-F | COtBu | 3-CHOHMe—Ph |

TABLE 2-continued

| 890 | 2-F | COtBu | 3-COH(Me)2—Ph |
| 891 | 2-F | COtBu | 3-Me—Ph |
| 892 | 2-F | COtBu | 3-Et—Ph |
| 893 | 2-F | COtBu | 3-iPr—Ph |
| 894 | 2-F | COtBu | 3-tBu—Ph |
| 895 | 2-F | COtBu | 3-CH2CO2Me—Ph |
| 896 | 2-F | COtBu | 3-(1-piperidinyl)-Ph |
| 897 | 2-F | COtBu | 3-(1-pyrrolidinyl)-Ph |
| 898 | 2-F | COtBu | 3-(2-imidazolyl)-Ph |
| 899 | 2-F | COtBu | 3-(1-imidazolyl)-Ph |
| 900 | 2-F | COtBu | 3-(2-thiazolyl)-Ph |
| 901 | 2-F | COtBu | 3-(3-pyrazolyl)-Ph |
| 902 | 2-F | COtBu | 3-(1-pyrazolyl)-Ph |
| 903 | 2-F | COtBu | 3-(5-Me-1-tetrazolyl)-Ph |
| 904 | 2-F | COtBu | 3-(1-Me-5-tetrazolyl)-Ph |
| 905 | 2-F | COtBu | 3-(2-pyridyl)-Ph |
| 906 | 2-F | COtBu | 3-(2-thienyl)-Ph |
| 907 | 2-F | COtBu | 3-(2-furanyl)-Ph |
| 908 | 2-F | COtBu | 4-CN—Ph |
| 909 | 2-F | COtBu | 4-COMe—Ph |
| 910 | 2-F | COtBu | 4-CO2Me—Ph |
| 911 | 2-F | COtBu | 4-CONH2—Ph |
| 912 | 2-F | COtBu | 4-CONHMe—Ph |
| 913 | 2-F | COtBu | 4-CONHPh—Ph |
| 914 | 2-F | COtBu | 4-F—Ph |
| 915 | 2-F | COtBu | 4-Cl—Ph |
| 916 | 2-F | COtBu | 4-Br—Ph |
| 917 | 2-F | COtBu | 4-SO2NH2—Ph |
| 918 | 2-F | COtBu | 4-SO2NHMe—Ph |
| 919 | 2-F | COtBu | 4-CF3—Ph |
| 920 | 2-F | COtBu | 4-OMe—Ph |
| 921 | 2-F | COtBu | 4-SMe—Ph |
| 922 | 2-F | COtBu | 4-SOMe—Ph |
| 923 | 2-F | COtBu | 4-SO2Me—Ph |
| 924 | 2-F | COtBu | 4-OH—Ph |
| 925 | 2-F | COtBu | 4-CH2OH—Ph |
| 926 | 2-F | COtBu | 4-CHOHMe—Ph |
| 927 | 2-F | COtBu | 4-COH(Me)2—Ph |
| 928 | 2-F | COtBu | 4-Me—Ph |
| 929 | 2-F | COtBu | 4-Et—Ph |
| 930 | 2-F | COtBu | 4-iPr—Ph |
| 931 | 2-F | COtBu | 4-tBu—Ph |
| 932 | 2-F | COtBu | 4-CH2CO2Me—Ph |
| 933 | 2-F | COtBu | 4-(1-piperidinyl)-Ph |
| 934 | 2-F | COtBu | 4-(1-pyrrolidinyl)-Ph |
| 935 | 2-F | COtBu | 4-(2-imidazolyl)-Ph |
| 936 | 2-F | COtBu | 4-(1-imidazolyl)-Ph |
| 937 | 2-F | COtBu | 4-(2-thiazolyl)-Ph |
| 938 | 2-F | COtBu | 4-(3-pyrazolyl)-Ph |
| 939 | 2-F | COtBu | 4-(1-pyrazolyl)-Ph |
| 940 | 2-F | COtBu | 4-(5-Me-1-tetrazolyl)-Ph |
| 941 | 2-F | COtBu | 4-(1-Me-5-tetrazolyl)-Ph |
| 942 | 2-F | COtBu | 4-(2-pyridyl)-Ph |
| 943 | 2-F | COtBu | 4-(2-thienyl)-Ph |
| 944 | 2-F | COtBu | 4-(2-furanyl)-Ph |
| 945 | 2-F | COtBu | 2-CN—Ph |
| 946 | 2-F | COtBu | 2-COMe—Ph |
| 947 | 2-F | COtBu | 2-CO2Me—Ph |
| 948 | 2-F | COtBu | 2-CONH2—Ph |
| 949 | 2-F | COtBu | 2-CONHMe—Ph |
| 950 | 2-F | COtBu | 2-F—Ph |
| 951 | 2-F | COtBu | 2-Cl—Ph |
| 952 | 2-F | COtBu | 2-Br—Ph |
| 953 | 2-F | COtBu | 2-SO2NH2—Ph |
| 954 | 2-F | COtBu | 2-SO2NHMe—Ph |
| 955 | 2-F | COtBu | 2-CF3—Ph |
| 956 | 2-F | COtBu | 2-OMe—Ph |
| 957 | 2-F | COtBu | 2-SMe—Ph |
| 958 | 2-F | COtBu | 2-SOMe—Ph |
| 959 | 2-F | COtBu | 2-SO2Me—Ph |
| 960 | 2-F | COtBu | 2-OH—Ph |
| 961 | 2-F | COtBu | 2-CH2OH—Ph |
| 962 | 2-F | COtBu | 2-CHOHMe—Ph |
| 963 | 2-F | COtBu | 2-COH(Me)2—Ph |
| 964 | 2-F | COtBu | 2-Me—Ph |
| 965 | 2-F | COtBu | 2-Et—Ph |
| 966 | 2-F | COtBu | 2-iPr—Ph |
| 967 | 2-F | COtBu | 2-tBu—Ph |
| 968 | 2-F | COtBu | 2-CH2CO2Me—Ph |
| 969 | 2-F | COtBu | 2-(1-piperidinyl)-Ph |
| 970 | 2-F | COtBu | 2-(1-pyrrolidinyl)-Ph |
| 971 | 2-F | COtBu | 2-(2-imidazolyl)-Ph |
| 972 | 2-F | COtBu | 2-(1-imidazolyl)-Ph |
| 973 | 2-F | COtBu | 2-(2-thiazolyl)-Ph |
| 974 | 2-F | COtBu | 2-(3-pyrazolyl)-Ph |
| 975 | 2-F | COtBu | 2-(1-pyrazolyl)-Ph |
| 976 | 2-F | COtBu | 2-(5-Me-1-tetrazolyl)-Ph |
| 977 | 2-F | COtBu | 2-(1-Me-5-tetrazolyl)-Ph |
| 978 | 2-F | COtBu | 2-(2-pyridyl)-Ph |
| 979 | 2-F | COtBu | 2-(2-thienyl)-Ph |
| 980 | 2-F | COtBu | 2-(2-furanyl)-Ph |
| 981 | 2-F | COtBu | 2,4-diF—Ph |
| 982 | 2-F | COtBu | 2,5-diF—Ph |
| 983 | 2-F | COtBu | 2,6-diF—Ph |
| 984 | 2-F | COtBu | 3,4-diF—Ph |
| 985 | 2-F | COtBu | 3,5-diF—Ph |
| 986 | 2-F | COtBu | 2,4-diCl—Ph |
| 987 | 2-F | COtBu | 2,5-diCl—Ph |
| 988 | 2-F | COtBu | 2,6-diCl—Ph |
| 989 | 2-F | COtBu | 3,4-diCl—Ph |
| 990 | 2-F | COtBu | 3,5-diCl—Ph |
| 991 | 2-F | COtBu | 3,4-diCF3—Ph |
| 992 | 2-F | COLBu | 3,5-diCF3—Ph |
| 993 | 2-F | COtBu | 5-Cl-2-MeO—Ph |
| 994 | 2-F | COtBu | 5-Cl-2-Me—Ph |
| 995 | 2-F | COtBu | 2-F-5-Me—Ph |
| 996 | 2-F | COtBu | 3-F-5-morpholino-Ph |
| 997 | 2-F | COtBu | 3,4-OCH2O—Ph |
| 998 | 2-F | COtBu | 3,4-OCH2CH2O—Ph |
| 999 | 2-F | COtBu | 2-MeO-5-CONH2—Ph |
| 1000 | 2-F | COtBu | 2-MeO-4-(1-Me-5-tetrazolyl)-Ph |
| 1001 | 2-F | COtBu | 2-MeO-5-(1-Me-5-tetrazolyl)-Ph |
| 1002 | 2-F | COtBu | 3-CONH2-5-(1-Me-5-tetrazolyl)-Ph |
| 1003 | 2-F | COtBu | 1-naphthyl |
| 1004 | 2-F | COtBu | 2-naphthyl |
| 1005 | 2-F | COtBu | 2-thienyl |
| 1006 | 2-F | COtBu | 3-thienyl |
| 1007 | 2-F | COtBu | 2-furanyl |
| 1Q08 | 2-F | COtBu | 3-furanyl |
| 1009 | 2-F | COtBu | 2-pyridyl |
| 1010 | 2-F | COtBu | 3-pyridyl |
| 1011 | 2-F | COtBu | 4-pyridyl |
| 1012 | 2-F | COtBu | 2-indolyl |
| 1013 | 2-F | COtBu | 3-indolyl |
| 1014 | 2-F | COtBu | 5-indolyl |
| 1015 | 2-F | COtBu | 6-indolyl |
| 1016 | 2-F | COtBu | 3-indazolyl |
| 1017 | 2-F | COtBu | 5-indazolyl |
| 1018 | 2-F | COtBu | 6-indazolyl |
| 1019 | 2-F | COtBu | 2-imidazolyl |
| 1020 | 2-F | COtBu | 3-isoxazoyl |
| 1021 | 2-F | COtBu | 3-pyrazolyl |
| 1022 | 2-F | COtBu | 2-thiadiazolyl |
| 1023 | 2-F | COtBu | 2-thiazolyl |
| 1024 | 2-F | COtBu | 5-Ac-4-Me-2-thiazolyl |
| 1025 | 2-F | COtBu | 5-tetrazolyl |
| 1026 | 2-F | COtBu | 2-benzimidazolyl |
| 1027 | 2-F | COtBu | 5-benzimidazolyl |
| 1028 | 2-F | COtBu | 2-benzothiazolyl |
| 1029 | 2-F | COtBu | 5-benzothiazolyl |
| 1030 | 2-F | COtBu | 2-benzoxazolyl |
| 1031 | 2-F | COtBu | 5-benzoxazolyl |
| 1032 | 2-F | COtBu | 1-adamantyl |
| 1033 | 2-F | COtBu | 2-adamantyl |
| 1034 | 2-F | COtBu | i-Pr |
| 1035 | 2-F | COtBu | t-Bu |
| 1036 | 2-F | COtBu | c-Hex |
| 1037 | 2-F | COtBu | CH2CH2OMe |
| 1038 | 2-F | COtBu | CH2CONH2 |
| 1039 | 2-F | COtBu | CH2CO2Me |
| 1040 | 2-F | COtBu | CH(CH2Ph)CO2Me |
| 1041 | 2-F | COtBu | CH2CH2NMe2 |
| 1042 | 2-F | COtBu | benzyl |
| 1043 | 2-F | COtBu | phenethyl |
| 1044 | 2-F | COtBu | 2-(morpholn-1-yl)-Et |
| 1045 | 2-F | SO2Me | Ph |
| 1046 | 2-F | SO2Me | 3-CN—Ph |
| 1047 | 2-F | SO2Ne | 3-COMe—Ph |

TABLE 2-continued

| | | | |
|---|---|---|---|
| 1048 | 2-F | SO2Me | 3-CO2Me—Ph |
| 1049 | 2-F | SO2Me | 3-CONH2—Ph |
| 1050 | 2-F | SO2Me | 3-CONHMe—Ph |
| 1051 | 2-F | SO2Me | 3-F—Ph |
| 1052 | 2-F | SO2Me | 3-Cl—Ph |
| 1053 | 2-F | SO2Me | 3-Br—Ph |
| 1054 | 2-F | SO2Me | 3-SO2NH2—Ph |
| 1055 | 2-F | SO2Me | 3-SO2NHMe—Ph |
| 1056 | 2-F | SO2Me | 3-CF3—Ph |
| 1057 | 2-F | SO2Me | 3-OMe—Ph |
| 1058 | 2-F | SO2Me | 3-SMe—Ph |
| 1059 | 2-F | SO2Me | 3-SOMe—Ph |
| 1060 | 2-F | SO2Me | 3-SO2Me—Ph |
| 1061 | 2-F | SO2Me | 3-OH—Ph |
| 1062 | 2-F | SO2Me | 3-CH2OH—Ph |
| 1063 | 2-F | SO2Me | 3-CHOHMe—Ph |
| 1064 | 2-F | SO2Me | 3-COH(Me)2—Ph |
| 1065 | 2-F | SO2Me | 3-Me—Ph |
| 1066 | 2-F | SO2Me | 3-Et—Ph |
| 1067 | 2-F | SO2Me | 3-iPr—Ph |
| 1068 | 2-F | SO2Me | 3-tBu—Ph |
| 1069 | 2-F | SO2Me | 3-CH2CO2Me—Ph |
| 1070 | 2-F | SO2Me | 3-(1-piperidinyl)-Ph |
| 1071 | 2-F | SO2Me | 3-(1-pyrrolidinyl)-Ph |
| 1072 | 2-F | SO2Me | 3-(2-imidazolyl)-Ph |
| 1073 | 2-F | SO2Me | 3-(1-imidazolyl)-Ph |
| 1074 | 2-F | SO2Me | 3-(2-thiazolyl)-Ph |
| 1075 | 2-F | SO2Me | 3-(3-pyrazolyl)-Ph |
| 1076 | 2-F | SO2Me | 3-(1-pyrazolyl)-Ph |
| 1077 | 2-F | SO2Me | 3-(5-Me-1-tetrazolyl)-Ph |
| 1078 | 2-F | SO2Me | 3-(1-Me-5-tetrazolyl)-Ph |
| 1079 | 2-F | SO2Me | 3-(2-pyridyl)-Ph |
| 1080 | 2-F | SO2Me | 3-(2-thienyl)-Ph |
| 1081 | 2-F | SO2Me | 3-(2-furanyl)-Ph |
| 1082 | 2-F | SO2Me | 4-CN—Ph |
| 1083 | 2-F | SO2Me | 4-COMe—Ph |
| 1084 | 2-F | SO2Me | 4-CO2Me—Ph |
| 1085 | 2-F | SO2Me | 4-CONH2—Ph |
| 1086 | 2-F | SO2Me | 4-CONHMe—Ph |
| 1087 | 2-F | SO2Me | 4-CONHPh—Ph |
| 1088 | 2-F | SO2Me | 4-F—Ph |
| 1089 | 2-F | SO2Me | 4-Cl—Ph |
| 1090 | 2-F | SO2Me | 4-Br—Ph |
| 1091 | 2-F | SO2Me | 4-SO2NH2—Ph |
| 1092 | 2-F | SO2Me | 4-SO2NHMe—Ph |
| 1093 | 2-F | SO2Me | 4-CF3—Ph |
| 1094 | 2-F | SO2Me | 4-OMe—Ph |
| 1095 | 2-F | SO2Me | 4-SMe—Ph |
| 1096 | 2-F | SO2Me | 4-SOMe—Ph |
| 1097 | 2-F | SO2Me | 4-SO2Me—Ph |
| 1098 | 2-F | SO2Me | 4-OH—Ph |
| 1099 | 2-F | SO2Me | 4-CH2OH—Ph |
| 1100 | 2-F | SO2Me | 4-CHOHMe—Ph |
| 1101 | 2-F | SO2Me | 4-COH(Me)2—Ph |
| 1102 | 2-F | SO2Me | 4-Me—Ph |
| 1103 | 2-F | SO2Me | 4-Et—Ph |
| 1104 | 2-F | SO2Me | 4-iPr—Ph |
| 1105 | 2-F | SO2Me | 4-tBu—Ph |
| 1106 | 2-F | SO2Me | 4-CH2CO2Me—Ph |
| 1107 | 2-F | SO2Me | 4-(1-piperidinyl)-Ph |
| 1108 | 2-F | SO2Me | 4-(1-pyrrolidinyl)-Ph |
| 1109 | 2-F | SO2Me | 4-(2-imidazolyl)-Ph |
| 1110 | 2-F | SO2Me | 4-(1-imidazolyl)-Ph |
| 1111 | 2-F | SO2Me | 4-(2-thiazolyl)-Ph |
| 1112 | 2-F | SO2Me | 4-(3-pyrazolyl)-Ph |
| 1113 | 2-F | SO2Me | 4-(1-pyrazolyl)-Ph |
| 1114 | 2-F | SO2Me | 4-(5-Me-1-tetrazolyl)-Ph |
| 1115 | 2-F | SO2Me | 4-(1-Me-5-tetrazolyl)-Ph |
| 1116 | 2-F | SO2Me | 4-(2-pyridyl)-Ph |
| 1117 | 2-F | SO2Me | 4-(2-thienyl)-Ph |
| 1118 | 2-F | SO2Me | 4-(2-furanyl)-Ph |
| 1119 | 2-F | SO2Me | 2-CN—Ph |
| 1120 | 2-F | SO2Me | 2-COMe—Ph |
| 1121 | 2-F | SO2Me | 2-CO2Me—Ph |
| 1122 | 2-F | SO2Me | 2-CONH2—Ph |
| 1123 | 2-F | SO2Me | 2-CONHMe—Ph |
| 1124 | 2-F | SO2Me | 2-F—Ph |
| 1125 | 2-F | SO2Me | 2-Cl—Ph |
| 1126 | 2-F | SO2Me | 2-Br—Ph |
| 1127 | 2-F | SO2Me | 2-SO2NH2—Ph |
| 1128 | 2-F | SO2Me | 2-SO2NHMe—Ph |
| 1129 | 2-F | SO2Me | 2-CF3—Ph |
| 1130 | 2-F | SO2Me | 2-OMe—Ph |
| 1131 | 2-F | SO2Me | 2-SMe—Ph |
| 1132 | 2-F | SO2Me | 2-SOMe—Ph |
| 1133 | 2-F | SO2Me | 2-SO2Me—Ph |
| 1134 | 2-F | SO2Me | 2-OH—Ph |
| 1135 | 2-F | SO2Me | 2-CH2OH—Ph |
| 1136 | 2-F | SO2Me | 2-CHOHM—Ph |
| 1137 | 2-F | SO2Me | 2-COH(Me)2—Ph |
| 1138 | 2-F | SO2Me | 2-Me—Ph |
| 1139 | 2-F | SO2Me | 2-Et—Ph |
| 1140 | 2-F | SO2Me | 2-iPr—Ph |
| 1141 | 2-F | SO2Me | 2-tBu—Ph |
| 1142 | 2-F | SO2Me | 2-CH2CO2Me—Ph |
| 1143 | 2-F | SO2Me | 2-(1-piperidinyl)-Ph |
| 1144 | 2-F | SO2Me | 2-(1-pyrrolidinyl)-Ph |
| 1145 | 2-F | SO2Me | 2-(2-imidazolyl)-Ph |
| 1146 | 2-F | SO2Me | 2-(1-imidazolyl)-Ph |
| 1147 | 2-F | SO2Me | 2-(2-thiazolyl)-Ph |
| 1148 | 2-F | SO2Me | 2-(3-pyrazolyl)-Ph |
| 1149 | 2-F | SO2Me | 2-(1-pyrazolyl)-Ph |
| 1150 | 2-F | SO2Me | 2-(5-Me-1-tetrazolyl)-Ph |
| 1151 | 2-F | SO2Me | 2-(1-Me-5-tetrazolyl)-Ph |
| 1152 | 2-F | SO2Me | 2-(2-pyridyl)-Ph |
| 1153 | 2-F | SO2Me | 2-(2-thienyl)-Ph |
| 1154 | 2-F | SO2Me | 2-(2-furanyl)-Ph |
| 1155 | 2-F | SO2Me | 2,4-diF—Ph |
| 1156 | 2-F | SO2Me | 2,5-diF—Ph |
| 1157 | 2-F | SO2Me | 2,6-diF—Ph |
| 1158 | 2-F | SO2Me | 3,4-diF—Ph |
| 1159 | 2-F | SO2Me | 3,5-diF—Ph |
| 1160 | 2-F | SO2Me | 2,4-diCl—Ph |
| 1161 | 2-F | SO2Me | 2,5-diCl—Ph |
| 1162 | 2-F | SO2Me | 2,6-diCl—Ph |
| 1163 | 2-F | SO2Me | 3,4-diCl—Ph |
| 1164 | 2-F | SO2Me | 3,5-diCl—Ph |
| 1165 | 2-F | SO2Me | 3,4-diCF3—Ph |
| 1166 | 2-F | SO2Me | 3,5-diCF3—Ph |
| 1167 | 2-F | SO2Me | 5-Cl-2-MeO—Ph |
| 1168 | 2-F | SO2Me | 5-Cl-2-Me—Ph |
| 1169 | 2-F | SO2Me | 2-F-S-Me—Ph |
| 1170 | 2-F | SO2Me | 3-F-5-morpholino-Ph |
| 1171 | 2-F | SO2Me | 3,4-OCH2O—Ph |
| 1172 | 2-F | SO2Me | 3,4-OCH2CH2O—Ph |
| 1173 | 2-F | SO2Me | 2-MeO-5-CONH2—Ph |
| 1174 | 2-F | SO2Me | 2-MeO-4-(1-Me-5-tetrazolyl)-Ph |
| 1175 | 2-F | SO2Me | 2-MeO-5-(1-Me-5-tetrazolyl)-Ph |
| 1176 | 2-F | SO2Me | 3-CONH2-5-(1-Me-5-tetrazolyl)-Ph |
| 1177 | 2-F | SO2Me | 1-naphthyl |
| 1178 | 2-F | SO2Me | 2-naphthyl |
| 1179 | 2-F | SO2Me | 2-thienyl |
| 1180 | 2-F | SO2Me | 3-thienyl |
| 1181 | 2-F | SO2Me | 2-furanyl |
| 1182 | 2-F | SO2Me | 3-furanyl |
| 1183 | 2-F | SO2Me | 2-pyridyl |
| 1184 | 2-F | SO2Me | 3-pyridyl |
| 1185 | 2-F | SO2Me | 4-pyridyl |
| 1186 | 2-F | SO2Me | 2-indolyl |
| 1187 | 2-F | SO2Me | 3-indolyl |
| 1188 | 2-F | SO2Me | 5-indolyl |
| 1189 | 2-F | SO2Me | 6-indolyl |
| 1190 | 2-F | SO2Me | 3-indazolyl |
| 1191 | 2-F | SO2Me | 5-indazolyl |
| 1192 | 2-F | SO2Me | 6-indazolyl |
| 1193 | 2-F | SO2Me | 2-imidazolyl |
| 1194 | 2-F | SO2Me | 3-isoxazoyl |
| 1195 | 2-F | SO2Me | 3-pyrazolyl |
| 1196 | 2-F | SO2Me | 2-thiadiazolyl |
| 1197 | 2-F | SO2Me | 2-thiazolyl |
| 1198 | 2-F | SO2Me | 5-Ac-4-Me-2-thiazolyl |
| 1199 | 2-F | SO2Me | 5-tetrazolyl |
| 1200 | 2-F | SO2Me | 2-benzimidazolyl |
| 1201 | 2-F | SO2Me | 5-benzimidazolyl |
| 1202 | 2-F | SO2Me | 2-benzothiazolyl |
| 1203 | 2-F | SO2Me | 5-benzothiazolyl |
| 1204 | 2-F | SO2Me | 2-benzoxazolyl |
| 1205 | 2-F | SO2Me | 5-benzoxazolyl |

TABLE 2-continued

| | | | |
|---|---|---|---|
| 1206 | 2-F | SO2Me | 1-adamantyl |
| 1207 | 2-F | SO2Me | 2-adamantyl |
| 1208 | 2-F | SO2Me | i-Pr |
| 1209 | 2-F | SO2Me | t-Bu |
| 1210 | 2-F | SO2Me | c-Hex |
| 1211 | 2-F | SO2Me | CH2CH2OMe |
| 1212 | 2-F | SO2Me | CH2CONH2 |
| 1213 | 2-F | SO2Me | CH2CO2Me |
| 1214 | 2-F | SO2Me | CH(CH2Ph)CO2Me |
| 1215 | 2-F | SO2Me | CH2CH2NMe2 |
| 1216 | 2-F | SO2Me | benzyl |
| 1217 | 2-F | SO2Me | phenethyl |
| 1218 | 2-F | SO2Me | 2-(morpholin-1-yl)-Et |
| 1219 | 2-F | CH2COMe | Ph |
| 1220 | 2-F | CH2COMe | 3-CN—Ph |
| 1221 | 2-F | CH2COMe | 3-COMe—Ph |
| 1222 | 2-F | CH2COMe | 3-CO2Me—Ph |
| 1223 | 2-F | CH2COMe | 3-CONH2—Ph |
| 1224 | 2-F | CH2COMe | 3-CONHMe—Ph |
| 1225 | 2-F | CH2COMe | 3-F—Ph |
| 1226 | 2-F | CH2COMe | 3-Cl—Ph |
| 1227 | 2-F | CH2COMe | 3-Br—Ph |
| 1228 | 2-F | CH2COMe | 3-SO2NH2—Ph |
| 1229 | 2-F | CH2COMe | 3-SO2NHMe—Ph |
| 1230 | 2-F | CH2COMe | 3-CF3—Ph |
| 1231 | 2-F | CH2COMe | 3-OMe—Ph |
| 1232 | 2-F | CH2COMe | 3-SMe—Ph |
| 1233 | 2-F | CH2COMe | 3-SOMe—Ph |
| 1234 | 2-F | CH2COMe | 3-SO2Me—Ph |
| 1235 | 2-F | CH2COMe | 3-OH—Ph |
| 1236 | 2-F | CH2COMe | 3-CH2OH—Ph |
| 1237 | 2-F | CH2COMe | 3-CHOHMe—Ph |
| 1238 | 2-F | CH2COMe | 3-COH(Me)2—Ph |
| 1239 | 2-F | CH2COMe | 3-Me—Ph |
| 1240 | 2-F | CH2COMe | 3-Et—Ph |
| 1241 | 2-F | CH2COMe | 3-iPr—Ph |
| 1242 | 2-F | CH2COMe | 3-tBu—Ph |
| 1243 | 2-F | CH2COMe | 3-CH2CO2Me—Ph |
| 1244 | 2-F | CH2COMe | 3-(1-piperidinyl)-Ph |
| 1245 | 2-F | CH2COMe | 3-(1-pyrrolidinyl)-Ph |
| 1246 | 2-F | CH2COMe | 3-(2-imidazolyl)-Ph |
| 1247 | 2-F | CH2COMe | 3-(1-imidazolyl)-Ph |
| 1248 | 2-F | CH2COMe | 3-(2-thiazolyl)-Ph |
| 1249 | 2-F | CH2COMe | 3-(3-pyrazolyl)-Ph |
| 1250 | 2-F | CH2COMe | 3-(1-pyrazolyl)-Ph |
| 1251 | 2-F | CH2COMe | 3-(5-Me-1-tetrazolyl)-Ph |
| 1252 | 2-F | CH2COMe | 3-(1-Me-5-tetrazolyl)-Ph |
| 1253 | 2-F | CH2COMe | 3-(2-pyridyl)-Ph |
| 1254 | 2-F | CH2COMe | 3-(2-thienyl)-Ph |
| 1255 | 2-F | CH2COMe | 3-(2-furanyl)-Ph |
| 1256 | 2-F | CH2COMe | 4-CN—Ph |
| 1257 | 2-F | CH2COMe | 4-COMe—Ph |
| 1258 | 2-F | CH2COMe | 4-CO2Me—Ph |
| 1259 | 2-F | CH2COMe | 4-CONH2—Ph |
| 1260 | 2-F | CH2COMe | 4-CONHMe—Ph |
| 1261 | 2-F | CH2COMe | 4-CONHPh—Ph |
| 1262 | 2-F | CH2COMe | 4-F—Ph |
| 1263 | 2-F | CH2COMe | 4-Cl—Ph |
| 1264 | 2-F | CH2COMe | 4-Br—Ph |
| 1265 | 2-F | CH2COMe | 4-SO2NH2—Ph |
| 1266 | 2-F | CH2COMe | 4-SO2NHMe—Ph |
| 1267 | 2-F | CH2COMe | 4-CF3—Ph |
| 1268 | 2-F | CH2COMe | 4-OMe—Ph |
| 1269 | 2-F | CH2COMe | 4-SMe—Ph |
| 1270 | 2-F | CH2COMe | 4-SOMe—Ph |
| 1271 | 2-F | CH2COMe | 4-SO2Me—Ph |
| 1272 | 2-F | CH2COMe | 4-OH—Ph |
| 1273 | 2-F | CH2COMe | 4-CH2OH—Ph |
| 1274 | 2-F | CH2COMe | 4-CHOHMe—Ph |
| 1275 | 2-F | CH2COMe | 4-COH(Me)2—Ph |
| 1276 | 2-F | CH2COMe | 4-Me—Ph |
| 1277 | 2-F | CH2COMe | 4-Et—Ph |
| 1278 | 2-F | CH2COMe | 4-iPr—Ph |
| 1279 | 2-F | CH2COMe | 4-tBu—Ph |
| 1280 | 2-F | CH2COMe | 4-CH2CO2Me—Ph |
| 1281 | 2-F | CH2COMe | 4-(1-piperidinyl)-Ph |
| 1282 | 2-F | CH2COMe | 4-(1-pyrrolidinyl)-Ph |
| 1283 | 2-F | CH2COMe | 4-(2-imidazolyl)-Ph |
| 1284 | 2-F | CH2COMe | 4-(1-imidazolyl)-Ph |
| 1285 | 2-F | CH2COMe | 4-(2-thiazolyl)-Ph |
| 1286 | 2-F | CH2COMe | 4-(3-pyrazolyl)-Ph |
| 1287 | 2-F | CH2COMe | 4-(1-pyrazolyl)-Ph |
| 1288 | 2-F | CH2COMe | 4-(5-Me-1-tetrazolyl)-Ph |
| 1289 | 2-F | CH2COMe | 4-(1-Me-5-tetrazolyl)-Ph |
| 1290 | 2-F | CH2COMe | 4-(2-pyridyl)-Ph |
| 1291 | 2-F | CH2COMe | 4-(2-thienyl)-Ph |
| 1292 | 2-F | CH2COMe | 4-(2-furanyl)-Ph |
| 1293 | 2-F | CH2COMe | 2-CN—Ph |
| 1294 | 2-F | CH2COMe | 2-COMe—Ph |
| 1295 | 2-F | CH2COMe | 2-CO2Me—Ph |
| 1296 | 2-F | CH2COMe | 2-CONH2—Ph |
| 1297 | 2-F | CH2COMe | 2-CONHMe—Ph |
| 1298 | 2-F | CH2COMe | 2-F—Ph |
| 1299 | 2-F | CH2COMe | 2-Cl—Ph |
| 1300 | 2-F | CH2COMe | 2-Br—Ph |
| 1301 | 2-F | CH2COMe | 2-SO2NH2—Ph |
| 1302 | 2-F | CH2COMe | 2-SO2NHMe—Ph |
| 1303 | 2-F | CH2COMe | 2-CF3—Ph |
| 1304 | 2-F | CH2COMe | 2-OMe—Ph |
| 1305 | 2-F | CH2COMe | 2-SMe—Ph |
| 1306 | 2-F | CH2COMe | 2-SOMe—Ph |
| 1307 | 2-F | CH2COMe | 2-SO2Me—Ph |
| 1308 | 2-F | CH2COMe | 2-OH—Ph |
| 1309 | 2-F | CH2COMe | 2-CH2OH—Ph |
| 1310 | 2-F | CH2COMe | 2-CHOHMe—Ph |
| 1311 | 2-F | CH2COMe | 2-COH(Me)2—Ph |
| 1312 | 2-F | CH2COMe | 2-Me—Ph |
| 1313 | 2-F | CH2COMe | 2-Et—Ph |
| 1314 | 2-F | CH2COMe | 2-iPr—Ph |
| 1315 | 2-F | CH2COMe | 2-tBu—Ph |
| 1316 | 2-F | CH2COMe | 2-CH2CO2Me—Ph |
| 1317 | 2-F | CH2COMe | 2-(1-piperidinyl)-Ph |
| 1318 | 2-F | CH2COMe | 2-(1-pyrrolidlnyl)-Ph |
| 1319 | 2-F | CH2COMe | 2-(2-imidazolyl)-Ph |
| 1320 | 2-F | CH2COMe | 2-(1-imidazolyl)-Ph |
| 1321 | 2-F | CH2COMe | 2-(2-thiazolyl)-Ph |
| 1322 | 2-F | CH2COMe | 2-(3-pyrazolyl)-Ph |
| 1323 | 2-F | CH2COMe | 2-(1-pyrazolyl)-Ph |
| 1324 | 2-F | CH2COMe | 2-(5-Me-1-tetrazolyl)-Ph |
| 1325 | 2-F | CH2COMe | 2-(1-Me-5-tetrazolyl)-Ph |
| 1326 | 2-F | CH2COMe | 2-(2-pyridyl)-Ph |
| 1327 | 2-F | CH2COMe | 2-(2-thienyl)-Ph |
| 1328 | 2-F | CH2COMe | 2-(2-furanyl)-Ph |
| 1329 | 2-F | CH2COMe | 2,4-diF—Ph |
| 1330 | 2-F | CH2COMe | 2,5-diF—Ph |
| 1331 | 2-F | CH2COMe | 2,6-diF—Ph |
| 1332 | 2-F | CH2COMe | 3,4-diF—Ph |
| 1333 | 2-F | CH2COMe | 3,5-diF—Ph |
| 1334 | 2-F | CH2COMe | 2,4-diCl—Ph |
| 1335 | 2-F | CH2COMe | 2,5-diCl—Ph |
| 1336 | 2-F | CH2COMe | 2,6-diCl—Ph |
| 1337 | 2-F | CH2COMe | 3,4-diCl—Ph |
| 1338 | 2-F | CH2COMe | 3,5-diCl—Ph |
| 1339 | 2-F | CH2COMe | 3,4-diCF3—Ph |
| 1340 | 2-F | CH2COMe | 3,5-diCF3—Ph |
| 1341 | 2-F | CH2COMe | 5-Cl-2-MeO—Ph |
| 1342 | 2-F | CH2COMe | 5-Cl-2-Me—Ph |
| 1343 | 2-F | CH2COMe | 2-F-5-Me—Ph |
| 1344 | 2-F | CH2COMe | 3-F-5-morpholino-Ph |
| 1345 | 2-F | CH2COMe | 3,4-OCH2O—Ph |
| 1346 | 2-F | CH2COMe | 3,4-OCH2CH2O—Ph |
| 1347 | 2-F | CH2COMe | 2-MeO-5-CONH2—Ph |
| 1348 | 2-F | CH2COMe | 2-MeO-4-(1-Me-5-tetrazolyl)-Ph |
| 1349 | 2-F | CH2COMe | 2-MeO-5-(1-Me-5-tetrazolyl)-Ph |
| 1350 | 2-F | CH2COMe | 3-CONH2-5-(1-Me-5-tetrazolyl)-Ph |
| 1351 | 2-F | CH2COMe | 1-naphthyl |
| 1352 | 2-F | CH2COMe | 2-naphthyl |
| 1353 | 2-F | CH2COMe | 2-thienyl |
| 1354 | 2-F | CH2COMe | 3-thienyl |
| 1355 | 2-F | CH2COMe | 2-furanyl |
| 1356 | 2-F | CH2COMe | 3-furanyl |
| 1357 | 2-F | CH2COMe | 2-pyridyl |
| 1358 | 2-F | CH2COMe | 3-pyridyl |
| 1359 | 2-F | CH2COMe | 4-pyridyl |
| 1360 | 2-F | CH2COMe | 2-indolyl |
| 1361 | 2-F | CH2COMe | 3-indolyl |
| 1362 | 2-F | CH2COMe | 5-indolyl |
| 1363 | 2-F | CH2COMe | 6-indolyl |

TABLE 2-continued

| | | | |
|---|---|---|---|
| 1364 | 2-F | CH2COMe | 3-indazolyl |
| 1365 | 2-F | CH2COMe | 5-indazolyl |
| 1366 | 2-F | CH2COMe | 6-indazolyl |
| 1367 | 2-F | CH2COMe | 2-imidazolyl |
| 1368 | 2-F | CH2COMe | 3-isoxazoyl |
| 1369 | 2-F | CH2COMe | 3-pyrazolyl |
| 1370 | 2-F | CH2COMe | 2-thiadiazolyl |
| 1371 | 2-F | CH2COMe | 2-thiazolyl |
| 1372 | 2-F | CH2COMe | 5-Ac-4-Me-2-thiazolyl |
| 1373 | 2-F | CH2COMe | 5-tetrazolyl |
| 1374 | 2-F | CH2COMe | 2-benzimidazolyl |
| 1375 | 2-F | CH2COMe | 5-benzimidazolyl |
| 1376 | 2-F | CH2COMe | 2-benzothiazolyl |
| 1377 | 2-F | CH2COMe | 5-benzothiazolyl |
| 1378 | 2-F | CH2COMe | 2-benzoxazolyl |
| 1379 | 2-F | CH2COMe | 5-benzoxazolyl |
| 1380 | 2-F | CH2COMe | 1-adamantyl |
| 1381 | 2-F | CH2COMe | 2-adamantyl |
| 1382 | 2-F | CH2COMe | i-Pr |
| 1383 | 2-F | CH2COMe | t-Bu |
| 1384 | 2-F | CH2COMe | c-Hex |
| 1385 | 2-F | CH2COMe | CH2CH2OMe |
| 1386 | 2-F | CH2COMe | CH2CONH2 |
| 1387 | 2-F | CH2COMe | CH2CO2Me |
| 1388 | 2-F | CH2COMe | CH(CH2Ph)CO2Me |
| 1389 | 2-F | CH2COMe | CH2CH2NMe2 |
| 1390 | 2-F | CH2COMe | benzyl |
| 1391 | 2-F | CH2COMe | phenethyl |
| 1392 | 2-F | CH2COMe | 2-(morpholin-1-yl)-Et |
| 1393 | 3-F | H | Ph |
| 1394 | 3-F | H | 3-CN—Ph |
| 1395 | 3-F | H | 3-COMe—Ph |
| 1396 | 3-F | H | 3-CO2Me—Ph |
| 1397 | 3-F | H | 3-CONH2—Ph |
| 1398 | 3-F | H | 3-CONHMe—Ph |
| 1399 | 3-F | H | 3-F—Ph |
| 1400 | 3-F | H | 3-Cl—Ph |
| 1401 | 3-F | H | 3-Br—Ph |
| 1402 | 3-F | H | 3-SO2NH2—Ph |
| 1403 | 3-F | H | 3-SO2NHMe—Ph |
| 1404 | 3-F | H | 3-CF3—Ph |
| 1405 | 3-F | H | 3-OMe—Ph |
| 1406 | 3-F | H | 3-SMe—Ph |
| 1407 | 3-F | H | 3-SOMe—Ph |
| 1408 | 3-F | H | 3-SO2Me—Ph |
| 1409 | 3-F | H | 3-OH—Ph |
| 1410 | 3-F | H | 3-CH2OH—Ph |
| 1411 | 3-F | H | 3-CHOHMe—Ph |
| 1412 | 3-F | H | 3-COH(Me)2—Ph |
| 1413 | 3-F | H | 3-Me—Ph |
| 1414 | 3-F | H | 3-Et—Ph |
| 1415 | 3-F | H | 3-iPr—Ph |
| 1416 | 3-F | H | 3-tBu—Ph |
| 1417 | 3-F | H | 3-CH2CO2Me—Ph |
| 1418 | 3-F | H | 3-(1-piperidinyl)-Ph |
| 1419 | 3-F | H | 3-(1-pyrrolidinyl)-Ph |
| 1420 | 3-F | H | 3-(2-imidazolyl)-Ph |
| 1421 | 3-F | H | 3-(1-imidazolyl)-Ph |
| 1422 | 3-F | H | 3-(2-thiazolyl)-Ph |
| 1423 | 3-F | H | 3-(3-pyrazolyl)-Ph |
| 1424 | 3-F | H | 3-(1-pyrazolyl)-Ph |
| 1425 | 3-F | H | 3-(5-Me-1-tetrazolyl)-Ph |
| 1426 | 3-F | H | 3-(1-Me-5-tetrazolyl)-Ph |
| 1427 | 3-F | H | 3-(2-pyridyl)-Ph |
| 1428 | 3-F | H | 3-(2-thienyl)-Ph |
| 1429 | 3-F | H | 3-(2-furanyl)-Ph |
| 1430 | 3-F | H | 4-CN—Ph |
| 1431 | 3-F | H | 4-COMe—Ph |
| 1432 | 3-F | H | 4-CO2Me—Ph |
| 1433 | 3-F | H | 4-CONH2—Ph |
| 1434 | 3-F | H | 4-CONHMe—Ph |
| 1435 | 3-F | H | 4-CONHPh—Ph |
| 1436 | 3-F | H | 4-F—Ph |
| 1437 | 3-F | H | 4-Cl—Ph |
| 1438 | 3-F | H | 4-Br—Ph |
| 1439 | 3-F | H | 4-SO2NH2—Ph |
| 1440 | 3-F | H | 4-SO2NHMe—Ph |
| 1441 | 3-F | H | 4-CF3—Ph |
| 1442 | 3-F | H | 4-OMe—Ph |
| 1443 | 3-F | H | 4-SMe—Ph |
| 1444 | 3-F | H | 4-SOMe—Ph |
| 1445 | 3-F | H | 4-SO2Me—Ph |
| 1446 | 3-F | H | 4-OH—Ph |
| 1447 | 3-F | H | 4-CH2OH—Ph |
| 1448 | 3-F | H | 4-CHOHMe—Ph |
| 1449 | 3-F | H | 4-COH(Me)2—Ph |
| 1450 | 3-F | H | 4-Me—Ph |
| 1451 | 3-F | H | 4-Et—Ph |
| 1452 | 3-F | H | 4-iPr—Ph |
| 1453 | 3-F | H | 4-tBu—Ph |
| 1454 | 3-F | H | 4-CH2CO2Me—Ph |
| 1455 | 3-F | H | 4-(1-piperidinyl)-Ph |
| 1456 | 3-F | H | 4-(1-pyrrolidinyl)-Ph |
| 1457 | 3-F | H | 4-(2-imidazolyl)-Ph |
| 1458 | 3-F | H | 4-(1-imidazolyl)-Ph |
| 1459 | 3-F | H | 4-(2-thiazolyl)-Ph |
| 1460 | 3-F | H | 4-(3-pyrazolyl)-Ph |
| 1461 | 3-F | H | 4-(1-pyrazolyl)-Ph |
| 1462 | 3-F | H | 4-(5-Me-1-tetrazolyl)-Ph |
| 1463 | 3-F | H | 4-(1-Me-5-tetrazolyl)-Ph |
| 1464 | 3-F | H | 4-(2-pyridyl)-Ph |
| 1465 | 3-F | H | 4-(2-thienyl)-Ph |
| 1466 | 3-F | H | 4-(2-furanyl)-Ph |
| 1467 | 3-F | H | 2-CN—Ph |
| 1468 | 3-F | H | 2-COMe—Ph |
| 1469 | 3-F | H | 2-CO2Me—Ph |
| 1470 | 3-F | H | 2-CONH2—Ph |
| 1471 | 3-F | H | 2-CONHMe—Ph |
| 1472 | 3-F | H | 2-F—Ph |
| 1473 | 3-F | H | 2-Cl—Ph |
| 1474 | 3-F | H | 2-Br—Ph |
| 1475 | 3-F | H | 2-SO2NH2—Ph |
| 1476 | 3-F | H | 2-SO2NHMe—Ph |
| 1477 | 3-F | H | 2-CF3—Ph |
| 1478 | 3-F | H | 2-OMe—Ph |
| 1479 | 3-F | H | 2-SMe—Ph |
| 1480 | 3-F | H | 2-SOMe—Ph |
| 1481 | 3-F | H | 2-SO2Me—Ph |
| 1482 | 3-F | H | 2-OH—Ph |
| 1483 | 3-F | H | 2-CH2OH—Ph |
| 1484 | 3-F | H | 2-CHOHMe—Ph |
| 1485 | 3-F | H | 2-COH(Me)2—Ph |
| 1486 | 3-F | H | 2-Me—Ph |
| 1487 | 3-F | H | 2-Et—Ph |
| 1488 | 3-F | H | 2-iPr—Ph |
| 1489 | 3-F | H | 2-tBu—Ph |
| 1490 | 3-F | H | 2-CH2CO2Me—Ph |
| 1491 | 3-F | H | 2-(1-piperidinyl)-Ph |
| 1492 | 3-F | H | 2-(1-pyrrolidinyl)-Ph |
| 1493 | 3-F | H | 2-(2-imidazolyl)-Ph |
| 1494 | 3-F | H | 2-(1-imidazolyl)-Ph |
| 1495 | 3-F | H | 2-(2-thiazolyl)-Ph |
| 1496 | 3-F | H | 2-(3-pyrazolyl)-Ph |
| 1497 | 3-F | H | 2-(1-pyrazolyl)-Ph |
| 1498 | 3-F | H | 2-(5-Me-1-tetrazolyl)-Ph |
| 1499 | 3-F | H | 2-(1-Me-5-tetrazolyl)-Ph |
| 1500 | 3-F | H | 2-(2-pyridyl)-Ph |
| 1501 | 3-F | H | 2-(2-thienyl)-Ph |
| 1502 | 3-F | H | 2-(2-furanyl)-Ph |
| 1503 | 3-F | H | 2,4-diF—Ph |
| 1504 | 3-F | H | 2,5-diF—Ph |
| 1505 | 3-F | H | 2,6-diF—Ph |
| 1506 | 3-F | H | 3,4-diF—Ph |
| 1507 | 3-F | H | 3,5-diF—Ph |
| 1508 | 3-F | H | 2,4-diCl—Ph |
| 1509 | 3-F | H | 2,5-diCl—Ph |
| 1510 | 3-F | H | 2,6-diCl—Ph |
| 1511 | 3-F | H | 3,4-diCl—Ph |
| 1512 | 3-F | H | 3,5-diCl—Ph |
| 1513 | 3-F | H | 3,4-diCF3—Ph |
| 1514 | 3-F | H | 3,5-diCF3—Ph |
| 1515 | 3-F | H | 5-Cl-2-MeO—Ph |
| 1516 | 3-F | H | 5-Cl-2-Me—Ph |
| 1517 | 3-F | H | 2-F-5-Me—Ph |
| 1518 | 3-F | H | 3-F-5-morpholino-Ph |
| 1519 | 3-F | H | 3,4-OCH2O—Ph |
| 1520 | 3-F | H | 3,4-OCH2CH2O—Ph |
| 1521 | 3-F | H | 2-MeO-5-CONH2—Ph |

TABLE 2-continued

| | | | |
|---|---|---|---|
| 1522 | 3-F | H | 2-MeO-4-(1-Me-5-tetraolyl)-Ph |
| 1523 | 3-F | H | 2-MeO-5-(1-Me-5-tetrazolyl)-Ph |
| 1524 | 3-F | H | 3-CONH2-5-(1-Me-5-tetrazolyl)-Ph |
| 1525 | 3-F | H | 1-naphthyl |
| 1526 | 3-F | H | 2-naphthyl |
| 1527 | 3-F | H | 2-thienyl |
| 1528 | 3-F | H | 3-thienyl |
| 1529 | 3-F | H | 2-furanyl |
| 1530 | 3-F | H | 3-furanyl |
| 1531 | 3-F | H | 2-pyridyl |
| 1532 | 3-F | H | 3-pyridyl |
| 1533 | 3-F | H | 4-pyridyl |
| 1534 | 3-F | H | 2-indolyl |
| 1535 | 3-F | H | 3-indolyl |
| 1536 | 3-F | H | 5-indolyl |
| 1537 | 3-F | H | 6-indolyl |
| 1538 | 3-F | H | 3-indazolyl |
| 1539 | 3-F | H | 5-indazolyl |
| 1540 | 3-F | H | 6-indazolyl |
| 1541 | 3-F | H | 2-imidazolyl |
| 1542 | 3-F | H | 3-isoxazoyl |
| 1543 | 3-F | H | 3-pyrazolyl |
| 1544 | 3-F | H | 2-thiadiazolyl |
| 1545 | 3-F | H | 2-thiazolyl |
| 1546 | 3-F | H | 5-Ac-4-Me-2-thlazolyl |
| 1547 | 3-F | H | 5-tetrazolyl |
| 1548 | 3-F | H | 2-benzimidazolyl |
| 1549 | 3-F | H | 5-benzimidazolyl |
| 1550 | 3-F | H | 2-benzothiazolyl |
| 1551 | 3-F | H | 5-benzothiazolyl |
| 1552 | 3-F | H | 2-benzoxazolyl |
| 1553 | 3-F | H | 5-benzoxazolyl |
| 1554 | 3-F | H | 1-adamantyl |
| 1555 | 3-F | H | 2-adamantyl |
| 1556 | 3-F | H | i-Pr |
| 1557 | 3-F | H | t-Bu |
| 1558 | 3-F | H | c-Hex |
| 1559 | 3-F | H | CH2CH2OMe |
| 1560 | 3-F | H | CH2CONH2 |
| 1561 | 3-F | H | CH2CO2Me |
| 1562 | 3-F | H | CH(CH2Ph)CO2Me |
| 1563 | 3-F | H | CH2CH2NMe2 |
| 1564 | 3-F | H | benzyl |
| 1565 | 3-F | H | phenethyl |
| 1566 | 3-F | H | 2-(morpholin-1-yl)-Et |
| 1567 | 3-F | Me | Ph |
| 1568 | 3-F | Me | 3-CN—Ph |
| 1569 | 3-F | Me | 3-COMe—Ph |
| 1570 | 3-F | Me | 3-CO2Me—Ph |
| 1571 | 3-F | Me | 3-CONH2—Ph |
| 1572 | 3-F | Me | 3-CONHMe—Ph |
| 1573 | 3-F | Me | 3-F—Ph |
| 1574 | 3-F | Me | 3-Cl—Ph |
| 1575 | 3-F | Me | 3-Br—Ph |
| 1576 | 3-F | Me | 3-SO2NH2—Ph |
| 1577 | 3-F | Me | 3-SO2NHMe—Ph |
| 1578 | 3-F | Me | 3-CF3—Ph |
| 1579 | 3-F | Me | 3-OMe—Ph |
| 1580 | 3-F | Me | 3-SMe—Ph |
| 1581 | 3-F | Me | 3-SOMe—Ph |
| 1582 | 3-F | Me | 3-SO2Me—Ph |
| 1583 | 3-F | Me | 3-OH—Ph |
| 1584 | 3-F | Me | 3-CH2OH—Ph |
| 1585 | 3-F | Me | 3-CHOHMe—Ph |
| 1586 | 3-F | Me | 3-COH(Me)2—Ph |
| 1587 | 3-F | Me | 3-Me—Ph |
| 1588 | 3-F | Me | 3-Et—Ph |
| 1589 | 3-F | Me | 3-iPr—Ph |
| 1590 | 3-F | Me | 3-tBu—Ph |
| 1591 | 3-F | Me | 3-CH2CO2Me—Ph |
| 1592 | 3-F | Me | 3-(1-piperidinyl)-Ph |
| 1593 | 3-F | Me | 3-(1-pyrrolidinyl)-Ph |
| 1594 | 3-F | Me | 3-(2-imidazolyl)-Ph |
| 1595 | 3-F | Me | 3-(1-imidazolyl)-Ph |
| 1596 | 3-F | Me | 3-(2-thiazolyl)-Ph |
| 1597 | 3-F | Me | 3-(3-pyrazolyl)-Ph |
| 1598 | 3-F | Me | 3-(1-pyrazolyl)-Ph |
| 1599 | 3-F | Me | 3-(5-Me-1-tetrazolyl)-Ph |
| 1600 | 3-F | Me | 3-(1-Me-5-tetrazolyl)-Ph |
| 1601 | 3-F | Me | 3-(2-pyridyl)-Ph |
| 1602 | 3-F | Me | 3-(2-thienyl)-Ph |
| 1603 | 3-F | Me | 3-(2-furanyl)-Ph |
| 1604 | 3-F | Me | 4-CN—Ph |
| 1605 | 3-F | Me | 4-COMe—Ph |
| 1606 | 3-F | Me | 4-CO2Me—Ph |
| 1607 | 3-F | Me | 4-CONH2—Ph |
| 1608 | 3-F | Me | 4-CONHMe—Ph |
| 1609 | 3-F | Me | 4-CONHPh—Ph |
| 1610 | 3-F | Me | 4-F—Ph |
| 1611 | 3-F | Me | 4-Cl—Ph |
| 1612 | 3-F | Me | 4-Br—Ph |
| 1613 | 3-F | Me | 4-SO2NH2—Ph |
| 1614 | 3-F | Me | 4-SO2NHMe—Ph |
| 1615 | 3-F | Me | 4-CF3—Ph |
| 1616 | 3-F | Me | 4-OMe—Ph |
| 1617 | 3-F | Me | 4-SMe—Ph |
| 1618 | 3-F | Me | 4-SOMe—Ph |
| 1619 | 3-F | Me | 4-SO2Me—Ph |
| 1620 | 3-F | Me | 4-OH—Ph |
| 1621 | 3-F | Me | 4-CH2OH—Ph |
| 1622 | 3-F | Me | 4-CHOHMe—Ph |
| 1623 | 3-F | Me | 4-COH(Me)2—Ph |
| 1624 | 3-F | Me | 4-Me—Ph |
| 1625 | 3-F | Me | 4-Et—Ph |
| 1626 | 3-F | Me | 4-iPr—Ph |
| 1627 | 3-F | Me | 4-tBu—Ph |
| 1628 | 3-F | Me | 4-CH2CO2Me—Ph |
| 1629 | 3-F | Me | 4-(1-piperidinyl)-Ph |
| 1630 | 3-F | Me | 4-(1-pyrrolidinyl)-Ph |
| 1631 | 3-F | Me | 4-(2-imidazolyl)-Ph |
| 1632 | 3-F | Me | 4-(1-imidazolyl)-Ph |
| 1633 | 3-F | Me | 4-(2-thiazolyl)-Ph |
| 1634 | 3-F | Me | 4-(3-pyrazolyl)-Ph |
| 1635 | 3-F | Me | 4-(1-pyrazolyl)-Ph |
| 1636 | 3-F | Me | 4-(5-Me-1-tetrazolyl)-Ph |
| 1637 | 3-F | Me | 4-(1-Me-5-tetrazolyl)-Ph |
| 1638 | 3-F | Me | 4-(2-pyridyl)-Ph |
| 1639 | 3-F | Me | 4-(2-thienyl)-Ph |
| 1640 | 3-F | Me | 4-(2-furanyl)-Ph |
| 1641 | 3-F | Me | 2-CN—Ph |
| 1642 | 3-F | Me | 2-COMe—Ph |
| 1643 | 3-F | Me | 2-CO2Me—Ph |
| 1644 | 3-F | Me | 2-CONH2—Ph |
| 1645 | 3-F | Me | 2-CONHMe—Ph |
| 1646 | 3-F | Me | 2-F—Ph |
| 1647 | 3-F | Me | 2-Cl—Ph |
| 1648 | 3-F | Me | 2-Br—Ph |
| 1649 | 3-F | Me | 2-SO2NH2—Ph |
| 1650 | 3-F | Me | 2-SO2NHMe—Ph |
| 1651 | 3-F | Me | 2-CF3—Ph |
| 1652 | 3-F | Me | 2-OMe—Ph |
| 1653 | 3-F | Me | 2-SMe—Ph |
| 1654 | 3-F | Me | 2-SOMe—Ph |
| 1655 | 3-F | Me | 2-SO2Me—Ph |
| 1656 | 3-F | Me | 2-OH—Ph |
| 1657 | 3-F | Me | 2-CH2OH—Ph |
| 1653 | 3-F | Me | 2-CHOHMe—Ph |
| 1659 | 3-F | Me | 2-COH(Me)2—Ph |
| 1660 | 3-F | Me | 2-Me—Ph |
| 1661 | 3-F | Me | 2-Et—Ph |
| 1662 | 3-F | Me | 2-iPr—Ph |
| 1663 | 3-F | Me | 2-tBu—Ph |
| 1664 | 3-F | Me | 2-CH2CO2Me—Ph |
| 1665 | 3-F | Me | 2-(1-piperidinyl)-Ph |
| 1666 | 3-F | Me | 2-(1-pyrrolidinyl)-Ph |
| 1667 | 3-F | Me | 2-(2-imidazolyl)-Ph |
| 1668 | 3-F | Me | 2-(1-imidazolyl)-Ph |
| 1669 | 3-F | Me | 2-(2-thiazolyl)-Ph |
| 1670 | 3-F | Me | 2-(3-pyrazolyl)-Ph |
| 1671 | 3-F | Me | 2-(1-pyrazolyl)-Ph |
| 1672 | 3-F | Me | 2-(5-Me-1-tetrazolyl)-Ph |
| 1673 | 3-F | Me | 2-(1-Me-5-tetrazolyl)-Ph |
| 1674 | 3-F | Me | 2-(2-pyridyl)-Ph |
| 1675 | 3-F | Me | 2-(2-thienyl)-Ph |
| 1676 | 3-F | Me | 2-(2-furanyl)-Ph |
| 1677 | 3-F | Me | 2,4-diF—Ph |
| 1678 | 3-F | Me | 2,5-diF—Ph |
| 1679 | 3-F | Me | 2,6-diF—Ph |

TABLE 2-continued

| | | | |
|---|---|---|---|
| 1680 | 3-F | Me | 3,4-diF—Ph |
| 1681 | 3-F | Me | 3,5-diF—Ph |
| 1682 | 3-F | Me | 2,4-diF—Ph |
| 1683 | 3-F | Me | 2,5-diCl—Ph |
| 1684 | 3-F | Me | 2,6-diCl—Ph |
| 1685 | 3-F | Me | 3,4-diCl—Ph |
| 1686 | 3-F | Me | 3,5-diCl—Ph |
| 1687 | 3-F | Me | 3,4-diCF3—Ph |
| 1688 | 3-F | Me | 3,5-diCF3—Ph |
| 1689 | 3-F | Me | 5-Cl-2-MeO—Ph |
| 1690 | 3-F | Me | 5-Cl-2-Me—Ph |
| 1691 | 3-F | Me | 2-F-S-Me—Ph |
| 1692 | 3-F | Me | 3-F-5-morpholino-Ph |
| 1693 | 3-F | Me | 3,4-OCH2O—Ph |
| 1694 | 3-F | Me | 3,4-OCH2CH2O—Ph |
| 1695 | 3-F | Me | 2-MeO-5-CONH2—Ph |
| 1696 | 3-F | Me | 2-MeO-4-(1-Me-5-tetrazolyl)-Ph |
| 1697 | 3-F | Me | 2-MeO-5-(1-Me-5-tetrazolyl)-Ph |
| 1698 | 3-F | Me | 3-CONH2-5-(1-Me-5-tetrazolyl)-Ph |
| 1699 | 3-F | Me | 1-naphthyl |
| 1700 | 3-F | Me | 2-naphthyl |
| 1701 | 3-F | Me | 2-thienyl |
| 1702 | 3-F | Me | 3-thienyl |
| 1703 | 3-F | Me | 2-furanyl |
| 1704 | 3-F | Me | 3-furanyl |
| 1705 | 3-F | Me | 2-pyridyl |
| 1706 | 3-F | Me | 3-pyridyl |
| 1707 | 3-F | Me | 4-pyridyl |
| 1708 | 3-F | Me | 2-indolyl |
| 1709 | 3-F | Me | 3-indolyl |
| 1710 | 3-F | Me | 5-indolyl |
| 1711 | 3-F | Me | 6-indolyl |
| 1712 | 3-F | Me | 3-indazolyl |
| 1713 | 3-F | Me | 5-indazolyl |
| 1714 | 3-F | Me | 6-indazolyl |
| 1715 | 3-F | Me | 2-imidazolyl |
| 1716 | 3-F | Me | 3-isoxazoyl |
| 1717 | 3-F | Me | 3-pyrazolyl |
| 1718 | 3-F | Me | 2-thiadiazolyl |
| 1719 | 3-F | Me | 2-thiazolyl |
| 1720 | 3-F | Me | 5-Ac-4-Me-2-thiazolyl |
| 1721 | 3-F | Me | 5-tetrazolyl |
| 1722 | 3-F | Me | 2-benzimidazolyl |
| 1723 | 3-F | Me | 5-benzimidazolyl |
| 1724 | 3-F | Me | 2-benzothiazolyl |
| 1725 | 3-F | Me | 5-benzothiazolyl |
| 1726 | 3-F | Me | 2-benzoxazolyl |
| 1727 | 3-F | Me | 5-benzoxazolyl |
| 1728 | 3-F | Me | 1-adamantyl |
| 1729 | 3-F | Me | 2-adamantyl |
| 1730 | 3-F | Me | i-Pr |
| 1731 | 3-F | Me | t-Bu |
| 1732 | 3-F | Me | c-Hex |
| 1733 | 3-F | Me | CH2CH2OMe |
| 1734 | 3-F | Me | CH2CONH2 |
| 1735 | 3-F | Me | CH2CO2Me |
| 1736 | 3-F | Me | CH(CH2Ph)CO2Me |
| 1737 | 3-F | Me | CH2CH2NMe2 |
| 1738 | 3-F | Me | benzyl |
| 1739 | 3-F | Me | phenethyl |
| 1740 | 3-F | Me | 2-(morpholin-1-yl)-Et |
| 1741 | 3-F | 2-F—Et | Ph |
| 1742 | 3-F | 2-F—Et | 3-CN—Ph |
| 1743 | 3-F | 2-F—Et | 3-COMe—Ph |
| 1744 | 3-F | 2-F—Et | 3-CO2Me—Ph |
| 1745 | 3-F | 2-F—Et | 3-CONH2—Ph |
| 1746 | 3-F | 2-F—Et | 3-CONHMe—Ph |
| 1747 | 3-F | 2-F—Et | 3-F—Ph |
| 1748 | 3-F | 2-F—Et | 3-Cl—Ph |
| 1749 | 3-F | 2-F—Et | 3-Br—Ph |
| 1750 | 3-F | 2-F—Et | 3-SO2NH2—Ph |
| 1751 | 3-F | 2-F—Et | 3-SO2NHMe—Ph |
| 1752 | 3-F | 2-F—Et | 3-CF3—Ph |
| 1753 | 3-F | 2-F—Et | 3-OMe—Ph |
| 1754 | 3-F | 2-F—Et | 3-SMe—Ph |
| 1755 | 3-F | 2-F—Et | 3-SOMe—Ph |
| 1756 | 3-F | 2-F—Et | 3-SO2Me—Ph |
| 1757 | 3-F | 2-F—Et | 3-OH—Ph |
| 1758 | 3-F | 2-F—Et | 3-CH2OH—Ph |
| 1759 | 3-F | 2-F—Et | 3-CHOHMe—Ph |
| 1760 | 3-F | 2-F—Et | 3-COH(Me)2—Ph |
| 1761 | 3-F | 2-F—Et | 3-Me—Ph |
| 1762 | 3-F | 2-F—Et | 3-Et-Ph |
| 1763 | 3-F | 2-F—Et | 3-iPr—Ph |
| 1764 | 3-F | 2-F—Et | 3-tBu—Ph |
| 1765 | 3-F | 2-F—Et | 3-CH2CO2Me—Ph |
| 1766 | 3-F | 2-F—Et | 3-(1-piperidinyl)-Ph |
| 1767 | 3-F | 2-F—Et | 3-(1-pyrrolidinyl)-Ph |
| 1768 | 3-F | 2-F—Et | 3-(2-imidazolyl)-Ph |
| 1769 | 3-F | 2-F—Et | 3-(1-imidazolyl)-Ph |
| 1770 | 3-F | 2-F—Et | 3-(2-thiazolyl)-Ph |
| 1771 | 3-F | 2-F—Et | 3-(3-pyrazolyl)-Ph |
| 1772 | 3-F | 2-F—Et | 3-(1-pyrazolyl)-Ph |
| 1773 | 3-F | 2-F—Et | 3-(5-Me-1-tetrazolyl)-Ph |
| 1774 | 3-F | 2-F—Et | 3-(1-Me-5-tetrazolyl)-Ph |
| 1775 | 3-F | 2-F—Et | 3-(2-pyridyl)-Ph |
| 1776 | 3-F | 2-F—Et | 3-(2-thienyl)-Ph |
| 1777 | 3-F | 2-F—Et | 3-(2-furanyl)-Ph |
| 1778 | 3-F | 2-F—Et | 4-CN—Ph |
| 1779 | 3-F | 2-F—Et | 4-COMe—Ph |
| 1780 | 3-F | 2-F—Et | 4-CO2Me—Ph |
| 1781 | 3-F | 2-F—Et | 4-CONH2—Ph |
| 1782 | 3-F | 2-F—Et | 4-CONHMe—Ph |
| 1783 | 3-F | 2-F—Et | 4-CONHPh—Ph |
| 1784 | 3-F | 2-F—Et | 4-F—Ph |
| 1785 | 3-F | 2-F—Et | 4-Cl—Ph |
| 1786 | 3-F | 2-F—Et | 4-Br—Ph |
| 1787 | 3-F | 2-F—Et | 4-SO2NH2—Ph |
| 1788 | 3-F | 2-F—Et | 4-SO2NHMe—Ph |
| 1789 | 3-F | 2-F—Et | 4-CF3—Ph |
| 1790 | 3-F | 2-F—Et | 4-OMe—Ph |
| 1791 | 3-F | 2-F—Et | 4-SMe—Ph |
| 1792 | 3-F | 2-F—Et | 4-SOMe—Ph |
| 1793 | 3-F | 2-F—Et | 4-SO2Me—Ph |
| 1794 | 3-F | 2-F—Et | 4-OH—Ph |
| 1795 | 3-F | 2-F—Et | 4-CH2OH—Ph |
| 1796 | 3-F | 2-F—Et | 4-CHOHMe—Ph |
| 1797 | 3-F | 2-F—Et | 4-COH(Me)2—Ph |
| 1798 | 3-F | 2-F—Et | 4-Me—Ph |
| 1799 | 3-F | 2-F—Et | 4-Et-Ph |
| 1800 | 3-F | 2-F—Et | 4-iPr—Ph |
| 1801 | 3-F | 2-F—Et | 4-tBu-Ph |
| 1802 | 3-F | 2-F—Et | 4-CH2CO2Me—Ph |
| 1803 | 3-F | 2-F—Et | 4-(1-piperidiriyl)-Ph |
| 1804 | 3-F | 2-F—Et | 4-(1-pyrrolidinyl)-Ph |
| 1805 | 3-F | 2-F—Et | 4-(2-imidazolyl)-Ph |
| 1806 | 3-F | 2-F—Et | 4-(1-imidazolyl)-Ph |
| 1807 | 3-F | 2-F—Et | 4-(2-thiazolyl)-Ph |
| 1808 | 3-F | 2-F—Et | 4-(3-pyrazolyl)-Ph |
| 1809 | 3-F | 2-F—Et | 4-(1-pyrazolyl)-Ph |
| 1810 | 3-F | 2-F—Et | 4-(5-Me-1-tetrazalyl)-Ph |
| 1811 | 3-F | 2-F—Et | 4-(1-Me-5-tetrazolyl)-Ph |
| 1812 | 3-F | 2-F—Et | 4-(2-pyridyl)-Ph |
| 1813 | 3-F | 2-F—Et | 4-(2-thienyl)-Ph |
| 1814 | 3-F | 2-F—Et | 4-(2-furanyl)-Ph |
| 1815 | 3-F | 2-F—Et | 2-CN—Ph |
| 1816 | 3-F | 2-F—Et | 2-COMe—Ph |
| 1817 | 3-F | 2-F—Et | 2-CO2Me—Ph |
| 1818 | 3-F | 2-F—Et | 2-CONH2—Ph |
| 1819 | 3-F | 2-F—Et | 2-CONHMe—Ph |
| 1820 | 3-F | 2-F—Et | 2-F—Ph |
| 1821 | 3-F | 2-F—Et | 2-Cl—Ph |
| 1822 | 3-F | 2-F—Et | 2-Br—Ph |
| 1823 | 3-F | 2-F—Et | 2-SO2NH2—Ph |
| 1824 | 3-F | 2-F—Et | 2-SO2NHMe—Ph |
| 1825 | 3-F | 2-F—Et | 2-CF3—Ph |
| 1826 | 3-F | 2-F—Et | 2-OMe—Ph |
| 1827 | 3-F | 2-F—Et | 2-SMe—Ph |
| 1828 | 3-F | 2-F—Et | 2-SOMe—Ph |
| 1829 | 3-F | 2-F—Et | 2-SO2Me—Ph |
| 1830 | 3-F | 2-F—Et | 2-OH—Ph |
| 1831 | 3-F | 2-F—Et | 2-CH2OH—Ph |
| 1832 | 3-F | 2-F—Et | 2-CHOHMe—Ph |
| 1833 | 3-F | 2-F—Et | 2-COH(Me)2—Ph |
| 1834 | 3-F | 2-F—Et | 2-Me—Ph |
| 1835 | 3-F | 2-F—Et | 2-Et-Ph |
| 1836 | 3-F | 2-F—Et | 2-iPr—Ph |
| 1837 | 3-F | 2-F—Et | 2-tBu—Ph |

TABLE 2-continued

| | | | |
|---|---|---|---|
| 1838 | 3-F | 2-F—Et | 2-CH2CO2Me—Ph |
| 1839 | 3-F | 2-F—Et | 2-(1-piperidinyl)-Ph |
| 1840 | 3-F | 2-F—Et | 2-(1-pyrrolidinyl)-Ph |
| 1841 | 3-F | 2-F—Et | 2-(2-imidazolyl)-Ph |
| 1842 | 3-F | 2-F—Et | 2-(1-imidazolyl)-Ph |
| 1843 | 3-F | 2-F—Et | 2-(2-thiazolyl)-Ph |
| 1844 | 3-F | 2-F—Et | 2-(3-pyrazolyl)-Ph |
| 1845 | 3-F | 2-F—Et | 2-(1-pyrazolyl)-Ph |
| 1846 | 3-F | 2-F—Et | 2-(5-Me-1-tetrazolyl)-Ph |
| 1847 | 3-F | 2-F—Et | 2-(1-Me-5-tetrazolyl)-Ph |
| 1848 | 3-F | 2-F—Et | 2-(2-pyridyl)-Ph |
| 1849 | 3-F | 2-F—Et | 2-(2-thienyl)-Ph |
| 1850 | 3-F | 2-F—Et | 2-(2-furanyl)-Ph |
| 1851 | 3-F | 2-F—Et | 2,4-diF—Ph |
| 1852 | 3-F | 2-F—Et | 2,5-diF—Ph |
| 1853 | 3-F | 2-F—Et | 2,6-diF—Ph |
| 1854 | 3-F | 2-F—Et | 3,4-diF—Ph |
| 1855 | 3-F | 2-F—Et | 3,5-diF—Ph |
| 1856 | 3-F | 2-F—Et | 2,4-diCl—Ph |
| 1857 | 3-F | 2-F—Et | 2,5-diCl—Ph |
| 1858 | 3-F | 2-F—Et | 2,6-diCl—Ph |
| 1859 | 3-F | 2-F—Et | 3,4-diCl—Ph |
| 1860 | 3-F | 2-F—Et | 3,5-diCl—Ph |
| 1861 | 3-F | 2-F—Et | 3,4-diCF3—Ph |
| 1862 | 3-F | 2-F—Et | 3,5-diCF3—Ph |
| 1863 | 3-F | 2-F—Et | 5-Cl-2-MeO—Ph |
| 1864 | 3-F | 2-F—Et | 5-Cl-2-Me—Ph |
| 1865 | 3-F | 2-F—Et | 2-F-5-Me—Ph |
| 1866 | 3-F | 2-F—Et | 3-F-5-morpholino-Ph |
| 1867 | 3-F | 2-F—Et | 3,4-OCH2O—Ph |
| 1868 | 3-F | 2-F—Et | 3,4-OCH2CH2O—Ph |
| 1869 | 3-F | 2-F—Et | 2-MeO-5-CONH2—Ph |
| 1870 | 3-F | 2-F—Et | 2-MeO-4-(1-Me-5-tetrazolyl)-Ph |
| 1871 | 3-F | 2-F—Et | 2-MeO-5-(1-Me-5-tetrazolyl)-Ph |
| 1872 | 3-F | 2-F—Et | 3-CONH2-5-(1-Me-5-tetrazolyl)-Ph |
| 1873 | 3-F | 2-F—Et | 1-naphthyl |
| 1874 | 3-F | 2-F—Et | 2-naphthyl |
| 1875 | 3-F | 2-F—Et | 2-thienyl |
| 1876 | 3-F | 2-F—Et | 3-thienyl |
| 1877 | 3-F | 2-F—Et | 2-furanyl |
| 1878 | 3-F | 2-F—Et | 3-furanyl |
| 1879 | 3-F | 2-F—Et | 2-pyridyl |
| 1880 | 3-F | 2-F—Et | 3-pyridyl |
| 1881 | 3-F | 2-F—Et | 4-pyridyl |
| 1882 | 3-F | 2-F—Et | 2-indolyl |
| 1883 | 3-F | 2-F—Et | 3-indolyl |
| 1884 | 3-F | 2-F—Et | 5-indolyl |
| 1885 | 3-F | 2-F—Et | 6-indolyl |
| 1886 | 3-F | 2-F—Et | 3-indazolyl |
| 1887 | 3-F | 2-F—Et | 5-indazolyl |
| 1888 | 3-F | 2-F—Et | 6-indazolyl |
| 1889 | 3-F | 2-F—Et | 2-imidazolyl |
| 1890 | 3-F | 2-F—Et | 3-isoxazoyl |
| 1891 | 3-F | 2-F—Et | 3-pyrazolyl |
| 1892 | 3-F | 2-F—Et | 2-thiadiazolyl |
| 1893 | 3-F | 2-F—Et | 2-thiazolyl |
| 1894 | 3-F | 2-F—Et | 5-Ac-4-Me-2-thiazolyl |
| 1895 | 3-F | 2-F—Et | 5-tetrazolyl |
| 1896 | 3-F | 2-F—Et | 2-benzimidazolyl |
| 1897 | 3-F | 2-F—Et | 5-benzimidazolyl |
| 1898 | 3-F | 2-F—Et | 2-benzothiazolyl |
| 1899 | 3-F | 2-F—Et | 5-benzothiazolyl |
| 1900 | 3-F | 2-F—Et | 2-benzoxazolyl |
| 1901 | 3-F | 2-F—Et | 5-benzoxazolyl |
| 1902 | 3-F | 2-F—Et | 1-adamantyl |
| 1903 | 3-F | 2-F—Et | 2-adamantyl |
| 1904 | 3-F | 2-F—Et | i-Pr |
| 1905 | 3-F | 2-F—Et | t-Bu |
| 1906 | 3-F | 2-F—Et | c-Hex |
| 1907 | 3-F | 2-F—Et | CH2CH2OMe |
| 1908 | 3-F | 2-F—Et | CH2CONH2 |
| 1909 | 3-F | 2-F—Et | CH2CO2Me |
| 1910 | 3-F | 2-F—Et | CH(CH2Ph)CO2Me |
| 1911 | 3-F | 2-F—Et | CH2CH2NMe2 |
| 1912 | 3-F | 2-F—Et | benzyl |
| 1913 | 3-F | 2-F—Et | phenethyl |
| 1914 | 3-F | 2-F—Et | 2-(morpholin-1-yl)-Et |
| 1915 | 3-F | CO2Me | Ph |
| 1916 | 3-F | CO2Me | 3-CN—Ph |
| 1917 | 3-F | CO2Me | 3-COMe—Ph |
| 1918 | 3-F | CO2Me | 3-CO2Me—Ph |
| 1919 | 3-F | CO2Me | 3-CONH2—Ph |
| 1920 | 3-F | CO2Me | 3-CONHMe—Ph |
| 1921 | 3-F | CO2Me | 3-F—Ph |
| 1922 | 3-F | CO2Me | 3-Cl—Ph |
| 1923 | 3-F | CO2Me | 3-Br—Ph |
| 1924 | 3-F | CO2Me | 3-SO2NH2—Ph |
| 1925 | 3-F | CO2Me | 3-SO2NHMe—Ph |
| 1926 | 3-F | CO2Me | 3-CF3—Ph |
| 1927 | 3-F | CO2Me | 3-OMe—Ph |
| 1928 | 3-F | CO2Me | 3-SMe—Ph |
| 1929 | 3-F | CO2Me | 3-SOMe—Ph |
| 1930 | 3-F | CO2Me | 3-SO2Me—Ph |
| 1931 | 3-F | CO2Me | 3-OH—Ph |
| 1932 | 3-F | CO2Me | 3-CH2OH—Ph |
| 1933 | 3-F | CO2Me | 3-CHOHMe—Ph |
| 1934 | 3-F | CO2Me | 3-COH(Me)2—Ph |
| 1935 | 3-F | CO2Me | 3-Me—Ph |
| 1936 | 3-F | CO2Me | 3-Et—Ph |
| 1937 | 3-F | CO2Me | 3-iPr—Ph |
| 1938 | 3-F | CO2Me | 3-tBu—Ph |
| 1939 | 3-F | CO2Me | 3-CH2CO2Me—Ph |
| 1940 | 3-F | CO2Me | 3-(1-piperidinyl)-Ph |
| 1941 | 3-F | CO2Me | 3-(1-pyrrolidinyl)-Ph |
| 1942 | 3-F | CO2Me | 3-(2-imidazolyl)-Ph |
| 1943 | 3-F | CO2Me | 3-(1-imidazolyl)-Ph |
| 1944 | 3-F | CO2Me | 3-(2-thiazolyl)-Ph |
| 1945 | 3-F | CO2Me | 3-(3-pyrazolyl)-Ph |
| 1946 | 3-F | CO2Me | 3-(1-pyrazolyl)-Ph |
| 1947 | 3-F | CO2Me | 3-(5-Me-1-tetrazolyl)-Ph |
| 1948 | 3-F | CO2Me | 3-(1-Me-5-tetrazolyl)-Ph |
| 1949 | 3-F | CO2Me | 3-(2-pyridyl)-Ph |
| 1950 | 3-F | CO2Me | 3-(2-thienyl)-Ph |
| 1951 | 3-F | CO2Me | 3-(2-furanyl)-Ph |
| 1952 | 3-F | CO2Me | 4-CN—Ph |
| 1953 | 3-F | CO2Me | 4-COMe—Ph |
| 1954 | 3-F | CO2Me | 4-CO2Me—Ph |
| 1955 | 3-F | CO2Me | 4-CONH2—Ph |
| 1956 | 3-F | CO2Me | 4-CONHMe—Ph |
| 1957 | 3-F | CO2Me | 4-CONHPh—Ph |
| 1958 | 3-F | CO2Me | 4-F—Ph |
| 1959 | 3-F | CO2Me | 4-Cl—Ph |
| 1960 | 3-F | CO2Me | 4-Br—Ph |
| 1961 | 3-F | CO2Me | 4-SO2NH2—Ph |
| 1962 | 3-F | CO2Me | 4-SO2NHMe—Ph |
| 1963 | 3-F | CO2Me | 4-CF3—Ph |
| 1964 | 3-F | CO2Me | 4-OMe—Ph |
| 1965 | 3-F | CO2Me | 4-SMe—Ph |
| 1966 | 3-F | CO2Me | 4-SOMe—Ph |
| 1967 | 3-F | CO2Me | 4-SO2Me—Ph |
| 1968 | 3-F | CO2Me | 4-OH—Ph |
| 1969 | 3-F | CO2Me | 4-CH2OH—Ph |
| 1970 | 3-F | CO2Me | 4-CHOHMe—Ph |
| 1971 | 3-F | CO2Me | 4-COH(Me)2—Ph |
| 1972 | 3-F | CO2Me | 4-Me—Ph |
| 1973 | 3-F | CO2Me | 4-Et—Ph |
| 1974 | 3-F | CO2Me | 4-iPr—Ph |
| 1975 | 3-F | CO2Me | 4-tBu—Ph |
| 1976 | 3-F | CO2Me | 4-CH2CO2Me—Ph |
| 1977 | 3-F | CO2Me | 4-(1-piperidinyl)-Ph |
| 1978 | 3-F | CO2Me | 4-(1-pyrrolidinyl)-Ph |
| 1979 | 3-F | CO2Me | 4-(2-imidazolyl)-Ph |
| 1980 | 3-F | CO2Me | 4-(1-imidazolyl)-Ph |
| 1981 | 3-F | CO2Me | 4-(2-thiazolyl)-Ph |
| 1982 | 3-F | CO2Me | 4-(3-pyrazolyl)-Ph |
| 1983 | 3-F | CO2Me | 4-(1-pyrazolyl)-Ph |
| 1984 | 3-F | CO2Me | 4-(5-Me-1-tetrazolyl)-Ph |
| 1985 | 3-F | CO2Me | 4-(1-Me-5-tetrazolyl)-Ph |
| 1985 | 3-F | CO2Me | 4-(2-pyridyl)-Ph |
| 1987 | 3-F | CO2Me | 4-(2-thienyl)-Ph |
| 1988 | 3-F | CO2Me | 4-(2-furanyl)-Ph |
| 1989 | 3-F | CO2Me | 2-CN—Ph |
| 1990 | 3-F | CO2Me | 2-COMe—Ph |
| 1991 | 3-F | CO2Me | 2-CO2Me—Ph |
| 1992 | 3-F | CO2Me | 2-CONH2—Ph |
| 1993 | 3-F | CO2Me | 2-CONHMe—Ph |
| 1994 | 3-F | CO2Me | 2-F—Ph |
| 1995 | 3-F | CO2Me | 2-Cl—Ph |

TABLE 2-continued

| | | | |
|---|---|---|---|
| 1996 | 3-F | CO2Me | 2-Br—Ph |
| 1997 | 3-F | CO2Me | 2-SO2NH2—Ph |
| 1998 | 3-F | CO2Me | 2-SO2NHMe—Ph |
| 1999 | 3-F | CO2Me | 2-CF3—Ph |
| 2CO0 | 3-F | CO2Me | 2-OMe—Ph |
| 2CO1 | 3-F | CO2Me | 2-SMe—Ph |
| 2CO2 | 3-F | CO2Me | 2-SOMe—Ph |
| 2CO3 | 3-F | CO2Me | 2-SO2Me—Ph |
| 2CO4 | 3-F | CO2Me | 2-OH—Ph |
| 2CO5 | 3-F | CO2Me | 2-CH2OH—Ph |
| 2CO6 | 3-F | CO2Me | 2-CHOHMe—Ph |
| 2CO7 | 3-F | CO2Me | 2-COH(Me)2—Ph |
| 2CO8 | 3-F | CO2Me | 2-Me—Ph |
| 2CO9 | 3-F | CO2Me | 2-Et—Ph |
| 2010 | 3-F | CO2Me | 2-iPr—Ph |
| 2011 | 3-F | CO2Me | 2-tBu—Ph |
| 2012 | 3-F | CO2Me | 2-CH2CO2Me—Ph |
| 2013 | 3-F | CO2Me | 2-(1-piperidinyl)-Ph |
| 2014 | 3-F | CO2Me | 2-(1-pyrrolidinyl)-Ph |
| 2015 | 3-F | CO2Me | 2-(2-imidazolyl)-Ph |
| 2016 | 3-F | CO2Me | 2-(1-imidazolyl)-Ph |
| 2017 | 3-F | CO2Me | 2-(2-thiazolyl)-Ph |
| 2018 | 3-F | CO2Me | 2-(3-pyrazolyl)-Ph |
| 2019 | 3-F | CO2Me | 2-(1-pyrazolyl)-Ph |
| 2020 | 3-F | CO2Me | 2-(5-Me-1-tetrazolyl)-Ph |
| 2021 | 3-F | CO2Me | 2-(1-Me-5-tetrazolyl)-Ph |
| 2022 | 3-F | CO2Me | 2-(2-pyridyl)-Ph |
| 2023 | 3-F | CO2Me | 2-(2-thienyl)-Ph |
| 2024 | 3-F | CO2Me | 2-(2-furanyl)-Ph |
| 2025 | 3-F | CO2Me | 2,4-diF—Ph |
| 2026 | 3-F | CO2Me | 2,5-diF—Ph |
| 2027 | 3-F | CO2Me | 2,6-diF—Ph |
| 2028 | 3-F | CO2Me | 3,4-diF—Ph |
| 2029 | 3-F | CO2Me | 3,5-diF—Ph |
| 2030 | 3-F | CO2Me | 2,4-diCl—Ph |
| 2031 | 3-F | CO2Me | 2,5-diCl—Ph |
| 2032 | 3-F | CO2Me | 2,6-diCl—Ph |
| 2033 | 3-F | CO2Me | 3,4-diCl—Ph |
| 2034 | 3-F | CO2Me | 3,5-diCl—Ph |
| 2035 | 3-F | CO2Me | 3,4-diCF3—Ph |
| 2036 | 3-F | CO2Me | 3,5-diCF3—Ph |
| 2037 | 3-F | CO2Me | 5-Cl-2-MeO—Ph |
| 2038 | 3-F | CO2Me | 5-Cl-2-Me—Ph |
| 2039 | 3-F | CO2Me | 2-F-5-Me—Ph |
| 2040 | 3-F | CO2Me | 3-F-5-morpholino-Ph |
| 2041 | 3-F | CO2Me | 3,4-OCH2O—Ph |
| 2042 | 3-F | CO2Me | 3,4-OCH2CH2O—Ph |
| 2043 | 3-F | CO2Me | 2-MeO-5-CONH2—Ph |
| 2044 | 3-F | CO2Me | 2-MeO-4-(1-Me-5-tetrazolyl)-Ph |
| 2045 | 3-F | CO2Me | 2-MeO-5-(1-Me-5-tetrazolyl)-Ph |
| 2046 | 3-F | CO2Me | 3-CONH2-5-(1-Me-5-tetrazolyl)-Ph |
| 2047 | 3-F | CO2Me | 1-naphthyl |
| 2048 | 3-F | CO2Me | 2-naphthyl |
| 2049 | 3-F | CO2Me | 2-thienyl |
| 2050 | 3-F | CO2Me | 3-thienyl |
| 2051 | 3-F | CO2Me | 2-furanyl |
| 2052 | 3-F | CO2Me | 3-furanyl |
| 2053 | 3-F | CO2Me | 2-pyridyl |
| 2054 | 3-F | CO2Me | 3-pyridyl |
| 2055 | 3-F | CO2Me | 4-pyridyl |
| 2056 | 3-F | CO2Me | 2-indolyl |
| 2057 | 3-F | CO2Me | 3-indolyl |
| 2058 | 3-F | CO2Me | 5-indolyl |
| 2059 | 3-F | CO2Me | 6-indolyl |
| 2060 | 3-F | CO2Me | 3-indazolyl |
| 2061 | 3-F | CO2Me | 5-indazolyl |
| 2062 | 3-F | CO2Me | 6-indazolyl |
| 2063 | 3-F | CO2Me | 2-imidazolyl |
| 2064 | 3-F | CO2Me | 3-isoxazolyl |
| 2065 | 3-F | CO2Me | 3-pyrazolyl |
| 2066 | 3-F | CO2Me | 2-thiadiazolyl |
| 2067 | 3-F | CO2Me | 2-thiazolyl |
| 2068 | 3-F | CO2Me | 5-Ac-4-Me-2-thlazolyl |
| 2069 | 3-F | CO2Me | 5-tetrazolyl |
| 2070 | 3-F | CO2Me | 2-benzimidazolyl |
| 2071 | 3-F | CO2Me | 5-benzimidazolyl |
| 2072 | 3-F | CO2Me | 2-benzothiazolyl |
| 2073 | 3-F | CO2Me | 5-benzothiazolyl |
| 2074 | 3-F | CO2Me | 2-benzoxazolyl |
| 2075 | 3-F | CO2Me | 5-benzoxazolyl |
| 2076 | 3-F | CO2Me | 1-adamantyl |
| 2077 | 3-F | CO2Me | 2-adamantyl |
| 2078 | 3-F | CO2Me | i-Pr |
| 2079 | 3-F | CO2Me | t-Bu |
| 2080 | 3-F | CO2Me | c-Hex |
| 2081 | 3-F | CO2Me | CH2CH2OMe |
| 2082 | 3-F | CO2Me | CH2CONH2 |
| 2083 | 3-F | CO2Me | CH2CO2Me |
| 2084 | 3-F | CO2Me | CH(CH2Ph)CO2Me |
| 2085 | 3-F | CO2Me | CH2CH2NMe2 |
| 2086 | 3-F | CO2Me | benzyl |
| 2087 | 3-F | CO2Me | phenethyl |
| 2088 | 3-F | CO2Me | 2-(morpholin-1-yl)-Et |
| 2089 | 3-F | Ac | Ph |
| 2090 | 3-F | Ac | 3-CN—Ph |
| 2091 | 3-F | Ac | 3-COMe—Ph |
| 2092 | 3-F | Ac | 3-CO2Me—Ph |
| 2093 | 3-F | Ac | 3-CONH2—Ph |
| 2094 | 3-F | Ac | 3-CONHMe—Ph |
| 2095 | 3-F | Ac | 3-F—Ph |
| 2096 | 3-F | Ac | 3-Cl—Ph |
| 2097 | 3-F | Ac | 3-Br—Ph |
| 2098 | 3-F | Ac | 3-SO2NH2—Ph |
| 2099 | 3-F | Ac | 3-SO2NHMe—Ph |
| 2100 | 3-F | Ac | 3-CF3—Ph |
| 2101 | 3-F | Ac | 3-OMe—Ph |
| 2102 | 3-F | Ac | 3-SMe—Ph |
| 2103 | 3-F | Ac | 3-SOMe—Ph |
| 2104 | 3-F | Ac | 3-SO2Me—Ph |
| 2105 | 3-F | Ac | 3-OH—Ph |
| 2106 | 3-F | Ac | 3-CH2OH—Ph |
| 2107 | 3-F | Ac | 3-CHOHMe—Ph |
| 2108 | 3-F | Ac | 3-COH(Me)2—Ph |
| 2109 | 3-F | Ac | 3-Me—Ph |
| 2110 | 3-F | Ac | 3-Et—Ph |
| 2111 | 3-F | Ac | 3-iPr—Ph |
| 2112 | 3-F | Ac | 3-tBu—Ph |
| 2113 | 3-F | Ac | 3-CH2CO2Me—Ph |
| 2114 | 3-F | Ac | 3-(1-piperidinyl)-Ph |
| 2115 | 3-F | Ac | 3-(1-pyrrolidinyl)-Ph |
| 2116 | 3-F | Ac | 3-(2-imidazolyl)-Ph |
| 2117 | 3-F | Ac | 3-(1-imidazalyl)-Ph |
| 2118 | 3-F | Ac | 3-(2-thiazolyl)-Ph |
| 2119 | 3-F | Ac | 3-(3-pyrazolyl)-Ph |
| 2120 | 3-F | Ac | 3-(1-pyrazolyl)-Ph |
| 2121 | 3-F | Ac | 3-(5-Me-1-tetrazolyl)-Ph |
| 2122 | 3-F | Ac | 3-(1-Me-5-tetrazolyl)-Ph |
| 2123 | 3-F | Ac | 3-(2-pyridyl)-Ph |
| 2124 | 3-F | Ac | 3-(2-thienyl)-Ph |
| 2125 | 3-F | Ac | 3-(2-furanyl)-Ph |
| 2126 | 3-F | Ac | 4-CN—Ph |
| 2127 | 3-F | Ac | 4-COMe—Ph |
| 2128 | 3-F | Ac | 4-CO2Me—Ph |
| 2129 | 3-F | Ac | 4-CONH2—Ph |
| 2130 | 3-F | Ac | 4-CONHMe—Ph |
| 2131 | 3-F | Ac | 4-CONHPh—Ph |
| 2132 | 3-F | Ac | 4-F—Ph |
| 2133 | 3-F | Ac | 4-Cl—Ph |
| 2134 | 3-F | Ac | 4-Br—Ph |
| 2135 | 3-F | Ac | 4-SO2NH2—Ph |
| 2136 | 3-F | Ac | 4-SO2NHMe—Ph |
| 2137 | 3-F | Ac | 4-CF3—Ph |
| 2138 | 3-F | Ac | 4-OMe—Ph |
| 2139 | 3-F | Ac | 4-SMe—Ph |
| 2140 | 3-F | Ac | 4-SOMe—Ph |
| 2141 | 3-F | Ac | 4-SO2Me—Ph |
| 2142 | 3-F | Ac | 4-OH—Ph |
| 2143 | 3-F | Ac | 4-CH2OH—Ph |
| 2144 | 3-F | Ac | 4-CHOHMe—Ph |
| 2145 | 3-F | Ac | 4-COH(Me)2—Ph |
| 2146 | 3-F | Ac | 4-Me—Ph |
| 2147 | 3-F | Ac | 4-Et—Ph |
| 2148 | 3-F | Ac | 4-iPr—Ph |
| 2149 | 3-F | Ac | 4-tBu—Ph |
| 2150 | 3-F | Ac | 4-CH2CO2Me—Ph |
| 2151 | 3-F | Ac | 4-(1-piperidinyl)-Ph |
| 2152 | 3-F | Ac | 4-(1-pyrrolidinyl)-Ph |
| 2153 | 3-F | Ac | 4-(2-imidazolyl)-Ph |

TABLE 2-continued

| | | | |
|---|---|---|---|
| 2154 | 3-F | Ac | 4-(1-imidazolyl)-Ph |
| 2155 | 3-F | Ac | 4-(2-thiazolyl)-Ph |
| 2156 | 3-F | Ac | 4-(3-pyrazolyl)-Ph |
| 2157 | 3-F | Ac | 4-(1-pyrazolyl)-Ph |
| 2158 | 3-F | Ac | 4-(5-Me-1-tetrazolyl)-Ph |
| 2159 | 3-F | Ac | 4-(1-Me-5-tetrazolyl)-Ph |
| 2160 | 3-F | Ac | 4-(2-pyridyl)-Ph |
| 2161 | 3-F | Ac | 4-(2-thienyl)-Ph |
| 2162 | 3-F | Ac | 4-(2-furanyl)-Ph |
| 2163 | 3-F | Ac | 2-CN—Ph |
| 2164 | 3-F | Ac | 2-COMe—Ph |
| 2165 | 3-F | Ac | 2-CO2Me—Ph |
| 2166 | 3-F | Ac | 2-CONH2—Ph |
| 2167 | 3-F | Ac | 2-CONHMe—Ph |
| 2168 | 3-F | Ac | 2-F—Ph |
| 2169 | 3-F | Ac | 2-Cl—Ph |
| 2170 | 3-F | Ac | 2-Br—Ph |
| 2171 | 3-F | Ac | 2-SO2NH2—Ph |
| 2172 | 3-F | Ac | 2-SO2NHMe—Ph |
| 2173 | 3-F | Ac | 2-CF3—Ph |
| 2174 | 3-F | Ac | 2-OMe—Ph |
| 2175 | 3-F | Ac | 2-SMe—Ph |
| 2176 | 3-F | Ac | 2-SOMe—Ph |
| 2177 | 3-F | Ac | 2-SO2Me—Ph |
| 2178 | 3-F | Ac | 2-OH—Ph |
| 2179 | 3-F | Ac | 2-CH2OH—Ph |
| 2180 | 3-F | Ac | 2-CHOHMe—Ph |
| 2181 | 3-F | Ac | 2-COH(Me)2—Ph |
| 2182 | 3-F | Ac | 2-Me—Ph |
| 2183 | 3-F | Ac | 2-Et—Ph |
| 2184 | 3-F | Ac | 2-iPr—Ph |
| 2185 | 3-F | Ac | 2-tBu—Ph |
| 2186 | 3-F | Ac | 2-CH2CO2Me—Ph |
| 2187 | 3-F | Ac | 2-(1-piperidinyl)-Ph |
| 2188 | 3-F | Ac | 2-(1-pyrrolidinyl)-Ph |
| 2189 | 3-F | Ac | 2-(2-imidazolyl)-Ph |
| 2190 | 3-F | Ac | 2-(1-imidazolyl)-Ph |
| 2191 | 3-F | Ac | 2-(2-thiazolyl)-Ph |
| 2192 | 3-F | Ac | 2-(3-pyrazolyl)-Ph |
| 2193 | 3-F | Ac | 2-(1-pyrazolyl)-Ph |
| 2194 | 3-F | Ac | 2-(5-Me-1-tetrazolyl)-Ph |
| 2195 | 3-F | Ac | 2-(1-Me-5-tetrazolyl)-Ph |
| 2196 | 3-F | Ac | 2-(2-pyridyl)-Ph |
| 2197 | 3-F | Ac | 2-(2-thienyl)-Ph |
| 2198 | 3-F | Ac | 2-(2-furanyl)-Ph |
| 2199 | 3-F | Ac | 2,4-diF—Ph |
| 2200 | 3-F | Ac | 2,5-diF—Ph |
| 2201 | 3-F | Ac | 2,6-diF—Ph |
| 2202 | 3-F | Ac | 3,4-diF—Ph |
| 2203 | 3-F | Ac | 3,5-diF—Ph |
| 2204 | 3-F | Ac | 2,4-diCl—Ph |
| 2205 | 3-F | Ac | 2,5-diCl—Ph |
| 2206 | 3-F | Ac | 2,6-diCl—Ph |
| 2207 | 3-F | Ac | 3,4-diCl—Ph |
| 2208 | 3-F | Ac | 3,5-diCl—Ph |
| 2209 | 3-F | Ac | 3,4-diCF3—Ph |
| 2210 | 3-F | Ac | 3,5-diCF3—Ph |
| 2211 | 3-F | Ac | 5-Cl-2-MeO—Ph |
| 2212 | 3-F | Ac | 5-Cl-2-Me—Ph |
| 2213 | 3-F | Ac | 2-F-5-Me—Ph |
| 2214 | 3-F | Ac | 3-F-5-morpholino-Ph |
| 2215 | 3-F | Ac | 3,4-OCH2O—Ph |
| 2216 | 3-F | Ac | 3,4-OCH2CH2O—Ph |
| 2217 | 3-F | Ac | 2-MeO-5-CONH2—Ph |
| 2218 | 3-F | Ac | 2-MeO-4-(1-Me-5-tetrazolyl)-Ph |
| 2219 | 3-F | Ac | 2-MeO-5-(1-Me-5-tetrazolyl)Ph |
| 2220 | 3-F | Ac | 3-CONH2-5-(1-Me-5-tetrazolyl)-Ph |
| 2221 | 3-F | Ac | 1-naphthyl |
| 2222 | 3-F | Ac | 2-naphthyl |
| 2223 | 3-F | Ac | 2-thienyl |
| 2224 | 3-F | Ac | 3-thienyl |
| 2225 | 3-F | Ac | 2-furanyl |
| 2226 | 3-F | Ac | 3-furanyl |
| 2227 | 3-F | Ac | 2-pyridyl |
| 2228 | 3-F | Ac | 3-pyridyl |
| 2229 | 3-F | Ac | 4-pyridyl |
| 2230 | 3-F | Ac | 2-indolyl |
| 2231 | 3-F | Ac | 3-indolyl |
| 2232 | 3-F | Ac | 5-indolyl |
| 2233 | 3-F | Ac | 6-indolyl |
| 2234 | 3-F | Ac | 3-indazolyl |
| 2235 | 3-F | Ac | 5-indazolyl |
| 2236 | 3-F | Ac | 6-indazolyl |
| 2237 | 3-F | Ac | 2-imidazolyl |
| 2238 | 3-F | Ac | 3-isoxazoyl |
| 2239 | 3-F | Ac | 3-pyrazolyl |
| 2240 | 3-F | Ac | 2-thiadiazolyl |
| 2241 | 3-F | Ac | 2-thiazolyl |
| 2242 | 3-F | Ac | 5-Ac-4-Me-2-thiazolyl |
| 2243 | 3-F | Ac | 5-tetrazolyl |
| 2244 | 3-F | Ac | 2-benzimidazolyl |
| 2245 | 3-F | Ac | 5-benzimidazolyl |
| 2246 | 3-F | Ac | 2-benzothiazolyl |
| 2247 | 3-F | Ac | 5-benzothiazolyl |
| 2248 | 3-F | Ac | 2-benzoxazolyl |
| 2249 | 3-F | Ac | 5-benzoxazolyl |
| 2250 | 3-F | Ac | 1-adamantyl |
| 2251 | 3-F | Ac | 2-adamantyl |
| 2252 | 3-F | Ac | i-Pr |
| 2253 | 3-F | Ac | t-Bu |
| 2254 | 3-F | Ac | c-Hex |
| 2255 | 3-F | Ac | CH2CH2OMe |
| 2256 | 3-F | Ac | CH2CONH2 |
| 2257 | 3-F | Ac | CH2CO2Me |
| 2258 | 3-F | Ac | CH(CH2Ph)CO2Me |
| 2259 | 3-F | Ac | CH2CH2NMe2 |
| 2260 | 3-F | Ac | benzyl |
| 2261 | 3-F | Ac | phenethyl |
| 2262 | 3-F | Ac | 2-(morpholin-1-yl)-Et |
| 2263 | 3-F | COtBu | Ph |
| 2264 | 3-F | COtBu | 3-CN—Ph |
| 2265 | 3-F | COtBu | 3-COMe—Ph |
| 2266 | 3-F | COtBu | 3-CO2Me—Ph |
| 2267 | 3-F | COtBu | 3-CONH2—Ph |
| 2268 | 3-F | COtBu | 3-CONHMe—Ph |
| 2269 | 3-F | COtBu | 3-F—Ph |
| 2270 | 3-F | COtBu | 3-Cl—Ph |
| 2271 | 3-F | COtBu | 3-Br—Ph |
| 2272 | 3-F | COtBu | 3-SO2NH2—Ph |
| 2273 | 3-F | COtBu | 3-SO2NHMe—Ph |
| 2274 | 3-F | COtBu | 3-CF3—Ph |
| 2275 | 3-F | COtBu | 3-OMe—Ph |
| 2276 | 3-F | COtBu | 3-SMe—Ph |
| 2277 | 3-F | COtBu | 3-SOMe—Ph |
| 2278 | 3-F | COtBu | 3-SO2Me—Ph |
| 2279 | 3-F | COtBu | 3-OH—Ph |
| 2280 | 3-F | COtBu | 3-CH2OH—Ph |
| 2281 | 3-F | COtBu | 3-CHOHMe—Ph |
| 2282 | 3-F | COtBu | 3-COH(Me)2—Ph |
| 2283 | 3-F | COtBu | 3-Me—Ph |
| 2284 | 3-F | COtBu | 3-Et—Ph |
| 2285 | 3-F | COtBu | 3-iPr—Ph |
| 2286 | 3-F | COtBu | 3-tBu—Ph |
| 2287 | 3-F | COtBu | 3-CH2CO2Me—Ph |
| 2288 | 3-F | COtBu | 3-(1-piperidinyl)-Ph |
| 2289 | 3-F | COtBu | 3-(1-pyrrolidinyl)-Ph |
| 2290 | 3-F | COtBu | 3-(2-imidazolyl)-Ph |
| 2291 | 3-F | COtBu | 3-(1-imidazolyl)-Ph |
| 2292 | 3-F | COtBu | 3-(2-thiazolyl)-Ph |
| 2293 | 3-F | COtBu | 3-(3-pyrazolyl)-Ph |
| 2294 | 3-F | COtBu | 3-(1-pyrazolyl)-Ph |
| 2295 | 3-F | COtBu | 3-(5-Me-1-tetrazolyl)-Ph |
| 2296 | 3-F | COtBu | 3-(1-Me-5-tetrazolyl)-Ph |
| 2297 | 3-F | COtBu | 3-(2-pyridyl)-Ph |
| 2298 | 3-F | COtBu | 3-(2-thienyl)-Ph |
| 2299 | 3-F | COtBu | 3-(2-furanyl)-Ph |
| 2300 | 3-F | COtBu | 4-CN—Ph |
| 2301 | 3-F | COtBu | 4-COMe—Ph |
| 2302 | 3-F | COtBu | 4-CO2Me—Ph |
| 2303 | 3-F | COtBu | 4-CONH2—Ph |
| 2304 | 3-F | COtBu | 4-CONHMe—Ph |
| 2305 | 3-F | COtBu | 4-CONHPh—Ph |
| 2306 | 3-F | COtBu | 4-F—Ph |
| 2307 | 3-F | COtBu | 4-Cl—Ph |
| 2308 | 3-F | COtBu | 4-Br—Ph |
| 2309 | 3-F | COtBu | 4-SO2NH2—Ph |
| 2310 | 3-F | COtBu | 4-SO2NHMe—Ph |
| 2311 | 3-F | COtBu | 4-CF3—Ph |

TABLE 2-continued

| | | | |
|---|---|---|---|
| 2312 | 3-F | COtBu | 4-OMe—Ph |
| 2313 | 3-F | COtBu | 4-SMe—Ph |
| 2314 | 3-F | COtBu | 4-SOMe—Ph |
| 2315 | 3-F | COtBu | 4-SO2Me—Ph |
| 2316 | 3-F | COtBu | 4-OH—Ph |
| 2317 | 3-F | COtBu | 4-CH2OH—Ph |
| 2318 | 3-F | COtBu | 4-CHOHMe—Ph |
| 2319 | 3-F | COtBu | 4-COH(Me)2—Ph |
| 2320 | 3-F | COtBu | 4-Me—Ph |
| 2321 | 3-F | COtBu | 4-Et—Ph |
| 2322 | 3-F | COtBu | 4-iPr—Ph |
| 2323 | 3-F | COtBu | 4-tBu—Ph |
| 2324 | 3-F | COtBu | 4-CH2CO2Me—Ph |
| 2325 | 3-F | COtBu | 4-(1-piperidinyl)-Ph |
| 2326 | 3-F | COtBu | 4-(1-pyrrolidinyl)-Ph |
| 2327 | 3-F | COtBu | 4-(2-imidazolyl)-Ph |
| 2328 | 3-F | COtBu | 4-(1-imidazolyl)-Ph |
| 2329 | 3-F | COtBu | 4-(2-thiazolyl)-Ph |
| 2330 | 3-F | COtBu | 4-(3-pyrazolyl)-Ph |
| 2331 | 3-F | COtBu | 4-(1-pyrazolyl)-Ph |
| 2332 | 3-F | COtBu | 4-(5-Me-1-tetrazolyl)-Ph |
| 2333 | 3-F | COtBu | 4-(1-Me-5-tetrazolyl)-Ph |
| 2334 | 3-F | COtBu | 4-(2-pyridyl)-Ph |
| 2335 | 3-F | COtBu | 4-(2-thienyl)-Ph |
| 2336 | 3-F | COtBu | 4-(2-furanyl)-Ph |
| 2337 | 3-F | COtBu | 2-CN—Ph |
| 2338 | 3-F | COtBu | 2-COMe—Ph |
| 2339 | 3-F | COtBu | 2-CO2Me—Ph |
| 2340 | 3-F | COtBu | 2-CONH2—Ph |
| 2341 | 3-F | COtBu | 2-CONHMe—Ph |
| 2342 | 3-F | COtBu | 2-F—Ph |
| 2343 | 3-F | COtBu | 2-Cl—Ph |
| 2344 | 3-F | COtBu | 2-Br—Ph |
| 2345 | 3-F | COtBu | 2-SO2NH2—Ph |
| 2346 | 3-F | COtBu | 2-SO2NHMe—Ph |
| 2347 | 3-F | COtBu | 2-CF3—Ph |
| 2348 | 3-F | COtBu | 2-OMe—Ph |
| 2349 | 3-F | COtBu | 2-SMe—Ph |
| 2350 | 3-F | COtBu | 2-SOMe—Ph |
| 2351 | 3-F | COtBu | 2-SO2Me—Ph |
| 2352 | 3-F | COtBu | 2-OH—Ph |
| 2353 | 3-F | COtBu | 2-CH2OH—Ph |
| 2354 | 3-F | COtBu | 2-CHOHMe—Ph |
| 2355 | 3-F | COtBu | 2-COH(Me)2—Ph |
| 2356 | 3-F | COtBu | 2-Me—Ph |
| 2357 | 3-F | COtBu | 2-Et—Ph |
| 2358 | 3-F | COtBu | 2-iPr—Ph |
| 2359 | 3-F | COtBu | 2-tBu—Ph |
| 2360 | 3-F | COtBu | 2-CH2CO2Me—Ph |
| 2361 | 3-F | COtBu | 2-(1-piperidinyl)-Ph |
| 2362 | 3-F | COtBu | 2-(1-pyrrolidinyl)-Ph |
| 2363 | 3-F | COtBu | 2-(2-imidazolyl)-Ph |
| 2364 | 3-F | COtBu | 2-(1-imidazolyl)-Ph |
| 2365 | 3-F | COtBu | 2-(2-thiazolyl)-Ph |
| 2366 | 3-F | COtBu | 2-(3-pyrazolyl)-Ph |
| 2367 | 3-F | COtBu | 2-(1-pyrazolyl)-Ph |
| 2368 | 3-F | COtBu | 2-(5-Me-1-tetrazolyl)-Ph |
| 2369 | 3-F | COtBu | 2-(1-Me-5-tetrazolyl)-Ph |
| 2370 | 3-F | COtBu | 2-(2-pyridyl)-Ph |
| 2371 | 3-F | COtBu | 2-(2-thienyl)-Ph |
| 2372 | 3-F | COtBu | 2-(2-furanyl)-Ph |
| 2373 | 3-F | COtBu | 2,4-diF—Ph |
| 2374 | 3-F | COtBu | 2,5-diF—Ph |
| 2375 | 3-F | COtBu | 2,6-diF—Ph |
| 2376 | 3-F | COtBu | 3,4-diF—Ph |
| 2377 | 3-F | COtBu | 3,5-diF—Ph |
| 2378 | 3-F | COtBu | 2,4-diCl—Ph |
| 2379 | 3-F | COtBu | 2,5-diCl—Ph |
| 2380 | 3-F | COtBu | 2,6-diCl—Ph |
| 2381 | 3-F | COtBu | 3,4-diCl—Ph |
| 2382 | 3-F | COtBu | 3,5-diCl—Ph |
| 2383 | 3-F | COtBu | 3,4-diCF3—Ph |
| 2384 | 3-F | COtBu | 3,5-diCF3—Ph |
| 2385 | 3-F | COtBu | 5-Cl-2-MeO—Ph |
| 2386 | 3-F | COtBu | 5-Cl-2-Me—Ph |
| 2387 | 3-F | COtBu | 2-F-5-Me—Ph |
| 2388 | 3-F | COtBu | 3-F-5-morpholino-Ph |
| 2389 | 3-F | COtBu | 3,4-OCH2O—Ph |
| 2390 | 3-F | COtBu | 3,4-OCH2CH2O—Ph |
| 2391 | 3-F | COtBu | 2-MeO-5-CONH2—Ph |
| 2392 | 3-F | COtBu | 2-MeO-4-(1-Me-5-tetrazolyl)-Ph |
| 2393 | 3-F | COtBu | 2-MeO-5-(1-Me-5-tetrazolyl)-Ph |
| 2394 | 3-F | COtBu | 3-CONH2-5-(1-Me-5-tetrazolyl)-Ph |
| 2395 | 3-F | COtBu | 1-naphthyl |
| 2396 | 3-F | COtBu | 2-naphthyl |
| 2397 | 3-F | COtBu | 2-thienyl |
| 2398 | 3-F | COtBu | 3-thienyl |
| 2399 | 3-F | COtBu | 2-furanyl |
| 2400 | 3-F | COtBu | 3-furanyl |
| 2401 | 3-F | COtBu | 2-pyridyl |
| 2402 | 3-F | COtBu | 3-pyridyl |
| 2403 | 3-F | COtBu | 4-pyridyl |
| 2404 | 3-F | COtBu | 2-indolyl |
| 2405 | 3-F | COtBu | 3-indolyl |
| 2406 | 3-F | COtBu | 5-indolyl |
| 2407 | 3-F | COtBu | 6-indolyl |
| 2408 | 3-F | COtBu | 3-indazolyl |
| 2409 | 3-F | COtBu | 5-indazolyl |
| 2410 | 3-F | COtBu | 6-indazolyl |
| 2411 | 3-F | COtBu | 2-imidazolyl |
| 2412 | 3-F | COtBu | 3-isoxazoyl |
| 2413 | 3-F | COtBu | 3-pyrazolyl |
| 2414 | 3-F | COtBu | 2-thiadiazolyl |
| 2415 | 3-F | COtBu | 2-thiazolyl |
| 2416 | 3-F | COtBu | 5-Ac-4-Me-2-thiazolyl |
| 2417 | 3-F | COtBu | 5-tetrazolyl |
| 2418 | 3-F | COtBu | 2-benzimidazolyl |
| 2419 | 3-F | COtBu | 5-benzimidazolyl |
| 2420 | 3-F | COtBu | 2-benzothiazolyl |
| 2421 | 3-F | COtBu | 5-benzothiazolyl |
| 2422 | 3-F | COtBu | 2-benzoxazolyl |
| 2423 | 3-F | COtBu | 5-benzoxazolyl |
| 2424 | 3-F | COtBu | 1-adamantyl |
| 2425 | 3-F | COtBu | 2-adamantyl |
| 2426 | 3-F | COtBu | i-Pr |
| 2427 | 3-F | COtBu | t-Bu |
| 2428 | 3-F | COtBu | c-Hex |
| 2429 | 3-F | COtBu | CH2CH2OMe |
| 2430 | 3-F | COtBu | CH2CONH2 |
| 2431 | 3-F | COtBu | CH2CO2Me |
| 2432 | 3-F | COtBu | CH(CH2Ph)CO2Me |
| 2433 | 3-F | COtBu | CH2CH2NMe2 |
| 2434 | 3-F | COtBu | benzyl |
| 2435 | 3-F | COtBu | phenethyl |
| 2436 | 3-F | COtBu | 2-(morpholin-1-yl)-Et |
| 2437 | 3-F | SO2Me | Ph |
| 2438 | 3-F | SO2Me | 3-CN—Ph |
| 2439 | 3-F | SO2Me | 3-COMe—Ph |
| 2440 | 3-F | SO2Me | 3-CO2Me—Ph |
| 2441 | 3-F | SO2Me | 3-CONH2—Ph |
| 2442 | 3-F | SO2Me | 3-CONHMe—Ph |
| 2443 | 3-F | SO2Me | 3-F—Ph |
| 2444 | 3-F | SO2Me | 3-Cl—Ph |
| 2445 | 3-F | SO2Me | 3-Br—Ph |
| 2446 | 3-F | SO2Me | 3-SO2NH2—Ph |
| 2447 | 3-F | SO2Me | 3-SO2NHMe—Ph |
| 2448 | 3-F | SO2Me | 3-CF3—Ph |
| 2449 | 3-F | SO2Me | 3-OMe—Ph |
| 2450 | 3-F | SO2Me | 3-SMe—Ph |
| 2451 | 3-F | SO2Me | 3-SOMe—Ph |
| 2452 | 3-F | SO2Me | 3-SO2Me—Ph |
| 2453 | 3-F | SO2Me | 3-OH—Ph |
| 2454 | 3-F | SO2Me | 3-CH2OH—Ph |
| 2455 | 3-F | SO2Me | 3-CHOHMe—Ph |
| 2456 | 3-F | SO2Me | 3-COH(Me)2—Ph |
| 2457 | 3-F | SO2Me | 3-Me—Ph |
| 2458 | 3-F | SO2Me | 3-Et—Ph |
| 2459 | 3-F | SO2Me | 3-iPr—Ph |
| 2460 | 3-F | SO2Me | 3-tBu—Ph |
| 2461 | 3-F | SO2Me | 3-CH2CO2Me—Ph |
| 2462 | 3-F | SO2Me | 3-(1-piperidinyl)-Ph |
| 2463 | 3-F | SO2Me | 3-(1-pyrrolidinyl)-Ph |
| 2464 | 3-F | SO2Me | 3-(2-imidazolyl)-Ph |
| 2465 | 3-F | SO2Me | 3-(1-imidazolyl)-Ph |
| 2466 | 3-F | SO2Me | 3-(2-thiazolyl)-Ph |
| 2467 | 3-F | SO2Me | 3-(3-pyrazolyl)-Ph |
| 2468 | 3-F | SO2Me | 3-(1-pyrazolyl)-Ph |
| 2469 | 3-F | SO2Me | 3-(5-Me-1-tetrazolyl)-Ph |

TABLE 2-continued

| | | | |
|---|---|---|---|
| 2470 | 3-F | SO2Me | 3-(1-Me-5-tetrazolyl)-Ph |
| 2471 | 3-F | SO2Me | 3-(2-pyridyl)-Ph |
| 2472 | 3-F | SO2Me | 3-(2-thienyl)-Ph |
| 2473 | 3-F | SO2Me | 3-(2-furanyl)-Ph |
| 2474 | 3-F | SO2Me | 4-CN—Ph |
| 2475 | 3-F | SO2Me | 4-COMe—Ph |
| 2476 | 3-F | SO2Me | 4-CO2Me—Ph |
| 2477 | 3-F | SO2Me | 4-CONH2—Ph |
| 2478 | 3-F | SO2Me | 4-CONHMe—Ph |
| 2479 | 3-F | SO2Me | 4-CONHPh—Ph |
| 2480 | 3-F | SO2Me | 4-F—Ph |
| 2481 | 3-F | SO2Me | 4-Cl—Ph |
| 2482 | 3-F | SO2Me | 4-Br—Ph |
| 2483 | 3-F | SO2Me | 4-SO2NH2—Ph |
| 2484 | 3-F | SO2Me | 4-SO2NHMe—Ph |
| 2485 | 3-F | SO2Me | 4-CF3—Ph |
| 2486 | 3-F | SO2Me | 4-OMe—Ph |
| 2487 | 3-F | SO2Me | 4-SMe—Ph |
| 2488 | 3-F | SO2Me | 4-SOMe—Ph |
| 2489 | 3-F | SO2Me | 4-SO2Me—Ph |
| 2490 | 3-F | SO2Me | 4-OH—Ph |
| 2491 | 3-F | SO2Me | 4-CH2OH—Ph |
| 2492 | 3-F | SO2Me | 4-CHOHMe—Ph |
| 2493 | 3-F | SO2Me | 4-COH(Me)2—Ph |
| 2494 | 3-F | SO2Me | 4-Me—Ph |
| 2495 | 3-F | SO2Me | 4-Et—Ph |
| 2496 | 3-F | SO2Me | 4-iPr—Ph |
| 2497 | 3-F | SO2Me | 4-tBu—Ph |
| 2498 | 3-F | SO2Me | 4-CH2CO2Me—Ph |
| 2499 | 3-F | SO2Me | 4-(1-piperidinyl)-Ph |
| 2500 | 3-F | SO2Me | 4-(1-pyrrolidinyl)-Ph |
| 2501 | 3-F | SO2Me | 4-(2-imidazolyl)-Ph |
| 2502 | 3-F | SO2Me | 4-(1-imidazolyl)-Ph |
| 2503 | 3-F | SO2Me | 4-(2-thiazolyl)-Ph |
| 2504 | 3-F | SO2Me | 4-(3-pyrazolyl)-Ph |
| 2505 | 3-F | SO2Me | 4-(1-pyrazolyl)-Ph |
| 2506 | 3-F | SO2Me | 4-(5-Me-1-tetrazolyl)-Ph |
| 2507 | 3-F | SO2Me | 4-(1-Me-5-tetrazolyl)-Ph |
| 2508 | 3-F | SO2Me | 4-(2-pyridyl)-Ph |
| 2509 | 3-F | SO2Me | 4-(2-thienyl)-Ph |
| 2510 | 3-F | SO2Me | 4-(2-furanyl)-Ph |
| 2511 | 3-F | SO2Me | 2-CN—Ph |
| 2512 | 3-F | SO2Me | 2-COMe—Ph |
| 2513 | 3-F | SO2Me | 2-CO2Me—Ph |
| 2514 | 3-F | SO2Me | 2-CONH2—Ph |
| 2515 | 3-F | SO2Me | 2-CONHMe—Ph |
| 2516 | 3-F | SO2Me | 2-F—Ph |
| 2517 | 3-F | SO2Me | 2-Cl—Ph |
| 2518 | 3-F | SO2Me | 2-Br—Ph |
| 2519 | 3-F | SO2Me | 2-SO2NH2—Ph |
| 2520 | 3-F | SO2Me | 2-SO2NHMe—Ph |
| 2521 | 3-F | SO2Me | 2-CF3—Ph |
| 2522 | 3-F | SO2Me | 2-OMe—Ph |
| 2523 | 3-F | SO2Me | 2-SMe—Ph |
| 2524 | 3-F | SO2Me | 2-SOMe—Ph |
| 2525 | 3-F | SO2Me | 2-SO2Me—Ph |
| 2526 | 3-F | SO2Me | 2-OH—Ph |
| 2527 | 3-F | SO2Me | 2-CH2OH—Ph |
| 2528 | 3-F | SO2Me | 2-CHOHMe—Ph |
| 2529 | 3-F | SO2Me | 2-COH(Me)2—Ph |
| 2530 | 3-F | SO2Me | 2-Me—Ph |
| 2531 | 3-F | SO2Me | 2-Et—Ph |
| 2532 | 3-F | SO2Me | 2-iPr—Ph |
| 2533 | 3-F | SO2Me | 2-tBu—Ph |
| 2534 | 3-F | SO2Me | 2-CH2CO2Me—Ph |
| 2535 | 3-F | SO2Me | 2-(1-piperidinyl)-Ph |
| 2536 | 3-F | SO2Me | 2-(1-pyrrolidinyl)-Ph |
| 2537 | 3-F | SO2Me | 2-(2-imidazolyl)-Ph |
| 2538 | 3-F | SO2Me | 2-(1-imidazolyl)-Ph |
| 2539 | 3-F | SO2Me | 2-(2-thiazolyl)-Ph |
| 2540 | 3-F | SO2Me | 2-(3-pyrazolyl)-Ph |
| 2541 | 3-F | SO2Me | 2-(1-pyrazolyl)-Ph |
| 2542 | 3-F | SO2Me | 2-(5-Me-1-tetrazolyl)-Ph |
| 2543 | 3-F | SO2Me | 2-(1-Me-5-tetrazolyl)-Ph |
| 2544 | 3-F | SO2Me | 2-(2-pyridyl)-Ph |
| 2545 | 3-F | SO2Me | 2-(2-thienyl)-Ph |
| 2546 | 3-F | SO2Me | 2-(2-furanyl)-Ph |
| 2547 | 3-F | SO2Me | 2,4-diF—Ph |
| 2548 | 3-F | SO2Me | 2,5-diF—Ph |
| 2549 | 3-F | SO2Me | 2,6-diF—Ph |
| 2550 | 3-F | SO2Me | 3,4-diF—Ph |
| 2551 | 3-F | SO2Me | 3,5-diF—Ph |
| 2552 | 3-F | SO2Me | 2,4-diCl—Ph |
| 2553 | 3-F | SO2Me | 2,5-diCl—Ph |
| 2554 | 3-F | SO2Me | 2,6-diCl—Ph |
| 2555 | 3-F | SO2Me | 3,4-diCl—Ph |
| 2556 | 3-F | SO2Me | 3,5-diCl—Ph |
| 2557 | 3-F | SO2Me | 3,4-diCF3—Ph |
| 2558 | 3-F | SO2Me | 3,5-diCF3—Ph |
| 2559 | 3-F | SO2Me | 5-Cl-2-MeO—Ph |
| 2560 | 3-F | SO2Me | 5-Cl-2-Me—Ph |
| 2561 | 3-F | SO2Me | 2-F-S-Me—Ph |
| 2562 | 3-F | SO2Me | 3-F-5-morpholino-Ph |
| 2563 | 3-F | SO2Me | 3,4-OCH2O—Ph |
| 2S64 | 3-F | SO2Me | 3,4-OCH2CH2O—Ph |
| 256S | 3-F | SO2Me | 2-MeO-5-CONH2—Ph |
| 2566 | 3-F | SO2Me | 2-MeO-4-(1-Me-5-tetrazolyl)-Ph |
| 2567 | 3-F | SO2Me | 2-MeO-5-(1-Me-5-tetrazolyl)-Ph |
| 2568 | 3-F | SO2Me | 3-CONH2-5-(1-Me-5-tetrazolyl)-Ph |
| 2569 | 3-F | SO2Me | 1-naphthyl |
| 2S70 | 3-F | SO2Me | 2-naphthyl |
| 2S71 | 3-F | SO2Me | 2-thienyl |
| 2S72 | 3-F | SO2Me | 3-thienyl |
| 2573 | 3-F | SO2Me | 2-furanyl |
| 2574 | 3-F | SO2Me | 3-furanyl |
| 2575 | 3-F | SO2Me | 2-pyridyl |
| 2S76 | 3-F | SO2Me | 3-pyridyl |
| 2577 | 3-F | SO2Me | 4-pyridyl |
| 2578 | 3-F | SO2Me | 2-indolyl |
| 2579 | 3-F | SO2Me | 3-indolyl |
| 2580 | 3-F | SO2Me | 5-indolyl |
| 2581 | 3-F | SO2Me | 6-indolyl |
| 2582 | 3-F | SO2Me | 3-indazolyl |
| 2583 | 3-F | SO2Me | 5-indazolyl |
| 2584 | 3-F | SO2Me | 6-indazolyl |
| 2S8S | 3-F | SO2Me | 2-imidazolyl |
| 2S86 | 3-F | SO2Me | 3-isoxazoyl |
| 2587 | 3-F | SO2Me | 3-pyrazolyl |
| 2588 | 3-F | SO2Me | 2-thiadiazolyl |
| 2S89 | 3-F | SO2Me | 2-thiazolyl |
| 2590 | 3-F | SO2Me | 5-Ac-4-Me-2-thiazolyl |
| 2591 | 3-F | SO2Me | 5-tetrazolyl |
| 2592 | 3-F | SO2Me | 2-benzimidazolyl |
| 2593 | 3-F | SO2Me | 5-benzimidazolyl |
| 2594 | 3-F | SO2Me | 2-benzothiazolyl |
| 2595 | 3-F | SO2Me | 5-benzothiazolyl |
| 2596 | 3-F | SO2Me | 2-benzoxazolyl |
| 2597 | 3-F | SO2Me | 5-benzoxazolyl |
| 2598 | 3-F | SO2Me | 1-adamantyl |
| 2599 | 3-F | SO2Me | 2-adamantyl |
| 2600 | 3-F | SO2Me | i-Pr |
| 2601 | 3-F | SO2Me | t-Bu |
| 2602 | 3-F | SO2Me | c-Hex |
| 2603 | 3-F | SO2Me | CH2CH2OMe |
| 2604 | 3-F | SO2Me | CH2CONH2 |
| 2605 | 3-F | SO2Me | CH2CO2Me |
| 2606 | 3-F | SO2Me | CH(CH2Ph)CO2Me |
| 2607 | 3-F | SO2Me | CH2CH2NMe2 |
| 2608 | 3-F | SO2Me | benzyl |
| 2609 | 3-F | SO2Me | phenethyl |
| 2610 | 3-F | SO2Me | 2-(morpholin-1-yl)-Et |
| 2611 | 3-F | CH2COMe | Ph |
| 2612 | 3-F | CH2COMe | 3-CN—Ph |
| 2613 | 3-F | CH2COMe | 3-COMe—Ph |
| 2614 | 3-F | CH2COMe | 3-CO2Me—Ph |
| 2615 | 3-F | CH2COMe | 3-CONH2—Ph |
| 2616 | 3-F | CH2COMe | 3-CONHMe—Ph |
| 2617 | 3-F | CH2COMe | 3-F—Ph |
| 2618 | 3-F | CH2COMe | 3-Cl—Ph |
| 2619 | 3-F | CH2COMe | 3-Br—Ph |
| 2620 | 3-F | CH2COMe | 3-SO2NH2—Ph |
| 2621 | 3-F | CH2COMe | 3-SO2NHMe—Ph |
| 2622 | 3-F | CH2COMe | 3-CF3—Ph |
| 2623 | 3-F | CH2COMe | 3-OMe—Ph |
| 2624 | 3-F | CH2COMe | 3-SMe—Ph |
| 2625 | 3-F | CH2COMe | 3-SOMe—Ph |
| 2626 | 3-F | CH2COMe | 3-SO2Me—Ph |
| 2627 | 3-F | CH2COMe | 3-OH—Ph |

TABLE 2-continued

| | | | |
|---|---|---|---|
| 2628 | 3-F | CH2COMe | 3-CH2OH—Ph |
| 2629 | 3-F | CH2COMe | 3-CHOHMe—Ph |
| 2630 | 3-F | CH2COMe | 3-COH(Me)2—Ph |
| 2631 | 3-F | CH2COMe | 3-Me—Ph |
| 2632 | 3-F | CH2COMe | 3-Et—Ph |
| 2633 | 3-F | CH2COMe | 3-iPr—Ph |
| 2634 | 3-F | CH2COMe | 3-tBu—Ph |
| 2635 | 3-F | CH2COMe | 3-CH2CO2Me—Ph |
| 2636 | 3-F | CH2COMe | 3-(1-piperidinyl)-Ph |
| 2637 | 3-F | CH2COMe | 3-(1-pyrrolidinyl)-Ph |
| 2638 | 3-F | CH2COMe | 3-(2-imidazolyl)-Ph |
| 2639 | 3-F | CH2COMe | 3-(1-imidazolyl)-Ph |
| 2640 | 3-F | CH2COMe | 3-(2-thiazolyl)-Ph |
| 2641 | 3-F | CH2COMe | 3-(3-pyrazolyl)-Ph |
| 2642 | 3-F | CH2COMe | 3-(1-pyrazolyl)-Ph |
| 2643 | 3-F | CH2COMe | 3-(5-Me-1-tetrazolyl)-Ph |
| 2644 | 3-F | CH2COMe | 3-(1-Me-5-tetrazolyl)-Ph |
| 2645 | 3-F | CH2COMe | 3-(2-pyridyl)-Ph |
| 2646 | 3-F | CH2COMe | 3-(2-thienyl)-Ph |
| 2647 | 3-F | CH2COMe | 3-(2-furanyl)-Ph |
| 2648 | 3-F | CH2COMe | 4-CN—Ph |
| 2649 | 3-F | CH2COMe | 4-COMe—Ph |
| 2650 | 3-F | CH2COMe | 4-CO2Me—Ph |
| 2651 | 3-F | CH2COMe | 4-CONH2—Ph |
| 2652 | 3-F | CH2COMe | 4-CONHMe—Ph |
| 2653 | 3-F | CH2COMe | 4-CONHPh—Ph |
| 2654 | 3-F | CH2COMe | 4-F—Ph |
| 2655 | 3-F | CH2COMe | 4-Cl—Ph |
| 2656 | 3-F | CH2COMe | 4-Br—Ph |
| 2657 | 3-F | CH2COMe | 4-SO2NH2—Ph |
| 2658 | 3-F | CH2COMe | 4-SO2NHMe—Ph |
| 2659 | 3-F | CH2COMe | 4-CF3—Ph |
| 2660 | 3-F | CH2COMe | 4-OMe—Ph |
| 2661 | 3-F | CH2COMe | 4-SMe—Ph |
| 2662 | 3-F | CH2COMe | 4-SOMe—Ph |
| 2663 | 3-F | CH2COMe | 4-SO2Me—Ph |
| 2664 | 3-F | CH2COMe | 4-OH—Ph |
| 2665 | 3-F | CH2COMe | 4-CH2OH—Ph |
| 2666 | 3-F | CH2COMe | 4-CHOHMe—Ph |
| 2667 | 3-F | CH2COMe | 4-COH(Me)2—Ph |
| 2668 | 3-F | CH2COMe | 4-Me—Ph |
| 2669 | 3-F | CH2COMe | 4-Et—Ph |
| 2670 | 3-F | CH2COMe | 4-iPr—Ph |
| 2671 | 3-F | CH2COMe | 4-tBu—Ph |
| 2672 | 3-F | CH2COMe | 4-CH2CO2Me—Ph |
| 2673 | 3-F | CH2COMe | 4-(1-piperidinyl)-Ph |
| 2674 | 3-F | CH2COMe | 4-(1-pyrrolidinyl)-Ph |
| 2675 | 3-F | CH2COMe | 4-(2-imidazolyl)-Ph |
| 2676 | 3-F | CH2COMe | 4-(1-imidazolyl)-Ph |
| 2677 | 3-F | CH2COMe | 4-(2-thiazolyl)-Ph |
| 2678 | 3-F | CH2COMe | 4-(3-pyrazolyl)-Ph |
| 2679 | 3-F | CH2COMe | 4-(1-pyrazolyl)-Ph |
| 2680 | 3-F | CH2COMe | 4-(5-Me-1-tetrazolyl)-Ph |
| 2681 | 3-F | CH2COMe | 4-(1-Me-5-tetrazolyl)-Ph |
| 2682 | 3-F | CH2COMe | 4-(2-pyridyl)-Ph |
| 2683 | 3-F | CH2COMe | 4-(2-thienyl)-Ph |
| 2684 | 3-F | CH2COMe | 4-(2-furanyl)-Ph |
| 2685 | 3-F | CH2COMe | 2-CN—Ph |
| 2686 | 3-F | CH2COMe | 2-COMe—Ph |
| 2687 | 3-F | CH2COMe | 2-CO2Me—Ph |
| 2688 | 3-F | CH2COMe | 2-CONH2—Ph |
| 2689 | 3-F | CH2COMe | 2-CONHMe—Ph |
| 2690 | 3-F | CH2COMe | 2-F—Ph |
| 2691 | 3-F | CH2COMe | 2-Cl—Ph |
| 2692 | 3-F | CH2COMe | 2-Br—Ph |
| 2693 | 3-F | CH2COMe | 2-SO2NH2—Ph |
| 2694 | 3-F | CH2COMe | 2-SO2NHMe—Ph |
| 2695 | 3-F | CH2COMe | 2-CF3—Ph |
| 2696 | 3-F | CH2COMe | 2-OMe—Ph |
| 2697 | 3-F | CH2COMe | 2-SMe—Ph |
| 2698 | 3-F | CH2COMe | 2-SOMe—Ph |
| 2699 | 3-F | CH2COMe | 2-SO2Me—Ph |
| 2700 | 3-F | CH2COMe | 2-OH—Ph |
| 2701 | 3-F | CH2COMe | 2-CH2OH—Ph |
| 2702 | 3-F | CH2COMe | 2-CHOHMe—Ph |
| 2703 | 3-F | CH2COMe | 2-COH(Me)2—Ph |
| 2704 | 3-F | CH2COMe | 2-Me—Ph |
| 2705 | 3-F | CH2COMe | 2-Et—Ph |
| 2706 | 3-F | CH2COMe | 2-iPr—Ph |
| 2707 | 3-F | CH2COMe | 2-tBu—Ph |
| 2703 | 3-F | CH2COMe | 2-CH2CO2Me—Ph |
| 2709 | 3-F | CH2COMe | 2-(1-piperidinyl)-Ph |
| 2710 | 3-F | CH2COMe | 2-(1-pyrrolidinyl)-Ph |
| 2711 | 3-F | CH2COMe | 2-(2-imidazolyl)-Ph |
| 2712 | 3-F | CH2COMe | 2-(1-imidazolyl)-Ph |
| 2713 | 3-F | CH2COMe | 2-(2-thiazolyl)-Ph |
| 2714 | 3-F | CH2COMe | 2-(3-pyrazolyl)-Ph |
| 2715 | 3-F | CH2COMe | 2-(1-pyrazolyl)-Ph |
| 2716 | 3-F | CH2COMe | 2-(5-Me-1-tetrazolyl)-Ph |
| 2717 | 3-F | CH2COMe | 2-(1-Me-5-tetrazolyl)-Ph |
| 2718 | 3-F | CH2COMe | 2-(2-pyridyl)-Ph |
| 2719 | 3-F | CH2COMe | 2-(2-thienyl)-Ph |
| 2720 | 3-F | CH2COMe | 2-(2-furanyl)-Ph |
| 2721 | 3-F | CH2COMe | 2,4-diF—Ph |
| 2722 | 3-F | CH2COMe | 2,5-diF—Ph |
| 2723 | 3-F | CH2COMe | 2,6-diF—Ph |
| 2724 | 3-F | CH2COMe | 3,4-diF—Ph |
| 2725 | 3-F | CH2COMe | 3,5-diF—Ph |
| 2726 | 3-F | CH2COMe | 2,4-diCl—Ph |
| 2727 | 3-F | CH2COMe | 2,5-diCl—Ph |
| 2728 | 3-F | CH2COMe | 2,6-diCl—Ph |
| 2729 | 3-F | CH2COMe | 3,4-diCl—Ph |
| 2730 | 3-F | CH2COMe | 3,5-diCl—Ph |
| 2731 | 3-F | CH2COMe | 3,4-diCF3—Ph |
| 2732 | 3-F | CH2COMe | 3,5-diCF3—Ph |
| 2733 | 3-F | CH2COMe | 5-Cl-2-MeO—Ph |
| 2734 | 3-F | CH2COMe | 5-Cl-2-Me—Ph |
| 2735 | 3-F | CH2COMe | 2-F-5-Me—Ph |
| 2736 | 3-F | CH2COMe | 3-F-5-morpholino-Ph |
| 2737 | 3-F | CH2COMe | 3,4-OCH2O—Ph |
| 2738 | 3-F | CH2COMe | 3,4-OCH2CH2O—Ph |
| 2739 | 3-F | CH2COMe | 2-MeO-5-CONH2—Ph |
| 2740 | 3-F | CH2COMe | 2-MeO-4-(1-Me-5-tetrazolyl)-Ph |
| 2741 | 3-F | CH2COMe | 2-MeO-5-(1-Me-5-tetrazolyl)-Ph |
| 2742 | 3-F | CH2COMe | 3-CONH2-5-(1-Me-5-tetrazolyl)-Ph |
| 2743 | 3-F | CH2COMe | 1-naphthyl |
| 2744 | 3-F | CH2COMe | 2-naphthyl |
| 2745 | 3-F | CH2COMe | 2-thienyl |
| 2746 | 3-F | CH2COMe | 3-thienyl |
| 2747 | 3-F | CH2COMe | 2-furanyl |
| 2748 | 3-F | CH2COMe | 3-furanyl |
| 2749 | 3-F | CH2COMe | 2-pyridyl |
| 2750 | 3-F | CH2COMe | 3-pyridyl |
| 2751 | 3-F | CH2COMe | 4-pyridyl |
| 2752 | 3-F | CH2COMe | 2-indolyl |
| 2753 | 3-F | CH2COMe | 3-indolyl |
| 2754 | 3-F | CH2COMe | 5-indolyl |
| 2755 | 3-F | CH2COMe | 6-indolyl |
| 2756 | 3-F | CH2COMe | 3-indazolyl |
| 2757 | 3-F | CH2COMe | 5-indazolyl |
| 2758 | 3-F | CH2COMe | 6-indazolyl |
| 2759 | 3-F | CH2COMe | 2-imidazolyl |
| 2760 | 3-F | CH2COMe | 3-isoxazoyl |
| 2761 | 3-F | CH2COMe | 3-pyrazolyl |
| 2762 | 3-F | CH2COMe | 2-thiadiazolyl |
| 2763 | 3-F | CH2COMe | 2-thiazolyl |
| 2764 | 3-F | CH2COMe | 5-Ac-4-Me-2-thiazolyl |
| 2765 | 3-F | CH2COMe | 5-tetrazolyl |
| 2766 | 3-F | CH2COMe | 2-benzimidazolyl |
| 2767 | 3-F | CH2COMe | 5-benzimidazolyl |
| 2768 | 3-F | CH2COMe | 2-benzothiazolyl |
| 2769 | 3-F | CH2COMe | 5-benzothiazolyl |
| 2770 | 3-F | CH2COMe | 2-benzoxazolyl |
| 2771 | 3-F | CH2COMe | 5-benzoxazolyl |
| 2772 | 3-F | CH2COMe | 1-adamantyl |
| 2773 | 3-F | CH2COMe | 2-adamantyl |
| 2774 | 3-F | CH2COMe | i-Pr |
| 2775 | 3-F | CH2COMe | t-Bu |
| 2776 | 3-F | CH2COMe | c-Hex |
| 2777 | 3-F | CH2COMe | CH2CH2OMe |
| 2778 | 3-F | CH2COMe | CH2CONH2 |
| 2779 | 3-F | CH2COMe | CH2CO2Me |
| 2780 | 3-F | CH2COMe | CH(CH2Ph)CO2Me |
| 2781 | 3-F | CH2COMe | CH2CH2NMe2 |
| 2782 | 3-F | CH2COMe | benzyl |
| 2783 | 3-F | CH2COMe | phenethyl |
| 2784 | 3-F | CH2COMe | 2-(morpholin-1-yl)-Et |
| 2785 | 4-F | H | Ph |

TABLE 2-continued

| | | | |
|---|---|---|---|
| 2786 | 4-F | H | 3-CN—Ph |
| 2787 | 4-F | H | 3-COMe—Ph |
| 2788 | 4-F | H | 3-CO2Me—Ph |
| 2789 | 4-F | H | 3-CONH2—Ph |
| 2790 | 4-F | H | 3-CONHMe—Ph |
| 2791 | 4-F | H | 3-F—Ph |
| 2792 | 4-F | H | 3-Cl—Ph |
| 2793 | 4-F | H | 3-Br—Ph |
| 2794 | 4-F | H | 3-SO2NH2—Ph |
| 2795 | 4-F | H | 3-SO2NHMe—Ph |
| 2796 | 4-F | H | 3-CF3—Ph |
| 2797 | 4-F | H | 3-OMe—Ph |
| 2798 | 4-F | H | 3-SMe—Ph |
| 2799 | 4-F | H | 3-SOMe—Ph |
| 2800 | 4-F | H | 3-SO2Me—Ph |
| 2801 | 4-F | H | 3-OH—Ph |
| 2802 | 4-F | H | 3-CH2OH—Ph |
| 2803 | 4-F | H | 3-CHOHMe—Ph |
| 2804 | 4-F | H | 3-COH(Me)2—Ph |
| 2805 | 4-F | H | 3-Me—Ph |
| 2806 | 4-F | H | 3-Et—Ph |
| 2807 | 4-F | H | 3-iPr—Ph |
| 2808 | 4-F | H | 3-tBu—Ph |
| 2809 | 4-F | H | 3-CH2CO2Me—Ph |
| 2810 | 4-F | H | 3-(1-piperidinyl)-Ph |
| 2811 | 4-F | H | 3-(1-pyrrolidinyl)-Ph |
| 2812 | 4-F | H | 3-(2-imidazolyl)-Ph |
| 2813 | 4-F | H | 3-(1-imidazolyl)-Ph |
| 2814 | 4-F | H | 3-(2-thiazolyl)-Ph |
| 2815 | 4-F | H | 3-(3-pyrazolyl)-Ph |
| 2816 | 4-F | H | 3-(1-pyrazolyl)-Ph |
| 2817 | 4-F | H | 3-(5-Me-1-tetrazolyl)-Ph |
| 2818 | 4-F | H | 3-(1-Me-5-tetrazolyl)-Ph |
| 2819 | 4-F | H | 3-(2-pyridyl)-Ph |
| 2820 | 4-F | H | 3-(2-thienyl)-Ph |
| 2821 | 4-F | H | 3-(2-furanyl)-Ph |
| 2822 | 4-F | H | 4-CN—Ph |
| 2823 | 4-F | H | 4-COMe—Ph |
| 2824 | 4-F | H | 4-CO2Me—Ph |
| 2825 | 4-F | H | 4-CONH2—Ph |
| 2826 | 4-F | H | 4-CONHMe—Ph |
| 2827 | 4-F | H | 4-CONHPh—Ph |
| 2828 | 4-F | H | 4-F—Ph |
| 2829 | 4-F | H | 4-Cl—Ph |
| 2830 | 4-F | H | 4-Br—Ph |
| 2831 | 4-F | H | 4-SO2NH2—Ph |
| 2832 | 4-F | H | 4-SO2NHMe—Ph |
| 2833 | 4-F | H | 4-CF3—Ph |
| 2834 | 4-F | H | 4-OMe—Ph |
| 2835 | 4-F | H | 4-SMe—Ph |
| 2836 | 4-F | H | 4-SOMe—Ph |
| 2837 | 4-F | H | 4-SO2Me—Ph |
| 2838 | 4-F | H | 4-OH—Ph |
| 2839 | 4-F | H | 4-CH2OH—Ph |
| 2840 | 4-F | H | 4-CHOHMe—Ph |
| 2841 | 4-F | H | 4-COH(Me)2—Ph |
| 2842 | 4-F | H | 4-Me—Ph |
| 2843 | 4-F | H | 4-Et—Ph |
| 2844 | 4-F | H | 4-iPr—Ph |
| 2845 | 4-F | H | 4-tBu—Ph |
| 2846 | 4-F | H | 4-CH2CO2Me—Ph |
| 2847 | 4-F | H | 4-(1-piperidinyl)-Ph |
| 2848 | 4-F | H | 4-(1-pyrrolidinyl)-Ph |
| 2849 | 4-F | H | 4-(2-imidazolyl)-Ph |
| 2850 | 4-F | H | 4-(1-imidazolyl)-Ph |
| 2851 | 4-F | H | 4-(2-thiazolyl)-Ph |
| 2852 | 4-F | H | 4-(3-pyrazolyl)-Ph |
| 2853 | 4-F | H | 4-(1-pyrazolyl)-Ph |
| 2854 | 4-F | H | 4-(5-Me-1-tetrazolyl)-Ph |
| 2855 | 4-F | H | 4-(1-Me-5-tetrazolyl)-Ph |
| 2856 | 4-F | H | 4-(2-pyridyl)-Ph |
| 2857 | 4-F | H | 4-(2-thienyl)-Ph |
| 2858 | 4-F | H | 4-(2-furanyl)-Ph |
| 2859 | 4-F | H | 2-CN—Ph |
| 2860 | 4-F | H | 2-COMe—Ph |
| 2861 | 4-F | H | 2-CO2Me—Ph |
| 2862 | 4-F | H | 2-CONH2—Ph |
| 2863 | 4-F | H | 2-CONHMe—Ph |
| 2864 | 4-F | H | 2-F—Ph |
| 2865 | 4-F | H | 2-Cl—Ph |
| 2866 | 4-F | H | 2-Br—Ph |
| 2867 | 4-F | H | 2-SO2NH2—Ph |
| 2868 | 4-F | H | 2-SO2NHMe—Ph |
| 2869 | 4-F | H | 2-CF3—Ph |
| 2870 | 4-F | H | 2-OMe—Ph |
| 2871 | 4-F | H | 2-SMe—Ph |
| 2872 | 4-F | H | 2-SOMe—Ph |
| 2873 | 4-F | H | 2-SO2Me—Ph |
| 2874 | 4-F | H | 2-OH—Ph |
| 2875 | 4-F | H | 2-CH2OH—Ph |
| 2876 | 4-F | H | 2-CHOHMe—Ph |
| 2877 | 4-F | H | 2-COH(Me)2—Ph |
| 2878 | 4-F | H | 2-Me—Ph |
| 2879 | 4-F | H | 2-Et—Ph |
| 2880 | 4-F | H | 2-iPr—Ph |
| 2881 | 4-F | H | 2-tBu—Ph |
| 2882 | 4-F | H | 2-CH2CO2Me—Ph |
| 2883 | 4-F | H | 2-(1-piperidinyl)-Ph |
| 2884 | 4-F | H | 2-(1-pyrrolidinyl)-Ph |
| 2885 | 4-F | H | 2-(2-imidazolyl)-Ph |
| 2886 | 4-F | H | 2-(1-imidazolyl)-Ph |
| 2887 | 4-F | H | 2-(2-thiazolyl)-Ph |
| 2888 | 4-F | H | 2-(3-pyrazolyl)-Ph |
| 2889 | 4-F | H | 2-(1-pyrazolyl)-Ph |
| 2890 | 4-F | H | 2-(5-Me-1-tetrazolyl)-Ph |
| 2891 | 4-F | H | 2-(1-Me-5-tetrazolyl)-Ph |
| 2892 | 4-F | H | 2-(2-pyridyl)-Ph |
| 2893 | 4-F | H | 2-(2-thienyl)-Ph |
| 2894 | 4-F | H | 2-(2-furanyl)-Ph |
| 2895 | 4-F | H | 2,4-diF—Ph |
| 2896 | 4-F | H | 2,5-diF—Ph |
| 2897 | 4-F | H | 2,6-diF—Ph |
| 2898 | 4-F | H | 3,4-diF—Ph |
| 2899 | 4-F | H | 3,5-diF—Ph |
| 2900 | 4-F | H | 2,4-diCl—Ph |
| 2901 | 4-F | H | 2,5-diCl—Ph |
| 2902 | 4-F | H | 2,6-diCl—Ph |
| 2903 | 4-F | H | 3,4-diCl—Ph |
| 2904 | 4-F | H | 3,5-diCl—Ph |
| 2905 | 4-F | H | 3,4-diCF3—Ph |
| 2906 | 4-F | H | 3,5-diCF3—Ph |
| 2907 | 4-F | H | 5-Cl-2-MeO—Ph |
| 2908 | 4-F | H | 5-Cl-2-Me—Ph |
| 2909 | 4-F | H | 2-F-5-Me—Ph |
| 2910 | 4-F | H | 3-F-5-morpholino-Ph |
| 2911 | 4-F | H | 3,4-OCH2O—Ph |
| 2912 | 4-F | H | 3,4-OCH2CH2O—Ph |
| 2913 | 4-F | H | 2-MeO-5-CONH2—Ph |
| 2914 | 4-F | H | 2-MeO-4-(1-Me-5-tetrazolyl)-Ph |
| 2915 | 4-F | H | 2-MeO-5-(1-Me-5-tetrazolyl)-Ph |
| 2916 | 4-F | H | 3-CONH2-5-(1-Me-5-tetrazolyl)-Ph |
| 2917 | 4-F | H | 1-naphthyl |
| 2918 | 4-F | H | 2-naphthyl |
| 2919 | 4-F | H | 2-thienyl |
| 2920 | 4-F | H | 3-thienyl |
| 2921 | 4-F | H | 2-furanyl |
| 2922 | 4-F | H | 3-furanyl |
| 2923 | 4-F | H | 2-pyridyl |
| 2924 | 4-F | H | 3-pyridyl |
| 2925 | 4-F | H | 4-pyridyl |
| 2926 | 4-F | H | 2-indolyl |
| 2927 | 4-F | H | 3-indolyl |
| 2928 | 4-F | H | 5-indolyl |
| 2929 | 4-F | H | 6-indolyl |
| 2930 | 4-F | H | 3-indazolyl |
| 2931 | 4-F | H | 5-indazolyl |
| 2932 | 4-F | H | 6-indazolyl |
| 2933 | 4-F | H | 2-imidazolyl |
| 2934 | 4-F | H | 3-isoxazoyl |
| 2935 | 4-F | H | 3-pyrazolyl |
| 2936 | 4-F | H | 2-thiadiazolyl |
| 2937 | 4-F | H | 2-thiazolyl |
| 2938 | 4-F | H | 5-Ac-4-Me-2-thiazolyl |
| 2939 | 4-F | H | 5-tetrazolyl |
| 2940 | 4-F | H | 2-benzimidazolyl |
| 2941 | 4-F | H | 5-benzimidazolyl |
| 2942 | 4-F | H | 2-benzothiazolyl |
| 2943 | 4-F | H | 5-benzothiazolyl |

TABLE 2-continued

| | | | |
|---|---|---|---|
| 2944 | 4-F | H | 2-benzoxazolyl |
| 2945 | 4-F | H | 5-benzoxazolyl |
| 2946 | 4-F | H | 1-adamantyl |
| 2947 | 4-F | H | 2-adamantyl |
| 2948 | 4-F | H | i-Pr |
| 2949 | 4-F | H | t-Bu |
| 2950 | 4-F | H | c-Hex |
| 2951 | 4-F | H | CH2CH2OMe |
| 2952 | 4-F | H | CH2CONH2 |
| 2953 | 4-F | H | CH2CO2Me |
| 2954 | 4-F | H | CH(CH2Ph)CO2Me |
| 2955 | 4-F | H | CH2CH2NMe2 |
| 2956 | 4-F | H | benzyl |
| 2957 | 4-F | H | phenethyl |
| 2958 | 4-F | H | 2-(morpholin-1-yl)-Et |
| 2959 | 4-F | Me | Ph |
| 2960 | 4-F | Me | 3-CN—Ph |
| 2961 | 4-F | Me | 3-COMe—Ph |
| 2962 | 4-F | Me | 3-CO2Me—Ph |
| 2963 | 4-F | Me | 3-CONH2—Ph |
| 2964 | 4-F | Me | 3-CONHMe—Ph |
| 2965 | 4-F | Me | 3-F—Ph |
| 2966 | 4-F | Me | 3-Cl—Ph |
| 2967 | 4-F | Me | 3-Br—Ph |
| 2968 | 4-F | Me | 3-SO2NH2—Ph |
| 2969 | 4-F | Me | 3-SO2NHMe—Ph |
| 2970 | 4-F | Me | 3-CF3—Ph |
| 2971 | 4-F | Me | 3-OMe—Ph |
| 2972 | 4-F | Me | 3-SMe—Ph |
| 2973 | 4-F | Me | 3-SOMe—Ph |
| 2974 | 4-F | Me | 3-SO2Me—Ph |
| 2975 | 4-F | Me | 3-OH—Ph |
| 2976 | 4-F | Me | 3-CH2OH—Ph |
| 2977 | 4-F | Me | 3-CHOHMe—Ph |
| 2978 | 4-F | Me | 3-COH(Me)2—Ph |
| 2979 | 4-F | Me | 3-Me—Ph |
| 2980 | 4-F | Me | 3-Et—Ph |
| 2981 | 4-F | Me | 3-iPr—Ph |
| 2982 | 4-F | Me | 3-tBu—Ph |
| 2983 | 4-F | Me | 3-CH2CO2Me—Ph |
| 2984 | 4-F | Me | 3-(1-piperidinyl)-Ph |
| 2985 | 4-F | Me | 3-(1-pyrrolidinyl)-Ph |
| 2986 | 4-F | Me | 3-(2-imidazolyl)-Ph |
| 2987 | 4-F | Me | 3-(1-imidazolyl)-Ph |
| 2988 | 4-F | Me | 3-(2-thiazolyl)-Ph |
| 2989 | 4-F | Me | 3-(3-pyrazolyl)-Ph |
| 2990 | 4-F | Me | 3-(1-pyrazolyl)-Ph |
| 2991 | 4-F | Me | 3-(5-Me-1-tetrazolyl)-Ph |
| 2992 | 4-F | Me | 3-(1-Me-5-tetrazolyl)-Ph |
| 2993 | 4-F | Me | 3-(2-pyridyl)-Ph |
| 2994 | 4-F | Me | 3-(2-thienyl)-Ph |
| 2995 | 4-F | Me | 3-(2-furanyl)-Ph |
| 2996 | 4-F | Me | 4-CN—Ph |
| 2997 | 4-F | Me | 4-COMe—Ph |
| 2998 | 4-F | Me | 4-CO2Me—Ph |
| 2999 | 4-F | Me | 4-CONH2—Ph |
| 3000 | 4-F | Me | 4-CONHMe—Ph |
| 3001 | 4-F | Me | 4-CONHPh—Ph |
| 3002 | 4-F | Me | 4-F—Ph |
| 3003 | 4-F | Me | 4-Cl—Ph |
| 3004 | 4-F | Me | 4-Br—Ph |
| 3005 | 4-F | Me | 4-SO2NH2—Ph |
| 3006 | 4-F | Me | 4-SO2NHMe—Ph |
| 3007 | 4-F | Me | 4-CF3—Ph |
| 3008 | 4-F | Me | 4-OMe—Ph |
| 3009 | 4-F | Me | 4-SMe—Ph |
| 3010 | 4-F | Me | 4-SOMe—Ph |
| 3011 | 4-F | Me | 4-SO2Me—Ph |
| 3012 | 4-F | Me | 4-OH—Ph |
| 3013 | 4-F | Me | 4-CH2OH—Ph |
| 3014 | 4-F | Me | 4-CHOHMe—Ph |
| 3015 | 4-F | Me | 4-COH(Me)2—Ph |
| 3016 | 4-F | Me | 4-Me—Ph |
| 3017 | 4-F | Me | 4-Et—Ph |
| 3018 | 4-F | Me | 4-iPr—Ph |
| 3019 | 4-F | Me | 4-tBu—Ph |
| 3020 | 4-F | Me | 4-CH2CO2Me—Ph |
| 3021 | 4-F | Me | 4-(1-piperidinyl)-Ph |
| 3022 | 4-F | Me | 4-(1-pyrrolidinyl)-Ph |
| 3023 | 4-F | Me | 4-(2-imidazolyl)-Ph |
| 3024 | 4-F | Me | 4-(1-imidazolyl)-Ph |
| 3025 | 4-F | Me | 4-(2-thiazolyl)-Ph |
| 3026 | 4-F | Me | 4-(3-pyrazolyl)-Ph |
| 3027 | 4-F | Me | 4-(1-pyrazolyl)-Ph |
| 3028 | 4-F | Me | 4-(5-Me-1-tetrazolyl)-Ph |
| 3029 | 4-F | Me | 4-(1-Me-5-tetrazolyl)-Ph |
| 3030 | 4-F | Me | 4-(2-pyridyl)-Ph |
| 3031 | 4-F | Me | 4-(2-thienyl)-Ph |
| 3032 | 4-F | Me | 4-(2-furanyl)-Ph |
| 3033 | 4-F | Me | 2-CN—Ph |
| 3034 | 4-F | Me | 2-COMe—Ph |
| 3035 | 4-F | Me | 2-CO2Me—Ph |
| 3036 | 4-F | Me | 2-CONH2—Ph |
| 3037 | 4-F | Me | 2-CONHMe—Ph |
| 3038 | 4-F | Me | 2-F—Ph |
| 3039 | 4-F | Me | 2-Cl—Ph |
| 3040 | 4-F | Me | 2-Br—Ph |
| 3041 | 4-F | Me | 2-SO2NH2—Ph |
| 3042 | 4-F | Me | 2-SO2NHMe—Ph |
| 3043 | 4-F | Me | 2-CF3—Ph |
| 3044 | 4-F | Me | 2-OMe—Ph |
| 3045 | 4-F | Me | 2-SMe—Ph |
| 3046 | 4-F | Me | 2-SOMe—Ph |
| 3047 | 4-F | Me | 2-SO2Me—Ph |
| 3048 | 4-F | Me | 2-OH—Ph |
| 3049 | 4-F | Me | 2-CH2OH—Ph |
| 3050 | 4-F | Me | 2-CHOHMe—Ph |
| 3051 | 4-F | Me | 2-COH(Me)2—Ph |
| 3052 | 4-F | Me | 2-Me—Ph |
| 3053 | 4-F | Me | 2-Et—Ph |
| 3054 | 4-F | Me | 2-iPr—Ph |
| 3055 | 4-F | Me | 2-tBu—Ph |
| 3056 | 4-F | Me | 2-CH2CO2Me—Ph |
| 3057 | 4-F | Me | 2-(1-piperidinyl)-Ph |
| 3058 | 4-F | Me | 2-(1-pyrrolidinyl)-Ph |
| 3059 | 4-F | Me | 2-(2-imidazolyl)-Ph |
| 3060 | 4-F | Me | 2-(1-imidazolyl)-Ph |
| 3061 | 4-F | Me | 2-(2-thiazolyl)-Ph |
| 3062 | 4-F | Me | 2-(3-pyrazolyl)-Ph |
| 3063 | 4-F | Me | 2-(1-pyrazolyl)-Ph |
| 3064 | 4-F | Me | 2-(5-Me-1-tetrazolyl)-Ph |
| 3065 | 4-F | Me | 2-(1-Me-5-tetrazolyl)-Ph |
| 3066 | 4-F | Me | 2-(2-pyridyl)-Ph |
| 3067 | 4-F | Me | 2-(2-thienyl)-Ph |
| 3068 | 4-F | Me | 2-(2-furanyl)-Ph |
| 3069 | 4-F | Me | 2,4-diF—Ph |
| 3070 | 4-F | Me | 2,5-diF—Ph |
| 3071 | 4-F | Me | 2,6-diF—Ph |
| 3072 | 4-F | Me | 3,4-diF—Ph |
| 3073 | 4-F | Me | 3,5-diF—Ph |
| 3074 | 4-F | Me | 2,4-diCl—Ph |
| 3075 | 4-F | Me | 2,5-diCl—Ph |
| 3076 | 4-F | Me | 2,6-diCl—Ph |
| 3077 | 4-F | Me | 3,4-diCl—Ph |
| 3078 | 4-F | Me | 3,5-diCl—Ph |
| 3079 | 4-F | Me | 3,4-diCF3—Ph |
| 3080 | 4-F | Me | 3,5-diCF3—Ph |
| 3081 | 4-F | Me | 5-Cl-2-MeO—Ph |
| 3082 | 4-F | Me | 5-Cl-2-Me—Ph |
| 3083 | 4-F | Me | 2-F-5-Me—Ph |
| 3084 | 4-F | Me | 3-F-5-morpholino-Ph |
| 3085 | 4-F | Me | 3,4-OCH2O—Ph |
| 3086 | 4-F | Me | 3,4-OCH2CH2O—Ph |
| 3087 | 4-F | Me | 2-MeO-5-CONH2—Ph |
| 3083 | 4-F | Me | 2-MeO-4-(1-Me-5-tetrazolyl)-Ph |
| 3089 | 4-F | Me | 2-MeO-5-(1-Me-5-tetrazolyl)-Ph |
| 3090 | 4-F | Me | 3-CONH2-5-(1-Me-5-tetrazolyl)-Ph |
| 3091 | 4-F | Me | 1-naphthyl |
| 3092 | 4-F | Me | 2-naphthyl |
| 3093 | 4-F | Me | 2-thienyl |
| 3094 | 4-F | Me | 3-thienyl |
| 3095 | 4-F | Me | 2-furanyl |
| 3096 | 4-F | Me | 3-furanyl |
| 3097 | 4-F | Me | 2-pyridyl |
| 3098 | 4-F | Me | 3-pyridyl |
| 3099 | 4-F | Me | 4-pyridyl |
| 3100 | 4-F | Me | 2-indolyl |
| 3101 | 4-F | Me | 3-indolyl |

TABLE 2-continued

| | | | |
|---|---|---|---|
| 3102 | 4-F | Me | 5-indolyl |
| 3103 | 4-F | Me | 6-indolyl |
| 3104 | 4-F | Me | 3-indazolyl |
| 3105 | 4-F | Me | 5-indazolyl |
| 3106 | 4-F | Me | 6-indazolyl |
| 3107 | 4-F | Me | 2-imidazolyl |
| 3108 | 4-F | Me | 3-isoxazoyl |
| 3109 | 4-F | Me | 3-pyrazolyl |
| 3110 | 4-F | Me | 2-thiadiazolyl |
| 3111 | 4-F | Me | 2-thiazolyl |
| 3112 | 4-F | Me | 5-Ac-4-Me-2-thiazolyl |
| 3113 | 4-F | Me | 5-tetrazolyl |
| 3114 | 4-F | Me | 2-benzimidazolyl |
| 3115 | 4-F | Me | 5-benzimidazolyl |
| 3116 | 4-F | Me | 2-benzothiazolyl |
| 3117 | 4-F | Me | 5-benzothiazolyl |
| 3118 | 4-F | Me | 2-benzoxazolyl |
| 3119 | 4-F | Me | 5-benzoxazolyl |
| 3120 | 4-F | Me | 1-adamantyl |
| 3121 | 4-F | Me | 2-adamantyl |
| 3122 | 4-F | Me | i-Pr |
| 3123 | 4-F | Me | t-Bu |
| 3124 | 4-F | Me | c-Hex |
| 3125 | 4-F | Me | CH2CH2OMe |
| 3126 | 4-F | Me | CH2CONH2 |
| 3127 | 4-F | Me | CH2CO2Me |
| 3128 | 4-F | Me | CH(CH2Ph)CO2Me |
| 3129 | 4-F | Me | CH2CH2NMe2 |
| 3130 | 4-F | Me | benzyl |
| 3131 | 4-F | Me | phenethyl |
| 3132 | 4-F | Me | 2-(morpholin-1-yl)-Et |
| 3133 | 4-F | 2-F—Et | Ph |
| 3134 | 4-F | 2-F—Et | 3-CN—Ph |
| 3135 | 4-F | 2-F—Et | 3-COMe—Ph |
| 3136 | 4-F | 2-F—Et | 3-CO2Me—Ph |
| 3137 | 4-F | 2-F—Et | 3-CONH2—Ph |
| 3138 | 4-F | 2-F—Et | 3-CONHMe—Ph |
| 3139 | 4-F | 2-F—Et | 3-F—Ph |
| 3140 | 4-F | 2-F—Et | 3-Cl—Ph |
| 3141 | 4-F | 2-F—Et | 3-Br—Ph |
| 3142 | 4-F | 2-F—Et | 3-SO2NH2—Ph |
| 3143 | 4-F | 2-F—Et | 3-SO2NHMe—Ph |
| 3144 | 4-F | 2-F—Et | 3-CF3—Ph |
| 3145 | 4-F | 2-F—Et | 3-OMe—Ph |
| 3146 | 4-F | 2-F—Et | 3-SMe—Ph |
| 3147 | 4-F | 2-F—Et | 3-SOMe—Ph |
| 3148 | 4-F | 2-F—Et | 3-SO2Me—Ph |
| 3149 | 4-F | 2-F—Et | 3-OH—Ph |
| 3150 | 4-F | 2-F—Et | 3-CH2OH—Ph |
| 3151 | 4-F | 2-F—Et | 3-CHOHMe—Ph |
| 3152 | 4-F | 2-F—Et | 3-COH(Me)2—Ph |
| 3153 | 4-F | 2-F—Et | 3-Me—Ph |
| 3154 | 4-F | 2-F—Et | 3-Et—Ph |
| 3155 | 4-F | 2-F—Et | 3-iPr—Ph |
| 3156 | 4-F | 2-F—Et | 3-tBu—Ph |
| 3157 | 4-F | 2-F—Et | 3-CH2CO2Me—Ph |
| 3158 | 4-F | 2-F—Et | 3-(1-piperidinyl)-Ph |
| 3159 | 4-F | 2-F—Et | 3-(1-pyrrolidinyl)-Ph |
| 3160 | 4-F | 2-F—Et | 3-(2-imidazolyl)-Ph |
| 3161 | 4-F | 2-F—Et | 3-(1-imidazolyl)-Ph |
| 3162 | 4-F | 2-F—Et | 3-(2-thiazolyl)-Ph |
| 3163 | 4-F | 2-F—Et | 3-(3-pyrazolyl)-Ph |
| 3164 | 4-F | 2-F—Et | 3-(1-pyrazolyl)-Ph |
| 3165 | 4-F | 2-F—Et | 3-(5-Me-1-tetrazolyl)-Ph |
| 3166 | 4-F | 2-F—Et | 3-(1-Me-5-tetrazolyl)-Ph |
| 3167 | 4-F | 2-F—Et | 3-(2-pyridyl)-Ph |
| 3168 | 4-F | 2-F—Et | 3- (2-thienyl)-Ph |
| 3169 | 4-F | 2-F—Et | 3-(2-furanyl)-Ph |
| 3170 | 4-F | 2-F—Et | 4-CN—Ph |
| 3171 | 4-F | 2-F—Et | 4-COMe—Ph |
| 3172 | 4-F | 2-F—Et | 4-CO2Me—Ph |
| 3173 | 4-F | 2-F—Et | 4-CONH2—Ph |
| 3174 | 4-F | 2-F—Et | 4-CONHMe—Ph |
| 3175 | 4-F | 2-F—Et | 4-CONHPh—Ph |
| 3176 | 4-F | 2-F—Et | 4-F—Ph |
| 3177 | 4-F | 2-F—Et | 4-Cl—Ph |
| 3178 | 4-F | 2-F—Et | 4-Br—Ph |
| 3179 | 4-F | 2-F—Et | 4-SO2NH2—Ph |
| 3180 | 4-F | 2-F—Et | 4-SO2NHMe—Ph |
| 3181 | 4-F | 2-F—Et | 4-CF3—Ph |
| 3182 | 4-F | 2-F—Et | 4-OMe—Ph |
| 3183 | 4-F | 2-F—Et | 4-SMe—Ph |
| 3184 | 4-F | 2-F—Et | 4-SOMe—Ph |
| 3185 | 4-F | 2-F—Et | 4-SO2Me—Ph |
| 3186 | 4-F | 2-F—Et | 4-OH—Ph |
| 3187 | 4-F | 2-F—Et | 4-CH2OH—Ph |
| 3188 | 4-F | 2-F—Et | 4-CHOHMe—Ph |
| 3189 | 4-F | 2-F—Et | 4-COH(Me)2—Ph |
| 3190 | 4-F | 2-F—Et | 4-Me—Ph |
| 3191 | 4-F | 2-F—Et | 4-Et—Ph |
| 3192 | 4-F | 2-F—Et | 4-iPr—Ph |
| 3193 | 4-F | 2-F—Et | 4-tBu—Ph |
| 3194 | 4-F | 2-F—Et | 4-CH2CO2Me—Ph |
| 3195 | 4-F | 2-F—Et | 4-(1-piperidinyl)-Ph |
| 3196 | 4-F | 2-F—Et | 4-(1-pyrrolidinyl)-Ph |
| 3197 | 4-F | 2-F—Et | 4-(2-imidazolyl)-Ph |
| 3198 | 4-F | 2-F—Et | 4-(1-imidazolyl)-Ph |
| 3199 | 4-F | 2-F—Et | 4-(2-thiazolyl)-Ph |
| 3200 | 4-F | 2-F—Et | 4-(3-pyrazolyl)-Ph |
| 3201 | 4-F | 2-F—Et | 4-(1-pyrazolyl)-Ph |
| 3202 | 4-F | 2-F—Et | 4-(5-Me-1-tetrazolyl)-Ph |
| 3203 | 4-F | 2-F—Et | 4-(1-Me-5-tetrazolyl)-Ph |
| 3204 | 4-F | 2-F—Et | 4-(2-pyridyl)-Ph |
| 3205 | 4-F | 2-F—Et | 4-(2-thienyl)-Ph |
| 3206 | 4-F | 2-F—Et | 4-(2-furanyl)-Ph |
| 3207 | 4-F | 2-F—Et | 2-CN—Ph |
| 3208 | 4-F | 2-F—Et | 2-COMe—Ph |
| 3209 | 4-F | 2-F—Et | 2-CO2Me—Ph |
| 3210 | 4-F | 2-F—Et | 2-CONH2—Ph |
| 3211 | 4-F | 2-F—Et | 2-CONHMe—Ph |
| 3212 | 4-F | 2-F—Et | 2-F—Ph |
| 3213 | 4-F | 2-F—Et | 2-Cl—Ph |
| 3214 | 4-F | 2-F—Et | 2-Br—Ph |
| 3215 | 4-F | 2-F—Et | 2-SO2NH2—Ph |
| 3216 | 4-F | 2-F—Et | 2-SO2NHMe—Ph |
| 3217 | 4-F | 2-F—Et | 2-CF3—Ph |
| 3218 | 4-F | 2-F—Et | 2-OMe—Ph |
| 3219 | 4-F | 2-F—Et | 2-SMe—Ph |
| 3220 | 4-F | 2-F—Et | 2-SOMe—Ph |
| 3221 | 4-F | 2-F—Et | 2-SO2Me—Ph |
| 3222 | 4-F | 2-F—Et | 2-OH—Ph |
| 3223 | 4-F | 2-F—Et | 2-CH2OH—Ph |
| 3224 | 4-F | 2-F—Et | 2-CHOHMe—Ph |
| 3225 | 4-F | 2-F—Et | 2-COH(Me)2—Ph |
| 3226 | 4-F | 2-F—Et | 2-Me—Ph |
| 3227 | 4-F | 2-F—Et | 2-Et—Ph |
| 3228 | 4-F | 2-F—Et | 2-iPr—Ph |
| 3229 | 4-F | 2-F—Et | 2-tBu—Ph |
| 3230 | 4-F | 2-F—Et | 2-CH2CO2Me—Ph |
| 3231 | 4-F | 2-F—Et | 2-(1-piperidinyl)-Ph |
| 3232 | 4-F | 2-F—Et | 2-(1-pyrrolidinyl)-Ph |
| 3233 | 4-F | 2-F—Et | 2-(2-imidazolyl)-Ph |
| 3234 | 4-F | 2-F—Et | 2-(1-imidazolyl)-Ph |
| 3235 | 4-F | 2-F—Et | 2-(2-thiazolyl)-Ph |
| 3236 | 4-F | 2-F—Et | 2-(3-pyrazolyl)-Ph |
| 3237 | 4-F | 2-F—Et | 2-(1-pyrazolyl)-Ph |
| 3238 | 4-F | 2-F—Et | 2-(5-Me-1-tetrazolyl)-Ph |
| 3239 | 4-F | 2-F—Et | 2-(1-Me-5-tetrazolyl)-Ph |
| 3240 | 4-F | 2-F—Et | 2-(2-pyridyl)-Ph |
| 3241 | 4-F | 2-F—Et | 2-(2-thienyl)-Ph |
| 3242 | 4-F | 2-F—Et | 2-(2-furanyl)-Ph |
| 3243 | 4-F | 2-F—Et | 2,4-diF—Ph |
| 3244 | 4-F | 2-F—Et | 2,5-diF—Ph |
| 3245 | 4-F | 2-F—Et | 2,6-diF—Ph |
| 3246 | 4-F | 2-F—Et | 3,4-diF—Ph |
| 3247 | 4-F | 2-F—Et | 3,5-diF—Ph |
| 3248 | 4-F | 2-F—Et | 2,4-diCl—Ph |
| 3249 | 4-F | 2-F—Et | 2,5-diCl—Ph |
| 3250 | 4-F | 2-F—Et | 2,6-diCl—Ph |
| 3251 | 4-F | 2-F—Et | 3,4-diCl—Ph |
| 3252 | 4-F | 2-F—Et | 3,5-diCl—Ph |
| 3253 | 4-F | 2-F—Et | 3,4-diCF3—Ph |
| 3254 | 4-F | 2-F—Et | 3,5-diCF3—Ph |
| 3255 | 4-F | 2-F—Et | 5-Cl-2-MeO—Ph |
| 3256 | 4-F | 2-F—Et | 5-Cl-2-Me—Ph |
| 3257 | 4-F | 2-F—Et | 2-F-5-Me—Ph |
| 3258 | 4-F | 2-F—Et | 3-F-5-morpholino-Ph |
| 3259 | 4-F | 2-F—Et | 3,4-OCH2O—Ph |

TABLE 2-continued

| | | | |
|---|---|---|---|
| 3260 | 4-F | 2-F—Et | 3,4-OCH2CH2O—Ph |
| 3261 | 4-F | 2-F—Et | 2-MeO-5-CONH2—Ph |
| 3262 | 4-F | 2-F—Et | 2-MeO-4-(1-Me-5-tetrazolyl)-Ph |
| 3263 | 4-F | 2-F—Et | 2-MeO-5-(1-Me-5-tetrazolyl)-Ph |
| 3264 | 4-F | 2-F—Et | 3-CONH2-5-(1-Me-5-tetrazolyl)-Ph |
| 3265 | 4-F | 2-F—Et | 1-naphthyl |
| 3266 | 4-F | 2-F—Et | 2-naphthyl |
| 3267 | 4-F | 2-F—Et | 2-thienyl |
| 3268 | 4-F | 2-F—Et | 3-thienyl |
| 3269 | 4-F | 2-F—Et | 2-furanyl |
| 3270 | 4-F | 2-F—Et | 3-furanyl |
| 3271 | 4-F | 2-F—Et | 2-pyridyl |
| 3272 | 4-F | 2-F—Et | 3-pyridyl |
| 3273 | 4-F | 2-F—Et | 4-pyridyl |
| 3274 | 4-F | 2-F—Et | 2-indolyl |
| 3275 | 4-F | 2-F—Et | 3-indolyl |
| 3276 | 4-F | 2-F—Et | 5-indolyl |
| 3277 | 4-F | 2-F—Et | 6-indolyl |
| 3278 | 4-F | 2-F—Et | 3-indazolyl |
| 3279 | 4-F | 2-F—Et | 5-indazolyl |
| 3280 | 4-F | 2-F—Et | 6-indazolyl |
| 3281 | 4-F | 2-F—Et | 2-imidazolyl |
| 3282 | 4-F | 2-F—Et | 3-isoxazoyl |
| 3283 | 4-F | 2-F—Et | 3-pyrazolyl |
| 3284 | 4-F | 2-F—Et | 2-thiadiazolyl |
| 3285 | 4-F | 2-F—Et | 2-thiazolyl |
| 3286 | 4-F | 2-F—Et | 5-Ac-4-Me-2-thiazolyl |
| 3287 | 4-F | 2-F—Et | 5-tetrazolyl |
| 3288 | 4-F | 2-F—Et | 2-benzimidazolyl |
| 3289 | 4-F | 2-F—Et | 5-benzimidazolyl |
| 3290 | 4-F | 2-F—Et | 2-benzothiazolyl |
| 3291 | 4-F | 2-F—Et | 5-benzothiazolyl |
| 3292 | 4-F | 2-F—Et | 2-benzoxazolyl |
| 3293 | 4-F | 2-F—Et | 5-benzoxazolyl |
| 3294 | 4-F | 2-F—Et | 1-adamantyl |
| 3295 | 4-F | 2-F—Et | 2-adamantyl |
| 3296 | 4-F | 2-F—Et | i-Pr |
| 3297 | 4-F | 2-F—Et | t-Bu |
| 3298 | 4-F | 2-F—Et | c-Hex |
| 3299 | 4-F | 2-F—Et | CH2CH2OMe |
| 3300 | 4-F | 2-F—Et | CH2CONH2 |
| 3301 | 4-F | 2-F—Et | CH2CO2Me |
| 3302 | 4-F | 2-F—Et | CH(CH2Ph)CO2Me |
| 3303 | 4-F | 2-F—Et | CH2CH2NMe2 |
| 3304 | 4-F | 2-F—Et | benzyl |
| 3305 | 4-F | 2-F—Et | phenethyl |
| 3306 | 4-F | 2-F—Et | 2-(morpholin-1-yl)-Et |
| 3307 | 4-F | CO2Me | Ph |
| 3308 | 4-F | CO2Me | 3-CN—Ph |
| 3309 | 4-F | CO2Me | 3-COMe—Ph |
| 3310 | 4-F | CO2Me | 3-CO2Me—Ph |
| 3311 | 4-F | CO2Me | 3-CONH2—Ph |
| 3312 | 4-F | CO2Me | 3-CONHMe—Ph |
| 3313 | 4-F | CO2Me | 3-F—Ph |
| 3314 | 4-F | CO2Me | 3-Cl—Ph |
| 3315 | 4-F | CO2Me | 3-Br—Ph |
| 3316 | 4-F | CO2Me | 3-SO2NH2—Ph |
| 3317 | 4-F | CO2Me | 3-SO2NHMe—Ph |
| 3318 | 4-F | CO2Me | 3-CF3—Ph |
| 3319 | 4-F | CO2Me | 3-OMe—Ph |
| 3320 | 4-F | CO2Me | 3-SMe—Ph |
| 3321 | 4-F | CO2Me | 3-SOMe—Ph |
| 3322 | 4-F | CO2Me | 3-SO2Me—Ph |
| 3323 | 4-F | CO2Me | 3-OH—Ph |
| 3324 | 4-F | CO2Me | 3-CH2OH—Ph |
| 3325 | 4-F | CO2Me | 3-CHoliNe-Ph |
| 3326 | 4-F | CO2Me | 3-COH(Me)2—Ph |
| 3327 | 4-F | CO2Me | 3-Me—Ph |
| 3328 | 4-F | CO2Me | 3-Et—Ph |
| 3329 | 4-F | CO2Me | 3-iPr—Ph |
| 3330 | 4-F | CO2Me | 3-tBu—Ph |
| 3331 | 4-F | CO2Me | 3-CH2CO2Me—Ph |
| 3332 | 4-F | CO2Me | 3-(1-piperidinyl)-Ph |
| 3333 | 4-F | CO2Me | 3-(1-pyrrolidinyl)-Ph |
| 3334 | 4-F | CO2Me | 3-(2-imidazolyl)-Ph |
| 3335 | 4-F | CO2Me | 3-(1-imidazolyl)-Ph |
| 3336 | 4-F | CO2Me | 3-(2-thiazolyl)-Ph |
| 3337 | 4-F | CO2Me | 3-(3-pyrazolyl)-Ph |
| 3338 | 4-F | CO2Me | 3-(1-pyrazolyl)-Ph |
| 3339 | 4-F | CO2Me | 3-(5-Me-1-tetrazolyl)-Ph |
| 3340 | 4-F | CO2Me | 3-(1-Me-5-tetrazolyl)-Ph |
| 3341 | 4-F | CO2Me | 3-(2-pyridyl)-Ph |
| 3342 | 4-F | CO2Me | 3-(2-thienyl)-Ph |
| 3343 | 4-F | CO2Me | 3-(2-furanyl)-Ph |
| 3344 | 4-F | CO2Me | 4-CN—Ph |
| 3345 | 4-F | CO2Me | 4-COMe—Ph |
| 3346 | 4-F | CO2Me | 4-CO2Me—Ph |
| 3347 | 4-F | CO2Me | 4-CONH2—Ph |
| 3348 | 4-F | CO2Me | 4-CONHMe—Ph |
| 3349 | 4-F | CO2Me | 4-CONHPh—Ph |
| 3350 | 4-F | CO2Me | 4-F—Ph |
| 3351 | 4-F | CO2Me | 4-Cl—Ph |
| 3352 | 4-F | CO2Me | 4-Br—Ph |
| 3353 | 4-F | CO2Me | 4-SO2NH2—Ph |
| 3354 | 4-F | CO2Me | 4-SO2NHMe—Ph |
| 3355 | 4-F | CO2Me | 4-CF3—Ph |
| 3356 | 4-F | CO2Me | 4-OMe—Ph |
| 3357 | 4-F | CO2Me | 4-SMe—Ph |
| 3358 | 4-F | CO2Me | 4-SOMe—Ph |
| 3359 | 4-F | CO2Me | 4-SO2Me—Ph |
| 3360 | 4-F | CO2Me | 4-OH—Ph |
| 3361 | 4-F | CO2Me | 4-CH2OH—Ph |
| 3362 | 4-F | CO2Me | 4-CHOHMe—Ph |
| 3363 | 4-F | CO2Me | 4-COH(Me)2—Ph |
| 3364 | 4-F | CO2Me | 4-Me—Ph |
| 3365 | 4-F | CO2Me | 4-Et—Ph |
| 3366 | 4-F | CO2Me | 4-iPr—Ph |
| 3367 | 4-F | CO2Me | 4-tBu—Ph |
| 3368 | 4-F | CO2Me | 4-CH2CO2Me—Ph |
| 3369 | 4-F | CO2Me | 4-(1-piperidinyl)-Ph |
| 3370 | 4-F | CO2Me | 4-(1-pyrrolidinyl)-Ph |
| 3371 | 4-F | CO2Me | 4-(2-imidazolyl)-Ph |
| 3372 | 4-F | CO2Me | 4-(1-iinidazolyl)-Ph |
| 3373 | 4-F | CO2Me | 4-(2-thiazolyl)-Ph |
| 3374 | 4-F | CO2Me | 4-(3-pyrazolyl)-Ph |
| 3375 | 4-F | CO2Me | 4-(1-pyrazolyl)-Ph |
| 3376 | 4-F | CO2Me | 4-(5-Me-1-tetrazolyl)-Ph |
| 3377 | 4-F | CO2Me | 4-(1-Me-5-tetrazolyl)-Ph |
| 3378 | 4-F | CO2Me | 4-(2-pyridyl)-Ph |
| 3379 | 4-F | CO2Me | 4-(2-thienyl)-Ph |
| 3380 | 4-F | CO2Me | 4-(2-furanyl)-Ph |
| 3381 | 4-F | CO2Me | 2-CN—Ph |
| 3382 | 4-F | CO2Me | 2-COMe—Ph |
| 3383 | 4-F | CO2Me | 2-CO2Me—Ph |
| 3384 | 4-F | CO2Me | 2-CONH2—Ph |
| 3385 | 4-F | CO2Me | 2-CONHMe—Ph |
| 3386 | 4-F | CO2Me | 2-F—Ph |
| 3387 | 4-F | CO2Me | 2-Cl—Ph |
| 3388 | 4-F | CO2Me | 2-Br—Ph |
| 3389 | 4-F | CO2Me | 2-SO2NH2—Ph |
| 3390 | 4-F | CO2Me | 2-SO2NHMe—Ph |
| 3391 | 4-F | CO2Me | 2-CF3—Ph |
| 3392 | 4-F | CO2Me | 2-OMe—Ph |
| 3393 | 4-F | CO2Me | 2-SMe—Ph |
| 3394 | 4-F | CO2Me | 2-SOMe—Ph |
| 3395 | 4-F | CO2Me | 2-SO2Me—Ph |
| 3396 | 4-F | CO2Me | 2-OH—Ph |
| 3397 | 4-F | CO2Me | 2-CH2OH—Ph |
| 3398 | 4-F | CO2Me | 2-CHOHMe—Ph |
| 3399 | 4-F | CO2Me | 2-COH(Me)2—Ph |
| 3400 | 4-F | CO2Me | 2-Me—Ph |
| 3401 | 4-F | CO2Me | 2-Et—Ph |
| 3402 | 4-F | CO2Me | 2-iPr—Ph |
| 3403 | 4-F | CO2Me | 2-tBu—Ph |
| 3404 | 4-F | CO2Me | 2-CH2CO2Me—Ph |
| 3405 | 4-F | CO2Me | 2-(1-piperidinyl)-Ph |
| 3406 | 4-F | CO2Me | 2-(1-pyrrolidinyl)-Ph |
| 3407 | 4-F | CO2Ne | 2-(2-imidazolyl)-Ph |
| 3408 | 4-F | CO2Me | 2-(1-imidazolyl)-Ph |
| 3409 | 4-F | CO2Me | 2-(2-thiazolyl)-Ph |
| 3410 | 4-F | CO2Me | 2-(3-pyrazolyl)-Ph |
| 3411 | 4-F | CO2Me | 2-(1-pyrazolyl)-Ph |
| 3412 | 4-F | CO2Me | 2-(5-Me-1-tetrazolyl)-Ph |
| 3413 | 4-F | CO2Me | 2-(1-Me-5-tetrazolyl)-Ph |
| 3414 | 4-F | CO2Me | 2-(2-pyridyl)-Ph |
| 3415 | 4-F | CO2Me | 2-(2-thienyl)-Ph |
| 3416 | 4-F | CO2Me | 2-(2-furanyl)-Ph |
| 3417 | 4-F | CO2Me | 2,4-diF—Ph |

TABLE 2-continued

| | | | |
|---|---|---|---|
| 3418 | 4-F | CO2Me | 2,5-diF—Ph |
| 3419 | 4-F | CO2Me | 2,6-diF—Ph |
| 3420 | 4-F | CO2Me | 3,4-diF—Ph |
| 3421 | 4-F | CO2Me | 3,5-diF—Ph |
| 3422 | 4-F | CO2Me | 2,4-diCl—Ph |
| 3423 | 4-F | CO2Me | 2,5-diCl—Ph |
| 3424 | 4-F | CO2Me | 2,6-diCl—Ph |
| 3425 | 4-F | CO2Me | 3,4-diCl—Ph |
| 3426 | 4-F | CO2Me | 3,5-diCl—Ph |
| 3427 | 4-F | CO2Me | 3,4-diCF3—Ph |
| 3428 | 4-F | CO2Me | 3,5-diCF3—Ph |
| 3429 | 4-F | CO2Me | 5-Cl-2-MeO—Ph |
| 3430 | 4-F | CO2Me | 5-Cl-2-Me—Ph |
| 3431 | 4-F | CO2Me | 2-F-5-Me—Ph |
| 3432 | 4-F | CO2Me | 3-F-5-morpholino-Ph |
| 3433 | 4-F | CO2Me | 3,4-OCH2O—Ph |
| 3434 | 4-F | CO2Me | 3,4-OCH2CH2O—Ph |
| 3435 | 4-F | CO2Me | 2-MeO-5-CONH2—Ph |
| 3436 | 4-F | CO2Me | 2-MeO-4-(1-Me-5-tetrazolyl)-Ph |
| 3437 | 4-F | CO2Me | 2-MeO-5-(1-Me-5-tetrazolyl)-Ph |
| 3438 | 4-F | CO2Me | 3-CONH2-5-(1-Me-5-tetrazolyl)-Ph |
| 3439 | 4-F | CO2Me | 1-naphthyl |
| 3440 | 4-F | CO2Me | 2-naphthyl |
| 3441 | 4-F | CO2Me | 2-thienyl |
| 3442 | 4-F | CO2Me | 3-thienyl |
| 3443 | 4-F | CO2Me | 2-furanyl |
| 3444 | 4-F | CO2Me | 3-furanyl |
| 3445 | 4-F | CO2Me | 2-pyridyl |
| 3446 | 4-F | CO2Me | 3-pyridyl |
| 3447 | 4-F | CO2Me | 4-pyridyl |
| 3448 | 4-F | CO2Me | 2-indolyl |
| 3449 | 4-F | CO2Me | 3-indolyl |
| 3450 | 4-F | CO2Me | 5-indolyl |
| 3451 | 4-F | CO2Me | 6-indolyl |
| 3452 | 4-F | CO2Me | 3-indazolyl |
| 3453 | 4-F | CO2Me | 5-indazolyl |
| 3454 | 4-F | CO2Me | 6-indazolyl |
| 3455 | 4-F | CO2Me | 2-imidazolyl |
| 3456 | 4-F | CO2Me | 3-isoxazoyl |
| 3457 | 4-F | CO2Me | 3-pyrazolyl |
| 3458 | 4-F | CO2Me | 2-thiadiazolyl |
| 3459 | 4-F | CO2Me | 2-thiazolyl |
| 3460 | 4-F | CO2Me | 5-Ac-4-Me-2-thiazolyl |
| 3461 | 4-F | CO2Me | 5-tetrazolyl |
| 3462 | 4-F | CO2Me | 2-benzimidazolyl |
| 3463 | 4-F | CO2Me | 5-benzimidazolyl |
| 3464 | 4-F | CO2Me | 2-benzothiazolyl |
| 3465 | 4-F | CO2Me | 5-benzothiazolyl |
| 3466 | 4-F | CO2Me | 2-benzoxazolyl |
| 3467 | 4-F | CO2Me | 5-benzoxazolyl |
| 3468 | 4-F | CO2Me | 1-adamantyl |
| 3469 | 4-F | CO2Me | 2-adamantyl |
| 3470 | 4-F | CO2Me | i-Pr |
| 3471 | 4-F | CO2Me | t-Bu |
| 3472 | 4-F | CO2Me | c-Hex |
| 3473 | 4-F | CO2Me | CH2CH2OMe |
| 3474 | 4-F | CO2Me | CH2CONH2 |
| 3475 | 4-F | CO2Me | CH2CO2Me |
| 3476 | 4-F | CO2Me | CH(CH2Ph)CO2Me |
| 3477 | 4-F | CO2Me | CH2CH2NTAe2 |
| 3478 | 4-F | CO2Me | benzyl |
| 3479 | 4-F | CO2Me | phenethyl |
| 3480 | 4-F | CO2Me | 2-(morpholin-1-yl)-Et |
| 3481 | 4-F | Ac | Ph |
| 3482 | 4-F | Ac | 3-CN—Ph |
| 3483 | 4-F | Ac | 3-COMe—Ph |
| 3484 | 4-F | Ac | 3-CO2Me—Ph |
| 3485 | 4-F | Ac | 3-CONH2—Ph |
| 3486 | 4-F | Ac | 3-CONHMe—Ph |
| 3487 | 4-F | Ac | 3-F—Ph |
| 3488 | 4-F | Ac | 3-Cl—Ph |
| 3489 | 4-F | Ac | 3-Br—Ph |
| 3490 | 4-F | Ac | 3-SO2NH2—Ph |
| 3491 | 4-F | Ac | 3-SO2NHMe—Ph |
| 3492 | 4-F | Ac | 3-CF3—Ph |
| 3493 | 4-F | Ac | 3-OMe—Ph |
| 3494 | 4-F | Ac | 3-SMe—Ph |
| 3495 | 4-F | Ac | 3-SOMe—Ph |
| 3496 | 4-F | Ac | 3-SO2Me—Ph |
| 3497 | 4-F | Ac | 3-OH—Ph |
| 3498 | 4-F | Ac | 3-CH2OH—Ph |
| 3499 | 4-F | Ac | 3-CHOHMe—Ph |
| 3500 | 4-F | Ac | 3-COH(Me)2—Ph |
| 3501 | 4-F | Ac | 3-Me—Ph |
| 3502 | 4-F | Ac | 3-Et—Ph |
| 3503 | 4-F | Ac | 3-iPr—Ph |
| 3504 | 4-F | Ac | 3-tBu—Ph |
| 3505 | 4-F | Ac | 3-CH2CO2Me—Ph |
| 3506 | 4-F | Ac | 3-(1-piperidinyl)-Ph |
| 3507 | 4-F | Ac | 3-(1-pyrrolidinyl)-Ph |
| 3508 | 4-F | Ac | 3-(2-imidazolyl)-Ph |
| 3509 | 4-F | Ac | 3-(1-imidazolyl)-Ph |
| 3510 | 4-F | Ac | 3-(2-thiazolyl)-Ph |
| 3511 | 4-F | Ac | 3-(3-pyrazolyl)-Ph |
| 3512 | 4-F | Ac | 3-(1-pyrazolyl)-Ph |
| 3513 | 4-F | Ac | 3-(5-Me-1-tetrazolyl)-Ph |
| 3514 | 4-F | Ac | 3-(1-Me-5-tetrazolyl)-Ph |
| 3515 | 4-F | Ac | 3-(2-pyridyl)-Ph |
| 3516 | 4-F | Ac | 3-(2-thienyl)-Ph |
| 3517 | 4-F | Ac | 3-(2-furanyl)-Ph |
| 3518 | 4-F | Ac | 4-CN—Ph |
| 3519 | 4-F | Ac | 4-COMe—Ph |
| 3520 | 4-F | Ac | 4-CO2Me—Ph |
| 3521 | 4-F | Ac | 4-CONH2—Ph |
| 3522 | 4-F | Ac | 4-CONHMe—Ph |
| 3523 | 4-F | Ac | 4-CONHPh—Ph |
| 3524 | 4-F | Ac | 4-F—Ph |
| 3525 | 4-F | Ac | 4-Cl—Ph |
| 3526 | 4-F | Ac | 4-Br—Ph |
| 3527 | 4-F | Ac | 4-SO2NH2—Ph |
| 3528 | 4-F | Ac | 4-SO2NHMe—Ph |
| 3529 | 4-F | Ac | 4-CF3—Ph |
| 3530 | 4-F | Ac | 4-OMe—Ph |
| 3531 | 4-F | Ac | 4-SMe—Ph |
| 3532 | 4-F | Ac | 4-SOMe—Ph |
| 3533 | 4-F | Ac | 4-SO2Me—Ph |
| 3534 | 4-F | Ac | 4-OH—Ph |
| 3535 | 4-F | Ac | 4-CH2OH—Ph |
| 3536 | 4-F | Ac | 4-CHOHMe—Ph |
| 3537 | 4-F | Ac | 4-COH(Me)2—Ph |
| 3538 | 4-F | Ac | 4-Me—Ph |
| 3539 | 4-F | Ac | 4-Et—Ph |
| 3540 | 4-F | Ac | 4-iPr—Ph |
| 3541 | 4-F | Ac | 4-tBu—Ph |
| 3542 | 4-F | Ac | 4-CH2CO2Me—Ph |
| 3543 | 4-F | Ac | 4-(1-piperidinyl)-Ph |
| 3544 | 4-F | Ac | 4-(1-pyrrolidinyl)-Ph |
| 3545 | 4-F | Ac | 4-(2-imidazolyl)-Ph |
| 3546 | 4-F | Ac | 4-(1-imidazolyl)-Ph |
| 3547 | 4-F | Ac | 4-(2-thiazolyl)-Ph |
| 3548 | 4-F | Ac | 4-(3-pyrazolyl)-Ph |
| 3549 | 4-F | Ac | 4-(1-pyrazolyl)-Ph |
| 3550 | 4-F | Ac | 4-(5-Me-1-tetrazolyl)-Ph |
| 3551 | 4-F | Ac | 4-(1-Me-5-tetrazolyl)-Ph |
| 3552 | 4-F | Ac | 4-(2-pyridyl)-Ph |
| 3553 | 4-F | Ac | 4-(2-thiefly)-Ph |
| 3554 | 4-F | Ac | 4-(2-furanyl)-Ph |
| 3555 | 4-F | Ac | 2-CN—Ph |
| 3556 | 4-F | Ac | 2-COMe—Ph |
| 3557 | 4-F | Ac | 2-CO2Me—Ph |
| 3558 | 4-F | Ac | 2-CONH2—Ph |
| 3559 | 4-F | Ac | 2-CONHMe—Ph |
| 3560 | 4-F | Ac | 2-F—Ph |
| 3561 | 4-F | Ac | 2-Cl—Ph |
| 3562 | 4-F | Ac | 2-Br—Ph |
| 3563 | 4-F | Ac | 2-SO2NH2—Ph |
| 3564 | 4-F | Ac | 2-SO2NHMe—Ph |
| 3565 | 4-F | Ac | 2-CF3—Ph |
| 3566 | 4-F | Ac | 2-OMe—Ph |
| 3567 | 4-F | Ac | 2-SMe—Ph |
| 3568 | 4-F | Ac | 2-SOMe—Ph |
| 3569 | 4-F | Ac | 2-SO2Me—Ph |
| 3570 | 4-F | Ac | 2-OH—Ph |
| 3571 | 4-F | Ac | 2-CH2OH—Ph |
| 3572 | 4-F | Ac | 2-CHOHMe—Ph |
| 3573 | 4-F | Ac | 2-COH(Me)2—Ph |
| 3574 | 4-F | Ac | 2-Me—Ph |
| 3575 | 4-F | Ac | 2-Et—Ph |

TABLE 2-continued

| | | | |
|---|---|---|---|
| 3576 | 4-F | Ac | 2-iPr—Ph |
| 3577 | 4-F | Ac | 2-tBu—Ph |
| 3578 | 4-F | Ac | 2-CH2CO2Me—Ph |
| 3579 | 4-F | Ac | 2-(1-piperidinyl)-Ph |
| 3580 | 4-F | Ac | 2-(1-pyrrolidinyl)-Ph |
| 3581 | 4-F | Ac | 2-(2-imidazolyl)-Ph |
| 3582 | 4-F | Ac | 2-(1-imidazolyl)-Ph |
| 3583 | 4-F | Ac | 2-(2-thiazolyl)-Ph |
| 3584 | 4-F | Ac | 2-(3-pyrazolyl)-Ph |
| 3585 | 4-F | Ac | 2-(1-pyrazolyl)-Ph |
| 3586 | 4-F | Ac | 2-(5-Me-1-tetrazolyl)-Ph |
| 3587 | 4-F | Ac | 2-(1-Me-5-tetrazolyl)-Ph |
| 3588 | 4-F | Ac | 2-(2-pyridyl)-Ph |
| 3589 | 4-F | Ac | 2-(2-thienyl)-Ph |
| 3590 | 4-F | Ac | 2-(2-furanyl)-Ph |
| 3591 | 4-F | Ac | 2,4-diF—Ph |
| 3592 | 4-F | Ac | 2,5-diF—Ph |
| 3593 | 4-F | Ac | 2,6-diF—Ph |
| 3594 | 4-F | Ac | 3,4-diF—Ph |
| 3595 | 4-F | Ac | 3,5-diF—Ph |
| 3596 | 4-F | Ac | 2,4-diCl—Ph |
| 3597 | 4-F | Ac | 2,5-diCl—Ph |
| 3598 | 4-F | Ac | 2,6-diCl—Ph |
| 3599 | 4-F | Ac | 3,4-diCl—Ph |
| 3600 | 4-F | Ac | 3,5-diCl—Ph |
| 3601 | 4-F | Ac | 3,4-diCF3—Ph |
| 3602 | 4-F | Ac | 3,5-diCF3—Ph |
| 3603 | 4-F | Ac | 5-Cl-2-MeO—Ph |
| 3604 | 4-F | Ac | 5-Cl-2-Me—Ph |
| 3605 | 4-F | Ac | 2-F-5-Me—Ph |
| 3606 | 4-F | Ac | 3-F-5-morpholino-Ph |
| 3607 | 4-F | Ac | 3,4-OCH2O—Ph |
| 3608 | 4-F | Ac | 3,4-OCH2CH2O—Ph |
| 3609 | 4-F | Ac | 2-MeO-5-CONH2—Ph |
| 3610 | 4-F | Ac | 2-MeO-4-(1-Me-5-tetrazolyl)-Ph |
| 3611 | 4-F | Ac | 2-MeO-5-(1-Me-5-tetrazolyl)-Ph |
| 3612 | 4-F | Ac | 3-CONH2-5-(1-Me-5-tetrazolyl)-Ph |
| 3613 | 4-F | Ac | 1-naphthyl |
| 3614 | 4-F | Ac | 2-naphthyl |
| 3615 | 4-F | Ac | 2-thienyl |
| 3616 | 4-F | Ac | 3-thienyl |
| 3617 | 4-F | Ac | 2-furanyl |
| 3618 | 4-F | Ac | 3-furanyl |
| 3619 | 4-F | Ac | 2-pyridyl |
| 3620 | 4-F | Ac | 3-pyridyl |
| 3621 | 4-F | Ac | 4-pyridyl |
| 3622 | 4-F | Ac | 2-indolyl |
| 3623 | 4-F | Ac | 3-indolyl |
| 3624 | 4-F | Ac | 5-indolyl |
| 3625 | 4-F | Ac | 6-indolyl |
| 3626 | 4-F | Ac | 3-indazolyl |
| 3627 | 4-F | Ac | 5-indazolyl |
| 3628 | 4-F | Ac | 6-indazolyl |
| 3629 | 4-F | Ac | 2-imidazolyl |
| 3630 | 4-F | Ac | 3-isoxazoyl |
| 3631 | 4-F | Ac | 3-pyrazolyl |
| 3632 | 4-F | Ac | 2-thiadiazolyl |
| 3633 | 4-F | Ac | 2-thiazolyl |
| 3634 | 4-F | Ac | 5-Ac-4-Me-2-thiazolyl |
| 3635 | 4-F | Ac | 5-tetrazolyl |
| 3636 | 4-F | Ac | 2-benzimidazolyl |
| 3637 | 4-F | Ac | 5-benzimidazolyl |
| 3633 | 4-F | Ac | 2-benzothiazolyl |
| 3639 | 4-F | Ac | 5-benzothiazolyl |
| 3640 | 4-F | Ac | 2-benzoxazolyl |
| 3641 | 4-F | Ac | 5-benzoxazolyl |
| 3642 | 4-F | Ac | 1-adamantyl |
| 3643 | 4-F | Ac | 2-adamantyl |
| 3644 | 4-F | Ac | i-Pr |
| 3645 | 4-F | Ac | t-Bu |
| 3646 | 4-F | Ac | c-Hex |
| 3647 | 4-F | Ac | CH2CH2OMe |
| 3648 | 4-F | Ac | CH2CONH2 |
| 3649 | 4-F | Ac | CH2CO2Me |
| 3650 | 4-F | Ac | CH(CH2Ph)CO2Me |
| 3651 | 4-F | Ac | CH2CH2NMe2 |
| 3652 | 4-F | Ac | benzyl |
| 3653 | 4-F | Ac | phenethyl |
| 3654 | 4-F | Ac | 2-(morpholin-1-yl)-Et |
| 3655 | 4-F | COtBu | Ph |
| 3656 | 4-F | COtBu | 3-CN—Ph |
| 3657 | 4-F | COtBu | 3-COMe—Ph |
| 3658 | 4-F | COtBu | 3-CO2Me—Ph |
| 3659 | 4-F | COtBu | 3-CONH2—Ph |
| 3660 | 4-F | COtBu | 3-CONHMe—Ph |
| 3661 | 4-F | COtBu | 3-F—Ph |
| 3662 | 4-F | COtBu | 3-Cl—Ph |
| 3663 | 4-F | COtBu | 3-Br—Ph |
| 3664 | 4-F | COtBu | 3-SO2NH2—Ph |
| 3665 | 4-F | COtBu | 3-SO2NHMe—Ph |
| 3666 | 4-F | COtBu | 3-CF3—Ph |
| 3667 | 4-F | COtBu | 3-OMe—Ph |
| 3668 | 4-F | COtBu | 3-SMe—Ph |
| 3669 | 4-F | COtBu | 3-SOMe—Ph |
| 3670 | 4-F | COtBu | 3-SO2Me—Ph |
| 3671 | 4-F | COtBu | 3-OH—Ph |
| 3672 | 4-F | COtBu | 3-CH2OH—Ph |
| 3673 | 4-F | COtBu | 3-CHOHMe—Ph |
| 3674 | 4-F | COtBu | 3-COH(Me)2—Ph |
| 3675 | 4-F | COtBu | 3-Me—Ph |
| 3676 | 4-F | COtBu | 3-Et—Ph |
| 3677 | 4-F | COtBu | 3-iPr—Ph |
| 3678 | 4-F | COtBu | 3-tBu—Ph |
| 3679 | 4-F | COtBu | 3-CH2CO2Me—Ph |
| 3680 | 4-F | COtBu | 3-(1-piperidinyl)-Ph |
| 3681 | 4-F | COtBu | 3-(1-pyrrolidinyl)-Ph |
| 3682 | 4-F | COtBu | 3-(2-imidazolyl)-Ph |
| 3683 | 4-F | COtBu | 3-(1-imidazolyl)-Ph |
| 3684 | 4-F | COtBu | 3-(2-thiazolyl)-Ph |
| 3685 | 4-F | COtBu | 3-(3-pyrazolyl)-Ph |
| 3686 | 4-F | COtBu | 3-(1-pyrazolyl)-Ph |
| 3687 | 4-F | COtBu | 3-(5-Me-1-tetrazolyl)-Ph |
| 3688 | 4-F | COtBu | 3-(1-Me-5-tetrazolyl)-Ph |
| 3689 | 4-F | COtBu | 3-(2-pyridyl)-Ph |
| 3690 | 4-F | COtBu | 3-(2-thienyl)-Ph |
| 3691 | 4-F | COtBu | 3-(2-furanyl)-Ph |
| 3692 | 4-F | COtBu | 4-CN—Ph |
| 3693 | 4-F | COtBu | 4-COMe—Ph |
| 3694 | 4-F | COtBu | 4-CO2Me—Ph |
| 3695 | 4-F | COtBu | 4-CONH2—Ph |
| 3696 | 4-F | COtBu | 4-CONHMe—Ph |
| 3697 | 4-F | COtBu | 4-CONHPh—Ph |
| 3698 | 4-F | COtBu | 4-F—Ph |
| 3699 | 4-F | COtBu | 4-Cl—Ph |
| 3700 | 4-F | COtBu | 4-Br—Ph |
| 3701 | 4-F | COtBu | 4-SO2NH2—Ph |
| 3702 | 4-F | COtBu | 4-SO2NHMe—Ph |
| 3703 | 4-F | COtBu | 4-CF3—Ph |
| 3704 | 4-F | COtBu | 4-OMe—Ph |
| 3705 | 4-F | COtBu | 4-SMe—Ph |
| 3706 | 4-F | COtBu | 4-SOMe—Ph |
| 3707 | 4-F | COtBu | 4-SO2Me—Ph |
| 3708 | 4-F | COtBu | 4-OH—Ph |
| 3709 | 4-F | COtBu | 4-CH2OH—Ph |
| 3710 | 4-F | COtBu | 4-CHOHMe—Ph |
| 3711 | 4-F | COtBu | 4-COH(Me)2—Ph |
| 3712 | 4-F | COtBu | 4-Me—Ph |
| 3713 | 4-F | COtBu | 4-Et—Ph |
| 3714 | 4-F | COtBu | 4-iPr—Ph |
| 3715 | 4-F | COtBu | 4-tBu—Ph |
| 3716 | 4-F | COtBu | 4-CH2CO2Me—Ph |
| 3717 | 4-F | COtBu | 4-(1-piperidinyl)-Ph |
| 3718 | 4-F | COtBu | 4-(1-pyrrolidinyl)-Ph |
| 3719 | 4-F | COtBu | 4-(2-imidazolyl)-Ph |
| 3720 | 4-F | COtBu | 4-(1-imidazolyl)-Ph |
| 3721 | 4-F | COtBu | 4-(2-thiazolyl)-Ph |
| 3722 | 4-F | COtBu | 4-(3-pyrazolyl)-Ph |
| 3723 | 4-F | COtBu | 4-(1-pyrazolyl)-Ph |
| 3724 | 4-F | COtBu | 4-(5-Me-1-tetrazolyl)-Ph |
| 3725 | 4-F | COtBu | 4-(1-Me-5-tetrazolyl)-Ph |
| 3726 | 4-F | COtBu | 4-(2-pyridyl)-Ph |
| 3727 | 4-F | COtBu | 4-(2-thienyl)-Ph |
| 3728 | 4-F | COtBu | 4-(2-furanyl)-Ph |
| 3729 | 4-F | COtBu | 2-CN—Ph |
| 3730 | 4-F | COtBu | 2-COMe—Ph |
| 3731 | 4-F | COtBu | 2-CO2Me—Ph |
| 3732 | 4-F | COtBu | 2-CONH2—Ph |
| 3733 | 4-F | COtBu | 2-CONHMe—Ph |

TABLE 2-continued

| | | | |
|---|---|---|---|
| 3734 | 4-F | COtBu | 2-F—Ph |
| 3735 | 4-F | COtBu | 2-Cl—Ph |
| 3736 | 4-F | COtBu | 2-Br—Ph |
| 3737 | 4-F | COtBu | 2-SO2NH2—Ph |
| 3738 | 4-F | COtBu | 2-SO2NHMe—Ph |
| 3739 | 4-F | COtBu | 2-CF3—Ph |
| 3740 | 4-F | COtBu | 2-OMe—Ph |
| 3741 | 4-F | COtBu | 2-SMe—Ph |
| 3742 | 4-F | COtBu | 2-SOMe—Ph |
| 3743 | 4-F | COtBu | 2-SO2Me—Ph |
| 3744 | 4-F | COtBu | 2-OH—Ph |
| 3745 | 4-F | COtBu | 2-CH2OH—Ph |
| 3746 | 4-F | COtBu | 2-CHOHMe—Ph |
| 3747 | 4-F | COtBu | 2-COH(Me)2—Ph |
| 3748 | 4-F | COtBu | 2-Me—Ph |
| 3749 | 4-F | COtBu | 2-Et—Ph |
| 3750 | 4-F | COtBu | 2-iPr—Ph |
| 3751 | 4-F | COtBu | 2-tBu—Ph |
| 3752 | 4-F | COtBu | 2-CH2CO2Me—Ph |
| 3753 | 4-F | COtBu | 2-(1-piperidinyl)-Ph |
| 3754 | 4-F | COtBu | 2-(1-pyrrolidinyl)-Ph |
| 3755 | 4-F | COtBu | 2-(2-imidazolyl)-Ph |
| 3756 | 4-F | COtBu | 2-(1-imidazolyl)-Ph |
| 3757 | 4-F | COtBu | 2-(2-thiazolyl)-Ph |
| 3758 | 4-F | COtBu | 2-(3-pyrazolyl)-Ph |
| 3759 | 4-F | COtBu | 2-(1-pyrazolyl)-Ph |
| 3760 | 4-F | COtBu | 2-(5-Me-1-tetrazolyl)-Ph |
| 3761 | 4-F | COtBu | 2-(1-Me-5-tetrazolyl)-Ph |
| 3762 | 4-F | COtBu | 2-(2-pyridyl)-Ph |
| 3763 | 4-F | COtBu | 2-(2-thienyl)-Ph |
| 3764 | 4-F | COtBu | 2-(2-furanyl)-Ph |
| 3765 | 4-F | COtBu | 2,4-diF—Ph |
| 3766 | 4-F | COtBu | 2,5-diF—Ph |
| 3767 | 4-F | COtBu | 2,6-diF—Ph |
| 3768 | 4-F | COtBu | 3,4-diF—Ph |
| 3769 | 4-F | COtBu | 3,5-diF—Ph |
| 3770 | 4-F | COtBu | 2,4-diCl—Ph |
| 3771 | 4-F | COtBu | 2,5-diCl—Ph |
| 3772 | 4-F | COtBu | 2,6-diCl—Ph |
| 3773 | 4-F | COtBu | 3,4-diCl—Ph |
| 3774 | 4-F | COtBu | 3,5-diCl—Ph |
| 3775 | 4-F | COtBu | 3,4-diCF3—Ph |
| 3776 | 4-F | COtBu | 3,5-diCF3—Ph |
| 3777 | 4-F | COtBu | 5-Cl-2-MeO—Ph |
| 3778 | 4-F | COtBu | 5-Cl-2-Me—Ph |
| 3779 | 4-F | COtBu | 2-F-5-Me—Ph |
| 3780 | 4-F | COtBu | 3-F-5-morpholino-Ph |
| 3781 | 4-F | COtBu | 3,4-OCH2O—Ph |
| 3782 | 4-F | COtBu | 3,4-OCH2CH2O—Ph |
| 3783 | 4-F | COtBu | 2-MeO-5-CONH2—Ph |
| 3784 | 4-F | COtBu | 2-MeO-4-(1-Me-5-tetrazolyl)-Ph |
| 3785 | 4-F | COtBu | 2-MeO-5-(1-Me-5-tetrazolyl)-Ph |
| 3786 | 4-F | COtBu | 3-CONH2-5-(1-Me-5-tetrazolyl)-Ph |
| 3787 | 4-F | COtBu | 1-naphthyl |
| 3788 | 4-F | COtBu | 2-naphthyl |
| 3789 | 4-F | COtBu | 2-thienyl |
| 3790 | 4-F | COtBu | 3-thienyl |
| 3791 | 4-F | COtBu | 2-furanyl |
| 3792 | 4-F | COtBu | 3-furanyl |
| 3793 | 4-F | COtBu | 2-pyridyl |
| 3794 | 4-F | COtBu | 3-pyridyl |
| 3795 | 4-F | COtBu | 4-pyridyl |
| 3796 | 4-F | COtBu | 2-indolyl |
| 3797 | 4-F | COtBu | 3-indolyl |
| 3798 | 4-F | COtBu | 5-indolyl |
| 3799 | 4-F | COtBu | 6-indolyl |
| 3800 | 4-F | COtBu | 3-indazolyl |
| 3801 | 4-F | COtBu | 5-indazolyl |
| 3802 | 4-F | COtBu | 6-indazolyl |
| 3803 | 4-F | COtBu | 2-imidazolyl |
| 3804 | 4-F | COtBu | 3-isoxazoyl |
| 3805 | 4-F | COtBu | 3-pyrazolyl |
| 3806 | 4-F | COtBu | 2-thiadiazolyl |
| 3807 | 4-F | COtBu | 2-thiazolyl |
| 3808 | 4-F | COtBu | 5-Ac-4-Me-2-thiazolyl |
| 3809 | 4-F | COtBu | 5-tetrazolyl |
| 3810 | 4-F | COtBu | 2-benzimidazolyl |
| 3811 | 4-F | COtBu | 5-benzimidazolyl |
| 3812 | 4-F | COtBu | 2-benzothiazolyl |
| 3813 | 4-F | COtBu | 5-benzothiazolyl |
| 3814 | 4-F | COtBu | 2-benzoxazolyl |
| 3815 | 4-F | COtBu | 5-benzoxazolyl |
| 3816 | 4-F | COtBu | 1-adamantyl |
| 3817 | 4-F | COtBu | 2-adamantyl |
| 3818 | 4-F | COtBu | i-Pr |
| 3819 | 4-F | COtBu | t-Bu |
| 3820 | 4-F | COtBu | c-Hex |
| 3821 | 4-F | COtBu | CH2CH2OMe |
| 3822 | 4-F | COtBu | CH2CONH2 |
| 3823 | 4-F | COtBu | CH2CO2Me |
| 3824 | 4-F | COtBu | CH(CH2Ph)CO2Me |
| 3825 | 4-F | COtBu | CH2CH2NMe2 |
| 3826 | 4-F | COtBu | benzyl |
| 3827 | 4-F | COtBu | phenethyl |
| 3828 | 4-F | COtBu | 2-(morpholin-1-yl)-Et |
| 3829 | 4-F | SO2Me | Ph |
| 3830 | 4-F | SO2Me | 3-CN—Ph |
| 3831 | 4-F | SO2Me | 3-COMe—Ph |
| 3832 | 4-F | SO2Me | 3-CO2Me—Ph |
| 3833 | 4-F | SO2Me | 3-CONH2—Ph |
| 3834 | 4-F | SO2Me | 3-CONHMe—Ph |
| 3835 | 4-F | SO2Me | 3-F—Ph |
| 3836 | 4-F | SO2Me | 3-Cl—Ph |
| 3837 | 4-F | SO2Me | 3-Br—Ph |
| 3838 | 4-F | SO2Me | 3-SO2NH2—Ph |
| 3839 | 4-F | SO2Me | 3-SO2NHMe—Ph |
| 3840 | 4-F | SO2Me | 3-CF3—Ph |
| 3841 | 4-F | SO2Me | 3-OMe—Ph |
| 3842 | 4-F | SO2Me | 3-SMe—Ph |
| 3843 | 4-F | SO2Me | 3-SOMe—Ph |
| 3844 | 4-F | SO2Me | 3-SO2Me—Ph |
| 3845 | 4-F | SO2Me | 3-OH—Ph |
| 3846 | 4-F | SO2Me | 3-CH2OH—Ph |
| 3847 | 4-F | SO2Me | 3-CHOHMe—Ph |
| 3848 | 4-F | SO2Me | 3-COH(Me)2—Ph |
| 3849 | 4-F | SO2Me | 3-Me—Ph |
| 3850 | 4-F | SO2Me | 3-Et—Ph |
| 3851 | 4-F | SO2Me | 3-iPr—Ph |
| 3852 | 4-F | SO2Me | 3-tBu—Ph |
| 3853 | 4-F | SO2Me | 3-CH2CO2Me—Ph |
| 3854 | 4-F | SO2Me | 3-(1-piperidinyl)-Ph |
| 3855 | 4-F | SO2Me | 3-(1-pyrrolidinyl)-Ph |
| 3856 | 4-F | SO2Me | 3-(2-imidazolyl)-Ph |
| 3857 | 4-F | SO2Me | 3-(1-imidazolyl)-Ph |
| 3858 | 4-F | SO2Me | 3-(2-thiazolyl)-Ph |
| 3859 | 4-F | SO2Me | 3-(3-pyrazolyl)-Ph |
| 3860 | 4-F | SO2Me | 3-(1-pyrazolyl)-Ph |
| 3861 | 4-F | SO2Me | 3-(5-Me-1-tetrazolyl)-Ph |
| 3862 | 4-F | SO2Me | 3-(1-Me-5-tetrazolyl)-Ph |
| 3863 | 4-F | SO2Me | 3-(2-pyridyl)-Ph |
| 3864 | 4-F | SO2Me | 3-(2-thienyl)-Ph |
| 3865 | 4-F | SO2Me | 3-(2-furanyl)-Ph |
| 3866 | 4-F | SO2Me | 4-CN—Ph |
| 3867 | 4-F | SO2Me | 4-COMe—Ph |
| 3868 | 4-F | SO2Me | 4-CO2Me—Ph |
| 3869 | 4-F | SO2Me | 4-CONH2—Ph |
| 3870 | 4-F | SO2Me | 4-CONHMe—Ph |
| 3871 | 4-F | SO2Me | 4-CONHPh—Ph |
| 3872 | 4-F | SO2Me | 4-F—Ph |
| 3873 | 4-F | SO2Me | 4-Cl—Ph |
| 3874 | 4-F | SO2Me | 4-Br—Ph |
| 3875 | 4-F | SO2Me | 4-SO2NH2—Ph |
| 3876 | 4-F | SO2Me | 4-SO2NHMe—Ph |
| 3877 | 4-F | SO2Me | 4-CF3—Ph |
| 3878 | 4-F | SO2Me | 4-OMe—Ph |
| 3879 | 4-F | SO2Me | 4-SMe—Ph |
| 3880 | 4-F | SO2Me | 4-SOMe—Ph |
| 3881 | 4-F | SO2Me | 4-SO2Me—Ph |
| 3882 | 4-F | SO2Me | 4-OH—Ph |
| 3883 | 4-F | SO2Me | 4-CH2OH—Ph |
| 3884 | 4-F | SO2Me | 4-CHOHMe—Ph |
| 3885 | 4-F | SO2Me | 4-COH(Me)2—Ph |
| 3886 | 4-F | SO2Me | 4-Me—Ph |
| 3887 | 4-F | SO2Me | 4-Et—Ph |
| 3888 | 4-F | SO2Me | 4-iPr—Ph |
| 3889 | 4-F | SO2Me | 4-tBu—Ph |
| 3890 | 4-F | SO2Me | 4-CH2CO2Me—Ph |
| 3891 | 4-F | SO2Me | 4-(1-piperidinyl)-Ph |

TABLE 2-continued

| | | | |
|---|---|---|---|
| 3892 | 4-F | SO2Me | 4-(1-pyrrolidinyl)-Ph |
| 3893 | 4-F | SO2Me | 4-(2-imidazolyl)-Ph |
| 3894 | 4-F | SO2Me | 4-(1-imidazolyl)-Ph |
| 3895 | 4-F | SO2Me | 4-(2-thiazolyl)-Ph |
| 3896 | 4-F | SO2Me | 4-(3-pyrazolyl)-Ph |
| 3897 | 4-F | SO2Me | 4-(1-pyrazolyl)-Ph |
| 3898 | 4-F | SO2Me | 4-(5-Me-1-tetrazolyl)-Ph |
| 3899 | 4-F | SO2Me | 4-(1-Me-5-tetrazolyl)-Ph |
| 3900 | 4-F | SO2Me | 4-(2-pyridyl)-Ph |
| 3901 | 4-F | SO2Me | 4-(2-thienyl)-Ph |
| 3902 | 4-F | SO2Me | 4-(2-furanyl)-Ph |
| 3903 | 4-F | SO2Me | 2-CN—Ph |
| 3904 | 4-F | SO2Me | 2-COMe—Ph |
| 3905 | 4-F | SO2Me | 2-CO2Me—Ph |
| 3906 | 4-F | SO2Me | 2-CONH2—Ph |
| 3907 | 4-F | SO2Me | 2-CONHMe—Ph |
| 3908 | 4-F | SO2Me | 2-F—Ph |
| 3909 | 4-F | SO2Me | 2-Cl—Ph |
| 3910 | 4-F | SO2Me | 2-Br—Ph |
| 3911 | 4-F | SO2Me | 2-SO2NH2—Ph |
| 3912 | 4-F | SO2Me | 2-SO2NHMe—Ph |
| 3913 | 4-F | SO2Me | 2-CF3—Ph |
| 3914 | 4-F | SO2Me | 2-OMe—Ph |
| 3915 | 4-F | SO2Me | 2-SMe—Ph |
| 3916 | 4-F | SO2Me | 2-SOMe—Ph |
| 3917 | 4-F | SO2Me | 2-SO2Me—Ph |
| 3918 | 4-F | SO2Me | 2-OH—Ph |
| 3919 | 4-F | SO2Me | 2-CH2OH—Ph |
| 3920 | 4-F | SO2Me | 2-CHOHMe—Ph |
| 3921 | 4-F | SO2Me | 2-COH(Me)2—Ph |
| 3922 | 4-F | SO2Me | 2-Me—Ph |
| 3923 | 4-F | SO2Me | 2-Et—Ph |
| 3924 | 4-F | SO2Me | 2-iPr—Ph |
| 3925 | 4-F | SO2Me | 2-tBu—Ph |
| 3926 | 4-F | SO2Me | 2-CH2CO2Me—Ph |
| 3927 | 4-F | SO2Me | 2-(1-piperidinyl)-Ph |
| 3928 | 4-F | SO2Me | 2-(1-pyrrolidinyl)-Ph |
| 3929 | 4-F | SO2Me | 2-(2-imidazolyl)-Ph |
| 3930 | 4-F | SO2Me | 2-(1-imidazolyl)-Ph |
| 3931 | 4-F | SO2Me | 2-(2-thiazolyl)-Ph |
| 3932 | 4-F | SO2Me | 2-(3-pyrazolyl)-Ph |
| 3933 | 4-F | SO2Me | 2-(1-pyrazolyl)-Ph |
| 3934 | 4-F | SO2Me | 2-(5-Me-1-tetrazolyl)-Ph |
| 3935 | 4-F | SO2Me | 2-(1-Me-5-tetrazolyl)-Ph |
| 3936 | 4-F | SO2Me | 2-(2-pyridyl)-Ph |
| 3937 | 4-F | SO2Me | 2-(2-thienyl)-Ph |
| 3938 | 4-F | SO2Me | 2-(2-furanyl)-Ph |
| 3939 | 4-F | SO2Me | 2,4-diF—Ph |
| 3940 | 4-F | SO2Me | 2,5-diF—Ph |
| 3941 | 4-F | SO2Me | 2,6-diF—Ph |
| 3942 | 4-F | SO2Me | 3,4-diF—Ph |
| 3943 | 4-F | SO2Me | 3,5-diF—Ph |
| 3944 | 4-F | SO2Me | 2,4-diCl—Ph |
| 3945 | 4-F | SO2Me | 2,5-diCl—Ph |
| 3946 | 4-F | SO2Me | 2,6-diCl—Ph |
| 3947 | 4-F | SO2Me | 3,4-diCl—Ph |
| 3948 | 4-F | SO2Me | 3,5-diCl—Ph |
| 3949 | 4-F | SO2Me | 3,4-diCF3—Ph |
| 3950 | 4-F | SO2Me | 3,5-diCF3—Ph |
| 3951 | 4-F | SO2Me | 5-Cl-2-MeO—Ph |
| 3952 | 4-F | SO2Me | 5-Cl-2-Me—Ph |
| 3953 | 4-F | SO2Me | 2-F-5-Me—Ph |
| 3954 | 4-F | SO2Me | 3-F-5-morpholino-Ph |
| 3955 | 4-F | SO2Me | 3,4-OCH2O—Ph |
| 3956 | 4-F | SO2Me | 3,4-OCH2CH2O—Ph |
| 3957 | 4-F | SO2Me | 2-MeO-5-CONH2—Ph |
| 3958 | 4-F | SO2Me | 2-MeO-4-(1-Me-5-tetrazolyl)-Ph |
| 3959 | 4-F | SO2Me | 2-MeO-5-(1-Me-5-tetrazolyl)-Ph |
| 3960 | 4-F | SO2Me | 3-CONH2-5-(1-Me-5-tetrazolyl)-Ph |
| 3961 | 4-F | SO2Me | 1-naphthyl |
| 3962 | 4-F | SO2Me | 2-naphthyl |
| 3963 | 4-F | SO2Me | 2-thienyl |
| 3964 | 4-F | SO2Me | 3-thienyl |
| 3965 | 4-F | SO2Me | 2-furanyl |
| 3966 | 4-F | SO2Me | 3-furanyl |
| 3967 | 4-F | SO2Me | 2-pyridyl |
| 3968 | 4-F | SO2Me | 3-pyridyl |
| 3969 | 4-F | SO2Me | 4-pyridyl |
| 3970 | 4-F | SO2Me | 2-indolyl |
| 3971 | 4-F | SO2Me | 3-indolyl |
| 3972 | 4-F | SO2Me | 5-indolyl |
| 3973 | 4-F | SO2Me | 6-indolyl |
| 3974 | 4-F | SO2Me | 3-indazolyl |
| 3975 | 4-F | SO2Me | 5-indazolyl |
| 3976 | 4-F | SO2Me | 6-indazolyl |
| 3977 | 4-F | SO2Me | 2-imidazolyl |
| 3978 | 4-F | SO2Me | 3-isoxazoyl |
| 3979 | 4-F | SO2Me | 3-pyrazolyl |
| 3980 | 4-F | SO2Me | 2-thiadiazolyl |
| 3981 | 4-F | SO2Me | 2-thiazolyl |
| 3982 | 4-F | SO2Me | 5-Ac-4-Me-2-thiazolyl |
| 3983 | 4-F | SO2Me | 5-tetrazolyl |
| 3984 | 4-F | SO2Me | 2-benzimidazolyl |
| 3985 | 4-F | SO2Me | 5-benzimidazolyl |
| 3986 | 4-F | SO2Me | 2-benzothiazolyl |
| 3987 | 4-F | SO2Me | 5-benzothiazolyl |
| 3988 | 4-F | SO2Me | 2-benzoxazolyl |
| 3989 | 4-F | SO2Me | 5-benzoxazolyl |
| 3990 | 4-F | SO2Me | 1-adamantyl |
| 3991 | 4-F | SO2Me | 2-adamantyl |
| 3992 | 4-F | SO2Me | i-Pr |
| 3993 | 4-F | SO2Me | t-Bu |
| 3994 | 4-F | SO2Me | c-Hex |
| 3995 | 4-F | SO2Me | CH2CH2OMe |
| 3996 | 4-F | SO2Me | CH2CONH2 |
| 3997 | 4-F | SO2Me | CH2CO2Me |
| 3998 | 4-F | SO2Me | CH(CH2Ph)CO2Me |
| 3999 | 4-F | SO2Me | CH2CH2NMe |
| 4000 | 4-F | SO2Me | benzyl |
| 4001 | 4-F | SO2Me | phenethyl |
| 4002 | 4-F | SO2Me | 2-(morpholin-1-yl)-Et |
| 4003 | 4-F | CH2COMe | Ph |
| 4004 | 4-F | CH2COMe | 3-CN—Ph |
| 4005 | 4-F | CH2COMe | 3-COMe—Ph |
| 4006 | 4-F | CH2COMe | 3-CO2Me—Ph |
| 4007 | 4-F | CH2COMe | 3-CONH2—Ph |
| 4008 | 4-F | CH2COMe | 3-CONHMe—Ph |
| 4009 | 4-F | CH2COMe | 3-F—Ph |
| 4010 | 4-F | CH2COMe | 3-Cl—Ph |
| 4011 | 4-F | CH2COMe | 3-Br—Ph |
| 4012 | 4-F | CH2COMe | 3-SO2NH2—Ph |
| 4013 | 4-F | CH2COMe | 3-SO2NHMe—Ph |
| 4014 | 4-F | CH2COMe | 3-CF3—Ph |
| 4015 | 4-F | CH2COMe | 3-OMe—Ph |
| 4016 | 4-F | CH2COMe | 3-SMe—Ph |
| 4017 | 4-F | CH2COMe | 3-SOMe—Ph |
| 4018 | 4-F | CH2COMe | 3-SO2Me—Ph |
| 4019 | 4-F | CH2COMe | 3-OH—Ph |
| 4020 | 4-F | CH2COMe | 3-CH2OH—Ph |
| 4021 | 4-F | CH2COMe | 3-CHOHMe—Ph |
| 4022 | 4-F | CH2COMe | 3-COH(Me)2—Ph |
| 4023 | 4-F | CH2COMe | 3-Me—Ph |
| 4024 | 4-F | CH2COMe | 3-Et—Ph |
| 4025 | 4-F | CH2COMe | 3-iPr—Ph |
| 4026 | 4-F | CH2COMe | 3-tBu—Ph |
| 4027 | 4-F | CH2COMe | 3-CH2CO2Me—Ph |
| 4028 | 4-F | CH2COMe | 3-(1-piperidinyl)-Ph |
| 4029 | 4-F | CH2COMe | 3-(1-pyrrolidinyl)-Ph |
| 4030 | 4-F | CH2COMe | 3-(2-imidazolyl)-Ph |
| 4031 | 4-F | CH2COMe | 3-(1-imidazolyl)-Ph |
| 4032 | 4-F | CH2COMe | 3-(2-thiazolyl)-Ph |
| 4033 | 4-F | CH2COMe | 3-(3-pyrazolyl)-Ph |
| 4034 | 4-F | CH2COMe | 3-(1-pyrazolyl)-Ph |
| 4035 | 4-F | CH2COMe | 3-(5-Me-1-tetrazolyl)-Ph |
| 4036 | 4-F | CH2COMe | 3-(1-Me-5-tetrazolyl)-Ph |
| 4037 | 4-F | CH2COMe | 3-(2-pyridyl)-Ph |
| 4038 | 4-F | CH2COMe | 3-(2-thienyl)-Ph |
| 4039 | 4-F | CH2COMe | 3-(2-furanyl)-Ph |
| 4040 | 4-F | CH2COMe | 4-CN—Ph |
| 4041 | 4-F | CH2COMe | 4-COMe—Ph |
| 4042 | 4-F | CH2COMe | 4-CO2Me—Ph |
| 4043 | 4-F | CH2COMe | 4-CONH2—Ph |
| 4044 | 4-F | CH2COMe | 4-CONHMe—Ph |
| 4045 | 4-F | CH2COMe | 4-CONHPh—Ph |
| 4046 | 4-F | CH2COMe | 4-F—Ph |
| 4047 | 4-F | CH2COMe | 4-Cl—Ph |
| 4048 | 4-F | CH2COMe | 4-Br—Ph |
| 4049 | 4-F | CH2COMe | 4-SO2NH2—Ph |

TABLE 2-continued

| | | | |
|---|---|---|---|
| 4050 | 4-F | CH2COMe | 4-SO2NHMe—Ph |
| 4051 | 4-F | CH2COMe | 4-CF3—Ph |
| 4052 | 4-F | CH2COMe | 4-OMe—Ph |
| 4053 | 4-F | CH2COMe | 4-SMe—Ph |
| 4054 | 4-F | CH2COMe | 4-SOMe—Ph |
| 4055 | 4-F | CH2COMe | 4-SO2Me—Ph |
| 4056 | 4-F | CH2COMe | 4-OH—Ph |
| 4057 | 4-F | CH2COMe | 4-CH2OH—Ph |
| 4058 | 4-F | CH2COMe | 4-CHOHMe—Ph |
| 4059 | 4-F | CH2COMe | 4-COH(Me)2—Ph |
| 4060 | 4-F | CH2COMe | 4-Me—Ph |
| 4061 | 4-F | CH2COMe | 4-Et—Ph |
| 4062 | 4-F | CH2COMe | 4-iPr—Ph |
| 4063 | 4-F | CH2COMe | 4-tBu—Ph |
| 4064 | 4-F | CH2COMe | 4-CH2CO2Me—Ph |
| 4065 | 4-F | CH2COMe | 4-(1-piperidinyl)-Ph |
| 4066 | 4-F | CH2COMe | 4-(1-pyrrolidinyl)-Ph |
| 4067 | 4-F | CH2COMe | 4-(2-imidazolyl)-Ph |
| 4068 | 4-F | CH2COMe | 4-(1-imidazolyl)-Ph |
| 4069 | 4-F | CH2COMe | 4-(2-thiazolyl)-Ph |
| 4070 | 4-F | CH2COMe | 4-(3-pyrazolyl)-Ph |
| 4071 | 4-F | CH2COMe | 4-(1-pyrazolyl)-Ph |
| 4072 | 4-F | CH2COMe | 4-(5-Me-1-tetrazolyl)-Ph |
| 4073 | 4-F | CH2COMe | 4-(1-Me-5-tetrazolyl)-Ph |
| 4074 | 4-F | CH2COMe | 4-(2-pyridyl)-Ph |
| 4075 | 4-F | CH2COMe | 4-(2-thienyl)-Ph |
| 4076 | 4-F | CH2COMe | 4-(2-furanyl)-Ph |
| 4077 | 4-F | CH2COMe | 2-CN—Ph |
| 4078 | 4-F | CH2COMe | 2-COMe—Ph |
| 4079 | 4-F | CH2COMe | 2-CO2Me—Ph |
| 4080 | 4-F | CH2COMe | 2-CONH2—Ph |
| 4081 | 4-F | CH2COMe | 2-CONHMe—Ph |
| 4082 | 4-F | CH2COMe | 2-F—Ph |
| 4083 | 4-F | CH2COMe | 2-Cl—Ph |
| 4084 | 4-F | CH2COMe | 2-Br—Ph |
| 4085 | 4-F | CH2COMe | 2-SO2NH2—Ph |
| 4086 | 4-F | CH2COMe | 2-SO2NHMe—Ph |
| 4087 | 4-F | CH2COMe | 2-CF3—Ph |
| 4088 | 4-F | CH2COMe | 2-OMe—Ph |
| 4089 | 4-F | CH2COMe | 2-SMe—Ph |
| 4090 | 4-F | CH2COMe | 2-SOMe—Ph |
| 4091 | 4-F | CH2COMe | 2-SO2Me—Ph |
| 4092 | 4-F | CH2COMe | 2-OH—Ph |
| 4093 | 4-F | CH2COMe | 2-CH2OH—Ph |
| 4094 | 4-F | CH2COMe | 2-CHOHMe—Ph |
| 4095 | 4-F | CH2COMe | 2-COH(Me)2—Ph |
| 4096 | 4-F | CH2COMe | 2-Me—Ph |
| 4097 | 4-F | CH2COMe | 2-Et—Ph |
| 4098 | 4-F | CH2COMe | 2-iPr—Ph |
| 4099 | 4-F | CH2COMe | 2-tBu—Ph |
| 4100 | 4-F | CH2COMe | 2-CH2CO2Me—Ph |
| 4101 | 4-F | CH2COMe | 2-(1-piperidinyl)-Ph |
| 4102 | 4-F | CH2COMe | 2-(1-pyrrolidinyl)-Ph |
| 4103 | 4-F | CH2COMe | 2-(2-imidazolyl)-Ph |
| 4104 | 4-F | CH2COMe | 2-(1-imidazolyl)-Ph |
| 4105 | 4-F | CH2COMe | 2-(2-thiazolyl)-Ph |
| 4106 | 4-F | CH2COMe | 2-(3-pyrazolyl)-Ph |
| 4107 | 4-F | CH2COMe | 2-(1-pyrazolyl)-Ph |
| 4108 | 4-F | CH2COMe | 2-(5-Me-1-tetrazolyl)-Ph |
| 4109 | 4-F | CH2COMe | 2-(1-Me-5-tetrazolyl)-Ph |
| 4110 | 4-F | CH2COMe | 2-(2-pyridyl)-Ph |
| 4111 | 4-F | CH2COMe | 2-(2-thienyl)-Ph |
| 4112 | 4-F | CH2COMe | 2-(2-furanyl)-Ph |
| 4113 | 4-F | CH2COMe | 2,4-diF—Ph |
| 4114 | 4-F | CH2COMe | 2,5-diF—Ph |
| 4115 | 4-F | CH2COMe | 2,6-diF—Ph |
| 4116 | 4-F | CH2COMe | 3,4-diF—Ph |
| 4117 | 4-F | CH2COMe | 3,5-diF—Ph |
| 4118 | 4-F | CH2COMe | 2,4-diCl—Ph |
| 4119 | 4-F | CH2COMe | 2,5-diCl—Ph |
| 4120 | 4-F | CH2COMe | 2,6-diCl—Ph |
| 4121 | 4-F | CH2COMe | 3,4-diCl—Ph |
| 4i22 | 4-F | CH2COMe | 3,5-diCl—Ph |
| 4123 | 4-F | CH2COMe | 3,4-diCF3—Ph |
| 4124 | 4-F | CH2COMe | 3,5-diCF3—Ph |
| 4125 | 4-F | CH2COMe | 5-Cl-2-MeO—Ph |
| 4126 | 4-F | CH2COMe | 5-Cl-2-Me—Ph |
| 4127 | 4-F | CH2COMe | 2-F-5-Me—Ph |
| 4128 | 4-F | CH2COMe | 3-F-5-morpholino-Ph |
| 4129 | 4-F | CH2COMe | 3,4-OCH2O—Ph |
| 4130 | 4-F | CH2COMe | 3,4-OCH2CH2O—Ph |
| 4131 | 4-F | CH2COMe | 2-MeO-5-CONH2—Ph |
| 4132 | 4-F | CH2COMe | 2-MeO-4-(1-Me-5-tetrazolyl)-Ph |
| 4133 | 4-F | CH2COMe | 2-MeO-5-(1-Me-5-tetrazolyl)-Ph |
| 4134 | 4-F | CH2COMe | 3-CONH2-5-(1-Me-5-tetrazolyl)-Ph |
| 4135 | 4-F | CH2COMe | 1-naphthyl |
| 4136 | 4-F | CH2COMe | 2-naphthyl |
| 4137 | 4-F | CH2COMe | 2-thienyl |
| 4138 | 4-F | CH2COMe | 3-thienyl |
| 4139 | 4-F | CH2COMe | 2-furanyl |
| 4140 | 4-F | CH2COMe | 3-furanyl |
| 4141 | 4-F | CH2COMe | 2-pyridyl |
| 4142 | 4-F | CH2COMe | 3-pyridyl |
| 4143 | 4-F | CH2COMe | 4-pyridyl |
| 4144 | 4-F | CH2COMe | 2-indolyl |
| 4145 | 4-F | CH2COMe | 3-indolyl |
| 4146 | 4-F | CH2COMe | 5-indolyl |
| 4147 | 4-F | CH2COMe | 6-indolyl |
| 4148 | 4-F | CH2COMe | 3-indazolyl |
| 4149 | 4-F | CH2COMe | 5-indazolyl |
| 4150 | 4-F | CH2COMe | 6-indazolyl |
| 4151 | 4-F | CH2COMe | 2-imidazolyl |
| 4152 | 4-F | CH2COMe | 3-isoxazoyl |
| 4153 | 4-F | CH2COMe | 3-pyrazolyl |
| 4154 | 4-F | CH2COMe | 2-thiadiazolyl |
| 4155 | 4-F | CH2COMe | 2-thiazolyl |
| 4156 | 4-F | CH2COMe | 5-Ac-4-Me-2-thiazolyl |
| 4157 | 4-F | CH2COMe | 5-tetrazolyl |
| 4158 | 4-F | CH2COMe | 2-benzimidazolyl |
| 4159 | 4-F | CH2COMe | 5-benzimidazolyl |
| 4160 | 4-F | CH2COMe | 2-benzothiazolyl |
| 4161 | 4-F | CH2COMe | 5-benzothiazolyl |
| 4162 | 4-F | CH2COMe | 2-benzoxazolyl |
| 4163 | 4-F | CH2COMe | 5-benzoxazolyl |
| 4164 | 4-F | CH2COMe | 1-adamantyl |
| 4165 | 4-F | CH2COMe | 2-adamantyl |
| 4166 | 4-F | CH2COMe | i-Pr |
| 4167 | 4-F | CH2COMe | t-Bu |
| 4168 | 4-F | CH2COMe | c-Hex |
| 4169 | 4-F | CH2COMe | CH2CH2OMe |
| 4170 | 4-F | CH2COMe | CH2CONH2 |
| 4171 | 4-F | CH2COMe | CH2CO2Me |
| 4172 | 4-F | CH2COMe | CH(CH2Ph)CO2Me |
| 4173 | 4-F | CH2COMe | CH2CH2NMe2 |
| 4174 | 4-F | CH2COMe | benzyl |
| 4175 | 4-F | CH2COMe | phenethyl |
| 4176 | 4-F | CH2COMe | 2-(morpholin-1-yl)-Et |
| 4177 | 4-Cl | H | Ph |
| 4178 | 4-Cl | H | 3-CN—Ph |
| 4179 | 4-Cl | H | 3-COMe—Ph |
| 4180 | 4-Cl | H | 3-CO2Me—Ph |
| 4181 | 4-Cl | H | 3-CONH2—Ph |
| 4182 | 4-Cl | H | 3-CONHMe—Ph |
| 4183 | 4-Cl | H | 3-F—Ph |
| 4184 | 4-Cl | H | 3-Cl—Ph |
| 4185 | 4-Cl | H | 3-Br—Ph |
| 4186 | 4-Cl | H | 3-SO2NH2—Ph |
| 4187 | 4-Cl | H | 3-SO2NHMe—Ph |
| 4188 | 4-Cl | H | 3-CF3—Ph |
| 4189 | 4-Cl | H | 3-OMe—Ph |
| 4190 | 4-Cl | H | 3-SMe—Ph |
| 4191 | 4-Cl | H | 3-SOMe—Ph |
| 4192 | 4-Cl | H | 3-SO2Me—Ph |
| 4193 | 4-Cl | H | 3-OH—Ph |
| 4194 | 4-Cl | H | 3-CH2OH—Ph |
| 4195 | 4-Cl | H | 3-CHOHMe—Ph |
| 4196 | 4-Cl | H | 3-COH(Me)2—Ph |
| 4197 | 4-Cl | H | 3-Me—Ph |
| 4198 | 4-Cl | H | 3-Et—Ph |
| 4199 | 4-Cl | H | 3-iPr—Ph |
| 4200 | 4-Cl | H | 3-tBu—Ph |
| 4201 | 4-Cl | H | 3-CH2CO2Me—Ph |
| 4202 | 4-Cl | H | 3-(1-piperidinyl)-Ph |
| 4203 | 4-Cl | H | 3-(1-pyrrolidinyl)-Ph |
| 4204 | 4-Cl | H | 3-(2-imidazolyl)-Ph |
| 4205 | 4-Cl | H | 3-(1-imidazolyl)-Ph |
| 4206 | 4-Cl | H | 3-(2-thiazolyl)-Ph |
| 4207 | 4-Cl | H | 3-(3-pyrazolyl)-Ph |

TABLE 2-continued

| | | | |
|---|---|---|---|
| 4208 | 4-Cl | H | 3-(1-pyrazolyl)-Ph |
| 4209 | 4-Cl | H | 3-(5-Me-1-tetrazolyl)-Ph |
| 4210 | 4-Cl | H | 3-(1-Me-5-tetrazolyl)-Ph |
| 4211 | 4-Cl | H | 3-(2-pyridyl)-Ph |
| 4212 | 4-Cl | H | 3-(2-thienyl)-Ph |
| 4213 | 4-Cl | H | 3-(2-furanyl)-Ph |
| 4214 | 4-Cl | H | 4-CN—Ph |
| 4215 | 4-Cl | H | 4-COMe—Ph |
| 4216 | 4-Cl | H | 4-CO2Me—Ph |
| 4217 | 4-Cl | H | 4-CONH2—Ph |
| 4218 | 4-Cl | H | 4-CONHMe—Ph |
| 4219 | 4-Cl | H | 4-CONHPh—Ph |
| 4220 | 4-Cl | H | 4-F—Ph |
| 4221 | 4-Cl | H | 4-Cl—Ph |
| 4222 | 4-Cl | H | 4-Br—Ph |
| 4223 | 4-Cl | H | 4-SO2NH2—Ph |
| 4224 | 4-Cl | H | 4-SO2NHMe—Ph |
| 4225 | 4-Cl | H | 4-CF3—Ph |
| 4226 | 4-Cl | H | 4-OMe—Ph |
| 4227 | 4-Cl | H | 4-SMe—Ph |
| 4228 | 4-Cl | H | 4-SOMe—Ph |
| 4229 | 4-Cl | H | 4-SO2Me—Ph |
| 4230 | 4-Cl | H | 4-OH—Ph |
| 4231 | 4-Cl | H | 4-CH2OH—Ph |
| 4232 | 4-Cl | H | 4-CHOHMe—Ph |
| 4233 | 4-Cl | H | 4-COH(Me)2—Ph |
| 4234 | 4-Cl | H | 4-Me—Ph |
| 4235 | 4-Cl | H | 4-Et—Ph |
| 4236 | 4-Cl | H | 4-iPr—Ph |
| 4237 | 4-Cl | H | 4-tBu—Ph |
| 4238 | 4-Cl | H | 4-CH2CO2Me—Ph |
| 4239 | 4-Cl | H | 4-(1-piperidinyl)-Ph |
| 4240 | 4-Cl | H | 4-(1-pyrrolidinyl)-Ph |
| 4241 | 4-Cl | H | 4-(2-imidazolyl)-Ph |
| 4242 | 4-Cl | H | 4-(1-imidazolyl)-Ph |
| 4243 | 4-Cl | H | 4-(2-thiazolyl)-Ph |
| 4244 | 4-Cl | H | 4-(3-pyrazolyl)-Ph |
| 4245 | 4-Cl | H | 4-(1-pyrazolyl)-Ph |
| 4246 | 4-Cl | H | 4-(5-Me-1-tetrazolyl)-Ph |
| 4247 | 4-Cl | H | 4-(1-Me-5-tetrazolyl)-Ph |
| 4248 | 4-Cl | H | 4-(2-pyridyl)-Ph |
| 4249 | 4-Cl | H | 4-(2-thienyl)-Ph |
| 4250 | 4-Cl | H | 4-(2-furanyl)-Ph |
| 4251 | 4-Cl | H | 2-CN—Ph |
| 4252 | 4-Cl | H | 2-COMe—Ph |
| 4253 | 4-Cl | H | 2-CO2Me—Ph |
| 4254 | 4-Cl | H | 2-CONH2—Ph |
| 4255 | 4-Cl | H | 2-CONHMe—Ph |
| 4256 | 4-Cl | H | 2-F—Ph |
| 4257 | 4-Cl | H | 2-Cl—Ph |
| 4258 | 4-Cl | H | 2-Br—Ph |
| 4259 | 4-Cl | H | 2-SO2NH2—Ph |
| 4260 | 4-Cl | H | 2-SO2NHMe—Ph |
| 4261 | 4-Cl | H | 2-CF3—Ph |
| 4262 | 4-Cl | H | 2-OMe—Ph |
| 4263 | 4-Cl | H | 2-SMe—Ph |
| 4264 | 4-Cl | H | 2-SOMe—Ph |
| 4265 | 4-Cl | H | 2-SO2Me—Ph |
| 4266 | 4-Cl | H | 2-OH—Ph |
| 4267 | 4-Cl | H | 2-CH2OH—Ph |
| 4268 | 4-Cl | H | 2-CHOHMe—Ph |
| 4269 | 4-Cl | H | 2-COH(Me)2—Ph |
| 4270 | 4-Cl | H | 2-Me—Ph |
| 4271 | 4-Cl | H | 2-Et—Ph |
| 4272 | 4-Cl | H | 2-iPr—Ph |
| 4273 | 4-Cl | H | 2-tBu—Ph |
| 4274 | 4-Cl | H | 2-CH2CO2Me—Ph |
| 4275 | 4-Cl | H | 2-(1-piperidinyl)-Ph |
| 4276 | 4-Cl | H | 2-(1-pyrrolidinyl)-Ph |
| 4277 | 4-Cl | H | 2-(2-imidazolyl)-Ph |
| 4278 | 4-Cl | H | 2-(1-imidazolyl)-Ph |
| 4279 | 4-Cl | H | 2-(2-thiazolyl)-Ph |
| 4280 | 4-Cl | H | 2-(3-pyrazolyl)-Ph |
| 4281 | 4-Cl | H | 2-(1-pyrazolyl)-Ph |
| 4282 | 4-Cl | H | 2-(5-Me-1-tetrazolyl)-Ph |
| 4283 | 4-Cl | H | 2-(1-Me-5-tetrazolyl)-Ph |
| 4284 | 4-Cl | H | 2-(2-pyridyl)-Ph |
| 4285 | 4-Cl | H | 2-(2-thienyl)-Ph |
| 4286 | 4-Cl | H | 2-(2-furanyl)-Ph |
| 4287 | 4-Cl | H | 2,4-diF—Ph |
| 4288 | 4-Cl | H | 2,5-diF—Ph |
| 4289 | 4-Cl | H | 2,6-diF—Ph |
| 4290 | 4-Cl | H | 3,4-diF—Ph |
| 4291 | 4-Cl | H | 3,5-diF—Ph |
| 4292 | 4-Cl | H | 2,4-diCl—Ph |
| 4293 | 4-Cl | H | 2,5-diCl—Ph |
| 4294 | 4-Cl | H | 2,6-diCl—Ph |
| 4295 | 4-Cl | H | 3,4-diCl—Ph |
| 4296 | 4-Cl | H | 3,5-diCl—Ph |
| 4297 | 4-Cl | H | 3,4-diCF3—Ph |
| 4298 | 4-Cl | H | 3,5-diCF3—Ph |
| 4299 | 4-Cl | H | 5-Cl-2-MeO—Ph |
| 4300 | 4-Cl | H | 5-Cl-2-Me—Ph |
| 4301 | 4-Cl | H | 2-F-5-Me—Ph |
| 4302 | 4-Cl | H | 3-F-5-morpholino-Ph |
| 4303 | 4-Cl | H | 3,4-OCH2O—Ph |
| 4304 | 4-Cl | H | 3,4-OCH2CH2O—Ph |
| 4305 | 4-Cl | H | 2-MeO-5-CONH2—Ph |
| 4306 | 4-Cl | H | 2-MeO-4-(1-Me-5-tetrazolyl)-Ph |
| 4307 | 4-Cl | H | 2-MeO-5-(1-Me-5-tetrazolyl)-Ph |
| 4308 | 4-Cl | H | 3-CONH2-5-(1-Me-5-tetrazolyl)-Ph |
| 4309 | 4-Cl | H | 1-naphthyl |
| 4310 | 4-Cl | H | 2-naphthyl |
| 4311 | 4-Cl | H | 2-thienyl |
| 4312 | 4-Cl | H | 3-thienyl |
| 4313 | 4-Cl | H | 2-furanyl |
| 4314 | 4-Cl | H | 3-furanyl |
| 4315 | 4-Cl | H | 2-pyridyl |
| 4316 | 4-Cl | H | 3-pyridyl |
| 4317 | 4-Cl | H | 4-pyridyl |
| 4318 | 4-Cl | H | 2-indolyl |
| 4319 | 4-Cl | H | 3-indolyl |
| 4320 | 4-Cl | H | 5-indolyl |
| 4321 | 4-Cl | H | 6-indolyl |
| 4322 | 4-Cl | H | 3-indazolyl |
| 4323 | 4-Cl | H | 5-indazolyl |
| 4324 | 4-Cl | H | 6-indazolyl |
| 4325 | 4-Cl | H | 2-imidazolyl |
| 4326 | 4-Cl | H | 3-isoxazoyl |
| 4327 | 4-Cl | H | 3-pyrazolyl |
| 4328 | 4-Cl | H | 2-thiadiazolyl |
| 4329 | 4-Cl | H | 2-thiazolyl |
| 4330 | 4-Cl | H | 5-Ac-4-Me-2-thiazolyl |
| 4331 | 4-Cl | H | 5-tetrazolyl |
| 4332 | 4-Cl | H | 2-benzimidazolyl |
| 4333 | 4-Cl | H | 5-benzimidazolyl |
| 4334 | 4-Cl | H | 2-benzothiazolyl |
| 4335 | 4-Cl | H | 5-benzothiazolyl |
| 4336 | 4-Cl | H | 2-benzoxazolyl |
| 4337 | 4-Cl | H | 5-benzoxazolyl |
| 4338 | 4-Cl | H | 1-adamantyl |
| 4339 | 4-Cl | H | 2-adamantyl |
| 4340 | 4-Cl | H | i-Pr |
| 4341 | 4-Cl | H | t-Bu |
| 4342 | 4-Cl | H | c-Hex |
| 4343 | 4-Cl | H | CH2CH2OMe |
| 4344 | 4-Cl | H | CH2CONH2 |
| 4345 | 4-Cl | H | CH2CO2Me |
| 4346 | 4-Cl | H | CH(CH2Ph)CO2Me |
| 4347 | 4-Cl | H | CH2CH2NMe2 |
| 4348 | 4-Cl | H | benzyl |
| 4349 | 4-Cl | H | phenethyl |
| 4350 | 4-Cl | H | 2-(morpholin-1-yl)-Et |
| 4351 | 4-Cl | Me | Ph |
| 4352 | 4-Cl | Me | 3-CN—Ph |
| 4353 | 4-Cl | Me | 3-COMe—Ph |
| 4354 | 4-Cl | Me | 3-CO2Me—Ph |
| 4355 | 4-Cl | Me | 3-CONH2—Ph |
| 4356 | 4-Cl | Me | 3-CONHMe—Ph |
| 4357 | 4-Cl | Me | 3-F—Ph |
| 4358 | 4-Cl | Me | 3-Cl—Ph |
| 4359 | 4-Cl | Me | 3-Br—Ph |
| 4360 | 4-Cl | Me | 3-SO2NH2—Ph |
| 4361 | 4-Cl | Me | 3-SO2NHMe—Ph |
| 4362 | 4-Cl | Me | 3-CF3—Ph |
| 4363 | 4-Cl | Me | 3-OMe—Ph |
| 4364 | 4-Cl | Me | 3-SMe—Ph |
| 4365 | 4-Cl | Me | 3-SOMe—Ph |

TABLE 2-continued

| | | | |
|---|---|---|---|
| 4366 | 4-Cl | Me | 3-SO2Me—Ph |
| 4367 | 4-Cl | Me | 3-OH—Ph |
| 4368 | 4-Cl | Me | 3-CH2OH—Ph |
| 4369 | 4-Cl | Me | 3-CHOHMe—Ph |
| 4370 | 4-Cl | Me | 3-COH(Me)2—Ph |
| 4371 | 4-Cl | Me | 3-Me—Ph |
| 4372 | 4-Cl | Me | 3-Et—Ph |
| 4373 | 4-Cl | Me | 3-iPr—Ph |
| 4374 | 4-Cl | Me | 3-tBu—Ph |
| 4375 | 4-Cl | Me | 3-cH2CO2Me—Ph |
| 4376 | 4-Cl | Me | 3-(1-piperidinyl)-Ph |
| 4377 | 4-Cl | Me | 3-(1-pyrrolidinyl)-Ph |
| 4378 | 4-Cl | Me | 3-(2-imidazolyl)-Ph |
| 4379 | 4-Cl | Me | 3-(1-imidazolyl)-Ph |
| 4380 | 4-Cl | Me | 3-(2-thiazolyl)-Ph |
| 4381 | 4-Cl | Me | 3-(3-pyrazolyl)-Ph |
| 4382 | 4-Cl | Me | 3-(1-pyrazolyl)-Ph |
| 4383 | 4-Cl | Me | 3-(5-Me-1-tetrazolyl)-Ph |
| 4384 | 4-Cl | Me | 3-(1-Me-5-tetrazolyl)-Ph |
| 4385 | 4-Cl | Me | 3-(2-pyridyl)-Ph |
| 4386 | 4-Cl | Me | 3-(2-thienyl)-Ph |
| 4387 | 4-Cl | Me | 3-(2-furanyl)-Ph |
| 4388 | 4-Cl | Me | 4-CN—Ph |
| 4389 | 4-Cl | Me | 4-COMe—Ph |
| 4390 | 4-Cl | Me | 4-CO2Me—Ph |
| 4391 | 4-Cl | Me | 4-CONH2—Ph |
| 4392 | 4-Cl | Me | 4-CONHMe—Ph |
| 4393 | 4-Cl | Me | 4-CONHPh—Ph |
| 4394 | 4-Cl | Me | 4-F—Ph |
| 4395 | 4-Cl | Me | 4-Cl—Ph |
| 4396 | 4-Cl | Me | 4-Br—Ph |
| 4397 | 4-Cl | Me | 4-SO2NH2—Ph |
| 4398 | 4-Cl | Me | 4-SO2NHMe—Ph |
| 4399 | 4-Cl | Me | 4-CF3—Ph |
| 4400 | 4-Cl | Me | 4-OMe—Ph |
| 4401 | 4-Cl | Me | 4-SMe—Ph |
| 4402 | 4-Cl | Me | 4-SOMe—Ph |
| 4403 | 4-Cl | Me | 4-SO2Me—Ph |
| 4404 | 4-Cl | Me | 4-OH—Ph |
| 4405 | 4-Cl | Me | 4-CH2OH—Ph |
| 4406 | 4-Cl | Me | 4-CHOHMe—Ph |
| 4407 | 4-Cl | Me | 4-COH(Me)2—Ph |
| 4408 | 4-Cl | Me | 4-Me—Ph |
| 4409 | 4-Cl | Me | 4-Et—Ph |
| 4410 | 4-Cl | Me | 4-iPr—Ph |
| 4411 | 4-Cl | Me | 4-tBu—Ph |
| 4412 | 4-Cl | Me | 4-CH2CO2Me—Ph |
| 4413 | 4-Cl | Me | 4-(1-piperidinyl)-Ph |
| 4414 | 4-Cl | Me | 4-(1-pyrrolidinyl)-Ph |
| 4415 | 4-Cl | Me | 4-(2-imidazolyl)-Ph |
| 4416 | 4-Cl | Me | 4-(1-imidazolyl)-Ph |
| 4417 | 4-Cl | Me | 4-(2-thiazolyl)-Ph |
| 4418 | 4-Cl | Me | 4-(3-pyrazolyl)-Ph |
| 4419 | 4-Cl | Me | 4-(1-pyrazolyl)-Ph |
| 4420 | 4-Cl | Me | 4-(5-Me-1-tetrazolyl)-Ph |
| 4421 | 4-Cl | Me | 4-(1-Me-5-tetrazolyl)-Ph |
| 4422 | 4-Cl | Me | 4-(2-pyridyl)-Ph |
| 4423 | 4-Cl | Me | 4-(2-thienyl)-Ph |
| 4424 | 4-Cl | Me | 4-(2-furanyl)-Ph |
| 4425 | 4-Cl | Me | 2-CN—Ph |
| 4426 | 4-Cl | Me | 2-COMe—Ph |
| 4427 | 4-Cl | Me | 2-CO2Me—Ph |
| 4428 | 4-Cl | Me | 2-CONH2—Ph |
| 4429 | 4-Cl | Me | 2-CONHMe—Ph |
| 4430 | 4-Cl | Me | 2-F—Ph |
| 4431 | 4-Cl | Me | 2-Cl—Ph |
| 4432 | 4-Cl | Me | 2-Br—Ph |
| 4433 | 4-Cl | Me | 2-SO2NH2—Ph |
| 4434 | 4-Cl | Me | 2-SO2NHMe—Ph |
| 4435 | 4-Cl | Me | 2-CF3—Ph |
| 4436 | 4-Cl | Me | 2-OMe—Ph |
| 4437 | 4-Cl | Me | 2-SMe—Ph |
| 4438 | 4-Cl | Me | 2-SOMe—Ph |
| 4439 | 4-Cl | Me | 2-SO2Me—Ph |
| 4440 | 4-Cl | Me | 2-OH—Ph |
| 4441 | 4-Cl | Me | 2-CH2OH—Ph |
| 4442 | 4-Cl | Me | 2-CHOHMe—Ph |
| 4443 | 4-Cl | Me | 2-COH(Me)2—Ph |
| 4444 | 4-Cl | Me | 2-Me—Ph |
| 4445 | 4-Cl | Me | 2-Et—Ph |
| 4446 | 4-Cl | Me | 2-iPr—Ph |
| 4447 | 4-Cl | Me | 2-tBu—Ph |
| 4448 | 4-Cl | Me | 2-CH2CO2Me—Ph |
| 4449 | 4-Cl | Me | 2-(1-piperidinyl)-Ph |
| 4450 | 4-Cl | Me | 2-(1-pyrrolidinyl)-Ph |
| 4451 | 4-Cl | Me | 2-(2-imidazolyl)-Ph |
| 4452 | 4-Cl | Me | 2-(1-imidazolyl)-Ph |
| 4453 | 4-Cl | Me | 2-(2-thiazolyl)-Ph |
| 4454 | 4-Cl | Me | 2-(3-pyrazolyl)-Ph |
| 4455 | 4-Cl | Me | 2-(1-pyrazolyl)-Ph |
| 4456 | 4-Cl | Me | 2-(5-Me-1-tetrazolyl)-Ph |
| 4457 | 4-Cl | Me | 2-(1-Me-5-tetrazolyl)-Ph |
| 4458 | 4-Cl | Me | 2-(2-pyridyl)-Ph |
| 4459 | 4-Cl | Me | 2-(2-thienyl)-Ph |
| 4460 | 4-Cl | Me | 2-(2-furanyl)-Ph |
| 4461 | 4-Cl | Me | 2,4-diF—Ph |
| 4462 | 4-Cl | Me | 2,5-diF—Ph |
| 4463 | 4-Cl | Me | 2,6-diF—Ph |
| 4464 | 4-Cl | Me | 3,4-diF—Ph |
| 4465 | 4-Cl | Me | 3,5-diF—Ph |
| 4466 | 4-Cl | Me | 2,4-diCl—Ph |
| 4467 | 4-Cl | Me | 2,5-diCl—Ph |
| 4468 | 4-Cl | Me | 2,6-diCl—Ph |
| 4469 | 4-Cl | Me | 3,4-diCl—Ph |
| 4470 | 4-Cl | Me | 3,5-diCl—Ph |
| 4471 | 4-Cl | Me | 3,4-diCF3—Ph |
| 4472 | 4-Cl | Me | 3,5-diCF3—Ph |
| 4473 | 4-Cl | Me | 5-Cl-2-MeO—Ph |
| 4474 | 4-Cl | Me | 5-Cl-2-Me—Ph |
| 4475 | 4-Cl | Me | 2-F-5-Me—Ph |
| 4476 | 4-Cl | Me | 3-F-5-morpholino-Ph |
| 4477 | 4-Cl | Me | 3,4-OCH2O—Ph |
| 4478 | 4-Cl | Me | 3,4-OCH2CH2O—Ph |
| 4479 | 4-Cl | Me | 2-MeO-5-CONH2—Ph |
| 4480 | 4-Cl | Me | 2-MeO-4-(1-Me-5-tetrazolyl)-Ph |
| 4481 | 4-Cl | Me | 2-MeO-5-(1-Me-5-tetrazolyl)-Ph |
| 4482 | 4-Cl | Me | 3-CONH2-5-(1-Me-5-tetrazolyl)-Ph |
| 4483 | 4-Cl | Me | 1-naphthyl |
| 4484 | 4-Cl | Me | 2-naphthyl |
| 4485 | 4-Cl | Me | 2-thienyl |
| 4486 | 4-Cl | Me | 3-thienyl |
| 4487 | 4-Cl | Me | 2-furanyl |
| 4488 | 4-Cl | Me | 3-furanyl |
| 4489 | 4-Cl | Me | 2-pyridyl |
| 4490 | 4-Cl | Me | 3-pyridyl |
| 4491 | 4-Cl | Me | 4-pyridyl |
| 4492 | 4-Cl | Me | 2-indolyl |
| 4493 | 4-Cl | Me | 3-indolyl |
| 4494 | 4-Cl | Me | 5-indolyl |
| 4495 | 4-Cl | Me | 6-indolyl |
| 4496 | 4-Cl | Me | 3-indazolyl |
| 4497 | 4-Cl | Me | 5-indazolyl |
| 4498 | 4-Cl | Me | 6-indazolyl |
| 4499 | 4-Cl | Me | 2-imidazolyl |
| 4500 | 4-Cl | Me | 3-isoxazoyl |
| 4501 | 4-Cl | Me | 3-pyrazolyl |
| 4502 | 4-Cl | Me | 2-thiadiazolyl |
| 4503 | 4-Cl | Me | 2-thiazolyl |
| 4504 | 4-Cl | Me | 5-Ac-4-Me-2-thiazolyl |
| 4505 | 4-Cl | Me | 5-tetrazolyl |
| 4506 | 4-Cl | Me | 2-benzinidazolyl |
| 4507 | 4-Cl | Me | 5-benzimidazolyl |
| 4508 | 4-Cl | Me | 2-benzothiazolyl |
| 4509 | 4-Cl | Me | 5-benzothiazolyl |
| 4510 | 4-Cl | Me | 2-benzoxazolyl |
| 4511 | 4-Cl | Me | 5-benzoxazolyl |
| 4512 | 4-Cl | Me | 1-adanantyl |
| 4513 | 4-Cl | Me | 2-adamantyl |
| 4514 | 4-Cl | Me | i-Pr |
| 4515 | 4-Cl | Me | t-Bu |
| 4516 | 4-Cl | Me | c-Hex |
| 4517 | 4-Cl | Me | CH2CH2OMe |
| 4518 | 4-Cl | Me | CH2CONH2 |
| 4519 | 4-Cl | Me | CH2CO2Me |
| 4520 | 4-Cl | Me | CH(CH2Ph)CO2Me |
| 4521 | 4-Cl | Me | CH2CH2NMe2 |
| 4522 | 4-Cl | Me | benzyl |
| 4523 | 4-Cl | Me | phenethyl |

TABLE 2-continued

| | | | |
|---|---|---|---|
| 4524 | 4-Cl | Me | 2-(morpholin-1-yl)-Et |
| 4525 | 4-Cl | 2-F—Et | Ph |
| 4526 | 4-Cl | 2-F—Et | 3-CN—Ph |
| 4527 | 4-Cl | 2-F—Et | 3-COMe—Ph |
| 4528 | 4-Cl | 2-F—Et | 3-CO2Me—Ph |
| 4529 | 4-Cl | 2-F—Et | 3-CONH2—Ph |
| 4530 | 4-Cl | 2-F—Et | 3-CONHMe—Ph |
| 4531 | 4-Cl | 2-F—Et | 3-F—Ph |
| 4532 | 4-Cl | 2-F—Et | 3-Cl—Ph |
| 4533 | 4-Cl | 2-F—Et | 3-Br—Ph |
| 4534 | 4-Cl | 2-F—Et | 3-SO2NH2—Ph |
| 4535 | 4-Cl | 2-F—Et | 3-SO2NHMe—Ph |
| 4536 | 4-Cl | 2-F—Et | 3-CF3—Ph |
| 4537 | 4-Cl | 2-F—Et | 3-OMe—Ph |
| 4538 | 4-Cl | 2-F—Et | 3-SMe—Ph |
| 4539 | 4-Cl | 2-F—Et | 3-SOMe—Ph |
| 4540 | 4-Cl | 2-F—Et | 3-SO2Me—Ph |
| 4541 | 4-Cl | 2-F—Et | 3-OH—Ph |
| 4542 | 4-Cl | 2-F—Et | 3-CH2OH—Ph |
| 4543 | 4-Cl | 2-F—Et | 3-CHOHMe—Ph |
| 4544 | 4-Cl | 2-F—Et | 3-COH(Me)2—Ph |
| 4545 | 4-Cl | 2-F—Et | 3-Me—Ph |
| 4546 | 4-Cl | 2-F—Et | 3-Et—Ph |
| 4547 | 4-Cl | 2-F—Et | 3-iPr—Ph |
| 4548 | 4-Cl | 2-F—Et | 3-LBu—Ph |
| 4549 | 4-Cl | 2-F—Et | 3-CH2CO2Me—Ph |
| 4550 | 4-Cl | 2-F—Et | 3-(1-piperidinyl)-Ph |
| 4551 | 4-Cl | 2-F—Et | 3-(1-pyrrolidinyl)-Ph |
| 4552 | 4-Cl | 2-F—Et | 3-(2-imidazolyl)-Ph |
| 4553 | 4-Cl | 2-F—Et | 3-(1-imidazolyl)-Ph |
| 4554 | 4-Cl | 2-F—Et | 3-(2-thiazolyl)-Ph |
| 4555 | 4-Cl | 2-F—Et | 3-(3-pyrazolyl)-Ph |
| 4556 | 4-Cl | 2-F—Et | 3-(1-pyrazolyl)-Ph |
| 4557 | 4-Cl | 2-F—Et | 3-(5-Me-1-tetrazolyl)-Ph |
| 4558 | 4-Cl | 2-F—Et | 3-(1-Me-5-tetrazolyl)-Ph |
| 4559 | 4-Cl | 2-F—Et | 3-(2-pyridyl)-Ph |
| 4560 | 4-Cl | 2-F—Et | 3-(2-thienyl)-Ph |
| 4561 | 4-Cl | 2-F—Et | 3- (2-furanyl)-Ph |
| 4562 | 4-Cl | 2-F—Et | 4-CN—Ph |
| 4563 | 4-Cl | 2-F—Et | 4-COMe—Ph |
| 4564 | 4-Cl | 2-F—Et | 4-CO2Me—Ph |
| 4565 | 4-Cl | 2-F—Et | 4-CONH2—Ph |
| 4566 | 4-Cl | 2-F—Et | 4-CONHrMTe-Ph |
| 4567 | 4-Cl | 2-F—Et | 4-CONHPh—Ph |
| 4568 | 4-Cl | 2-F—Et | 4-F—Ph |
| 4569 | 4-Cl | 2-F—Et | 4-Cl—Ph |
| 4570 | 4-Cl | 2-F—Et | 4-Br—Ph |
| 4571 | 4-Cl | 2-F—Et | 4-SO2NH2—Ph |
| 4572 | 4-Cl | 2-F—Et | 4-SO2NHMe—Ph |
| 4573 | 4-Cl | 2-F—Et | 4-CF3—Ph |
| 4574 | 4-Cl | 2-F—Et | 4-OMe—Ph |
| 4575 | 4-Cl | 2-F—Et | 4-SMe—Ph |
| 4576 | 4-Cl | 2-F—Et | 4-SOMe—Ph |
| 4577 | 4-Cl | 2-F—Et | 4-SO2Me—Ph |
| 4578 | 4-Cl | 2-F—Et | 4-OH—Ph |
| 4579 | 4-Cl | 2-F—Et | 4-CH2OH—Ph |
| 4580 | 4-Cl | 2-F—Et | 4-CHOHMe—Ph |
| 4581 | 4-Cl | 2-F—Et | 4-COH(Me)2—Ph |
| 4582 | 4-Cl | 2-F—Et | 4-Me—Ph |
| 4583 | 4-Cl | 2-F—Et | 4-Et—Ph |
| 4584 | 4-Cl | 2-F—Et | 4-iPr—Ph |
| 4585 | 4-Cl | 2-F—Et | 4-tBu—Ph |
| 4586 | 4-Cl | 2-F—Et | 4-CH2CO2Me—Ph |
| 4587 | 4-Cl | 2-F—Et | 4-(1-piperidinyl)-Ph |
| 4588 | 4-Cl | 2-F—Et | 4-(1-pyrrolidinyl)-Ph |
| 4589 | 4-Cl | 2-F—Et | 4-(2-imidazolyl)-Ph |
| 4590 | 4-Cl | 2-F—Et | 4-(1-imidazolyl)-Ph |
| 4591 | 4-Cl | 2-F—Et | 4-(2-thiazolyl)-Ph |
| 4592 | 4-Cl | 2-F—Et | 4-(3-pyrazolyl)-Ph |
| 4593 | 4-Cl | 2-F—Et | 4-(1-pyrazolyl)-Ph |
| 4594 | 4-Cl | 2-F—Et | 4-(5-Me-1-tetrazolyl)-Ph |
| 4595 | 4-Cl | 2-F—Et | 4-(1-Me-5-tetrazolyl)-Ph |
| 4596 | 4-Cl | 2-F—Et | 4-(2-pyridyl)-Ph |
| 4597 | 4-Cl | 2-F—Et | 4-(2-thienyl)-Ph |
| 4598 | 4-Cl | 2-F—Et | 4-(2-furanyl)-Ph |
| 4599 | 4-Cl | 2-F—Et | 2-CN—Ph |
| 4600 | 4-Cl | 2-F—Et | 2-COMe—Ph |
| 4601 | 4-Cl | 2-F—Et | 2-CO2Me—Ph |
| 4602 | 4-Cl | 2-F—Et | 2-CONH2—Ph |
| 4603 | 4-Cl | 2-F—Et | 2-CONHMe—Ph |
| 4604 | 4-Cl | 2-F—Et | 2-F—Ph |
| 4605 | 4-Cl | 2-F—Et | 2-Cl—Ph |
| 4606 | 4-Cl | 2-F—Et | 2-Br—Ph |
| 4607 | 4-Cl | 2-F—Et | 2-SO2NH2—Ph |
| 4608 | 4-Cl | 2-F—Et | 2-SO2NHMe—Ph |
| 4609 | 4-Cl | 2-F—Et | 2-CF3—Ph |
| 4610 | 4-Cl | 2-F—Et | 2-OMe—Ph |
| 4611 | 4-Cl | 2-F—Et | 2-SMe—Ph |
| 4612 | 4-Cl | 2-F—Et | 2-SOMe—Ph |
| 4613 | 4-Cl | 2-F—Et | 2-SO2Me—Ph |
| 4614 | 4-Cl | 2-F—Et | 2-OH—Ph |
| 4615 | 4-Cl | 2-F—Et | 2-CH2OH—Ph |
| 4616 | 4-Cl | 2-F—Et | 2-CHOHMe—Ph |
| 4617 | 4-Cl | 2-F—Et | 2-COH(Me)2—Ph |
| 4618 | 4-Cl | 2-F—Et | 2-Me—Ph |
| 4619 | 4-Cl | 2-F—Et | 2-Et—Ph |
| 4620 | 4-Cl | 2-F—Et | 2-iPr—Ph |
| 4621 | 4-Cl | 2-F—Et | 2-tBu—Ph |
| 4622 | 4-Cl | 2-F—Et | 2-CH2CO2Me—Ph |
| 4623 | 4-Cl | 2-F—Et | 2-(1-piperidinyl)-Ph |
| 4624 | 4-Cl | 2-F—Et | 2-(1-pyrrolidinyl)-Ph |
| 4625 | 4-Cl | 2-F—Et | 2-(2-imidazolyl)-Ph |
| 4626 | 4-Cl | 2-F—Et | 2-(1-imidazolyl)-Ph |
| 4627 | 4-Cl | 2-F—Et | 2-(2-thiazolyl)-Ph |
| 4623 | 4-Cl | 2-F—Et | 2-(3-pyrazolyl)-Ph |
| 4629 | 4-Cl | 2-F—Et | 2-(1-pyrazolyl)-Ph |
| 4630 | 4-Cl | 2-F—Et | 2-(5-Me-1-tetrazolyl)-Ph |
| 4631 | 4-Cl | 2-F—Et | 2-(1-Me-5-tetrazolyl)-Ph |
| 4632 | 4-Cl | 2-F—Et | 2-(2-pyridyl)-Ph |
| 4633 | 4-Cl | 2-F—Et | 2-(2-thienyl)-Ph |
| 4634 | 4-Cl | 2-F—Et | 2-(2-furanyl)-Ph |
| 4635 | 4-Cl | 2-F—Et | 2,4-diF—Ph |
| 4636 | 4-Cl | 2-F—Et | 2,5-diF—Ph |
| 4637 | 4-Cl | 2-F—Et | 2,6-diF—Ph |
| 4638 | 4-Cl | 2-F—Et | 3,4-diF—Ph |
| 4639 | 4-Cl | 2-F—Et | 3,5-diF—Ph |
| 4640 | 4-Cl | 2-F—Et | 2,4-diCl—Ph |
| 4641 | 4-Cl | 2-F—Et | 2,5-diCl—Ph |
| 4642 | 4-Cl | 2-F—Et | 2,6-diCl—Ph |
| 4643 | 4-Cl | 2-F—Et | 3,4-diCl—Ph |
| 4644 | 4-Cl | 2-F—Et | 3,5-diCl—Ph |
| 4645 | 4-Cl | 2-F—Et | 3,4-diCF3—Ph |
| 4646 | 4-Cl | 2-F—Et | 3,5-diCF3—Ph |
| 4647 | 4-Cl | 2-F—Et | 5-Cl-2-MeO—Ph |
| 4648 | 4-Cl | 2-F—Et | 5-Cl-2-Me—Ph |
| 4649 | 4-Cl | 2-F—Et | 2-F-5-Me—Ph |
| 4650 | 4-Cl | 2-F—Et | 3-F-5-morpholino-Ph |
| 4651 | 4-Cl | 2-F—Et | 3,4-OCH2O—Ph |
| 4652 | 4-Cl | 2-F—Et | 3,4-OCH2CH2O—Ph |
| 4653 | 4-Cl | 2-F—Et | 2-MeO-5-CONM2-Ph |
| 4654 | 4-Cl | 2-F—Et | 2-MeO-4-(1-Me-5-tetrazolyl)-Ph |
| 4655 | 4-Cl | 2-F—Et | 2-MeO-5-(1-Me-5-tetrazolyl)-Ph |
| 4656 | 4-Cl | 2-F—Et | 3-CONH2-5-(1-Me-5-tetrazolyl)-Ph |
| 4657 | 4-Cl | 2-F—Et | 1-naphthyl |
| 4658 | 4-Cl | 2-F—Et | 2-naphthyl |
| 4659 | 4-Cl | 2-F—Et | 2-thienyl |
| 4660 | 4-Cl | 2-F—Et | 3-thienyl |
| 4661 | 4-Cl | 2-F—Et | 2-furanyl |
| 4662 | 4-Cl | 2-F—Et | 3-furanyl |
| 4663 | 4-Cl | 2-F—Et | 2-pyridyl |
| 4664 | 4-Cl | 2-F—Et | 3-pyridyl |
| 4665 | 4-Cl | 2-F—Et | 4-pyridyl |
| 4666 | 4-Cl | 2-F—Et | 2-indolyl |
| 4667 | 4-Cl | 2-F—Et | 3-indolyl |
| 4668 | 4-Cl | 2-F—Et | 5-indolyl |
| 4669 | 4-Cl | 2-F—Et | 6-indolyl |
| 4670 | 4-Cl | 2-F—Et | 3-indazolyl |
| 4671 | 4-Cl | 2-F—Et | 5-indazolyl |
| 4672 | 4-Cl | 2-F—Et | 6-indazolyl |
| 4673 | 4-Cl | 2-F—Et | 2-imidazolyl |
| 4674 | 4-Cl | 2-F—Et | 3-isoxazoyl |
| 4675 | 4-Cl | 2-F—Et | 3-pyrazolyl |
| 4676 | 4-Cl | 2-F—Et | 2-thiadiazolyl |
| 4677 | 4-Cl | 2-F—Et | 2-thiazolyl |
| 4678 | 4-Cl | 2-F—Et | 5-Ac-4-Me-2-thiazolyl |
| 4679 | 4-Cl | 2-F—Et | 5-tetrazolyl |
| 4680 | 4-Cl | 2-F—Et | 2-benzimidazolyl |
| 4681 | 4-Cl | 2-F—Et | 5-benzimidazolyl |

TABLE 2-continued

| | | | |
|---|---|---|---|
| 4682 | 4-Cl | 2-F—Et | 2-benzothiazolyl |
| 4683 | 4-Cl | 2-F—Et | 5-benzothiazolyl |
| 4684 | 4-Cl | 2-F—Et | 2-benzoxazolyl |
| 4685 | 4-Cl | 2-F—Et | 5-benzoxazolyl |
| 4686 | 4-Cl | 2-F—Et | 1-adamantyl |
| 4687 | 4-Cl | 2-F—Et | 2-adamantyl |
| 4688 | 4-Cl | 2-F—Et | i-Pr |
| 4689 | 4-Cl | 2-F—Et | t-Bu |
| 4690 | 4-Cl | 2-F—Et | c-Hex |
| 4691 | 4-Cl | 2-F—Et | CH2CH2OMe |
| 4692 | 4-Cl | 2-F—Et | CH2CONH2 |
| 4693 | 4-Cl | 2-F—Et | cH2CO2Me |
| 4694 | 4-Cl | 2-F—Et | cH(CH2Ph)CO2Me |
| 4695 | 4-Cl | 2-F—Et | CH2CH2NMe2 |
| 4696 | 4-Cl | 2-F—Et | benzyl |
| 4697 | 4-Cl | 2-F—Et | phenethyl |
| 4698 | 4-Cl | 2-F—Et | 2-(morpholin-1-yl)-Et |
| 4699 | 4-Cl | CO2Me | Ph |
| 4700 | 4-Cl | CO2Me | 3-CN—Ph |
| 4701 | 4-Cl | CO2Me | 3-COMe—Ph |
| 4702 | 4-Cl | CO2Me | 3-CO2Me—Ph |
| 4703 | 4-Cl | CO2Me | 3-CONH2—Ph |
| 4704 | 4-Cl | CO2Me | 3-CONHMe—Ph |
| 4705 | 4-Cl | CO2Me | 3-F—Ph |
| 4706 | 4-Cl | CO2Me | 3-Cl—Ph |
| 4707 | 4-Cl | CO2Me | 3-Br—Ph |
| 4708 | 4-Cl | CO2Me | 3-SO2NH2—Ph |
| 4709 | 4-Cl | CO2Me | 3-SO2NHMe—Ph |
| 4710 | 4-Cl | CO2Me | 3-CF3—Ph |
| 4711 | 4-Cl | CO2Me | 3-OMe—Ph |
| 4712 | 4-Cl | CO2Me | 3-SMe—Ph |
| 4713 | 4-Cl | CO2Me | 3-SOMe—Ph |
| 4714 | 4-Cl | CO2Me | 3-SO2Me—Ph |
| 4715 | 4-Cl | CO2Me | 3-OH—Ph |
| 4716 | 4-Cl | CO2Me | 3-CH2OH—Ph |
| 4717 | 4-Cl | CO2Me | 3-CHOHMe—Ph |
| 4718 | 4-Cl | CO2Me | 3-COH(Me)2—Ph |
| 4719 | 4-Cl | CO2Me | 3-Me—Ph |
| 4720 | 4-Cl | CO2Me | 3-Et—Ph |
| 4721 | 4-Cl | CO2Me | 3-iPr—Ph |
| 4722 | 4-Cl | CO2Me | 3-tBu—Ph |
| 4723 | 4-Cl | CO2Me | 3-CH2CO2Me—Ph |
| 4724 | 4-Cl | CO2Me | 3-(1-piperidinyl)-Ph |
| 4725 | 4-Cl | CO2Me | 3-(1-pyrrolidinyl)-Ph |
| 4726 | 4-Cl | CO2Me | 3-(2-imidazolyl)-Ph |
| 4727 | 4-Cl | CO2Me | 3-(1-imidazolyl)-Ph |
| 4728 | 4-Cl | CO2Me | 3-(2-thiazolyl)-Ph |
| 4729 | 4-Cl | CO2Me | 3-(3-pyrazolyl)-Ph |
| 4730 | 4-Cl | CO2Me | 3-(1-pyrazolyl)-Ph |
| 4731 | 4-Cl | CO2Me | 3-(5-Me-1-tetrazolyl)-Ph |
| 4732 | 4-Cl | CO2Me | 3-(1-Me-5-tetrazolyl)-Ph |
| 4733 | 4-Cl | CO2Me | 3-(2-pyridyl)-Ph |
| 4734 | 4-Cl | CO2Me | 3-(2-thienyl)-Ph |
| 4735 | 4-Cl | CO2Me | 3-(2-furanyl)-Ph |
| 4736 | 4-Cl | CO2Me | 4-CN—Ph |
| 4737 | 4-Cl | CO2Me | 4-COMe—Ph |
| 4738 | 4-Cl | CO2Me | 4-CO2Me—Ph |
| 4739 | 4-Cl | CO2Me | 4-CONH2—Ph |
| 4740 | 4-Cl | CO2Me | 4-CONHMe—Ph |
| 4741 | 4-Cl | CO2Me | 4-CONHPh—Ph |
| 4742 | 4-Cl | CO2Me | 4-F—Ph |
| 4743 | 4-Cl | CO2Me | 4-Cl—Ph |
| 4744 | 4-Cl | CO2Me | 4-Br—Ph |
| 4745 | 4-Cl | CO2Me | 4-SO2NH2—Ph |
| 4746 | 4-Cl | CO2Me | 4-SO2NHMe—Ph |
| 4747 | 4-Cl | CO2Me | 4-CF3—Ph |
| 4748 | 4-Cl | CO2Me | 4-OMe—Ph |
| 4749 | 4-Cl | CO2Me | 4-SMe—Ph |
| 4750 | 4-Cl | CO2Me | 4-SOMe—Ph |
| 4751 | 4-Cl | CO2Me | 4-SO2Me—Ph |
| 4752 | 4-Cl | CO2Me | 4-OH—Ph |
| 4753 | 4-Cl | CO2Me | 4-CH2OH—Ph |
| 4754 | 4-Cl | CO2Me | 4-CHOHMe—Ph |
| 4755 | 4-Cl | CO2Me | 4-COH(Me)2—Ph |
| 4756 | 4-Cl | CO2Me | 4-Me—Ph |
| 4757 | 4-Cl | CO2Me | 4-Et—Ph |
| 4758 | 4-Cl | CO2Me | 4-iPr—Ph |
| 4759 | 4-Cl | CO2Me | 4-tBu—Ph |
| 4760 | 4-Cl | CO2Me | 4-CH2CO2Me—Ph |
| 4761 | 4-Cl | CO2Me | 4-(1-piperidinyl)-Ph |
| 4762 | 4-Cl | CO2Me | 4-(1-pyrrolidinyl)-Ph |
| 4763 | 4-Cl | CO2Me | 4-(2-imidazolyl)-Ph |
| 4764 | 4-Cl | CO2Me | 4-(1-imidazolyl)-Ph |
| 4765 | 4-Cl | CO2Me | 4-(2-thiazolyl)-Ph |
| 4766 | 4-Cl | CO2Me | 4-(3-pyrazolyl)-Ph |
| 4767 | 4-Cl | CO2Me | 4-(1-pyrazolyl)-Ph |
| 4768 | 4-Cl | CO2Me | 4-(5-Me-1-tetrazolyl)-Ph |
| 4769 | 4-Cl | CO2Me | 4-(1-Me-5-tetrazolyl)-Ph |
| 4770 | 4-Cl | CO2Me | 4-(2-pyridyl)-Ph |
| 4771 | 4-Cl | CO2Me | 4-(2-thienyl)-Ph |
| 4772 | 4-Cl | CO2Me | 4-(2-furanyl)-Ph |
| 4773 | 4-Cl | CO2Me | 2-CN—Ph |
| 4774 | 4-Cl | CO2Me | 2-COMe—Ph |
| 4775 | 4-Cl | CO2Me | 2-CO2Me—Ph |
| 4776 | 4-Cl | CO2Me | 2-CONH2—Ph |
| 4777 | 4-Cl | CO2Me | 2-CONHMe—Ph |
| 4778 | 4-Cl | CO2Me | 2-F—Ph |
| 4779 | 4-Cl | CO2Me | 2-Cl—Ph |
| 4780 | 4-Cl | CO2Me | 2-Br—Ph |
| 4781 | 4-Cl | CO2Me | 2-SO2NH2—Ph |
| 4782 | 4-Cl | CO2Me | 2-SO2NHMe—Ph |
| 4783 | 4-Cl | CO2Me | 2-CF3—Ph |
| 4784 | 4-Cl | CO2Me | 2-OMe—Ph |
| 4785 | 4-Cl | CO2Me | 2-SMe—Ph |
| 4786 | 4-Cl | CO2Me | 2-SOMe—Ph |
| 4787 | 4-Cl | CO2Me | 2-SO2Me—Ph |
| 4788 | 4-Cl | CO2Me | 2-OH—Ph |
| 4789 | 4-Cl | CO2Me | 2-CH2OH—Ph |
| 4790 | 4-Cl | CO2Me | 2-CHOHMe—Ph |
| 4791 | 4-Cl | CO2Me | 2-COH(Me)2—Ph |
| 4792 | 4-Cl | CO2Me | 2-Me—Ph |
| 4793 | 4-Cl | CO2Me | 2-Et—Ph |
| 4794 | 4-Cl | CO2Me | 2-iPr—Ph |
| 4795 | 4-Cl | CO2Me | 2-tBu—Ph |
| 4796 | 4-Cl | CO2Me | 2-CH2CO2Me—Ph |
| 4797 | 4-Cl | CO2Me | 2-(1-piperidinyl)-Ph |
| 4798 | 4-Cl | CO2Me | 2-(1-pyrrolidinyl)-Ph |
| 4799 | 4-Cl | CO2Me | 2-(2-imidazolyl)-Ph |
| 4800 | 4-Cl | CO2Me | 2-(1-imidazolyl)-Ph |
| 4801 | 4-Cl | CO2Me | 2-(2-thiazolyl)-Ph |
| 4802 | 4-Cl | CO2Me | 2-(3-pyrazolyl)-Ph |
| 4803 | 4-Cl | CO2Me | 2-(1-pyrazolyl)-Ph |
| 4804 | 4-Cl | CO2Me | 2-(5-Me-1-tetrazolyl)-Ph |
| 4805 | 4-Cl | CO2Me | 2-(1-Me-5-tetrazolyl)-Ph |
| 4806 | 4-Cl | CO2Me | 2-(2-pyridyl)-Ph |
| 4807 | 4-Cl | CO2Me | 2-(2-thienyl)-Ph |
| 4808 | 4-Cl | CO2Me | 2-(2-furanyl)-Ph |
| 4809 | 4-Cl | CO2Me | 2,4-diF—Ph |
| 4810 | 4-Cl | CO2Me | 2,5-diF—Ph |
| 4811 | 4-Cl | CO2Me | 2,6-diF—Ph |
| 4812 | 4-Cl | CO2Me | 3,4-diF—Ph |
| 4813 | 4-Cl | CO2Me | 3, 5-diF—Ph |
| 4814 | 4-Cl | CO2Me | 2,4-diCl—Ph |
| 4815 | 4-Cl | CO2Me | 2,5-diCl—Ph |
| 4816 | 4-Cl | CO2Me | 2,6-diCl—Ph |
| 4817 | 4-Cl | CO2Me | 3,4-diCl—Ph |
| 4818 | 4-Cl | CO2Me | 3,5-diCl—Ph |
| 4819 | 4-Cl | CO2Me | 3, 4-diCF3—Ph |
| 4820 | 4-Cl | CO2Me | 3,5-diCF3—Ph |
| 4821 | 4-Cl | CO2Me | 5-Cl-2-MeO—Ph |
| 4822 | 4-Cl | CO2Me | 5-Cl-2-Me—Ph |
| 4823 | 4-Cl | CO2Me | 2-F-5-Me—Ph |
| 4824 | 4-Cl | CO2Me | 3-F-5-morpholino-Ph |
| 4825 | 4-Cl | CO2Me | 3,4-OCH2O—Ph |
| 4826 | 4-Cl | CO2Me | 3,4-OCH2CH2O—Ph |
| 4827 | 4-Cl | CO2Me | 2-MeO-5-CONH2—Ph |
| 4828 | 4-Cl | CO2Me | 2-MeO-4-(1-Me-5-tetrazolyl)-Ph |
| 4829 | 4-Cl | CO2Me | 2-MeO-5-(1-Me-5-tetrazolyl)-Ph |
| 4830 | 4-Cl | CO2Me | 3-CONH2-5-(1-Me-5-tetrazolyl)-Ph |
| 4831 | 4-Cl | CO2Me | 1-naphthyl |
| 4832 | 4-Cl | CO2Me | 2-naphthyl |
| 4833 | 4-Cl | CO2Me | 2-thienyl |
| 4834 | 4-Cl | CO2Me | 3-thienyl |
| 4835 | 4-Cl | CO2Me | 2-furanyl |
| 4836 | 4-Cl | CO2Me | 3-furanyl |
| 4837 | 4-Cl | CO2Me | 2-pyridyl |
| 4838 | 4-Cl | CO2Me | 3-pyridyl |
| 4839 | 4-Cl | CO2Me | 4-pyridyl |

TABLE 2-continued

| | | | |
|---|---|---|---|
| 4840 | 4-Cl | CO2Me | 2-indolyl |
| 4841 | 4-Cl | CO2Me | 3-indolyl |
| 4842 | 4-Cl | CO2Me | 5-indolyl |
| 4843 | 4-Cl | CO2Me | 6-indolyl |
| 4844 | 4-Cl | CO2Me | 3-indazolyl |
| 4845 | 4-Cl | CO2Me | 5-indazolyl |
| 4846 | 4-Cl | CO2Me | 6-indazolyl |
| 4847 | 4-Cl | CO2Me | 2-imidazolyl |
| 4848 | 4-Cl | CO2Me | 3-isoxazoyl |
| 4849 | 4-Cl | CO2Me | 3-pyrazolyl |
| 4850 | 4-Cl | CO2Me | 2-thiadiazolyl |
| 4851 | 4-Cl | CO2Me | 2-thiazolyl |
| 4852 | 4-Cl | CO2Me | 5-Ac-4-Me-2-thiazolyl |
| 4853 | 4-Cl | CO2Me | 5-tetrazolyl |
| 4854 | 4-Cl | CO2Me | 2-benzimidazolyl |
| 4855 | 4-Cl | CO2Me | 5-benzimidazolyl |
| 4856 | 4-Cl | CO2Me | 2-benzothiazolyl |
| 4857 | 4-Cl | CO2Me | 5-benzothiazolyl |
| 4858 | 4-Cl | CO2Me | 2-benzoxazolyl |
| 4859 | 4-Cl | CO2Me | 5-benzoxazolyl |
| 4860 | 4-Cl | CO2Me | 1-adamantyl |
| 4861 | 4-Cl | CO2Me | 2-adamantyl |
| 4862 | 4-Cl | CO2Me | i-Pr |
| 4863 | 4-Cl | CO2Me | t-Bu |
| 4864 | 4-Cl | CO2Me | c-Hex |
| 4865 | 4-Cl | CO2Me | CH2CH2OMe |
| 4866 | 4-Cl | CO2Me | CH2CONH2 |
| 4867 | 4-Cl | CO2Me | CH2CO2Me |
| 4868 | 4-Cl | CO2Me | CH(CH2Ph)CO2Me |
| 4869 | 4-Cl | CO2Me | CH2CH2NMe2 |
| 4870 | 4-Cl | CO2Me | benzyl |
| 4871 | 4-Cl | CO2Me | phenethyl |
| 4872 | 4-Cl | CO2Me | 2-(morpholin-1-yl)-Et |
| 4873 | 4-Cl | Ac | Ph |
| 4874 | 4-Cl | Ac | 3-CN—Ph |
| 4875 | 4-Cl | Ac | 3-COMe—Ph |
| 4876 | 4-Cl | Ac | 3-CO2Me—Ph |
| 4877 | 4-Cl | Ac | 3-CONH2—Ph |
| 4878 | 4-Cl | Ac | 3-CONHMe—Ph |
| 4879 | 4-Cl | Ac | 3-F—Ph |
| 4880 | 4-Cl | Ac | 3-Cl—Ph |
| 4881 | 4-Cl | Ac | 3-Br—Ph |
| 4882 | 4-Cl | Ac | 3-SO2NH2—Ph |
| 4883 | 4-Cl | Ac | 3-SO2NHMe—Ph |
| 4884 | 4-Cl | Ac | 3-CF3—Ph |
| 4885 | 4-Cl | Ac | 3-OMe—Ph |
| 4886 | 4-Cl | Ac | 3-SMe—Ph |
| 4887 | 4-Cl | Ac | 3-SOMe—Ph |
| 4888 | 4-Cl | Ac | 3-SO2Me—Ph |
| 4889 | 4-Cl | Ac | 3-OH—Ph |
| 4890 | 4-Cl | Ac | 3-CH2OH—Ph |
| 4891 | 4-Cl | Ac | 3-CHOHMe—Ph |
| 4892 | 4-Cl | Ac | 3-COH(Me)2—Ph |
| 4893 | 4-Cl | Ac | 3-Me—Ph |
| 4894 | 4-Cl | Ac | 3-Et—Ph |
| 4895 | 4-Cl | Ac | 3-iPr—Ph |
| 4896 | 4-Cl | Ac | 3-tBu—Ph |
| 4897 | 4-Cl | Ac | 3-CH2CO2Me—Ph |
| 4898 | 4-Cl | Ac | 3-(1-piperidinyl)-Ph |
| 4899 | 4-Cl | Ac | 3-(1-pyrrolidinyl)-Ph |
| 4900 | 4-Cl | Ac | 3-(2-imidazolyl)-Ph |
| 4901 | 4-Cl | Ac | 3-(1-imidazolyl)-Ph |
| 4902 | 4-Cl | Ac | 3-(2-thiazolyl)-Ph |
| 4903 | 4-Cl | Ac | 3-(3-pyrazolyl)-Ph |
| 4904 | 4-Cl | Ac | 3-(1-pyrazolyl)-Ph |
| 4905 | 4-Cl | Ac | 3-(5-Me-1-tetrazolyl)-Ph |
| 4906 | 4-Cl | Ac | 3-(1-Me-5-tetrazolyl)-Ph |
| 4907 | 4-Cl | Ac | 3-(2-pyridyl)-Ph |
| 4908 | 4-Cl | Ac | 3-(2-thienyl)-Ph |
| 4909 | 4-Cl | Ac | 3-(2-furanyl)-Ph |
| 4910 | 4-Cl | Ac | 4-CN—Ph |
| 4911 | 4-Cl | Ac | 4-COMe—Ph |
| 4912 | 4-Cl | Ac | 4-CO2Me—Ph |
| 4913 | 4-Cl | Ac | 4-CONH2—Ph |
| 4914 | 4-Cl | Ac | 4-CONHMe—Ph |
| 4915 | 4-Cl | Ac | 4-CONHPh—Ph |
| 4916 | 4-Cl | Ac | 4-F—Ph |
| 4917 | 4-Cl | Ac | 4-Cl—Ph |
| 4918 | 4-Cl | Ac | 4-Br—Ph |
| 4919 | 4-Cl | Ac | 4-SO2NH2—Ph |
| 4920 | 4-Cl | Ac | 4-SO2NHMe—Ph |
| 4921 | 4-Cl | Ac | 4-CF3—Ph |
| 4922 | 4-Cl | Ac | 4-OMe—Ph |
| 4923 | 4-Cl | Ac | 4-SMe—Ph |
| 4924 | 4-Cl | Ac | 4-SOMe—Ph |
| 4925 | 4-Cl | Ac | 4-SO2Me—Ph |
| 4926 | 4-Cl | Ac | 4-OH—Ph |
| 4927 | 4-Cl | Ac | 4-CH2OH—Ph |
| 4928 | 4-Cl | Ac | 4-CHOHMe—Ph |
| 4929 | 4-Cl | Ac | 4-COH(Me)2—Ph |
| 4930 | 4-Cl | Ac | 4-Me—Ph |
| 4931 | 4-Cl | Ac | 4-Et—Ph |
| 4932 | 4-Cl | Ac | 4-iPr—Ph |
| 4933 | 4-Cl | Ac | 4-tBu—Ph |
| 4934 | 4-Cl | Ac | 4-CH2CO2Me—Ph |
| 4935 | 4-Cl | Ac | 4-(1-piperidinyl)-Ph |
| 4936 | 4-Cl | Ac | 4-(1-pyrrolidinyl)-Ph |
| 4937 | 4-Cl | Ac | 4-(2-imidazolyl)-Ph |
| 4938 | 4-Cl | Ac | 4-(1-imidazolyl)-Ph |
| 4939 | 4-Cl | Ac | 4-(2-thiazolyl)-Ph |
| 4940 | 4-Cl | Ac | 4-(3-pyrazolyl)-Ph |
| 4941 | 4-Cl | Ac | 4-(1-pyrazolyl)-Ph |
| 4942 | 4-Cl | Ac | 4-(5-Me-1-tetrazolyl)-Ph |
| 4943 | 4-Cl | Ac | 4-(1-Me-5-tetrazolyl)-ph |
| 4944 | 4-Cl | Ac | 4-(2-pyridyl)-Ph |
| 4945 | 4-Cl | Ac | 4-(2-thienyl)-ph |
| 4946 | 4-Cl | Ac | 4-(2-furanyl)-Ph |
| 4947 | 4-Cl | Ac | 2-CN—Ph |
| 4948 | 4-Cl | Ac | 2-COMe—Ph |
| 4949 | 4-Cl | Ac | 2-CO2Me—Ph |
| 4950 | 4-Cl | Ac | 2-CONH2—Ph |
| 4951 | 4-Cl | Ac | 2-CONHMe—Ph |
| 4952 | 4-Cl | Ac | 2-F—Ph |
| 4953 | 4-Cl | Ac | 2-Cl—Ph |
| 4954 | 4-Cl | Ac | 2-Br—Ph |
| 4955 | 4-Cl | Ac | 2-SO2NH2—Ph |
| 4956 | 4-Cl | Ac | 2-SO2NHMe—Ph |
| 4957 | 4-Cl | Ac | 2-CF3—Ph |
| 4958 | 4-Cl | Ac | 2-OMe—Ph |
| 4959 | 4-Cl | Ac | 2-SMe—Ph |
| 4960 | 4-Cl | Ac | 2-SOMe—Ph |
| 4961 | 4-Cl | Ac | 2-SO2Me—Ph |
| 4962 | 4-Cl | Ac | 2-OH—Ph |
| 4963 | 4-Cl | Ac | 2-CH2OH—Ph |
| 4964 | 4-Cl | Ac | 2-CHOHMe—Ph |
| 4965 | 4-Cl | Ac | 2-COH(Me)2—Ph |
| 4966 | 4-Cl | Ac | 2-Me—Ph |
| 4967 | 4-Cl | Ac | 2-Et—Ph |
| 4968 | 4-Cl | Ac | 2-iPr—Ph |
| 4969 | 4-Cl | Ac | 2-tBu—Ph |
| 4970 | 4-Cl | Ac | 2-CH2CO2Me—Ph |
| 4971 | 4-Cl | Ac | 2-(1-piperidinyl)-Ph |
| 4972 | 4-Cl | Ac | 2-(1-pyrrolidinyl)-Ph |
| 4973 | 4-Cl | Ac | 2-(2-imidazolyl)-Ph |
| 4974 | 4-Cl | Ac | 2-(1-imidazolyl)-Ph |
| 4975 | 4-Cl | Ac | 2-(2-thiazolyl)-Ph |
| 4976 | 4-Cl | Ac | 2-(3-pyrazolyl)-Ph |
| 4977 | 4-Cl | Ac | 2-(1-pyrazolyl)-Ph |
| 4978 | 4-Cl | Ac | 2-(5-Me-1-tetrazolyl)-Ph |
| 4979 | 4-Cl | Ac | 2-(1-Me-5-tetrazolyl)-Ph |
| 4980 | 4-Cl | Ac | 2-(2-pyridyl)-Ph |
| 4981 | 4-Cl | Ac | 2-(2-thienyl)-Ph |
| 4982 | 4-Cl | Ac | 2-(2-furanyl)-Ph |
| 4983 | 4-Cl | Ac | 2,4-diF—Ph |
| 4984 | 4-Cl | Ac | 2,5-diF—Ph |
| 4985 | 4-Cl | Ac | 2,6-diF—Ph |
| 4986 | 4-Cl | Ac | 3,4-diF—Ph |
| 4987 | 4-Cl | Ac | 3,5-diF—Ph |
| 4988 | 4-Cl | Ac | 2,4-diCl—Ph |
| 4989 | 4-Cl | Ac | 2,5-diCl—Ph |
| 4990 | 4-Cl | Ac | 2,6-diCl—Ph |
| 4991 | 4-Cl | Ac | 3,4-diCl—Ph |
| 4992 | 4-Cl | Ac | 3,5-diCl—Ph |
| 4993 | 4-Cl | Ac | 3,4-diCF3—Ph |
| 4994 | 4-Cl | Ac | 3,5-diCF3—Ph |
| 4995 | 4-Cl | Ac | 5-Cl-2-MeO—Ph |
| 4996 | 4-Cl | Ac | 5-Cl-2-Me—Ph |
| 4997 | 4-Cl | Ac | 2-F-5-Me—Ph |

TABLE 2-continued

| | | | |
|---|---|---|---|
| 4998 | 4-Cl | Ac | 3-F-5-morpholino-Ph |
| 4999 | 4-Cl | Ac | 3,4-OCH2O—Ph |
| 5000 | 4-Cl | Ac | 3,4-OCH2CH2O—Ph |
| 5001 | 4-Cl | Ac | 2-MeO-5-CONH2—Ph |
| 5002 | 4-Cl | Ac | 2-MeO-4-(1-Me-5-tetrazolyl)-Ph |
| 5003 | 4-Cl | Ac | 2-MeO-5-(1-Me-5-tetrazolyl)-Ph |
| 5004 | 4-Cl | Ac | 3-CONH2-5-(1-Me-5-tetrazolyl)-Ph |
| 5005 | 4-Cl | Ac | 1-naphthyl |
| 5006 | 4-Cl | Ac | 2-naphthyl |
| 5007 | 4-Cl | Ac | 2-thienyl |
| 5008 | 4-Cl | Ac | 3-thienyl |
| 5009 | 4-Cl | Ac | 2-furanyl |
| 5010 | 4-Cl | Ac | 3-furanyl |
| 5011 | 4-Cl | Ac | 2-pyridyl |
| 5012 | 4-Cl | Ac | 3-pyridyl |
| 5013 | 4-Cl | Ac | 4-pyridyl |
| 5014 | 4-Cl | Ac | 2-indolyl |
| 5015 | 4-Cl | Ac | 3-indolyl |
| 5016 | 4-Cl | Ac | 5-indolyl |
| 5017 | 4-Cl | Ac | 6-indolyl |
| 5018 | 4-Cl | Ac | 3-indazolyl |
| 5019 | 4-Cl | Ac | 5-indazolyl |
| 5020 | 4-Cl | Ac | 6-indazolyl |
| 5021 | 4-Cl | Ac | 2-imidazolyl |
| 5022 | 4-Cl | Ac | 3-isoxazoyl |
| 5023 | 4-Cl | Ac | 3-pyrazolyl |
| 5024 | 4-Cl | Ac | 2-thiadiazolyl |
| 5025 | 4-Cl | Ac | 2-thiazolyl |
| 5026 | 4-Cl | Ac | 5-Ac-4-Me-2-thiazolyl |
| 5027 | 4-Cl | Ac | 5-tetrazolyl |
| 5028 | 4-Cl | Ac | 2-benzimidazolyl |
| 5029 | 4-Cl | Ac | 5-benzimidazolyl |
| 5030 | 4-Cl | Ac | 2-benzothiazolyl |
| 5031 | 4-Cl | Ac | 5-benzothiazolyl |
| 5032 | 4-Cl | Ac | 2-benzoxazolyl |
| 5033 | 4-Cl | Ac | 5-benzoxazolyl |
| 5034 | 4-Cl | Ac | 1-adamantyl |
| 5035 | 4-Cl | Ac | 2-adamantyl |
| 5036 | 4-Cl | Ac | i-Pr |
| 5037 | 4-Cl | Ac | t-Bu |
| 5038 | 4-Cl | Ac | c-Hex |
| 5039 | 4-Cl | Ac | CH2CH2OMe |
| 5040 | 4-Cl | Ac | CH2CONH2 |
| 5041 | 4-Cl | Ac | CH2CO2Me |
| 5042 | 4-Cl | Ac | CH(CH2Ph)CO2Me |
| 5043 | 4-Cl | Ac | CH2CH2NMe2 |
| 5044 | 4-Cl | Ac | benzyl |
| 5045 | 4-Cl | Ac | phenethyl |
| 5046 | 4-Cl | Ac | 2-(morpholin-1-yl)-Et |
| 5047 | 4-Cl | COtBu | Ph |
| 5048 | 4-Cl | COtBu | 3-CN—Ph |
| 5049 | 4-Cl | COtBu | 3-COMe—Ph |
| 5050 | 4-Cl | COtBu | 3-CO2Me—Ph |
| 5051 | 4-Cl | COtBu | 3-CONH2—Ph |
| 5052 | 4-Cl | COtBu | 3-CONHMe—Ph |
| 5053 | 4-Cl | COtBu | 3-F—Ph |
| 5054 | 4-Cl | COtBu | 3-Cl—Ph |
| 5055 | 4-Cl | COtBu | 3-Br—Ph |
| 5056 | 4-Cl | COtBu | 3-SO2NH2—Ph |
| 5057 | 4-Cl | COtBu | 3-SO2NHMe—Ph |
| 5058 | 4-Cl | COtBu | 3-CF3—Ph |
| 5059 | 4-Cl | COtBu | 3-OMe—Ph |
| 5060 | 4-Cl | COtBu | 3-SMe—Ph |
| 5061 | 4-Cl | COtBu | 3-SOMe—Ph |
| 5062 | 4-Cl | COtBu | 3-SO2Me—Ph |
| 5063 | 4-Cl | COtBu | 3-OH—Ph |
| 5064 | 4-Cl | COtBu | 3-CH2OH—Ph |
| 5065 | 4-Cl | COtBu | 3-CHOHMe—Ph |
| 5066 | 4-Cl | COtBu | 3-COH(Me)2—Ph |
| 5067 | 4-Cl | COtBu | 3-Me—Ph |
| 5068 | 4-Cl | COtBu | 3-Et—Ph |
| 5069 | 4-Cl | COtBu | 3-iPr—Ph |
| 5070 | 4-Cl | COtBu | 3-tBu—Ph |
| 5071 | 4-Cl | COtBu | 3-CH2CO2Me—Ph |
| 5072 | 4-Cl | COtBu | 3-(1-piperidinyl)-Ph |
| 5073 | 4-Cl | COtBu | 3-(1-pyrrolidinyl)-Ph |
| 5074 | 4-Cl | COtBu | 3-(2-imidazolyl)-Ph |
| 5075 | 4-Cl | COtBu | 3-(1-imidazolyl)-Ph |
| 5076 | 4-Cl | COtBu | 3-(2-thiazolyl)-Ph |
| 5077 | 4-Cl | COtBu | 3-(3-pyrazolyl)-Ph |
| 5078 | 4-Cl | COtBu | 3-(1-pyrazolyl)-Ph |
| 5079 | 4-Cl | COtBu | 3-(5-Me-1-tetrazolyl)-Ph |
| 5080 | 4-Cl | COtBu | 3-(1-Me-5-tetrazolyl)-Ph |
| 5081 | 4-Cl | COtBu | 3-(2-pyridyl)-Ph |
| 5082 | 4-Cl | COtBu | 3-(2-thienyl)-Ph |
| 5083 | 4-Cl | COtBu | 3-(2-furanyl)-Ph |
| 5084 | 4-Cl | COtBu | 4-CN—Ph |
| 5085 | 4-Cl | COtBu | 4-COMe—Ph |
| 5086 | 4-Cl | COtBu | 4-CO2Me—Ph |
| 5087 | 4-Cl | COtBu | 4-CONH2—Ph |
| 5088 | 4-Cl | COtBu | 4-CONHMe—Ph |
| 5089 | 4-Cl | COtBu | 4-CONHPh—Ph |
| 5090 | 4-Cl | COtBu | 4-F—Ph |
| 5091 | 4-Cl | COtBu | 4-Cl—Ph |
| 5092 | 4-Cl | COtBu | 4-Br—Ph |
| 5093 | 4-Cl | COtBu | 4-SO2NH2—Ph |
| 5094 | 4-Cl | COtBu | 4-SO2NHMe—Ph |
| 5095 | 4-Cl | COtBu | 4-CF3—Ph |
| 5096 | 4-Cl | COtBu | 4-OMe—Ph |
| 5097 | 4-Cl | COtBu | 4-SMe—Ph |
| 5098 | 4-Cl | COtBu | 4-SOMe—Ph |
| 5099 | 4-Cl | COtBu | 4-SO2Me—Ph |
| 5100 | 4-Cl | COtBu | 4-OH—Ph |
| 5101 | 4-Cl | COtBu | 4-CH2OH—Ph |
| 5102 | 4-Cl | COtBu | 4-CHOHMe—Ph |
| 5103 | 4-Cl | COtBu | 4-COH(Me)2—Ph |
| 5104 | 4-Cl | COtBu | 4-Me—Ph |
| 5105 | 4-Cl | COtBu | 4-Et—Ph |
| 5106 | 4-Cl | COtBu | 4-iPr—Ph |
| 5107 | 4-Cl | COtBu | 4-tBu—Ph |
| 5108 | 4-Cl | COtBu | 4-CH2CO2Me—Ph |
| 5109 | 4-Cl | COtBu | 4-(1-piperidinyl)-Ph |
| 5110 | 4-Cl | COtBu | 4-(1-pyrrolidinyl)-Ph |
| 5111 | 4-Cl | COtBu | 4-(2-imidazolyl)-Ph |
| 5112 | 4-Cl | COtBu | 4-(1-imidazolyl)-Ph |
| 5113 | 4-Cl | COtBu | 4-(2-thiazolyl)-Ph |
| 5114 | 4-Cl | COtBu | 4-(3-pyrazolyl)-Ph |
| 5115 | 4-Cl | COtBu | 4-(1-pyrazolyl)-Ph |
| 5116 | 4-Cl | COtBu | 4-(5-Me-1-tetrazolyl)-Ph |
| 5117 | 4-Cl | COtBu | 4-(1-Me-5-tetrazolyl)-Ph |
| 5118 | 4-Cl | COtBu | 4-(2-pyridyl)-Ph |
| 5119 | 4-Cl | COtBu | 4-(2-thienyl)-Ph |
| 5120 | 4-Cl | COtBu | 4-(2-furanyl)-Ph |
| 5121 | 4-Cl | COtBu | 2-CN—Ph |
| 5122 | 4-Cl | COtBu | 2-COMe—Ph |
| 5123 | 4-Cl | COtBu | 2-CO2Me—Ph |
| 5124 | 4-Cl | COtBu | 2-CONH2—Ph |
| 5125 | 4-Cl | COtBu | 2-CONHMe—Ph |
| 5126 | 4-Cl | COtBu | 2-F—Ph |
| 5127 | 4-Cl | COtBu | 2-Cl—Ph |
| 5128 | 4-Cl | COtBu | 2-Br—Ph |
| 5129 | 4-Cl | COtBu | 2-SO2NH2—Ph |
| 5130 | 4-Cl | COtBu | 2-SO2NHIMe—Ph |
| 5131 | 4-Cl | COtBu | 2-CF3—Ph |
| 5132 | 4-Cl | COtBu | 2-OMe—Ph |
| 5133 | 4-Cl | COtBu | 2-SMe—Ph |
| 5134 | 4-Cl | COtBu | 2-SOMe—Ph |
| 5135 | 4-Cl | COtBu | 2-SO2Me—Ph |
| 5136 | 4-Cl | COtBu | 2-OH—Ph |
| 5137 | 4-Cl | COtBu | 2-CH2OH—Ph |
| 5138 | 4-Cl | COtBu | 2-CHOHMe—Ph |
| 5139 | 4-Cl | COtBu | 2-COH(Me)2—Ph |
| 5140 | 4-Cl | COtBu | 2-Me—Ph |
| 5141 | 4-Cl | COtBu | 2-Et—Ph |
| 5142 | 4-Cl | COtBu | 2-iPr—Ph |
| 5143 | 4-Cl | COtBu | 2-tBu—Ph |
| 5144 | 4-Cl | COtBu | 2-CH2CO2Me—Ph |
| 5145 | 4-Cl | COtBu | 2-(1-piperidinyl)-Ph |
| 5146 | 4-Cl | COtBu | 2-(1-pyrrolidinyl)-Ph |
| 5147 | 4-Cl | COtBu | 2-(2-imidazolyl)-Ph |
| 5148 | 4-Cl | COtBu | 2-(1-imidazolyl)-Ph |
| 5149 | 4-Cl | COtBu | 2-(2-thiazolyl)-Ph |
| 5150 | 4-Cl | COtBu | 2-(3-pyrazolyl)-ph |
| 5151 | 4-Cl | COtBu | 2-(1-pyrazolyl)-Ph |
| 5152 | 4-Cl | COtBu | 2-(5-Me-1-tetrazolyl)-Ph |
| 5153 | 4-Cl | COtBu | 2-(1-Me-5-tetrazolyl)-Ph |
| 5154 | 4-Cl | COtBu | 2-(2-pyridyl)-Ph |
| 5155 | 4-Cl | COtBu | 2-(2-thienyl)-Ph |

TABLE 2-continued

| | | | |
|---|---|---|---|
| 5156 | 4-Cl | COtBu | 2-(2-furanyl)-Ph |
| 5157 | 4-Cl | COtBu | 2,4-diF—Ph |
| 5158 | 4-Cl | COtBu | 2,5-diF—Ph |
| 5159 | 4-Cl | COtBu | 2,6-diF—Ph |
| 5160 | 4-Cl | COtBu | 3,4-diF—Ph |
| 5161 | 4-Cl | COtBu | 3,5-diF—Ph |
| 5162 | 4-Cl | COtBu | 2,4-diCl—Ph |
| 5163 | 4-Cl | COtBu | 2,5-diCl—Ph |
| 5164 | 4-Cl | COtBu | 2,6-diCl—Ph |
| 5165 | 4-Cl | COtBu | 3,4-diCl—Ph |
| 5166 | 4-Cl | COtBu | 3,5-diCl—Ph |
| 5167 | 4-Cl | COtBu | 3,4-diCF3—Ph |
| 5168 | 4-Cl | COtBu | 3,5-diCF3—Ph |
| 5169 | 4-Cl | COtBu | 5-Cl-2-MeO—Ph |
| 5170 | 4-Cl | COtBu | 5-Cl-2-Me—Ph |
| 5171 | 4-Cl | COtBu | 2-F-5-Me—Ph |
| 5172 | 4-Cl | COtBu | 3-F-5-morpholino-Ph |
| 5173 | 4-Cl | COtBu | 3,4-OCH2O—Ph |
| 5174 | 4-Cl | COtBu | 3,4-OCH2CH2O—Ph |
| 5175 | 4-Cl | COtBu | 2-MeO-5-CONH2—Ph |
| 5176 | 4-Cl | COtBu | 2-MeO-4-(1-Me-5-tetrazolyl)-Ph |
| 5177 | 4-Cl | COtBu | 2-MeO-5-(1-Me-5-tetrazolyl)-Ph |
| 5178 | 4-Cl | COtBu | 3-CONH2-5-(1-Me-5-tetrazolyl)-ph |
| 5179 | 4-Cl | COtBu | 1-naphthyl |
| 5180 | 4-Cl | COtBu | 2-naphthyl |
| 5181 | 4-Cl | COtBu | 2-thienyl |
| 5182 | 4-Cl | COtBu | 3-thienyl |
| 5183 | 4-Cl | COtBu | 2-furanyl |
| 5184 | 4-Cl | COtBu | 3-furanyl |
| 5185 | 4-Cl | COtBu | 2-pyridyl |
| 5186 | 4-Cl | COtBu | 3-pyridyl |
| 5187 | 4-Cl | COtBu | 4-pyridyl |
| 5188 | 4-Cl | COtBu | 2-indolyl |
| 5189 | 4-Cl | COtBu | 3-indolyl |
| 5190 | 4-Cl | COtBu | 5-indolyl |
| 5191 | 4-Cl | COtBu | 6-indolyl |
| 5192 | 4-Cl | COtBu | 3-indazolyl |
| 5193 | 4-Cl | COtBu | 5-indazolyl |
| 5194 | 4-Cl | COtBu | 6-indazolyl |
| 5195 | 4-Cl | COtBu | 2-imidazolyl |
| 5196 | 4-Cl | COtBu | 3-isoxazoyl |
| 5197 | 4-Cl | COtBu | 3-pyrazolyl |
| 5198 | 4-Cl | COtBu | 2-thiadiazolyl |
| 5199 | 4-Cl | COtBu | 2-thiazolyl |
| 5200 | 4-Cl | COtBu | 5-Ac-4-Me-2-thiazolyl |
| 5201 | 4-Cl | COtBu | 5-tetrazolyl |
| 5202 | 4-Cl | COtBu | 2-benzimidazolyl |
| 5203 | 4-Cl | COtBu | 5-benzimidazolyl |
| 5204 | 4-Cl | COtBu | 2-benzothiazolyl |
| 5205 | 4-Cl | COtBu | 5-benzothiazolyl |
| 5206 | 4-Cl | COtBu | 2-benzoxazolyl |
| 5207 | 4-Cl | COtBu | 5-benzoxazolyl |
| 5208 | 4-Cl | COtBu | 1-adamantyl |
| 5209 | 4-Cl | COtBu | 2-adamantyl |
| 5210 | 4-Cl | COtBu | i-Pr |
| 5211 | 4-Cl | COtBu | t-Bu |
| 5212 | 4-Cl | COtBu | c-Hex |
| 5213 | 4-Cl | COtBu | CH2CH2OMe |
| 5214 | 4-Cl | COtBu | CH2CONH2 |
| 5215 | 4-Cl | COtBu | CH2CO2Me |
| 5216 | 4-Cl | COtBu | CH(CH2Ph)CO2Me |
| 5217 | 4-Cl | COtBu | CH2CH2NMe2 |
| 5218 | 4-Cl | COtBu | benzyl |
| 5219 | 4-Cl | COtBu | phenethyl |
| 5220 | 4-Cl | COtBu | 2-(morpholin-1-yl)-Et |
| 5221 | 4-Cl | SO2Me | Ph |
| 5222 | 4-Cl | SO2Me | 3-CN—Ph |
| 5223 | 4-Cl | SO2Me | 3-COMe—Ph |
| 5224 | 4-Cl | SO2Me | 3-CO2Me—Ph |
| 5225 | 4-Cl | SO2Me | 3-CONH2—Ph |
| 5226 | 4-Cl | SO2Me | 3-CONHMe—Ph |
| 5227 | 4-Cl | SO2Me | 3-F—Ph |
| 5228 | 4-Cl | SO2Me | 3-Cl—Ph |
| 5229 | 4-Cl | SO2Me | 3-Br—Ph |
| 5230 | 4-Cl | SO2Me | 3-SO2NH2—Ph |
| 5231 | 4-Cl | SO2Me | 3-SO2NHMe—Ph |
| 5232 | 4-Cl | SO2Me | 3-CF3—Ph |
| 5233 | 4-Cl | SO2Me | 3-OMe—Ph |
| 5234 | 4-Cl | SO2Me | 3-SMe—Ph |
| 5235 | 4-Cl | SO2Me | 3-SOMe—Ph |
| 5236 | 4-Cl | SO2Me | 3-SO2Me—Ph |
| 5237 | 4-Cl | SO2Me | 3-OH—Ph |
| 5238 | 4-Cl | SO2Me | 3-CH2OH—Ph |
| 5239 | 4-Cl | SO2Me | 3-CHOHMe—Ph |
| 5240 | 4-Cl | SO2Me | 3-COH(Me)2—Ph |
| 5241 | 4-Cl | SO2Me | 3-Me—Ph |
| 5242 | 4-Cl | SO2Me | 3-Et—Ph |
| 5243 | 4-Cl | SO2Me | 3-iPr—Ph |
| 5244 | 4-Cl | SO2Me | 3-tBu—Ph |
| 5245 | 4-Cl | SO2Me | 3-CH2CO2Me—Ph |
| 5246 | 4-Cl | SO2Me | 3-(1-piperidinyl)-Ph |
| 5247 | 4-Cl | SO2Me | 3-(1-pyrrolidinyl)-Ph |
| 5248 | 4-Cl | SO2Me | 3-(2-imidazolyl)-Ph |
| 5249 | 4-Cl | SO2Me | 3-(1-imidazolyl)-Ph |
| 5250 | 4-Cl | SO2Me | 3-(2-thiazolyl)-Ph |
| 5251 | 4-Cl | SO2Me | 3-(3-pyrazolyl)-Ph |
| 5252 | 4-Cl | SO2Me | 3-(1-pyrazolyl)-Ph |
| 5253 | 4-Cl | SO2Me | 3-(5-Me-1-tetrazolyl)-ph |
| 5254 | 4-Cl | SO2Me | 3-(1-Me-5-tetrazolyl)-Ph |
| 5255 | 4-Cl | SO2Me | 3-(2-pyridyl)-Ph |
| 5256 | 4-Cl | SO2Me | 3-(2-thienyl)-Ph |
| 5257 | 4-Cl | SO2Me | 3-(2-furanyl)-Ph |
| 5258 | 4-Cl | SO2Me | 4-CN—Ph |
| 5259 | 4-Cl | SO2Me | 4-COMe—Ph |
| 5260 | 4-Cl | SO2Me | 4-CO2Me—Ph |
| 5261 | 4-Cl | SO2Me | 4-CONH2—Ph |
| 5262 | 4-Cl | SO2Me | 4-CONHMe—Ph |
| 5263 | 4-Cl | SO2Me | 4-CONHPh—Ph |
| 5264 | 4-Cl | SO2Me | 4-F—Ph |
| 5265 | 4-Cl | SO2Me | 4-Cl—Ph |
| 5266 | 4-Cl | SO2Me | 4-Br—Ph |
| 5267 | 4-Cl | SO2Me | 4-SO2NH2—Ph |
| 5268 | 4-Cl | SO2Me | 4-SO2NHMe—Ph |
| 5269 | 4-Cl | SO2Me | 4-CF3—Ph |
| 5270 | 4-Cl | SO2Me | 4-OMe—Ph |
| 5271 | 4-Cl | SO2Me | 4-SMe—Ph |
| 5272 | 4-Cl | SO2Me | 4-SOMe—Ph |
| 5273 | 4-Cl | SO2Me | 4-SO2Me—Ph |
| 5274 | 4-Cl | SO2Me | 4-OH—Ph |
| 5275 | 4-Cl | SO2Me | 4-CH2OH—Ph |
| 5276 | 4-Cl | SO2Me | 4-CHOHMe—Ph |
| 5277 | 4-Cl | SO2Me | 4-COH(Me)2—Ph |
| 5278 | 4-Cl | SO2Me | 4-Me—Ph |
| 5279 | 4-Cl | SO2Me | 4-Et—Ph |
| 5280 | 4-Cl | SO2Me | 4-iPr—Ph |
| 5281 | 4-Cl | SO2Me | 4-tBu—Ph |
| 5282 | 4-Cl | SO2Me | 4-CH2CO2Me—Ph |
| 5283 | 4-Cl | SO2Me | 4-(1-piperidinyl)-Ph |
| 5284 | 4-Cl | SO2Me | 4-(1-pyrrolidinyl)-ph |
| 5285 | 4-Cl | SO2Me | 4-(2-imidazolyl)-Ph |
| 5286 | 4-Cl | SO2Me | 4-(1-imidazolyl)-Ph |
| 5287 | 4-Cl | SO2Me | 4-(2-thiazolyl)-Ph |
| 5288 | 4-Cl | SO2Me | 4-(3-pyrazolyl)-Ph |
| 5289 | 4-Cl | SO2Me | 4-(1-pyrazolyl)-Ph |
| 5290 | 4-Cl | SO2Me | 4-(5-Me-1-tetrazolyl)-Ph |
| 5291 | 4-Cl | SO2Me | 4-(1-Me-5-tetrazolyl)-Ph |
| 5292 | 4-Cl | SO2Me | 4-(2-pyridyl)-Ph |
| 5293 | 4-Cl | SO2Me | 4-(2-thienyl)-Ph |
| 5294 | 4-Cl | SO2Me | 4-(2-furanyl)-Ph |
| 5295 | 4-Cl | SO2Me | 2-CN—Ph |
| 5296 | 4-Cl | SO2Me | 2-COMe—Ph |
| 5297 | 4-Cl | SO2Me | 2-CO2Me—Ph |
| 5298 | 4-Cl | SO2Me | 2-CONH2-Ph |
| 5299 | 4-Cl | SO2Me | 2-CONHMe—Ph |
| 5300 | 4-Cl | SO2Me | 2-F—Ph |
| 5301 | 4-Cl | SO2Me | 2-Cl—Ph |
| 5302 | 4-Cl | SO2Me | 2-Br—Ph |
| 5303 | 4-Cl | SO2Me | 2-SO2NH2—Ph |
| 5304 | 4-Cl | SO2Me | 2-SO2NHMe—Ph |
| 5305 | 4-Cl | SO2Me | 2-CF3—Ph |
| 5306 | 4-Cl | SO2Me | 2-OMe—Ph |
| 5307 | 4-Cl | SO2Me | 2-SMe—Ph |
| 5308 | 4-Cl | SO2Me | 2-SOMe—Ph |
| 5309 | 4-Cl | SO2Me | 2-SO2Me—Ph |
| 5310 | 4-Cl | SO2Me | 2-OH—Ph |
| 5311 | 4-Cl | SO2Me | 2-CH2OH—Ph |
| 5312 | 4-Cl | SO2Me | 2-CHOHMe—Ph |
| 5313 | 4-Cl | SO2Me | 2-COH(Me)2—Ph |

TABLE 2-continued

| | | | |
|---|---|---|---|
| 5314 | 4-Cl | SO2Me | 2-Me—Ph |
| 5315 | 4-Cl | SO2Me | 2-Et—Ph |
| 5316 | 4-Cl | SO2Me | 2-iPr—Ph |
| 5317 | 4-Cl | SO2Me | 2-tBu—Ph |
| 5318 | 4-Cl | SO2Me | 2-CH2CO2Me—Ph |
| 5319 | 4-Cl | SO2Me | 2-(1-piperidinyl)-Ph |
| 5320 | 4-Cl | SO2Me | 2-(1-pyrrolidinyl)-ph |
| 5321 | 4-Cl | SO2Me | 2-(2-imidazolyl)-Ph |
| 5322 | 4-Cl | SO2Me | 2-(1-imidazolyl)-Ph |
| 5323 | 4-Cl | SO2Me | 2-(2-thiazolyl)-Ph |
| 5324 | 4-Cl | SO2Me | 2-(3-pyrazolyl)-Ph |
| 5325 | 4-Cl | SO2Me | 2-(1-pyrazolyl)-Ph |
| 5326 | 4-Cl | SO2Me | 2-(5-Me-1-tetrazolyl)-Ph |
| 5327 | 4-Cl | SO2Me | 2-(1-Me-5-tetrazolyl)-Ph |
| 5328 | 4-Cl | SO2Me | 2-(2-pyridyl)-Ph |
| 5329 | 4-Cl | SO2Me | 2-(2-thienyl)-Ph |
| 5330 | 4-Cl | SO2Me | 2-(2-turanyl)-Ph |
| 5331 | 4-Cl | SO2Me | 2,4-diF—Ph |
| 5332 | 4-Cl | SO2Me | 2,5-diF—Ph |
| 5333 | 4-Cl | SO2Me | 2,6-diF—Ph |
| 5334 | 4-Cl | SO2Me | 3,4-diF—Ph |
| 5335 | 4-Cl | SO2Me | 3,5-diF—Ph |
| 5336 | 4-Cl | SO2Me | 2,4-diCl—Ph |
| 5337 | 4-Cl | SO2Me | 2,5-diCl—Ph |
| 5338 | 4-Cl | SO2Me | 2,6-diCl—Ph |
| 5339 | 4-Cl | SO2Me | 3,4-diCl—Ph |
| 5340 | 4-Cl | SO2Me | 3,5-diCl—Ph |
| 5341 | 4-Cl | SO2Me | 3,4-diCF3—Ph |
| 5342 | 4-Cl | SO2Me | 3,5-diCF3—Ph |
| 5343 | 4-Cl | SO2Me | 5-Cl-2-MeO—Ph |
| 5344 | 4-Cl | SO2Me | 5-Cl-2-Me—Ph |
| 5345 | 4-Cl | SO2Me | 2-F-5-Me—Ph |
| 5346 | 4-Cl | SO2Me | 3-F-5-morpholino-Ph |
| 5347 | 4-Cl | SO2Me | 3,4-OCH2O—Ph |
| 5348 | 4-Cl | SO2Me | 3,4-OCH2CH2O—Ph |
| 5349 | 4-Cl | SO2Me | 2-MeO-5-CONH2—Ph |
| 5350 | 4-Cl | SO2Me | 2-MeO-4-(1-Me-5-tetrazolyl)-Ph |
| 5351 | 4-Cl | SO2Me | 2-MeO-5-(1-Me-5-tetrazolyl)-Ph |
| 5352 | 4-Cl | SO2Me | 3-CONH2-5-(1-Me-5-tetrazolyl)-Ph |
| 5353 | 4-Cl | SO2Me | 1-naphthyl |
| 5354 | 4-Cl | SO2Me | 2-naphthyl |
| 5355 | 4-Cl | SO2Me | 2-thienyl |
| 5356 | 4-Cl | SO2Me | 3-thienyl |
| 5357 | 4-Cl | SO2Me | 2-furanyl |
| 5358 | 4-Cl | SO2Me | 3-furanyl |
| 5359 | 4-Cl | SO2Me | 2-pyridyl |
| 5360 | 4-Cl | SO2Me | 3-pyridyl |
| 5361 | 4-Cl | SO2Me | 4-pyridyl |
| 5362 | 4-Cl | SO2Me | 2-indolyl |
| 5363 | 4-Cl | SO2Me | 3-indolyl |
| 5364 | 4-Cl | SO2Me | 5-indolyl |
| 5365 | 4-Cl | SO2Me | 6-indolyl |
| 5366 | 4-Cl | SO2Me | 3-indazolyl |
| 5367 | 4-Cl | SO2Me | 5-indazolyl |
| 5368 | 4-Cl | SO2Me | 6-indazolyl |
| 5369 | 4-Cl | SO2Me | 2-imidazolyl |
| 5370 | 4-Cl | SO2Me | 3-isoxazoyl |
| 5371 | 4-Cl | SO2Me | 3-pyrazolyl |
| 5372 | 4-Cl | SO2Me | 2-thiadiazolyl |
| 5373 | 4-Cl | SO2Me | 2-thiazolyl |
| 5374 | 4-Cl | SO2Me | 5-Ac-4-Me-2-thiazolyl |
| 5375 | 4-Cl | SO2Me | 5-tetrazolyl |
| 5376 | 4-Cl | SO2Me | 2-benzimidazolyl |
| 5377 | 4-Cl | SO2Me | 5-benzimidazolyl |
| 5378 | 4-Cl | SO2Me | 2-benzothiazolyl |
| 5379 | 4-Cl | SO2Me | 5-benzothiazolyl |
| 5380 | 4-Cl | SO2Me | 2-benzoxazolyl |
| 5381 | 4-Cl | SO2Me | 5-benzoxazolyl |
| 5382 | 4-Cl | SO2Me | 1-adamantyl |
| 5383 | 4-Cl | SO2Me | 2-adamantyl |
| 5384 | 4-Cl | SO2Me | i-Pr |
| 5385 | 4-Cl | SO2Me | t-Bu |
| 5386 | 4-Cl | SO2Me | c-Hex |
| 5387 | 4-Cl | SO2Me | CH2CH2OMe |
| 5388 | 4-Cl | SO2Me | CH2CONH2 |
| 5389 | 4-Cl | SO2Me | CH2CO2Me |
| 5390 | 4-Cl | SO2Me | CH(CH2Ph)CO2Me |
| 5391 | 4-Cl | SO2Me | CH2CH2NMe2 |
| 5392 | 4-Cl | SO2Me | benzyl |
| 5393 | 4-Cl | SO2Me | phenethyl |
| 5394 | 4-Cl | SO2Me | 2-(morpholin-1-yl)-Et |
| 5395 | 4-Cl | CH2COMe | Ph |
| 5396 | 4-Cl | CH2COMe | 3-CN—Ph |
| 5397 | 4-Cl | CH2COMe | 3-COMe—Ph |
| 5398 | 4-Cl | CH2COMe | 3-CO2Me—Ph |
| 5399 | 4-Cl | CH2COMe | 3-CONH2—Ph |
| 5400 | 4-Cl | CH2COMe | 3-CONHMe—Ph |
| 5401 | 4-Cl | CH2COMe | 3-F—Ph |
| 5402 | 4-Cl | CH2COMe | 3-Cl—Ph |
| 5403 | 4-Cl | CH2COMe | 3-Br—Ph |
| 5404 | 4-Cl | CH2COMe | 3-SO2NH2—Ph |
| 5405 | 4-Cl | CH2COMe | 3-SO2NHMe—Ph |
| 5406 | 4-Cl | CH2COMe | 3-CF3—Ph |
| 5407 | 4-Cl | CH2COMe | 3-OMe—Ph |
| 5408 | 4-Cl | CH2COMe | 3-SMe—Ph |
| 5409 | 4-Cl | CH2COMe | 3-SOMe—Ph |
| 5410 | 4-Cl | CH2COMe | 3-SO2Me—Ph |
| 5411 | 4-Cl | CH2COMe | 3-OH—Ph |
| 5412 | 4-Cl | CH2COMe | 3-CH2OH—Ph |
| 5413 | 4-Cl | CH2COMe | 3-CHOHMe—Ph |
| 5414 | 4-Cl | CH2COMe | 3-COH(Me)2—Ph |
| 5415 | 4-Cl | CH2COMe | 3-Me—Ph |
| 5416 | 4-Cl | CH2COMe | 3-Et—Ph |
| 5417 | 4-Cl | CH2COMe | 3-iPr—Ph |
| 5418 | 4-Cl | CH2COMe | 3-tBu—Ph |
| 5419 | 4-Cl | CH2COMe | 3-CH2CO2Me—Ph |
| 5420 | 4-Cl | CH2COMe | 3-(1-piperidinyl)-Ph |
| 5421 | 4-Cl | CH2COMe | 3-(1-pyrrolidinyl)-Ph |
| 5422 | 4-Cl | CH2COMe | 3-(2-imidazolyl)-Ph |
| 5423 | 4-Cl | CH2COMe | 3-(1-imidazolyl)-Ph |
| 5424 | 4-Cl | CH2COMe | 3-(2-thiazolyl)-Ph |
| 5425 | 4-Cl | CH2COMe | 3-(3-pyrazolyl)-Ph |
| 5426 | 4-Cl | CH2COMe | 3-(1-pyrazolyl)-Ph |
| 5427 | 4-Cl | CH2COMe | 3-(5-Me-1-tetrazolyl)-Ph |
| 5428 | 4-Cl | CH2COMe | 3-(1-Me-5-tetrazolyl)-Ph |
| 5429 | 4-Cl | CH2COMe | 3-(2-pyridyl)-Ph |
| 5430 | 4-Cl | CH2COMe | 3- (2-thienyl)-Ph |
| 5431 | 4-Cl | CH2COMe | 3-(2-furanyl)-ph |
| 5432 | 4-Cl | CH2COMe | 4-CN—Ph |
| 5433 | 4-Cl | CH2COMe | 4-COMe—Ph |
| 5434 | 4-Cl | CH2COMe | 4-CO2Me—Ph |
| 5435 | 4-Cl | CH2COMe | 4-CONH2—Ph |
| 5436 | 4-Cl | CH2COMe | 4-CONHMe—Ph |
| 5437 | 4-Cl | CH2COMe | 4-CONHPh—Ph |
| 5438 | 4-Cl | CH2COMe | 4-F—Ph |
| 5439 | 4-Cl | CH2COMe | 4-Cl—Ph |
| 5440 | 4-Cl | CH2COMe | 4-Br—Ph |
| 5441 | 4-Cl | CH2COMe | 4-SO2NH2—Ph |
| 5442 | 4-Cl | CH2COMe | 4-SO2NHMe—Ph |
| 5443 | 4-Cl | CH2COMe | 4-CF3—Ph |
| 5444 | 4-Cl | CH2COMe | 4-OMe—Ph |
| 5445 | 4-Cl | CH2COMe | 4-SMe—Ph |
| 5446 | 4-Cl | CH2COMe | 4-SOMe—Ph |
| 5447 | 4-Cl | CH2COMe | 4-SO2Me—Ph |
| 5448 | 4-Cl | CH2COMe | 4-OH—Ph |
| 5449 | 4-Cl | CH2COMe | 4-CH2OH—Ph |
| 5450 | 4-Cl | CH2COMe | 4-CHOHMe—Ph |
| 5451 | 4-Cl | CH2COMe | 4-COH(Me)2—Ph |
| 5452 | 4-Cl | CH2COMe | 4-Me—Ph |
| 5453 | 4-Cl | CH2COMe | 4-Et—Ph |
| 5454 | 4-Cl | CH2COMe | 4-iPr—Ph |
| 5455 | 4-Cl | CH2COMe | 4-tBu—Ph |
| 5456 | 4-Cl | CH2COMe | 4-CH2CO2Me—Ph |
| 5457 | 4-Cl | CH2COMe | 4-(1-piperidinyl)-Ph |
| 5458 | 4-Cl | CH2COMe | 4-(1-pyrrolidinyl)-Ph |
| 5459 | 4-Cl | CH2COMe | 4-(2-imidazolyl)-Ph |
| 5460 | 4-Cl | CH2COMe | 4-(1-imidazolyl)-Ph |
| 5461 | 4-Cl | CH2COMe | 4-(2-thiazolyl)-Ph |
| 5462 | 4-Cl | CH2COMe | 4-(3-pyrazolyl)-Ph |
| 5463 | 4-Cl | CH2COMe | 4-(1-pyrazolyl)-Ph |
| 5464 | 4-Cl | CH2COMe | 4-(5-Me-1-tetrazolyl)-Ph |
| 5465 | 4-Cl | CH2COMe | 4-(1-Me-5-tetrazolyl)-Ph |
| 5466 | 4-Cl | CH2COMe | 4-(2-pyridyl)-Ph |
| 5467 | 4-Cl | CH2COMe | 4-(2-thienyl)-Ph |
| 5468 | 4-Cl | CH2COMe | 4-(2-furanyl)-Ph |
| 5469 | 4-Cl | CH2COMe | 2-CN—Ph |
| 5470 | 4-Cl | CH2COMe | 2-COMe—Ph |

TABLE 2-continued

| | | | |
|---|---|---|---|
| 5471 | 4-Cl | CH2COMe | 2-CO2Me—Ph |
| 5472 | 4-Cl | CH2COMe | 2-CONH2—Ph |
| 5473 | 4-Cl | CH2COMe | 2-CONHMe—Ph |
| 5474 | 4-Cl | CH2COMe | 2-F—Ph |
| 5475 | 4-Cl | CH2COMe | 2-Cl—Ph |
| 5476 | 4-Cl | CH2COMe | 2-Br—Ph |
| 5477 | 4-Cl | CH2COMe | 2-SO2NH2—Ph |
| 5478 | 4-Cl | CH2COMe | 2-SO2NHMe—Ph |
| 5479 | 4-Cl | CH2COMe | 2-CF3—Ph |
| 5480 | 4-Cl | CH2COMe | 2-OMe—Ph |
| 5481 | 4-Cl | CH2COMe | 2-SMe—Ph |
| 5482 | 4-Cl | CH2COMe | 2-SOMe—Ph |
| 5483 | 4-Cl | CH2COMe | 2-SO2Me—Ph |
| 5484 | 4-Cl | CH2COMe | 2-OH—Ph |
| 5485 | 4-Cl | CH2COMe | 2-CH2OH—Ph |
| 5486 | 4-Cl | CH2COMe | 2-CHOHMe—Ph |
| 5487 | 4-Cl | CH2COMe | 2-COH(Me)2—Ph |
| 5488 | 4-Cl | CH2COMe | 2-Me—Ph |
| 5489 | 4-Cl | CH2COMe | 2-Et—Ph |
| 5490 | 4-Cl | CH2COMe | 2-iPr—Ph |
| 5491 | 4-Cl | CH2COMe | 2-tBu—Ph |
| 5492 | 4-Cl | CH2COMe | 2-CH2CO2Me—Ph |
| 5493 | 4-Cl | CH2COMe | 2-(1-piperidinyl)-Ph |
| 5494 | 4-Cl | CH2COMe | 2-(1-pyrrolidinyl)-Ph |
| 5495 | 4-Cl | CH2COMe | 2-(2-imidazolyl)-Ph |
| 5496 | 4-Cl | CH2COMe | 2-(1-imidazolyl)-Ph |
| 5497 | 4-Cl | CH2COMe | 2-(2-thiazolyl)-Ph |
| 5498 | 4-Cl | CH2COMe | 2-(3-pyrazolyl)-Ph |
| 5499 | 4-Cl | CH2COMe | 2-(1-pyrazolyl)-Ph |
| 5500 | 4-Cl | CH2COMe | 2-(5-Me-1-tetrazolyl)-Ph |
| 5501 | 4-Cl | CH2COMe | 2-(1-Me-5-tetrazolyl)-Ph |
| 5502 | 4-Cl | CH2COMe | 2-(2-pyridyl)-Ph |
| 5503 | 4-Cl | CH2COMe | 2-(2-thienyl)-Ph |
| 5504 | 4-Cl | CH2COMe | 2-(2-furanyl)-Ph |
| 5505 | 4-Cl | CH2COMe | 2,4-diF—Ph |
| 5506 | 4-Cl | CH2COMe | 2,5-diF—Ph |
| 5507 | 4-Cl | CH2COMe | 2,6-diF—Ph |
| 5508 | 4-Cl | CH2COMe | 3,4-diF—Ph |
| 5509 | 4-Cl | CH2COMe | 3,5-diF—Ph |
| 5510 | 4-Cl | CH2COMe | 2,4-diCl—Ph |
| 5511 | 4-Cl | CH2COMe | 2,5-diCl—Ph |
| 5512 | 4-Cl | CH2COMe | 2,6-diCl—Ph |
| 5513 | 4-Cl | CH2COMe | 3,4-diCl—Ph |
| 5514 | 4-Cl | CH2COMe | 3,5-diCl—Ph |
| 5515 | 4-Cl | CH2COMe | 3,4-diCF3—Ph |
| 5516 | 4-Cl | CH2COMe | 3,5-diCF3—Ph |
| 5517 | 4-Cl | CH2COMe | 5-Cl-2-MeO—Ph |
| 5518 | 4-Cl | CH2COMe | 5-Cl-2-Me—Ph |
| 5519 | 4-Cl | CH2COMe | 2-F-5-Me—Ph |
| 5520 | 4-Cl | CH2COMe | 3-F-5-morpholino-Ph |
| 5521 | 4-Cl | CH2COMe | 3,4-OCH2O—Ph |
| 5522 | 4-Cl | CH2COMe | 3,4-OCH2CH2O—Ph |
| 5523 | 4-Cl | CH2COMe | 2-MeO-5-CONH2—Ph |
| 5524 | 4-Cl | CH2COMe | 2-MeO-4-(1-Me-5-tetrazolyl)-Ph |
| 5525 | 4-Cl | CH2COMe | 2-MeO-5-(1-Me-5-tetrazolyl)-Ph |
| 5526 | 4-Cl | CH2COMe | 3-CONH2-5-(1-Me-5-tetrazolyl)-Ph |
| 5527 | 4-Cl | CH2COMe | 1-naphthyl |
| 5528 | 4-Cl | CH2COMe | 2-naphthyl |
| 5529 | 4-Cl | CH2COMe | 2-thienyl |
| 5530 | 4-Cl | CH2COMe | 3-thienyl |
| 5531 | 4-Cl | CH2COMe | 2-furanyl |
| 5532 | 4-Cl | CH2COMe | 3-furanyl |
| 5533 | 4-Cl | CH2COMe | 2-pyridyl |
| 5534 | 4-Cl | CH2COMe | 3-pyridyl |
| 5535 | 4-Cl | CH2COMe | 4-pyridyl |
| 5536 | 4-Cl | CH2COMe | 2-indolyl |
| 5537 | 4-Cl | CH2COMe | 3-indolyl |
| 5538 | 4-Cl | CH2COMe | 5-indolyl |
| 5539 | 4-Cl | CH2COMe | 6-indolyl |
| 5540 | 4-Cl | CH2COMe | 3-indazolyl |
| 5541 | 4-Cl | CH2COMe | 5-indazolyl |
| 5542 | 4-Cl | CH2COMe | 6-indazolyl |
| 5543 | 4-Cl | CH2COMe | 2-imidazolyl |
| 5544 | 4-Cl | CH2COMe | 3-isoxazoyl |
| 5545 | 4-Cl | CH2COMe | 3-pyrazolyl |
| 5546 | 4-Cl | CH2COMe | 2-thiadiazolyl |
| 5547 | 4-Cl | CH2COMe | 2-thiazolyl |
| 5548 | 4-Cl | CH2COMe | 5-Ac-4-Me-2-thiazolyl |
| 5549 | 4-Cl | CH2COMe | 5-tetrazolyl |

TABLE 2-continued

| | | | |
|---|---|---|---|
| 5550 | 4-Cl | CH2COMe | 2-benzimidazolyl |
| 5551 | 4-Cl | CH2COMe | 5-benzimidazolyl |
| 5552 | 4-Cl | CH2COMe | 2-benzothiazolyl |
| 5553 | 4-Cl | CH2COMe | 5-benzothiazolyl |
| 5554 | 4-Cl | CH2COMe | 2-benzoxazolyl |
| 5555 | 4-Cl | CH2COMe | 5-benzoxazolyl |
| 5556 | 4-Cl | CH2COMe | 1-adamantyl |
| 5557 | 4-Cl | CH2COMe | 2-adamantyl |
| 5558 | 4-Cl | CH2COMe | i-Pr |
| 5559 | 4-Cl | CH2COMe | t-Bu |
| 5560 | 4-Cl | CH2COMe | c-Hex |
| 5561 | 4-Cl | CH2COMe | CH2CH2OMe |
| 5562 | 4-Cl | CH2COMe | CH2CONH2 |
| 5563 | 4-Cl | CH2COMe | CH2CO2Me |
| 5564 | 4-Cl | CH2COMe | CH(CH2Ph)CO2Me |
| 5565 | 4-Cl | CH2COMe | CH2CH2NMe2 |
| 5566 | 4-Cl | CH2COMe | benzyl |
| 5567 | 4-Cl | CH2COMe | phenethyl |
| 5568 | 4-Cl | CH2COMe | 2-(morpholin-1-yl)-Et |

TABLE 3

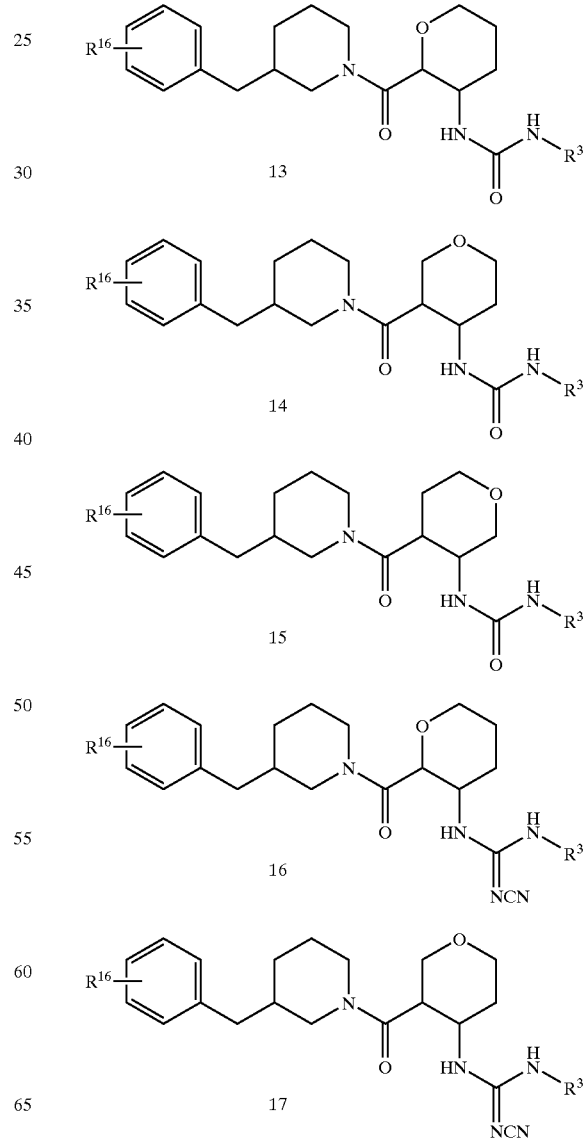

TABLE 3-continued
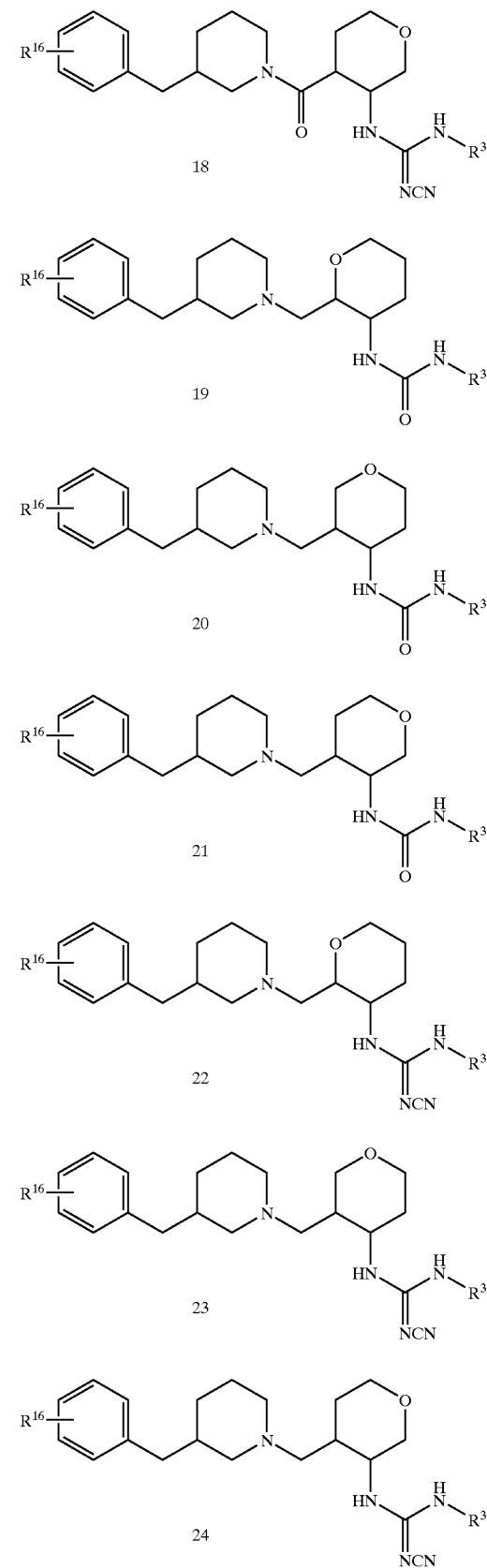
TABLE 3-continued
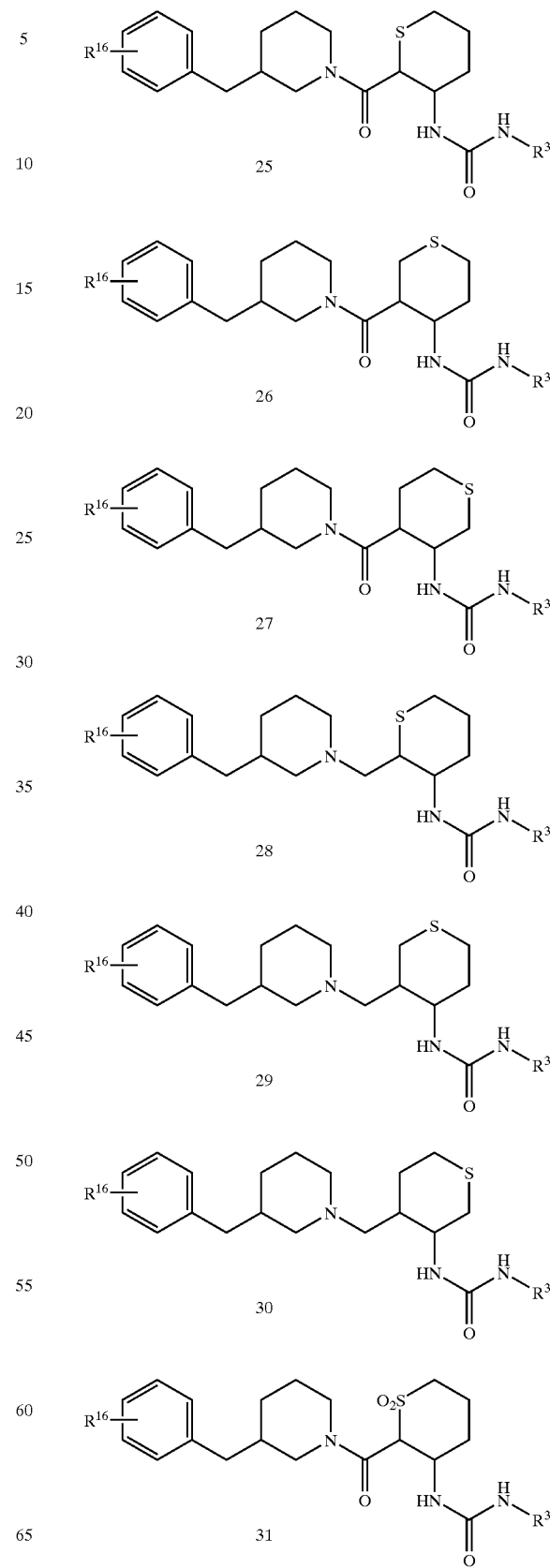

TABLE 3-continued
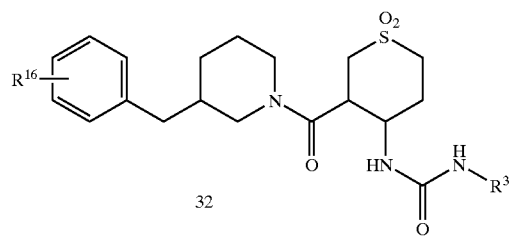
32
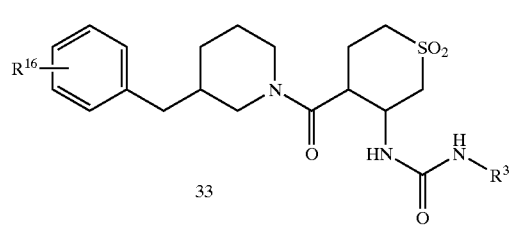
33
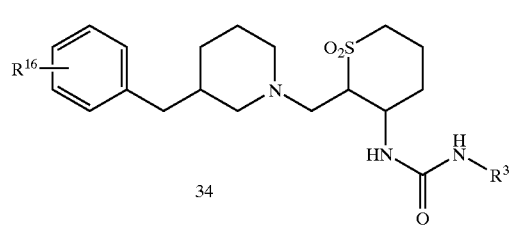
34
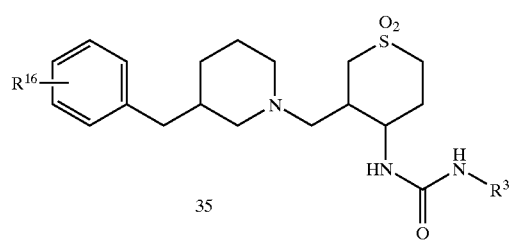
35
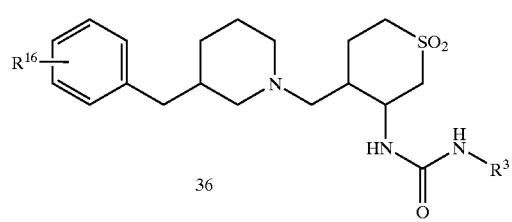
36
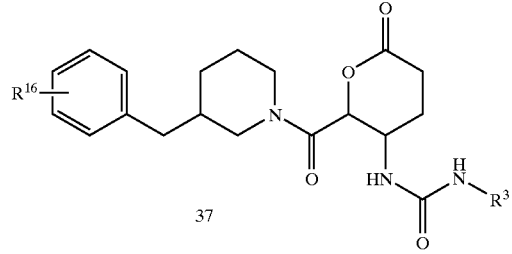
37
TABLE 3-continued
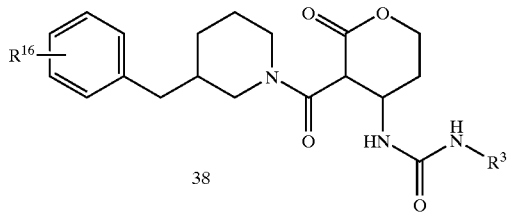
38
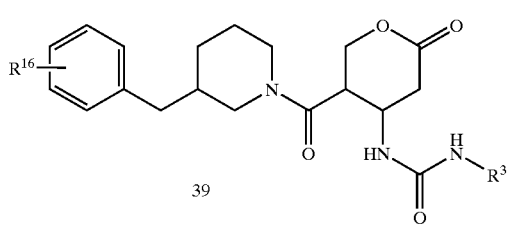
39
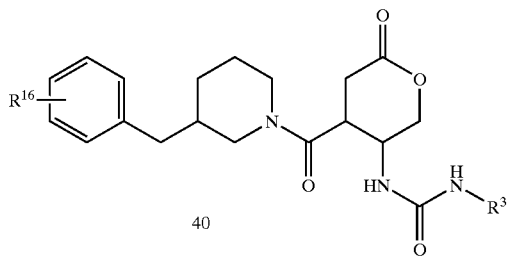
40
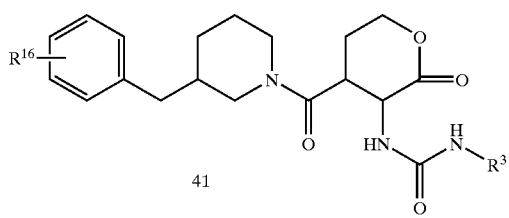
41
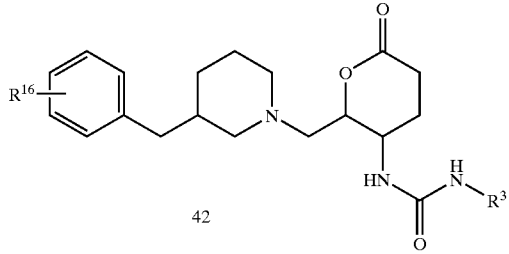
42
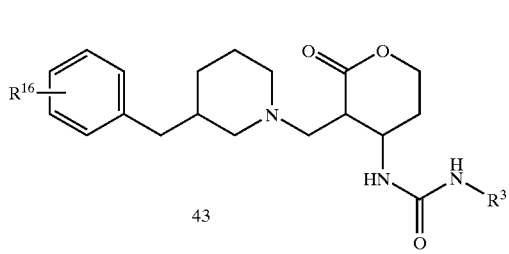
43

TABLE 3-continued
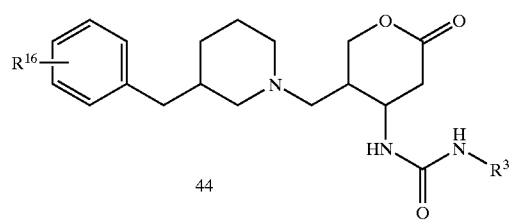
44
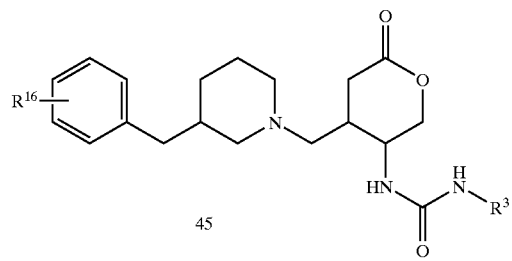
45
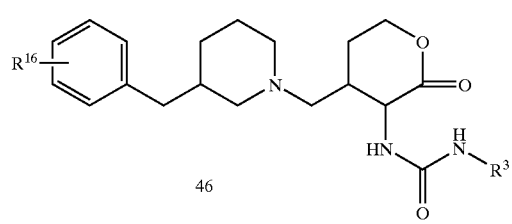
46
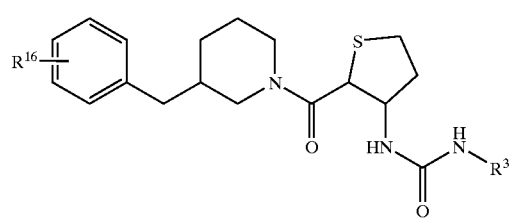
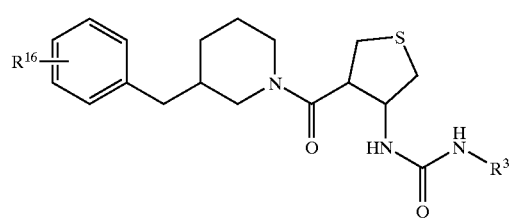
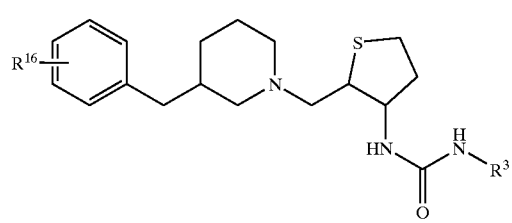
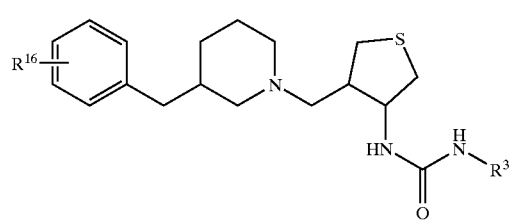
TABLE 3-continued
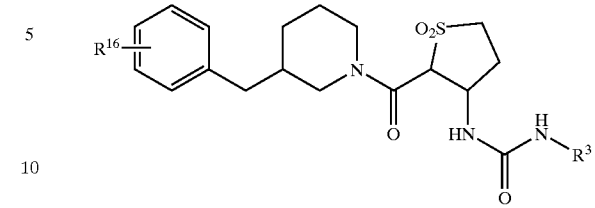
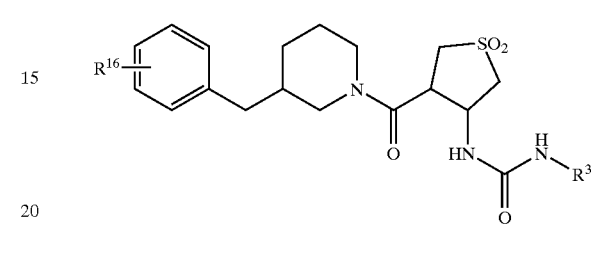
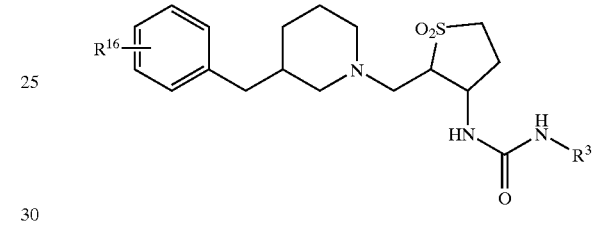
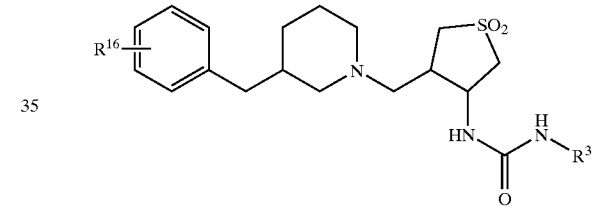
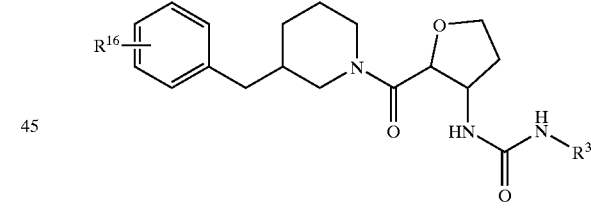
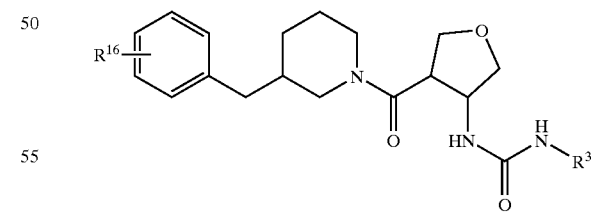
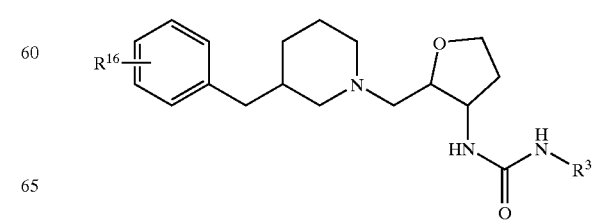

TABLE 3-continued

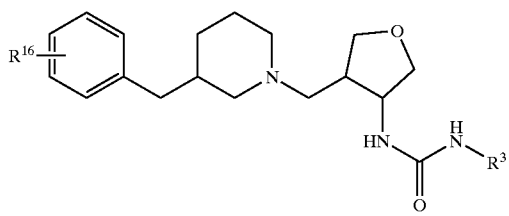

| Entry | R16 | R3 |
|---|---|---|
| 1 | 2-F | Ph |
| 2 | 2-F | 3-CN—Ph |
| 3 | 2-F | 3-COMe—Ph |
| 4 | 2-F | 3-CO2Me—Ph |
| 5 | 2-F | 3-CONH2—Ph |
| 6 | 2-F | 3-CONHMe—Ph |
| 7 | 2-F | 3-F—Ph |
| 8 | 2-F | 3-Cl—Ph |
| 9 | 2-F | 3-Br—Ph |
| 10 | 2-F | 3-SO2NH2—Ph |
| 11 | 2-F | 3-SO2NHMe—Ph |
| 12 | 2-F | 3-CF3—Ph |
| 13 | 2-F | 3-OMe—Ph |
| 14 | 2-F | 3-SMe—Ph |
| 15 | 2-F | 3-SOMe—Ph |
| 16 | 2-F | 3-SO2Me—Ph |
| 17 | 2-F | 3-OH—Ph |
| 18 | 2-F | 3-CH2OH—Ph |
| 19 | 2-F | 3-CHOHMe—Ph |
| 20 | 2-F | 3-COH(Me)2—Ph |
| 21 | 2-F | 3-Me—Ph |
| 22 | 2-F | 3-Et—Ph |
| 23 | 2-F | 3-iPr-Ph |
| 24 | 2-F | 3-tBu-Ph |
| 25 | 2-F | 3-CH2CO2Me—Ph |
| 26 | 2-F | 3-(1-piperidinyl)-Ph |
| 27 | 2-F | 3-(1-pyrrolidinyl)-Ph |
| 28 | 2-F | 3-(2-imidazolyl)-Ph |
| 29 | 2-F | 3-(1-imidazolyl)-Ph |
| 30 | 2-F | 3-(2-thiazolyl)-Ph |
| 31 | 2-F | 3-(3-pyrazolyl)-Ph |
| 32 | 2-F | 3-(1-pyrazolyl)-Ph |
| 33 | 2-F | 3-(5-Me-1-tetrazolyl)-Ph |
| 34 | 2-F | 3-(1-Me-5-tetrazolyl)-Ph |
| 35 | 2-F | 3-(2-pyridyl)-Ph |
| 36 | 2-F | 3-(2-thienyl)-Ph |
| 37 | 2-F | 3-(2-furanyl)-Ph |
| 38 | 2-F | 4-CN—Ph |
| 39 | 2-F | 4-COMe—Ph |
| 40 | 2-F | 4-CO2Me—Ph |
| 41 | 2-F | 4-CONH2—Ph |
| 42 | 2-F | 4-CONHMe—Ph |
| 43 | 2-F | 4-CONHPh—Ph |
| 44 | 2-F | 4-F—Ph |
| 45 | 2-F | 4-Cl—Ph |
| 46 | 2-F | 4-Br—Ph |
| 47 | 2-F | 4-SO2NH2—Ph |
| 48 | 2-F | 4-SO2NHMe—Ph |
| 49 | 2-F | 4-CF3—Ph |
| 50 | 2-F | 4-OMe—Ph |
| 51 | 2-F | 4-SMe—Ph |
| 52 | 2-F | 4-SOMe—Ph |
| 53 | 2-F | 4-SO2Me—Ph |
| 54 | 2-F | 4-OH—Ph |
| 55 | 2-F | 4-CH2OH—Ph |
| 56 | 2-F | 4-CHOHMe—Ph |
| 57 | 2-F | 4-COH(Me)2—Ph |
| 58 | 2-F | 4-Me—Ph |
| 59 | 2-F | 4-Et—Ph |
| 60 | 2-F | 4-iPr-Ph |
| 61 | 2-F | 4-tBu-Ph |
| 62 | 2-F | 4-CH2CO2Me—Ph |
| 63 | 2-F | 4-(1-piperidinyl)-Ph |
| 64 | 2-F | 4-(1-pyrrolidinyl)-Ph |
| 65 | 2-F | 4-(2-imidazolyl)-Ph |
| 66 | 2-F | 4-(1-imidazolyl)-Ph |
| 67 | 2-F | 4-(2-thiazolyl)-Ph |
| 68 | 2-F | 4-(3-pyrazolyl)-Ph |
| 69 | 2-F | 4-(1-pyrazolyl)-Ph |
| 70 | 2-F | 4-(5-Me-1-tetrazolyl)-Ph |
| 71 | 2-F | 4-(1-Me-5-tetrazolyl)-Ph |
| 72 | 2-F | 4-(2-pyridyl)-Ph |
| 73 | 2-F | 4-(2-thienyl)-Ph |
| 74 | 2-F | 4-(2-furanyl)-Ph |
| 75 | 2-F | 2-CN—Ph |
| 76 | 2-F | 2-COMe—Ph |
| 77 | 2-F | 2-CO2Me—Ph |
| 78 | 2-F | 2-CONH2—Ph |
| 79 | 2-F | 2-CONHMe—Ph |
| 80 | 2-F | 2-F—Ph |
| 81 | 2-F | 2-Cl—Ph |
| 82 | 2-F | 2-Br—Ph |
| 83 | 2-F | 2-SO2NH2—Ph |
| 84 | 2-F | 2-SO2NHMe—Ph |
| 85 | 2-F | 2-CF3—Ph |
| 86 | 2-F | 2-OMe—Ph |
| 87 | 2-F | 2-SMe—Ph |
| 88 | 2-F | 2-SOMe—Ph |
| 89 | 2-F | 2-SO2Me—Ph |
| 90 | 2-F | 2-OH—Ph |
| 91 | 2-F | 2-CH2OH—Ph |
| 92 | 2-F | 2-CHOHMe—Ph |
| 93 | 2-F | 2-COH(Me)2—Ph |
| 94 | 2-F | 2-Me—Ph |
| 95 | 2-F | 2-Et—Ph |
| 96 | 2-F | 2-iPr-Ph |
| 97 | 2-F | 2-tBu-Ph |
| 98 | 2-F | 2-CH2CO2Me—Ph |
| 99 | 2-F | 2-(1-piperidinyl)-Ph |
| 100 | 2-F | 2-(1-pyrrolidinyl)-Ph |
| 101 | 2-F | 2-(2-imidazolyl)-Ph |
| 102 | 2-F | 2-(1-imidazolyl)-Ph |
| 103 | 2-F | 2-(2-thiazolyl)-Ph |
| 104 | 2-F | 2-(3-pyrazolyl)-Ph |
| 105 | 2-F | 2-(1-pyrazolyl)-Ph |
| 106 | 2-F | 2-(5-Me-1-tetrazolyl)-Ph |
| 107 | 2-F | 2-(1-Me-5-tetrazolyl)-Ph |
| 108 | 2-F | 2-(2-pyridyl)-Ph |
| 109 | 2-F | 2-(2-thienyl)-Ph |
| 110 | 2-F | 2-(2-furanyl)-Ph |
| 111 | 2-F | 2,4-diF—Ph |
| 112 | 2-F | 2,5-diF—Ph |
| 113 | 2-F | 2,6-diF—Ph |
| 114 | 2-F | 3,4-diF—Ph |
| 115 | 2-F | 3,5-diF—Ph |
| 116 | 2-F | 2,4-diCl—Ph |
| 117 | 2-F | 2,5-diCl—Ph |
| 118 | 2-F | 2,6-diCl—Ph |
| 119 | 2-F | 3,4-diCl—Ph |
| 120 | 2-F | 3,5-diCl—Ph |
| 121 | 2-F | 3,4-diCF3—Ph |
| 122 | 2-F | 3,5-diCF3—Ph |
| 123 | 2-F | 5-Cl-2-MeO—Ph |
| 124 | 2-F | 5-Cl-2-Me—Ph |
| 125 | 2-F | 2-F-5-Me—Ph |
| 126 | 2-F | 3-F-5-morpholino-Ph |
| 127 | 2-F | 3,4-OCH2O—Ph |
| 128 | 2-F | 3,4-OCH2CH2O—Ph |
| 129 | 2-F | 2-MeO-5-CONH2—Ph |
| 130 | 2-F | 2-MeO-4-(1-Me-5-tetrazolyl)-Ph |
| 131 | 2-F | 2-MeO-5-(1-Me-5-tetrazolyl)-Ph |
| 132 | 2-F | 3-CONH2-5-(1-Me-5-tetrazolyl)-Ph |
| 133 | 2-F | 1-naphthyl |
| 134 | 2-F | 2-naphthyl |
| 135 | 2-F | 2-thienyl |
| 136 | 2-F | 3-thienyl |
| 137 | 2-F | 2-furanyl |
| 138 | 2-F | 3-furanyl |
| 139 | 2-F | 2-pyridyl |
| 140 | 2-F | 3-pyridyl |
| 141 | 2-F | 4-pyridyl |
| 142 | 2-F | 2-indolyl |
| 143 | 2-F | 3-indolyl |
| 144 | 2-F | 5-indolyl |
| 145 | 2-F | 6-indolyl |

TABLE 3-continued

| | | |
|---|---|---|
| 146 | 2-F | 3-indazolyl |
| 147 | 2-F | 5-indazolyl |
| 148 | 2-F | 6-indazolyl |
| 149 | 2-F | 2-imidazolyl |
| 150 | 2-F | 3-isoxazoyl |
| 151 | 2-F | 3-pyrazolyl |
| 152 | 2-F | 2-thiadiazolyl |
| 153 | 2-F | 2-thiazolyl |
| 154 | 2-F | 5-Ac-4-Me-2-thiazolyl |
| 155 | 2-F | 5-tetrazolyl |
| 156 | 2-F | 2-benzimidazolyl |
| 157 | 2-F | 5-benzimidazolyl |
| 158 | 2-F | 2-benzothiazolyl |
| 159 | 2-F | 5-benzothiazolyl |
| 160 | 2-F | 2-benzoxazolyl |
| 161 | 2-F | 5-benzoxazolyl |
| 162 | 2-F | 1-adamantyl |
| 163 | 2-F | 2-adamantyl |
| 164 | 2-F | i-Pr |
| 165 | 2-F | t-Bu |
| 166 | 2-F | c-Hex |
| 167 | 2-F | CH2CH2OMe |
| 168 | 2-F | CH2CONH2 |
| 169 | 2-F | CH2CO2Me |
| 170 | 2-F | CH(CH2Ph)CO2Me |
| 171 | 2-F | CH2CH2NMe2 |
| 172 | 2-F | benzyl |
| 173 | 2-F | phenethyl |
| 174 | 2-F | 2-(morpholin-1-yl)-Et |
| 175 | 3-F | Ph |
| 176 | 3-F | 3-CN—Ph |
| 177 | 3-F | 3-COMe—Ph |
| 178 | 3-F | 3-CO2Me—Ph |
| 179 | 3-F | 3-CONH2—Ph |
| 180 | 3-F | 3-CONHMe—Ph |
| 181 | 3-F | 3-F—Ph |
| 182 | 3-F | 3-Cl—Ph |
| 183 | 3-F | 3-Br—Ph |
| 184 | 3-F | 3-SO2NH2—Ph |
| 185 | 3-F | 3-SO2NHMe—Ph |
| 186 | 3-F | 3-CF3—Ph |
| 187 | 3-F | 3-OMe—Ph |
| 188 | 3-F | 3-SMe—Ph |
| 189 | 3-F | 3-SOMe—Ph |
| 190 | 3-F | 3-SO2Me—Ph |
| 191 | 3-F | 3-OH—Ph |
| 192 | 3-F | 3-CH2OH—Ph |
| 193 | 3-F | 3-CHOHMe—Ph |
| 194 | 3-F | 3-COH(Me)2—Ph |
| 195 | 3-F | 3-Me—Ph |
| 196 | 3-F | 3-Et—Ph |
| 197 | 3-F | 3-iPr-Ph |
| 198 | 3-F | 3-tBu-Ph |
| 199 | 3-F | 3-CH2CO2Me—Ph |
| 200 | 3-F | 3-(1-piperidinyl)-Ph |
| 201 | 3-F | 3-(1-pyrrolidinyl)-Ph |
| 202 | 3-F | 3-(2-imidazolyl)-Ph |
| 203 | 3-F | 3-(1-imidazolyl)-Ph |
| 204 | 3-F | 3-(2-thiazolyl)-Ph |
| 205 | 3-F | 3-(3-pyrazolyl)-Ph |
| 206 | 3-F | 3-(1-pyrazolyl)-Ph |
| 207 | 3-F | 3-(5-Me-1-tetrazolyl)-Ph |
| 208 | 3-F | 3-(1-Me-5-tetrazolyl)-Ph |
| 209 | 3-F | 3-(2-pyridyl)-Ph |
| 210 | 3-F | 3-(2-thienyl)-Ph |
| 211 | 3-F | 3-(2-furanyl)-Ph |
| 212 | 3-F | 4-CN—Ph |
| 213 | 3-F | 4-COMe—Ph |
| 214 | 3-F | 4-CO2Me—Ph |
| 215 | 3-F | 4-CONH2—Ph |
| 216 | 3-F | 4-CONHMe—Ph |
| 217 | 3-F | 4-CONHPh—Ph |
| 218 | 3-F | 4-F—Ph |
| 219 | 3-F | 4-Cl—Ph |
| 220 | 3-F | 4-Br—Ph |
| 221 | 3-F | 4-SO2NH2—Ph |
| 222 | 3-F | 4-SO2NHMe—Ph |
| 223 | 3-F | 4-CF3—Ph |
| 224 | 3-F | 4-OMe—Ph |
| 225 | 3-F | 4-SMe—Ph |
| 226 | 3-F | 4-SOMe—Ph |
| 227 | 3-F | 4-SO2Me—Ph |
| 228 | 3-F | 4-OH—Ph |
| 229 | 3-F | 4-CH2OH—Ph |
| 230 | 3-F | 4-CHOHMe—Ph |
| 231 | 3-F | 4-COH(Me)2—Ph |
| 232 | 3-F | 4-Me—Ph |
| 233 | 3-F | 4-Et—Ph |
| 234 | 3-F | 4-iPr-Ph |
| 235 | 3-F | 4-tBu-Ph |
| 236 | 3-F | 4-CH2CO2Me—Ph |
| 237 | 3-F | 4-(1-piperidinyl)-Ph |
| 238 | 3-F | 4-(1-pyrrolidinyl)-Ph |
| 239 | 3-F | 4-(2-imidazolyl)-Ph |
| 240 | 3-F | 4-(1-imidazolyl)-Ph |
| 241 | 3-F | 4-(2-thiazolyl)-Ph |
| 242 | 3-F | 4-(3-pyrazolyl)-Ph |
| 243 | 3-F | 4-(1-pyrazolyl)-Ph |
| 244 | 3-F | 4-(5-Me-1-tetrazolyl)-Ph |
| 245 | 3-F | 4-(1-Me-5-tetrazolyl)-Ph |
| 246 | 3-F | 4-(2-pyridyl)-Ph |
| 247 | 3-F | 4-(2-thienyl)-Ph |
| 248 | 3-F | 4-(2-furanyl)-Ph |
| 249 | 3-F | 2-CN—Ph |
| 250 | 3-F | 2-COMe—Ph |
| 251 | 3-F | 2-CO2Me—Ph |
| 252 | 3-F | 2-CONH2—Ph |
| 253 | 3-F | 2-CONHMe—Ph |
| 254 | 3-F | 2-F—Ph |
| 255 | 3-F | 2-Cl—Ph |
| 256 | 3-F | 2-Br—Ph |
| 257 | 3-F | 2-SO2NH2—Ph |
| 258 | 3-F | 2-SO2NHMe—Ph |
| 259 | 3-F | 2-CF3—Ph |
| 260 | 3-F | 2-OMe—Ph |
| 261 | 3-F | 2-SMe—Ph |
| 262 | 3-F | 2-SOMe—Ph |
| 263 | 3-F | 2-SO2Me—Ph |
| 264 | 3-F | 2-OH—Ph |
| 265 | 3-F | 2-CH2OH—Ph |
| 266 | 3-F | 2-CHOHMe—Ph |
| 267 | 3-F | 2-COH(Me)2—Ph |
| 268 | 3-F | 2-Me—Ph |
| 269 | 3-F | 2-Et—Ph |
| 270 | 3-F | 2-iPr-Ph |
| 271 | 3-F | 2-tBu-Ph |
| 272 | 3-F | 2-CH2CO2Me—Ph |
| 273 | 3-F | 2-(1-piperidinyl)-Ph |
| 274 | 3-F | 2-(1-pyrrolidinyl)-Ph |
| 275 | 3-F | 2-(2-imidazolyl)-Ph |
| 276 | 3-F | 2-(1-imidazolyl)-Ph |
| 277 | 3-F | 2-(2-thiazolyl)-Ph |
| 278 | 3-F | 2-(3-pyrazolyl)-Ph |
| 279 | 3-F | 2-(1-pyrazolyl)-Ph |
| 280 | 3-F | 2-(5-Me-1-tetrazolyl)-Ph |
| 281 | 3-F | 2-(1-Me-5-tetrazolyl)-Ph |
| 282 | 3-F | 2-(2-pyridyl)-Ph |
| 283 | 3-F | 2-(2-thienyl)-Ph |
| 284 | 3-F | 2-(2-furanyl)-Ph |
| 285 | 3-F | 2,4-diF—Ph |
| 286 | 3-F | 2,5-diF—Ph |
| 287 | 3-F | 2,6-diF—Ph |
| 288 | 3-F | 3,4-diF—Ph |
| 289 | 3-F | 3,5-diF—Ph |
| 290 | 3-F | 2,4-diCl—Ph |
| 291 | 3-F | 2,5-diCl—Ph |
| 292 | 3-F | 2,6-diCl—Ph |
| 293 | 3-F | 3,4-diCl—Ph |
| 294 | 3-F | 3,5-diCl—Ph |
| 295 | 3-F | 3,4-diCF3—Ph |
| 296 | 3-F | 3,5-diCF3—Ph |
| 297 | 3-F | 5-Cl-2-MeO—Ph |
| 298 | 3-F | 5-Cl-2-Me—Ph |
| 299 | 3-F | 2-F-5-Me—Ph |
| 300 | 3-F | 3-F-5-morpholino-Ph |
| 301 | 3-F | 3,4-OCH2O—Ph |
| 302 | 3-F | 3,4-OCH2CH2O—Ph |
| 303 | 3-F | 2-MeO-5-CONH2—Ph |

TABLE 3-continued

| | | |
|---|---|---|
| 304 | 3-F | 2-MeO-4-(1-Me-5-tetrazolyl)-Ph |
| 305 | 3-F | 2-MeO-5-(1-Me-5-tetrazolyl)-Ph |
| 306 | 3-F | 3-CONH2-5-(1-Me-5-tetrazolyl)-Ph |
| 307 | 3-F | 1-naphthyl |
| 308 | 3-F | 2-naphthyl |
| 309 | 3-F | 2-thienyl |
| 310 | 3-F | 3-thienyl |
| 311 | 3-F | 2-furanyl |
| 312 | 3-F | 3-furanyl |
| 313 | 3-F | 2-pyridyl |
| 314 | 3-F | 3-pyridyl |
| 315 | 3-F | 4-pyridyl |
| 316 | 3-F | 2-indolyl |
| 317 | 3-F | 3-indolyl |
| 318 | 3-F | 5-indolyl |
| 319 | 3-F | 6-indolyl |
| 320 | 3-F | 3-indazolyl |
| 321 | 3-F | 5-indazolyl |
| 322 | 3-F | 6-indazolyl |
| 323 | 3-F | 2-imidazolyl |
| 324 | 3-F | 3-isoxazoyl |
| 325 | 3-F | 3-pyrazolyl |
| 326 | 3-F | 2-thiadiazolyl |
| 327 | 3-F | 2-thiazolyl |
| 328 | 3-F | 5-Ac-4-Me-2-thiazolyl |
| 329 | 3-F | 5-tetrazolyl |
| 330 | 3-F | 2-benzimidazolyl |
| 331 | 3-F | 5-benzimidazolyl |
| 332 | 3-F | 2-benzothiazolyl |
| 333 | 3-F | 5-benzothiazolyl |
| 334 | 3-F | 2-benzoxazolyl |
| 335 | 3-F | 5-benzoxazolyl |
| 336 | 3-F | 1-adamantyl |
| 337 | 3-F | 2-adamantyl |
| 338 | 3-F | i-Pr |
| 339 | 3-F | t-Bu |
| 340 | 3-F | c-Hex |
| 341 | 3-F | CH2CH2OMe |
| 342 | 3-F | CH2CONH2 |
| 343 | 3-F | CH2CO2Me |
| 344 | 3-F | CH(CH2Ph)CO2Me |
| 345 | 3-F | CH2CH2NMe2 |
| 346 | 3-F | benzyl |
| 347 | 3-F | phenethyl |
| 348 | 3-F | 2-(morpholin-1-yl)-Et |
| 349 | 4-F | Ph |
| 350 | 4-F | 3-CN—Ph |
| 351 | 4-F | 3-COMe—Ph |
| 352 | 4-F | 3-CO2Me—Ph |
| 353 | 4-F | 3-CONH2—Ph |
| 354 | 4-F | 3-CONHMe—Ph |
| 355 | 4-F | 3-F—Ph |
| 356 | 4-F | 3-Cl—Ph |
| 357 | 4-F | 3-Br—Ph |
| 358 | 4-F | 3-SO2NH2—Ph |
| 359 | 4-F | 3-SO2NHMe—Ph |
| 360 | 4-F | 3-CF3—Ph |
| 361 | 4-F | 3-OMe—Ph |
| 362 | 4-F | 3-SMe—Ph |
| 363 | 4-F | 3-SOMe—Ph |
| 364 | 4-F | 3-SO2Me—Ph |
| 365 | 4-F | 3-OH—Ph |
| 366 | 4-F | 3-CH2OH—Ph |
| 367 | 4-F | 3-CHOHMe—Ph |
| 368 | 4-F | 3-COH(Me)2—Ph |
| 369 | 4-F | 3-Me—Ph |
| 370 | 4-F | 3-Et—Ph |
| 371 | 4-F | 3-iPr-Ph |
| 372 | 4-F | 3-tBu-Ph |
| 373 | 4-F | 3-CH2CO2Me—Ph |
| 374 | 4-F | 3-(1-piperidinyl)-Ph |
| 375 | 4-F | 3-(1-pyrrolidinyl)-Ph |
| 376 | 4-F | 3-(2-imidazolyl)-Ph |
| 377 | 4-F | 3-(1-imidazolyl)-Ph |
| 378 | 4-F | 3-(2-thiazolyl)-Ph |
| 379 | 4-F | 3-(3-pyrazolyl)-Ph |
| 380 | 4-F | 3-(1-pyrazolyl)-Ph |
| 381 | 4-F | 3-(5-Me-1-tetrazolyl)-Ph |
| 382 | 4-F | 3-(1-Me-5-tetrazolyl)-Ph |
| 383 | 4-F | 3-(2-pyridyl)-Ph |
| 384 | 4-F | 3-(2-thienyl)-Ph |
| 385 | 4-F | 3-(2-furanyl)-Ph |
| 386 | 4-F | 4-CN—Ph |
| 387 | 4-F | 4-COMe—Ph |
| 388 | 4-F | 4-CO2Me—Ph |
| 389 | 4-F | 4-CONH2—Ph |
| 390 | 4-F | 4-CONHMe—Ph |
| 391 | 4-F | 4-CONHPh—Ph |
| 392 | 4-F | 4-F—Ph |
| 393 | 4-F | 4-Cl—Ph |
| 394 | 4-F | 4-Br—Ph |
| 395 | 4-F | 4-SO2NH2—Ph |
| 396 | 4-F | 4-SO2NHMe—Ph |
| 397 | 4-F | 4-CF3—Ph |
| 398 | 4-F | 4-OMe—Ph |
| 399 | 4-F | 4-SMe—Ph |
| 400 | 4-F | 4-SOMe—Ph |
| 401 | 4-F | 4-SO2Me—Ph |
| 402 | 4-F | 4-OH—Ph |
| 403 | 4-F | 4-CH2OH—Ph |
| 404 | 4-F | 4-CHOHMe—Ph |
| 405 | 4-F | 4-COH(Me)2—Ph |
| 406 | 4-F | 4-Me—Ph |
| 407 | 4-F | 4-Et—Ph |
| 408 | 4-F | 4-iPr-Ph |
| 409 | 4-F | 4-tBu-Ph |
| 410 | 4-F | 4-CH2CO2Me—Ph |
| 411 | 4-F | 4-(1-piperidinyl)-Ph |
| 412 | 4-F | 4-(1-pyrrolidinyl)-Ph |
| 413 | 4-F | 4-(2-imidazolyl)-Ph |
| 414 | 4-F | 4-(1-imidazolyl)-Ph |
| 415 | 4-F | 4-(2-thiazolyl)-Ph |
| 416 | 4-F | 4-(3-pyrazolyl)-Ph |
| 417 | 4-F | 4-(1-pyrazolyl)-Ph |
| 418 | 4-F | 4-(5-Me-1-tetrazolyl)-Ph |
| 419 | 4-F | 4-(1-Me-5-tetrazolyl)-Ph |
| 420 | 4-F | 4-(2-pyridyl)-Ph |
| 421 | 4-F | 4-(2-thienyl)-Ph |
| 422 | 4-F | 4-(2-furanyl)-Ph |
| 423 | 4-F | 2-CN—Ph |
| 424 | 4-F | 2-COMe—Ph |
| 425 | 4-F | 2-CO2Me—Ph |
| 426 | 4-F | 2-CONH2—Ph |
| 427 | 4-F | 2-CONHMe—Ph |
| 428 | 4-F | 2-F—Ph |
| 429 | 4-F | 2-Cl—Ph |
| 430 | 4-F | 2-Br—Ph |
| 431 | 4-F | 2-SO2NH2—Ph |
| 432 | 4-F | 2-SO2NHMe—Ph |
| 433 | 4-F | 2-CF3—Ph |
| 434 | 4-F | 2-OMe—Ph |
| 435 | 4-F | 2-SMe—Ph |
| 436 | 4-F | 2-SOMe—Ph |
| 437 | 4-F | 2-SO2Me—Ph |
| 438 | 4-F | 2-OH—Ph |
| 439 | 4-F | 2-CH2OH—Ph |
| 440 | 4-F | 2-CHOHMe—Ph |
| 441 | 4-F | 2-COH(Me)2—Ph |
| 442 | 4-F | 2-Me—Ph |
| 443 | 4-F | 2-Et—Ph |
| 444 | 4-F | 2-iPr-Ph |
| 445 | 4-F | 2-tBu-Ph |
| 446 | 4-F | 2-CH2CO2Me—Ph |
| 447 | 4-F | 2-(1-piperidinyl)-Ph |
| 448 | 4-F | 2-(1-pyrrolidinyl)-Ph |
| 449 | 4-F | 2-(2-imidazolyl)-Ph |
| 450 | 4-F | 2-(1-imidazolyl)-Ph |
| 451 | 4-F | 2-(2-thiazolyl)-Ph |
| 452 | 4-F | 2-(3-pyrazolyl)-Ph |
| 453 | 4-F | 2-(1-pyrazolyl)-Ph |
| 454 | 4-F | 2-(5-Me-1-tetrazolyl)-Ph |
| 455 | 4-F | 2-(1-Me-5-tetrazolyl)-Ph |
| 456 | 4-F | 2-(2-pyridyl)-Ph |
| 457 | 4-F | 2-(2-thienyl)-Ph |
| 458 | 4-F | 2-(2-furanyl)-Ph |
| 459 | 4-F | 2,4-diF—Ph |
| 460 | 4-F | 2,5-diF—Ph |
| 461 | 4-F | 2,6-diF—Ph |

TABLE 3-continued

| | | |
|---|---|---|
| 462 | 4-F | 3,4-diF—Ph |
| 463 | 4-F | 3,5-diF—Ph |
| 464 | 4-F | 2,4-diCl—Ph |
| 465 | 4-F | 2,5-diCl—Ph |
| 466 | 4-F | 2,6-diCl—Ph |
| 467 | 4-F | 3,4-diCl—Ph |
| 468 | 4-F | 3,5-diCl—Ph |
| 469 | 4-F | 3,4-diCF3—Ph |
| 470 | 4-F | 3,5-diCF3—Ph |
| 471 | 4-F | 5-Cl-2-MeO—Ph |
| 472 | 4-F | 5-Cl-2-Me—Ph |
| 473 | 4-F | 2-F-5-Me—Ph |
| 474 | 4-F | 3-F-5-morpholino-Ph |
| 475 | 4-F | 3,4-OCH2O—Ph |
| 476 | 4-F | 3,4-OCH2CH2O—Ph |
| 477 | 4-F | 2-MeO-5-CONH2—Ph |
| 478 | 4-F | 2-MeO-4-(1-Me-5-tetrazolyl)-Ph |
| 479 | 4-F | 2-MeO-5-(1-Me-5-tetrazolyl)-Ph |
| 480 | 4-F | 3-CONH2-5-(1-Me-5-tetrazolyl)-Ph |
| 481 | 4-F | 1-naphthyl |
| 482 | 4-F | 2-naphthyl |
| 483 | 4-F | 2-thienyl |
| 484 | 4-F | 3-thienyl |
| 485 | 4-F | 2-furanyl |
| 486 | 4-F | 3-furanyl |
| 487 | 4-F | 2-pyridyl |
| 488 | 4-F | 3-pyridyl |
| 489 | 4-F | 4-pyridyl |
| 490 | 4-F | 2-indolyl |
| 491 | 4-F | 3-indolyl |
| 492 | 4-F | 5-indolyl |
| 493 | 4-F | 6-indolyl |
| 494 | 4-F | 3-indazolyl |
| 495 | 4-F | 5-indazolyl |
| 496 | 4-F | 6-indazolyl |
| 497 | 4-F | 2-imidazolyl |
| 498 | 4-F | 3-isoxazoyl |
| 499 | 4-F | 3-pyrazolyl |
| 500 | 4-F | 2-thiadiazolyl |
| 501 | 4-F | 2-thiazolyl |
| 502 | 4-F | 5-Ac-4-Me-2-thiazolyl |
| 503 | 4-F | 5-tetrazolyl |
| 504 | 4-F | 2-benzimidazolyl |
| 505 | 4-F | 5-benzimidazolyl |
| 506 | 4-F | 2-benzothiazolyl |
| 507 | 4-F | 5-benzothiazolyl |
| 508 | 4-F | 2-benzoxazolyl |
| 509 | 4-F | 5-benzoxazolyl |
| 510 | 4-F | 1-adamantyl |
| 511 | 4-F | 2-adamantyl |
| 512 | 4-F | i-Pr |
| 513 | 4-F | t-Bu |
| 514 | 4-F | c-Hex |
| 515 | 4-F | CH2CH2OMe |
| 516 | 4-F | CH2CONH2 |
| 517 | 4-F | CH2CO2Me |
| 518 | 4-F | CH(CH2Ph)CO2Me |
| 519 | 4-F | CH2CH2NMe2 |
| 520 | 4-F | benzyl |
| 521 | 4-F | phenethyl |
| 522 | 4-F | 2-(morpholin-1-yl)-Et |
| 523 | 3-Cl | Ph |
| 524 | 3-Cl | 3-CN—Ph |
| 525 | 3-Cl | 3-COMe—Ph |
| 526 | 3-Cl | 3-CO2Me—Ph |
| 527 | 3-Cl | 3-CONH2—Ph |
| 528 | 3-Cl | 3-CONHMe—Ph |
| 529 | 3-Cl | 3-F—Ph |
| 530 | 3-Cl | 3-Cl—Ph |
| 531 | 3-Cl | 3-Br—Ph |
| 532 | 3-Cl | 3-SO2NH2—Ph |
| 533 | 3-Cl | 3-SO2NHMe—Ph |
| 534 | 3-Cl | 3-CF3—Ph |
| 535 | 3-Cl | 3-OMe—Ph |
| 536 | 3-Cl | 3-SMe—Ph |
| 537 | 3-Cl | 3-SOMe—Ph |
| 538 | 3-Cl | 3-SO2Me—Ph |
| 539 | 3-Cl | 3-OH—Ph |
| 540 | 3-Cl | 3-CH2OH—Ph |
| 541 | 3-Cl | 3-CHOHMe—Ph |
| 542 | 3-Cl | 3-COH(Me)2—Ph |
| 543 | 3-Cl | 3-Me—Ph |
| 544 | 3-Cl | 3-Et—Ph |
| 545 | 3-Cl | 3-iPr-Ph |
| 546 | 3-Cl | 3-tBu-Ph |
| 547 | 3-Cl | 3-CH2CO2Me—Ph |
| 548 | 3-Cl | 3-(1-piperidinyl)-Ph |
| 549 | 3-Cl | 3-(1-pyrrolidinyl)-Ph |
| 550 | 3-Cl | 3-(2-imidazolyl)-Ph |
| 551 | 3-Cl | 3-(1-imidazolyl)-Ph |
| 552 | 3-Cl | 3-(2-thiazolyl)-Ph |
| 553 | 3-Cl | 3-(3-pyrazolyl)-Ph |
| 554 | 3-Cl | 3-(1-pyrazolyl)-Ph |
| 555 | 3-Cl | 3-(5-Me-1-tetrazolyl)-Ph |
| 556 | 3-Cl | 3-(1-Me-5-tetrazolyl)-Ph |
| 557 | 3-Cl | 3-(2-pyridyl)-Ph |
| 558 | 3-Cl | 3-(2-thienyl)-Ph |
| 559 | 3-Cl | 3-(2-furanyl)-Ph |
| 560 | 3-Cl | 4-CN—Ph |
| 561 | 3-Cl | 4-COMe—Ph |
| 562 | 3-Cl | 4-CO2Me—Ph |
| 563 | 3-Cl | 4-CONH2—Ph |
| 564 | 3-Cl | 4-CONHMe—Ph |
| 565 | 3-Cl | 4-CONHPh—Ph |
| 566 | 3-Cl | 4-F—Ph |
| 567 | 3-Cl | 4-Cl—Ph |
| 568 | 3-Cl | 4-Br—Ph |
| 569 | 3-Cl | 4-SO2NH2—Ph |
| 570 | 3-Cl | 4-SO2NHMe—Ph |
| 571 | 3-Cl | 4-CF3—Ph |
| 572 | 3-Cl | 4-OMe—Ph |
| 573 | 3-Cl | 4-SMe—Ph |
| 574 | 3-Cl | 4-SOMe—Ph |
| 575 | 3-Cl | 4-SO2Me—Ph |
| 576 | 3-Cl | 4-OH—Ph |
| 577 | 3-Cl | 4-CH2OH—Ph |
| 578 | 3-Cl | 4-CHOHMe—Ph |
| 579 | 3-Cl | 4-COH(Me)2—Ph |
| 580 | 3-Cl | 4-Me—Ph |
| 581 | 3-Cl | 4-Et—Ph |
| 582 | 3-Cl | 4-iPr-Ph |
| 583 | 3-Cl | 4-tBu-Ph |
| 584 | 3-Cl | 4-CH2CO2Me—Ph |
| 585 | 3-Cl | 4-(1-piperidinyl)-Ph |
| 586 | 3-Cl | 4-(1-pyrrolidinyl)-Ph |
| 587 | 3-Cl | 4-(2-imidazolyl)-Ph |
| 588 | 3-Cl | 4-(1-imidazolyl)-Ph |
| 589 | 3-Cl | 4-(2-thiazolyl)-Ph |
| 590 | 3-Cl | 4-(3-pyrazolyl)-Ph |
| 591 | 3-Cl | 4-(1-pyrazolyl)-Ph |
| 592 | 3-Cl | 4-(5-Me-1-tetrazolyl)-Ph |
| 593 | 3-Cl | 4-(1-Me-5-tetrazolyl)-Ph |
| 594 | 3-Cl | 4-(2-pyridyl)-Ph |
| 595 | 3-Cl | 4-(2-thienyl)-Ph |
| 596 | 3-Cl | 4-(2-furanyl)-Ph |
| 597 | 3-Cl | 2-CN—Ph |
| 598 | 3-Cl | 2-COMe—Ph |
| 599 | 3-Cl | 2-CO2Me—Ph |
| 600 | 3-Cl | 2-CONH2—Ph |
| 601 | 3-Cl | 2-CONHMe—Ph |
| 602 | 3-Cl | 2-F—Ph |
| 603 | 3-Cl | 2-Cl—Ph |
| 604 | 3-Cl | 2-Br—Ph |
| 605 | 3-Cl | 2-SO2NH2—Ph |
| 606 | 3-Cl | 2-SO2NHMe—Ph |
| 607 | 3-Cl | 2-CF3—Ph |
| 608 | 3-Cl | 2-OMe—Ph |
| 609 | 3-Cl | 2-SMe—Ph |
| 610 | 3-Cl | 2-SOMe—Ph |
| 611 | 3-Cl | 2-SO2Me—Ph |
| 612 | 3-Cl | 2-OH—Ph |
| 613 | 3-Cl | 2-CH2OH—Ph |
| 614 | 3-Cl | 2-CHOHMe—Ph |
| 615 | 3-Cl | 2-COH(Me)2—Ph |
| 616 | 3-Cl | 2-Me—Ph |
| 617 | 3-Cl | 2-Et—Ph |
| 618 | 3-Cl | 2-iPr-Ph |
| 619 | 3-Cl | 2-tBu-Ph |

TABLE 3-continued

| | | |
|---|---|---|
| 620 | 3-Cl | 2-CH2CO2Me—Ph |
| 621 | 3-Cl | 2-(1-piperidinyl)-Ph |
| 622 | 3-Cl | 2-(1-pyrrolidinyl)-Ph |
| 623 | 3-Cl | 2-(2-imidazolyl)-Ph |
| 624 | 3-Cl | 2-(1-imidazolyl)-Ph |
| 625 | 3-Cl | 2-(2-thiazolyl)-Ph |
| 626 | 3-Cl | 2-(3-pyrazolyl)-Ph |
| 627 | 3-Cl | 2-(1-pyrazolyl)-Ph |
| 628 | 3-Cl | 2-(5-Me-1-tetrazolyl)-Ph |
| 629 | 3-Cl | 2-(1-Me-5-tetrazolyl)-Ph |
| 630 | 3-Cl | 2-(2-pyridyl)-Ph |
| 631 | 3-Cl | 2-(2-thienyl)-Ph |
| 632 | 3-Cl | 2-(2-furanyl)-Ph |
| 633 | 3-Cl | 2,4-diF—Ph |
| 634 | 3-Cl | 2,5-diF—Ph |
| 635 | 3-Cl | 2,6-diF—Ph |
| 636 | 3-Cl | 3,4-diF—Ph |
| 637 | 3-Cl | 3,5-diF—Ph |
| 638 | 3-Cl | 2,4-diCl—Ph |
| 639 | 3-Cl | 2,5-diCl—Ph |
| 640 | 3-Cl | 2,6-diCl—Ph |
| 641 | 3-Cl | 3,4-diCl—Ph |
| 642 | 3-Cl | 3,5-diCl—Ph |
| 643 | 3-Cl | 3,4-diCF3—Ph |
| 644 | 3-Cl | 3,5-diCF3—Ph |
| 645 | 3-Cl | 5-Cl-2-MeO—Ph |
| 646 | 3-Cl | 5-Cl-2-Me—Ph |
| 647 | 3-Cl | 2-F-5-Me—Ph |
| 648 | 3-Cl | 3-F-5-morpholino-Ph |
| 649 | 3-Cl | 3,4-OCH2O—Ph |
| 650 | 3-Cl | 3,4-OCH2CH2O—Ph |
| 651 | 3-Cl | 2-MeO-5-CONH2—Ph |
| 652 | 3-Cl | 2-MeO-4-(1-Me-5-tetrazolyl)-Ph |
| 653 | 3-Cl | 2-MeO-5-(1-Me-5-tetrazolyl)-Ph |
| 654 | 3-Cl | 3-CONH2-5-(1-Me-5-tetrazolyl)-Ph |
| 655 | 3-Cl | 1-naphthyl |
| 656 | 3-Cl | 2-naphthyl |
| 657 | 3-Cl | 2-thienyl |
| 658 | 3-Cl | 3-thienyl |
| 659 | 3-Cl | 2-furanyl |
| 660 | 3-Cl | 3-furanyl |
| 661 | 3-Cl | 2-pyridyl |
| 662 | 3-Cl | 3-pyridyl |
| 663 | 3-Cl | 4-pyridyl |
| 664 | 3-Cl | 2-indolyl |
| 665 | 3-Cl | 3-indolyl |
| 666 | 3-Cl | 5-indolyl |
| 667 | 3-Cl | 6-indolyl |
| 668 | 3-Cl | 3-indazolyl |
| 669 | 3-Cl | 5-indazolyl |
| 670 | 3-Cl | 6-indazolyl |
| 671 | 3-Cl | 2-imidazolyl |
| 672 | 3-Cl | 3-isoxazoyl |
| 673 | 3-Cl | 3-pyrazolyl |
| 674 | 3-Cl | 2-thiadiazolyl |
| 675 | 3-Cl | 2-thiazolyl |
| 676 | 3-Cl | 5-Ac-4-Me-2-thiazolyl |
| 677 | 3-Cl | 5-tetrazolyl |
| 678 | 3-Cl | 2-benzimidazolyl |
| 679 | 3-Cl | 5-benzimidazolyl |
| 680 | 3-Cl | 2-benzothiazolyl |
| 681 | 3-Cl | 5-benzothiazolyl |
| 682 | 3-Cl | 2-benzoxazolyl |
| 683 | 3-Cl | 5-benzoxazolyl |
| 684 | 3-Cl | 1-adamantyl |
| 685 | 3-Cl | 2-adamantyl |
| 686 | 3-Cl | i-Pr |
| 687 | 3-Cl | t-Bu |
| 688 | 3-Cl | c-Hex |
| 689 | 3-Cl | CH2CH2OMe |
| 690 | 3-Cl | CH2CONH2 |
| 691 | 3-Cl | CH2CO2Me |
| 692 | 3-Cl | CH(CH2Ph)CO2Me |
| 693 | 3-Cl | CH2CH2NMe2 |
| 694 | 3-Cl | benzyl |
| 695 | 3-Cl | phenethyl |
| 696 | 3-Cl | 2-(morpholin-1-yl)-Et |
| 697 | 4-Cl | Ph |
| 698 | 4-Cl | 3-CN—Ph |
| 699 | 4-Cl | 3-COMe—Ph |
| 700 | 4-Cl | 3-CO2Me—Ph |
| 701 | 4-Cl | 3-CONH2—Ph |
| 702 | 4-Cl | 3-CONHMe—Ph |
| 703 | 4-Cl | 3-F—Ph |
| 704 | 4-Cl | 3-Cl—Ph |
| 705 | 4-Cl | 3-Br—Ph |
| 706 | 4-Cl | 3-SO2NH2—Ph |
| 707 | 4-Cl | 3-SO2NHMe—Ph |
| 708 | 4-Cl | 3-CF3—Ph |
| 709 | 4-Cl | 3-OMe—Ph |
| 710 | 4-Cl | 3-SMe—Ph |
| 711 | 4-Cl | 3-SOMe—Ph |
| 712 | 4-Cl | 3-SO2Me—Ph |
| 713 | 4-Cl | 3-OH—Ph |
| 714 | 4-Cl | 3-CH2OH—Ph |
| 715 | 4-Cl | 3-CHOHMe—Ph |
| 716 | 4-Cl | 3-COH(Me)2—Ph |
| 717 | 4-Cl | 3-Me—Ph |
| 718 | 4-Cl | 3-Et—Ph |
| 719 | 4-Cl | 3-iPr-Ph |
| 720 | 4-Cl | 3-tBu-Ph |
| 721 | 4-Cl | 3-CH2CO2Me—Ph |
| 722 | 4-Cl | 3-(1-piperidinyl)-Ph |
| 723 | 4-Cl | 3-(1-pyrrolidinyl)-Ph |
| 724 | 4-Cl | 3-(2-imidazolyl)-Ph |
| 725 | 4-Cl | 3-(1-imidazolyl)-Ph |
| 726 | 4-Cl | 3-(2-thiazolyl)-Ph |
| 727 | 4-Cl | 3-(3-pyrazolyl)-Ph |
| 728 | 4-Cl | 3-(1-pyrazolyl)-Ph |
| 729 | 4-Cl | 3-(5-Me-1-tetrazolyl)-Ph |
| 730 | 4-Cl | 3-(1-Me-5-tetrazolyl)-Ph |
| 731 | 4-Cl | 3-(2-pyridyl)-Ph |
| 732 | 4-Cl | 3-(2-thienyl)-Ph |
| 733 | 4-Cl | 3-(2-furanyl)-Ph |
| 734 | 4-Cl | 4-CN—Ph |
| 735 | 4-Cl | 4-COMe—Ph |
| 736 | 4-Cl | 4-CO2Me—Ph |
| 737 | 4-Cl | 4-CONH2—Ph |
| 738 | 4-Cl | 4-CONHMe—Ph |
| 739 | 4-Cl | 4-CONHPh—Ph |
| 740 | 4-Cl | 4-F—Ph |
| 741 | 4-Cl | 4-Cl—Ph |
| 742 | 4-Cl | 4-Br—Ph |
| 743 | 4-Cl | 4-SO2NH2—Ph |
| 744 | 4-Cl | 4-SO2NHMe—Ph |
| 745 | 4-Cl | 4-CF3—Ph |
| 746 | 4-Cl | 4-OMe—Ph |
| 747 | 4-Cl | 4-SMe—Ph |
| 748 | 4-Cl | 4-SOMe—Ph |
| 749 | 4-Cl | 4-SO2Me—Ph |
| 750 | 4-Cl | 4-OH—Ph |
| 751 | 4-Cl | 4-CH2OH—Ph |
| 752 | 4-Cl | 4-CHOHMe—Ph |
| 753 | 4-Cl | 4-COH(Me)2—Ph |
| 754 | 4-Cl | 4-Me—Ph |
| 755 | 4-Cl | 4-Et—Ph |
| 756 | 4-Cl | 4-iPr-Ph |
| 757 | 4-Cl | 4-tBu-Ph |
| 758 | 4-Cl | 4-CH2CO2Me—Ph |
| 759 | 4-Cl | 4-(1-piperidinyl)-Ph |
| 760 | 4-Cl | 4-(1-pyrrolidinyl)-Ph |
| 761 | 4-Cl | 4-(2-imidazolyl)-Ph |
| 762 | 4-Cl | 4-(1-imidazolyl)-Ph |
| 763 | 4-Cl | 4-(2-thiazolyl)-Ph |
| 764 | 4-Cl | 4-(3-pyrazolyl)-Ph |
| 765 | 4-Cl | 4-(1-pyrazolyl)-Ph |
| 766 | 4-Cl | 4-(5-Me-1-tetrazolyl)-Ph |
| 767 | 4-Cl | 4-(1-Me-5-tetrazolyl)-Ph |
| 768 | 4-Cl | 4-(2-pyridyl)-Ph |
| 769 | 4-Cl | 4-(2-thienyl)-Ph |
| 770 | 4-Cl | 4-(2-furanyl)-Ph |
| 771 | 4-Cl | 2-CN—Ph |
| 772 | 4-Cl | 2-COMe—Ph |
| 773 | 4-Cl | 2-CO2Me—Ph |
| 774 | 4-Cl | 2-CONH2—Ph |
| 775 | 4-Cl | 2-CONHMe—Ph |
| 776 | 4-Cl | 2-F—Ph |
| 777 | 4-Cl | 2-Cl—Ph |

TABLE 3-continued

| | | |
|---|---|---|
| 778 | 4-Cl | 2-Br—Ph |
| 779 | 4-Cl | 2-SO2NH2—Ph |
| 780 | 4-Cl | 2-SO2NHMe—Ph |
| 781 | 4-Cl | 2-CF3—Ph |
| 782 | 4-Cl | 2-OMe—Ph |
| 783 | 4-Cl | 2-SMe—Ph |
| 784 | 4-Cl | 2-SOMe—Ph |
| 785 | 4-Cl | 2-SO2Me—Ph |
| 786 | 4-Cl | 2-OH—Ph |
| 787 | 4-Cl | 2-CH2OH—Ph |
| 788 | 4-Cl | 2-CHOHMe—Ph |
| 789 | 4-Cl | 2-COH(Me)2—Ph |
| 790 | 4-Cl | 2-Me—Ph |
| 791 | 4-Cl | 2-Et—Ph |
| 792 | 4-Cl | 2-iPr-Ph |
| 793 | 4-Cl | 2-tBu-Ph |
| 794 | 4-Cl | 2-CH2CO2Me—Ph |
| 795 | 4-Cl | 2-(1-piperidinyl)-Ph |
| 796 | 4-Cl | 2-(1-pyrrolidinyl)-Ph |
| 797 | 4-Cl | 2-(2-imidazolyl)-Ph |
| 798 | 4-Cl | 2-(1-imidazolyl)-Ph |
| 799 | 4-Cl | 2-(2-thiazolyl)-Ph |
| 800 | 4-Cl | 2-(3-pyrazolyl)-Ph |
| 801 | 4-Cl | 2-(1-pyrazolyl)-Ph |
| 802 | 4-Cl | 2-(5-Me-1-tetrazolyl)-Ph |
| 803 | 4-Cl | 2-(1-Me-5-tetrazolyl)-Ph |
| 804 | 4-Cl | 2-(2-pyridyl)-Ph |
| 805 | 4-Cl | 2-(2-thienyl)-Ph |
| 806 | 4-Cl | 2-(2-furanyl)-Ph |
| 807 | 4-Cl | 2,4-diF—Ph |
| 808 | 4-Cl | 2,5-diF—Ph |
| 809 | 4-Cl | 2,6-diF—Ph |
| 810 | 4-Cl | 3,4-diF—Ph |
| 811 | 4-Cl | 3,5-diF—Ph |
| 812 | 4-Cl | 2,4-diCl—Ph |
| 813 | 4-Cl | 2,5-diCl—Ph |
| 814 | 4-Cl | 2,6-diCl—Ph |
| 815 | 4-Cl | 3,4-diCl—Ph |
| 816 | 4-Cl | 3,5-diCl—Ph |
| 817 | 4-Cl | 3,4-diCF3—Ph |
| 818 | 4-Cl | 3,5-diCF3—Ph |
| 819 | 4-Cl | 5-Cl-2-MeO—Ph |
| 820 | 4-Cl | 5-Cl-2-Me—Ph |
| 821 | 4-Cl | 2-F-5-Me—Ph |
| 822 | 4-Cl | 3-F-5-morpholino-Ph |
| 823 | 4-Cl | 3,4-OCH2O—Ph |
| 824 | 4-Cl | 3,4-OCH2CH2O—Ph |
| 825 | 4-Cl | 2-MeO-5-CONH2—Ph |
| 826 | 4-Cl | 2-MeO-4-(1-Me-5-tetrazolyl)-Ph |
| 827 | 4-Cl | 2-MeO-5-(1-Me-5-tetrazolyl)-Ph |
| 828 | 4-Cl | 3-CONH2-5-(1-Me-5-tetrazolyl)-Ph |
| 829 | 4-Cl | 1-naphthyl |
| 830 | 4-Cl | 2-naphthyl |
| 831 | 4-Cl | 2-thienyl |
| 832 | 4-Cl | 3-thienyl |
| 833 | 4-Cl | 2-furanyl |
| 834 | 4-Cl | 3-furanyl |
| 835 | 4-Cl | 2-pyridyl |
| 836 | 4-Cl | 3-pyridyl |
| 837 | 4-Cl | 4-pyridyl |
| 838 | 4-Cl | 2-indolyl |
| 839 | 4-Cl | 3-indolyl |
| 840 | 4-Cl | 5-indolyl |
| 841 | 4-Cl | 6-indolyl |
| 842 | 4-Cl | 3-indazolyl |
| 843 | 4-Cl | 5-indazolyl |
| 844 | 4-Cl | 6-indazolyl |
| 845 | 4-Cl | 2-imidazolyl |
| 846 | 4-Cl | 3-isoxazoyl |
| 847 | 4-Cl | 3-pyrazolyl |
| 848 | 4-Cl | 2-thiadiazolyl |
| 849 | 4-Cl | 2-thiazolyl |
| 850 | 4-Cl | 5-Ac-4-Me-2-thiazolyl |
| 851 | 4-Cl | 5-tetrazolyl |
| 852 | 4-Cl | 2-benzimidazolyl |
| 853 | 4-Cl | 5-benzimidazolyl |
| 854 | 4-Cl | 2-benzothiazolyl |
| 855 | 4-Cl | 5-benzothiazolyl |
| 856 | 4-Cl | 2-benzoxazolyl |
| 857 | 4-Cl | 5-benzoxazolyl |
| 858 | 4-Cl | 1-adamantyl |
| 859 | 4-Cl | 2-adamantyl |
| 860 | 4-Cl | i-Pr |
| 861 | 4-Cl | t-Bu |
| 862 | 4-Cl | c-Hex |
| 863 | 4-Cl | CH2CH2OMe |
| 864 | 4-Cl | CH2CONH2 |
| 865 | 4-Cl | CH2CO2Me |
| 866 | 4-Cl | CH(CH2Ph)CO2Me |
| 867 | 4-Cl | CH2CH2NMe2 |
| 868 | 4-Cl | benzyl |
| 869 | 4-Cl | phenethyl |
| 870 | 4-Cl | 2-(morpholin-1-yl)-Et |

TABLE 4

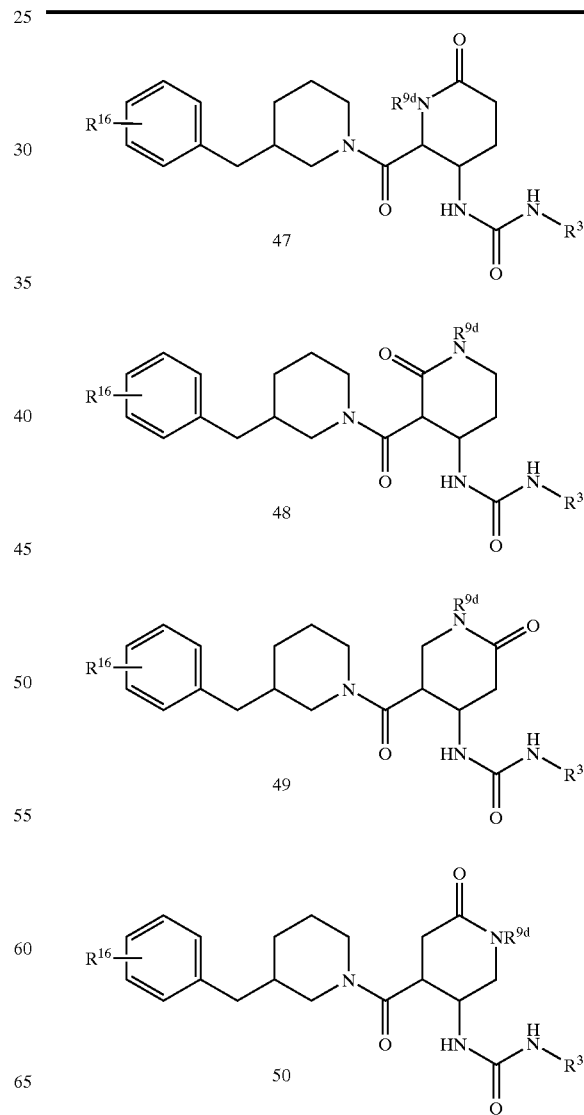

47

48

49

50

TABLE 4-continued
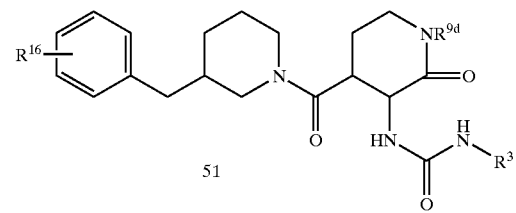
51
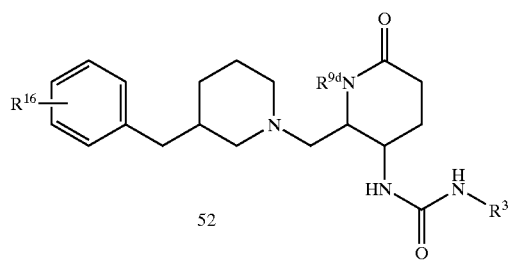
52
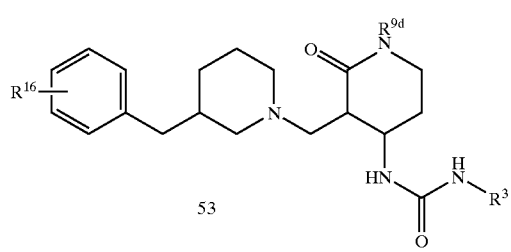
53
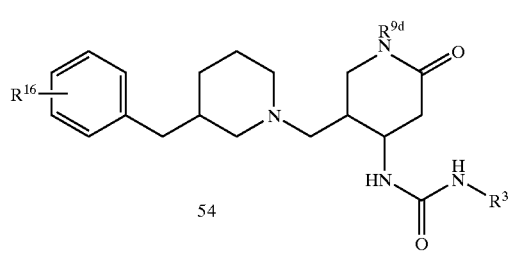
54
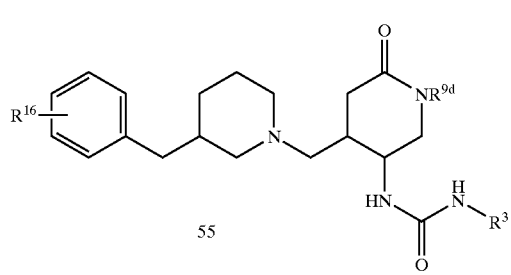
55
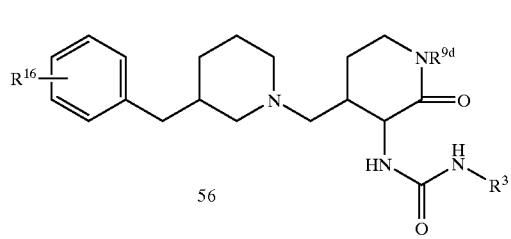
56
TABLE 4-continued
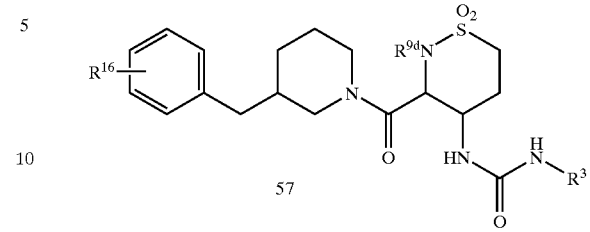
57
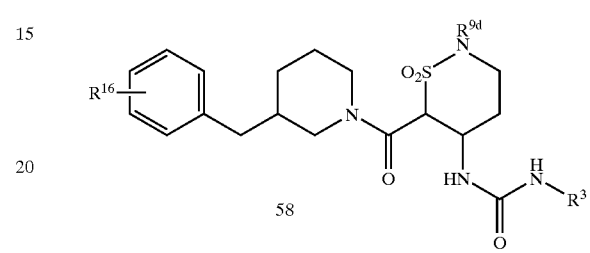
58
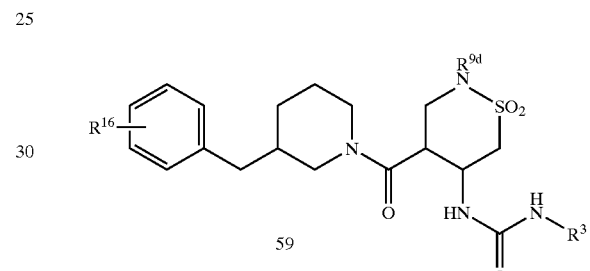
59
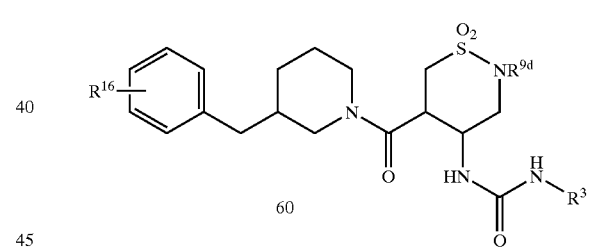
60
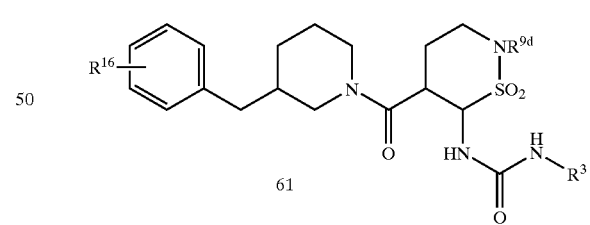
61
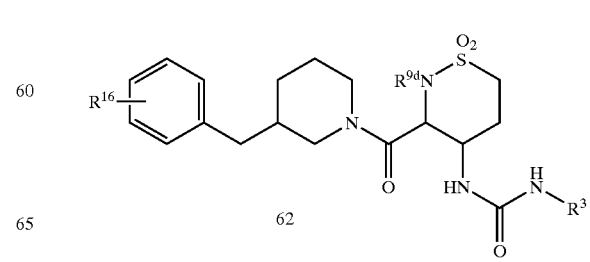
62

TABLE 4-continued

Structure 63: R16-substituted phenyl-CH2-piperidinyl-C(O)- attached to a 6-membered ring containing N-SO2 (N-R9d, O2S), with HN-C(O)-NH-R3 substituent.

Structure 64: R16-substituted phenyl-CH2-piperidinyl-C(O)- attached to a 6-membered ring containing N-R9d and SO2, with HN-C(O)-NH-R3 substituent.

Structure 65: R16-substituted phenyl-CH2-piperidinyl-C(O)- attached to a 6-membered ring containing SO2-NR9d, with HN-C(O)-NH-R3 substituent.

Structure 66: R16-substituted phenyl-CH2-piperidinyl-C(O)- attached to a 6-membered ring containing NR9d-SO2, with HN-C(O)-NH-R3 substituent.

| Entry | R16 | R9d | R3 |
|---|---|---|---|
| 1 | 2-F | H | Ph |
| 2 | 2-F | H | 3-CN—Ph |
| 3 | 2-F | H | 3-COMe—Ph |
| 4 | 2-F | H | 3-CO2Me—Ph |
| 5 | 2-F | H | 3-CONH2—Ph |
| 6 | 2-F | H | 3-CONHMe—Ph |
| 7 | 2-F | H | 3-F—Ph |
| 8 | 2-F | H | 3-Cl—Ph |
| 9 | 2-F | H | 3-Br—Ph |
| 10 | 2-F | H | 3-SO2NH—Ph |
| 11 | 2-F | H | 3-SO2NHMe—Ph |
| 12 | 2-F | H | 3-CF3—Ph |
| 13 | 2-F | H | 3-OMe—Ph |
| 14 | 2-F | H | 3-SMe—Ph |
| 15 | 2-F | H | 3-SOMe—Ph |
| 16 | 2-F | H | 3-SO2Me—Ph |
| 17 | 2-F | H | 3-OH—Ph |
| 18 | 2-F | H | 3-CH2OH—Ph |
| 19 | 2-F | H | 3-CHOHMe—Ph |
| 20 | 2-F | H | 3-COH(Me)2—Ph |
| 21 | 2-F | H | 3-Me—Ph |
| 22 | 2-F | H | 3-Et—Ph |
| 23 | 2-F | H | 3-iPr-Ph |
| 24 | 2-F | H | 3-tBu-Ph |
| 25 | 2-F | H | 3-CH2CO2Me—Ph |
| 26 | 2-F | H | 3-(1-piperidinyl)-Ph |
| 27 | 2-F | H | 3-(1-pyrrolidinyl)-Ph |
| 28 | 2-F | H | 3-(2-imidazolyl)-Ph |
| 29 | 2-F | H | 3-(1-imidazolyl)-Ph |
| 30 | 2-F | H | 3-(2-thiazolyl)-Ph |
| 31 | 2-F | H | 3-(3-pyrazolyl)-Ph |
| 32 | 2-F | H | 3-(1-pyrazolyl)-Ph |
| 33 | 2-F | H | 3-(5-Me-1-tetrazolyl)-Ph |
| 34 | 2-F | H | 3-(1-Me-5-tetrazolyl)-Ph |
| 35 | 2-F | H | 3-(2-pyridyl)-Ph |
| 36 | 2-F | H | 3-(2-thienyl)-Ph |
| 37 | 2-F | H | 3-(2-furanyl)-Ph |
| 38 | 2-F | H | 4-CN—Ph |
| 39 | 2-F | H | 4-COMe—Ph |
| 40 | 2-F | H | 4-CO2Me—Ph |
| 41 | 2-F | H | 4-CONH2—Ph |
| 42 | 2-F | H | 4-CONHMe—Ph |
| 43 | 2-F | H | 4-CONHPh—Ph |
| 44 | 2-F | H | 4-F—Ph |
| 45 | 2-F | H | 4-Cl—Ph |
| 46 | 2-F | H | 4-Br—Ph |
| 47 | 2-F | H | 4-SO2NH2—Ph |
| 48 | 2-F | H | 4-SO2NHMe—Ph |
| 49 | 2-F | H | 4-CF3—Ph |
| 50 | 2-F | H | 4-OMe—Ph |
| 51 | 2-F | H | 4-SMe—Ph |
| 52 | 2-F | H | 4-SOMe—Ph |
| 53 | 2-F | H | 4-SO2Me—Ph |
| 54 | 2-F | H | 4-OH—Ph |
| 55 | 2-F | H | 4-CH2OH—Ph |
| 56 | 2-F | H | 4-CHOHMe—Ph |
| 57 | 2-F | H | 4-COH(Me)2—Ph |
| 58 | 2-F | H | 4-Me—Ph |
| 59 | 2-F | H | 4-Et—Ph |
| 60 | 2-F | H | 4-iPr-Ph |
| 61 | 2-F | H | 4-tBu-Ph |
| 62 | 2-F | H | 4-CH2CO2Me—Ph |
| 63 | 2-F | H | 4-(1-piperidinyl)-Ph |
| 64 | 2-F | H | 4-(1-pyrrolidinyl)-Ph |
| 65 | 2-F | H | 4-(2-imidazolyl)-Ph |
| 66 | 2-F | H | 4-(1-imidazolyl)-Ph |
| 67 | 2-F | H | 4-(2-thiazolyl)-Ph |
| 68 | 2-F | H | 4-(3-pyrazolyl)-Ph |
| 69 | 2-F | H | 4-(1-pyrazolyl)-Ph |
| 70 | 2-F | H | 4-(5-Me-1-tetrazolyl)-Ph |
| 71 | 2-F | H | 4-(1-Me-5-tetrazolyl)-Ph |
| 72 | 2-F | H | 4-(2-pyridyl)-Ph |
| 73 | 2-F | H | 4-(2-thienyl)-Ph |
| 74 | 2-F | H | 4-(2-furanyl)-Ph |
| 75 | 2-F | H | 2-CN—Ph |
| 76 | 2-F | H | 2-COMe—Ph |
| 77 | 2-F | H | 2-CO2Me—Ph |
| 78 | 2-F | H | 2-CONH2—Ph |
| 79 | 2-F | H | 2-CONHMe—Ph |
| 80 | 2-F | H | 2-F—Ph |
| 81 | 2-F | H | 2-Cl—Ph |
| 82 | 2-F | H | 2-Br—Ph |
| 83 | 2-F | H | 2-SO2NH2—Ph |
| 84 | 2-F | H | 2-SO2NHMe—Ph |
| 85 | 2-F | H | 2-CF3—Ph |
| 86 | 2-F | H | 2-OMe—Ph |
| 87 | 2-F | H | 2-SMe—Ph |
| 88 | 2-F | H | 2-SOMe—Ph |
| 89 | 2-F | H | 2-SO2Me—Ph |
| 90 | 2-F | H | 2-OH—Ph |
| 91 | 2-F | H | 2-CH2OH—Ph |
| 92 | 2-F | H | 2-CHOHMe—Ph |
| 93 | 2-F | H | 2-COH(Me)2—Ph |
| 94 | 2-F | H | 2-Me—Ph |
| 95 | 2-F | H | 2-Et—Ph |
| 96 | 2-F | H | 2-iPr-Ph |
| 97 | 2-F | H | 2-tBu-Ph |
| 98 | 2-F | H | 2-CH2CO2Me—Ph |
| 99 | 2-F | H | 2-(1-piperidinyl)-Ph |
| 100 | 2-F | H | 2-(1-pyrrolidinyl)-Ph |
| 101 | 2-F | H | 2-(2-imidazolyl)-Ph |
| 102 | 2-F | H | 2-(1-imidazolyl)-Ph |
| 103 | 2-F | H | 2-(2-thiazolyl)-Ph |
| 104 | 2-F | H | 2-(3-pyrazolyl)-Ph |
| 105 | 2-F | H | 2-(1-pyrazolyl)-Ph |
| 106 | 2-F | H | 2-(5-Me-1-tetrazolyl)-Ph |
| 107 | 2-F | H | 2-(1-Me-5-tetrazolyl)-Ph |
| 108 | 2-F | H | 2-(2-pyridyl)-Ph |

TABLE 4-continued

| | | | |
|---|---|---|---|
| 109 | 2-F | H | 2-(2-thienyl)-Ph |
| 110 | 2-F | H | 2-(2-furanyl)-Ph |
| 111 | 2-F | H | 2,4-diF—Ph |
| 112 | 2-F | H | 2,5-diF—Ph |
| 113 | 2-F | H | 2,6-diF—Ph |
| 114 | 2-F | H | 3,4-diF—Ph |
| 115 | 2-F | H | 3,5-diF—Ph |
| 116 | 2-F | H | 2,4-diCl—Ph |
| 117 | 2-F | H | 2,5-diCl—Ph |
| 118 | 2-F | H | 2,6-diCl—Ph |
| 119 | 2-F | H | 3,4-diCl—Ph |
| 120 | 2-F | H | 3,5-diCl—Ph |
| 121 | 2-F | H | 3,4-diCF3—Ph |
| 122 | 2-F | H | 3,5-diCF3—Ph |
| 123 | 2-F | H | 5-Cl-2-MeO—Ph |
| 124 | 2-F | H | 5-Cl-2-Me—Ph |
| 125 | 2-F | H | 2-F-5-Me—Ph |
| 126 | 2-F | H | 3-F-5-morpholino-Ph |
| 127 | 2-F | H | 3,4-OCH2O—Ph |
| 128 | 2-F | H | 3,4-OCH2CH2O—Ph |
| 129 | 2-F | H | 2-MeO-5-CONH2—Ph |
| 130 | 2-F | H | 2-MeO-4-(1-Me-5-tetrazolyl)-Ph |
| 131 | 2-F | H | 2-MeO-5-(1-Me-5-tetrazolyl)-Ph |
| 132 | 2-F | H | 3-CONH2-5-(1-Me-5-tetrazolyl)-Ph |
| 133 | 2-F | H | 1-naphthyl |
| 134 | 2-F | H | 2-naphthyl |
| 135 | 2-F | H | 2-thienyl |
| 136 | 2-F | H | 3-thienyl |
| 137 | 2-F | H | 2-furanyl |
| 138 | 2-F | H | 3-furanyl |
| 139 | 2-F | H | 2-pyridyl |
| 140 | 2-F | H | 3-pyridyl |
| 141 | 2-F | H | 4-pyridyl |
| 142 | 2-F | H | 2-indolyl |
| 143 | 2-F | H | 3-indolyl |
| 144 | 2-F | H | 5-indolyl |
| 145 | 2-F | H | 6-indolyl |
| 146 | 2-F | H | 3-indazolyl |
| 147 | 2-F | H | 5-indazolyl |
| 148 | 2-F | H | 6-indazolyl |
| 149 | 2-F | H | 2-imidazolyl |
| 150 | 2-F | H | 3-isoxazoyl |
| 151 | 2-F | H | 3-pyrazolyl |
| 152 | 2-F | H | 2-thiadiazolyl |
| 153 | 2-F | H | 2-thiazolyl |
| 154 | 2-F | H | 5-Ac-4-Me-2-thiazolyl |
| 155 | 2-F | H | 5-tetrazolyl |
| 156 | 2-F | H | 2-benzimidazolyl |
| 157 | 2-F | H | 5-benzimidazolyl |
| 158 | 2-F | H | 2-benzothiazolyl |
| 159 | 2-F | H | 5-benzothiazolyl |
| 160 | 2-F | H | 2-benzoxazolyl |
| 161 | 2-F | H | 5-benzoxazolyl |
| 162 | 2-F | H | 1-adamantyl |
| 163 | 2-F | H | 2-adamantyl |
| 164 | 2-F | H | i-Pr |
| 165 | 2-F | H | t-Bu |
| 166 | 2-F | H | c-Hex |
| 167 | 2-F | H | CH2CH2OMe |
| 168 | 2-F | H | CH2CONH2 |
| 169 | 2-F | H | CH2CO2Me |
| 170 | 2-F | H | CH(CH2Ph)CO2Me |
| 171 | 2-F | H | CH2CH2NMe2 |
| 172 | 2-F | H | benzyl |
| 173 | 2-F | H | phenethyl |
| 174 | 2-F | H | 2-(morpholin-1-yl)-Et |
| 175 | 3-F | H | Ph |
| 176 | 3-F | H | 3-CN—Ph |
| 177 | 3-F | H | 3-COMe—Ph |
| 178 | 3-F | H | 3-CO2Me—Ph |
| 179 | 3-F | H | 3-CONH2—Ph |
| 180 | 3-F | H | 3-CONHMe—Ph |
| 181 | 3-F | H | 3-F—Ph |
| 182 | 3-F | H | 3-Cl—Ph |
| 183 | 3-F | H | 3-Br—Ph |
| 184 | 3-F | H | 3-SO2NH2—Ph |
| 185 | 3-F | H | 3-SO2NHMe—Ph |
| 186 | 3-F | H | 3-CF3—Ph |
| 187 | 3-F | H | 3-OMe—Ph |
| 188 | 3-F | H | 3-SMe—Ph |
| 189 | 3-F | H | 3-SOMe—Ph |
| 190 | 3-F | H | 3-SO2Me—Ph |
| 191 | 3-F | H | 3-OH—Ph |
| 192 | 3-F | H | 3-CH2OH—Ph |
| 193 | 3-F | H | 3-CHOHMe—Ph |
| 194 | 3-F | H | 3-COH(Me)2—Ph |
| 195 | 3-F | H | 3-Me—Ph |
| 196 | 3-F | H | 3-Et—Ph |
| 197 | 3-F | H | 3-iPr-Ph |
| 198 | 3-F | H | 3-tBu-Ph |
| 199 | 3-F | H | 3-CH2CO2Me—Ph |
| 200 | 3-F | H | 3-(1-piperidinyl)-Ph |
| 201 | 3-F | H | 3-(1-pyrrolidinyl)-Ph |
| 202 | 3-F | H | 3-(2-imidazolyl)-Ph |
| 203 | 3-F | H | 3-(1-imidazolyl)-Ph |
| 204 | 3-F | H | 3-(2-thiazolyl)-Ph |
| 205 | 3-F | H | 3-(3-pyrazolyl)-Ph |
| 206 | 3-F | H | 3-(1-pyrazolyl)-Ph |
| 207 | 3-F | H | 3-(5-Me-1-tetrazolyl)-Ph |
| 208 | 3-F | H | 3-(1-Me-5-tetrazolyl)-Ph |
| 209 | 3-F | H | 3-(2-pyridyl)-Ph |
| 210 | 3-F | H | 3-(2-thienyl)-Ph |
| 211 | 3-F | H | 3-(2-furanyl)-Ph |
| 212 | 3-F | H | 4-CN—Ph |
| 213 | 3-F | H | 4-COMe—Ph |
| 214 | 3-F | H | 4-CO2Me—Ph |
| 215 | 3-F | H | 4-CONH2—Ph |
| 216 | 3-F | H | 4-CONHMe—Ph |
| 217 | 3-F | H | 4-CONHPh—Ph |
| 218 | 3-F | H | 4-F—Ph |
| 219 | 3-F | H | 4-Cl—Ph |
| 220 | 3-F | H | 4-Br—Ph |
| 221 | 3-F | H | 4-SO2NH2—Ph |
| 222 | 3-F | H | 4-SO2NHMe—Ph |
| 223 | 3-F | H | 4-CF3—Ph |
| 224 | 3-F | H | 4-OMe—Ph |
| 225 | 3-F | H | 4-SMe—Ph |
| 226 | 3-F | H | 4-SOMe—Ph |
| 227 | 3-F | H | 4-SO2Me—Ph |
| 228 | 3-F | H | 4-OH—Ph |
| 229 | 3-F | H | 4-CH2OH—Ph |
| 230 | 3-F | H | 4-CHOHMe—Ph |
| 231 | 3-F | H | 4-COH(Me)2—Ph |
| 232 | 3-F | H | 4-Me—Ph |
| 233 | 3-F | H | 4-Et—Ph |
| 234 | 3-F | H | 4-iPr-Ph |
| 235 | 3-F | H | 4-tBu-Ph |
| 236 | 3-F | H | 4-CH2CO2Me—Ph |
| 237 | 3-F | H | 4-(1-piperidinyl)-Ph |
| 238 | 3-F | H | 4-(1-pyrrolidinyl)-Ph |
| 239 | 3-F | H | 4-(2-imidazolyl)-Ph |
| 240 | 3-F | H | 4-(1-imidazolyl)-Ph |
| 241 | 3-F | H | 4-(2-thiazolyl)-Ph |
| 242 | 3-F | H | 4-(3-pyrazolyl)-Ph |
| 243 | 3-F | H | 4-(1-pyrazolyl)-Ph |
| 244 | 3-F | H | 4-(5-Me-1-tetrazolyl)-Ph |
| 245 | 3-F | H | 4-(1-Me-5-tetrazolyl)-Ph |
| 246 | 3-F | H | 4-(2-pyridyl)-Ph |
| 247 | 3-F | H | 4-(2-thienyl)-Ph |
| 248 | 3-F | H | 4-(2-furanyl)-Ph |
| 249 | 3-F | H | 2-CN—Ph |
| 250 | 3-F | H | 2-COMe—Ph |
| 251 | 3-F | H | 2-CO2Me—Ph |
| 252 | 3-F | H | 2-CONH2—Ph |
| 253 | 3-F | H | 2-CONHMe—Ph |
| 254 | 3-F | H | 2-F—Ph |
| 255 | 3-F | H | 2-Cl—Ph |
| 256 | 3-F | H | 2-Br—Ph |
| 257 | 3-F | H | 2-SO2NH2—Ph |
| 258 | 3-F | H | 2-SO2NHMe—Ph |
| 259 | 3-F | H | 2-CF3—Ph |
| 260 | 3-F | H | 2-OMe—Ph |
| 261 | 3-F | H | 2-SMe—Ph |
| 262 | 3-F | H | 2-SOMe—Ph |
| 263 | 3-F | H | 2-SO2Me—Ph |
| 264 | 3-F | H | 2-OH—Ph |
| 265 | 3-F | H | 2-CH2OH—Ph |
| 266 | 3-F | H | 2-CHOHMe—Ph |

TABLE 4-continued

| | | | |
|---|---|---|---|
| 267 | 3-F | H | 2-COH(Me)2—Ph |
| 268 | 3-F | H | 2-Me—Ph |
| 269 | 3-F | H | 2-Et—Ph |
| 270 | 3-F | H | 2-iPr-Ph |
| 271 | 3-F | H | 2-tBu-Ph |
| 272 | 3-F | H | 2-CH2CO2Me—Ph |
| 273 | 3-F | H | 2-(1-piperidinyl)-Ph |
| 274 | 3-F | H | 2-(1-pyrrolidinyl)-Ph |
| 275 | 3-F | H | 2-(2-imidazolyl)-Ph |
| 276 | 3-F | H | 2-(1-imidazolyl)-Ph |
| 277 | 3-F | H | 2-(2-thiazolyl)-Ph |
| 278 | 3-F | H | 2-(3-pyrazolyl)-Ph |
| 279 | 3-F | H | 2-(1-pyrazolyl)-Ph |
| 280 | 3-F | H | 2-(5-Me-1-tetrazolyl)-Ph |
| 281 | 3-F | H | 2-(1-Me-5-tetrazolyl)-Ph |
| 282 | 3-F | H | 2-(2-pyridyl)-Ph |
| 283 | 3-F | H | 2-(2-thienyl)-Ph |
| 284 | 3-F | H | 2-(2-furanyl)-Ph |
| 285 | 3-F | H | 2,4-diF—Ph |
| 286 | 3-F | H | 2,5-diF—Ph |
| 287 | 3-F | H | 2,6-diF—Ph |
| 288 | 3-F | H | 3,4-diF—Ph |
| 289 | 3-F | H | 3,5-diF—Ph |
| 290 | 3-F | H | 2,4-diCl—Ph |
| 291 | 3-F | H | 2,5-diCl—Ph |
| 292 | 3-F | H | 2,6-diCl—Ph |
| 293 | 3-F | H | 3,4-diCl—Ph |
| 294 | 3-F | H | 3,5-diCl—Ph |
| 295 | 3-F | H | 3,4-diCF3—Ph |
| 296 | 3-F | H | 3,5-diCF3—Ph |
| 297 | 3-F | H | 5-Cl-2-MeO—Ph |
| 298 | 3-F | H | 5-Cl-2-Me—Ph |
| 299 | 3-F | H | 2-F-5-Me—Ph |
| 300 | 3-F | H | 3-F-5-morpholino-Ph |
| 301 | 3-F | H | 3,4-OCH2O—Ph |
| 302 | 3-F | H | 3,4-OCH2CH2O—Ph |
| 303 | 3-F | H | 2-MeO-5-CONH2—Ph |
| 304 | 3-F | H | 2-MeO-4-(1-Me-5-tetrazolyl)-Ph |
| 305 | 3-F | H | 2-MeO-5-(1-Me-5-tetrazolyl)-Ph |
| 306 | 3-F | H | 3-CONH2-5-(1-Me-5-tetrazolyl)-Ph |
| 307 | 3-F | H | 1-naphthyl |
| 308 | 3-F | H | 2-naphthyl |
| 309 | 3-F | H | 2-thienyl |
| 310 | 3-F | H | 3-thienyl |
| 311 | 3-F | H | 2-furanyl |
| 312 | 3-F | H | 3-furanyl |
| 313 | 3-F | H | 2-pyridyl |
| 314 | 3-F | H | 3-pyridyl |
| 315 | 3-F | H | 4-pyridyl |
| 316 | 3-F | H | 2-indolyl |
| 317 | 3-F | H | 3-indolyl |
| 318 | 3-F | H | 5-indolyl |
| 319 | 3-F | H | 6-indolyl |
| 320 | 3-F | H | 3-indazolyl |
| 321 | 3-F | H | 5-indazolyl |
| 322 | 3-F | H | 6-indazolyl |
| 323 | 3-F | H | 2-imidazolyl |
| 324 | 3-F | H | 3-isoxazoyl |
| 325 | 3-F | H | 3-pyrazolyl |
| 326 | 3-F | H | 2-thiadiazolyl |
| 327 | 3-F | H | 2-thiazolyl |
| 328 | 3-F | H | 5-Ac-4-Me-2-thiazolyl |
| 329 | 3-F | H | 5-tetrazolyl |
| 330 | 3-F | H | 2-benzimidazolyl |
| 331 | 3-F | H | 5-benzimidazolyl |
| 332 | 3-F | H | 2-benzothiazolyl |
| 333 | 3-F | H | 5-benzothiazolyl |
| 334 | 3-F | H | 2-benzoxazolyl |
| 335 | 3-F | H | 5-benzoxazolyl |
| 336 | 3-F | H | 1-adamantyl |
| 337 | 3-F | H | 2-adamantyl |
| 338 | 3-F | H | i-Pr |
| 339 | 3-F | H | t-Bu |
| 340 | 3-F | H | c-Hex |
| 341 | 3-F | H | CH2CH2OMe |
| 342 | 3-F | H | CH2CONH2 |
| 343 | 3-F | H | CH2CO2Me |
| 344 | 3-F | H | CH(CH2Ph)CO2Me |
| 345 | 3-F | H | CH2CH2NMe2 |
| 346 | 3-F | H | benzyl |
| 347 | 3-F | H | phenethyl |
| 348 | 3-F | H | 2-(morpholin-1-yl)-Et |
| 349 | 4-F | H | Ph |
| 350 | 4-F | H | 3-CN—Ph |
| 351 | 4-F | H | 3-COMe—Ph |
| 352 | 4-F | H | 3-CO2Me—Ph |
| 353 | 4-F | H | 3-CONH2—Ph |
| 354 | 4-F | H | 3-CONHMe—Ph |
| 355 | 4-F | H | 3-F—Ph |
| 356 | 4-F | H | 3-Cl—Ph |
| 357 | 4-F | H | 3-Br—Ph |
| 358 | 4-F | H | 3-SO2NH2—Ph |
| 359 | 4-F | H | 3-SO2NHMe—Ph |
| 360 | 4-F | H | 3-CF3—Ph |
| 361 | 4-F | H | 3-OMe—Ph |
| 362 | 4-F | H | 3-SMe—Ph |
| 363 | 4-F | H | 3-SOMe—Ph |
| 364 | 4-F | H | 3-SO2Me—Ph |
| 365 | 4-F | H | 3-OH—Ph |
| 366 | 4-F | H | 3-CH2OH—Ph |
| 367 | 4-F | H | 3-CHOHMe—Ph |
| 368 | 4-F | H | 3-COH(Me)2—Ph |
| 369 | 4-F | H | 3-Me—Ph |
| 370 | 4-F | H | 3-Et—Ph |
| 371 | 4-F | H | 3-iPr-Ph |
| 372 | 4-F | H | 3-tBu-Ph |
| 373 | 4-F | H | 3-CH2CO2Me—Ph |
| 374 | 4-F | H | 3-(1-piperidinyl)-Ph |
| 375 | 4-F | H | 3-(1-pyrrolidinyl)-Ph |
| 376 | 4-F | H | 3-(2-imidazolyl)-Ph |
| 377 | 4-F | H | 3-(1-imidazolyl)-Ph |
| 378 | 4-F | H | 3-(2-thiazolyl)-Ph |
| 379 | 4-F | H | 3-(3-pyrazolyl)-Ph |
| 380 | 4-F | H | 3-(1-pyrazolyl)-Ph |
| 381 | 4-F | H | 3-(5-Me-1-tetrazolyl)-Ph |
| 382 | 4-F | H | 3-(1-Me-5-tetrazolyl)-Ph |
| 383 | 4-F | H | 3-(2-pyridyl)-Ph |
| 384 | 4-F | H | 3-(2-thienyl)-Ph |
| 385 | 4-F | H | 3-(2-furanyl)-Ph |
| 386 | 4-F | H | 4-CN—Ph |
| 387 | 4-F | H | 4-COMe—Ph |
| 388 | 4-F | H | 4-CO2Me—Ph |
| 389 | 4-F | H | 4-CONH2—Ph |
| 390 | 4-F | H | 4-CONHMe—Ph |
| 391 | 4-F | H | 4-CONHPh—Ph |
| 392 | 4-F | H | 4-F—Ph |
| 393 | 4-F | H | 4-Cl—Ph |
| 394 | 4-F | H | 4-Br—Ph |
| 395 | 4-F | H | 4-SO2NH2—Ph |
| 396 | 4-F | H | 4-SO2NHMe—Ph |
| 397 | 4-F | H | 4-CF3—Ph |
| 398 | 4-F | H | 4-OMe—Ph |
| 399 | 4-F | H | 4-SMe—Ph |
| 400 | 4-F | H | 4-SOMe—Ph |
| 401 | 4-F | H | 4-SO2Me—Ph |
| 402 | 4-F | H | 4-OH—Ph |
| 403 | 4-F | H | 4-CH2OH—Ph |
| 404 | 4-F | H | 4-CHOHMe—Ph |
| 405 | 4-F | H | 4-COH(Me)2—Ph |
| 406 | 4-F | H | 4-Me—Ph |
| 407 | 4-F | H | 4-Et—Ph |
| 408 | 4-F | H | 4-iPr-Ph |
| 409 | 4-F | H | 4-tBu-Ph |
| 410 | 4-F | H | 4-CH2CO2Me—Ph |
| 411 | 4-F | H | 4-(1-piperidinyl)-Ph |
| 412 | 4-F | H | 4-(1-pyrrolidinyl)-Ph |
| 413 | 4-F | H | 4-(2-imidazolyl)-Ph |
| 414 | 4-F | H | 4-(1-imidazolyl)-Ph |
| 415 | 4-F | H | 4-(2-thiazolyl)-Ph |
| 416 | 4-F | H | 4-(3-pyrazolyl)-Ph |
| 417 | 4-F | H | 4-(1-pyrazolyl)-Ph |
| 418 | 4-F | H | 4-(5-Me-1-tetrazolyl)-Ph |
| 419 | 4-F | H | 4-(1-Me-5-tetrazolyl)-Ph |
| 420 | 4-F | H | 4-(2-pyridyl)-Ph |
| 421 | 4-F | H | 4-(2-thienyl)-Ph |
| 422 | 4-F | H | 4-(2-furanyl)-Ph |
| 423 | 4-F | H | 2-CN—Ph |
| 424 | 4-F | H | 2-COMe—Ph |

TABLE 4-continued

| | | | |
|---|---|---|---|
| 425 | 4-F | H | 2-CO2Me—Ph |
| 426 | 4-F | H | 2-CONH2—Ph |
| 427 | 4-F | H | 2-CONHMe—Ph |
| 428 | 4-F | H | 2-F—Ph |
| 429 | 4-F | H | 2-Cl—Ph |
| 430 | 4-F | H | 2-Br—Ph |
| 431 | 4-F | H | 2-SO2NH2—Ph |
| 432 | 4-F | H | 2-SO2NHMe—Ph |
| 433 | 4-F | H | 2-CF3—Ph |
| 434 | 4-F | H | 2-OMe—Ph |
| 435 | 4-F | H | 2-SMe—Ph |
| 436 | 4-F | H | 2-SOMe—Ph |
| 437 | 4-F | H | 2-SO2Me—Ph |
| 438 | 4-F | H | 2-OH—Ph |
| 439 | 4-F | H | 2-CH2OH—Ph |
| 440 | 4-F | H | 2-CHOHMe—Ph |
| 441 | 4-F | H | 2-COH(Me)2—Ph |
| 442 | 4-F | H | 2-Me—Ph |
| 443 | 4-F | H | 2-Et—Ph |
| 444 | 4-F | H | 2-iPr-Ph |
| 445 | 4-F | H | 2-tBu-Ph |
| 446 | 4-F | H | 2-CH2CO2Me—Ph |
| 447 | 4-F | H | 2-(1-piperidinyl)-Ph |
| 448 | 4-F | H | 2-(1-pyrrolidinyl)-Ph |
| 449 | 4-F | H | 2-(2-imidazolyl)-Ph |
| 450 | 4-F | H | 2-(1-imidazolyl)-Ph |
| 451 | 4-F | H | 2-(2-thiazolyl)-Ph |
| 452 | 4-F | H | 2-(3-pyrazolyl)-Ph |
| 453 | 4-F | H | 2-(1-pyrazolyl)-Ph |
| 454 | 4-F | H | 2-(5-Me-1-tetrazolyl)-Ph |
| 455 | 4-F | H | 2-(1-Me-5-tetrazolyl)-Ph |
| 456 | 4-F | H | 2-(2-pyridyl)-Ph |
| 457 | 4-F | H | 2-(2-thienyl)-Ph |
| 458 | 4-F | H | 2-(2-furanyl)-Ph |
| 459 | 4-F | H | 2,4-diF—Ph |
| 460 | 4-F | H | 2,5-diF—Ph |
| 461 | 4-F | H | 2,6-diF—Ph |
| 462 | 4-F | H | 3,4-diF—Ph |
| 463 | 4-F | H | 3,5-diF—Ph |
| 464 | 4-F | H | 2,4-diCl—Ph |
| 465 | 4-F | H | 2,5-diCl—Ph |
| 466 | 4-F | H | 2,6-diCl—Ph |
| 467 | 4-F | H | 3,4-diCl—Ph |
| 468 | 4-F | H | 3,5-diCl—Ph |
| 469 | 4-F | H | 3,4-diCF3—Ph |
| 470 | 4-F | H | 3,5-diCF3—Ph |
| 471 | 4-F | H | 5-Cl-2-MeO—Ph |
| 472 | 4-F | H | 5-Cl-2-Me—Ph |
| 473 | 4-F | H | 2-F-5-Me—Ph |
| 474 | 4-F | H | 3-F-5-morpholino-Ph |
| 475 | 4-F | H | 3,4-OCH2O—Ph |
| 476 | 4-F | H | 3,4-OCH2CH2O—Ph |
| 477 | 4-F | H | 2-MeO-5-CONH2—Ph |
| 478 | 4-F | H | 2-MeO-4-(1-Me-5-tetrazolyl)-Ph |
| 479 | 4-F | H | 2-MeO-5-(1-Me-5-tetrazolyl)-Ph |
| 480 | 4-F | H | 3-CONH2-5-(1-Me-5-tetrazolyl)-Ph |
| 481 | 4-F | H | 1-naphthyl |
| 482 | 4-F | H | 2-naphthyl |
| 483 | 4-F | H | 2-thienyl |
| 484 | 4-F | H | 3-thienyl |
| 485 | 4-F | H | 2-furanyl |
| 486 | 4-F | H | 3-furanyl |
| 487 | 4-F | H | 2-pyridyl |
| 488 | 4-F | H | 3-pyridyl |
| 489 | 4-F | H | 4-pyridyl |
| 490 | 4-F | H | 2-indolyl |
| 491 | 4-F | H | 3-indolyl |
| 492 | 4-F | H | 5-indolyl |
| 493 | 4-F | H | 6-indolyl |
| 494 | 4-F | H | 3-indazolyl |
| 495 | 4-F | H | 5-indazolyl |
| 496 | 4-F | H | 6-indazolyl |
| 497 | 4-F | H | 2-imidazolyl |
| 498 | 4-F | H | 3-isoxazoyl |
| 499 | 4-F | H | 3-pyrazolyl |
| 500 | 4-F | H | 2-thiadiazolyl |
| 501 | 4-F | H | 2-thiazolyl |
| 502 | 4-F | H | 5-Ac-4-Me-2-thiazolyl |
| 503 | 4-F | H | 5-tetrazolyl |
| 504 | 4-F | H | 2-benzimidazolyl |
| 505 | 4-F | H | 5-benzimidazolyl |
| 506 | 4-F | H | 2-benzothiazolyl |
| 507 | 4-F | H | 5-benzothiazolyl |
| 508 | 4-F | H | 2-benzoxazolyl |
| 509 | 4-F | H | 5-benzoxazolyl |
| 510 | 4-F | H | 1-adamantyl |
| 511 | 4-F | H | 2-adamantyl |
| 512 | 4-F | H | i-Pr |
| 513 | 4-F | H | t-Bu |
| 514 | 4-F | H | c-Hex |
| 515 | 4-F | H | CH2CH2OMe |
| 516 | 4-F | H | CH2CONH2 |
| 517 | 4-F | H | CH2CO2Me |
| 518 | 4-F | H | CH(CH2Ph)CO2Me |
| 519 | 4-F | H | CH2CH2NMe2 |
| 520 | 4-F | H | benzyl |
| 521 | 4-F | H | phenethyl |
| 522 | 4-F | H | 2-(morpholin-1-yl)-Et |
| 523 | 3-Cl | H | Ph |
| 524 | 3-Cl | H | 3-CN—Ph |
| 525 | 3-Cl | H | 3-COMe—Ph |
| 526 | 3-Cl | H | 3-CO2Me—Ph |
| 527 | 3-Cl | H | 3-CONH2—Ph |
| 528 | 3-Cl | H | 3-CONHMe—Ph |
| 529 | 3-Cl | H | 3-F—Ph |
| 530 | 3-Cl | H | 3-Cl—Ph |
| 531 | 3-Cl | H | 3-Br—Ph |
| 532 | 3-Cl | H | 3-SO2NH2—Ph |
| 533 | 3-Cl | H | 3-SO2NHMe—Ph |
| 534 | 3-Cl | H | 3-CF3—Ph |
| 535 | 3-Cl | H | 3-OMe—Ph |
| 536 | 3-Cl | H | 3-SMe—Ph |
| 537 | 3-Cl | H | 3-SOMe—Ph |
| 538 | 3-Cl | H | 3-SO2Me—Ph |
| 539 | 3-Cl | H | 3-OH—Ph |
| 540 | 3-Cl | H | 3-CH2OH—Ph |
| 541 | 3-Cl | H | 3-CHOHMe—Ph |
| 542 | 3-Cl | H | 3-COH(Me)2—Ph |
| 543 | 3-Cl | H | 3-Me—Ph |
| 544 | 3-Cl | H | 3-Et—Ph |
| 545 | 3-Cl | H | 3-iPr-Ph |
| 546 | 3-Cl | H | 3-tBu-Ph |
| 547 | 3-Cl | H | 3-CH2CO2Me—Ph |
| 548 | 3-Cl | H | 3-(1-piperidinyl)-Ph |
| 549 | 3-Cl | H | 3-(1-pyrrolidinyl)-Ph |
| 550 | 3-Cl | H | 3-(2-imidazolyl)-Ph |
| 551 | 3-Cl | H | 3-(1-imidazolyl)-Ph |
| 552 | 3-Cl | H | 3-(2-thiazolyl)-Ph |
| 553 | 3-Cl | H | 3-(3-pyrazolyl)-Ph |
| 554 | 3-Cl | H | 3-(1-pyrazolyl)-Ph |
| 555 | 3-Cl | H | 3-(5-Me-1-tetrazolyl)-Ph |
| 556 | 3-Cl | H | 3-(1-Me-5-tetrazolyl)-Ph |
| 557 | 3-Cl | H | 3-(2-pyridyl)-Ph |
| 558 | 3-Cl | H | 3-(2-thienyl)-Ph |
| 559 | 3-Cl | H | 3-(2-furanyl)-Ph |
| 560 | 3-Cl | H | 4-CN—Ph |
| 561 | 3-Cl | H | 4-COMe—Ph |
| 562 | 3-Cl | H | 4-CO2Me—Ph |
| 563 | 3-Cl | H | 4-CONH2—Ph |
| 564 | 3-Cl | H | 4-CONHMe—Ph |
| 565 | 3-Cl | H | 4-CONHPh—Ph |
| 566 | 3-Cl | H | 4-F—Ph |
| 567 | 3-Cl | H | 4-Cl—Ph |
| 568 | 3-Cl | H | 4-Br—Ph |
| 569 | 3-Cl | H | 4-SO2NH2—Ph |
| 570 | 3-Cl | H | 4-SO2NHMe—Ph |
| 571 | 3-Cl | H | 4-CF3—Ph |
| 572 | 3-Cl | H | 4-OMe—Ph |
| 573 | 3-Cl | H | 4-SMe—Ph |
| 574 | 3-Cl | H | 4-SOMe—Ph |
| 575 | 3-Cl | H | 4-SO2Me—Ph |
| 576 | 3-Cl | H | 4-OH—Ph |
| 577 | 3-Cl | H | 4-CH2OH—Ph |
| 578 | 3-Cl | H | 4-CHOHMe—Ph |
| 579 | 3-Cl | H | 4-COH(Me)2—Ph |
| 580 | 3-Cl | H | 4-Me—Ph |
| 581 | 3-Cl | H | 4-Et—Ph |
| 582 | 3-Cl | H | 4-iPr-Ph |

TABLE 4-continued

| | | | |
|---|---|---|---|
| 583 | 3-Cl | H | 4-tBu-Ph |
| 584 | 3-Cl | H | 4-CH2CO2Me—Ph |
| 585 | 3-Cl | H | 4-(1-piperidinyl)-Ph |
| 586 | 3-Cl | H | 4-(1-pyrrolidinyl)-Ph |
| 587 | 3-Cl | H | 4-(2-imidazolyl)-Ph |
| 588 | 3-Cl | H | 4-(1-imidazolyl)-Ph |
| 589 | 3-Cl | H | 4-(2-thiazolyl)-Ph |
| 590 | 3-Cl | H | 4-(3-pyrazolyl)-Ph |
| 591 | 3-Cl | H | 4-(1-pyrazolyl)-Ph |
| 592 | 3-Cl | H | 4-(5-Me-1-tetrazolyl)-Ph |
| 593 | 3-Cl | H | 4-(1-Me-5-tetrazolyl)-Ph |
| 594 | 3-Cl | H | 4-(2-pyridyl)-Ph |
| 595 | 3-Cl | H | 4-(2-thienyl)-Ph |
| 596 | 3-Cl | H | 4-(2-furanyl)-Ph |
| 597 | 3-Cl | H | 2-CN—Ph |
| 598 | 3-Cl | H | 2-COMe—Ph |
| 599 | 3-Cl | H | 2-CO2Me—Ph |
| 600 | 3-Cl | H | 2-CONH2—Ph |
| 601 | 3-Cl | H | 2-CONHMe—Ph |
| 602 | 3-Cl | H | 2-F—Ph |
| 603 | 3-Cl | H | 2-Cl—Ph |
| 604 | 3-Cl | H | 2-Br—Ph |
| 605 | 3-Cl | H | 2-SO2NH2—Ph |
| 606 | 3-Cl | H | 2-SO2NHMe—Ph |
| 607 | 3-Cl | H | 2-CF3—Ph |
| 608 | 3-Cl | H | 2-OMe—Ph |
| 609 | 3-Cl | H | 2-SMe—Ph |
| 610 | 3-Cl | H | 2-SOMe—Ph |
| 611 | 3-Cl | H | 2-SO2Me—Ph |
| 612 | 3-Cl | H | 2-OH—Ph |
| 613 | 3-Cl | H | 2-CH2OH—Ph |
| 614 | 3-Cl | H | 2-CHOHMe—Ph |
| 615 | 3-Cl | H | 2-COH(Me)2—Ph |
| 616 | 3-Cl | H | 2-Me—Ph |
| 617 | 3-Cl | H | 2-Et—Ph |
| 618 | 3-Cl | H | 2-iPr-Ph |
| 619 | 3-Cl | H | 2-tBu-Ph |
| 620 | 3-Cl | H | 2-CH2CO2Me—Ph |
| 621 | 3-Cl | H | 2-(1-piperidinyl)-Ph |
| 622 | 3-Cl | H | 2-(1-pyrrolidinyl)-Ph |
| 623 | 3-Cl | H | 2-(2-imidazolyl)-Ph |
| 624 | 3-Cl | H | 2-(1-imidazolyl)-Ph |
| 625 | 3-Cl | H | 2-(2-thiazolyl)-Ph |
| 626 | 3-Cl | H | 2-(3-pyrazolyl)-Ph |
| 627 | 3-Cl | H | 2-(1-pyrazolyl)-Ph |
| 628 | 3-Cl | H | 2-(5-Me-1-tetrazolyl)-Ph |
| 629 | 3-Cl | H | 2-(1-Me-5-tetrazolyl)-Ph |
| 630 | 3-Cl | H | 2-(2-pyridyl)-Ph |
| 631 | 3-Cl | H | 2-(2-thienyl)-Ph |
| 632 | 3-Cl | H | 2-(2-furanyl)-Ph |
| 633 | 3-Cl | H | 2,4-diF—Ph |
| 634 | 3-Cl | H | 2,5-diF—Ph |
| 635 | 3-Cl | H | 2,6-diF—Ph |
| 636 | 3-Cl | H | 3,4-diF—Ph |
| 637 | 3-Cl | H | 3,5-diF—Ph |
| 638 | 3-Cl | H | 2,4-diCl—Ph |
| 639 | 3-Cl | H | 2,5-diCl—Ph |
| 640 | 3-Cl | H | 2,6-diCl—Ph |
| 641 | 3-Cl | H | 3,4-diCl—Ph |
| 642 | 3-Cl | H | 3,5-diCl—Ph |
| 643 | 3-Cl | H | 3,4-diCF3—Ph |
| 644 | 3-Cl | H | 3,5-diCF3—Ph |
| 645 | 3-Cl | H | 5-Cl-2-MeO—Ph |
| 646 | 3-Cl | H | 5-Cl-2-Me—Ph |
| 647 | 3-Cl | H | 2-F-5-Me—Ph |
| 648 | 3-Cl | H | 3-F-5-morpholino-Ph |
| 649 | 3-Cl | H | 3,4-OCH2O—Ph |
| 650 | 3-Cl | H | 3,4-OCH2CH2O—Ph |
| 651 | 3-Cl | H | 2-MeO-5-CONH2—Ph |
| 652 | 3-Cl | H | 2-MeO-4-(1-Me-5-tetrazolyl)-Ph |
| 653 | 3-Cl | H | 2-MeO-5-(1-Me-5-tetrazolyl)-Ph |
| 654 | 3-Cl | H | 3-CONH2-5-(1-Me-5-tetrazolyl)-Ph |
| 655 | 3-Cl | H | 1-naphthyl |
| 656 | 3-Cl | H | 2-naphthyl |
| 657 | 3-Cl | H | 2-thienyl |
| 658 | 3-Cl | H | 3-thienyl |
| 659 | 3-Cl | H | 2-furanyl |
| 660 | 3-Cl | H | 3-furanyl |
| 661 | 3-Cl | H | 2-pyridyl |
| 662 | 3-Cl | H | 3-pyridyl |
| 663 | 3-Cl | H | 4-pyridyl |
| 664 | 3-Cl | H | 2-indolyl |
| 665 | 3-Cl | H | 3-indolyl |
| 666 | 3-Cl | H | 5-indolyl |
| 667 | 3-Cl | H | 6-indolyl |
| 668 | 3-Cl | H | 3-indazolyl |
| 669 | 3-Cl | H | 5-indazolyl |
| 670 | 3-Cl | H | 6-indazolyl |
| 671 | 3-Cl | H | 2-imidazolyl |
| 672 | 3-Cl | H | 3-isoxazoyl |
| 673 | 3-Cl | H | 3-pyrazolyl |
| 674 | 3-Cl | H | 2-thiadiazolyl |
| 675 | 3-Cl | H | 2-thiazolyl |
| 676 | 3-Cl | H | 5-Ac-4-Me-2-thiazolyl |
| 677 | 3-Cl | H | 5-tetrazolyl |
| 678 | 3-Cl | H | 2-benzimidazolyl |
| 679 | 3-Cl | H | 5-benzimidazolyl |
| 680 | 3-Cl | H | 2-benzothiazolyl |
| 681 | 3-Cl | H | 5-benzothiazolyl |
| 682 | 3-Cl | H | 2-benzoxazolyl |
| 683 | 3-Cl | H | 5-benzoxazolyl |
| 684 | 3-Cl | H | 1-adamantyl |
| 685 | 3-Cl | H | 2-adamantyl |
| 686 | 3-Cl | H | i-Pr |
| 687 | 3-Cl | H | t-Bu |
| 688 | 3-Cl | H | c-Hex |
| 689 | 3-Cl | H | CH2CH2OMe |
| 690 | 3-Cl | H | CH2CONH2 |
| 691 | 3-Cl | H | CH2CO2Me |
| 692 | 3-Cl | H | CH(CH2Ph)CO2Me |
| 693 | 3-Cl | H | CH2CH2NMe2 |
| 694 | 3-Cl | H | benzyl |
| 695 | 3-Cl | H | phenethyl |
| 696 | 3-Cl | H | 2-(morpholin-1-yl)-Et |
| 697 | 4-Cl | H | Ph |
| 698 | 4-Cl | H | 3-CN—Ph |
| 699 | 4-Cl | H | 3-COMe—Ph |
| 700 | 4-Cl | H | 3-CO2Me—Ph |
| 701 | 4-Cl | H | 3-CONH2—Ph |
| 702 | 4-Cl | H | 3-CONHMe—Ph |
| 703 | 4-Cl | H | 3-F—Ph |
| 704 | 4-Cl | H | 3-Cl—Ph |
| 705 | 4-Cl | H | 3-Br—Ph |
| 706 | 4-Cl | H | 3-SO2NH2—Ph |
| 707 | 4-Cl | H | 3-SO2NHMe—Ph |
| 708 | 4-Cl | H | 3-CF3—Ph |
| 709 | 4-Cl | H | 3-OMe—Ph |
| 710 | 4-Cl | H | 3-SMe—Ph |
| 711 | 4-Cl | H | 3-SOMe—Ph |
| 712 | 4-Cl | H | 3-SO2Me—Ph |
| 713 | 4-Cl | H | 3-OH—Ph |
| 714 | 4-Cl | H | 3-CH2OH—Ph |
| 715 | 4-Cl | H | 3-CHOHMe—Ph |
| 716 | 4-Cl | H | 3-COH(Me)2—Ph |
| 717 | 4-Cl | H | 3-Me—Ph |
| 718 | 4-Cl | H | 3-Et—Ph |
| 719 | 4-Cl | H | 3-iPr-Ph |
| 720 | 4-Cl | H | 3-tBu-Ph |
| 721 | 4-Cl | H | 3-CH2CO2Me—Ph |
| 722 | 4-Cl | H | 3-(1-piperidinyl)-Ph |
| 723 | 4-Cl | H | 3-(1-pyrrolidinyl)-Ph |
| 724 | 4-Cl | H | 3-(2-imidazolyl)-Ph |
| 725 | 4-Cl | H | 3-(1-imidazolyl)-Ph |
| 726 | 4-Cl | H | 3-(2-thiazolyl)-Ph |
| 727 | 4-Cl | H | 3-(3-pyrazolyl)-Ph |
| 728 | 4-Cl | H | 3-(1-pyrazolyl)-Ph |
| 729 | 4-Cl | H | 3-(5-Me-1-tetrazolyl)-Ph |
| 730 | 4-Cl | H | 3-(1-Me-5-tetrazolyl)-Ph |
| 731 | 4-Cl | H | 3-(2-pyridyl)-Ph |
| 732 | 4-Cl | H | 3-(2-thienyl)-Ph |
| 733 | 4-Cl | H | 3-(2-furanyl)-Ph |
| 734 | 4-Cl | H | 4-CN—Ph |
| 735 | 4-Cl | H | 4-COMe—Ph |
| 736 | 4-Cl | H | 4-CO2Me—Ph |
| 737 | 4-Cl | H | 4-CONH2—Ph |
| 738 | 4-Cl | H | 4-CONHMe—Ph |
| 739 | 4-Cl | H | 4-CONHPh—Ph |
| 740 | 4-Cl | H | 4-F—Ph |

TABLE 4-continued

| | | | |
|---|---|---|---|
| 741 | 4-Cl | H | 4-Cl—Ph |
| 742 | 4-Cl | H | 4-Br—Ph |
| 743 | 4-Cl | H | 4-SO2NH2—Ph |
| 744 | 4-Cl | H | 4-SO2NHMe—Ph |
| 745 | 4-Cl | H | 4-CF3—Ph |
| 746 | 4-Cl | H | 4-OMe—Ph |
| 747 | 4-Cl | H | 4-SMe—Ph |
| 748 | 4-Cl | H | 4-SOMe—Ph |
| 749 | 4-Cl | H | 4-SO2Me—Ph |
| 750 | 4-Cl | H | 4-OH—Ph |
| 751 | 4-Cl | H | 4-CH2OH—Ph |
| 752 | 4-Cl | H | 4-CHOHMe—Ph |
| 753 | 4-Cl | H | 4-COH(Me)2—Ph |
| 754 | 4-Cl | H | 4-Me—Ph |
| 755 | 4-Cl | H | 4-Et—Ph |
| 756 | 4-Cl | H | 4-iPr-Ph |
| 757 | 4-Cl | H | 4-tBu-Ph |
| 758 | 4-Cl | H | 4-CH2CO2Me—Ph |
| 759 | 4-Cl | H | 4-(1-piperidinyl)-Ph |
| 760 | 4-Cl | H | 4-(1-pyrrolidinyl)-Ph |
| 761 | 4-Cl | H | 4-(2-imidazolyl)-Ph |
| 762 | 4-Cl | H | 4-(1-imidazolyl)-Ph |
| 763 | 4-Cl | H | 4-(2-thiazolyl)-Ph |
| 764 | 4-Cl | H | 4-(3-pyrazolyl)-Ph |
| 765 | 4-Cl | H | 4-(1-pyrazolyl)-Ph |
| 766 | 4-Cl | H | 4-(5-Me-1-tetrazolyl)-Ph |
| 767 | 4-Cl | H | 4-(1-Me-5-tetrazolyl)-Ph |
| 768 | 4-Cl | H | 4-(2-pyridyl)-Ph |
| 769 | 4-Cl | H | 4-(2-thienyl)-Ph |
| 770 | 4-Cl | H | 4-(2-furanyl)-Ph |
| 771 | 4-Cl | H | 2-CN—Ph |
| 772 | 4-Cl | H | 2-COMe—Ph |
| 773 | 4-Cl | H | 2-CO2Me—Ph |
| 774 | 4-Cl | H | 2-CONH2—Ph |
| 775 | 4-Cl | H | 2-CONHMe—Ph |
| 776 | 4-Cl | H | 2-F—Ph |
| 777 | 4-Cl | H | 2-Cl—Ph |
| 778 | 4-Cl | H | 2-Br—Ph |
| 779 | 4-Cl | H | 2-SO2NH2—Ph |
| 780 | 4-Cl | H | 2-SO2NHMe—Ph |
| 781 | 4-Cl | H | 2-CF3—Ph |
| 782 | 4-Cl | H | 2-OMe—Ph |
| 783 | 4-Cl | H | 2-SMe—Ph |
| 784 | 4-Cl | H | 2-SOMe—Ph |
| 785 | 4-Cl | H | 2-SO2Me—Ph |
| 786 | 4-Cl | H | 2-OH—Ph |
| 787 | 4-Cl | H | 2-CH2OH—Ph |
| 788 | 4-Cl | H | 2-CHOHMe—Ph |
| 789 | 4-Cl | H | 2-COH(Me)2—Ph |
| 790 | 4-Cl | H | 2-Me—Ph |
| 791 | 4-Cl | H | 2-Et—Ph |
| 792 | 4-Cl | H | 2-iPr-Ph |
| 793 | 4-Cl | H | 2-tBu-Ph |
| 794 | 4-Cl | H | 2-CH2CO2Me—Ph |
| 795 | 4-Cl | H | 2-(1-piperidinyl)-Ph |
| 796 | 4-Cl | H | 2-(1-pyrrolidinyl)-Ph |
| 797 | 4-Cl | H | 2-(2-imidazolyl)-Ph |
| 798 | 4-Cl | H | 2-(1-imidazolyl)-Ph |
| 799 | 4-Cl | H | 2-(2-thiazolyl)-Ph |
| 800 | 4-Cl | H | 2-(3-pyrazolyl)-Ph |
| 801 | 4-Cl | H | 2-(1-pyrazolyl)-Ph |
| 802 | 4-Cl | H | 2-(5-Me-1-tetrazolyl)-Ph |
| 803 | 4-Cl | H | 2-(1-Me-5-tetrazolyl)-Ph |
| 804 | 4-Cl | H | 2-(2-pyridyl)-Ph |
| 805 | 4-Cl | H | 2-(2-thienyl)-Ph |
| 806 | 4-Cl | H | 2-(2-furanyl)-Ph |
| 807 | 4-Cl | H | 2,4-diF—Ph |
| 808 | 4-Cl | H | 2,5-diF—Ph |
| 809 | 4-Cl | H | 2,6-diF—Ph |
| 810 | 4-Cl | H | 3,4-diF—Ph |
| 811 | 4-Cl | H | 3,5-diF—Ph |
| 812 | 4-Cl | H | 2,4-diCl—Ph |
| 813 | 4-Cl | H | 2,5-diCl—Ph |
| 814 | 4-Cl | H | 2,6-diCl—Ph |
| 815 | 4-Cl | H | 3,4-diCl—Ph |
| 816 | 4-Cl | H | 3,5-diCl—Ph |
| 817 | 4-Cl | H | 3,4-diCF3—Ph |
| 818 | 4-Cl | H | 3,5-diCF3—Ph |
| 819 | 4-Cl | H | 5-Cl-2-MeO—Ph |
| 820 | 4-Cl | H | 5-Cl-2-Me—Ph |
| 821 | 4-Cl | H | 2-F-5-Me—Ph |
| 822 | 4-Cl | H | 3-F-5-morpholino-Ph |
| 823 | 4-Cl | H | 3,4-OCH2O—Ph |
| 824 | 4-Cl | H | 3,4-OCH2CH2O—Ph |
| 825 | 4-Cl | H | 2-MeO-5-CONH2—Ph |
| 826 | 4-Cl | H | 2-MeO-4-(1-Me-5-tetrazolyl)-Ph |
| 827 | 4-Cl | H | 2-MeO-5-(1-Me-5-tetrazolyl)-Ph |
| 828 | 4-Cl | H | 3-CONH2-5-(1-Me-5-tetrazolyl)-Ph |
| 829 | 4-Cl | H | 1-naphthyl |
| 830 | 4-Cl | H | 2-naphthyl |
| 831 | 4-Cl | H | 2-thienyl |
| 832 | 4-Cl | H | 3-thienyl |
| 833 | 4-Cl | H | 2-furanyl |
| 834 | 4-Cl | H | 3-furanyl |
| 835 | 4-Cl | H | 2-pyridyl |
| 836 | 4-Cl | H | 3-pyridyl |
| 837 | 4-Cl | H | 4-pyridyl |
| 838 | 4-Cl | H | 2-indolyl |
| 839 | 4-Cl | H | 3-indolyl |
| 840 | 4-Cl | H | 5-indolyl |
| 841 | 4-Cl | H | 6-indolyl |
| 842 | 4-Cl | H | 3-indazolyl |
| 843 | 4-Cl | H | 5-indazolyl |
| 844 | 4-Cl | H | 6-indazolyl |
| 845 | 4-Cl | H | 2-imidazolyl |
| 846 | 4-Cl | H | 3-isoxazoyl |
| 847 | 4-Cl | H | 3-pyrazolyl |
| 848 | 4-Cl | H | 2-thiadiazolyl |
| 849 | 4-Cl | H | 2-thiazolyl |
| 850 | 4-Cl | H | 5-Ac-4-Me-2-thiazolyl |
| 851 | 4-Cl | H | 5-tetrazolyl |
| 852 | 4-Cl | H | 2-benzimidazolyl |
| 853 | 4-Cl | H | 5-benzimidazolyl |
| 854 | 4-Cl | H | 2-benzothiazolyl |
| 855 | 4-Cl | H | 5-benzothiazolyl |
| 856 | 4-Cl | H | 2-benzoxazolyl |
| 857 | 4-Cl | H | 5-benzoxazolyl |
| 858 | 4-Cl | H | 1-adamantyl |
| 859 | 4-Cl | H | 2-adamantyl |
| 860 | 4-Cl | H | i-Pr |
| 861 | 4-Cl | H | t-Bu |
| 862 | 4-Cl | H | c-Hex |
| 863 | 4-Cl | H | CH2CH2OMe |
| 864 | 4-Cl | H | CH2CONH2 |
| 865 | 4-Cl | H | CH2CO2Me |
| 866 | 4-Cl | H | CH(CH2Ph)CO2Me |
| 867 | 4-Cl | H | CH2CH2NMe2 |
| 868 | 4-Cl | H | benzyl |
| 869 | 4-Cl | H | phenethyl |
| 870 | 4-Cl | H | 2-(morpholin-1-yl)-Et |
| 871 | 2-F | Me | Ph |
| 872 | 2-F | Me | 3-CN—Ph |
| 873 | 2-F | Me | 3-COMe—Ph |
| 874 | 2-F | Me | 3-CO2Me—Ph |
| 875 | 2-F | Me | 3-CONH2—Ph |
| 876 | 2-F | Me | 3-CONHMe—Ph |
| 877 | 2-F | Me | 3-F—Ph |
| 878 | 2-F | Me | 3-Cl—Ph |
| 879 | 2-F | Me | 3-Br—Ph |
| 880 | 2-F | Me | 3-SO2NH2—Ph |
| 881 | 2-F | Me | 3-SO2NHMe—Ph |
| 882 | 2-F | Me | 3-CF3—Ph |
| 883 | 2-F | Me | 3-OMe—Ph |
| 884 | 2-F | Me | 3-SMe—Ph |
| 885 | 2-F | Me | 3-SOMe—Ph |
| 886 | 2-F | Me | 3-SO2Me—Ph |
| 887 | 2-F | Me | 3-OH—Ph |
| 888 | 2-F | Me | 3-CH2OH—Ph |
| 889 | 2-F | Me | 3-CHOHMe—Ph |
| 890 | 2-F | Me | 3-COH(Me)2—Ph |
| 891 | 2-F | Me | 3-Me—Ph |
| 892 | 2-F | Me | 3-Et—Ph |
| 893 | 2-F | Me | 3-iPr-Ph |
| 894 | 2-F | Me | 3-tBu-Ph |
| 895 | 2-F | Me | 3-CH2CO2Me—Ph |
| 896 | 2-F | Me | 3-(1-piperidinyl)-Ph |
| 897 | 2-F | Me | 3-(1-pyrrolidinyl)-Ph |
| 898 | 2-F | Me | 3-(2-imidazolyl)-Ph |

TABLE 4-continued

| | | | |
|---|---|---|---|
| 899 | 2-F | Me | 3-(1-imidazolyl)-Ph |
| 900 | 2-F | Me | 3-(2-thiazolyl)-Ph |
| 901 | 2-F | Me | 3-(3-pyrazolyl)-Ph |
| 902 | 2-F | Me | 3-(1-pyrazolyl)-Ph |
| 903 | 2-F | Me | 3-(5-Me-1-tetrazolyl)-Ph |
| 904 | 2-F | Me | 3-(1-Me-5-tetrazolyl)-Ph |
| 905 | 2-F | Me | 3-(2-pyridyl)-Ph |
| 906 | 2-F | Me | 3-(2-thienyl)-Ph |
| 907 | 2-F | Me | 3-(2-furanyl)-Ph |
| 908 | 2-F | Me | 4-CN—Ph |
| 909 | 2-F | Me | 4-COMe—Ph |
| 910 | 2-F | Me | 4-CO2Me—Ph |
| 911 | 2-F | Me | 4-CONH2—Ph |
| 912 | 2-F | Me | 4-CONHMe—Ph |
| 913 | 2-F | Me | 4-CONHPh—Ph |
| 914 | 2-F | Me | 4-F—Ph |
| 915 | 2-F | Me | 4-Cl—Ph |
| 916 | 2-F | Me | 4-Br—Ph |
| 917 | 2-F | Me | 4-SO2NH2—Ph |
| 918 | 2-F | Me | 4-SO2NHMe—Ph |
| 919 | 2-F | Me | 4-CF3—Ph |
| 920 | 2-F | Me | 4-OMe—Ph |
| 921 | 2-F | Me | 4-SMe—Ph |
| 922 | 2-F | Me | 4-SOMe—Ph |
| 923 | 2-F | Me | 4-SO2Me—Ph |
| 924 | 2-F | Me | 4-OH—Ph |
| 925 | 2-F | Me | 4-CH2OH—Ph |
| 926 | 2-F | Me | 4-CHOHMe—Ph |
| 927 | 2-F | Me | 4-COH(Me)2—Ph |
| 928 | 2-F | Me | 4-Me—Ph |
| 929 | 2-F | Me | 4-Et—Ph |
| 930 | 2-F | Me | 4-iPr-Ph |
| 931 | 2-F | Me | 4-tBu-Ph |
| 932 | 2-F | Me | 4-CH2CO2Me—Ph |
| 933 | 2-F | Me | 4-(1-piperidinyl)-Ph |
| 934 | 2-F | Me | 4-(1-pyrrolidinyl)-Ph |
| 935 | 2-F | Me | 4-(2-imidazolyl)-Ph |
| 936 | 2-F | Me | 4-(1-imidazolyl)-Ph |
| 937 | 2-F | Me | 4-(2-thiazolyl)-Ph |
| 938 | 2-F | Me | 4-(3-pyrazolyl)-Ph |
| 939 | 2-F | Me | 4-(1-pyrazolyl)-Ph |
| 940 | 2-F | Me | 4-(5-Me-1-tetrazolyl)-Ph |
| 941 | 2-F | Me | 4-(1-Me-5-tetrazolyl)-Ph |
| 942 | 2-F | Me | 4-(2-pyridyl)-Ph |
| 943 | 2-F | Me | 4-(2-thienyl)-Ph |
| 944 | 2-F | Me | 4-(2-furanyl)-Ph |
| 945 | 2-F | Me | 2-CN—Ph |
| 946 | 2-F | Me | 2-COMe—Ph |
| 947 | 2-F | Me | 2-CO2Me—Ph |
| 948 | 2-F | Me | 2-CONH2—Ph |
| 949 | 2-F | Me | 2-CONHMe—Ph |
| 950 | 2-F | Me | 2-F—Ph |
| 951 | 2-F | Me | 2-Cl—Ph |
| 952 | 2-F | Me | 2-Br—Ph |
| 953 | 2-F | Me | 2-SO2NH—Ph |
| 954 | 2-F | Me | 2-SO2NHMe—Ph |
| 955 | 2-F | Me | 2-CF3—Ph |
| 956 | 2-F | Me | 2-OMe—Ph |
| 957 | 2-F | Me | 2-SMe—Ph |
| 958 | 2-F | Me | 2-SOMe—Ph |
| 959 | 2-F | Me | 2-SO2Me—Ph |
| 960 | 2-F | Me | 2-OH—Ph |
| 961 | 2-F | Me | 2-CH2OH—Ph |
| 962 | 2-F | Me | 2-CHOHMe—Ph |
| 963 | 2-F | Me | 2-COH(Me)2—Ph |
| 964 | 2-F | Me | 2-Me—Ph |
| 965 | 2-F | Me | 2-Et—Ph |
| 966 | 2-F | Me | 2-iPr-Ph |
| 967 | 2-F | Me | 2-tBu-Ph |
| 968 | 2-F | Me | 2-CH2CO2Me—Ph |
| 969 | 2-F | Me | 2-(1-piperidinyl)-Ph |
| 970 | 2-F | Me | 2-(1-pyrrolidinyl)-Ph |
| 971 | 2-F | Me | 2-(2-imidazolyl)-Ph |
| 972 | 2-F | Me | 2-(1-imidazolyl)-Ph |
| 973 | 2-F | Me | 2-(2-thiazolyl)-Ph |
| 974 | 2-F | Me | 2-(3-pyrazolyl)-Ph |
| 975 | 2-F | Me | 2-(1-pyrazolyl)-Ph |
| 976 | 2-F | Me | 2-(5-Me-1-tetrazolyl)-Ph |
| 977 | 2-F | Me | 2-(1-Me-5-tetrazolyl)-Ph |
| 978 | 2-F | Me | 2-(2-pyridyl)-Ph |
| 979 | 2-F | Me | 2-(2-thienyl)-Ph |
| 980 | 2-F | Me | 2-(2-furanyl)-Ph |
| 981 | 2-F | Me | 2,4-diF—Ph |
| 982 | 2-F | Me | 2,5-diF—Ph |
| 983 | 2-F | Me | 2,6-diF—Ph |
| 984 | 2-F | Me | 3,4-diF—Ph |
| 985 | 2-F | Me | 3,5-diF—Ph |
| 986 | 2-F | Me | 2,4-diCl—Ph |
| 987 | 2-F | Me | 2,5-diCl—Ph |
| 988 | 2-F | Me | 2,6-diCl—Ph |
| 989 | 2-F | Me | 3,4-diCl—Ph |
| 990 | 2-F | Me | 3,5-diCl—Ph |
| 991 | 2-F | Me | 3,4-diCF3—Ph |
| 992 | 2-F | Me | 3,5-diCF3—Ph |
| 993 | 2-F | Me | 5-Cl-2-MeO—Ph |
| 994 | 2-F | Me | 5-Cl-2-Me—Ph |
| 995 | 2-F | Me | 2-F-5-Me—Ph |
| 996 | 2-F | Me | 3-F-5-morpholino-Ph |
| 997 | 2-F | Me | 3,4-OCH2O—Ph |
| 998 | 2-F | Me | 3,4-OCH2CH2O—Ph |
| 999 | 2-F | Me | 2-MeO-5-CONH2—Ph |
| 1000 | 2-F | Me | 2-MeO-4-(1-Me-5-tetrazolyl)-Ph |
| 1001 | 2-F | Me | 2-MeO-5-(1-Me-5-tetrazolyl)-Ph |
| 1002 | 2-F | Me | 3-CONH2-5-(1-Me-5-tetrazolyl)-Ph |
| 1003 | 2-F | Me | 1-naphthyl |
| 1004 | 2-F | Me | 2-naphthyl |
| 1005 | 2-F | Me | 2-thienyl |
| 1006 | 2-F | Me | 3-thienyl |
| 1007 | 2-F | Me | 2-furanyl |
| 1008 | 2-F | Me | 3-furanyl |
| 1009 | 2-F | Me | 2-pyridyl |
| 1010 | 2-F | Me | 3-pyridyl |
| 1011 | 2-F | Me | 4-pyridyl |
| 1012 | 2-F | Me | 2-indolyl |
| 1013 | 2-F | Me | 3-indolyl |
| 1014 | 2-F | Me | 5-indolyl |
| 1015 | 2-F | Me | 6-indolyl |
| 1016 | 2-F | Me | 3-indazolyl |
| 1017 | 2-F | Me | 5-indazolyl |
| 1018 | 2-F | Me | 6-indazolyl |
| 1019 | 2-F | Me | 2-imidazolyl |
| 1020 | 2-F | Me | 3-isoxazoyl |
| 1021 | 2-F | Me | 3-pyrazolyl |
| 1022 | 2-F | Me | 2-thiadiazolyl |
| 1023 | 2-F | Me | 2-thiazolyl |
| 1024 | 2-F | Me | 5-Ac-4-Me-2-thiazolyl |
| 1025 | 2-F | Me | 5-tetrazolyl |
| 1026 | 2-F | Me | 2-benzimidazolyl |
| 1027 | 2-F | Me | 5-benzimidazolyl |
| 1028 | 2-F | Me | 2-benzothiazolyl |
| 1029 | 2-F | Me | 5-benzothiazolyl |
| 1030 | 2-F | Me | 2-benzoxazolyl |
| 1031 | 2-F | Me | 5-benzoxazolyl |
| 1032 | 2-F | Me | 1-adamantyl |
| 1033 | 2-F | Me | 2-adamantyl |
| 1034 | 2-F | Me | i-Pr |
| 1035 | 2-F | Me | t-Bu |
| 1036 | 2-F | Me | c-Hex |
| 1037 | 2-F | Me | CH2CH2OMe |
| 1038 | 2-F | Me | CH2CONH2 |
| 1039 | 2-F | Me | CH2CO2Me |
| 1040 | 2-F | Me | CH(CH2Ph)CO2Me |
| 1041 | 2-F | Me | CH2CH2NMe2 |
| 1042 | 2-F | Me | benzyl |
| 1043 | 2-F | Me | phenethyl |
| 1044 | 2-F | Me | 2-(morpholin-1-yl)-Et |
| 1045 | 3-F | Me | Ph |
| 1046 | 3-F | Me | 3-CN—Ph |
| 1047 | 3-F | Me | 3-COMe—Ph |
| 1048 | 3-F | Me | 3-CO2Me—Ph |
| 1049 | 3-F | Me | 3-CONH2—Ph |
| 1050 | 3-F | Me | 3-CONHMe—Ph |
| 1051 | 3-F | Me | 3-F—Ph |
| 1052 | 3-F | Me | 3-Cl—Ph |
| 1053 | 3-F | Me | 3-Br—Ph |
| 1054 | 3-F | Me | 3-SO2NH2—Ph |
| 1055 | 3-F | Me | 3-SO2NHMe—Ph |
| 1056 | 3-F | Me | 3-CF3—Ph |

TABLE 4-continued

| | | | |
|---|---|---|---|
| 1057 | 3-F | Me | 3-OMe—Ph |
| 1058 | 3-F | Me | 3-SMe—Ph |
| 1059 | 3-F | Me | 3-SOMe—Ph |
| 1060 | 3-F | Me | 3-SO2Me—Ph |
| 1061 | 3-F | Me | 3-OH—Ph |
| 1062 | 3-F | Me | 3-CH2OH—Ph |
| 1063 | 3-F | Me | 3-CHOHMe—Ph |
| 1064 | 3-F | Me | 3-COH(Me)2—Ph |
| 1065 | 3-F | Me | 3-Me—Ph |
| 1066 | 3-F | Me | 3-Et—Ph |
| 1067 | 3-F | Me | 3-iPr-Ph |
| 1068 | 3-F | Me | 3-tBu-Ph |
| 1069 | 3-F | Me | 3-CH2CO2Me—Ph |
| 1070 | 3-F | Me | 3-(1-piperidinyl)-Ph |
| 1071 | 3-F | Me | 3-(1-pyrrolidinyl)-Ph |
| 1072 | 3-F | Me | 3-(2-imidazolyl)-Ph |
| 1073 | 3-F | Me | 3-(1-imidazolyl)-Ph |
| 1074 | 3-F | Me | 3-(2-thiazolyl)-Ph |
| 1075 | 3-F | Me | 3-(3-pyrazolyl)-Ph |
| 1076 | 3-F | Me | 3-(1-pyrazolyl)-Ph |
| 1077 | 3-F | Me | 3-(5-Me-1-tetrazolyl)-Ph |
| 1078 | 3-F | Me | 3-(1-Me-5-tetrazolyl)-Ph |
| 1079 | 3-F | Me | 3-(2-pyridyl)-Ph |
| 1080 | 3-F | Me | 3-(2-thienyl)-Ph |
| 1081 | 3-F | Me | 3-(2-furanyl)-Ph |
| 1082 | 3-F | Me | 4-CN—Ph |
| 1083 | 3-F | Me | 4-COMe—Ph |
| 1084 | 3-F | Me | 4-CO2Me—Ph |
| 1085 | 3-F | Me | 4-CONH2—Ph |
| 1086 | 3-F | Me | 4-CONHMe—Ph |
| 1087 | 3-F | Me | 4-CONHPh—Ph |
| 1088 | 3-F | Me | 4-F—Ph |
| 1089 | 3-F | Me | 4-Cl—Ph |
| 1090 | 3-F | Me | 4-Br—Ph |
| 1091 | 3-F | Me | 4-SO2NH2—Ph |
| 1092 | 3-F | Me | 4-SO2NHMe—Ph |
| 1093 | 3-F | Me | 4-CF3—Ph |
| 1094 | 3-F | Me | 4-OMe—Ph |
| 1095 | 3-F | Me | 4-SMe—Ph |
| 1096 | 3-F | Me | 4-SOMe—Ph |
| 1097 | 3-F | Me | 4-SO2Me—Ph |
| 1098 | 3-F | Me | 4-OH—Ph |
| 1099 | 3-F | Me | 4-CH2OH—Ph |
| 1100 | 3-F | Me | 4-CHOHMe—Ph |
| 1101 | 3-F | Me | 4-COH(Me)2—Ph |
| 1102 | 3-F | Me | 4-Me—Ph |
| 1103 | 3-F | Me | 4-Et—Ph |
| 1104 | 3-F | Me | 4-iPr-Ph |
| 1105 | 3-F | Me | 4-tBu-Ph |
| 1106 | 3-F | Me | 4-CH2CO2Me—Ph |
| 1107 | 3-F | Me | 4-(1-piperidinyl)-Ph |
| 1108 | 3-F | Me | 4-(1-pyrrolidinyl)-Ph |
| 1109 | 3-F | Me | 4-(2-imidazolyl)-Ph |
| 1110 | 3-F | Me | 4-(1-imidazolyl)-Ph |
| 1111 | 3-F | Me | 4-(2-thiazolyl)-Ph |
| 1112 | 3-F | Me | 4-(3-pyrazolyl)-Ph |
| 1113 | 3-F | Me | 4-(1-pyrazolyl)-Ph |
| 1114 | 3-F | Me | 4-(5-Me-1-tetrazolyl)-Ph |
| 1115 | 3-F | Me | 4-(1-Me-5-tetrazolyl)-Ph |
| 1116 | 3-F | Me | 4-(2-pyridyl)-Ph |
| 1117 | 3-F | Me | 4-(2-thienyl)-Ph |
| 1118 | 3-F | Me | 4-(2-furanyl)-Ph |
| 1119 | 3-F | Me | 2-CN—Ph |
| 1120 | 3-F | Me | 2-COMe—Ph |
| 1121 | 3-F | Me | 2-CO2Me—Ph |
| 1122 | 3-F | Me | 2-CONH2—Ph |
| 1123 | 3-F | Me | 2-CONHMe—Ph |
| 1124 | 3-F | Me | 2-F—Ph |
| 1125 | 3-F | Me | 2-Cl—Ph |
| 1126 | 3-F | Me | 2-Br—Ph |
| 1127 | 3-F | Me | 2-SO2NH—Ph |
| 1128 | 3-F | Me | 2-SO2NHMe—Ph |
| 1129 | 3-F | Me | 2-CF3—Ph |
| 1130 | 3-F | Me | 2-OMe—Ph |
| 1131 | 3-F | Me | 2-SMe—Ph |
| 1132 | 3-F | Me | 2-SOMe—Ph |
| 1133 | 3-F | Me | 2-SO2Me—Ph |
| 1134 | 3-F | Me | 2-OH—Ph |
| 1135 | 3-F | Me | 2-CH2OH—Ph |
| 1136 | 3-F | Me | 2-CHOHMe—Ph |
| 1137 | 3-F | Me | 2-COH(Me)2—Ph |
| 1138 | 3-F | Me | 2-Me—Ph |
| 1139 | 3-F | Me | 2-Et—Ph |
| 1140 | 3-F | Me | 2-iPr-Ph |
| 1141 | 3-F | Me | 2-tBu-Ph |
| 1142 | 3-F | Me | 2-CH2CO2Me—Ph |
| 1143 | 3-F | Me | 2-(1-piperidinyl)-Ph |
| 1144 | 3-F | Me | 2-(1-pyrrolidinyl)-Ph |
| 1145 | 3-F | Me | 2-(2-imidazolyl)-Ph |
| 1146 | 3-F | Me | 2-(1-imidazolyl)-Ph |
| 1147 | 3-F | Me | 2-(2-thiazolyl)-Ph |
| 1148 | 3-F | Me | 2-(3-pyrazolyl)-Ph |
| 1149 | 3-F | Me | 2-(1-pyrazolyl)-Ph |
| 1140 | 3-F | Me | 2-(5-Me-1-tetrazolyl)-Ph |
| 1151 | 3-F | Me | 2-(1-Me-5-tetrazolyl)-Ph |
| 1152 | 3-F | Me | 2-(2-pyridyl)-Ph |
| 1153 | 3-F | Me | 2-(2-thienyl)-Ph |
| 1154 | 3-F | Me | 2-(2-furanyl)-Ph |
| 1155 | 3-F | Me | 2,4-diF—Ph |
| 1156 | 3-F | Me | 2,5-diF—Ph |
| 1157 | 3-F | Me | 2,6-diF—Ph |
| 1158 | 3-F | Me | 3,4-diF—Ph |
| 1159 | 3-F | Me | 3,5-diF—Ph |
| 1160 | 3-F | Me | 2,4-diCl—Ph |
| 1161 | 3-F | Me | 2,5-diCl—Ph |
| 1162 | 3-F | Me | 2,6-diCl—Ph |
| 1163 | 3-F | Me | 3,4-diCl—Ph |
| 1164 | 3-F | Me | 3,5-diCl—Ph |
| 1165 | 3-F | Me | 3,4-diCF3—Ph |
| 1166 | 3-F | Me | 3,5-diCF3—Ph |
| 1167 | 3-F | Me | 5-Cl-2-MeO—Ph |
| 1168 | 3-F | Me | 5-Cl-2-Me—Ph |
| 1169 | 3-F | Me | 2-F-5-Me—Ph |
| 1170 | 3-F | Me | 3-F-5-morpholino-Ph |
| 1171 | 3-F | Me | 3,4-OCH2O—Ph |
| 1172 | 3-F | Me | 3,4-OCH2CH2O—Ph |
| 1173 | 3-F | Me | 2-MeO-5-CONH2—Ph |
| 1174 | 3-F | Me | 2-MeO-4-(1-Me-5-tetrazolyl)-Ph |
| 1175 | 3-F | Me | 2-MeO-5-(1-Me-5-tetrazolyl)-Ph |
| 1176 | 3-F | Me | 3-CONH2-5-(1-Me-5-tetrazolyl)-Ph |
| 1177 | 3-F | Me | 1-naphthyl |
| 1178 | 3-F | Me | 2-naphthyl |
| 1179 | 3-F | Me | 2-thienyl |
| 1180 | 3-F | Me | 3-thienyl |
| 1181 | 3-F | Me | 2-furanyl |
| 1182 | 3-F | Me | 3-furanyl |
| 1183 | 3-F | Me | 2-pyridyl |
| 1184 | 3-F | Me | 3-pyridyl |
| 1185 | 3-F | Me | 4-pyridyl |
| 1186 | 3-F | Me | 2-indolyl |
| 1187 | 3-F | Me | 3-indolyl |
| 1188 | 3-F | Me | 5-indolyl |
| 1189 | 3-F | Me | 6-indolyl |
| 1190 | 3-F | Me | 3-indazolyl |
| 1191 | 3-F | Me | 5-indazolyl |
| 1192 | 3-F | Me | 6-indazolyl |
| 1193 | 3-F | Me | 2-imidazolyl |
| 1194 | 3-F | Me | 3-isoxazoyl |
| 1195 | 3-F | Me | 3-pyrazolyl |
| 1196 | 3-F | Me | 2-thiadiazolyl |
| 1197 | 3-F | Me | 2-thiazolyl |
| 1198 | 3-F | Me | 5-Ac-4-Me-2-thiazolyl |
| 1199 | 3-F | Me | 5-tetrazolyl |
| 1200 | 3-F | Me | 2-benzimidazolyl |
| 1201 | 3-F | Me | 5-benzimidazolyl |
| 1202 | 3-F | Me | 2-benzothiazolyl |
| 1203 | 3-F | Me | 5-benzothiazolyl |
| 1204 | 3-F | Me | 2-benzoxazolyl |
| 1205 | 3-F | Me | 5-benzoxazolyl |
| 1206 | 3-F | Me | 1-adamantyl |
| 1207 | 3-F | Me | 2-adamantyl |
| 1208 | 3-F | Me | i-Pr |
| 1209 | 3-F | Me | t-Bu |
| 1210 | 3-F | Me | c-Hex |
| 1211 | 3-F | Me | CH2CH2OMe |
| 1212 | 3-F | Me | CH2CONH2 |
| 1213 | 3-F | Me | CH2CO2Me |
| 1214 | 3-F | Me | CH(CH2Ph)CO2Me |

TABLE 4-continued

| | | | |
|---|---|---|---|
| 1215 | 3-F | Me | CH2CH2NMe2 |
| 1216 | 3-F | Me | benzyl |
| 1217 | 3-F | Me | phenethyl |
| 1218 | 3-F | Me | 2-(morpholin-1-yl)-Et |
| 1219 | 4-F | Me | Ph |
| 1220 | 4-F | Me | 3-CN—Ph |
| 1221 | 4-F | Me | 3-COMe—Ph |
| 1222 | 4-F | Me | 3-CO2Me—Ph |
| 1223 | 4-F | Me | 3-CONH2—Ph |
| 1224 | 4-F | Me | 3-CONHMe—Ph |
| 1225 | 4-F | Me | 3-F—Ph |
| 1226 | 4-F | Me | 3-Cl—Ph |
| 1227 | 4-F | Me | 3-Br—Ph |
| 1228 | 4-F | Me | 3-SO2NH2—Ph |
| 1229 | 4-F | Me | 3-SO2NHMe—Ph |
| 1230 | 4-F | Me | 3-CF3—Ph |
| 1231 | 4-F | Me | 3-OMe—Ph |
| 1232 | 4-F | Me | 3-SMe—Ph |
| 1233 | 4-F | Me | 3-SOMe—Ph |
| 1234 | 4-F | Me | 3-SO2Me—Ph |
| 1235 | 4-F | Me | 3-OH—Ph |
| 1236 | 4-F | Me | 3-CH2OH—Ph |
| 1237 | 4-F | Me | 3-CHOHMe—Ph |
| 1238 | 4-F | Me | 3-COH(Me)2—Ph |
| 1239 | 4-F | Me | 3-Me—Ph |
| 1240 | 4-F | Me | 3-Et—Ph |
| 1241 | 4-F | Me | 3-iPr—Ph |
| 1242 | 4-F | Me | 3-tBu-Ph |
| 1243 | 4-F | Me | 3-CH2CO2Me—Ph |
| 1244 | 4-F | Me | 3-(1-piperidinyl)-Ph |
| 1245 | 4-F | Me | 3-(1-pyrrolidinyl)-Ph |
| 1246 | 4-F | Me | 3-(2-imidazolyl)-Ph |
| 1247 | 4-F | Me | 3-(1-imidazolyl)-Ph |
| 1248 | 4-F | Me | 3-(2-thiazolyl)-Ph |
| 1249 | 4-F | Me | 3-(3-pyrazolyl)-Ph |
| 1250 | 4-F | Me | 3-(1-pyrazolyl)-Ph |
| 1251 | 4-F | Me | 3-(5-Me-1-tetrazolyl)-Ph |
| 1252 | 4-F | Me | 3-(1-Me-5-tetrazolyl)-Ph |
| 1253 | 4-F | Me | 3-(2-pyridyl)-Ph |
| 1254 | 4-F | Me | 3-(2-thienyl)-Ph |
| 1255 | 4-F | Me | 3-(2-furanyl)-Ph |
| 1256 | 4-F | Me | 4-CN—Ph |
| 1257 | 4-F | Me | 4-COMe—Ph |
| 1258 | 4-F | Me | 4-CO2Me—Ph |
| 1259 | 4-F | Me | 4-CONH2—Ph |
| 1260 | 4-F | Me | 4-CONHMe—Ph |
| 1261 | 4-F | Me | 4-CONHPh—Ph |
| 1262 | 4-F | Me | 4-F—Ph |
| 1263 | 4-F | Me | 4-Cl—Ph |
| 1264 | 4-F | Me | 4-Br—Ph |
| 1265 | 4-F | Me | 4-SO2NH2—Ph |
| 1266 | 4-F | Me | 4-SO2NHMe—Ph |
| 1267 | 4-F | Me | 4-CF3—Ph |
| 1268 | 4-F | Me | 4-OMe—Ph |
| 1269 | 4-F | Me | 4-SMe—Ph |
| 1270 | 4-F | Me | 4-SOMe—Ph |
| 1271 | 4-F | Me | 4-SO2Me—Ph |
| 1272 | 4-F | Me | 4-OH—Ph |
| 1273 | 4-F | Me | 4-CH2OH—Ph |
| 1274 | 4-F | Me | 4-CHOHMe—Ph |
| 1275 | 4-F | Me | 4-COH(Me)2—Ph |
| 1276 | 4-F | Me | 4-Me—Ph |
| 1277 | 4-F | Me | 4-Et—Ph |
| 1278 | 4-F | Me | 4-iPr-Ph |
| 1279 | 4-F | Me | 4-tBu-Ph |
| 1280 | 4-F | Me | 4-CH2CO2Me—Ph |
| 1281 | 4-F | Me | 4-(1-piperidinyl)-Ph |
| 1282 | 4-F | Me | 4-(1-pyrrolidinyl)-Ph |
| 1283 | 4-F | Me | 4-(2-imidazolyl)-Ph |
| 1284 | 4-F | Me | 4-(1-imidazolyl)-Ph |
| 1285 | 4-F | Me | 4-(2-thiazolyl)-Ph |
| 1286 | 4-F | Me | 4-(3-pyrazolyl)-Ph |
| 1287 | 4-F | Me | 4-(1-pyrazolyl)-Ph |
| 1288 | 4-F | Me | 4-(5-Me-1-tetrazolyl)-Ph |
| 1289 | 4-F | Me | 4-(1-Me-5-tetrazolyl)-Ph |
| 1290 | 4-F | Me | 4-(2-pyridyl)-Ph |
| 1291 | 4-F | Me | 4-(2-thienyl)-Ph |
| 1292 | 4-F | Me | 4-(2-furanyl)-Ph |
| 1293 | 4-F | Me | 2-CN—Ph |
| 1294 | 4-F | Me | 2-COMe—Ph |
| 1295 | 4-F | Me | 2-CO2Me—Ph |
| 1296 | 4-F | Me | 2-CONH2—Ph |
| 1297 | 4-F | Me | 2-CONHMe—Ph |
| 1298 | 4-F | Me | 2-F—Ph |
| 1299 | 4-F | Me | 2-Cl—Ph |
| 1300 | 4-F | Me | 2-Br—Ph |
| 1301 | 4-F | Me | 2-SO2NH2—Ph |
| 1302 | 4-F | Me | 2-SO2NHMe—Ph |
| 1303 | 4-F | Me | 2-CF3—Ph |
| 1304 | 4-F | Me | 2-OMe—Ph |
| 1305 | 4-F | Me | 2-SMe—Ph |
| 1306 | 4-F | Me | 2-SOMe—Ph |
| 1307 | 4-F | Me | 2-SO2Me—Ph |
| 1308 | 4-F | Me | 2-OH—Ph |
| 1309 | 4-F | Me | 2-CH2OH—Ph |
| 1310 | 4-F | Me | 2-CHOHMe—Ph |
| 1311 | 4-F | Me | 2-COH(Me)2—Ph |
| 1312 | 4-F | Me | 2-Me—Ph |
| 1313 | 4-F | Me | 2-Et—Ph |
| 1314 | 4-F | Me | 2-iPr-Ph |
| 1315 | 4-F | Me | 2-tBu-Ph |
| 1316 | 4-F | Me | 2-CH2CO2Me—Ph |
| 1317 | 4-F | Me | 2-(1-piperidinyl)-Ph |
| 1318 | 4-F | Me | 2-(1-pyrrolidinyl)-Ph |
| 1319 | 4-F | Me | 2-(2-imidazolyl)-Ph |
| 1320 | 4-F | Me | 2-(1-imidazolyl)-Ph |
| 1321 | 4-F | Me | 2-(2-thiazolyl)-Ph |
| 1322 | 4-F | Me | 2-(3-pyrazolyl)-Ph |
| 1323 | 4-F | Me | 2-(1-pyrazolyl)-Ph |
| 1324 | 4-F | Me | 2-(5-Me-1-tetrazolyl)-Ph |
| 1325 | 4-F | Me | 2-(1-Me-5-tetrazolyl)-Ph |
| 1326 | 4-F | Me | 2-(2-pyridyl)-Ph |
| 1327 | 4-F | Me | 2-(2-thienyl)-Ph |
| 1328 | 4-F | Me | 2-(2-furanyl)-Ph |
| 1329 | 4-F | Me | 2,4-diF—Ph |
| 1330 | 4-F | Me | 2,5-diF—Ph |
| 1331 | 4-F | Me | 2,6-diF—Ph |
| 1332 | 4-F | Me | 3,4-diF—Ph |
| 1333 | 4-F | Me | 3,5-diF—Ph |
| 1334 | 4-F | Me | 2,4-diCl—Ph |
| 1335 | 4-F | Me | 2,5-diCl—Ph |
| 1336 | 4-F | Me | 2,6-diCl—Ph |
| 1337 | 4-F | Me | 3,4-diCl—Ph |
| 1338 | 4-F | Me | 3,5-diCl—Ph |
| 1339 | 4-F | Me | 3,4-diCF3—Ph |
| 1340 | 4-F | Me | 3,5-diCF3—Ph |
| 1341 | 4-F | Me | 5-Cl-2-MeO—Ph |
| 1342 | 4-F | Me | 5-Cl-2-Me—Ph |
| 1343 | 4-F | Me | 2-F-5-Me—Ph |
| 1344 | 4-F | Me | 3-F-5-morpholino-Ph |
| 1345 | 4-F | Me | 3,4-OCH2O—Ph |
| 1346 | 4-F | Me | 3,4-OCH2CH2O—Ph |
| 1347 | 4-F | Me | 2-MeO-5-CONH2—Ph |
| 1348 | 4-F | Me | 2-MeO-4-(1-Me-5-tetrazolyl)-Ph |
| 1349 | 4-F | Me | 2-MeO-5-(1-Me-5-tetrazolyl)-Ph |
| 1350 | 4-F | Me | 3-CONH2-5-(1-Me-5-tetrazolyl)-Ph |
| 1351 | 4-F | Me | 1-naphthyl |
| 1352 | 4-F | Me | 2-naphthyl |
| 1353 | 4-F | Me | 2-thienyl |
| 1354 | 4-F | Me | 3-thienyl |
| 1355 | 4-F | Me | 2-furanyl |
| 1356 | 4-F | Me | 3-furanyl |
| 1357 | 4-F | Me | 2-pyridyl |
| 1358 | 4-F | Me | 3-pyridyl |
| 1359 | 4-F | Me | 4-pyridyl |
| 1360 | 4-F | Me | 2-indolyl |
| 1361 | 4-F | Me | 3-indolyl |
| 1362 | 4-F | Me | 5-indolyl |
| 1363 | 4-F | Me | 6-indolyl |
| 1364 | 4-F | Me | 3-indazolyl |
| 1365 | 4-F | Me | 5-indazolyl |
| 1366 | 4-F | Me | 6-indazolyl |
| 1367 | 4-F | Me | 2-imidazolyl |
| 1368 | 4-F | Me | 3-isoxazoyl |
| 1369 | 4-F | Me | 3-pyrazolyl |
| 1370 | 4-F | Me | 2-thiadiazolyl |
| 1371 | 4-F | Me | 2-thiazolyl |
| 1372 | 4-F | Me | 5-Ac-4-Me-2-thiazolyl |

TABLE 4-continued

| | | | |
|---|---|---|---|
| 1373 | 4-F | Me | 5-tetrazolyl |
| 1374 | 4-F | Me | 2-benzimidazolyl |
| 1375 | 4-F | Me | 5-benzimidazolyl |
| 1376 | 4-F | Me | 2-benzothiazolyl |
| 1377 | 4-F | Me | 5-benzothiazolyl |
| 1378 | 4-F | Me | 2-benzoxazolyl |
| 1379 | 4-F | Me | 5-benzoxazolyl |
| 1380 | 4-F | Me | 1-adamantyl |
| 1381 | 4-F | Me | 2-adamantyl |
| 1382 | 4-F | Me | i-Pr |
| 1383 | 4-F | Me | t-Bu |
| 1384 | 4-F | Me | c-Hex |
| 1385 | 4-F | Me | CH2CH2OMe |
| 1386 | 4-F | Me | CH2CONH2 |
| 1387 | 4-F | Me | CH2CO2Me |
| 1388 | 4-F | Me | CH(CH2Ph)CO2Me |
| 1389 | 4-F | Me | CH2CH2NMe2 |
| 1390 | 4-F | Me | benzyl |
| 1391 | 4-F | Me | phenethyl |
| 1392 | 4-F | Me | 2-(morpholin-1-yl)-Et |
| 1393 | 3-Cl | Me | Ph |
| 1394 | 3-Cl | Me | 3-CN—Ph |
| 1395 | 3-Cl | Me | 3-COMe—Ph |
| 1396 | 3-Cl | Me | 3-CO2Me—Ph |
| 1397 | 3-Cl | Me | 3-CONH2—Ph |
| 1398 | 3-Cl | Me | 3-CONHMe—Ph |
| 1399 | 3-Cl | Me | 3-F—Ph |
| 1400 | 3-Cl | Me | 3-Cl—Ph |
| 1401 | 3-Cl | Me | 3-Br—Ph |
| 1402 | 3-Cl | Me | 3-SO2NH2—Ph |
| 1403 | 3-Cl | Me | 3-SO2NHMe—Ph |
| 1404 | 3-Cl | Me | 3-CF3—Ph |
| 1405 | 3-Cl | Me | 3-OMe—Ph |
| 1406 | 3-Cl | Me | 3-SMe—Ph |
| 1407 | 3-Cl | Me | 3-SOMe—Ph |
| 1408 | 3-Cl | Me | 3-SO2Me—Ph |
| 1409 | 3-Cl | Me | 3-OH—Ph |
| 1410 | 3-Cl | Me | 3-CH2OH—Ph |
| 1411 | 3-Cl | Me | 3-CHOHMe—Ph |
| 1412 | 3-Cl | Me | 3-COH(Me)2—Ph |
| 1413 | 3-Cl | Me | 3-Me—Ph |
| 1414 | 3-Cl | Me | 3-Et—Ph |
| 1415 | 3-Cl | Me | 3-iPr-Ph |
| 1416 | 3-Cl | Me | 3-tBu-Ph |
| 1417 | 3-Cl | Me | 3-CH2CO2Me—Ph |
| 1418 | 3-Cl | Me | 3-(1-piperidinyl)-Ph |
| 1419 | 3-Cl | Me | 3-(1-pyrrolidinyl)-Ph |
| 1420 | 3-Cl | Me | 3-(2-imidazolyl)-Ph |
| 1421 | 3-Cl | Me | 3-(1-imidazolyl)-Ph |
| 1422 | 3-Cl | Me | 3-(2-thiazolyl)-Ph |
| 1423 | 3-Cl | Me | 3-(3-pyrazolyl)-Ph |
| 1424 | 3-Cl | Me | 3-(1-pyrazolyl)-Ph |
| 1425 | 3-Cl | Me | 3-(5-Me-1-tetrazolyl)-Ph |
| 1426 | 3-Cl | Me | 3-(1-Me-5-tetrazolyl)-Ph |
| 1427 | 3-Cl | Me | 3-(2-pyridyl)-Ph |
| 1428 | 3-Cl | Me | 3-(2-thienyl)-Ph |
| 1429 | 3-Cl | Me | 3-(2-furanyl)-Ph |
| 1430 | 3-Cl | Me | 4-CN—Ph |
| 1431 | 3-Cl | Me | 4-COMe—Ph |
| 1432 | 3-Cl | Me | 4-CO2Me—Ph |
| 1433 | 3-Cl | Me | 4-CONH2—Ph |
| 1434 | 3-Cl | Me | 4-CONHMe—Ph |
| 1435 | 3-Cl | Me | 4-CONHPh—Ph |
| 1436 | 3-Cl | Me | 4-F—Ph |
| 1437 | 3-Cl | Me | 4-Cl—Ph |
| 1438 | 3-Cl | Me | 4-Br—Ph |
| 1439 | 3-Cl | Me | 4-SO2NH—Ph |
| 1440 | 3-Cl | Me | 4-SO2NHMe—Ph |
| 1441 | 3-Cl | Me | 4-CF3—Ph |
| 1442 | 3-Cl | Me | 4-OMe—Ph |
| 1443 | 3-Cl | Me | 4-SMe—Ph |
| 1444 | 3-Cl | Me | 4-SOMe—Ph |
| 1445 | 3-Cl | Me | 4-SO2Me—Ph |
| 1446 | 3-Cl | Me | 4-OH—Ph |
| 1447 | 3-Cl | Me | 4-CH2OH—Ph |
| 1448 | 3-Cl | Me | 4-CHOHMe—Ph |
| 1449 | 3-Cl | Me | 4-COH(Me)2—Ph |
| 1450 | 3-Cl | Me | 4-Me—Ph |
| 1451 | 3-Cl | Me | 4-Et—Ph |
| 1452 | 3-Cl | Me | 4-iPr-Ph |
| 1453 | 3-Cl | Me | 4-tBu-Ph |
| 1454 | 3-Cl | Me | 4-CH2CO2Me—Ph |
| 1455 | 3-Cl | Me | 4-(1-piperidinyl)-Ph |
| 1456 | 3-Cl | Me | 4-(1-pyrrolidinyl)-Ph |
| 1457 | 3-Cl | Me | 4-(2-imidazolyl)-Ph |
| 1458 | 3-Cl | Me | 4-(1-imidazolyl)-Ph |
| 1459 | 3-Cl | Me | 4-(2-thiazolyl)-Ph |
| 1460 | 3-Cl | Me | 4-(3-pyrazolyl)-Ph |
| 1461 | 3-Cl | Me | 4-(1-pyrazolyl)-Ph |
| 1462 | 3-Cl | Me | 4-(5-Me-1-tetrazolyl)-Ph |
| 1463 | 3-Cl | Me | 4-(1-Me-5-tetrazolyl)-Ph |
| 1464 | 3-Cl | Me | 4-(2-pyridyl)-Ph |
| 1465 | 3-Cl | Me | 4-(2-thienyl)-Ph |
| 1466 | 3-Cl | Me | 4-(2-furanyl)-Ph |
| 1467 | 3-Cl | Me | 2-CN—Ph |
| 1468 | 3-Cl | Me | 2-COMe—Ph |
| 1469 | 3-Cl | Me | 2-CO2Me—Ph |
| 1470 | 3-Cl | Me | 2-CONH2—Ph |
| 1471 | 3-Cl | Me | 2-CONHMe—Ph |
| 1472 | 3-Cl | Me | 2-F—Ph |
| 1473 | 3-Cl | Me | 2-Cl—Ph |
| 1474 | 3-Cl | Me | 2-Br—Ph |
| 1475 | 3-Cl | Me | 2-SO2NH2—Ph |
| 1476 | 3-Cl | Me | 2-SO2NHMe—Ph |
| 1477 | 3-Cl | Me | 2-CF3—Ph |
| 1478 | 3-Cl | Me | 2-OMe—Ph |
| 1479 | 3-Cl | Me | 2-SMe—Ph |
| 1480 | 3-Cl | Me | 2-SOMe—Ph |
| 1481 | 3-Cl | Me | 2-SO2Me—Ph |
| 1482 | 3-Cl | Me | 2-OH—Ph |
| 1483 | 3-Cl | Me | 2-CH2OH—Ph |
| 1484 | 3-Cl | Me | 2-CHOHMe—Ph |
| 1485 | 3-Cl | Me | 2-COH(Me)2—Ph |
| 1486 | 3-Cl | Me | 2-Me—Ph |
| 1487 | 3-Cl | Me | 2-Et—Ph |
| 1488 | 3-Cl | Me | 2-iPr-Ph |
| 1489 | 3-Cl | Me | 2-tBu-Ph |
| 1490 | 3-Cl | Me | 2-CH2CO2Me—Ph |
| 1491 | 3-Cl | Me | 2-(1-piperidinyl)-Ph |
| 1492 | 3-Cl | Me | 2-(1-pyrrolidinyl)-Ph |
| 1493 | 3-Cl | Me | 2-(2-imidazolyl)-Ph |
| 1494 | 3-Cl | Me | 2-(1-imidazolyl)-Ph |
| 1495 | 3-Cl | Me | 2-(2-thiazolyl)-Ph |
| 1496 | 3-Cl | Me | 2-(3-pyrazolyl)-Ph |
| 1497 | 3-Cl | Me | 2-(1-pyrazolyl)-Ph |
| 1498 | 3-Cl | Me | 2-(5-Me-1-tetrazolyl)-Ph |
| 1499 | 3-Cl | Me | 2-(1-Me-5-tetrazolyl)-Ph |
| 1500 | 3-Cl | Me | 2-(2-pyridyl)-Ph |
| 1501 | 3-Cl | Me | 2-(2-thienyl)-Ph |
| 1502 | 3-Cl | Me | 2-(2-furanyl)-Ph |
| 1503 | 3-Cl | Me | 2,4-diF—Ph |
| 1504 | 3-Cl | Me | 2,5-diF—Ph |
| 1505 | 3-Cl | Me | 2,6-diF—Ph |
| 1506 | 3-Cl | Me | 3,4-diF—Ph |
| 1507 | 3-Cl | Me | 3,5-diF—Ph |
| 1508 | 3-Cl | Me | 2,4-diCl—Ph |
| 1509 | 3-Cl | Me | 2,5-diCl—Ph |
| 1510 | 3-Cl | Me | 2,6-diCl—Ph |
| 1511 | 3-Cl | Me | 3,4-diCl—Ph |
| 1512 | 3-Cl | Me | 3,5-diCl—Ph |
| 1513 | 3-Cl | Me | 3,4-diCF3—Ph |
| 1514 | 3-Cl | Me | 3,5-diCF3—Ph |
| 1515 | 3-Cl | Me | 5-Cl-2-MeO—Ph |
| 1516 | 3-Cl | Me | 5-Cl-2-Me—Ph |
| 1517 | 3-Cl | Me | 2-F-5-Me—Ph |
| 1518 | 3-Cl | Me | 3-F-5-morpholino-Ph |
| 1519 | 3-Cl | Me | 3,4-OCH2O—Ph |
| 1520 | 3-Cl | Me | 3,4-OCH2CH2O—Ph |
| 1521 | 3-Cl | Me | 2-MeO-5-CONH2—Ph |
| 1522 | 3-Cl | Me | 2-MeO-4-(1-Me-5-tetrazolyl)-Ph |
| 1523 | 3-Cl | Me | 2-MeO-5-(1-Me-5-tetrazolyl)-Ph |
| 1524 | 3-Cl | Me | 3-CONH2-5-(1-Me-5-tetrazolyl)-Ph |
| 1525 | 3-Cl | Me | 1-naphthyl |
| 1526 | 3-Cl | Me | 2-naphthyl |
| 1527 | 3-Cl | Me | 2-thienyl |
| 1528 | 3-Cl | Me | 3-thienyl |
| 1529 | 3-Cl | Me | 2-furanyl |
| 1530 | 3-Cl | Me | 3-furanyl |

TABLE 4-continued

| | | | |
|---|---|---|---|
| 1531 | 3-Cl | Me | 2-pyridyl |
| 1532 | 3-Cl | Me | 3-pyridyl |
| 1533 | 3-Cl | Me | 4-pyridyl |
| 1534 | 3-Cl | Me | 2-indolyl |
| 1535 | 3-Cl | Me | 3-indolyl |
| 1536 | 3-Cl | Me | 5-indolyl |
| 1537 | 3-Cl | Me | 6-indolyl |
| 1538 | 3-Cl | Me | 3-indazolyl |
| 1539 | 3-Cl | Me | 5-indazolyl |
| 1540 | 3-Cl | Me | 6-indazolyl |
| 1541 | 3-Cl | Me | 2-imidazolyl |
| 1542 | 3-Cl | Me | 3-isoxazoyl |
| 1543 | 3-Cl | Me | 3-pyrazolyl |
| 1544 | 3-Cl | Me | 2-thiadiazolyl |
| 1545 | 3-Cl | Me | 2-thiazolyl |
| 1546 | 3-Cl | Me | 5-Ac-4-Me-2-thiazolyl |
| 1547 | 3-Cl | Me | 5-tetrazolyl |
| 1548 | 3-Cl | Me | 2-benzimidazolyl |
| 1549 | 3-Cl | Me | 5-benzimidazolyl |
| 1550 | 3-Cl | Me | 2-benzothiazolyl |
| 1551 | 3-Cl | Me | 5-benzothiazolyl |
| 1552 | 3-Cl | Me | 2-benzoxazolyl |
| 1553 | 3-Cl | Me | 5-benzoxazolyl |
| 1554 | 3-Cl | Me | 1-adamantyl |
| 1555 | 3-Cl | Me | 2-adamantyl |
| 1556 | 3-Cl | Me | i-Pr |
| 1557 | 3-Cl | Me | t-Bu |
| 1558 | 3-Cl | Me | c-Hex |
| 1559 | 3-Cl | Me | CH2CH2OMe |
| 1560 | 3-Cl | Me | CH2CONH2 |
| 1561 | 3-Cl | Me | CH2CO2Me |
| 1562 | 3-Cl | Me | CH(CH2Ph)CO2Me |
| 1563 | 3-Cl | Me | CH2CH2NMe2 |
| 1564 | 3-Cl | Me | benzyl |
| 1565 | 3-Cl | Me | phenethyl |
| 1566 | 3-Cl | Me | 2-(morpholin-1-yl)-Et |
| 1567 | 4-Cl | Me | Ph |
| 1568 | 4-Cl | Me | 3-CN—Ph |
| 1569 | 4-Cl | Me | 3-COMe—Ph |
| 1570 | 4-Cl | Me | 3-CO2Me—Ph |
| 1571 | 4-Cl | Me | 3-CONH2—Ph |
| 1572 | 4-Cl | Me | 3-CONHMe—Ph |
| 1573 | 4-Cl | Me | 3-F—Ph |
| 1574 | 4-Cl | Me | 3-Cl—Ph |
| 1575 | 4-Cl | Me | 3-Br—Ph |
| 1576 | 4-Cl | Me | 3-SO2NH2—Ph |
| 1577 | 4-Cl | Me | 3-SO2NHMe—Ph |
| 1578 | 4-Cl | Me | 3-CF3—Ph |
| 1579 | 4-Cl | Me | 3-OMe—Ph |
| 1580 | 4-Cl | Me | 3-SMe—Ph |
| 1581 | 4-Cl | Me | 3-SOMe—Ph |
| 1582 | 4-Cl | Me | 3-SO2Me—Ph |
| 1583 | 4-Cl | Me | 3-OH—Ph |
| 1584 | 4-Cl | Me | 3-CH2OH—Ph |
| 1585 | 4-Cl | Me | 3-CHOHMe—Ph |
| 1586 | 4-Cl | Me | 3-COH(Me)2—Ph |
| 1587 | 4-Cl | Me | 3-Me—Ph |
| 1588 | 4-Cl | Me | 3-Et—Ph |
| 1589 | 4-Cl | Me | 3-iPr-Ph |
| 1590 | 4-Cl | Me | 3-tBu-Ph |
| 1591 | 4-Cl | Me | 3-CH2CO2Me—Ph |
| 1592 | 4-Cl | Me | 3-(1-piperidinyl)-Ph |
| 1593 | 4-Cl | Me | 3-(1-pyrrolidinyl)-Ph |
| 1594 | 4-Cl | Me | 3-(2-imidazolyl)-Ph |
| 1595 | 4-Cl | Me | 3-(1-imidazolyl)-Ph |
| 1596 | 4-Cl | Me | 3-(2-thiazolyl)-Ph |
| 1597 | 4-Cl | Me | 3-(3-pyrazolyl)-Ph |
| 1598 | 4-Cl | Me | 3-(1-pyrazolyl)-Ph |
| 1599 | 4-Cl | Me | 3-(5-Me-1-tetrazolyl)-Ph |
| 1600 | 4-Cl | Me | 3-(1-Me-5-tetrazolyl)-Ph |
| 1601 | 4-Cl | Me | 3-(2-pyridyl)-Ph |
| 1602 | 4-Cl | Me | 3-(2-thienyl)-Ph |
| 1603 | 4-Cl | Me | 3-(2-furanyl)-Ph |
| 1604 | 4-Cl | Me | 4-CN—Ph |
| 1605 | 4-Cl | Me | 4-COMe—Ph |
| 1606 | 4-Cl | Me | 4-CO2Me—Ph |
| 1607 | 4-Cl | Me | 4-CONH2—Ph |
| 1608 | 4-Cl | Me | 4-CONHMe—Ph |
| 1609 | 4-Cl | Me | 4-CONHPh—Ph |
| 1610 | 4-Cl | Me | 4-F—Ph |
| 1611 | 4-Cl | Me | 4-Cl—Ph |
| 1612 | 4-Cl | Me | 4-Br—Ph |
| 1613 | 4-Cl | Me | 4-SO2NH2—Ph |
| 1614 | 4-Cl | Me | 4-SO2NHMe—Ph |
| 1615 | 4-Cl | Me | 4-CF3—Ph |
| 1616 | 4-Cl | Me | 4-OMe—Ph |
| 1617 | 4-Cl | Me | 4-SMe—Ph |
| 1618 | 4-Cl | Me | 4-SOMe—Ph |
| 1619 | 4-Cl | Me | 4-SO2Me—Ph |
| 1620 | 4-Cl | Me | 4-OH—Ph |
| 1621 | 4-Cl | Me | 4-CH2OH—Ph |
| 1622 | 4-Cl | Me | 4-CHOHMe—Ph |
| 1623 | 4-Cl | Me | 4-COH(Me)2—Ph |
| 1624 | 4-Cl | Me | 4-Me—Ph |
| 1625 | 4-Cl | Me | 4-Et—Ph |
| 1626 | 4-Cl | Me | 4-iPr-Ph |
| 1627 | 4-Cl | Me | 4-tBu-Ph |
| 1628 | 4-Cl | Me | 4-CH2CO2Me—Ph |
| 1629 | 4-Cl | Me | 4-(1-piperidinyl)-Ph |
| 1630 | 4-Cl | Me | 4-(1-pyrrolidinyl)-Ph |
| 1631 | 4-Cl | Me | 4-(2-imidazolyl)-Ph |
| 1632 | 4-Cl | Me | 4-(1-imidazolyl)-Ph |
| 1633 | 4-Cl | Me | 4-(2-thiazolyl)-Ph |
| 1634 | 4-Cl | Me | 4-(3-pyrazolyl)-Ph |
| 1635 | 4-Cl | Me | 4-(1-pyrazolyl)-Ph |
| 1636 | 4-Cl | Me | 4-(5-Me-1-tetrazolyl)-Ph |
| 1637 | 4-Cl | Me | 4-(1-Me-5-tetrazolyl)-Ph |
| 1638 | 4-Cl | Me | 4-(2-pyridyl)-Ph |
| 1639 | 4-Cl | Me | 4-(2-thienyl)-Ph |
| 1640 | 4-Cl | Me | 4-(2-furanyl)-Ph |
| 1641 | 4-Cl | Me | 2-CN—Ph |
| 1642 | 4-Cl | Me | 2-COMe—Ph |
| 1643 | 4-Cl | Me | 2-CO2Me—Ph |
| 1644 | 4-Cl | Me | 2-CONH2—Ph |
| 1645 | 4-Cl | Me | 2-CONHMe—Ph |
| 1646 | 4-Cl | Me | 2-F—Ph |
| 1647 | 4-Cl | Me | 2-Cl—Ph |
| 1648 | 4-Cl | Me | 2-Br—Ph |
| 1649 | 4-Cl | Me | 2-SO2NH2—Ph |
| 1650 | 4-Cl | Me | 2-SO2NHMe—Ph |
| 1651 | 4-Cl | Me | 2-CF3—Ph |
| 1652 | 4-Cl | Me | 2-OMe—Ph |
| 1653 | 4-Cl | Me | 2-SMe—Ph |
| 1654 | 4-Cl | Me | 2-SOMe—Ph |
| 1655 | 4-Cl | Me | 2-SO2Me—Ph |
| 1656 | 4-Cl | Me | 2-OH—Ph |
| 1657 | 4-Cl | Me | 2-CH2OH—Ph |
| 1658 | 4-Cl | Me | 2-CHOHMe—Ph |
| 1659 | 4-Cl | Me | 2-COH(Me)2—Ph |
| 1660 | 4-Cl | Me | 2-Me—Ph |
| 1661 | 4-Cl | Me | 2-Et—Ph |
| 1662 | 4-Cl | Me | 2-iPr-Ph |
| 1663 | 4-Cl | Me | 2-tBu-Ph |
| 1664 | 4-Cl | Me | 2-CH2CO2Me—Ph |
| 1665 | 4-Cl | Me | 2-(1-piperidinyl)-Ph |
| 1666 | 4-Cl | Me | 2-(1-pyrrolidinyl)-Ph |
| 1667 | 4-Cl | Me | 2-(2-imidazolyl)-Ph |
| 1668 | 4-Cl | Me | 2-(1-imidazolyl)-Ph |
| 1669 | 4-Cl | Me | 2-(2-thiazolyl)-Ph |
| 1670 | 4-Cl | Me | 2-(3-pyrazolyl)-Ph |
| 1671 | 4-Cl | Me | 2-(1-pyrazolyl)-Ph |
| 1672 | 4-Cl | Me | 2-(5-Me-1-tetrazolyl)-Ph |
| 1673 | 4-Cl | Me | 2-(1-Me-5-tetrazolyl)-Ph |
| 1674 | 4-Cl | Me | 2-(2-pyridyl)-Ph |
| 1675 | 4-Cl | Me | 2-(2-thienyl)-Ph |
| 1676 | 4-Cl | Me | 2-(2-furanyl)-Ph |
| 1677 | 4-Cl | Me | 2,4-diF—Ph |
| 1678 | 4-Cl | Me | 2,5-diF—Ph |
| 1679 | 4-Cl | Me | 2,6-diF—Ph |
| 1680 | 4-Cl | Me | 3,4-diF—Ph |
| 1681 | 4-Cl | Me | 3,5-diF—Ph |
| 1682 | 4-Cl | Me | 2,4-diCl—Ph |
| 1683 | 4-Cl | Me | 2,5-diCl—Ph |
| 1684 | 4-Cl | Me | 2,6-diCl—Ph |
| 1685 | 4-Cl | Me | 3,4-diCl—Ph |
| 1686 | 4-Cl | Me | 3,5-diCl—Ph |
| 1687 | 4-Cl | Me | 3,4-diCF3—Ph |
| 1688 | 4-Cl | Me | 3,5-diCF3—Ph |

TABLE 4-continued

| | | | |
|---|---|---|---|
| 1689 | 4-Cl | Me | 5-Cl-2-MeO—Ph |
| 1690 | 4-Cl | Me | 5-Cl-2-Me—Ph |
| 1691 | 4-Cl | Me | 2-F-5-Me—Ph |
| 1692 | 4-Cl | Me | 3-F-5-morpholino-Ph |
| 1693 | 4-Cl | Me | 3,4-OCH2O—Ph |
| 1694 | 4-Cl | Me | 3,4-OCH2CH2O—Ph |
| 1695 | 4-Cl | Me | 2-MeO-5-CONH2—Ph |
| 1696 | 4-Cl | Me | 2-MeO-4-(1-Me-5-tetrazolyl)-Ph |
| 1697 | 4-Cl | Me | 2-MeO-5-(1-Me-5-tetrazolyl)-Ph |
| 1698 | 4-Cl | Me | 3-CONH2-5-(1-Me-5-tetrazolyl)-Ph |
| 1699 | 4-Cl | Me | 1-naphthyl |
| 1700 | 4-Cl | Me | 2-naphthyl |
| 1701 | 4-Cl | Me | 2-thienyl |
| 1702 | 4-Cl | Me | 3-thienyl |
| 1703 | 4-Cl | Me | 2-furanyl |
| 1704 | 4-Cl | Me | 3-furanyl |
| 1705 | 4-Cl | Me | 2-pyridyl |
| 1706 | 4-Cl | Me | 3-pyridyl |
| 1707 | 4-Cl | Me | 4-pyridyl |
| 1708 | 4-Cl | Me | 2-indolyl |
| 1709 | 4-Cl | Me | 3-indolyl |
| 1710 | 4-Cl | Me | 5-indolyl |
| 1711 | 4-Cl | Me | 6-indolyl |
| 1712 | 4-Cl | Me | 3-indazolyl |
| 1713 | 4-Cl | Me | 5-indazolyl |
| 1714 | 4-Cl | Me | 6-indazolyl |
| 1715 | 4-Cl | Me | 2-imidazolyl |
| 1716 | 4-Cl | Me | 3-isoxazoyl |
| 1717 | 4-Cl | Me | 3-pyrazolyl |
| 1718 | 4-Cl | Me | 2-thiadiazolyl |
| 1719 | 4-Cl | Me | 2-thiazolyl |
| 1720 | 4-Cl | Me | 5-Ac-4-Me-2-thiazolyl |
| 1721 | 4-Cl | Me | 5-tetrazolyl |
| 1722 | 4-Cl | Me | 2-benzimidazolyl |
| 1723 | 4-Cl | Me | 5-benzimidazolyl |
| 1724 | 4-Cl | Me | 2-benzothiazolyl |
| 1725 | 4-Cl | Me | 5-benzothiazolyl |
| 1726 | 4-Cl | Me | 2-benzoxazolyl |
| 1727 | 4-Cl | Me | 5-benzoxazolyl |
| 1728 | 4-Cl | Me | 1-adamantyl |
| 1729 | 4-Cl | Me | 2-adamantyl |
| 1730 | 4-Cl | Me | i-Pr |
| 1731 | 4-Cl | Me | t-Bu |
| 1732 | 4-Cl | Me | c-Hex |
| 1733 | 4-Cl | Me | CH2CH2OMe |
| 1734 | 4-Cl | Me | CH2CONH2 |
| 1735 | 4-Cl | Me | CH2CO2Me |
| 1736 | 4-Cl | Me | CH(CH2Ph)CO2Me |
| 1737 | 4-Cl | Me | CH2CH2NMe2 |
| 1738 | 4-Cl | Me | benzyl |
| 1739 | 4-Cl | Me | phenethyl |
| 1740 | 4-Cl | Me | 2-(morpholin-1-yl)-Et |

Utility

The utility of the compounds in accordance with the present invention as modulators of chemokine receptor activity may be demonstrated by methodology known in the art, such as the assays for CCR-2 and CCR-3 ligand binding, as disclosed by Ponath et al., J. Exp. Med., 183, 2437–2448 (1996) and Uguccioni et al., J. Clin. Invest., 100, 1137–1143 (1997). Cell lines for expressing the receptor of interest include those naturally expressing the chemokine receptor, such as EOL-3 or THP-1, those induced to express the chemokine receptor by the addition of chemical or protein agents, such as HL-60 or AML14.3D10 cells treated with, for example, butyric acid with interleukin-5 present, or a cell engineered to express a recombinant chemokine receptor, such as CHO or HEK-293. Finally, blood or tissue cells, for example human peripheral blood eosinophils, isolated using methods as described by Hansel et al., J. Immunol. Methods, 145, 105–110 (1991), can be utilized in such assays. In particular, the compound of the present invention have activity in binding to the CCR-3 receptor in the aforementioned assays. As used herein, "activity" is intended to mean a compound demonstrating an IC50 of 10 $\mu$M or lower in concentration when measured in the aforementioned assays. Such a result is indicative of the intrinsic activity of the compounds as modulators of chemokine receptor activity. A general binding protocol is described below.

CCR3-Receptor Binding Protocol

Millipore filter plates (#MABVN1250) are treated with 5 $\mu$g/ml protamine in phosphate buffered saline, pH 7.2, for ten minutes at room temperature. Plates are washed three times with phosphate buffered saline and incubated with phosphate buffered saline for thirty minutes at room temperature. For binding, 50 $\mu$l of binding buffer (0.5% bovine serum albumen, 20 mM HEPES buffer and 5 mM magnesium chloride in RPMI 1640 media) with or without a test concentration of a compound present at a known concentration is combined with 50 $\mu$l of 125-I labeled human eotaxin (to give a final concentration of 150 pM radioligand) and 50 $\mu$l of cell suspension in binding buffer containing $5\times10^5$ total cells. Cells used for such binding assays can include cell lines transfected with a gene expressing CCR$^3$ such as that described by Daugherty et al. (1996), isolated human eosinophils such as described by Hansel et al. (1991) or the AML14.3D10 cell line after differentiation with butyric acid as described by Tiffany et al. (1998). The mixture of compound, cells and radioligand are incubated at room temperature for thirty minutes. Plates are placed onto a vacuum manifold, vacuum applied, and plates washed three times with binding buffer with 0.5M NaCl added. The plastic skirt is removed from the plate, the plate allowed to air dry, the wells punch out and CPM counted. The percent inhibition of binding is calculated using the total count obtained in the absence of any competing compound or chemokine ligand and the background binding determined by addition of 100 nM eotaxin in place of the test compound.

The utility of the compounds in accordance with the present invention as inhibitors of the migration of eosinophils or cell lines expressing the chemokine receptors may be demonstrated by methodology known in the art, such as the chemotaxis assay disclosed by Bacon et al., Brit. J. Pharmacol., 95, 966–974 (1988). In particular, the compound of the present invention have activity in inhibition of the migration of eosinophils in the aforementioned assays. As used herein, "activity" is intended to mean a compound demonstrating an IC50 of 10 $\mu$M or lower in concentration when measured in the aforementioned assays. Such a result is indicative of the intrinsic activity of the compounds as modulators of chemokine receptor activity. A human eosinophil chemotaxis assay protocol is described below.

Human Eosinophil Chemotaxis Assay

Neuroprobe MBA96 96-well chemotaxis chambers with Neuroprobe polyvinylpyrrolidone-free polycarbonate PFD5 5-micron filters in place are warmed in a 37° C. incubator prior to assay. Freshly isolated human eosinophils, isolated according to a method such as that described by Hansel et al. (1991), are suspended in RPMI 1640 with 0.1% bovine serum albumin at $1\times10^6$ cells/ml and warmed in a 37° C. incubator prior to assay. A 20 nM solution of human eotaxin in RPMI 1640 with 0.1% bovine serum albumin is warmed in a 37° C. incubator prior to assay. The eosinophil suspension and the 20 nM eotaxin solution are each mixed 1:1 with prewarmed RPMI 1640 with 0.1% bovine serum albumin with or without a dilution of a test compound that is at two fold the desired final concentration. These mixtures are warmed in a 37° C. incubator prior to assay. The filter is separated from the prewarmed Neuroprobe chemotaxis chamber and the eotaxin/compound mixture is placed into a Polyfiltronics MPC 96 well plate that has been placed in the bottom part of the Neuro Probe chemotaxis chamber. The approximate volume is 370 microliters and there should be a positive meniscus after dispensing. The filter is replaced above the 96 well plate, the rubber gasket is attached to the bottom of the upper chamber, and the chamber assembled. A 200 µl volume of the cell suspension/compound mixture is added to the appropriate wells of the upper chamber. The upper chamber is covered with a plate sealer, and the assembled unit placed in a 37° C. incubator for 45 minutes. After incubation, the plate sealer is removed and all remaining cell suspension is aspirated off. The chamber is disassembled and, while holding the filter by the sides at a 90-degree angle, unmigrated cells are washed away using a gentle stream of phosphate buffered saline dispensed from a squirt bottle and then the filter wiped with a rubber tipped squeegee. The filter is allowed to completely dry and immersed completely in Wright Giemsa stain for 30–45 seconds. The filter is rinsed with distilled water for 7 minutes, rinsed once with water briefly, and allowed to dry. Migrated cells are enumerated by microscopy.

Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited. For example, eosinophilic infiltration to inflammatory sites (e.g., in asthma or allergic rhinitis) can be inhibited according to the present method. In particular, the compound of the following examples has activity in blocking the migration of cells expressing the CCR-3 receptor using the appropriate chemokines in the aforementioned assays. As used herein, "activity" is intended to mean a compound demonstrating an IC50 of 10 µM or lower in concentration when measured in the aforementioned assays. Such a result is also indicative of the intrinsic activity of the compounds as modulators of chemokine receptor activity.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, *Taeniasis saginata*, Cysticercosis); visceral worms, visceral larva migraines (e.g., Toxocara), eosinophilic gastroenteritis (e.g., Anisaki sp., Phocanema sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases. In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102,203), leukotriene biosynthesis inhibitors (zileuton, BAY-1005); (f) non-steroidal antiinflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (I) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone ad pioglitazone); (l) preparations of interferons (interferon alpha-2a, interferon-2B, interferon alpha-N3, interferon beta-1a, interferon beta-1b,interferon gamma-1b); (m) anti-viral compounds such as efavirenz, nevirapine, indinavir, ganciclovir, lamivudine, famciclovir, and zalcitabine; (o) other compound such as 5-aminosalicylic acid an prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective doses of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient,and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

As will be apparent to one skilled in the art, numerous modifications and variations of the present invention are possible in light of the above teachings. It is therefore to be understood that within the scope of the appended claims, the invention may be practiced otherwise than as specifically described herein.

What is claimed is:
1. A compound of formula (I):

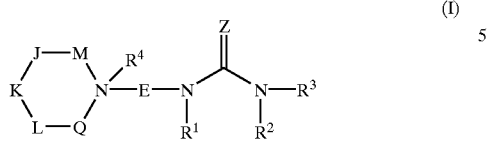

or a stereoisomer or a pharmaceutically acceptable salt thereof, wherein:

M is selected from $CH_2$, $CHR^5$, $CHR^{13}$, $CR^{13}R^{13}$, and $CR^5R^{13}$;

Q is selected from $CH_2$, $CHR^5$, $CHR^{13}$, $CR^{13}R^{13}$, and $CR^5R^{13}$;

J and K are independently selected from $CH_2$, $CHR^5$, $CHR^6$, $CR^6R^6$ and $CR^5R^6$;

L is selected from $CHR^5$ and $CR^5R^6$;

Z is selected from O, S, $NR^{1a}$, $C(CN)_2$, $CH(NO_2)$, and CHCN;

$R^{1a}$ is selected from H, $C_{1-6}$ alkyl, $C_{3-6}$ cycloalkyl, $CONR^{1b}R^{1b}$, $OR^{1b}$, CN, $NO_2$, and $(CH_2)_n$phenyl;

$R^{1b}$ is independently selected from H, $C_{1-3}$ alkyl, $C_{3-6}$ cycloalkyl, and phenyl;

E is

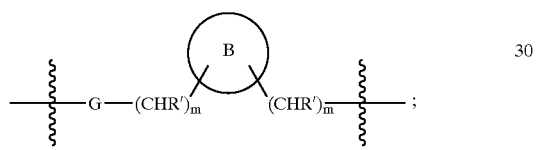

G is selected from a bond, C=O, and $SO_2$;

Ring B is a 5, 6, or 7 membered saturated heterocyclic ring wherein one of the heterocycle ring atoms is selected from $-NR^9-$, $-O-$, and $-S(O)_p-$, or two of the heterocycle ring atoms are selected from $-NR^{9d}C(O)-$, $-C(O)NR^{9d}-$, $-C(O)O-$, $-OC(O)-$, $-NR^{9d}S(O)_2-$, and $-S(O)_2NR^{9d}$, the heterocycle ring being selected from piperidine, tetrahydropyran, tetrahydrothiopyran, tetrahydrothiopyran 1,1-dioxide, tetrahydrothiopyran 1-monooxide, piperidin-2-one, tetrahydropyran-2-one, [1,2]thiazinane 1,1-dioxide, pyrrolidine, tetrahydrofuran, tetrahydrothiophene, pyrrolidin-2-one, dihydrofuran-2-one, and isothiazolidine 1,1-dioxide, and being optionally substituted by 0–2 $R^8$;

$R^1$ and $R^2$ are independently selected from H, $C_{1-8}$ alkyl, $C_{3-8}$ alkenyl, $C_{3-8}$ alkynyl, and $(CH_2)_rC_{3-6}$ cycloalkyl;

$R^3$ is selected from methyl substituted with 0–1 $R^{10}$, $C_{2-8}$ alkyl substituted with 0–3 $R^7$, $C_{3-8}$ alkenyl substituted with 0–3 $R^7$, $C_{3-8}$ alkynyl substituted with 0–3 $R^7$, $C_2$ fluoroalkyl, $C_{3-8}$ haloalkyl, a $(CR^{3'}R^{3''})_r$—$C_{3-10}$ carbocyclic residue substituted with 0–5 $R^{15}$ and a $(CR^{3'}R^{3''})_r$-5–19 membered heterocyclic system, wherein the heterocyclic system is selected from 1H-indazole, 2-pyrrolidonyl, 2H, 6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H, 6H-1,5,2-dithiazinyl, dihydrofuran-2-one, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolidine 1,1-dioxide, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidin-2-one, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, Pyridoimidazole, pyridothiazole, pyridinyl, pyridyl, pyrimidinyl, pyrrolidin-2-one, pyrrolidinyl, Pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydropyranyl (THP), tetrahydroquinolinyl, tetrahydropyran-2-one, tetrahydrothiophenyl, 1-oxo-hexahydro-1$\alpha^4$-thiopyranyl, 1,1-dioxo-hexahydro-1$\alpha^6$-thiopyranyl, tetrahydrothiopyranyl (THTP), 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,1-dioxo-1$\alpha^6$-[1,2]thiazinanyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl;

$R^{3'}$ and $R^{3''}$, at each occurrence, are selected from H, $C_{1-6}$ alkyl, $(CH_2)_rC_{3-6}$ cycloalkyl, and phenyl;

$R^4$ is absent, taken with the nitrogen to which it is attached to form an N-oxide, or selected from $C_{1-8}$ alkyl, $C_{3-8}$ alkenyl, $C_{3-8}$ alkynyl, $(CH_2)_rC_{3-6}$ cycloalkyl, $(CH_2)_qC(O)R^{4b}$, $(CH_2)_qC(O)NR^{4a}R^{4a'}$, $(CH_2)_qC(O)OR^{4b}$, and a $(CH_2)_r$—$C_{3-10}$ carbocyclic residue substituted with 0–3 $R^{4c}$;

$R^{4a}$ and $R^{4a'}$, at each occurrence, are selected from H, $C_{1-6}$ alkyl, $(CH_2)_rC_{3-6}$ cycloalkyl, and phenyl;

$R^{4b}$, at each occurrence, is selected from $C_{1-6}$ alkyl, $C_{3-8}$ alkenyl, $(CH_2)_rC_{3-6}$ cycloalkyl, $C_{3-8}$ alkynyl, and phenyl;

$R^{4c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_r$OH, $(CH_2)_rSC_{1-5}$ alkyl, $(CH_2)_rNR^{4a}R^{4a'}$, and $(CH_2)_r$phenyl;

$R^5$ is selected from a $(CR^{5'}R^{5''})_t$—$C_{3-10}$ carbocyclic residue substituted with 0–5 $R^{16}$ and a $(CR^{5'}R^{5''})_t$-5–10 membered heterocyclic system containing 1–4 heteroatoms selected from N, O, and S, substituted with 0–3 $R^{16}$;

$R^{5'}$ and $R^{5''}$, at each occurrence, are selected from H, $C_{1-6}$ alkyl, $(CH_2)_rC_{3-6}$ cycloalkyl and phenyl;

$R^6$, at each occurrence, is selected from $C_{1-6}$ alkyl, $C_{2-8}$ alkenyl, $C_{2-8}$ alkynyl, $(CH_2)_rC_{3-6}$ cycloalkyl, $(CF_2)_rCF_3$, CN, $(CH_2)_rNR^{6a}R^{6a'}$, $(CH_2)_r$OH, $(CH_2)_rOR^{6b}$, $(CH_2)_r$SH, $(CH_2)_rSR^{6b}$, $(CH_2)_rC(O)OH$, $(CH_2)_rC(O)R^{6b}$, $(CH_2)_rC(O)NR^{6a}R^{6a'}$, $(CH_2)_rNR^{6d}C(O)R^{6a}$, $(CH_2)_rC(O)OR^{6b}$, $(CH_2)_rOC(O)R^{6b}$, $(CH_2)_rS(O)_p R^{6b}$, $(CH_2)_rS(O)_2NR^{6a}R^{6a'}$, $(CH_2)_rNR^{6d}S(O)_2R^{6b}$, and $(CH_2)_r$phenyl substituted with 0–3 $R^{6c}$;

$R^{6a}$ and $R^{6a'}$, at each occurrence, are selected from H, $C_{1-6}$ alkyl, $C_{3-6}$ cycloalkyl, and phenyl substituted with 0–3 $R^{6c}$;

$R^{6b}$, at each occurrence, is selected f yam $C_{1-6}$ alkyl, $C_{3-6}$ cycloalkyl, and phenyl substituted with 0–3 $R^{6c}$;

$R^{6c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{6d}R^{6d}$;

$R^{6d}$, at each occurrence, is selected from H, $C_{1-6}$ alkyl, and $C_{3-6}$ cycloalkyl;

with the proviso that when any of J or is $CR^6R^6$ and $R^6$ is cyano, or bonded to the carbon to which it is attached through a heteroatom, the other $R^6$ is not cyano, or bonded to the carbon to which it is attached through a heteroatom;

$R^7$ is selected from $NO_2$, CN, $NR^{7a}R^{7a'}$, OH, $OR^{7d}$, C(O)H, C(O)OH, $C(O)R^{7b}$, $C(O)NR^{7a}R^{7a'}$, $NR^{7f}C(O)OR^{7d}$, $OC(O)NR^{7a}R^{7a'}$, $NR^{7f}C(O)R^{7b}$, $NR^{7f}C(O)NR^{7f}R^{7f}$, $C(O)OR^{7d}$, $OC(O)R^{7b}$, $C(=NR^{7f})NR^{7a}R^{7a'}$, $NHC(=NR^{7f})NR^{7f}R^{7f}$, $S(O)_pR^{7b}$, $S(O)_2^{7a}R^{7a'}$, $NR^{7f}S(O)_2NR^{7b}$, $C_{1-6}$ haloalkyl;

$R^{7a}$ and $R^{7a'}$, at each occurrence, are selected from H, $C_{1-6}$ alkyl, $C_{3-8}$ alkenyl, $C_{3-8}$ alkenyl, a $(CH_2)_r$—$C_{3-10}$ carbocyclic residue substituted with 0–5 $R^{7e}$, and a $(CH_2)_r$-5-10 membered heterocyclic system containing 1–4 heteroatoms selected from N, O, and S, substituted with 0–2 $R^{7e}$;

alternatively, $R^{7a}$ and $R^{7a'}$, along with the N to which they are attached, join to form a 5–6 membered heterocyclic system containing 1–2 heteroatoms selected from $NR^{7h}$, O, and S and optionally fused with a benzene ring or a 6-membered aromatic heterocycle;

$R^{7b}$, at each occurrence, is selected from H, $C_{1-6}$ alkyl, $C_{3-8}$ alkenyl, $C_{3-8}$ alkynyl, a $(CH_2)_r$—$C_{3-6}$ carbocyclic residue substituted with 0–3 $R^{7e}$, and $(CH_2)_r$-5-6 membered heterocyclic system containing 1–4 heteroatoms selected from N, O, and S, substituted with 0–2 $R^{7e}$;

$R^{7d}$, at each occurrence, is selected from $C_{3-8}$ alkenyl, $C_{3-8}$ alkynyl, methyl, $CF_3$, $C_{2-6}$ alkyl substituted with 0–3 $R^{7e}$, a $(CH_2)_r$—$C_{3-10}$ carbocyclic residue substituted with 0–3 $R^{7e}$, and a $(CH_2)_r$5-6 membered heterocyclic system containing 1–4 heteroatoms selected from N, O, and S, substituted with 0–3 $R^{7e}$;

$R^{7e}$, at each occurrence, is selected from $C_{1-6}$ alkyl, $C_{2-8}$ alkenyl, $C_{2-8}$ alkynyl, $(CH_2)_rC_{3-6}$ Cycloalkyl, $C(O)C_{1-6}$ alkyl, $C(O)OC_{1-6}$ alkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{7f}R^{7f}$, $(CH_2)_r$phenyl, and a heterocycle substituted with 0–1 $R^{7g}$, wherein the heterocycle is selected from imidazole, thiazole, oxazole, pyrazole, 1,2,4-triazole, 1,2,3-triazole, isoxazole, and tetrazole,;

$R^{7f}$, at each occurrence, is selected from H, $C_{1-6}$ alkyl, $C_{3-6}$ cycloalkyl, and phenyl;

$R^{7g}$ is selected from methyl, ethyl, acetyl, and $CF_3$;

$R^{7h}$ is selected from H, $C_{1-6}$ alkyl, $C_{3-6}$ cycloalkyl, $(CH_2)_r$phenyl, $C(O)R^{7f}$, $C(O)OR^{7i}$, and $SO_2R^{7i}$;

$R^{7i}$, at each occurrence, is selected from $C_{1-6}$ alkyl, $C_{3-6}$ cycloalkyl;

$R^8$ is selected from $C_{1-6}$ alkyl, $C_{2-8}$ alkenyl, $C_{2-8}$ alkynyl, $C_{1-6}$ haloalkyl, a $(CH_2)_r$—$C_{3-10}$ carbocyclic residue substituted with 0–3 $R^{8c}$, and a $(CH_2)_r$-5-10 membered heterocyclic system containing 1–4 heteroatoms selected from N, O, and S, substituted with 0–2 $R^{8c}$;

$R^{8a}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{8e}$, and a $(CH_2)_r$-5-10 membered heterocyclic system containing 1–4 heteroatoms selected from N, O, and S, substituted with 0–3 $R^{8e}$;

$R^{8b}$, at each occurrence, is selected from $C_{1-6}$ alkyl, $C_{3-8}$ alkenyl, $C_{3-8}$ alkynyl, a $(CH_2)_r$—$C_{3-6}$ carbocyclic residue substituted with 0–2 $R^{8e}$, and a $(CH_2)_r$-5-6 membered heterocyclic system containing 1–4 heteroatoms selected from N, O, and S, substituted with 0–3 $R^{8e}$;

$R^{8c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{8f}R^{8f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{8a}$, $(CH_2)_rC(O)NR^{8f}R^{8f}$, $(CH_2)_rNR^{8f}C(O)R^{8a}$, $(CH_2)_rC(O)OC_{1-4}$ alkyl, $(CH_2)_rOC(O)R^{8b}$, $(CH_2)_rS(O)_pR^{8b}$, $(CH_2)_rS(O)_2NR^{8f}R^{8f}$, $(CH_2)_rNR^{8f}S(O)_2R^{8b}$, and $(CH_2)_r$phenyl substituted with 0–3 $R^{8e}$;

$R^{8e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_r OH$, $(CH_2)_rSH$, $(CH_2)_rSC_{1-5}$ alkyl, $(CH_2)_rNR^{8f}R^{8f}$, and $(CH_2)_r$phenyl;

$R^{8f}$, at each occurrence, is selected from H, $C_{1-6}$ alkyl, and $C_{3-6}$ cycloalkyl;

$R^9$ is selected from H, $CH_3$, $C_{2-6}$ alkyl substituted with 0–3 $R^{9a}$, $C_{3-8}$ alkenyl, $C_{3-8}$ alkynyl, $C_{1-6}$ haloalkyl, $(CHR')_rC(O)C_{1-6}$ alkyl substituted with 0–3 $R^{9j}$, $(CHR')_rC(O)OC_{1-6}$ alkyl substituted with 0–3 $R^{9b}$, $(CHR')_rC(O)NR^{9d}R^{9d'}$, $(CHR')_rS(O)_2C_{1-6}$ alkyl, $S(O)_2C_{1-6}$ haloalkyl, $(CHR')_rS(O)_2NR^{9d}R^{9d}$, $R^{9'}$, $(CHR')_rC(O)R^{9'}$, $(CHR')_rC(O)NR^{9d}R^{9'}$, $(CHR')_rS(O)_2R^{9'}$, and $(CHR')_rS(O)_2NR^{9d}R^{9'}$;

$R^{9'}$, at each occurrence, is independently selected from $(CHR')_rC_{3-6}$ cycloalkyl substituted with 0–3 $R^{9e}$, $(CHR')_r$phenyl substituted with 0–3 $R^{9c}$, $(CHR')_r$-5–10 membered heterocyclic system containing 1–4 heteroatoms selected from N, O, and S, substituted with 0–3 $R^{9c}$, $R^{9a}$, at each occurrence, is selected from CN, $NO_2$, $OC_{1-5}$ alkyl, $CF_3$, OH, $OC_{1-5}$ alkyl, OC(O)$C_{1-5}$ alkyl, $SC_{1-5}$ alkyl, $S(O)_pC_{1-5}$ alkyl, and $NR^{9d}R^{9d'}$;

$R^{9b}$, at each occurrence, is selected from $C_{3-6}$ cycloalkyl, CN, $(CF_2)_rCF_3$, $(CH_2)_qOC_{1-5}$ alkyl, $(CH_2)_qOH$, $(CH_2)_qSC_{1-5}$ alkyl, $(CH_2)_rS(O)_pC_{1-5}$ alkyl, and $(CH_2)_qNR^{9d}R^{9d'}$;

$R^{9c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CHR')_rC(O)C_{1-5}$ alkyl, $(CHR')_rC(O)OC_{1-5}$ alkyl, $(CHR')_rC(O)NR^{9d}R^{9d'}$, $(CH_2)_rOH$, $(CH_2)_rSC_{1-5}$ alkyl, $(CH_2)_rS(O)_pC_{1-5}$ alkyl, and $(CH_2)_rNR^{9d}R^{9d'}$;

provided that if $R^{9c}$ is attached to a carbon attached to the nitrogen on Ring B, then $R^{9c}$ is selected from $(CH_2)_qOH$, $(CH_2)_qOC_{1-5}$ alkyl, $(CH_2)_qSC_{1-5}$ alkyl, $(CH_2)_qS(O)_pC_{1-5}$ alkyl, and $(CH_2)_qNR^{9d}R^{9d'}$;

$R^{9d}$ and $R^{9d'}$, at each occurrence, are independently selected from H, $C_{1-6}$ alkyl, $C_{3-6}$ cycloalkyl, and phenyl;

alternatively, $R^{9d}$ and $R^{9d'}$, along with the N to which they are attached, join to form a 5–6 membered heterocyclic system containing 1–2 heteroatoms selected from $NR^{9h}$, O, and S and optionally fused with a benzene ring or a 6-membered aromatic heterocycle;

$R^{9e}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CHR')_rC(O)OC_{1-5}$ alkyl, $(CHR')_rC(O)NR^{9d}R^{9d'}$, $(CH_2)_rOH$, $(CH_2)_rSC_{1-5}$ alkyl, $(CH_2)_rS(O)_pC_{1-5}$ alkyl, and $(CH_2)_rNR^{9d}R^{9d'}$, or alternatively, two $R^{9e}$ on the same carbon atom form =O;

$R^{9h}$ is selected from H, $C_{1-6}$ alkyl, $C_{3-6}$ cycloalkyl, $(CH_2)_r$phenyl, $C(O)R^{9f}$, $C(O)0R^{9i}$, and $SO_2R^{9i}$;

$R^{9i}$, at each occurrence, is selected from $C_{1-6}$ alkyl, $C_{3-6}$ cycloalkyl;

$R^{9j}$, at each occurrence, is selected from $C_{3-6}$ cycloalkyl, ON, $(CF_2)_rCF_3$, $(CH_2)_rOC_{1-5}$ alkyl, $(CH_2)_rOH$, $(CH_2)_rSC_{1-5}$ alkyl, $(CH_2)_rS(O)_pC_{1-5}$ alkyl, and $(CH_2)_rNR^{9d}R^{9d'}$;

$R^{10}$ is selected from $C(O)H$, $C(O)OH$, $C(O)R^{10b}$, $C(O)NR^{10a}R^{10a'}$, $C(O)OR^{10d}$, $C(=NR^{10f})NR^{10a}R^{10a'}$, $S(O)R^{10b}$, $S(O)_2R^{10b}$, $S(O)_2NR^{10a}R^{10a'}$;

$R^{10a}$ and $R^{10a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0–5 $R^{10e}$, and a $(CH_2)_r$-5–10 membered heterocyclic system containing 1–4 heteroatoms selected from N, O, and S, substituted with 0–2 $R^{10e}$;

alternatively, $R^{10a}$ and $R^{10a'}$, along with the N to which they are attached, join to form a 5–6 membered heterocyclic system containing 1–2 heteroatoms selected from $NR^{10h}$, O, and S and optionally fused with a benzene ring or a 6-membered aromatic heterocycle;

$R^{10b}$, at each occurrence, is selected from $C_{1-6}$ alkyl, $C_{3-8}$ alkenyl, $C_{3-8}$ alkynyl, a $(CH_2)_r$—$C_{3-6}$ carbocyclic residue substituted with 0–3 $R^{10e}$, and $(CH_2)_r$-5–6 membered heterocyclic system containing 1–4 heteroatoms selected from N, O, and S, substituted with 0–2 $R^{10e}$;

$R^{10d}$, at each occurrence, is selected from $C_{3-8}$ alkenyl, $C_{3-8}$ alkynyl, methyl, $CF_3$, $C_{2-6}$ alkyl substituted with 0–3 $R^{10e}$, a $(CH_2)_r$—$C_{3-10}$ carbocyclic residue substituted with 0–3 $R^{10e}$, and a $(CH_2)_r$5–6 membered heterocyclic system containing 1–4 heteroatoms selected from N, O, and S, substituted with 0–3 $R^{10e}$;

$R^{10e}$, at each occurrence, is selected from $C_{1-6}$ alkyl, $C_{2-8}$ alkenyl, $C_{2-8}$ alkynyl, $(CH_2)_rC_{3-6}$ cycloalkyl, $C(O)C_{1-6}$ alkyl, $C(O)OC_{1-6}$ alkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{10f}R^{10f}$, $(CH_2)_r$phenyl, and a heterocycle substituted with 0–1 $R^{10g}$, wherein the heterocycle is selected from imidazole, thiazole, oxazole, pyrazole, 1,2,4-triazole, 1,2,3-triazole, isoxazole, and tetrazole;

$R^{10f}$, at each occurrence, is selected from H, $C_{1-6}$ alkyl, $C_{3-6}$ cycloalkyl, and phenyl;

$R^{10g}$ is selected from methyl, ethyl, acetyl, and $CF_3$;

$R^{10h}$ is selected from H, $C_{1-6}$ alkyl, $C_{3-6}$ cycloalkyl, $(CH_2)_r$phenyl, $C(O)R^{10f}$, $C(O)OR^{10i}$ and $SO_2R^{10i}$;

$R^{10i}$, at each occurrence, is selected from $C_{1-6}$ alkyl, $C_{3-6}$ cycloalkyl;

$R^{13}$, at each occurrence, is selected from $C_{1-6}$ alkyl, $C_{2-8}$ alkenyl, $C_{2-8}$ alkynyl, $C_{3-6}$ cycloalkyl, $(CF_2)_wCF_3$, $(CH_2)_qNR^{13a}R^{13a'}$, $(CH_2)_qOH$, $(CH_2)_qOR^{13b}$, $(CH_2)_qSH$, $(CH_2)_qSR^{13b}$, $(CH_2)_wC(O)OH$, $(CH_2)_wC(O)R^{13b}$, $(CH_2)_wC(O)NR^{13a}R^{13a'}$, $(CH_2)_qNR^{13d}C(O)R^{13a}$, $(CH_2)_wC(O)OR^{13b}$, $(CH_2)_qOC(O)R^{13b}$, $(CH_2)_wS(O)_pR^{13b}$, $(CH_2)_wS(O)_2NR^{13a}R^{13a'}$, $(CH_2)_qNR^{13d}S(O)_2R^{13b}$, and $(CH_2)_w$-phenyl substituted with 0–3 $R^{13c}$;

$R^{13a}$ and $R^{13a'}$, at each occurrence, are selected from H, $C_{1-6}$ alkyl, $C_{3-6}$ cycloalkyl, and phenyl substituted with 0–3 $R^{13c}$;

$R^{13b}$, at each occurrence, is selected from $C_{1-6}$ alkyl, $C_{3-6}$ cycloalkyl, and phenyl substituted with 0–3 $R^{13c}$;

$R^{13c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{13d}R^{13d}$;

$R^{13d}$, at each occurrence, is selected from H, $C_{1-6}$ alkyl, and $C_{3-6}$ cycloalkyl;

$R^{15}$, at each occurrence, is selected from =O $C_{1-8}$ alkyl, $(CH_2)_rC_{3-6}$ cycloalkyl, Cl, Br, I, F, $NO_2$, CN, $(CHR')_rNR^{15a}R^{15a'}$, $(CHR')_rOH$, $(CHR')_rO(CHR')_rR^{15d}$, $(CHR')_rSH$, $(CHR')_rC(O)H$, $(CHR')_rC(O)OH$, $(CHR')_rC(O)(CHR')_rR^{15b}$, $(CHR')_rC(O)NR^{15a}R^{15a'}$, $(CHR')_rNR^{15f}C(O)O(CHR')_rR^{15d}$, $(CHR')_rOC(O)NR^{15a}R^{15a'}$, $(CHR')_rNR^{15f}C(O)(CHR')_rR^{15b}$, $(CHR')_rNR^{15f}C(O)NR^{15f}R^{15f}$, $(CHR')_rC(O)0(CHR')_rR^{15d}$, $(CHR')_rOC(O)(CHR')_rR^{15b}$, $(CHR')_rC(=NR^{15f})NR^{15a}R^{15a'}$, $(CHR')_r$ $NHC(=NR^{15f})NR^{15f}R^{15f}$, $(CHR')_rS(O)_p$ $(CHR')_rR^{15b}$, $(CHR')_rS(p)_2NR^{15a}R^{15a'}$, $(CHR')_rNR^{15f}S(O)_2(CHR')_rR^{15b}$, $C_{1-6}$ haloalkyl, $C_{2-8}$ alkenyl substituted with 0–3 R', $C_{2-8}$ alkynyl substituted with 0–3 R', $(CHR')_r$phenyl substituted with 0–3 $R^{15e}$, and a $(CH_2)_r$-5–10 membered heterocyclic system containing 1–4 heteroatoms selected from N, O, and S, substituted with 0–2 $R^{15e}$;

R', at each occurrence, is independently selected from H, $C_{1-6}$ alkyl, $C_{3-8}$ alkenyl, $C_{3-8}$ alkynyl, $(CH_2)_rC_{3-6}$ cycloalkyl, and $(CH_2)_r$phenyl substituted with $R^{15e}$;

$R^{15a}$ and $R^{15a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0–5 $R^{15e}$, and a $(CH_2)_r$-5–10 membered heterocyclic system containing 1–4 heteroatoms selected from N, O, and S, substituted with 0–2 $R^{15e}$;

alternatively, $R^{15a}$ and $R^{15a'}$, along with the N to which they are attached, join to form a 5–6 membered heterocyclic system containing 1–2 heteroatoms selected from $NR^{15h}$, O, and S and optionally fused with a benzene ring or a 6-membered aromatic heterocycle;

$R^{15b}$, at each occurrence, is selected from $C_{1-6}$ alkyl, $C_{3-8}$ alkenyl, $C_{3-8}$ alkynyl, a $(CH_2)_r$—$C_{3-6}$ carbocyclic residue substituted with 0–3 $R^{15e}$, and $(CH_2)_r$-5–6 membered heterocyclic system containing 1–4 heteroatoms selected from N, O, and S, substituted with 0–2 $R^{15e}$;

$R^{15d}$, at each occurrence, is selected from $C_{3-8}$ alkenyl, $C_{3-8}$ alkynyl, methyl, $CF_3$, $C_{2-6}$ alkyl substituted with 0–3 $R^{15e}$, a $(CH_2)_r$—$C_{3-10}$ carbocyclic residue substituted with 0–3 $R^{15e}$, and a $(CH_2)_r$5–6 membered heterocyclic system containing 1–4 heteroatoms selected from N, O, and S, substituted with 0–3 $R^{15e}$;

$R^{15e}$, at each occurrence, is selected from $C_{1-6}$ alkyl, $C_{2-8}$ alkenyl, $C_{2-8}$ alkynyl, $(CH_2)_rC_{3-6}$ cycloalkyl, $C(O)C_{1-6}$ alkyl, $C(O)OC_{1-6}$ alkyl, Cl, F, Br, I, CN, $NO_2$, $(CF_2)_rCF_3$, $(CH_2)_rOC_{1-5}$ alkyl OH, SH, $(CH_2)_rSC_{1-5}$ alkyl, $(CH_2)_rNR^{15f}R^{15f}$, $(CH_2)_r$phenyl, and a heterocycle substituted with 0–1 $R^{15g}$, wherein the heterocycle is selected from imidazole, thiazole, oxazole, pyrazole, 1,2,4-triazole, 1,2,3-triazole, isoxazole, and tetrazole;

$R^{15f}$, at each occurrence, is selected from H, $C_{1-6}$ alkyl, $C_{3-6}$ cycloalkyl, and phenyl;

$R^{15g}$ is selected from methyl, ethyl, acetyl, and $CF_3$;

$R^{15h}$ is selected from H, $C_{1-6}$ alkyl, $C_{3-6}$ cycloalkyl, $(CH_2)_r$phenyl, $C(O)R^{15f}$, $C(O)OR^{15i}$ and $SO_2R^{15i}$;

$R^{15i}$, at each occurrence, is selected from $C_{1-6}$ alkyl, $C_{3-6}$ cycloalkyl;

$R^{16}$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{16a}R^{16a'}$, $(CHR')_r$ OH, $(CHR')_rO(CHR')_rR^{16d}$, $(CHR')_rSH$, $(CHR')_rC(O)H$, $(CHR')_rC(O)OH$, $(CHR')_rC(O)$ $(CHR')_rR^{16b}$, $(CHR')_rC(O)NR^{16a}R^{16a'}$, $(CHR')_rNR^{16f}C(O)$ $(CHR')_rR^{16b}$, $(CHR')_rC(O)O(CHR')_rR^{16d}$, $(CHR')_r OC(O)$ $(CHR')_rR^{16b}$, $(CHR')_rC(=NR^{16f})$ $NR^{16a}R^{16a'}$, $(CHR')_rNHC=(NR^{16f})NR^{16f}R^{16f}$, $(CHR')_rS(O)_p(CHR')_rR^{16b}$, $(CHR')_rS(O)_2 NR^{16a}R^{16a'}$, $(CHR')_rNR^{16f}S(O)_2(CHR')_rR^{16b}$, $C_{1-6}$ haloalkyl, $C_{2-8}$ alkenyl substituted with 0–3 R', $C_{2-8}$ alkynyl substituted with 0–3 R', and $(CHR')_r$phenyl substituted with 0–3 $R^{16e}$;

$R^{16a}$ and $R^{16a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0–5 $R^{16e}$, and a $(CH_2)_r$-5–10 membered heterocyclic system containing 1–4 heteroatoms selected from N, O, and S, substituted with 0–2 $R^{16e}$;

alternatively, $R^{16a}$ and $R^{16a'}$, along with the N to which they are attached, join to arm a 5–6 membered heterocyclic system containing 1–2 heteroatoms selected from $NR^{16h}$, O, and S and optionally fused with a benzene ring or a 6-membered aromatic heterocycle;

$R^{16b}$, at each occurrence, is selected from $C_{1-6}$ alkyl, $C_{3-8}$ alkenyl, $C_{3-8}$ alkynyl, a $(CH_2)_rC_{3-6}$ carbocyclic residue substituted with 0–3 $R^{16e}$, and a $(CH_2)_r$-5–6 membered heterocyclic system containing 1–4 heteroatoms selected from N, O, and S, substituted with 0–2 $R^{16e}$;

$R^{16d}$, at each occurrence, is selected from $C_{3-8}$ alkenyl, $C_{3-8}$ alkynyl, $C_{1-6}$ alkyl substituted with 0–3 $R^{16e}$, a $(CH_2)_r$—$C_{3-10}$ carbocyclic residue substituted with 0–3 $R^{16e}$, and a $(CH_2)_r$-5–6 membered heterocyclic system containing 1–4 heteroatoms selected from N, O, and S, substituted with 0–3 $R^{16e}$;

$R^{16e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{16f}R^{16f}$, and $(CH_2)_r$phenyl;

$R^{16f}$, at each occurrence, is selected from H, $c_{1-5}$ alkyl, and $C_{3-6}$ cycloalkyl, and phenyl;

$R^{16h}$ is selected from H, $C_{1-6}$ alkyl, $C_{3-6}$ cycloalkyl, $(CH_2)_r$phenyl, $C(O)R^{16f}$, $C(O)OR^{16i}$, and $SO_2R^{16i}$;

$R^{16i}$, at each occurrence, is selected from $C_{1-6}$ alkyl, $C_{3-6}$ cycloalkyl;

m, at each occurrence, is independently selected from 0, 1, and 2;

t, at each occurrence, is independently selected from 1 and 2;

w, at each occurrence, is independently selected from 0 and 1;

r, at each occurrence, is independently selected from 0, 1, 2, 3, 4, and 5;

q, at each occurrence, is independently selected from 1, 2, 3, 4, and 5; and p, at each occurrence, is independently selected from 0, 1, and 2.

2. The compound of claim 1, wherein:

$R^4$ is absent, taken with the nitrogen to which it is attached to form an N-oxide, or selected from $C_{1-8}$ alkyl, $(CH_2)_r C_{3-6}$ cycloalkyl, and $(CH_2)_r$-phenyl substituted with 0–3 $R^{4c}$;

$R^{4c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, $(CH_2)_rNR^{4a}R^{4a'}$, and $(CH_2)_r$phenyl;

$R^1$ and $R^2$ are independently selected from H and $C_{1-4}$ alkyl;

$R^6$, at each occurrence, is selected from $C_{1-4}$ alkyl, $C_{2-8}$ alkenyl, $C_{2-8}$ alkynyl, $(CH_2)_rC_{3-6}$ cycloalkyl, $(CF_2)_r CF_3$, CN, $(CH_2)_rOH$, $(CH_2)_rOR^{6b}$, $(CH_2)_rC(O)R^{6b}$, $(CH_2)_rC(O)NR^{6a}R^{6a'}$, $(CH_2)_rNR^{6d}C(O)R^{6a}$, and $(CH_2)_r$phenyl substituted with 0–3 $R^{6c}$;

$R^{6a}$ and $R^{6a'}$, at each occurrence, are selected from H, $C_{1-6}$ alkyl, $C_{3-6}$ cycloalkyl, and phenyl substituted with 0–3 $R^{6c}$;

$R^{6b}$, at each occurrence, is selected from $C_{1-6}$ alkyl, $C_{3-6}$ cycloalkyl, and phenyl substituted with 0–3 $R^{6c}$;

$R^{6c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_r OC_{1-5}$ alkyl, $(CH_2)_rOH$, $(CH_2)_rSC_{1-5}$ alkyl, and $(CH_2)_r NR^{6d}R^{6d}$;

$R^{6d}$, at each occurrence, is selected from H, $C_{1-6}$ alkyl, and $C_{3-6}$ cycloalkyl;

$R^{13}$, at each occurrence, is selected from $C_{1-4}$ alkyl, $C_{3-6}$ cycloalkyl, $(CH_2)NR^{13a}R^{13a'}$, $(CH_2)OH$, $(CH_2)OR^{13b}$, $(CH_2)_wC(O)R^{13b}$, $(CH_2)_wC(O)NR^{13a}R^{13a'}$, $(CH_2)NR^{13d}C(O)R^{13a}$, $(CH_2)_wS(O)_2NR^{13a}R^{13a'}$, $(CH_2)NR^{13d}S(O)_2R^{13b}$, and $(CH_2)_w$-phenyl substituted with 0–3 $R^{13c}$;

$R^{13a}$ and $R^{13a'}$, at each occurrence, are selected from H, $C_{1-6}$ alkyl, $C_{3-6}$ cycloalkyl, and phenyl substituted with 0–3 $R^{13c}$;

$R^{13b}$, at each occurrence, is selected from $C_{1-6}$ alkyl, $C_{3-6}$ cycloalkyl, and phenyl substituted with 0–3 $R^{13c}$;

$R^{13c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_r OC_{1-5}$ alkyl, $(CH_2)_rOH$, and $(CH_2)_rNR^{13d}R^{13d}$;

$R^{13d}$, at each occurrence, is selected from H, $C_{1-6}$ alkyl, and $C_{3-6}$ cycloalkyl;

q is selected from 1, 2, and 3; and r is selected from 0, 1, 2, and 3.

3. The compound of claim 2, wherein:

$R^3$ is selected from a methyl substituted with 0–1 $R^{10}$, $C_{2-8}$ alkyl substituted with 0–3 $R^7$, $(CR^3'H)r$-carbocyclic residue substituted with 0–5 $R^{15}$, wherein the carbocyclic residue is selected from phenyl, $C_{3-6}$ cycloalkyl, naphthyl, and adamantyl; and a $(CR^3'H)r$-heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzoxazolyl, benzisoxazolyl, quinolinyl, isoquinolinyl, imidazolyl, indazolyl, isoxazolinyl, morpholinyl, pyrrolidinyl, tetrahydropyranyl, tetrahydrofuranyl, indolyl, indolinyl, isoindolyl, isothiadiazolyl, isoxazolyl, piperidinyl, pyrrazolyl, 1,2, 4-triazolyl, 1,2,3-triazolyl, tetrazolyl, thiadiazolyl, thiazolyl, oxazolyl, pyrazinyl, and pyrimidinyl; and $R^5$ is selected from $(CR^{5'}H)_r$-phenyl substituted with 0–5 $R^{16}$; and a $(CR^{5'}H)_r$-heterocyclic system substituted with 0–3 $R^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

4. The compound of claim 3, wherein $R^9$ is selected from H, $CH_3$, $C_{2-6}$ alkyl substituted with 0–3 $R^{9a}$, $C_{3-8}$ alkenyl, $C_{3-8}$ alkynyl, $C_{1-3}$ haloalkyl, $(CH_2)_rC(O)C_{1-6}$ alkyl substituted with 0–2 $R^{9j}$, $(CH_2)_r C(O)OC_{1-6}$ alkyl substituted with 0–3 $R^{9b}$, $(CH_2)_rC(O) NR^{9d}R^{9d'}$, $(CH_2)_rS(O)_2C_{1-6}$ alkyl, $S(O)_2C_{1-6}$ trifluoromethyl, $(CH_2)_rC(O)R^{9'}$, and $(CH_2)_rC(O) NR^{9d}R^{9'}$, $(CH_2)_rS(O)_2R^{9'}$, $R^{9'}$, and $(CH_2)_rS(O)_2 NR^{9d}R^{9'}$;

$R^{9'}$, at each occurrence, is independently selected from $(CHR')_rC_{3-6}$ cycloalkyl substitutes with 0–3 $R^{9e}$, wherein the cycloalkyl is selected from cyclopropyl, cyclobutyl, cyclopentyl, and cyclohexyl, $(CHR')_r$phenyl substituted with 0–3 $R^{9c}$, $(CHR')_r$5–6 membered heterocycle system containing 1–4 heteroatoms selected from N, O, and S, substituted with 0–3 $R^{9c}$, wherein the heterocycle is selected from oxadiazolyl, morpholinyl, piperidinyl, tetrahydropyranyl, tetrahydrothiopyranyl, tetrahydrothiopyranyl dioxide, thiophene, imidazolyl, pyrrolidinyl pyrrolyl, thiazolyl, and furanyl, and $(CHR')_r$ phenyl substituted with 0–3 $R^{9c}$;

$R^{9a}$, at each occurrence, is selected from CN, O-methyl, O-ethyl, $CF_3$, OH, OC(O)-methyl, S-methyl, s-ethyl, S-propyl, $S(O)_p$-methyl, $S(O)_p$-ethyl $S(O)_p$-propyl, and $NR^{9d}R^{9d'}$;

$R^{9b}$, at each occurrence, is selected from cyclopropyl, cyclbutyl, cyclpentyl, CN, $CF_3$, $CH_2$-$OC_{1-5}$ alkyl, $CH_2$-OH, $CH_2$$SC_{1-5}$ alkyl, and $CH_2$-$NR^{9d}R^{9d'}$;

$R^{9c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_r OC_{1-5}$ alkyl, $(CH_2)_rC(O)OC_{1-5}$ alkyl, $(CH_2)_rC(O)C_{1-5}$ alkyl, $(CH_2)_rC(O)NR^{9d}R^{9d'}$, $(CH_2)_rOH$, $(CH_2)_rSC_{1-5}$ alkyl, $(CH_2)_rS(O)_pC_{1-5}$ alkyl, and $(CH_2)_rNR^{9d}R^{9d'}$;

provided that if $R^{9c}$ is attached to a carbon attached to the nitrogen on Ring B, then $R^{9c}$ is selected from $(CH_2)_q$ OH, $(CH_2)_qOC_{1-5}$ alkyl, $(CH_2)_qSC_{1-5}$ alkyl, $(CH_2)_qS (O)_qC_{1-5}$ alkyl, and $(CH_2)_qNR^{9d}R^{9d'}$;

$R^{9d}$ and $R^{9d'}$, at each occurrence, are independently selected from H, methyl, ethyl, propyl, i-propyl, butyl, cyclopropyl, cyclobutyl, cyclopentyl, cyclohexyl and phenyl;

$R^{9e}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_r OC_{1-5}$ alkyl, $(CH_2)_rC(O)OC_{1-5}$ alkyl, $(CH_2)_rC(O) NR^{9d}R^{9d'}$, $(CH_2)_rOH$, $(CH_2)_rSC_{1-5}$ alkyl, $(CH_2)_rS(O)_p C_{1-5}$ alkyl, and $(CH_2)_rNR^{9d}R^{9d'}$, or alternatively, two $R^{9e}$ on the same carbon atom form $=O$; and $R^{9j}$, at each occurrence, is selected prom cyclpropyl, cyclobutyl, cyclopentyl, CN, $CF_3$, O-methyl, O-ethyl, O-propyl, O-i-propyl, O-butyl, OH, S-methyl, S-ethyl, and $NR^{9d}R^{9d'}$.

5. The compound of claim 4, wherein the compound of formula (I) is:

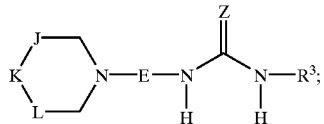

Z is selected from O, S, NCN, and $NCONH_2$;

$R^{16}$, at each occurrence, is selected from $C_{1-8}$ alkyl, $(CH_2)_rC_{3-6}$ cycloalkyl, $CF_3$, Cl, Br, I, F, $(CH_2)_r NR^{16a}R^{16a'}$, $NO_2$, CN, OH, $(CH_2)_rOR^{16d}$, $(CH_2)_rC (O)R^{16b}$, $(CH_2)_rC(O)NR^{16a}R^{16a'}$, $(CH_2)_rNR^{16f}C(O) R^{16b}$, $(CH_2)_rS(O)_pR^{16b}$, $(CH_2)_rS(O)_2NR^{16a}R^{16a'}$, $(CH_2)_rNR^{16f}S(O)_2R^{16b}$, and $(CH_2)_r$phenyl substituted with 0–3 $R^{16e}$;

$R^{16a}$ and $R^{16a'}$, at each occurrence, are selected from H, $C_{1-6}$ alkyl, $C_{3-6}$ cycloalkyl, and $(CH_2)_r$phenyl substituted with 0–3 $R^{16e}$;

$R^{16b}$, at each occurrence, is selected from H, $C_{1-6}$ alkyl, $C_{3-6}$ cycloalkyl, and $(CH_2)_r$phenyl substituted with 0–3 $R^{16e}$;

$R^{16d}$, at each occurrence, is selected from $C_{1-6}$ alkyl and phenyl;

$R^{16e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{16f}$, at each occurrence, is selected from H, and $C_{1-5}$ alkyl.

6. The compound of claim 5, wherein:

$R^5$ is $CH_2$phenyl substituted with 0–3 $R^{16}$;

r is selected from 0, 1, and 2.

7. The compound of claim 6, wherein:

J is selected from $CH_2$ and $CHR^5$;

K is selected from $CH_2$ and $CHR^5$;

L is $CHR^5$;

$R^3$ is selected from a $C_{3-10}$ carbocyclic residue substituted with 0–3 $R^{15}$, wherein the carbocyclic residue is selected from cyclopropyl, cyclobutyl, cyclopentyl, cyclohexyl, phenyl, naphthyl and adamantyl, and a $(CR^{3'}H)_r$-heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzoxazolyl, benzisoxazolyl, quinolinyl, isoquinolinyl, imidazolyl, indolyl, indolinyl, indazolyl, isoxazolinyl, morpholinyl, pyrrolidinyl, tetrahydropyranyl, tetrahydrofuranyl, isoindolyl, isothiadiazolyl, isoxazolyl, piperidinyl, pyrrazolyl, 1,2, 4-triazolyl, 1,2,3-triazolyl, tetrazolyl, thiadiazolyl, thiazolyl, oxazolyl, pyrazinyl, and pyrimidinyl;

$R^{15}$, at each occurrence, is selected from $C_{1-8}$ alkyl, $(CH_2)_rC_{3-6}$ cycloalkyl, $CF_3$, Cl, Br, I, F, $(CH_2)_r NR^{15a}R^{15a'}$, $NO_2$, CN, OH, $(CH_2)_rOR^{15d}$, $(CH_2)_rC(O) R^{15b}$, $(CH_2)_rC(O)NR^{15a}R^{15a'}$, $(CH_2)_rNR^{15f}C(O)R^{15b}$, $(CH_2)_rNR^{15f}C(O)O(CHR')_rR^{15d}$, $(CH_2)_rOC(O) NR^{15a}R^{15a'}$, $(CH_2)_rS(O)_pR^{15b}$, $(CH_2)_rS(O)_2 NR^{15a}R^{15a'}$, $(CH_2)_rNR^{15f}S(O)_2R^{15b}$, $(CH_2)_r$phenyl substituted with 0–3 $R^{15e}$, and a $(CH_2)_r$-5–6 membered heterocyclic system containing 1–4 heteroatoms selected from N, O, and S, substituted with 0–2 $R^{15e}$, wherein the heterocyclic system is selected from tetrazolyl, piperidinyl, pyrrolidinyl, imidazolyl, thiazolyl, pyrazolyl, pyridyl, thienyl, furanyl, pyrrolyl, oxazolyl, isoxazolyl, triazolyl, pyridazinyl, pyrimidinyl, pyrazinyl, morpholinyl, oxadiazolyl, and thiadiazolyl;

$R^{15a}$ and $R^{15a'}$, at each occurrence, are selected from H, $C_{1-6}$ alkyl, $C_{3-6}$ cycloalkyl, and $(CH_2)_r$phenyl substituted with 0–3 $R^{15e}$;

alternatively, $R^{15a}$ and $R^{15a'}$, along With the N to which they are attached, join to form 5–6 membered heterocyclic system containing 1–2 heteroatoms selected from $NR^{15h}$, O, and S and optionally fused with a benzene ring or a 6-membered aromatic heterocycle;

$R^{15b}$, at each occurrence, is selected from H, $C_{1-6}$ alkyl, $C_{3-6}$ cycloalkyl, and $(CH_2)_r$Phenyl substituted with 0–3 $R^{15e}$;

$R^{15d}$, at each occurrence, is selected from $C_{1-6}$ alkyl and phenyl;

$R^{15e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{15f}$, at each occurrence, is selected from H, and $C_{1-5}$ alkyl.

8. The compound of claim 5, wherein the compound of formula (I) is:

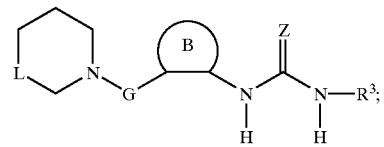

G is selected from $CH_2$ and C=O;

L is $CHR^5$;

B is selected from piperidine, tetrahydropyran, tetrahydrothiopyran, pyrrolidinyl, tetrahydrofuranyl, tetrahydrothiophenyl, tetrahydrothiophene 1-oxide, and tetrahydrothiophene 1,1-dioxide;

$R^3$ is selected from phenyl substituted with 1–2 $R^{15}$, —$CH_2$—$CH_2$-morpholin-1-yl substituted with 1–2 $R^{15}$, indazolyl substituted with 1–2 $R^{15}$, pyrazolyl substituted with 1–2 $R^{15}$ or thiazolyl substituted with 1–2 $R^{15}$;

$R^5$ is selected from a $CH_2$-phenyl substituted with 1–2 $R^{16'}$;

$R^9$ is selected from H, $C_{2-6}$ alkyl substituted with 0–3 $R^{9a}$, wherein the alkyl is selected from methyl, ethyl, propyl, i-propyl, butyl, i-butyl, s-butyl, t-butyl, neopentyl; —$CH_2CH=CH_2$;

—$CH_2C\equiv CH$; 2-fluoroethyl, 2,2-difluoroethyl, 2,2,2-trifluoroethyl, $(CH_2)_rC(O)C_{1-6}$ alkyl substituted with 0–2 $R^{9j}$, wherein the alkyl is selected from methyl, ethyl, propyl, i-propyl, butyl, t-butyl;

C(O)Omethyl, C(O)Ot-butyl, $SO_2$methyl, $SO_2$ethyl, $SO_2$propyl, $SO_2$i-propyl, $SO_2$t-butyl, $SO_2CF_3$, $(CH_2)_rC(O)NR^{9d}R^{9d'}$;

$(CH_2)_rC(O)R^{9'}$, $(CH_2)_rC(O)NR^{9d}R^{9'}$, $(CH_2)_rS(O)_2R^{9'}$, $R^{9'}$, and $(CH_2)_rS(O)_2NR^{9d}R^{9'}$;

$R^{9'}$, at each occurrence, is independently selected from $(CHR')_rC_{3-6}$ cycloalkyl, wherein the cycloalkyl is selected from cyclopropyl, cyclobutyl, cyclopentyl, and cyclohexyl, $(CHR')_r$phenyl substituted with 0–3 $R^{9c}$, $(CHR')_r$5–6 membered heterocycle system containing 1–4 heteroatoms selected from N, O, and S, substituted with 0–3 $R^{9c}$, wherein the heterocycle is selected from oxadiazolyl, morpholinyl, piperidinyl, tetrahydropyranyl, tetrahydrothiopyranyl, tetrahydrothiopyranyl dioxide, thiophene, imidazolyl, pyrrolidinyl, pyrrolyl, thiazolyl, and furanyl, and $(CHR')_r$phenyl substituted with 0–3 $R^{9c}$;

$R^{9a}$, at each occurrence, is selected from CN, O-methyl, O-ethyl, $CF_3$, OH, OC(O)-methyl, S-methyl, S-ethyl, S-propyl, $S(O)_p$-methyl, $S(O)_p$-ethyl, $S(O)_p$-propyl, and $NR^{9d}R^{9d'}$;

$R^{9c}$, at each occurrence, is selected from methyl, ethyl, propyl, C(O)-methyl, C(O)O-t-butyl;

$R^{9d}$ and $R^{9d'}$, at each occurrence, are independently selected from H, methyl, ethyl, propyl, i-propyl, butyl, t-butyl;

$R^{9j}$, at each occurrence, is selected from O-methyl, O-ethyl, and $NR^{9d}R^{9d'}$;

$R^{15}$ is selected from Me, $CF_3$, OMe, $OCF_3$, F, Cl, Br, OH, OMe, C(O)Me, CH(OH)Me, CN, $CO_2Me$, $CO_2Et$, $SO_2NH_2$, NHC(O)Me, $C(O)NH_2$, C(O)NHMe, $C(O)NHCH_2CH_2OMe$, C(O)piperidinyl, C(O)pyrrolidinyl, C(O)morpholinyl, and a 5–6 membered heterocyclic system, wherein the heterocyclic system is selected from tetrazolyl, indazolyl, pyrazolyl, triazolyl, morpholinyl, and thiazolyl, the heterocyclic system substituted with 0–2 $R^{15e}$;

$R^{15e}$ is selected from methyl, ethyl, propyl, i-propyl, cyclopropyl, cyclopropylmethyl, acetyl, and t-butoxycarbonyl;

$R^{16}$ is selected from F, Cl, Br, and I/O.

9. The compound of claim 1 wherein the compound is selected from:

(3R,4R)-4-[3-(3-acetyl-phenyl)-ureido]-3-[(S)-3-(4-fluoro-benzyl)-piperidine-1-carbonyl]-piperidine-1-carboxylic acid t-butyl ester;

1-(3-acetyl-phenyl)-3-{(3R,4R)-3-[(S)-3-(4-fluoro-benzyl)-piperidine-1-carbonyl]-piperidin-4-yl}-urea;

(3R,4R)-3-[(S)-3-(4-fluoro-benzyl)-piperidine-1-carbonyl]-4-{3-[3-(1-methyl-1H-tetrazol-5-yl)-phenyl]-ureido}-piperidine-1-carboxylic acid t-butyl ester;

1-{(3R,4R)-3-[(S)-3-(4-fluoro-benzyl)-piperidine-1-carbonyl]-piperidin-4-yl}-3-[3-(1-methyl-1H-tetrazol-5-yl)-phenyl]-urea;

1-{1-(2,2-Dimethyl-propionyl)-3-[(3R,4R)-3-((S)-4-fluoro-benzyl)-piperidine-1-carbonyl]-piperidin-4-yl}-3-[3-(1-methyl-1H-tetrazol-5-yl)-phenyl]-urea;

1-{1-Acetyl-3-[(3R,4R)-3-((S)-4-fluoro-benzyl)-piperidine-1-carbonyl]-piperidin-4-yl}-3-[3-(1-methyl-1H-tetrazol-5-yl)-phenyl]-urea;

1-{(3R,4R)-3-[(S)-3-(4-Fluoro-benzyl)-piperidine-1-carbonyl]-1-methanesulfonyl-piperidin-4-yl}-3-[3-(1-methyl-1H-tetrazol-5-yl)-phenyl]-urea;

1-{(3R,4R)-3-[(S)-3-(4-Fluoro-benzyl)-piperidine-1-carbonyl]-1-methyl-piperidin-4-yl}-3-[3-(1-methyl-1H-tetrazol-5-yl)-phenyl]-urea;

5-(3-{(3R,4R)-1-tert-butoxycarbonyl-3-[(S)-3-(4-fluoro-benzyl)-piperidine-1-carbonyl]-piperidin-4-yl}-ureido)-indazole-1-carboxylic acid t-butyl ester;

5-(3-{(3R,4R)-3-[(S)-3-(4-fluoro-benzyl)-piperidine-1-carbonyl]-piperidin-4-yl}-ureido)-indazole-1-carboxylic acid t-butyl ester;

(3R,4R)-4-[3-(5-acetyl-4-methyl-thiazol-2-yl)-ureido]-3-[(S)-3-(4-fluoro-benzyl)-piperidine-1-carbonyl]-piperidine-1-carboxylic acid t-butyl ester;

1-(5-acetyl-4-methyl-thiazol-2-yl)-3-{(3R,4R)-3-[(S)-3-(4-fluoro-benzyl)-piperidine-1-carbonyl]-piperidin-4-yl}-urea;

(3R,4S)-3-[3-(3-acetyl-phenyl)-ureido]-4-[(S)-3-(4-fluoro-benzyl)-piperidine-1-carbonyl]-piperidine-1-carboxylic acid t-butyl ester;

1-(3-acetyl-phenyl)-3-{(3R,4R)-4-[(S)-3-(4-fluoro-benzyl)-piperidine-1-carbonyl]-piperidin-3-yl}-urea;

(3R,4R)-4-[3-(3-acetyl-phenyl)-ureido]-3-[(S)-3-(4-fluoro-benzyl)-piperidin-1-ylmethyl]-piperidine-1-carboxylic acid t-butyl ester;

1-(3-acetyl-phenyl)-3-{(3S,4R)-3-[(S)-3-(4-fluoro-benzyl)-piperidin-1-ylmethyl]-piperidin-4-yl}-urea;

1-{(3R,4R)-1-acetyl-3-[(S)-3-(4-fluoro-benzyl)-piperidin-1-ylmethyl]-piperidin-4-yl}-3-(3-acetyl-phenyl)-urea;

1-(3-acetyl-phenyl)-3-{(3R,4R)-3-[(S)-3-(4-fluoro-benzyl)-piperidin-1-ylmethyl]-1-methanesulfonyl-piperidin-4-yl}-urea;

1-(3-acetyl-phenyl)-3-{(3S,4R)-3-[(S)-3-(4-fluoro-benzyl)-piperidin-1-ylmethyl]-1-methyl-piperidin-4-yl}-urea;

1-(3-acetyl-phenyl)-3-{(3R,4R)-3-[(S)-3-(4-fluoro-benzyl)-piperidin-1-ylmethyl]-1-isobutyl-piperidin-4-yl}-urea;

(3R,4R)-3-[(S)-3-(4-fluoro-benzyl)-piperidin-1-ylmethyl]-4-{3-[3-(1-methyl-1H-tetrazol-5-yl)-phenyl]-ureido}-piperidine-1-carboxylic acid t-butyl ester;

1-{(3S,4R)-3-[(S)-3-(4-fluoro-benzyl)-piperidin-1-ylmethyl]-piperidin-4-yl}-3-[3-(1-methyl-1H-tetrazol-5-yl)-phenyl]-urea;

5-(3-{(3R,4R)-1-t-butoxycarbonyl-3-[(S)-3-(4-fluoro-benzyl)-piperidin-1-ylmethyl]-piperidin-4-yl}-ureido)-indazole-1-carboxylic acid t-butyl ester;

5-(3-{(3S,4R)-3-[(S)-3-(4-Fluoro-benzyl)-piperidin-1-ylmethyl]-piperidin-4-yl}-ureido)-indazole-1-carboxylic acid t-butyl ester;

(3R,4R)-4-[3-(5-acetyl-4-methyl-thiazol-2-yl)-ureido]-3-[(S)-3-(4-fluoro-benzyl)-piperidin-1-ylmethyl]-piperidine-1-carboxylic acid t-butyl ester;

1-(5-acetyl-4-methyl-thiazol-2-yl)-3-{(3S,4R)-3-[(S)-3-(4-fluoro-benzyl)-piperidin-1-ylmethyl]-piperidin-4-yl}-urea;

(3R,4R)-4-[3-(3-acetyl-phenyl)-ureido]-3-[(S)-3-(4-fluoro-benzyl)-piperidin-1-ylmethyl]-piperidine-1-carboxylic acid t-butyl ester;

1-(3-acetyl-phenyl)-3-{(3R,4S)-4-[(S)-3-(4-fluoro-benzyl)-piperidin-1-ylmethyl]-piperidin-3-yl}-urea;

(3S,4R)-4-[3-(3-acetyl-phenyl)-ureido]-3-[(S)-3-(4-fluoro-benzyl)-piperidine-1-carbonyl]-piperidine-1-carboxylic acid t-butyl ester;

1-(3-acetyl-phenyl)-3-{(3S,4R)-3-[(S)-3-(4-fluoro-benzyl)-piperidine-1-carbonyl]-piperidin-4-yl}-urea;

(3R,4R)-4-[3-(3-acetyl-phenyl)-ureido]-3-[(S)-3-(4-fluoro-benzyl)-piperidin-1-ylmethyl]-piperidine-1-carboxylic acid methyl ester;

1-(3-acetyl-phenyl)-3-{(3R,4R)-1-(2,2-dimethyl-propionyl)-3-[(S)-3-(4-fluoro-benzyl)-piperidin-1-ylmethyl]-piperidin-4-yl}-urea;

(3R,4S)-3-[3-(5-acetyl-4-methyl-thiazol-2-yl)-ureido]-4-[(S)-3-(4-fluoro-benzyl)-piperidine-1-carbonyl]-piperidine-1-carboxylic acid t-butyl ester;

1-(3-acetyl-phenyl)-3-{(3R,4R)-3-[(S)-3-(4-fluoro-benzyl)-piperidin-1-ylmethyl]-1-(2-fluoro-ethyl)-piperidin-4-yl}-urea;

1-(3-acetyl-phenyl)-3-{(3R,4R)-3-[(S)-3-(4-fluoro-benzyl)-piperidin-1-ylmethyl]-1-(2-oxo-propyl)-piperidin-4-yl}-urea;

1-(3-acetyl-phenyl)-3-{(3R,4S)-4-[(S)-3-(4-fluoro-benzyl)-piperidin-1-ylmethyl]-1-methyl-piperidin-3-yl}-urea;

1-{(3R,4S)-1-Acetyl-4-[(S)-3-(4-fluoro-benzyl)-piperidin-1-ylmethyl]-piperidin-3-yl}-3-(3-acetyl-phenyl)-urea;

1-{(3R,4R)-1-acetyl-3-[(S)-3-(4-fluoro-benzyl)-piperidin-1-ylmethyl]-piperidin-4-yl}-3-(1-methyl-1H-tetrazol-5-yl)-urea;

1-{(3S,4R)-3-[(S)-3-(4-fluoro-benzyl)-piperidin-1-ylmethyl]-1-methyl-piperidin-4-yl}-3-(1-methyl-1H-tetrazol-5-yl)-urea;

1-{(3R,4R)-3-[(S)-3-(4-fluoro-benzyl)-piperidin-1-ylmethyl]-1-methanesulfonyl-piperidin-4-yl}-3-(1-methyl-1H-tetrazol-5-yl)-urea;

1-{(3R,4R)-3-[(S)-3-(4-Fluoro-benzyl)-piperidine-1-carbonyl]-1-(2-oxo-propyl)-piperidin-4-yl}-3-[3-(1-methyl-1H-tetrazol-5-yl)-phenyl]-urea;

1-{(3R,4R)-3-[(S)-3-(4-Fluoro-benzyl)-piperidine-1-carbonyl]-1-(2-fluoro-ethyl)-piperidin-4-yl}-3-[3-(1-methyl-1H-tetrazol-5-yl)-phenyl]-urea;

1-{(3R,4R)-3-[(S)-3-(4-Fluoro-benzyl)-piperidine-1-carbonyl]-1-trifluoromethanesulfonyl-piperidin-4-yl}-3-[3-(1-methyl-1H-tetrazol-5-yl)-phenyl]-urea;

1-(3-Acetyl-phenyl)-3-{(2S,3R)-2-[(S)-3-(4-fluoro-benzyl)-piperidin-1-ylmethyl]-tetrahydro-pyran-3-yl}-urea;

1-{(2S,3R)-2-[(S)-3-(4-Fluoro-benzyl)-piperidin-1-ylmethyl]-tetrahydro-pyran-3-yl}-3-[3-(1-methyl-1H-tetrazol-5-yl)-phenyl]-urea;

1-{(2S,3R)-2-[(S)-3-(4-Fluoro-benzyl)-piperidin-1-ylmethyl]-tetrahydro-pyran-3-yl}-3-(5-acetyl-4-methyl-thiazol-2-yl)-urea;

1-(3-Acetyl-phenyl)-3-{(2S,3R)-2-[(S)-3-(4-fluoro-benzyl)-piperidine-1-carbonyl]-tetrahydro-pyran-3-yl}-urea;

1-{(2S,3R)-2-[(S)-3-(4-Fluoro-benzyl)-piperidine-1-carbonyl]-tetrahydro-pyran-3-yl}-3-[3-(1-methyl-1H-tetrazol-5-yl)-phenyl]-urea;

1-{(2S,3R)-2-[(S)-3-(4-Fluoro-benzyl)-piperidine-1-carbonyl]-tetrahydro-pyran-3-yl}-3-(5-acetyl-4-methyl-thiazol-2-yl)-urea;

1-{(3S,4R)-3-[(S)-3-(4-fluoro-benzyl)-piperidin-1-ylmethyl]-1-methyl-piperidin-4-yl}-3-(5-acetyl-4-methyl-thiazol-2-yl)-urea;

1-{(3R,4R)-1-acetyl-3-[(S)-3-(4-fluoro-benzyl)-piperidin-1-ylmethyl]-piperidin-4-yl}-3-(5-acetyl-4-methyl-thiazol-2-yl)-urea;

1-(5-Acetyl-4-methyl-thiazol-2-yl)-3-{(3R,4R)-3-[(S)-3-(4-fluoro-benzyl)-piperidin-1-ylmethyl]-1-isobutyryl-piperidin-4-yl}-urea;

1-{(3R,4R)-3-[(S)-3-(4-fluoro-benzyl)-piperidin-1-ylmethyl]-1-methanesulfonyl-piperidin-4-yl}-3-(5-acetyl-4-methyl-thiazol-2-yl)-urea;

1-{(3S,4R)-3-[(S)-3-(4-fluoro-benzyl)-piperidin-1-ylmethyl]-1-(2-fluoroethyl)-piperidin-4-yl}-3-(5-acetyl-4-methyl-thiazol-2-yl)-urea;

1-{(3R,4R)-3-[(S)-3-(4-fluoro-benzyl)-piperidin-1-ylmethyl]-1-(2-oxopropyl)-piperidin-4-yl}-3-(5-acetyl-4-methyl-thiazol-2-yl)-urea;

1-(3-Acetyl-phenyl)-3-{(3R,4R)-3-[(S)-3-(4-fluoro-benzyl)-piperidin-1-ylmethyl]-tetrahydro-pyran-4-yl}-urea;

1-{(3R,4R)-3-[(S)3-(4-Fluoro-benzyl)-piperidin-1-ylmethyl]-tetrahydro-pyran-4-yl}-3-[3-(1-methyl-1H-tetrazol-5-yl)-phenyl]-urea;

1-{(3R,4R)-3-[(S)3-(4-Fluoro-benzyl)-piperidin-1-ylmethyl]-tetrahydro-pyran-4-yl}-3-(5-acetyl-4-methyl-thiazol-2-yl)-urea;

1-(3-Acetyl-phenyl)-3-{(3R,4R)-3-[(S)-3-(4-fluoro-benzyl)-piperidine-1-carbonyl]-tetrahydro-pyran-4-yl}-urea;

1-{(3R,4R)-3-[(S)3-(4-Fluoro-benzyl)-piperidine-1-carbonyl]-tetrahydro-pyran-4-yl}-3-[3-(1-methyl-1H-tetrazol-5-yl)-phenyl]-urea;

1-{(3R,4R)-3-[(S)3-(4-Fluoro-benzyl)-piperidine-1-carbonyl]-tetrahydro-pyran-4-yl}-3-(5-acetyl-4-methyl-thiazol-2-yl)-urea;

1-{(3S,4R)-3-[(S)-3-(4-fluoro-benzyl)-piperidin-1-ylmethyl]-piperidin-4-yl}-3-(4-fluoro-phenyl)-urea;

(3R,4R)-3-[(S)-3-(4-fluoro-benzyl)-piperidin-1-ylmethyl]-4-[3-(4-fluoro-phenyl)-ureido]-piperidine-1-carboxylic acid t-butyl ester;

1-{(3R,4R)-1-acetyl-3-[(S)-3-(4-fluoro-benzyl)-piperidin-1-ylmethyl]-piperidin-4-yl}-3-(4-fluoro-phenyl)-urea;

1-{(3S,4R)-3-[(S)-3-(4-fluoro-benzyl)-piperidin-1-ylmethyl]-1-methyl-piperidin-4-yl}-3-(4-fluoro-phenyl)-urea;

1-{(3S,4R)-3-[(S)-3-(4-fluoro-benzyl)-piperidin-1-ylmethyl]-1-ethyl-piperidin-4-yl}-3-(4-fluoro-phenyl)-urea;

1-{(3R,4R)-3-[(S)-3-(4-fluoro-benzyl)-piperidin-1-ylmethyl]-1-[1,2,4]oxadiazol-3-ylmethyl-piperidin-4-yl}-3-(4-fluoro-phenyl)-urea;

2-{(3R,4R)-3-[(S)-3-(4-fluoro-benzyl)-piperidin-1-ylmethyl]-4-[3-(4-fluoro-phenyl)-ureido]-piperidin-1-yl}-N-isopropyl-acetamide;

1-{(3R,4R)-3-[(S)-3-(4-fluoro-benzyl)-piperidin-1-ylmethyl]-1-prop-2-ynyl-piperidin-4-yl}-3-(4-fluoro-phenyl)-urea;

1-(3-acetyl-phenyl)-3-{(3R,4R)-3-[(S)-3-(4-fluoro-benzyl)-piperidin-1-ylmethyl]-[1,4']bipiperidinyl-4-yl}-urea;

1-{(3R,4R)-1'-acetyl-3-[(S)-3-(4-fluoro-benzyl)-piperidin-1-ylmethyl]-[1,4']bipiperidinyl-4-yl}-3-(3-acetyl-phenyl)-urea;

1-(3-acetyl-phenyl)-3-{(3R,4R)-3-[(S)-3-(4-fluoro-benzyl)-piperidin-1-ylmethyl]-1'-methyl-[1,4']bipiperidinyl-4-yl}-urea;

1-(3,5-diacetyl-phenyl)-3-{(3S,4R)-3-[(S)-3-(4-fluoro-benzyl)-piperidin-1-ylmethyl]-piperidin-4-yl}-urea;

(3R,4R)-3-[(S)-3-(4-fluoro-benzyl)-piperidin-1-ylmethyl]-4-[3-(3,5-diacetyl-phenyl)-ureido]-piperidine-1-carboxylic acid t-butyl ester;

1-(3,5-diacetyl-phenyl)-3-{(3R,4R)-1-acetyl-3-[(S)-3-(4-fluoro-benzyl)-piperidin-1-ylmethyl]-piperidin-4-yl}-urea;

1-(3,5-diacetyl-phenyl)-3-{(3S,4R)-3-[(S)-3-(4-fluoro-benzyl)-piperidin-1-ylmethyl]-1-methyl-piperidin-4-yl}-urea;

1-(3,5-diacetyl-phenyl)-3-{(3S,4R)-3-[(S)-3-(4-fluoro-benzyl)-piperidin-1-ylmethyl]-1-ethyl-piperidin-4-yl}-urea;

1-(3,5-diacetyl-phenyl)-3-{(3R,4R)-3-[(S)-3-(4-fluoro-benzyl)-piperidin-1-ylmethyl]-1-[1,2,4]oxadiazol-3-ylmethyl-piperidin-4-yl}-urea;

2-{(3R,4R)-3-[(S)-3-(4-Fluoro-benzyl)-piperidin-1-ylmethyl]-4-[3-(3,5-diacetyl-phenyl)-ureido]-piperidin-1-yl}-N-isopropyl-acetamide;

1-(3,5-diacetyl-phenyl)-3-{(3R,4R)-3-[(S)-3-(4-fluoro-benzyl)-piperidin-1-ylmethyl]-1-propargyl-piperidin-4-yl}-urea;

(3R,4R)-3-[(S)-3-(4-fluoro-benzyl)-piperidin-1-ylmethyl]-4-{3-[3-(1-methyl-1H-tetrazol-5-yl)-phenyl]-ureido}-piperidine-1-carboxylic acid methyl ester;

1-{(3S,4R)-3-[(S)-3-(4-fluoro-benzyl)-piperidin-1-ylmethyl]-piperidin-4-yl}-5-[3-methyl-5-(1-methyl-1H-tetrazol-5-yl)-phenyl]-urea;

(3R,4R)-3-[(S)-3-(4-fluoro-benzyl)-piperidin-1-ylmethyl]-4-{3-[3-methyl-5-(1-methyl-1H-tetrazol-5-yl)-phenyl]-ureido}-piperidine-1-carboxylic acid t-butyl ester;

1-{(3R,4R)-1-acetyl-3-[(S)-3-(4-fluoro-benzyl)-piperidin-1-ylmethyl]-piperidin-4-yl}-3-[3-methyl-5-(1-methyl-1H-tetrazol-5-yl)-phenyl]-urea;

1-{(3S,4R)-3-[(S)-3-(4-fluoro-benzyl)-piperidin-1-ylmethyl]-1-methyl-piperidin-4-yl}-3-[3-methyl-5-(1-methyl-1H-tetrazol-5-yl)-phenyl]-urea;

1-{(3S,4R)-3-[(S)-3-(4-fluoro-benzyl)-piperidin-1-ylmethyl]-1-ethyl-piperidin-4-yl}-3-[3-methyl-5-(1-methyl-1H-tetrazol-5-yl)-phenyl]-urea;

1-{(3R,4R)-3-[(S)-3-(4-fluoro-benzyl)-piperidin-1-ylmethyl]-1-[1,2,4]oxadiazol-3-ylmethyl-piperidin-4-yl}-3-[3-methyl-5-(1-methyl-1H-tetrazol-5-yl)-phenyl]-urea;

2-{(3R,4R)-3-[(S)-3-(4-fluoro-benzyl)-piperidin-1-ylmethyl]-4-{3-[3-methyl-5-(1-methyl-1H-tetrazol-5-yl)-phenyl]-ureido}-piperidin-1-yl}-N-isopropyl-acetamide;

1-{(3R,4R)-3-[(S)-3-(4-fluoro-benzyl)-piperidin-1-ylmethyl]-1-prop-2-ynyl-piperidin-4-yl}-3-[3-methyl-5-(1-methyl-1H-tetrazol-5-yl)-phenyl]-urea;

1-{(3S,4R)-3-[(S)-3-(4-fluoro-benzyl)-piperidin-1-ylmethyl]-piperidin-4-yl}-3-[3-bromo-5-(1-methyl-1H-tetrazol-5-yl)-phenyl]-urea;

(3R,4R)-3-[(S)-3-(4-fluoro-benzyl)-piperidin-1-ylmethyl]-4-{3-[3-bromo-5-(1-methyl-1H-tetrazol-5-yl)-phenyl]-ureido}-piperidine-1-carboxylic acid t-butyl ester;

1-{(3R,4R)-1-acetyl-3-[(S)-3-(4-fluoro-benzyl)-piperidin-1-ylmethyl]-piperidin-4-yl}-3-[3-bromo-5-(1-methyl-1H-tetrazol-5-yl)-phenyl]-urea;

1-{(3S,4R)-3-[(S)-3-(4-fluoro-benzyl)-piperidin-1-ylmethyl]-1-methyl-piperidin-4-yl}-3-[3-bromo-5-(1-methyl-1H-tetrazol-5-yl)-phenyl]-urea;

1-{(3S,4R)-3-[(S)-3-(4-fluoro-benzyl)-piperidin-1-ylmethyl]-1-ethyl-piperidin-4-yl}-3-[3-bromo-5-(1-methyl-1H-tetrazol-5-yl)-phenyl]-urea;

1-{(3R,4R)-3-[(S)-3-(4-fluoro-benzyl)-piperidin-1-ylmethyl]-1-[1,2,4]oxadiazol-3-ylmethyl-piperidin-4-yl}-3-[3-bromo-5-(1-methyl-1H-tetrazol-5-yl)-phenyl]-urea;

2-{(3R,4R)-3-[(S)-3-(4-fluoro-benzyl)-piperidin-1-ylmethyl]-4-{3-[3-bromo-5-(1-methyl-1H-tetrazol-5-yl)-phenyl]-ureido}-piperidin-1-yl}-N-isopropyl-acetamide;

1-{(3R,4R)-3-[(S)-3-(4-fluoro-benzyl)-piperidin-1-ylmethyl]-1-prop-2-ynyl-piperidin-4-yl}-3-[3bromo-5-(1-methyl-1H-tetrazol-5-yl)-phenyl]-urea;

1-[(3R,4R)-3-[(S)-3-(4-fluoro-benzyl)-piperidin-1-ylmethyl]-1-(2-oxo-propyl)-piperidin-4-yl]-3-[3-(1-methyl-1H-tetrazol-5-yl)-phenyl]-urea;

1-{(3R,4R)-3-[(S)-3-(4-fluoro-benzyl)-piperidin-1-ylmethyl]-1-(2-oxo-propyl)-piperidin-4-yl}-3-(1-methyl-pyrazol-3-yl)-urea;

1-{(3R,4R)-3-[(S)-3-(4-fluoro-benzyl)-piperidin-1-ylmethyl]-1-(2-oxo-propyl)-piperidin-4-yl}-3-(thiazol-2-yl)-urea;

2-{3-[(3R,4R)-3-[(S)-3-(4-fluoro-benzyl)-piperidin-1-ylmethyl]-1-(2-oxo-propyl)-piperidin-4-yl]-ureido}-4-methyl-thiazole-5-carboxylic acid ethyl ester;

(3R,4R)-3-[(S)-3-(4-fluoro-benzyl)-piperidin-1-ylmethyl]-4-(5-acetyl-4-methyl-thiazol-2-yl)-ureido}-piperidine-1-carboxylic acid methyl ester;

(3R,4R)-4-[3-(5-acetyl-4-methyl-thiazol-2-yl)-ureido]-3-[(S)-3-(4-fluoro-benzyl)-piperidin-1-ylmethyl]-piperidine-1-carboxylic acid 3-hydroxy-2,2-dimethyl-propyl ester;

1-(5-acetyl-4-methyl-thiazol-2-yl)-3-{(3R,4R)-3-[(S)-3-(4-fluoro-benzyl)-piperidin-1-ylmethyl]-1-propionyl-piperidin-4-yl}-urea;

1-(5-acetyl-4-methyl-thiazol-2-yl)-3-{(3R, 4R)-1-cyclopropanecarbonyl-3-[(S)-3-(4-fluoro-benzyl)-piperidin-1-ylmethyl]-piperidin-4-yl}-urea;

1-(5-acetyl-4-methyl-thiazol-2-yl)-3-{(3R,4R)-1-cyclopentanecarbonyl-3-[(S)-3-(4-fluoro-benzyl)-piperidin-1-ylmethyl]-piperidin-4-yl}-urea;

1-(5-acetyl-4-methyl-thiazol-2-yl)-3-[(3R, 4R)-3-[(S)-3-(4-fluoro-benzyl)-piperidin-1-ylmethyl]-1-(tetrahydro-pyran-4-carbonyl)-piperidin-4-yl]-urea;

1-(5-acetyl-4-methyl-thiazol-2-yl)-3-[(3R,4R)-3-[(S)-3-(4-fluoro-benzyl)-piperidin-1-ylmethyl]-1-(2-methoxy-acetyl)-piperidin-4-yl]-urea;

1-(5-acetyl-4-methyl-thiazol-2-yl)-3-[(3R,4R)-3-[(S)-3-(4-fluoro-benzyl)-piperidin-1-ylmethyl]-1-(2-dimethylamino-acetyl)-piperidin-4-yl]-urea;

(3R,4R)-4-[3-(5-acetyl-4-methyl-thiazol-2-yl)-ureido]-3-[(S)-3-(4-fluoro-benzyl)-piperidin-1-ylmethyl]-piperidine-1-carboxylic acid methylamide;

(3R,4R)-4-[3-(5-acetyl-4-methyl-thiazol-2-yl)-ureido]-3-[(S)-3-(4-fluoro-benzyl)-piperidin-1-ylmethyl]-piperidine-1-carboxylic acid dimethylamide;

(3R,4R)-4-[3-(5-acetyl-4-methyl-thiazol-2-yl)-ureido]-3-[(S)-3-(4-fluoro-benzyl)-piperidin-1-ylmethyl]-piperidine-1-carboxylic acid ethylamide;

1-(5-acetyl-4-methyl-thiazol-2-yl)-3-{(3S,4R)-1-ethyl-3-[(S)-3-(4-fluoro-benzyl)-piperidin-1-ylmethyl]-piperidin-4-yl}-urea;

1-(5-acetyl-4-methyl-thiazol-2-yl)-3-{(3S, 4R)-3-[(S)-3-(4-fluoro-benzyl)-piperidin-1-ylmethyl]-1-propyl-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-isopropyl-piperidin-4-yl}-urea;

1-(5-acetyl-4-methyl-thiazol-2-yl)-3-{(3R,4R)-1-cyclobutyl-3-[(S)-3-(4-fluoro-benzyl)-piperidin-1-ylmethyl]-piperidin-4-yl}-urea;

1-(5-acetyl-4-methyl-thiazol-2-yl)-3-{(3R,4R)-1-cyclopentyl-3-[(S)-3-(4-fluoro-benzyl)-piperidin-1-ylmethyl]-piperidin-4-yl}-urea;

1-(5-acetyl-4-methyl-thiazol-2-yl)-3-[(3R,4R)-3-[(S)-3-(4-fluoro-benzyl)-piperidin-1-ylmethyl]-1-(tetrahydro-pyran-4-yl)-piperidin-4-yl]-urea;

1-(5-acetyl-4-methyl-thiazol-2-yl)-3-[(3R,4R)-3-[(S)-3-(4-fluoro-benzyl)-piperidin-1-ylmethyl]-1-(tetrahydro-thiopyran-4-yl)-piperidin-4-yl]-urea;

1-(5-acetyl-4-methyl-thiazol-2-yl)-3-{(3R,4R)-1-(1,1-dioxo-hexahydro-1λ6-thiopyran-4-yl)-3-[(S)-3-(4-fluoro-benzyl)-piperidin-1-ylmethyl]-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-[1,4']bipiperidinyl-4-yl}-urea;

(3R,4R)-4-[3-(5-acetyl-4-methyl-thiazol-2-yl)-ureido]-3-[(S)-3-(4-fluoro-benzyl)-piperidin-1-ylmethyl]-[1,4']bipiperidinyl-1'-carboxylic acid tert-butyl ester;

1-{(3R,4R)-1'-acetyl-3-[(S)-3-(4-fluoro-benzyl)-piperidin-1-ylmethyl]-[1,4']bipiperidinyl-4-yl}-3-(5-acetyl-4-methyl-thiazol-2-yl)-urea;

1-(5-acetyl-4-methyl-thiazol-2-yl)-3-{(3R,4R)-3-[(S)-3-(4-fluoro-benzyl)-piperidin-1-ylmethyl]-1'-methyl-[1,4']bipiperidinyl-4-yl}-urea;

1-(5-acetyl-4-methyl-thiazol-2-yl)-3-{(3R,4R)-1-cyclopropylmethyl-3-[(S)-3-(4-fluoro-benzyl)-piperidin-1-ylmethyl]-piperidin-4-yl}-urea;

1-(5-acetyl-4-methyl-thiazol-2-yl)-3-{(3R,4R)-1-cyclobutylmethyl-3-[(S)-3-(4-fluoro-benzyl)-piperidin-1-ylmethyl]-piperidin-4-yl}-urea;

1-(5-acetyl-4-methyl-thiazol-2-yl)-3-{(3R,4R)-1-benzyl-3-[(S)-3-(4-fluoro-benzyl)-piperidin-1-ylmethyl]-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-furan-2-ylmethyl-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-furan-3-ylmethyl-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-thiophen-2-ylmethyl-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-thiophen-3-ylmethyl-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-imidazol-2-ylmethyl-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-imidazol-4-ylmethyl-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-thiazol-2-ylmethyl-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-[1,2,4]oxadiazol-3-ylmethyl-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-(2-hydroxyethyl)-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-(2-hydroxy-2-methylpropyl)-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-(2-hydroxy-3,3,3-trifluoropropyl)-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-(2-methoxy-ethyl)-piperidin-4-yl}-urea;

1-(5-acetyl-4-methyl-thiazol-2-yl)-3-{(3R,4R)-1-(2-ethoxy-ethyl)-3-[(S)-3-(4-fluoro-benzyl)-piperidin-1-ylmethyl]-piperidin-4-yl}-urea;

1-(5-acetyl-4-methyl-thiazol-2-yl)-3-{(3R,4R)-1-(2-ethylsulfanyl-ethyl)-3-[(S)-3-(4-fluoro-benzyl)-piperidin-1-ylmethyl]-piperidin-4-yl}-urea;

1-(5-acetyl-4-methyl-thiazol-2-yl)-3-{(3R,4R)-1-(2-ethanesulfonyl-ethyl)-3-[(S)-3-(4-fluoro-benzyl)-piperidin-1-ylmethyl]-piperidin-4-yl}-urea;

1-(5-acetyl-4-methyl-thiazol-2-yl)-3-{(3R,4R)-1-(2-acetoxy-ethyl)-3-[(S)-3-(4-fluoro-benzyl)-piperidin-1-ylmethyl]-piperidin-4-yl}-urea;

1-(5-acetyl-4-methyl-thiazol-2-yl)-3-{(3R,4R)-1-cyanomethyl-3-[(S)-3-(4-fluoro-benzyl)-piperidin-1-ylmethyl]-piperidin-4-yl}-urea;

1-(5-acetyl-4-methyl-thiazol-2-yl)-3-{(3R,4R)-1-(2-dimethylamino-ethyl)-3-[(S)-3-(4-fluoro-benzyl)-piperidin-1-ylmethyl]-piperidin-4-yl}-urea;

1-(5-acetyl-4-methyl-thiazol-2-yl)-3-{(3R,4R)-1-(2-diethylamino-ethyl)-3-[(S)-3-(4-fluoro-benzyl)-piperidin-1-ylmethyl]-piperidin-4-yl}-urea;

1-(5-acetyl-4-methyl-thiazol-2-yl)-3-[(3R,4R)-3-[(S)-3-(4-fluoro-benzyl)-piperidin-1-ylmethyl]-1-(2-pyrrolidin-1-yl-ethyl)-piperidin-4-yl]-urea;

1-(5-acetyl-4-methyl-thiazol-2-yl)-3-[(3R,4R)-3-[(S)-3-(4-fluoro-benzyl)-piperidin-1-ylmethyl]-1-(2-morpholin-1-yl-ethyl)-piperidin-4-yl]-urea;

1-(5-acetyl-4-methyl-thiazol-2-yl)-3-[(3R,4R)-3-[(S)-3-(4-fluoro-benzyl)-piperidin-1-ylmethyl]-1-(2-pyrrol-1-yl-ethyl)-piperidin-4-yl]-urea;

1-(5-acetyl-4-methyl-thiazol-2-yl)-3-[(3R,4R)-3-[(S)-3-(4-fluoro-benzyl)-piperidin-1-ylmethyl]-1-(3-oxo-butyl)-piperidin-4-yl]-urea;

1-(5-acetyl-4-methyl-thiazol-2-yl)-3-[(3R,4R)-3-[(S)-3-(4-fluoro-benzyl)-piperidin-1-ylmethyl]-1-(2-methyl-3-oxo-butyl)-piperidin-4-yl]-urea;

1-(5-acetyl-4-methyl-thiazol-2-yl)-3-[(3R,4R)-3-[(S)-3-(4-fluoro-benzyl)-piperidin-1-ylmethyl]-1-(3-hydroxypropyl)-piperidin-4-yl]-urea;

1-(5-acetyl-4-methyl-thiazol-2-yl)-3-{(3R,4R)-3-[(S)-3-(4-fluoro-benzyl)-piperidin-1-ylmethyl]-1-[(S)-3-hydroxy-2-methylpropyl]-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-[(R)-3-hydroxy-2-methylpropyl]-piperidin-4-yl}-urea;

1-(5-acetyl-4-methyl-thiazol-2-yl)-3-{(3R,4R)-1-(3,3-dimethyl-2-oxo-butyl)-3-[(S)-3-(4-fluoro-benzyl)-piperidin-1-ylmethyl]-piperidin-4-yl}-urea;

2-{(3R,4R)-4-[3-(5-acetyl-4-methyl-thiazol-2-yl)-ureido]-3-[(S)-3-(4-fluoro-benzyl)-piperidin-1-ylmethyl]-piperidin-1-yl}-N-methyl-acetamide;

2-{(3R,4R)-4-[3-(5-acetyl-4-methyl-thiazol-2-yl)-ureido]-3-[(S)-3-(4-fluoro-benzyl)-piperidin-1-ylmethyl]-piperidin-1-yl}-N-isopropyl-acetamide;

2-{(3R,4R)-4-[3-(5-acetyl-4-methyl-thiazol-2-yl)-ureido]-3-[(S)-3-(4-fluoro-benzyl)-piperidin-1-ylmethyl]-piperidin-1-yl}-N-tert-butyl-acetamide;

2-{(3R,4R)-4-[3-(5-acetyl-4-methyl-thiazol-2-yl)-ureido]-3-[(S)-3-(4-fluoro-benzyl)-piperidin-1-ylmethyl]-piperidin-1-yl}-N,N-dimethyl-acetamide;

1-(5-acetyl-4-methyl-thiazol-2-yl)-3-[(3R,4R)-3-[(S)-3-(4-fluoro-benzyl)-piperidin-1-ylmethyl]-1-(2-oxo-cyclopentyl)-piperidin-4-yl]-urea;

1-(5-acetyl-4-methyl-thiazol-2-yl)-3-{(3R,4R)-1-allyl-3-[(S)-3-(4-fluoro-benzyl)-piperidin-1-ylmethyl]-piperidin-4-yl}-urea;

1-(5-acetyl-4-methyl-thiazol-2-yl)-3-{(3R,4R)-3-[(S)-3-(4-fluoro-benzyl)-piperidin-1-ylmethyl]-1-prop-2-ynyl-piperidin-4-yl}-urea;

1-{(3R,4S)-4-[(S)-3-(4-fluoro-benzyl)-piperidin-1-ylmethyl]-piperidin-3-yl}-3-(4-fluoro-phenyl)-urea;

1-{(3R,4S)-1-acetyl-4-[(S)-3-(4-fluoro-benzyl)-piperidin-1-ylmethyl]-piperidin-3-yl}-3-(4-fluoro-phenyl)-urea;

1-[(3R,4S)-4-[(S)-3-(4-fluoro-benzyl)-piperidin-1-ylmethyl]-1-(2-methoxy-acetyl)-piperidin-3-yl]-3-(4-fluoro-phenyl)-urea;

1-{(3R,4S)-1-cyclopropylmethyl-4-[(S)-3-(4-fluoro-benzyl)-piperidin-1-ylmethyl]-piperidin-3-yl}-3-(4-fluoro-phenyl)-urea;

1-[(3R,4S)-4-[(S)-3-(4-fluoro-benzyl)-piperidin-1-ylmethyl]-1-(2-hydroxy-ethyl)-piperidin-3-yl]-3-(4-fluoro-phenyl)-urea;

1-(3-acetyl-phenyl)-3-[(3R,4S)-4-[(S)-3-(4-fluoro-benzyl)-piperidin-1-ylmethyl]-1-(2-methoxy-acetyl)-piperidin-3-yl]-urea;

1-(3-acetyl-phenyl)-3-{(3R,4S)-1-(2-dimethylamino-acetyl)-4-[(S)-3-(4-fluoro-benzyl)-piperidin-1-ylmethyl]-piperidin-3-yl}-urea;

(3R,4S)-3-[3-(3-acetyl-phenyl)-ureido]-4-[(S)-3-(4-fluoro-benzyl)-piperidin-1-ylmethyl]-piperidine-1-carboxylic acid ethylamide;

1-(3-acetyl-phenyl)-3-[(3R,4S)-4-[(S)-3-(4-fluoro-benzyl)-piperidin-1-ylmethyl]-1-(2-hydroxy-ethyl)-piperidin-3-yl]-urea;

(3R,4S)-4-[(S)-3-(4-fluoro-benzyl)-piperidin-1-ylmethyl]-3-{3-[3-(1-methyl-1H-tetrazol-5-yl)-phenyl]-ureido}-piperidine-1-carboxylic acid tert-butyl ester;

1-{(3R,4S)-1-acetyl-4-[(S)-3-(4-fluoro-benzyl)-piperidin-1-ylmethyl]-piperidin-3-yl}-3-[3-(1-methyl-1H-tetrazol-5-yl)-phenyl]-urea;

1-{(3R,4S)-1-(2,2-dimethyl-propionyl)-4-[(S)-3-(4-fluoro-benzyl)-piperidin-1-ylmethyl]-piperidin-3-yl}-3-[3-(1-methyl-1H-tetrazol-5-yl)-phenyl]-urea;

1-{(3R,4S)-4-[(S)-3-(4-fluoro-benzyl)-piperidin-1-ylmethyl]-1-methyl-piperidin-3-yl}-3-[3-(1-methyl-1H-tetrazol-5-yl)-phenyl]-urea;

1-{(3R,4S)-4-[(S)-3-(4-fluoro-benzyl)-piperidin-1-ylmethyl]-piperidin-3-yl}-3-[3-methyl-5-(1-methyl-1H-tetrazol-5-yl)-phenyl]-urea;

1-[(3R,4S)-4-[(S)-3-(4-fluoro-benzyl)-piperidin-1-ylmethyl]-1-(2-hydroxy-ethyl)-piperidin-3-yl]-3-[3-methyl-5-(1-methyl-1H-tetrazol-5-yl)-phenyl]-urea;

1-[3-bromo-5-(1-methyl-1H-tetrazol-5-yl)-phenyl]-3-{(3R,4S)-4-[(S)-3-(4-fluoro-benzyl)-piperidin-1-ylmethyl]-piperidin-3-yl}-urea;

1-[3-bromo-5-(1-methyl-1H-tetrazol-5-yl)-phenyl]-3-[(3R,4S)-4-[(S)-3-(4-fluoro-benzyl)-piperidin-1-ylmethyl]-1-(2-hydroxy-ethyl)-piperidin-3-yl]-urea;

1-{(3R,4S)-1-acetyl-4-[(S)-3-(4-fluoro-benzyl)-piperidin-1-ylmethyl]-piperidin-3-yl}-3-[3-(5-methyl-tetrazol-1-yl)-phenyl]-urea;

1-{(3R,4S)-1-acetyl-4-[(S)-3-(4-fluoro-benzyl)-piperidin-1-ylmethyl]-piperidin-3-yl}-3-(1-methyl-pyrazol-3-yl)-urea;

1-{(3R,4S)-1-acetyl-4-[(S)-3-(4-fluoro-benzyl)-piperidin-1-ylmethyl]-piperidin-3-yl}-3-(thiazol-2-yl)-urea;

2-(3-{(3R,4S)-1-acetyl-4-[(S)-3-(4-fluoro-benzyl)-piperidin-1-ylmethyl]-piperidin-3-yl}-ureido)-4-methyl-thiazole-5-carboxylic acid ethyl ester;

1-(5-acetyl-4-methyl-thiazol-2-yl)-3-{(3R,4S)-4-[(S)-3-(4-fluoro-benzyl)-piperidin-1-ylmethyl]-piperidin-3-yl}-urea;

(3R,4S)-3-[3-(5-acetyl-4-methyl-thiazol-2-yl)-ureido]-4-[(S)-3-(4-fluoro-benzyl)-piperidin-1-ylmethyl]-piperidine-1-carboxylic acid methyl ester;

(3R,4S)-3-[3-(5-acetyl-4-methyl-thiazol-2-yl)-ureido]-4-[(S)-3-(4-fluoro-benzyl)-piperidin-1-ylmethyl]-piperidine-1-carboxylic acid tert-butyl ester;

1-{(3R,4S)-1-acetyl-4-[(S)-3-(4-fluoro-benzyl)-piperidin-1-ylmethyl]-piperidin-3-yl}-3-(5-acetyl-4-methyl-thiazol-2-yl)-urea;

1-(5-acetyl-4-methyl-thiazol-2-yl)-3-{(3R,4S)-4-[(S)-3-(4-fluoro-benzyl)-piperidin-1-ylmethyl]-1-propionyl-piperidin-3-yl}-urea;

1-(5-acetyl-4-methyl-thiazol-2-yl)-3-{(3R,4S)-4-[(S)-3-(4-fluoro-benzyl)-piperidin-1-ylmethyl]-1-(2-methyl-propionyl)-piperidin-3-yl}-urea;

1-(5-acetyl-4-methyl-thiazol-2-yl)-3-{(3R,4S)-1-(2,2-dimethyl-propionyl)-4-[(S)-3-(4-fluoro-benzyl)-piperidin-1-ylmethyl]-piperidin-3-yl}-urea;

1-(5-acetyl-4-methyl-thiazol-2-yl)-3-{(3R,4S)-1-cyclopropanecarbonyl-4-[(S)-3-(4-fluoro-benzyl)-piperidin-1-ylmethyl]-piperidin-3-yl}-urea;

1-(5-acetyl-4-methyl-thiazol-2-yl)-3-{(3R,4S)-1-cyclobutanecarbonyl-4-[(S)-3-(4-fluoro-benzyl)-piperidin-1-ylmethyl]-piperidin-3-yl}-urea;

1-(5-acetyl-4-methyl-thiazol-2-yl)-3-{(3R,4S)-1-cyclopentanecarbonyl-4-[(S)-3-(4-fluoro-benzyl)-piperidin-1-ylmethyl]-piperidin-3-yl}-urea;

1-(5-acetyl-4-methyl-thiazol-2-yl)-3-{(3R,4S)-1-cyclohexanecarbonyl-4-[(S)-3-(4-fluoro-benzyl)-piperidin-1-ylmethyl]-piperidin-3-yl}-urea;

1-(5-acetyl-4-methyl-thiazol-2-yl)-3-{(3R,4S)-4-[(S)-3-(4-fluoro-benzyl)-piperidin-1-ylmethyl]-1-(tetrahydro-pyran-4-carbonyl)-piperidin-3-yl}-urea;

1-(5-acetyl-4-methyl-thiazol-2-yl)-3-{(3R,4S)-4-[(S)-3-(4-fluoro-benzyl)-piperidin-1-ylmethyl]-1-(2-methoxy-acetyl)-piperidin-3-yl}-urea;

1-(5-acetyl-4-methyl-thiazol-2-yl)-3-{(3R,4S)-1-(2-dimethylamino-acetyl)-4-[(S)-3-(4-fluoro-benzyl)-piperidin-1-ylmethyl]-piperidin-3-yl}-urea;

(3R,4S)-3-[3-(5-acetyl-4-methyl-thiazol-2-yl)-ureido]-4-[(S)-3-(4-fluoro-benzyl)-piperidin-1-ylmethyl]-piperidine-1-carboxylic acid methylamide;

(3R,4S)-3-[3-(5-acetyl-4-methyl-thiazol-2-yl)-ureido]-4-[(S)-3-(4-fluoro-benzyl)-piperidin-1-ylmethyl]-piperidine-1-carboxylic acid ethylamide;

(3R,4S)-3-[3-(5-acetyl-4-methyl-thiazol-2-yl)-ureido]-4-[(S)-3-(4-fluoro-benzyl)-piperidin-1-ylmethyl]-piperidine-1-carboxylic acid propylamide;

(3R, 4S)-3-[3-(5-acetyl-4-methyl-thiazol-2-yl)-ureido]-4-[(S)-3-(4-fluoro-benzyl)-piperidin-1-ylmethyl]-piperidine-1-carboxylic acid isopropylamide;

(3R,4S)-3-[3-(5-acetyl-4-methyl-thiazol-2-yl)-ureido]-4-[(S)-3-(4-fluoro-benzyl)-piperidin-1-ylmethyl]-piperidine-1-carboxylic acid allylamide;

(3R,4S)-3-[3-(5-acetyl-4-methyl-thiazol-2-yl)-ureido]-4-[(S)-3-(4-fluoro-benzyl)-piperidin-1-ylmethyl]-piperidine-1-carboxylic acid (5-acetyl-4-methyl-thiazol-2-yl)-amide;

1-(5-acetyl-4-methyl-thiazol-2-yl)-3-{(3R,4S)-4-[(S)-3-(4-fluoro-benzyl)-piperidin-1-ylmethyl]-1-methyl-piperidin-3-yl}-urea;

1-(5-acetyl-4-methyl-thiazol-2-yl)-3-{(3R,4S)-4-[(S)-3-(4-fluoro-benzyl)-piperidin-1-ylmethyl]-[1,4']bipiperidinyl-3-yl}-urea;

1-{(3R,4S)-1'-acetyl-4-[(S)-3-(4-fluoro-benzyl)-piperidin-1-ylmethyl]-[1,4']bipiperidinyl-3-yl}-3-(5-acetyl-4-methyl-thiazol-2-yl)-urea;

1-(5-acetyl-4-methyl-thiazol-2-yl)-3-{(3R,4S)-4-[(S)-3-(4-fluoro-benzyl)-piperidin-1-ylmethyl]-1'-methyl-[1,4']bipiperidinyl-3-yl}-urea;

1-(5-acetyl-4-methyl-thiazol-2-yl)-3-{(3R,4S)-1-cyclopropylmethyl-4-[(S)-3-(4-fluoro-benzyl)-piperidin-1-ylmethyl]-piperidin-3-yl}-urea;

1-(5-acetyl-4-methyl-thiazol-2-yl)-3-[(3R,4S)-4-[(S)-3-(4-fluoro-benzyl)-piperidin-1-ylmethyl]-1-(tetrahydro-pyran-2-ylmethyl)-piperidin-3-yl]-urea;

1-(5-acetyl-4-methyl-thiazol-2-yl)-3-{(3R,4S)-4-[(S)-3-(4-fluoro-benzyl)-piperidin-1-ylmethyl]-1-furan-2-ylmethyl-piperidin-3-yl}-urea;

1-(5-acetyl-4-methyl-thiazol-2-yl)-3-{(3R,4S)-4-[(S)-3-(4-fluoro-benzyl)-piperidin-1-ylmethyl]-1-furan-3-ylmethyl-piperidin-3-yl}-urea;

1-(5-acetyl-4-methyl-thiazol-2-yl)-3-{(3R,4S)-4-[(S)-3-(4-fluoro-benzyl)-piperidin-1-ylmethyl]-1-[1,2,4]oxadiazol-3-ylmethyl-piperidin-3-yl}-urea;

1-(5-acetyl-4-methyl-thiazol-2-yl)-3-{(3R,4S)-4-[(S)-3-(4-fluoro-benzyl)-piperidin-1-ylmethyl]-1-(2-fluoro-ethyl)-piperidin-3-yl}-urea;

1-(5-acetyl-4-methyl-thiazol-2-yl)-3-{(3R,4S)-4-[(S)-3-(4-fluoro-benzyl)-piperidin-1-ylmethyl]-1(2-hydroxy-ethyl)-piperidin-3-yl}-urea;

1-(5-acetyl-4-methyl-thiazol-2-yl)-3-{(3R,4S)-1-(2-ethanesulfonyl-ethyl)-4-[(S)-3-(4-fluoro-benzyl)-piperidin-1-ylmethyl]-piperidin-3-yl}-urea;

1-(5-acetyl-4-methyl-thiazol-2-yl)-3-{(3R,4S)-1-cyanomethyl-4-[(S)-3-(4-fluoro-benzyl)-piperidin-1-ylmethyl]-piperidin-3-yl}-urea;

1-(5-acetyl-4-methyl-thiazol-2-yl)-3-{(3R,4S)-4-[(S)-3-(4-fluoro-benzyl)-piperidin-1-ylmethyl]-1-(2-hydroxy-propyl)-piperidin-3-yl}-urea;

1-(5-acetyl-4-methyl-thiazol-2-yl)-3-{(3R,4S)-4-[(S)-3-(4-fluoro-benzyl)-piperidin-1-ylmethyl]-1-[(S)-2-hydroxy-2-methyl-propyl]-piperidin-3-yl}-urea;

1-(5-acetyl-4-methyl-thiazol-2-yl)-3-{(3R,4S)-4-[(S)-3-(4-fluoro-benzyl)-piperidin-1-ylmethyl]-1-[(R)-2-hydroxy-2-methyl-propyl]-piperidin-3-yl}-urea;

1-(5-acetyl-4-methyl-thiazol-2-yl)-3-{(3R,4S)-4-[(S)-3-(4-fluoro-benzyl)-piperidin-1-ylmethyl]-1-(2-oxo-propyl)-piperidin-3-yl}-urea;

2-{(3R,4S)-3-[3-(5-acetyl-4-methyl-thiazol-2-yl)-ureido]-4-[(S)-3-(4-fluoro-benzyl)-piperidin-1-ylmethyl]-piperidin-1-yl}-N,N-dimethyl-acetamide;

1-{(3R,4S)-4-[(S)-3-(4-fluoro-benzyl)-piperidin-1-ylmethyl]-1-isobutyryl-piperidin-3-yl}-3-[3-(1-methyl-1H-tetrazol-5-yl)-phenyl]-urea;

1-{(3R,4S)-1-benzoyl-4-[(S)-3-(4-fluoro-benzyl)-piperidin-1-ylmethyl]-piperidin-3-yl}-3-[3-(1-methyl-1H-tetrazol-5-yl)-phenyl]-urea;

1-{(3R,4S)-4-[(S)-3-(4-fluoro-benzyl)-piperidin-1-ylmethyl]-1-(propane-2-sulfonyl)-piperidin-3-yl}-3-[3-(1-methyl-1H-tetrazol-5-yl)-phenyl]-urea;

1-{(3R,4S)-4-[(S)-3-(4-fluoro-benzyl)-piperidin-1-ylmethyl]-piperidin-3-yl}-3-(2-morpholin-4-yl-ethyl)-urea;

(3R,4S)-4-[(S)-3-(4-fluoro-benzyl)-piperidin-1-ylmethyl]-3-[3-(2-morpholin-4-yl-ethyl)-ureido]-piperidine-1-carboxylic acid methyl ester;

1-{(3R,4S)-1-acetyl-4-[(S)-3-(4-fluoro-benzyl)-piperidin-1-ylmethyl]-piperidin-3-yl}-3-(2-morpholin-4-yl-ethyl)-urea;

1-{(3R,4S)-4-[(S)-3-(4-fluoro-benzyl)-piperidin-1-ylmethyl]-1-propionyl-piperidin-3-yl}-3-(2-morpholin-4-yl-ethyl)-urea;

1-{(3R,4S)-1-(2,2-dimethyl-propionyl)-4-[(S)-3-(4-fluoro-benzyl)-piperidin-1-ylmethyl]-piperidin-3-yl}-3-(2-morpholin-4-yl-ethyl)-urea;

1-{(3R,4S)-1-cyclobutanecarbonyl-4-[(S)-3-(4-fluoro-benzyl)-piperidin-1-ylmethyl]-piperidin-3-yl}-3-(2-morpholin-4-yl-ethyl)-urea;

1-{(3R,4S)-4-[(S)-3-(4-fluoro-benzyl)-piperidin-1-ylmethyl]-1-(tetrahydro-pyran-4-carbonyl)-piperidin-3-yl}-3-(2-morpholin-4-yl-ethyl)-urea;

1-{(3R,4S)-4-[(S)-3-(4-fluoro-benzyl)-piperidin-1-ylmethyl]-1-(2-methoxy-acetyl)-piperidin-3-yl}-3-(2-morpholin-4-yl-ethyl)-urea;

(3R,4S)-4-[(S)-3-(4-fluoro-benzyl)-piperidin-1-ylmethyl]-3-[3-(2-morpholin-4-yl-ethyl)-ureido]-piperidine-1-carboxylic acid dimethylamide;

(3R,4S)-4-[(S)-3-(4-fluoro-benzyl)-piperidin-1-ylmethyl]-3-[3-(2-morpholin-4-yl-ethyl)-ureido]-piperidine-1-carboxylic acid ethylamide;

1-{(3R,4S)-4-[(S)-3-(4-fluoro-benzyl)-piperidin-1-ylmethyl]-1-methanesulfonyl-piperidin-3-yl}-3-(2-morpholin-4-yl-ethyl)-urea;

1-{(3R,4S)-4-[(S)-3-(4-fluoro-benzyl)-piperidin-1-ylmethyl]-1-methyl-piperidin-3-yl}-3-(2-morpholin-4-yl-ethyl)-urea;

1-{(3R,4S)-1-ethyl-4-[(S)-3-(4-fluoro-benzyl)-piperidin-1-ylmethyl]-piperidin-3-yl}-3-(2-morpholin-4-yl-ethyl)-urea;

1-{(3R,4S)-4-[(S)-3-(4-fluoro-benzyl)-piperidin-1-ylmethyl]-1-isopropyl-piperidin-3-yl}-3-(2-morpholin-4-yl-ethyl)-urea;

1-{(3R,4S)-1-cyclopropylmethyl-4-[(S)-3-(4-fluoro-benzyl)-piperidin-1-ylmethyl]-piperidin-3-yl}-3-(2-morpholin-4-yl-ethyl)-urea;

1-{(3R,4S)-4-[(S)-3-(4-fluoro-benzyl)-piperidin-1-ylmethyl]-1-(2-oxo-propyl)-piperidin-3-yl}-3-(2-morpholin-4-yl-ethyl)-urea;

1-{(3R,4S)-4-[(S)-3-(4-fluoro-benzyl)-piperidin-1-ylmethyl]-tetrahydro-pyran-3-yl}-3-[3-(1-methyl-1H-tetrazol-5-yl)-phenyl]-urea;

1-{(3R,4S)-4-[(S)-3-(4-fluoro-benzyl)-piperidin-1-ylmethyl]-tetrahydro-pyran-3-yl}-3-[3-methyl-5-(1-methyl-1H-tetrazol-5-yl)-phenyl]-urea;

1-(5-acetyl-4-methyl-thiazol-2-yl)-3-{(3R,4S)-4-[(S)-3-(4-fluoro-benzyl)-piperidin-1-ylmethyl]-tetrahydro-pyran-3-yl}-urea;

(3R,4R)-3-[(S)-3-(4-fluoro-benzyl)-piperidin-1-ylmethyl]-4-[3-(4-fluoro-phenyl)-ureido]-piperidine-1-carboxylic acid methyl ester;

1-{(3R,4R)-1-(2-dimethylamino-acetyl)-3-[(S)-3-(4-fluoro-benzyl)-piperidin-1-ylmethyl]-piperidin-4-yl}-3-(4-fluoro-phenyl)-urea;

1-{(3R,4R)-3-[(S)-3-(4-fluoro-benzyl)-piperidin-1-ylmethyl]-1-methanesulfonyl-piperidin-4-yl}-3-(4-fluoro-phenyl)-urea;

1-{(3R,4R)-3-[(S)-3-(4-fluoro-benzyl)-piperidin-1-ylmethyl]-1-thiazol-2-ylmethyl-piperidin-4-yl}-3-(4-fluoro-phenyl)-urea;

1-[(3R, 4R)-3-[(S)-3-(4-fluoro-benzyl)-piperidin-1-ylmethyl]-1-(2-hydroxy-ethyl)-piperidin-4-yl]-3-(4-fluoro-phenyl)-urea;

1-[(3R,4R)-3-[(S)-3-(4-fluoro-benzyl)-piperidin-1-ylmethyl]-1-(2-methoxy-ethyl)-piperidin-4-yl]-3-(4-fluoro-phenyl)-urea;

1-[(3R,4R)-3-[(S)-3-(4-fluoro-benzyl)-piperidin-1-ylmethyl]-1-(2-morpholin-4-yl-ethyl)-piperidin-4-yl]-3-(4-fluoro -phenyl)-urea;

1-[(3S,4R)-3-[(S)-3-(4-fluoro-benzyl)-piperidin-1-ylmethyl]-1-(2-hydroxy-propyl )-piperidin-4-yl]-3-(4-fluoro-phenyl)-urea;

(3R,4R)-4-[3-(3,5-diacetyl-phenyl)-ureido]-3-[(S)-3-(4-fluoro-benzyl)-piperidin-1-ylmethyl]-piperidine-1-carboxylic acid methyl ester;

1-(3,5-diacetyl-phenyl)-3-{(3R,4R)-1-(2-dimethylamino-acetyl)-3-[(S)-3-(4-fluoro-benzyl)-piperidin-1-ylmethyl]-piperidin-4-yl}-urea;

1-(3,5-diacetyl-phenyl)-3-{(3R,4R)-3-[(S)-3-(4-fluoro-benzyl)-piperidin-1-ylmethyl]-1-methanesulfonyl-piperidin-4-yl}-urea;

1-(3,5-diacetyl-phenyl)-3-{(3R,4R)-1-(1,1-dioxo-hexahydro-1λ6-thiopyran-4-yl)-3-[(S)-3-(4-fluoro-benzyl)-piperidin-1-ylmethyl]-piperidin-4-yl}-urea;

1-(3,5-diacetyl-phenyl)-3-{(3R,4R)-3-[(S)-3-(4-fluoro-benzyl)-piperidin-1-ylmethyl]-1-thiazol-2-ylmethyl-piperidin-4-yl}-urea;

1-(3,5-diacetyl-phenyl)-3-[(3R,4R)-3-[(S)-3-(4-fluoro-benzyl)-piperidin-1-ylmethyl]-1-(2-hydroxy-ethyl)-piperidin-4-yl]-urea;

1-(3,5-diacetyl-phenyl)-3-[(3R,4R)-3-[(S)-3-(4-fluoro-benzyl)-piperidin-1-ylmethyl]-1-(2-methoxy-ethyl)-piperidin-4-yl]-urea;

1-(3,5-diacetyl-phenyl)-3-[(3R,4R)-3-[(S)-3-(4-fluoro-benzyl)-piperidin-1-ylmethyl]-1-(2-morpholin-4-yl-ethyl)-piperidin-4-yl]-urea;

1-(3,5-diacetyl-phenyl)-3-[(3S,4R)-3-[(S)-3-(4-fluoro-benzyl)-piperidin-1-ylmethyl]-1-(2-hydroxy-propyl)-piperidin-4-yl]-urea;

(3R,4R)-3-[(S)-3-(4-fluoro-benzyl)-piperidin-1-ylmethyl]-4-{3-[3-methyl-5-(1-methyl-1H-tetrazol-5-yl)-phenyl]-ureido}-piperidine-1-carboxylic acid methyl ester;

1-{(3R,4R)-1-(2-dimethylamino-acetyl)-3-[(S)-3-(4-fluoro-benzyl)-piperidin-1-ylmethyl]-piperidin-4-yl}-3-[3-methyl-5-(1-methyl-1H-tetrazol-5-yl)-phenyl]-urea;

1-{(3R,4R)-3-[(S)-3-(4-fluoro-benzyl)-piperidin-1-ylmethyl]-1-methanesulfonyl-piperidin-4-yl}-3-[3-methyl-5-(1-methyl-1H-tetrazol-5-yl)-phenyl]-urea;

1-{(3R,4R)-3-[(S)-3-(4-fluoro-benzyl)-piperidin-1-ylmethyl]-1-thiazol-2-ylmethyl-piperidin-4-yl}-3-[3-methyl-5-(1-methyl-1H-tetrazol-5-yl)-phenyl]-urea;

1-[(3R,4R)-3-[(S)-3-(4-fluoro-benzyl)-piperidin-1-ylmethyl]-1-(2-hydroxy-ethyl)-piperidin-4-yl]-3-[3-methyl-5-(1-methyl-1H-tetrazol-5-yl)-phenyl]-urea;

1-[(3R,4R)-3-[(S)-3-(4-fluoro-benzyl)-piperidin-1-ylmethyl]-1-(2-methoxy-ethyl)-piperidin-4-yl]-3-[3-methyl-5-(1-methyl-1H-tetrazol-5-yl)-phenyl]-urea;

1-[(3R,4R)-3-[(S)-3-(4-fluoro-benzyl)-piperidin-1-ylmethyl]-1-(2-morpholin-4-yl-ethyl)-piperidin-4-yl]-3-[3-methyl-5-(1-methyl-1H-tetrazol-5-yl)-phenyl]-urea;

1-[(3S,4R)-3-[(S)-3-(4-fluoro-benzyl)-piperidin-1-ylmethyl]-1-(2-hydroxy-propyl)-piperidin-4-yl]-3-[3-methyl-5-(1-methyl-1H-tetrazol-5-yl)-phenyl]-urea;

(3R,4R)-3-[(S)-3-(4-fluoro-benzyl)-piperidin-1-ylmethyl]-4-{3-[3-bromo-5-(1-methyl-1H-tetrazol-5-yl)-phenyl]-ureido}-piperidine-1-carboxylic acid methyl ester;

1-{(3R,4R)-1-(2-dimethylamino-acetyl)-3-[(S)-3-(4-fluoro-benzyl)-piperidin-1-ylmethyl]-piperidin-4-yl}-3-[3-bromo-5-(1-methyl-1H-tetrazol-5-yl)-phenyl]-urea;

1-{(3R,4R)-3-[(S)-3-(4-fluoro-benzyl)-piperidin-1-ylmethyl]-1-methanesulfonyl-piperidin-4-yl}-3-[3-bromo-5-(1-methyl-1H-tetrazol-5-yl)-phenyl]-urea;

1-{(3R,4R)-3-[(S)-3-(4-fluoro-benzyl)-piperidin-1-ylmethyl]-1-thiazol-2-ylmethyl-piperidin-4-yl}-3-[3-bromo-5-(1-methyl-1H-tetrazol-5-yl)-phenyl]-urea;

1-[(3R,4R)-3-[(S)-3-(4-fluoro-benzyl)-piperidin-1-ylmethyl]-1-(2-hydroxy-ethyl)-piperidin-4-yl]-3-[3-bromo-5-(1-methyl-1H-tetrazol-5-yl)-phenyl]-urea;

1-[(3R,4R)-3-[(S)-3-(4-fluoro-benzyl)-piperidin-1-ylmethyl]-1-(2-methoxy-ethyl)-piperidin-4-yl]-3-[3-bromo-5-(1-methyl-1H-tetrazol-5-yl)-phenyl]-urea;

1-[(3R,4R)-3-[(S)-3-(4-fluoro-benzyl)-piperidin-1-ylmethyl]-1-(2-morpholin-4-yl-ethyl)-piperidin-4-yl]-3-[3-bromo-5-(1-methyl-1H-tetrazol-5-yl)-phenyl]-urea;

1-[(3S,4R)-3-[(S)-3-(4-fluoro-benzyl)-piperidin-1-ylmethyl]-1-(2-hydroxy-propyl)-piperidin-4-yl]-3-[3-bromo-5-(1-methyl-1H-tetrazol-5-yl)-phenyl]-urea;

(3R,4S)-3-(3-benzyl-ureido)-4-[(S)-3-(4-fluoro-benzyl)-piperidin-1-ylmethyl]-piperidine-1-carboxylic acid tert-butyl ester;

1-benzyl-3-{(3R,4S)-4-[(S)-3-(4-fluoro-benzyl)-piperidin-1-ylmethyl]-piperidin-3-yl}-urea;

(3R,4S)-4-[(S)-3-(4-fluoro-benzyl)-piperidin-1-ylmethyl]-3-[3-(tetrahydro-pyran-4-ylmethyl)-ureido]-piperidine-1-carboxylic acid tert-butyl ester;

1-{(3R,4S)-4-[(S)-3-(4-fluoro-benzyl)-piperidin-1-ylmethyl]-piperidin-3-yl}-3-(tetrahydro-pyran-4-ylmethyl)-urea;

(3R,4S)-4-[(S)-3-(4-fluoro-benzyl)-piperidin-1-ylmethyl]-3-{3-[2-(tetrahydro-pyran-4-yl)-ethyl]-ureido}-piperidine-1-carboxylic acid tert-butyl ester;

1-{(3R,4S)-4-[(S)-3-(4-fluoro-benzyl)-piperidin-1-ylmethyl]-piperidin-3-yl}-3-[2-(tetrahydro-pyran-4-yl)-ethyl]-urea;

1-{(3S,4S)-4-[(S)-3-(4-Fluoro-benzyl)-piperidin-1-ylmethyl]-tetrahydro-pyran-3-yl}-3-[3-methyl-5-(1-methyl-1H-tetrazol-5-yl)-phenyl]-urea;

1-{(3S,4S)-4-[(S)-3-(4-fluoro-benzyl)-piperidin-1-ylmethyl]-tetrahydro-pyran-3-yl}-3-[3-(1-methyl-1H-tetrazol-5-yl)-phenyl]-urea;

1-{(3S,4S)-4-[(S)-3-(4-fluorobenzyl)-piperidin-1-ylmethyl]-tetrahydro-pyran-3-yl}-3-[5-acetyl-4-methylthiazol-2-yl]-urea;

1-{(3S,4S)-4-[(S)-3-(4-fluorobenzyl)-piperidin-1-ylmethyl]-tetrahydro-pyran-3-yl}-3-(3-acetylphenyl)-urea;

1-{(3S,4S)-4-[(S)-3-(4-fluorobenzyl)-piperidin-1-ylmethyl]-tetrahydro-pyran-3-yl}-3-(2-morpholin-4-yl-ethyl)-urea;

1-{(3S,4S)-4-[(S)-3-(4-fluorobenzyl)-piperidin-1-ylmethyl]-1,1-dioxo-tetrahydrothiophen-3-yl}-3-[5-acetyl-4-methylthiazol-2-yl]-urea;

1-{(3S,4S)-4-[(S)-3-(4-fluorobenzyl)-piperidin-1-ylmethyl]-1,1-dioxo-tetrahydrothiophen-3-yl}-3-[3-(1-methyl-1H-tetrazol-5-yl)-phenyl]-urea;

1-{(3S,4S)-4-[(S)-3-(4-fluorobenzyl)-piperidin-1-ylmethyl]-1,1-dioxo-tetrahydrothiophen-3-yl}-3-[3-acetylphenyl]-urea;

1-{(3S,4S)-4-[(S)-3-(4-fluorobenzyl)-piperidin-1-ylmethyl]-1,1-dioxo-tetrahydrothiophen-3-yl}-3-(2-morpholin-4-yl-ethyl)-urea;

1-(5-acetyl-4-methyl-thiazol-2-yl)-3-{(3R,4S)-4-[(S)-3-(4-fluorobenzyl)-piperidine-1-carbonyl]-1,1-dioxo-tetrahydro-1λ6-thiophen-3-yl}-urea;

1-{(3R,4S)-4-[(S)-3-(4-fluorobenzyl)-piperidine-1-carbonyl]-1,1-dioxo-tetrahydrothiophen-3-yl}-3-(2-morpholin-4-yl-ethyl)-urea;

(3S,4S)-3-[(S)-3-(4-fluorobenzyl)-piperidin-1-ylmethyl]-4-{3-[3-methyl-5-(1-methyl-1H-tetrazol-5-yl)-phenyl]-ureido}-pyrrolidine-1-carboxylic acid tert-butyl ester;

1-(5-acetyl-4-methylthiazol-2-yl)-3-{(3S,4S)-4-[(S)-3-(4-fluorobenzyl)-piperidin-1-ylmethyl]-pyrrolidin-3-yl}-urea.

10. A pharmaceutical composition, comprising a pharmaceutically acceptable carrier and a therapeutically effective amount of a compound according to claim 1.

11. A method for inhibiting the chemokine receptor activity comprising administering to a patient in need thereof a chemokine receptor inhibitory amount of a compound according to claim 1.

12. A method for treating asthma, comprising administering to a patient in need thereof a therapeutically effective amount of a compound according to claim 1.

13. A pharmaceutical composition comprising a pharmaceutically acceptable carrier and a therapeutically effective amount of a compound according to claim 9, or a pharmaceutically acceptable salt thereof.

14. The method of claim 11 wherein the chemokine wherein the chemokine receptor is $CCR^3$.

15. A method for treating an inflammatory disorder comprising administering to a patient in need thereof a therapeutically effective amount of a compound according to claim 9, or a pharmaceutically acceptable salt thereof.

16. A method according to claim 15, wherein the disorder is selected from asthma, allergic rhinitis, atopic dermatitis, inflammatory bowel diseases, idiopathic pulmonary fibrosis, bullous pemphigoid, allergic colitis, eczema, conjunctivitis, familial eosinophilia, eosinophilic cellulitis, eosinophilic pneumonias, eosinophilic fasciitis, and eosinophilic gastroenteritis.

17. The method according to claim 16, wherein the disorder is selected from asthma, allergic rhinitis, atopic dermatitis, and inflammatory bowel diseases.

18. A method for inhibiting the chemokine receptor activity comprising administering to a patient in need thereof a chemokine receptor inhibitory amount of a compound of formula (I):

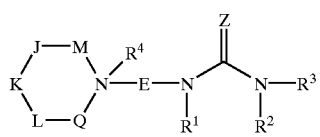
(I)

or stereoisomer or pharmaceutically acceptable salt thereof, wherein:

M is selected from $CH_2$, $CHR^5$, $CHR^{13}$, $CR^{13}R^{13}$, and $CR^5R^{13}$;

Q is selected from $CH_2$, $CHR^5$, $CHR^{13}$, $CR^{13}R^{13}$, and $CR^5R^{13}$;

J and K are independently selected from $CH_2$, $CHR^5$, $CHR^6$, $CR^6R^6$ and $CR^5R^6$;

L is selected from $CHR^5$ and $CR^5R^6$;

Z is selected from O, S $NR^{1a}$, $C(CN)_2$, $CH(NO_2)$, and CHCN;

$R^{1a}$ is selected from H, $C_{1-6}$ alkyl, $C_{3-6}$ cycloalkyl, $CONR^{1b}R^{1b}$, $OR^{1b}$, CN, $NO_2$, and $(CH_2)_w$phenyl;

$R^{1b}$ is independently selected from H, $C_{1-3}$ alkyl, $C_{3-6}$ cycloalkyl, and phenyl;

E is

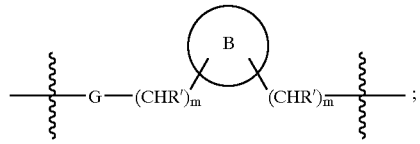

G is selected from a bond, C=O, and $SO_2$;

Ring B is a 5, 6, or 7 membered saturated heterocyclic ring wherein one of the heterocycle ring atoms is selected from $-NR^9-$, $-O-$, and $-S(O)_p-$, or two of the heterocycle ring atoms are selected from $-NR^{9d}C(O)-$, $-C(O)NR^{9d}-$, $-C(O)O-$, $-OC(O)-$, $-NRR^{9d}S(O)_2-$, and $-S(O)_2NR^{9d}$, the heterocycle ring being selected from piperidine, tetrahydropyran, tetrahydrothiopyran, tetrahydrothiopyran 1,1-dioxide, tetrahydrothiopyran 1-monooxide, piperidin-2-ones tetrahydropyran-2-one, [1,2]thiazinane 1,1-dioxide, pyrrolidine, tetrahydrofuran, tetrahydrothiophene, pyrrolidin-2-one, dihydrofuran-2-one, and isothiazolidine 1,1-dioxide, and being optionally substituted by 0–2 $R^8$;

$R^1$ and $R^2$ are independently selected from H, $C_{1-8}$ alkyl, $C_{3-8}$ alkenyl, $C_{3-8}$ alkynyl, and $(CH_2)_rC_{3-6}$ cycloalkyl;

$R^3$ is selected from methyl substituted with 0–1 $R^{10}$, $C_{2-8}$ alkyl substituted with 0–3 $R^7$, $C_{3-8}$ alkenyl substituted with 0–3 $R^7$, $C_{3-8}$ alkynyl substituted with 0–3 $R^7$, $C_2$ fluoroalkyl, $C_{3-8}$ haloalkyl, a $(CR^{3'}R^{3"})_r$—$C_{3-10}$ carbocyclic residue substituted with 0–5 $R^{15}$ and a $(CR^{3'}R^{3"})_r$-5–10 membered heterocyclic system containing 1–4 heteroatoms selected from N, O, and S, substituted with 0–3 $R^{15}$;

$R^{3'}$ and $R^{3"}$, at each occurrence, are selected from H, $C_{1-6}$ alkyl, $(CH_2)_rC_{3-6}$ cycloalkyl, and phenyl;

$R^4$ is absent, taken with the nitrogen to which it is attached to form an N-oxide, or selected from $C_{1-8}$ alkyl, $C_{3-8}$ alkenyl, $C_{3-8}$ alkynyl, $(CH_2)_rC_{3-6}$ cycloalkyl, $(CH_2)_qC(O)R^{4b}$, $(CH_2)_qC(O)NR^{4a}R^{4a'}$, $(CH_2)_qC(O)OR^{4b}$, and a $(CH_2)_r$—$C_{3-10}$ carbocyclic residue substituted with 0–3 $R^{4c}$;

$R^{4a}$ and $R^{4a'}$, at each occurrence, are selected from H, $C_{1-6}$ alkyl, $(CH_2)_rC_{3-6}$ cycloalkyl, and phenyl;

$R^{4b}$, at each occurrence, is selected from $C_{1-6}$ alkyl, $C_{3-8}$ alkenyl, $(CH_2)_rC_{3-6}$ cycloalkyl, $C_{3-8}$ alkynyl, and phenyl;

$R^{4c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, $(CH_2)_rNR^{4a}R^{4a'}$, and $(CH_2)_r$phenyl;

$R^5$ is selected from a $(CR^{5'}R^{5"})_r$—$C_{3-10}$ carbocyclic residue substituted with 0–5 $R^{16}$ and a $(CR^{5'}R^{5"})_r$-5–10 membered heterocyclic system containing 1–4 heteroatoms selected from N, O, and S, substituted with 0–3 $R^{16}$;

$R^{5'}$ and $R^{5"}$, at each occurrence, are selected from H, $C_{1-6}$ alkyl, $(CH_2)_rC_{3-6}$ cycloalkyl, and phenyl;

$R^6$, at each occurrence, is selected from $C_{1-6}$ alkyl, $C_{2-8}$ alkenyl, $C_{2-8}$ alkynyl, $(CH_2)_rC_{3-6}$ cycloalkyl, $(CF_2)_rCF_3$, CN, $(CH_2)_rNR^{6a}R^{6a'}$, $(CH_2)_rOH$, $(CH_2)_rOR^{6b}$, $(CH_2)_rSH$, $(CH_2)_rSR^{6b}$, $(CH_2)_rC(O)OH$, $(CH_2)_rC(O)R^{6b}$, $(CH_2)_rC(O)NR^{6a}R^{6a}$, $(CH_2)_rNR^{6d}C(O)R^{6a}$, $(CH_2)_rC(O)OR^{6b}$, $(CH_2)_rOC(O)R^{6b}$, $(CH_2)_rS(O)_pR^{6b}$, $(CH_2)_rS(O)_2NR^{6a}R^{6a}$, $(CH_2)_rNR^{6d}S(O)_2R^{6b}$, and $(CH_2)_r$phenyl substituted with 0–3 $R^{6c}$;

$R^{6a}$ and $R^{6a'}$, at each occurrence, are selected from H, $C_{1-6}$ alkyl, $C_{3-6}$ cycloalkyl, and phenyl substituted with 0–3 $R^{6c}$;

$R^{6b}$, at each occurrence, is selected from $C_{1-6}$ alkyl, $C_{3-6}$ cycloalkyl, and phenyl substituted with 0–3 $R^{6c}$;

$R^{6c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{6d}R^{6d}$;

$R^{6d}$, at each occurrence, is selected from H, $C_{1-6}$ alkyl, and $C_{3-6}$ cycloalkyl;

with the proviso that when any of J or K is $CR^6R^6$ and $R^6$ is cyano, or bonded to the carbon to which it is attached through a heteroatom, the other $R^6$ is not cyano, or bonded to the carbon to which it is attached through a heteroatom;

$R^7$ is selected from $NO_2$, CN, $NR^{7a}R^{7a'}$, OH, $OR^{7d}$, $C(O)H$, $C(O)OH$, $C(O)R^{7b}$, $C(O)NR^{7a}R^{7a'}$, $NR^{7f}C(O)OR^{7d}$, $OC(O)NR^{7a}R^{7a'}$, $NR^{7f}C(O)R^{7b}$, $NR^{7f}C(O)NR^{7f}R^{7f}$, $C(O)OR^{7d}$, $OC(O)R^{7b}$, $C(=NR^{7f})NR^{7a}R^{7a'}$, $NHC(=NR^{7f})NR^{7f}R^{7f}$, $S(O)_pR^{7b}$, $S(O)_2NR^{7a}R^{7a'}$, $NR^{7f}S(O)_2R^{7b}$, $C_{1-6}$ haloalkyl;

$R^{7a}$ and $R^{7a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0–5 $R^{7e}$, and a $(CH_2)_r$-5–10 membered heterocyclic system containing 1–4 heteroatoms selected from N, O, and S, substituted with 0–2 $R^{7e}$;

alternatively, $R^{7a}$ and $R^{7a'}$, along with the N to which they are attached, join to form a 5–6 membered heterocyclic system containing 1–2 heteroatoms selected from $NR^{7h}$, O, and S and optionally fused with a benzene ring or a 6-membered aromatic heterocycle;

$R^{7b}$, at each occurrence, is selected from H, $C_{1-6}$ alkyl, $C_{3-8}$ alkenyl, $C_{3-8}$ alkynyl, a $(CH_2)_r$—$C_{3-6}$ carbocyclic residue substituted with 0–3 $R^{7e}$, and $(CH_2)_r$-5–6 membered heterocyclic system containing 1–4 heteroatoms selected from N, O, and S, substituted with 0–2 $R^{7e}$;

$R^{7d}$, at each occurrence, is selected from $C_{3-8}$ alkenyl, $C_{3-8}$ alkynyl, methyl, $CF_3$, $C_{2-6}$ alkyl substituted with 0–3 $R^{7e}$, a $(CH_2)_r$—$C_{3-10}$ carbocyclic residue substituted with 0–3 $R^{7e}$, and a $(CH_2)_r$5–membered heterocyclic system containing 1–4 heteroatoms selected from N, O, and S, substituted with 0–3 $R^{7e}$;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, $C(O)C_{1-6}$ alkyl, $C(O)OC_{1-6}$ alkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{7f}R^{7f}$, $(CH_2)_r$phenyl, and a heterocycle substituted with 0–1 $R^{7g}$, wherein the heterocycle is selected from imidazole, thiazole, oxazole, pyrazole, 1,2,4-triazole, 1,2,3-triazole, isoxazole, and tetrazole;

$R^{7f}$, at each occurrence, is selected from H, $C_{1-6}$ alkyl, $C_{3-6}$ cycloalkyl, and phenyl;

$R^{7g}$ is selected from methyl, ethyl, acetyl, and $CF_3$;

$R^{7h}$ is selected from H, $C_{1-6}$ alkyl, $C_{3-6}$ cycloalkyl, $(CH_2)_r$phenyl, $C(O)R^{7f}$, $C(O)OR^{7i}$, and $SO_2R^{7i}$;

$R^{7i}$, at each occurrence, is selected from $C_{1-6}$ alkyl, $C_{3-6}$ cycloalkyl;

$R^8$ is selected from $C_{1-6}$ alkyl, $C_{2-8}$ alkenyl, $C_{2-8}$ alkynyl, $C_{1-6}$ haloalkyl, a $(CH_2)_r$—$C_{3-10}$ carbocyclic residue substituted with 0–3 $R^{8c}$, and a $(CH_2)_r$-5–10 membered heterocyclic system containing 1–4 heteroatoms selected from N, O, and S, substituted with 0–2 $R^{8c}$;

$R^{8a}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{8e}$, and a $(CH_2)_r$-5–10 membered heterocyclic system containing 1–4 heteroatoms selected from N, O, and S, substituted with 0–3 $R^{8e}$;

$R^{8b}$, at each occurrence, is selected from $C_{1-6}$ alkyl, $C_{3-8}$ alkenyl, $C_{3-8}$ alkynyl, a $(CH_2)_r$—$C_{3-6}$ carbocyclic residue substituted with 0–2 $R^{8e}$, and a $(CH_2)_r$-5–membered heterocyclic system containing 1–4 heteroatoms selected from N, O, and S, substituted with 0–3 $R^{8e}$;

$R^{8c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{8f}R^{8f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{8a}$, $(CH_2)_rC(O)$ $NR^{8f}R^{8f}$, $(CH_2)_rNR^{8f}C(O)R^{8a}$, $(CH_2)_rC(O)OC_{1-4}$ alkyl, $(CH_2)_rOC(O)R^{8b}$, $(CH_2)_rS(O)_pR^{8b}$, $(CH_2)_rS(O)_2NR^{8f}R^{8f}$, $(CH_2)_rNR^{8f}S(O)_2R^{8b}$, and $(CH_2)_r$phenyl substituted with 0–3 $R^{8e}$;

$R^{8e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_r$ OH, $(CH_2)_r$SH, $(CH_2)_rSC_{1-5}$ alkyl, $(CH_2)_rNR^{8f}R^{8f}$, and $(CH_2)_r$phenyl;

$R^{8f}$, at each occurrence, is selected from H, $C_{1-6}$ alkyl, and $C_{3-6}$ cycloalkyl;

$R^9$ is selected from H, $CH_3$, $C_{2-6}$ alkyl substituted with 0–3 $R^{9a}$, $C_{3-8}$ alkenyl, $C_{3-8}$ alkynyl, $C_{1-6}$ haloalkyl, $(CHR')_rC(O)C_{1-6}$ alkyl substituted with 0–3 $R^{9j}$, $(CHR')_rC(O)OC_{1-6}$ alkyl substituted with 0–3 $R^{9b}$, $(CHR')_rC(O)NR^{9d}R^{9d'}$, $(CHR')_rS(O)_2C_{1-6}$ alkyl, $S(O)_2C_{1-6}$ haloalkyl, $(CHR')_rS(O)_2NR^{9d}R^{9d}$, $R^{9'}$, $(CHR')_rC(O)R^{9'}$, $(CHR')_rC(O)NR^{9d}R^{9'}$, $(CHR')_rS(O)_2R^{9'}$, and $(CHR')_rS(O)_2NR^{9d}R^{9'}$;

$R^{9'}$, at each occurrence, is independently selected from $(CHR')_rC_{3-6}$ cycloalkyl substituted with 0–3 $R^{9e}$, $(CHR')_r$phenyl substituted with 0–3 $R^{9c}$, $(CHR')_r$-5–10 membered heterocyclic system containing 1–4 heteroatoms selected from N, O, and S, substituted with 0–3 $R^{9c}$, $R^{9a}$, at each occurrence, is selected from ON, $NO_2$, $OC_{1-5}$ alkyl, $CF_3$, OH, $OC_{1-5}$ alkyl, $OC(O)C_{1-5}$ alkyl, $SC_{1-5}$ alkyl, $S(O)_pC_{1-5}$ alkyl, and $NR^{9d}R^{9d'}$;

$R^{9b}$, at each occurrence, is selected from $C_{3-6}$ cycloalkyl, CN, $(CF_2)_rCF_3$, $(CH_2)_qOC_{1-5}$ alkyl, $(CH_2)_qOH$, $(CH_2)_qSC_{1-5}$ alkyl, $(CH_2)_rS(O)_pC_{1-5}$ alkyl, and $(CH_2)_qNR^{9d}R^{9d'}$;

$R^{9c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CHR')_rC(O)C_{1-5}$ alkyl, $(CHR')_r$ $C(O)OC_{1-5}$ alkyl, $(CHR')_rC(O)NR^{9d}R^{9d'}$, $(CH_2)_r$ OH, $(CH_2)_rSC_{1-5}$ alkyl, $(CH_2)_rS(O)_pC_{1-5}$ alkyl, and $(CH_2)_rNR^{9d}R^{9d'}$;

provided that if $R^{9c}$ is attached to a carbon attached to the nitrogen on Ring B, then $R^{9c}$ is selected from $(CH_2)_qOH$, $(CH_2)_qOC_{1-5}$ alkyl, $(CH_2)_qSC_{1-5}$ alkyl, $(CH_2)_qS(O)_qC_{1-5}$ alkyl, and $(CH_2)_qNR^{9d}R^{9d'}$;

$R^{9d}$ and $R^{9d'}$, at each occurrence, are independently selected from H, $C_{1-6}$ alkyl, $C_{3-6}$ cycloalkyl, and phenyl;

alternatively, $R^{9d}$ and $R^{9d'}$, along with the N to which they are attached, join to form a 5–6 membered heterocyclic system containing 1–2 heteroatoms selected from $NR^{9h}$, O, and S and optionally fused with a benzene ring or a 6-membered aromatic heterocycle;

$R^{9e}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CHR')_rC(O)OC_{1-5}$ alkyl, $(CHR')_rC(O)NR^{9d}R^{9d'}$, $(CH_2)_rOH$, $(CH_2)_rSC_{1-5}$ alkyl, $(CH_2)_rS(O)_pC_{1-5}$ alkyl, and $(CH_2)_rNR^{9d}R^{9d'}$, or alternatively, two $R^{9e}$ on the same carbon atom form $=O$;

$R^{9h}$ is selected from H, $C_{1-6}$ alkyl, $C_{3-6}$ cycloalkyl, $(CH_2)_r$phenyl, $C(O)R^{9f}$, $C(O)OR^{9i}$, and $SO_2R^{9i}$;

$R^{9i}$, at each occurrence, is selected from $C_{1-6}$ alkyl, $C_{3-6}$ cycloalkyl;

$R^{9j}$, at each occurrence, is selected from $C_{3-6}$ cycloalkyl, CN, $(CF_2)_rCF_3$, $(CH_2)_rOC_{1-5}$ alkyl, $(CH_2)_rOH$, $(CH_2)_rSC_{1-5}$ alkyl, $(CH_2)_rS(O)_pC_{1-5}$ alkyl, and $(CH_2)_rNR^{9d}R^{9d'}$;

$R^{10}$ is selected from C(O)H, C(O)OH, $C(O)R^{10b}$, $C(O)NR^{10a}R^{10a'}$, $C(O)OR^{10d}$, $C(=NR^{10f})NR^{10a}R^{10a'}$, $S(O)R^{10b}$, $S(O)_2R^{10b}$, $S(O)_2NR^{10a}R^{10a'}$; $R^{10a}$ and $R^{10a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0–5 $R^{10e}$, and a $(CH_2)_r$-5–10 membered heterocyclic system containing 1–4 heteroatoms selected from N, O, and S, substituted with 0–2 $R^{10e}$;

alternatively, $R^{10a}$ and $R^{10a'}$, along With the N to which they are attached, join to form a 5–6 membered heterocyclic system containing 1–2 heteroatoms selected from $NR^{10h}$, O, and S and optionally fused with a benzene ring or a 6-membered aromatic heterocycle;

$R^{10b}$, at each occurrence, is selected from $C_{1-6}$ alkyl, $C_{3-8}$ alkenyl, $C_{3-8}$ alkynyl, a $(CH_2)_r$—$C_{3-6}$ carbocyclic residue substituted with 0–3 $R^{10e}$, and $(CH_2)_r$-5–6 membered heterocyclic system containing 1–4 heteroatoms selected from N, O, and S, substituted with 0–2 $R^{10e}$;

$R^{10d}$, at each occurrence, is selected from $C_{3-8}$ alkenyl, $C_{3-8}$ alkynyl, methyl, $CF_3$, $C_{2-6}$ alkyl substituted with 0–3 $R^{10e}$, a $(CH_2)_r$—$C_{3-10}$ carbocyclic residue substituted with 0–3 $R^{10e}$, and a $(CH_2)_r$5–6 membered heterocyclic system containing 1–4 heteroatoms selected from N, O, and S, substituted with 0–3 $R^{10e}$;

$R^{10e}$, at each occurrence, is selected from $C_{1-6}$ alkyl, $C_{2-8}$ alkenyl, $C_{2-8}$ alkynyl, $(CH_2)_rC_{3-6}$ cycloalkyl, C(O)C$_{1-6}$ alkyl, C(O)OC$_{1-6}$ alkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{10f}$R$^{10f}$, (CH$_2$)$_r$phenyl, and a heterocycle substituted with 0–1 R$^{10g}$, wherein the heterocycle is selected from imidazole, thiazole, oxazole, pyrazole, 1,2,4-triazole, 1,2,3-triazole, isoxazole, and tetrazole,;

R$^{10f}$, at each occurrence, is selected from H, C$_{1-6}$ alkyl, C$_{3-6}$ cycloalkyl, and phenyl;

R$^{10g}$ is selected from methyl, ethyl, acetyl, and CF$_3$;

R$^{10h}$ is selected from H, C$_{1-6}$ alkyl, C$_{3-6}$ cycloalkyl, (CH$_2$)$_r$phenyl, C(O)R$^{10f}$, C(O)OR$^{10i}$, and SO$_2$R$^{10i}$;

R$^{10i}$, at each occurrence, is selected from C$_{1-6}$ alkyl, C$_{3-6}$ cycloalkyl;

R$^{13}$, at each occurrence, is selected from C$_{1-6}$ alkyl, C$_{2-8}$ alkenyl, C$_{2-8}$ alkynyl, C$_{3-6}$ cycloalkyl, (CF$_2$)$_w$CF$_3$, (CH$_2$)$_q$NR$^{13a}$R$^{13a'}$, (CH$_2$)$_q$OH, (CH$_2$)$_q$OR$^{13b}$, (CH$_2$)$_q$SH, (CH$_2$)$_q$SR$^{13b}$, (CH$_2$)$_w$C(O)OH, (CH$_2$)$_w$C(O)R$^{13b}$, (CH$_2$)$_w$C(O)NR$^{13a}$R$^{13a'}$, (CH$_2$)$_q$NR$^{13d}$C(O)R$^{13a}$, (CH$_2$)$_w$C(O)OR$^{13b}$, (CH$_2$)$_q$OC(O)R$^{13b}$, (CH$_2$)$_w$S(O)$_p$R$^{13b}$, (CH$_2$)$_w$S(O)$_2$NR$^{13a}$R$^{13a'}$, (CH$_2$)$_q$NR$^{13d}$S(O)$_2$R$^{13b}$, and (CH$_2$)$_w$-phenyl substituted with 0–3 R$^{13c}$;

R$^{13a}$ and R$^{13a'}$, at each occurrence, are selected from H, C$_{1-6}$ alkyl, C$_{3-6}$ cycloalkyl, and phenyl substituted with 0–3 R$^{13c}$;

R$^{13b}$, at each occurrence, is selected from C$_{1-6}$ alkyl, C$_{3-6}$ cycloalkyl, and phenyl substituted with 0–3 R$^{13c}$;

R$^{13c}$, at each occurrence, is selected from C$_{1-6}$ alkyl, C$_{3-6}$ cycloalkyl, Cl, F, Br, I, CN, NO$_2$, (CF$_2$)$_r$CF$_3$, (CH$_2$)$_r$OC$_{1-5}$ alkyl, (CH$_2$)$_r$OH, (CH$_2$)$_r$SC$_{1-5}$ alkyl, and (CH$_2$)$_r$NR$^{13d}$R$^{13d}$;

R$^{13d}$, at each occurrence, is selected from H, C$_{1-6}$ alkyl, and C$_{3-6}$ cycloalkyl;

R$^{15}$, at each occurrence, is selected from =O, C$_{1-8}$ alkyl, (CH$_2$)$_r$C$_{3-6}$ cycloalkyl, Cl, Br, I, F, NO$_2$, CN, (CHR')$_r$NR$^{15a}$R$^{15a'}$, (CHR')$_r$OH, (CHR')$_r$O(CHR')$_r$R$^{15d}$, (CHR')$_r$SH, (CHR')$_r$C(O)H, (CHR')$_r$C(O)OH, (CHR')$_r$C(O) (CHR')$_r$R$^{15b}$, (CHR')$_r$C(O) (CHR')$_r$R$^{15b}$, (CHR')$_r$C(O)NR$^{15a}$R$^{15a'}$, (CHR')$_r$NR$^{15f}$C(O)O(CHR')$_r$R$^{15d}$, (CHR')$_r$OC(O)NR$^{15a}$R$^{15a'}$, (CHR')$_r$NR$^{15f}$C(O) (CHR')$_r$R$^{15b}$, (CHR')$_r$NR$^{15f}$C(O)NR$^{15f}$R$^{15f}$, (CHR')$_r$C(O)O(CHR')$_r$R$^{15d}$, (CHR')$_r$OC(O) (CHR')$_r$R$^{15b}$, (CHR')$_r$C(=NR$^{15f}$)NR$^{15a}$R$^{15a'}$, (CHR')$_r$NHC(=NR$^{15f}$)NR$^{15f}$R$^{15f}$, (CHR')$_r$S(O)$_p$(CHR')$_r$R$^{15b}$, (CHR')$_r$S(O)$_2$NR$^{15a}$R$^{15a'}$, (CHR')$_r$NR$^{15f}$S(O)$_2$ (CHR')$_r$R$^{15b}$, C$_{1-6}$ haloalkyl, C$_{2-8}$ alkenyl substituted with 0–3 R', C$_{2-8}$ alkynyl substituted with 0–3 R', (CHR')$_r$phenyl substituted with 0–3 R$^{15e}$, and a (CH$_2$)$_r$-5–10 membered heterocyclic system containing 1–4 heteroatoms selected from N, O, and S, substituted with 0–2 R$^{15e}$;

R', at each occurrence, is independently selected from H, C$_{1-6}$ alkyl, C$_{3-8}$ alkenyl, C$_{3-8}$ alkynyl, (CH$_2$)$_r$C$_{3-6}$ cycloalkyl, and (CH$_2$)$_r$phenyl substituted with R$^{15e}$;

R$^{15a}$ and R$^{15a'}$, at each occurrence, are selected from H, C$_{1-6}$ alkyl, C$_{3-8}$ alkenyl, C$_{3-8}$ alkynyl, a (CH$_2$)$_r$—C$_{3-10}$ carbocyclic residue substituted with 0–5 R$^{15e}$, and a (CH$_2$)$_r$-5–10 membered heterocyclic system containing 1–4 heteroatoms selected from N, O, and S, substituted with 0–2 R$^{15e}$;

alternatively, R$^{15a}$ and R$^{15a'}$, along with the N to which they are attached, join to form a 5–6 membered heterocyclic system containing 1–2 heteroatoms selected from NR$^{15h}$, O, and S and optionally fused with a benzene ring or a 6-membered aromatic heterocycle;

R$^{15b}$, at each occurrence, is selected from C$_{1-6}$ alkyl, C$_{3-8}$ alkenyl, C$_{3-8}$ alkynyl, a (CH$_2$)$_r$—C$_{3-6}$ carbocyclic residue substituted with 0–3 R$^{15e}$, and (CH$_2$)$_r$-5–membered heterocyclic system containing 1–4 heteroatoms selected from N, O, and S, substituted with 0–2 R$^{15e}$;

R$^{15d}$, at each occurrence, is selected from C$_{3-8}$ alkenyl, C$_{3-8}$ alkynyl, methyl, CF$_3$, C$_{2-6}$ alkyl substituted with 0–3 R$^{15e}$, a (CH$_2$)$_r$—C$_{3-10}$ carbocyclic residue substituted with 0–3 R$^{15e}$, and a (CH$_2$)$_r$5–6 membered heterocyclic system containing 1–4 heteroatoms selected from N, O, and S, substituted with 0–3 R$^{15e}$;

R$^{15e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, C(O)C$_{1-6}$ alkyl, C(O)OC$_{1-6}$ alkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{15f}$R$^{15f}$, (CH$_2$)$_r$phenyl, and a heterocycle substituted with 0–1 R$^{15g}$, wherein the heterocycle is selected from imidazole, thiazole, oxazole, pyrazole, 1,2,4-triazole, 1,2,3-triazole, isoxazole, and tetrazole;

R$^{15f}$, at each occurrence, is selected from H, C$_{1-6}$ alkyl, C$_{3-6}$ cycloalkyl, and phenyl;

R$^{15g}$ is selected from methyl, ethyl, acetyl, and CF$_3$;

R$^{15h}$ is selected from H, C$_{1-6}$ alkyl, C$_{3-6}$ cycloalkyl, (CH$_2$)$_r$phenyl, C(O)R$^{15f}$, C(O)OR$^{15i}$, and SO$_2$R$^{15i}$;

R$^{15i}$, is each occurrence, is selected from C$_{16-6}$ alkyl, C$_{3-6}$ cycloalkyl;

R$^{16}$, at each occurrence, is selected from C$_{1-8}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CHR')$_r$NR$^{16a}$R$^{16a'}$, (CHR')$_r$OH, (CHR')$_r$O(CHR')$_r$R$^{16d}$, (CHR')$_r$SH, (CHR')$_r$C(O)H, (CHR')$_r$C(O)OH, (CHR')$_r$C(O) (CHR')$_r$R$^{16b}$, (CHR')$_r$C(O)NR$^{16a}$R$^{16a'}$, (CHR')$_r$NR$^{16f}$C(O) (CHR')$_r$R$^{16b}$, (CHR')$_r$C(O)O(CHR')$_r$R$^{16d}$, (CHR')$_r$OC(O) (CHR')$_r$R$^{16b}$, (CHR')$_r$C(=NR$^{16f}$)NR$^{16a}$R$^{16a'}$, (CHR')$_r$NHC(=NR$^{16f}$)NR$^{16f}$R$^{16f}$, (CHR')$_r$S(O)$_p$(CHR')$_r$R$^{16b}$, (CHR')$_r$S(O)$_2$NR$^{16a}$R$^{16a'}$, (CHR')$_r$NR$^{16f}$S(O)$_2$(CHR')$_r$R$^{16b}$, C$_{1-6}$ haloalkyl, C$_{2-8}$ alkenyl substituted with 0–3 R', C$_{2-8}$ alkynyl substituted with 0–3 R', and (CHR')$_r$phenyl substituted with 0–3 R$^{16e}$;

R$^{16a}$ and R$^{16a'}$, at each occurrence, are selected from H, C$_{1-6}$ alkyl, C$_{3-8}$ alkenyl, C$_{3-8}$ alkynyl, a (CH$_2$)$_r$—C$_{3-10}$ carbocyclic residue substituted with 0–5 R$^{16e}$, and a (CH$_2$)$_r$-5–10 membered heterocyclic system containing 1–4 heteroatoms selected from N, O, and S, substituted with 0–2 R$^{16e}$;

alternatively, R$^{16a}$ and R$^{16a'}$, along with the N to which they are attached, join to form a 5–6 membered heterocyclic system containing 1–2 heteroatoms selected from NR$^{16h}$, O, and S and optionally fused with a benzene ring or a 6-membered aromatic heterocycle;

R$^{16b}$, at each occurrence, is selected from C$_{1-6}$ alkyl, C$_{3-8}$ alkenyl, C$_{3-8}$ alkynyl, a (CH$_2$)$_r$C$_{3-6}$ carbocyclic residue substituted with 0–3 R$^{16e}$, and a (CH$_2$)$_r$-5–membered heterocyclic system containing 1–4 heteroatoms selected from N, O, and S, substituted with 0–2 R$^{16e}$;

R$^{16d}$, at each occurrence, is selected from C$_{3-8}$ alkenyl, C$_{3-8}$ alkynyl, C$_{1-6}$ alkyl substituted with 0–3 R$^{16e}$, a (CH$_2$)$_r$—C$_{3-10}$ carbocyclic residue substituted with 0–3 R$^{16e}$, and a (CH$_2$)$_r$-5–membered heterocyclic system containing 1–4 heteroatoms selected from N, O, and S, substituted with 0–3 R$^{16e}$;

$R^{16e}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, F, Br, I, CN, $NO_2$, $(CF_2)_r CF_3$, $(CH_2)_r OC_{1-5}$ alkyl, OH, SH, $(CH_2)_r SC_{1-5}$ alkyl, $(CH_2)_r NR^{16f} R^{16f}$, and $(CH_2)_r$phenyl;

$R^{16f}$, at each occurrence, is selected from H, $C_{1-5}$ alkyl, and $C_{3-6}$ cycloalkyl, and phenyl;

$R^{16h}$ is selected from H, $C_{1-6}$ alkyl, $C_{3-6}$ cycloalkyl, $(CH_2)_r$phenyl, $C(O)R^{16f}$, $C(O)OR^{16i}$, and $SO_2 R^{16i}$;

$R^{16i}$, at each occurrence, is selected from $C_{1-6}$ alkyl, $C_{3-6}$ cycloalkyl;

m, at each occurrence, is independently selected from 0, 1, and 2;

t, at each occurrence, is independently selected from 1 and 2;

w, at each occurrence, is independently selected from 0 and 1;

r, at each occurrence, is independently selected from 0, 1, 2, 3, 4, and 5;

q, at each occurrence, is independently selected from 1, 2, 3, 4, and 5; and p, at each occurrence, is independently selected from 0, 1, and 2.

19. The method of claim 18 wherein the chemokine receptor is CCR3.

20. A method for inhibiting the chemokine receptor activity comprising administering to a patient in need thereof a chemokine receptor inhibitory amount of a compound according to claim 7.

21. A method for treating asthma, comprising administering to a patient in need thereof a therapeutically effective amount of a compound according to claim 7.

22. The method of claim 20 wherein the chemokine receptor is CCR3.

23. A method for treating an inflammatory disorder comprising administering to a patient in need thereof a therapeutically effective amount of a compound according to claim 7, or a pharmaceutically acceptable salt thereof.

24. A method according to claim 23, wherein the disorder is selected from asthma, allergic rhinitis, atopic dermatitis, inflammatory bowel diseases, idiopathic pulmonary fibrosis, bullous pemphigoid, allergic colitis, eczema, conjunctivitis, familial eosinophilia, eosinophilic cellulitis, eosinophilic pneumonias, eosinophilic fasciitis, and eosinophilic gastroenteritis.

* * * * *